US012102687B2

(12) United States Patent
Subramanian et al.

(10) Patent No.: US 12,102,687 B2
(45) Date of Patent: *Oct. 1, 2024

(54) MUSCLE TARGETING COMPLEXES AND USES THEREOF FOR TREATING MYOTONIC DYSTROPHY

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US); Cody A. Desjardins, Waltham, MA (US); Brendan Quinn, Waltham, MA (US); John Najim, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/609,032

(22) Filed: Mar. 19, 2024

(65) Prior Publication Data

US 2024/0238435 A1    Jul. 18, 2024

Related U.S. Application Data

(63) Continuation of application No. 18/495,086, filed on Oct. 26, 2023, now Pat. No. 11,969,475, which is a continuation-in-part of application No. 18/490,905, filed on Oct. 20, 2023, now abandoned, which is a continuation of application No. 18/181,795, filed on Mar. 10, 2023, now Pat. No. 11,839,660, which is a continuation of application No. 17/811,401, filed on Jul. 8, 2022, now Pat. No. 11,672,872, said application No. 18/495,086 is a continuation-in-part of application No. 18/349,631, filed on Jul. 10, 2023, now Pat. No. 11,986,537, which is a continuation of application No. 17/811,370, filed on Jul. 8, 2022, now Pat. No. 11,771,776, said application No. 18/495,086 is a continuation-in-part of application No. 18/329,781, filed on Jun. 6, 2023, now Pat. No. 11,844,843, which is a continuation of application No. 18/063,795, filed on Dec. 9, 2022, now Pat. No. 11,679,161, which is a continuation of application No. 17/811,380, filed on Jul. 8, 2022, now Pat. No. 11,638,761, said application No. 18/495,086 is a continuation-in-part of application No. 18/181,700, filed on Mar. 10, 2023, now abandoned, which is a continuation of application No. 17/811,424, filed on Jul. 8, 2022, now Pat. No. 11,633,498.

(60) Provisional application No. 63/220,043, filed on Jul. 9, 2021, provisional application No. 63/220,262, filed on Jul. 9, 2021, provisional application No.
(Continued)

(51) Int. Cl.
| | |
|---|---|
| A61K 39/395 | (2006.01) |
| A61K 47/68 | (2017.01) |
| C07K 14/47 | (2006.01) |
| C07K 16/28 | (2006.01) |
| C12N 15/113 | (2010.01) |
| A61K 38/00 | (2006.01) |
| A61K 39/00 | (2006.01) |

(52) U.S. Cl.
CPC ...... *A61K 47/6807* (2017.08); *A61K 47/6849* (2017.08); *C07K 14/4707* (2013.01); *C07K 16/2881* (2013.01); *C12N 15/113* (2013.01); *A61K 38/00* (2013.01); *A61K 2039/505* (2013.01); *C07K 2317/24* (2013.01); *C07K 2317/33* (2013.01); *C07K 2317/55* (2013.01); *C07K 2317/77* (2013.01); *C07K 2317/92* (2013.01); *C07K 2317/94* (2013.01); *C12N 2310/11* (2013.01); *C12N 2310/14* (2013.01); *C12N 2310/3513* (2013.01)

(58) Field of Classification Search
None
See application file for complete search history.

(56) References Cited

U.S. PATENT DOCUMENTS

| | | |
|---|---|---|
| 2,631,173 A | 3/1953 | Hillyer et al. |
| 6,214,345 B1 | 4/2001 | Firestone et al. |
| | (Continued) | |

FOREIGN PATENT DOCUMENTS

| | | |
|---|---|---|
| CN | 103443125 A | 12/2013 |
| CN | 103732259 A | 4/2014 |
| | (Continued) | |

OTHER PUBLICATIONS

[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.

(Continued)

*Primary Examiner* — Meera Natarajan
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits expression or activity of a DMPK allele comprising a disease-associated-repeat. In some embodiments, the molecular payload is an oligonucleotide, such as an antisense oligonucleotide or RNAi oligonucleotide.

30 Claims, 61 Drawing Sheets

Specification includes a Sequence Listing.

Related U.S. Application Data

63/220,155, filed on Jul. 9, 2021, provisional application No. 63/220,144, filed on Jul. 9, 2021.

(56) References Cited

U.S. PATENT DOCUMENTS

| | | |
|---|---|---|
| 7,015,315 B1 | 3/2006 | Cook et al. |
| 7,064,142 B2 | 6/2006 | Sato et al. |
| 7,265,131 B2 | 9/2007 | Johnson et al. |
| 7,575,886 B2 | 8/2009 | Venkataraman et al. |
| 8,580,756 B2 | 11/2013 | Hansen et al. |
| 8,846,639 B2 | 9/2014 | Swayze et al. |
| 8,859,629 B2 | 10/2014 | van Delft et al. |
| 8,952,147 B2 | 2/2015 | Bouchard et al. |
| 9,045,754 B2 | 6/2015 | Bhanot et al. |
| 9,222,940 B2 | 12/2015 | van Delft et al. |
| 9,260,371 B2 | 2/2016 | Bertozzi et al. |
| 9,428,534 B2 | 8/2016 | Christensen et al. |
| 9,504,758 B2 | 11/2016 | van Delft et al. |
| 9,550,834 B2 | 1/2017 | Shirai et al. |
| 9,550,988 B2 | 1/2017 | Swayze |
| 9,610,362 B2 | 4/2017 | Armstrong |
| 9,617,540 B2 | 4/2017 | Bhanot et al. |
| 9,695,418 B2 | 7/2017 | Seth et al. |
| 9,708,406 B2 | 7/2017 | Zhang et al. |
| 9,708,614 B2 | 7/2017 | Christensen et al. |
| 9,765,338 B2 | 9/2017 | Bennett et al. |
| 10,131,682 B2 | 11/2018 | Zhao |
| 10,238,753 B2 | 3/2019 | Armstrong |
| 10,239,807 B2 | 3/2019 | van Delft et al. |
| 10,266,502 B2 | 4/2019 | van Delft et al. |
| 10,434,111 B2 | 10/2019 | Bertozzi et al. |
| 10,493,092 B2 | 12/2019 | Swayze |
| 10,550,188 B2 | 2/2020 | Geall et al. |
| 10,881,743 B2 | 1/2021 | Geall et al. |
| 11,111,309 B2 | 9/2021 | Subramanian et al. |
| 11,168,141 B2 | 11/2021 | Subramanian et al. |
| 11,230,605 B2 * | 1/2022 | Launay ................... A61P 35/00 |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 11,497,815 B2 | 11/2022 | Subramanian et al. |
| 11,518,816 B2 | 12/2022 | Subramanian et al. |
| 11,633,496 B2 | 4/2023 | Subramanian et al. |
| 11,633,498 B2 | 4/2023 | Subramanian et al. |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,759,525 B1 | 9/2023 | Subramanian et al. |
| 11,771,776 B2 | 10/2023 | Subramanian et al. |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 11,911,484 B2 | 2/2024 | Subramanian et al. |
| 11,931,421 B2 | 3/2024 | Hilderbrand et al. |
| 11,969,475 B2 | 4/2024 | Subramanian et al. |
| 11,986,537 B2 | 5/2024 | Subramanian et al. |
| 12,005,124 B2 | 6/2024 | Subramanian et al. |
| 2004/0063654 A1 | 4/2004 | Davis et al. |
| 2004/0191243 A1 | 9/2004 | Chen et al. |
| 2005/0084906 A1 | 4/2005 | Goetsch et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2011/0009471 A1 | 1/2011 | Kaneko et al. |
| 2011/0250199 A1 | 10/2011 | Fitzgerald et al. |
| 2011/0256157 A1 | 10/2011 | Howard et al. |
| 2012/0122801 A1 | 5/2012 | Platenburg |
| 2012/0201809 A1 | 8/2012 | Bhat et al. |
| 2012/0225013 A1 | 9/2012 | Dennis et al. |
| 2013/0028891 A1 | 1/2013 | Penichet et al. |
| 2013/0066063 A1 | 3/2013 | Berry et al. |
| 2013/0137763 A1 | 5/2013 | van Delft et al. |
| 2013/0177579 A1 | 7/2013 | Lin et al. |
| 2013/0237585 A1 | 9/2013 | Bennett et al. |
| 2014/0193436 A1 | 7/2014 | Prudent |
| 2014/0323552 A1 | 10/2014 | Burghes et al. |
| 2015/0064181 A1 | 3/2015 | Armstrong |
| 2015/0225722 A1 | 8/2015 | Ozsolak |
| 2015/0258210 A1 | 9/2015 | van Delft et al. |
| 2016/0015828 A1 | 1/2016 | Torgov et al. |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0250347 A1 | 9/2016 | van Delft et al. |
| 2016/0272973 A1 | 9/2016 | Shehadeh |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2017/0342169 A1 | 11/2017 | Akamatsu et al. |
| 2017/0348416 A1 | 12/2017 | Hasler et al. |
| 2018/0002433 A1 | 1/2018 | Zhang et al. |
| 2018/0021449 A1 | 1/2018 | Armstrong |
| 2018/0134797 A1 | 5/2018 | Zhang et al. |
| 2018/0369400 A1 | 12/2018 | Levin et al. |
| 2019/0000986 A1 | 1/2019 | Levin et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0153083 A1 | 5/2019 | Juste et al. |
| 2019/0211362 A1 | 7/2019 | Lundberg et al. |
| 2019/0240346 A1 | 8/2019 | Sugo et al. |
| 2019/0298847 A1 | 10/2019 | Geall et al. |
| 2019/0336615 A1 | 11/2019 | Thompson et al. |
| 2020/0046742 A1 | 2/2020 | Bertozzi et al. |
| 2020/0048174 A1 | 2/2020 | van Delft et al. |
| 2020/0123267 A1 | 4/2020 | Zhang et al. |
| 2020/0282074 A1 | 9/2020 | Levin et al. |
| 2020/0325237 A1 | 10/2020 | Darimont et al. |
| 2021/0038739 A1 | 2/2021 | Takahashi et al. |
| 2021/0130486 A1 | 5/2021 | Darimont et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |

(56) References Cited

U.S. PATENT DOCUMENTS

| | | |
|---|---|---|
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016950 A1 | 1/2024 | Weeden et al. |
| 2024/0016952 A1 | 1/2024 | Subramanian et al. |
| 2024/0066139 A1 | 2/2024 | Subramanian et al. |
| 2024/0066140 A1 | 2/2024 | Subramanian et al. |
| 2024/0067743 A1 | 2/2024 | Subramanian et al. |
| 2024/0067744 A1 | 2/2024 | Subramanian et al. |
| 2024/0100177 A1 | 3/2024 | Hildebrand et al. |
| 2024/0110184 A1 | 4/2024 | Brown et al. |
| 2024/0117356 A1 | 4/2024 | Subramanian et al. |
| 2024/0148891 A1 | 5/2024 | Subramanian et al. |

FOREIGN PATENT DOCUMENTS

| | | |
|---|---|---|
| EP | 2149605 A2 | 2/2010 |
| EP | 2410053 A1 | 1/2012 |
| EP | 2410054 A1 | 1/2012 |
| EP | 3031920 A1 | 6/2016 |
| EP | 3067421 A1 | 9/2016 |
| EP | 2623609 B1 | 1/2017 |
| EP | 3202905 A1 | 8/2017 |
| EP | 2922818 B1 | 9/2018 |
| EP | 3473270 A1 | 4/2019 |
| EP | 3489360 A2 | 5/2019 |
| EP | 3560958 A1 | 10/2019 |
| IL | 54795 A | 10/1980 |
| JP | 2002-253259 A | 9/2002 |
| JP | 2010-532168 | 10/2010 |
| JP | 2013-538560 A | 1/2012 |
| JP | 2015-532264 A | 11/2015 |
| JP | 2015-534996 A | 12/2015 |
| JP | 2016-528258 A | 9/2016 |
| WO | WO 1989/007970 A1 | 9/1989 |
| WO | WO 1991/004753 A1 | 4/1991 |
| WO | WO 2003/059951 A2 | 7/2003 |
| WO | WO 2004/069991 A2 | 8/2004 |
| WO | WO 2005/023825 A2 | 3/2005 |
| WO | WO 2006/022688 A1 | 3/2006 |
| WO | WO 2007/089612 A2 | 8/2007 |
| WO | WO 2008/018795 A1 | 2/2008 |
| WO | WO 2008/049085 A1 | 4/2008 |
| WO | WO 2009/005793 A2 | 1/2009 |
| WO | WO 2009/144481 A2 | 12/2009 |
| WO | WO 2010/048586 A1 | 4/2010 |
| WO | WO 2011/136645 A1 | 11/2011 |
| WO | WO 2012/012443 A2 | 1/2012 |
| WO | WO 2012/012467 A2 | 1/2012 |
| WO | WO 2012/075037 A1 | 6/2012 |
| WO | WO 2012/144906 A1 | 10/2012 |
| WO | WO 2013/085550 A2 | 6/2013 |
| WO | WO 2013/126746 A2 | 8/2013 |
| WO | WO 2013/138662 A1 | 9/2013 |
| WO | WO 2013/162363 A1 | 10/2013 |
| WO | WO 2014/052276 A1 | 4/2014 |
| WO | WO 2014/065661 A1 | 5/2014 |
| WO | WO/2015/021457 * | 2/2015 |
| WO | WO 2015/021457 A2 | 2/2015 |
| WO | WO 2015/023937 A1 | 2/2015 |
| WO | WO 2015/042581 A1 | 3/2015 |
| WO | WO 2015/179741 A1 | 11/2015 |
| WO | WO 2016/081643 A1 | 5/2016 |
| WO | WO 2016/081670 A2 | 5/2016 |
| WO | WO 2016/187425 A1 | 11/2016 |
| WO | WO 2017/100467 A2 | 6/2017 |
| WO | WO 2017/106643 A1 | 6/2017 |
| WO | WO 2017/143156 A1 | 8/2017 |
| WO | WO 2017/173408 A1 | 10/2017 |
| WO | WO 2017/192679 A1 | 11/2017 |
| WO | WO 2017/205191 A1 | 11/2017 |
| WO | WO 2017/221883 A1 | 12/2017 |
| WO | WO 2018/129384 A1 | 7/2018 |
| WO | WO 2018/226861 A1 | 12/2018 |
| WO | WO 2019/060775 A1 | 3/2019 |
| WO | WO 2019/071028 A1 | 4/2019 |
| WO | WO 2019/113393 A1 | 6/2019 |
| WO | WO 2019/136180 A2 | 7/2019 |
| WO | WO 2019/151539 A1 | 8/2019 |
| WO | WO 2019/157224 A1 | 8/2019 |
| WO | WO 2019/215175 A1 | 11/2019 |
| WO | WO 2019/229658 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/163817 A1 | 8/2020 |
| WO | WO 2020/247738 A1 | 12/2020 |
| WO | WO 2020/247782 A1 | 12/2020 |
| WO | WO 2020/247818 A1 | 12/2020 |
| WO | WO2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051665 A1 | 3/2022 |
| WO | WO 2022/056266 A2 | 3/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |
| WO | WO 2023/044398 A1 | 3/2023 |
| WO | WO 2023/077120 A1 | 5/2023 |
| WO | WO 2023/086864 A1 | 5/2023 |
| WO | WO 2023/201318 A1 | 10/2023 |
| WO | WO 2023/201324 A1 | 10/2023 |

(56) References Cited

FOREIGN PATENT DOCUMENTS

| | | |
|---|---|---|
| WO | WO 2023/201332 A1 | 10/2023 |
| WO | WO 2024/011135 A1 | 1/2024 |
| WO | WO 2024/011150 A1 | 1/2024 |
| WO | WO 2024/097644 A1 | 5/2024 |

OTHER PUBLICATIONS

[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.

[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.

[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.

[No Author Listed], Baliforsen—Ionis Pharmaceuticals Drug Profile. Springer Nature Switzerland AG. Nov. 15, 2016. 9 pages.

[No Author Listed], Building the world's leading muscle disease company. Dyne Company Overview. Jun. 2021. 42 pages.

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.

[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.

Agard et al., A Comparative Study of Bioorthogonal Reactions with Azides. ACS Chem. Biol. 2006;1(10):644-8. Epub Oct. 20, 2006.

Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.

Altshuler et al., Generation of recombinant antibodies and means for increasing their affinity. Biochemistry (Mosc). Dec. 2010;75(13):1584-605.

Anciaux et al., Transition-metal-catalyzed reactions of diazo compounds. 1. Cyclopropanation of double bonds. The Journal of Organic Chemistry. Feb. 1980;45(4):695-702.

Antony-Mayer et al., Bicyclo[6.1.0]nonynes. Chemische Berichte. Nov. 1988;121(11):2013-8.

Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.

Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.

Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.

Ast et al., Estergruppenhaltige Polyalkenylene durch Olefin-Metathese. Die Makromolekulare Chemie. May 1976;177(5):1349-55.

Barfield et al., A Novel HER2-targeted Antibody-drug Conjugate Offers the Possibility of Clinical Dosing at Trastuzumab-equivalent Exposure Levels. Mol Cancer Ther. Sep. 2020;19(9):1866-1874. doi: 10.1158/1535-7163.MCT-20-0190. Epub Jul. 10, 2020.

Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.

Baskin et al., Copper-free click chemistry for dynamic in vivo imaging. PNAS. Oct. 2007; 104(43):16793-7.

Behlke, Chemical modification of siRNAs for in vivo use. Oligonucleotides. Dec. 2008;18(4):305-19.

Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.

Beskrovnaya, Forcetm platform delivers exon skipping PMO, leads to durable increases in dystrophin protein in mdx mice and is well tolerated NHPs. Presented at Muscle Study Group Annual Scientific Meeting. Oct. 1, 2021. 29 pages.

Bien-Ly et al., Transferrin receptor (TfR) trafficking determines brain uptake of TfR antibody affinity variants. J Exp Med. Feb. 10, 2014;211(2):233-44. Epub Jan. 27, 2014.

Black, 9.13.4.1.1.3.2 Variation 2: C-Alkylation (and Arylation) by Carbenes and Free Radicals. Science of Synthesis. 2001;9:514.

Brown et al., Tolerance to single, but not multiple, amino acid replacements in antibody VH CDR 2: a means of minimizing B cell wastage from somatic hypermutation? J Immunol. May 1, 1996;156(9):3285-91.

Buntz et al., Quantitative fluorescence imaging determines the absolute No. of locked nucleic acid oligonucleotides needed for suppression of target gene expression. Nucleic Acids Res. Jan. 25, 2019;47(2):953-969. doi: 10.1093/nar/gky1158.

Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.

Candelaria et al., Antibodies Targeting the Transferrin Receptor 1 (TfR1) as Direct Anti-cancer Agents. Front Immunol. Mar. 17, 2021;12:607692.

Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.

Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Cho et al., Myotonic dystrophy: emerging mechanisms for DM1 and DM2. Biochim Biophys Acta. Feb. 2007;1772(2):195-204. Epub Jun. 20, 2006.

Chothia et al., Canonical structures for the hypervariable regions of immunoglobulins. J Mol Biol. Aug. 20, 1987;196(4):901-17. doi: 10.1016/0022-2836(87)90412-8.

Clark et al., Increased brain uptake of targeted nanoparticles by adding an acid-cleavable linkage between transferrin and the nanoparticle core. PNAS. Oct. 2015;112(40):12486-91.

Codelli et al., Second-Generation Difluorinated Cyclooctynes for Copper-Free Click Chemistry. J. Am. Chem. Soc. 2008;130(34):11486-11493. Epub Aug. 5, 2008.

Coico et al., Immunology: A short course. 2008 (originally published 2003): 61-2. 8 pages (including English translation).

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., Antisense research and applications. 1993. p. 15-35.

Crooke et al., Kinetic characteristics of Escherichia coli RNase H1: cleavage of various antisense oligonucleotide-RNA duplexes. Biochem J . Dec. 1, 1995;312(Pt 2):599-608. doi: 10.1042/bj3120599.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

(56) References Cited

OTHER PUBLICATIONS

Danis et al., Potential therapeutic application of antisense oligonucleotides in the treatment of ocular diseases. Expert Opin Pharmacother. Feb. 2001;2(2):277-91.
Darimont et al., A novel antibody-oligonucleotide conjugate (AOC) platform enables efficient regulation of muscle targets in mice. Abstract. 8-05. J. Cach Sarcopen Musc. 2017; 8: 1065-66.
Davis et al., Improved targeting of miRNA with antisense oligonucleotides. Nucleic Acids Res. May 11, 2006;34(8):2294-304. doi: 10.1093/nar/gkl183. Print 2006.
Debets et al., Bioorthogonal labelling of biomolecules: new functional handles and ligation methods. Org Biomol Chem. Oct. 14, 2013;11(38):6439-55. Epub Aug. 23, 2013.
Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.
Desjardins et al., Building a FORCETM platform-based DMD franchise for the treatment of individuals with mutations amenable to exon skipping. Neuromusc Dis. Oct. 2022; 32: S101-2. Abstract.
Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.
Desjardins et al., ForceTM platform achieves robust exon skipping, restores dystrophin at the sarcolemma and halts progression of fibrosis in the severe D2-mdx model of DMD. Abstract. Mar. 2023. 1 page.
Desjardins et al., ForceTM platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19- 22, 2023. 1 page.
Dommerholt et al., Readily accessible bicyclononynes for bioorthogonal labeling and three-dimensional imaging of living cells. Angew Chem Int Ed. Dec. 3, 2010;49(49):9422-5.
Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.
Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.
Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.
Elangkovan et al., Gene Therapy for Duchenne Muscular Dystrophy. J Neuromuscul Dis. 2021;8(s2):S303-S316.
Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.
Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.
Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.
Furling et al., Abstract R.P.1.01 Therapeutic RNA strategies for myotonic dystrophy with CTG repeats. Neuromuscular Disorders. 2004;14:585. 2 pages total.
Furling et al., Viral vector producing antisense RNA restores myotonic dystrophy myoblast functions. Gene Ther. May 2003;10(9):795-802.
Gagnon et al., RNAi factors are present and active in human cell nuclei. Cell Rep. Jan. 16, 2014;6(1):211-21. Epub Jan. 2, 2014.
Galderisi et al., Myotonic dystrophy: antisense oligonucleotide inhibition of DMPK gene expression in vitro. Biochem Biophys Res Commun. Apr. 25, 1996;221(3):750-4.
Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.
Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.
Giles et al., Enhanced RNase H activity with methylphosphonodiester/phosphodiester chimeric antisense oligodeoxynucleotides. Anticancer Drug Des. Feb. 1992;7(1):37-48.
Girones et al. Comparison of the kinetics of cycling of the transferrin receptor in the presence or absence of bound diferric transferrin. Biochem J. Nov. 15, 1989;264(1):35-46.
Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.
Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.
Gray et al., Combinatorial peptide libraries: mining for cell-binding peptides. Chem Rev. Jan. 22, 2014;114(2):1020-81.
Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.
Iwaki et al., Preparation of Chiral Stationary Phase via Activated Carbamate Intermediate for Liquid Chromatographic Optical Resolution. Chromatographia. Oct. 1987;23:727-30.
Jain et al., Current ADC Linker Chemistry. Pharm Res. Nov. 2015;32(11):3526-40. Epub Mar. 11, 2015.
Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.
Jeara Wiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.
Jepsen et al., Locked nucleic acid: a potent nucleic acid analog in therapeutics and biotechnology. Oligonucleotides. 2004;14(2):130-46. doi: 10.1089/1545457041526317.
Juliano, The delivery of therapeutic oligonucleotides. Nucleic Acids Res. Aug. 19, 2016;44(14):6518-48. doi: 10.1093/nar/gkw236. Epub Apr. 15, 2016.
Kher et al., Antisense Oligonucleotides and RNA Interference. Challenges in Delivery of Therapeutic Genomics and Proteomics. Aug. 2011:325-86.
Kline et al., Methods to Make Homogenous Antibody Drug Conjugates. Pharm Res. Nov. 2015;32(11):3480-93. Epub Dec. 16, 2014.
Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

(56) References Cited

OTHER PUBLICATIONS

Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.
Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.
Kurreck et al., Design of antisense oligonucleotides stabilized by locked nucleic acids. Nucleic Acids Res. May 1, 2002;30(9):1911-8. doi: 10.1093/nar/30.9.1911.
Kurreck, Antisense technologies. Improvement through novel chemical modifications. Eur J Biochem. Apr. 2003;270(8):1628-44.
Lai et al., Mechanism of action and spectrum of cell lines sensitive to a doxorubicin-transferrin conjugate. Cancer Chemother Pharmacol. 1998;41(2):155-60. doi: 10.1007/s002800050722.
Langlois et al., Abstract 831—Ribozyme and Antisense RNA-Based Gene Therapies for Myotonic Dystrophy. Molecular Therapy. May 2003;7(5, Part 2):S320.
Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.
Langlois et al., Hammerhead ribozyme-mediated destruction of nuclear foci in myotonic dystrophy myoblasts. Mol Ther. May 2003;7(5 Pt 1):670-80.
Lawrence et al., Crystal structure of the ectodomain of human transferrin receptor. Science. Oct. 22, 1999;286(5440):779-82. doi: 10.1126/science.286.5440.779.
Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.
Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.
Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.
Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.
Levin, Targeting Therapeutic Oligonucleotides. N Engl J Med. Jan. 5, 2017;376(1):86-88. doi: 10.1056/NEJMcibr1613559.
Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.
Liang et al., Targeted delivery of plasmid DNA to myogenic cells via transferrin-conjugated peptide nucleic acid. Mol Ther. Mar. 2000; 1(3):236-43. doi: 10.1006/mthe.2000.0043.
Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.
Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.
Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.
Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.
Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.
Meeuwissen et al., Cofactor regeneration in polymersome nanoreactors: Enzymatically catalysed Baeyer-Villiger reactions. Journal of Materials Chemistry. Dec. 2011;21(47):18923-6.
Mignon, Update on Ionis-DMPKRX Program. 2018 MDF Annual Conference. Nashville, TN. Sep. 14-15, 2018:22 pages.
Mojsov et al., A Quantitative Evaluation of Methods for Coupling Asparagine. The Journal of Organic Chemistry. Feb. 1980;45(4):555-60.
Monia et al., Evaluation of 2'-modified oligonucleotides containing 2'-deoxy gaps as antisense inhibitors of gene expression. J Biol Chem. Jul. 5, 1993;268(19):14514-22.
Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.
Mulders et al., Molecular therapy in myotonic dystrophy: focus on RNA gain-of-function. Human Molecular Genetics. 2010;19(1):R90-7. Epub Apr. 20, 2010.
Mulders et al., Triplet-repeat oligonucleotide-mediated reversal of RNA toxicity in myotonic dystrophy. PNAS. Aug. 18, 2009;106(33):13915-20. Supporting information included. 13 pages.
Murray et al., Human Biochemistry. "Mir." Moscow. 1993; 1:34. 5 pages (including English translation).
Naylor et al., Deliver, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.
Naylor et al., Deliver, a randomized, double-blind, placebo controlled, multiple ascending dose study of DYNE-251 in boys with DMD amenable to Exon 51 skipping. Abstract. Mar. 2023. 1 page.
Overby et al., RNA-mediated therapies in myotonic dystrophy. Drug Discov Today. Dec. 2018;23(12):2013-2022. Epub Aug. 4, 2018.
Padlan et al., A possible procedure for reducing the immunogenicity of antibody variable domains while preserving their ligand-binding properties. Molecular Immunology. Apr.-May 1991;28(4-5):489-98.
Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.
Panowski et al., Site-specific antibody drug conjugates for cancer therapy. MAbs. Jan.-Feb. 2014;6(1):34-45.
Picariello et al., Dyne-101 achieves durable knockdown of toxic human nuclear DMPK RNA and correction of splicing in the hTfR1/DMSXL mouse model of DM1. Presented at The Muscular Dystrophy Association Clinical and Scientific Conference. Mar. 13-16, 2022. 1 page.
Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.
Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.
Qian et al., Targeted drug delivery via the transferrin receptor-mediated endocytosis pathway. Pharmacol Rev. Dec. 2002;54(4):561-87. doi: 10.1124/pr.54.4.561.
Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.

(56) References Cited

OTHER PUBLICATIONS

Roberts et al., Advances in oligonucleotide drug delivery. Nat Rev Drug Discov. Oct. 2020;19(10):673-694. doi: 10.1038/s41573-020-0075-7. Epub Aug. 11, 2020.
Roberts et al., The Halogenation of Ethylenes. J. Am. Chem. Soc. May 1937;59(5):947-8.
Sahenk et al., The muscular dystrophies: distinct pathogenic mechanisms invite novel therapeutic approaches. Curr Rheumatol Rep. Jun. 2011;13(3):199-207.
Samoylova et al., Elucidation of muscle-binding peptides by phage display screening. Muscle Nerve. Apr. 1999;22(4):460-6.
Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.
Scanlon, Anti-genes: siRNA, ribozymes and antisense. Curr Pharm Biotechnol. Oct. 2004;5(5):415-20.
Scherr et al., Detection of antisense and ribozyme accessible sites on native mRNAs: application to NCOA3 mRNA. Mol Ther. Nov. 2001;4(5):454-60.
Schneider et al., Structural features of the cell surface receptor for transferrin that is recognized by the monoclonal antibody OKT9. J Biol Chem. Jul. 25, 1982;257(14):8516-22.
Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Chemistry, mechanism and clinical status of antisense oligonucleotides and duplex RNAs. Nucleic Acids Res. Feb. 28, 2018;46(4):1584-1600.
Singh et al., Catalytic Enantioselective Cyclopropanation of Olefins Using Carbenoid Chemistry. Synthesis. Feb. 1997;137-49.
Stein, The experimental use of antisense oligonucleotides: a guide for the perplexed. J Clin Invest. Sep. 2001;108(5):641-4.
Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.
Strop et al., Location matters: site of conjugation modulates stability and pharmacokinetics of antibody drug conjugates. Chem Biol. Feb. 21, 2013;20(2):161-7.
Subramanian et al., Abstract 1074. Targeted delivery of oligonucleotide therapeutics to muscle demonstrates potential to treat duchenne muscular dystrophy. Abstract. Mol Ther. 28(4S1): 465. (2020) 1 page.
Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.
Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.
Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.
Swayze et al., The medicinal chemistry of oligonucleotides. In: Antisense Drug Technology, Second Edition. 2007. Crooke, Ed. Chapter 6: 143-182.
Thomas et al., Myotonic Dystrophy and Developmental Regulation of RNA Processing. Comprehensive Physiology. Apr. 2018;8(2):509-53. Epub Mar. 25, 2018.
Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.
Tron et al., Click chemistry reactions in medicinal chemistry: applications of the 1,3-dipolar cycloaddition between azides and alkynes. Med Res Rev. Mar. 2008;28(2):278-308.
Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.
Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
Wagner et al., Transferrin-polycation conjugates as carriers for DNA uptake into cells. Proc Natl Acad Sci U S A. May 1990;87(9):3410-4. doi: 10.1073/pnas.87.9.3410.
Walder et al., Role of RNase H in hybrid-arrested translation by antisense oligonucleotides. Proc. Natl. Acad. Sci. Jul. 1988;85:5011-5.
Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.
Walles et al., ADME and Safety Aspects of Non-cleavable Linkers in Drug Discovery and Development. Curr Top Med Chem. 2017;17(32):3463-3475. doi: 10.2174/1568026618666180118153502.
Wheeler et al., Reversal of RNA dominance by displacement of protein sequestered on triplet repeat RNA. Science. Jul. 17, 2009;325(5938):336-9.
Wheeler et al., Targeting nuclear RNA for in vivo correction of myotonic dystrophy. Nature. Aug. 2, 2012;488(7409):111-5. doi: 10.1038/nature11362.
Wheeler, Myotonic dystrophy: therapeutic strategies for the future. Neurotherapeutics. Oct. 2008;5(4):592-600.
Wilton et al., Exon skipping and Duchenne muscular dystrophy: hope, hype and how feasible? Neurol India. Jul.-Sep. 2008;56(3):254-62. doi: 10.4103/0028-3886.43443.
Wolf et al., Achieve trial, a randomized, placebo-controlled, multiple ascending dose study of Dyne-101 in individuals with myotonic dystrophy Type 1 (DM1). Abstract. Mar. 2023. 1 page.
Wolf et al., Achieve trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.
Wu et al., Determination of the role of the human RNase H1 in the pharmacology of DNA-like antisense drugs. J Biol Chem. Apr. 23, 2004;279(17):17181-9. Epub Feb. 11, 2004.
Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.
Yao et al., Targeted Delivery of ASOs Demonstrates Potential to Treat Duchenne Muscular Dystrophy. Poster. Presented at ASGCT; May 12, 2020. 1 page.
Ye et al., Generation and functional characterization of the anti-transferrin receptor single-chain antibody-GAL4 (TfRscFv-GAL4) fusion protein. BMC Biotechnol. Nov. 28, 2012;12:91.
Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.
Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.
Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.
Zanotti et al., Abstract 82. The ForceTM platform delivers oligonucleotides to the brain in a DM1 mouse model and in NHPs. Mol Ther. Apr. 2023; 31(4S1): 44.
Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.

(56) References Cited

OTHER PUBLICATIONS

Zanotti et al., DYNE-101 achieves durable knockdown of toxic human nuclear DMPK RNA and correction of splicing in the hTfR1/DMSXL mouse model of DM1. Abstract. Mar. 2022. 1 page.

Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.

Zanotti, Repeat dosing with DYNE-101 is Well Tolerated and Leads to a Sustained Reduction of DMPK RNA expression in key muscles for DM1 pathology in hTfR1/DMSXL mice and NHPs. Presented at American Society of Gene & Cell Therapy Conference. May 16, 2022. 15 pages.

Zanotti, The ForceTM platform delivers oligonucleotides to the brain in a DM1 mouse model and in NHPs. Presented at American Society of Gene & Cell Therapy Conference. May 17, 2023. 16 pages.

Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.

\* cited by examiner

| Oligo | 50% DMPK KD (nM) | 80% DMPK KD (nM) |
|---|---|---|
| DMPK-ASO-1 | 17.23 | 230.3 |
| DMPK-ASO-2 | 28.34 | 522.04 |
| DMPK-ASO-3 | 15.66 | 169.89 |
| ASO300 (tool) | 52.6 | ~10324 (extrapolated) |

| Oligo | 50% DMPK KD (nM) | 80% DMPK KD (nM) |
|---|---|---|
| DMPK-ASO-1 | 54 | 709 |
| DMPK-ASO-2 | 31 | 461 |
| DMPK-ASO-3 | 83 | 558 |
| ASO300 (tool) | 37 | 141 |

SEQUENCE LISTING

```
Sequence total quantity: 638
SEQ ID NO: 1                 moltype = AA  length = 8
FEATURE                      Location/Qualifiers
REGION                       1..8
                             note = Synthetic
source                       1..8
                             mol_type = protein
                             organism = synthetic construct
SEQUENCE: 1
GFNIKDDY                                                                   8

SEQ ID NO: 2                 moltype = AA  length = 8
FEATURE                      Location/Qualifiers
REGION                       1..8
                             note = Synthetic
source                       1..8
                             mol_type = protein
                             organism = synthetic construct
SEQUENCE: 2
IDPENGDT                                                                   8

SEQ ID NO: 3                 moltype = AA  length = 10
FEATURE                      Location/Qualifiers
REGION                       1..10
                             note = Synthetic
source                       1..10
                             mol_type = protein
                             organism = synthetic construct
SEQUENCE: 3
TLWLRRGLDY                                                                10

SEQ ID NO: 4                 moltype = AA  length = 11
FEATURE                      Location/Qualifiers
REGION                       1..11
                             note = Synthetic
source                       1..11
                             mol_type = protein
                             organism = synthetic construct
SEQUENCE: 4
KSLLHSNGYT Y                                                              11

SEQ ID NO: 5                 moltype =   length =
SEQUENCE: 5
000

SEQ ID NO: 6                 moltype = AA  length = 9
FEATURE                      Location/Qualifiers
REGION                       1..9
                             note = Synthetic
source                       1..9
                             mol_type = protein
                             organism = synthetic construct
SEQUENCE: 6
MQHLEYPFT                                                                  9

SEQ ID NO: 7                 moltype = AA  length = 5
FEATURE                      Location/Qualifiers
REGION                       1..5
                             note = Synthetic
source                       1..5
                             mol_type = protein
                             organism = synthetic construct
SEQUENCE: 7
DDYMY                                                                      5

SEQ ID NO: 8                 moltype = AA  length = 17
FEATURE                      Location/Qualifiers
REGION                       1..17
                             note = Synthetic
source                       1..17
                             mol_type = protein
                             organism = synthetic construct
SEQUENCE: 8
WIDPENGDTE YASKFQD                                                        17

SEQ ID NO: 9                 moltype = AA  length = 8
FEATURE                      Location/Qualifiers
REGION                       1..8
```

```
                    note = Synthetic
source              1..8
                    mol_type = protein
                    organism = synthetic construct
SEQUENCE: 9
WLRRGLDY                                                                8

SEQ ID NO: 10       moltype = AA   length = 16
FEATURE             Location/Qualifiers
REGION              1..16
                    note = Synthetic
source              1..16
                    mol_type = protein
                    organism = synthetic construct
SEQUENCE: 10
RSSKSLLHSN GYTYLF                                                       16

SEQ ID NO: 11       moltype = AA   length = 7
FEATURE             Location/Qualifiers
REGION              1..7
                    note = Synthetic
source              1..7
                    mol_type = protein
                    organism = synthetic construct
SEQUENCE: 11
RMSNLAS                                                                 7

SEQ ID NO: 12       moltype = AA   length = 7
FEATURE             Location/Qualifiers
REGION              1..7
                    note = Synthetic
source              1..7
                    mol_type = protein
                    organism = synthetic construct
SEQUENCE: 12
GFNIKDD                                                                 7

SEQ ID NO: 13       moltype =    length =
SEQUENCE: 13
000

SEQ ID NO: 14       moltype = AA   length = 6
FEATURE             Location/Qualifiers
REGION              1..6
                    note = Synthetic
source              1..6
                    mol_type = protein
                    organism = synthetic construct
SEQUENCE: 14
LRRGLD                                                                  6

SEQ ID NO: 15       moltype = AA   length = 12
FEATURE             Location/Qualifiers
REGION              1..12
                    note = Synthetic
source              1..12
                    mol_type = protein
                    organism = synthetic construct
SEQUENCE: 15
SKSLLHSNGY TY                                                           12

SEQ ID NO: 16       moltype = AA   length = 6
FEATURE             Location/Qualifiers
REGION              1..6
                    note = Synthetic
source              1..6
                    mol_type = protein
                    organism = synthetic construct
SEQUENCE: 16
HLEYPF                                                                  6

SEQ ID NO: 17       moltype = AA   length = 117
FEATURE             Location/Qualifiers
REGION              1..117
                    note = Synthetic
source              1..117
                    mol_type = protein
                    organism = synthetic construct
SEQUENCE: 17
```

```
EVQLQQSGAE LVRPGASVKL SCTASGFNIK DDYMYWVKQR PEQGLEWIGW IDPENGDTEY    60
ASKFQDKATV TADTSSNTAY LQLSSLTSED TAVYYCTLWL RRGLDYWGQG TSVTVSS      117

SEQ ID NO: 18           moltype = AA  length = 112
FEATURE                 Location/Qualifiers
REGION                  1..112
                        note = Synthetic
source                  1..112
                        mol_type = protein
                        organism = synthetic construct
SEQUENCE: 18
DIVMTQAAPS VPVTPGESVS ISCRSSKSLL HSNGYTYLFW FLQRPGQSPQ LLIYRMSNLA    60
SGVPDRFSGS GSGTAFTLRI SRVEAEDVGV YYCMQHLEYP FTFGGGTKLE IK           112

SEQ ID NO: 19           moltype = AA  length = 8
FEATURE                 Location/Qualifiers
REGION                  1..8
                        note = Synthetic
source                  1..8
                        mol_type = protein
                        organism = synthetic construct
SEQUENCE: 19
IDPETGDT                                                            8

SEQ ID NO: 20           moltype = AA  length = 17
FEATURE                 Location/Qualifiers
REGION                  1..17
                        note = Synthetic
source                  1..17
                        mol_type = protein
                        organism = synthetic construct
SEQUENCE: 20
WIDPETGDTE YASKFQD                                                  17

SEQ ID NO: 21           moltype =     length =
SEQUENCE: 21
000

SEQ ID NO: 22           moltype = AA  length = 117
FEATURE                 Location/Qualifiers
REGION                  1..117
                        note = Synthetic
source                  1..117
                        mol_type = protein
                        organism = synthetic construct
SEQUENCE: 22
EVQLQQSGAE LVRPGASVKL SCTASGFNIK DDYMYWVKQR PEQGLEWIGW IDPETGDTEY    60
ASKFQDKATV TADTSSNTAY LQLSSLTSED TAVYYCTLWL RRGLDYWGQG TSVTVSS      117

SEQ ID NO: 23           moltype = AA  length = 8
FEATURE                 Location/Qualifiers
REGION                  1..8
                        note = Synthetic
source                  1..8
                        mol_type = protein
                        organism = synthetic construct
SEQUENCE: 23
IDPESGDT                                                            8

SEQ ID NO: 24           moltype = AA  length = 17
FEATURE                 Location/Qualifiers
REGION                  1..17
                        note = Synthetic
source                  1..17
                        mol_type = protein
                        organism = synthetic construct
SEQUENCE: 24
WIDPESGDTE YASKFQD                                                  17

SEQ ID NO: 25           moltype =     length =
SEQUENCE: 25
000

SEQ ID NO: 26           moltype = AA  length = 117
FEATURE                 Location/Qualifiers
REGION                  1..117
                        note = Synthetic
source                  1..117
                        mol_type = protein
```

```
                                 organism = synthetic construct
SEQUENCE: 26
EVQLQQSGAE LVRPGASVKL SCTASGFNIK DDYMYWVKQR PEQGLEWIGW IDPESGDTEY    60
ASKFQDKATV TADTSSNTAY LQLSSLTSED TAVYYCTLWL RRGLDYWGQG TSVTVSS      117

SEQ ID NO: 27            moltype = AA   length = 9
FEATURE                  Location/Qualifiers
REGION                   1..9
                         note = Synthetic
source                   1..9
                         mol_type = protein
                         organism = synthetic construct
SEQUENCE: 27
GYSITSGYY                                                             9

SEQ ID NO: 28            moltype = AA   length = 7
FEATURE                  Location/Qualifiers
REGION                   1..7
                         note = Synthetic
source                   1..7
                         mol_type = protein
                         organism = synthetic construct
SEQUENCE: 28
ITFDGAN                                                               7

SEQ ID NO: 29            moltype = AA   length = 12
FEATURE                  Location/Qualifiers
REGION                   1..12
                         note = Synthetic
source                   1..12
                         mol_type = protein
                         organism = synthetic construct
SEQUENCE: 29
TRSSYDYDVL DY                                                        12

SEQ ID NO: 30            moltype = AA   length = 6
FEATURE                  Location/Qualifiers
REGION                   1..6
                         note = Synthetic
source                   1..6
                         mol_type = protein
                         organism = synthetic construct
SEQUENCE: 30
QDISNF                                                                6

SEQ ID NO: 31            moltype =     length =
SEQUENCE: 31
000

SEQ ID NO: 32            moltype = AA   length = 9
FEATURE                  Location/Qualifiers
REGION                   1..9
                         note = Synthetic
source                   1..9
                         mol_type = protein
                         organism = synthetic construct
SEQUENCE: 32
QQGHTLPYT                                                             9

SEQ ID NO: 33            moltype = AA   length = 6
FEATURE                  Location/Qualifiers
REGION                   1..6
                         note = Synthetic
source                   1..6
                         mol_type = protein
                         organism = synthetic construct
SEQUENCE: 33
SGYYWN                                                                6

SEQ ID NO: 34            moltype = AA   length = 16
FEATURE                  Location/Qualifiers
REGION                   1..16
                         note = Synthetic
source                   1..16
                         mol_type = protein
                         organism = synthetic construct
SEQUENCE: 34
YITFDGANNY NPSLKN                                                    16
```

| | | |
|---|---|---|
| SEQ ID NO: 35 | moltype = AA   length = 10 | |
| FEATURE | Location/Qualifiers | |
| REGION | 1..10 | |
| | note = Synthetic | |
| source | 1..10 | |
| | mol_type = protein | |
| | organism = synthetic construct | |
| SEQUENCE: 35 | | |
| SSYDYDVLDY | | 10 |
| | | |
| SEQ ID NO: 36 | moltype = AA   length = 11 | |
| FEATURE | Location/Qualifiers | |
| REGION | 1..11 | |
| | note = Synthetic | |
| source | 1..11 | |
| | mol_type = protein | |
| | organism = synthetic construct | |
| SEQUENCE: 36 | | |
| RASQDISNFL N | | 11 |
| | | |
| SEQ ID NO: 37 | moltype = AA   length = 7 | |
| FEATURE | Location/Qualifiers | |
| REGION | 1..7 | |
| | note = Synthetic | |
| source | 1..7 | |
| | mol_type = protein | |
| | organism = synthetic construct | |
| SEQUENCE: 37 | | |
| YTSRLHS | | 7 |
| | | |
| SEQ ID NO: 38 | moltype = AA   length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 38 | | |
| GYSITSGY | | 8 |
| | | |
| SEQ ID NO: 39 | moltype =     length = | |
| SEQUENCE: 39 | | |
| 000 | | |
| | | |
| SEQ ID NO: 40 | moltype = AA   length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 40 | | |
| SYDYDVLD | | 8 |
| | | |
| SEQ ID NO: 41 | moltype = AA   length = 7 | |
| FEATURE | Location/Qualifiers | |
| REGION | 1..7 | |
| | note = Synthetic | |
| source | 1..7 | |
| | mol_type = protein | |
| | organism = synthetic construct | |
| SEQUENCE: 41 | | |
| SQDISNF | | 7 |
| | | |
| SEQ ID NO: 42 | moltype = AA   length = 6 | |
| FEATURE | Location/Qualifiers | |
| REGION | 1..6 | |
| | note = Synthetic | |
| source | 1..6 | |
| | mol_type = protein | |
| | organism = synthetic construct | |
| SEQUENCE: 42 | | |
| GHTLPY | | 6 |
| | | |
| SEQ ID NO: 43 | moltype = AA   length = 119 | |
| FEATURE | Location/Qualifiers | |
| REGION | 1..119 | |
| | note = Synthetic | |
| source | 1..119 | |

```
                            mol_type = protein
                            organism = synthetic construct
SEQUENCE: 43
DVQLQESGPG LVKPSQSLSL TCSVTGYSIT SGYYWNWIRQ FPGNKLEWMG YITFDGANNY        60
NPSLKNRISI TRDTSKNQFF LKLTSVTTED TATYYCTRSS YDYDVLDYWG QGTTLTVSS        119

SEQ ID NO: 44               moltype = AA   length = 107
FEATURE                     Location/Qualifiers
REGION                      1..107
                            note = Synthetic
source                      1..107
                            mol_type = protein
                            organism = synthetic construct
SEQUENCE: 44
DIQMTQTTSS LSASLGDRVT ISCRASQDIS NFLNWYQQRP DGTVKLLIYY TSRLHSGVPS        60
RFSGSGSGTD FSLTVSNLEQ EDIATYFCQQ GHTLPYTFGG GTKLEIK                    107

SEQ ID NO: 45               moltype = AA   length = 8
FEATURE                     Location/Qualifiers
REGION                      1..8
                            note = Synthetic
source                      1..8
                            mol_type = protein
                            organism = synthetic construct
SEQUENCE: 45
GYSFTDYC                                                                  8

SEQ ID NO: 46               moltype = AA   length = 8
FEATURE                     Location/Qualifiers
REGION                      1..8
                            note = Synthetic
source                      1..8
                            mol_type = protein
                            organism = synthetic construct
SEQUENCE: 46
IYPGSGNT                                                                  8

SEQ ID NO: 47               moltype = AA   length = 13
FEATURE                     Location/Qualifiers
REGION                      1..13
                            note = Synthetic
source                      1..13
                            mol_type = protein
                            organism = synthetic construct
SEQUENCE: 47
AREDYYPYHG MDY                                                           13

SEQ ID NO: 48               moltype = AA   length = 10
FEATURE                     Location/Qualifiers
REGION                      1..10
                            note = Synthetic
source                      1..10
                            mol_type = protein
                            organism = synthetic construct
SEQUENCE: 48
ESVDGYDNSF                                                               10

SEQ ID NO: 49               moltype =     length =
SEQUENCE: 49
000

SEQ ID NO: 50               moltype = AA   length = 9
FEATURE                     Location/Qualifiers
REGION                      1..9
                            note = Synthetic
source                      1..9
                            mol_type = protein
                            organism = synthetic construct
SEQUENCE: 50
QQSSEDPWT                                                                 9

SEQ ID NO: 51               moltype = AA   length = 5
FEATURE                     Location/Qualifiers
REGION                      1..5
                            note = Synthetic
source                      1..5
                            mol_type = protein
                            organism = synthetic construct
SEQUENCE: 51
```

-continued

```
DYCIN                                                                  5

SEQ ID NO: 52           moltype = AA  length = 17
FEATURE                 Location/Qualifiers
REGION                  1..17
                        note = Synthetic
source                  1..17
                        mol_type = protein
                        organism = synthetic construct
SEQUENCE: 52
WIYPGSGNTR YSERFKG                                                    17

SEQ ID NO: 53           moltype = AA  length = 11
FEATURE                 Location/Qualifiers
REGION                  1..11
                        note = Synthetic
source                  1..11
                        mol_type = protein
                        organism = synthetic construct
SEQUENCE: 53
EDYYPYHGMD Y                                                          11

SEQ ID NO: 54           moltype = AA  length = 15
FEATURE                 Location/Qualifiers
REGION                  1..15
                        note = Synthetic
source                  1..15
                        mol_type = protein
                        organism = synthetic construct
SEQUENCE: 54
RASESVDGYD NSFMH                                                      15

SEQ ID NO: 55           moltype = AA  length = 7
FEATURE                 Location/Qualifiers
REGION                  1..7
                        note = Synthetic
source                  1..7
                        mol_type = protein
                        organism = synthetic construct
SEQUENCE: 55
RASNLES                                                                7

SEQ ID NO: 56           moltype = AA  length = 7
FEATURE                 Location/Qualifiers
REGION                  1..7
                        note = Synthetic
source                  1..7
                        mol_type = protein
                        organism = synthetic construct
SEQUENCE: 56
GYSFTDY                                                                7

SEQ ID NO: 57           moltype =     length =
SEQUENCE: 57
000

SEQ ID NO: 58           moltype = AA  length = 9
FEATURE                 Location/Qualifiers
REGION                  1..9
                        note = Synthetic
source                  1..9
                        mol_type = protein
                        organism = synthetic construct
SEQUENCE: 58
DYYPYHGMD                                                              9

SEQ ID NO: 59           moltype = AA  length = 11
FEATURE                 Location/Qualifiers
REGION                  1..11
                        note = Synthetic
source                  1..11
                        mol_type = protein
                        organism = synthetic construct
SEQUENCE: 59
SESVDGYDNS F                                                          11

SEQ ID NO: 60           moltype = AA  length = 6
FEATURE                 Location/Qualifiers
REGION                  1..6
```

```
                        note = Synthetic
source                  1..6
                        mol_type = protein
                        organism = synthetic construct
SEQUENCE: 60
SSEDPW                                                                        6

SEQ ID NO: 61           moltype = AA   length = 120
FEATURE                 Location/Qualifiers
REGION                  1..120
                        note = Synthetic
source                  1..120
                        mol_type = protein
                        organism = synthetic construct
SEQUENCE: 61
QIQLQQSGPE LVRPGASVKI SCKASGYSFT DYCINWVNQR PGQGLEWIGW IYPGSGNTRY   60
SERFKGKATL TVDTSSNTAY MQLSSLTSED SAVYFCARED YYPYHGMDYW GQGTSVTVSS  120

SEQ ID NO: 62           moltype = AA   length = 111
FEATURE                 Location/Qualifiers
REGION                  1..111
                        note = Synthetic
source                  1..111
                        mol_type = protein
                        organism = synthetic construct
SEQUENCE: 62
DIVLTQSPTS LAVSLGQRAT ISCRASESVD GYDNSFMHWY QQKPGQPPKL LIFRASNLES   60
GIPARFSGSG SRTDFTLTIN PVEAADVATY YCQQSSEDPW TFGGGTKLEI K          111

SEQ ID NO: 63           moltype = AA   length = 8
FEATURE                 Location/Qualifiers
REGION                  1..8
                        note = Synthetic
source                  1..8
                        mol_type = protein
                        organism = synthetic construct
SEQUENCE: 63
GYSFTDYY                                                                      8

SEQ ID NO: 64           moltype = AA   length = 5
FEATURE                 Location/Qualifiers
REGION                  1..5
                        note = Synthetic
source                  1..5
                        mol_type = protein
                        organism = synthetic construct
SEQUENCE: 64
DYYIN                                                                         5

SEQ ID NO: 65           moltype = AA   length = 120
FEATURE                 Location/Qualifiers
REGION                  1..120
                        note = Synthetic
source                  1..120
                        mol_type = protein
                        organism = synthetic construct
SEQUENCE: 65
QIQLQQSGPE LVRPGASVKI SCKASGYSFT DYYINWVNQR PGQGLEWIGW IYPGSGNTRY   60
SERFKGKATL TVDTSSNTAY MQLSSLTSED SAVYFCARED YYPYHGMDYW GQGTSVTVSS  120

SEQ ID NO: 66           moltype = AA   length = 8
FEATURE                 Location/Qualifiers
REGION                  1..8
                        note = Synthetic
source                  1..8
                        mol_type = protein
                        organism = synthetic construct
SEQUENCE: 66
GYSFTDYD                                                                      8

SEQ ID NO: 67           moltype = AA   length = 5
FEATURE                 Location/Qualifiers
REGION                  1..5
                        note = Synthetic
source                  1..5
                        mol_type = protein
                        organism = synthetic construct
SEQUENCE: 67
DYDIN                                                                         5
```

```
SEQ ID NO: 68            moltype = AA   length = 120
FEATURE                  Location/Qualifiers
REGION                   1..120
                         note = Synthetic
source                   1..120
                         mol_type = protein
                         organism = synthetic construct
SEQUENCE: 68
QIQLQQSGPE LVRPGASVKI SCKASGYSFT DYDINWVNQR PGQGLEWIGW IYPGSGNTRY    60
SERFKGKATL TVDTSSNTAY MQLSSLTSED SAVYFCARED YYPYHGMDYW GQGTSVTVSS   120

SEQ ID NO: 69            moltype = AA   length = 117
FEATURE                  Location/Qualifiers
REGION                   1..117
                         note = Synthetic
source                   1..117
                         mol_type = protein
                         organism = synthetic construct
SEQUENCE: 69
EVQLVQSGSE LKKPGASVKV SCTASGFNIK DDYMYWVRQP PGKGLEWIGW IDPETGDTEY    60
ASKFQDRVTV TADTSTNTAY MELSSLRSED TAVYYCTLWL RRGLDYWGQG TLVTVSS      117

SEQ ID NO: 70            moltype = AA   length = 112
FEATURE                  Location/Qualifiers
REGION                   1..112
                         note = Synthetic
source                   1..112
                         mol_type = protein
                         organism = synthetic construct
SEQUENCE: 70
DIVMTQSPLS LPVTPGEPAS ISCRSSKSLL HSNGYTYLFW FQQRPGQSPR LLIYRMSNLA    60
SGVPDRFSGS GSGTDFTLKI SRVEAEDVGV YYCMQHLEYP FTFGGGTKVE IK           112

SEQ ID NO: 71            moltype = AA   length = 117
FEATURE                  Location/Qualifiers
REGION                   1..117
                         note = Synthetic
source                   1..117
                         mol_type = protein
                         organism = synthetic construct
SEQUENCE: 71
EVQLVQSGSE LKKPGASVKV SCTASGFNIK DDYMYWVRQP PGKGLEWIGW IDPESGDTEY    60
ASKFQDRVTV TADTSTNTAY MELSSLRSED TAVYYCTLWL RRGLDYWGQG TLVTVSS      117

SEQ ID NO: 72            moltype = AA   length = 117
FEATURE                  Location/Qualifiers
REGION                   1..117
                         note = Synthetic
source                   1..117
                         mol_type = protein
                         organism = synthetic construct
SEQUENCE: 72
EVQLVQSGSE LKKPGASVKV SCTASGFNIK DDYMYWVRQP PGKGLEWIGW IDPENGDTEY    60
ASKFQDRVTV TADTSTNTAY MELSSLRSED TAVYYCTLWL RRGLDYWGQG TLVTVSS      117

SEQ ID NO: 73            moltype = AA   length = 119
FEATURE                  Location/Qualifiers
REGION                   1..119
                         note = Synthetic
source                   1..119
                         mol_type = protein
                         organism = synthetic construct
SEQUENCE: 73
QVQLQESGPG LVKPSQTLSL TCSVTGYSIT SGYYWNWIRQ PPGKGLEWMG YITFDGANNY    60
NPSLKNRVSI SRDTSKNQFS LKLSSVTAED TATYYCTRSS YDYDVLDYWG QGTTVTVSS    119

SEQ ID NO: 74            moltype = AA   length = 107
FEATURE                  Location/Qualifiers
REGION                   1..107
                         note = Synthetic
source                   1..107
                         mol_type = protein
                         organism = synthetic construct
SEQUENCE: 74
DIQMTQSPSS LSASVGDRVT ITCRASQDIS NFLNWYQQKP GQPVKLLIYY TSRLHSGVPS    60
RFSGSGSGTD FTLTISSLQP EDFATYFCQQ GHTLPYTFGQ GTKLEIK                 107

SEQ ID NO: 75            moltype = AA   length = 107
```

```
FEATURE                 Location/Qualifiers
REGION                  1..107
                        note = Synthetic
source                  1..107
                        mol_type = protein
                        organism = synthetic construct
SEQUENCE: 75
DIQMTQSPSS LSASVGDRVT ITCRASQDIS NFLNWYQQKP GQPVKLLIYY TSRLHSGVPS    60
RFSGSGSGTD FTLTISSLQP EDFATYYCQQ GHTLPYTFGQ GTKLEIK                 107

SEQ ID NO: 76           moltype = AA  length = 119
FEATURE                 Location/Qualifiers
REGION                  1..119
                        note = Synthetic
source                  1..119
                        mol_type = protein
                        organism = synthetic construct
SEQUENCE: 76
QVQLQESGPG LVKPSQTLSL TCTVTGYSIT SGYYWNWIRQ PPGKGLEWIG YITFDGANNY    60
NPSLKNRVSI SRDTSKNQFS LKLSSVTAED TATYYCTRSS YDYDVLDYWG QGTTVTVSS    119

SEQ ID NO: 77           moltype = AA  length = 120
FEATURE                 Location/Qualifiers
REGION                  1..120
                        note = Synthetic
source                  1..120
                        mol_type = protein
                        organism = synthetic construct
SEQUENCE: 77
QVQLVQSGAE VKKPGASVKV SCKASGYSFT DYYINWVRQA PGQGLEWMGW IYPGSGNTRY    60
SERFKGRVTI TRDTSASTAY MELSSLRSED TAVYYCARED YYPYHGMDYW GQGTLVTVSS   120

SEQ ID NO: 78           moltype = AA  length = 111
FEATURE                 Location/Qualifiers
REGION                  1..111
                        note = Synthetic
source                  1..111
                        mol_type = protein
                        organism = synthetic construct
SEQUENCE: 78
DIVLTQSPDS LAVSLGERAT INCRASESVD GYDNSFMHWY QQKPGQPPKL LIFRASNLES    60
GVPDRFSGSG SRTDFTLTIS SLQAEDVAVY YCQQSSEDPW TFGQGTKLEI K            111

SEQ ID NO: 79           moltype = AA  length = 120
FEATURE                 Location/Qualifiers
REGION                  1..120
                        note = Synthetic
source                  1..120
                        mol_type = protein
                        organism = synthetic construct
SEQUENCE: 79
QVQLVQSGAE VKKPGASVKV SCKASGYSFT DYDINWVRQA PGQGLEWMGW IYPGSGNTRY    60
SERFKGRVTI TRDTSASTAY MELSSLRSED TAVYYCARED YYPYHGMDYW GQGTLVTVSS   120

SEQ ID NO: 80           moltype = AA  length = 111
FEATURE                 Location/Qualifiers
REGION                  1..111
                        note = Synthetic
source                  1..111
                        mol_type = protein
                        organism = synthetic construct
SEQUENCE: 80
DIVMTQSPDS LAVSLGERAT INCRASESVD GYDNSFMHWY QQKPGQPPKL LIFRASNLES    60
GVPDRFSGSG SGTDFTLTIS SLQAEDVAVY YCQQSSEDPW TFGQGTKLEI K            111

SEQ ID NO: 81           moltype = AA  length = 330
FEATURE                 Location/Qualifiers
source                  1..330
                        mol_type = protein
                        organism = Homo sapiens
SEQUENCE: 81
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 82           moltype = AA  length = 330
```

```
FEATURE                 Location/Qualifiers
REGION                  1..330
                        note = Synthetic
source                  1..330
                        mol_type = protein
                        organism = synthetic construct
SEQUENCE: 82
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 83           moltype = AA  length = 107
FEATURE                 Location/Qualifiers
REGION                  1..107
                        note = Synthetic
source                  1..107
                        mol_type = protein
                        organism = synthetic construct
SEQUENCE: 83
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 84           moltype = AA  length = 447
FEATURE                 Location/Qualifiers
REGION                  1..447
                        note = Synthetic
source                  1..447
                        mol_type = protein
                        organism = synthetic construct
SEQUENCE: 84
EVQLVQSGSE LKKPGASVKV SCTASGFNIK DDYMYWVRQP PGKGLEWIGW IDPETGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 85           moltype = AA  length = 219
FEATURE                 Location/Qualifiers
REGION                  1..219
                        note = Synthetic
source                  1..219
                        mol_type = protein
                        organism = synthetic construct
SEQUENCE: 85
DIVMTQSPLS LPVTPGEPAS ISCRSSKSLL HSNGYTYLFW FQQRPGQSPR LLIYRMSNLA    60
SGVPDRFSGS GSGTDFTLKI SRVEAEDVGV YYCMQHLEYP FTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219

SEQ ID NO: 86           moltype = AA  length = 447
FEATURE                 Location/Qualifiers
REGION                  1..447
                        note = Synthetic
source                  1..447
                        mol_type = protein
                        organism = synthetic construct
SEQUENCE: 86
EVQLVQSGSE LKKPGASVKV SCTASGFNIK DDYMYWVRQP PGKGLEWIGW IDPESGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 87           moltype = AA  length = 447
FEATURE                 Location/Qualifiers
REGION                  1..447
                        note = Synthetic
source                  1..447
                        mol_type = protein
                        organism = synthetic construct
```

```
SEQUENCE: 87
EVQLVQSGSE LKKPGASVKV SCTASGFNIK DDYMYWVRQP PGKGLEWIGW IDPENGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 88           moltype = AA   length = 449
FEATURE                 Location/Qualifiers
REGION                  1..449
                        note = Synthetic
source                  1..449
                        mol_type = protein
                        organism = synthetic construct
SEQUENCE: 88
QVQLQESGPG LVKPSQTLSL TCSVTGYSIT SGYYWNWIRQ PPGKGLEWMG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 89           moltype = AA   length = 214
FEATURE                 Location/Qualifiers
REGION                  1..214
                        note = Synthetic
source                  1..214
                        mol_type = protein
                        organism = synthetic construct
SEQUENCE: 89
DIQMTQSPSS LSASVGDRVT ITCRASQDIS NFLNWYQQKP GQPVKLLIYY TSRLHSGVPS    60
RFSGSGSGTD FTLTISSLQP EDFATYFCQQ GHTLPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 90           moltype = AA   length = 214
FEATURE                 Location/Qualifiers
REGION                  1..214
                        note = Synthetic
source                  1..214
                        mol_type = protein
                        organism = synthetic construct
SEQUENCE: 90
DIQMTQSPSS LSASVGDRVT ITCRASQDIS NFLNWYQQKP GQPVKLLIYY TSRLHSGVPS    60
RFSGSGSGTD FTLTISSLQP EDFATYYCQQ GHTLPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 91           moltype = AA   length = 449
FEATURE                 Location/Qualifiers
REGION                  1..449
                        note = Synthetic
source                  1..449
                        mol_type = protein
                        organism = synthetic construct
SEQUENCE: 91
QVQLQESGPG LVKPSQTLSL TCTVTGYSIT SGYYWNWIRQ PPGKGLEWIG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 92           moltype = AA   length = 450
FEATURE                 Location/Qualifiers
REGION                  1..450
                        note = Synthetic
source                  1..450
                        mol_type = protein
                        organism = synthetic construct
SEQUENCE: 92
QVQLVQSGAE VKKPGASVKV SCKASGYSFT DYYINWVRQA PGQGLEWMGW IYPGSGNTRY    60
```

```
SERFKGRVTI TRDTSASTAY MELSSLRSED TAVYYCARED YYPYHGMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 93           moltype = AA   length = 218
FEATURE                 Location/Qualifiers
REGION                  1..218
                        note = Synthetic
source                  1..218
                        mol_type = protein
                        organism = synthetic construct
SEQUENCE: 93
DIVLTQSPDS LAVSLGERAT INCRASESVD GYDNSFMHWY QQKPGQPPKL LIFRASNLES     60
GVPDRFSGSG SRTDFTLTIS SLQAEDVAVY YCQQSSEDPW TFGQGTKLEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                           218

SEQ ID NO: 94           moltype = AA   length = 450
FEATURE                 Location/Qualifiers
REGION                  1..450
                        note = Synthetic
source                  1..450
                        mol_type = protein
                        organism = synthetic construct
SEQUENCE: 94
QVQLVQSGAE VKKPGASVKV SCKASGYSFT DYDINWVRQA PGQGLEWMGW IYPGSGNTRY     60
SERFKGRVTI TRDTSASTAY MELSSLRSED TAVYYCARED YYPYHGMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 95           moltype = AA   length = 218
FEATURE                 Location/Qualifiers
REGION                  1..218
                        note = Synthetic
source                  1..218
                        mol_type = protein
                        organism = synthetic construct
SEQUENCE: 95
DIVMTQSPDS LAVSLGERAT INCRASESVD GYDNSFMHWY QQKPGQPPKL LIFRASNLES     60
GVPDRFSGSG SGTDFTLTIS SLQAEDVAVY YCQQSSEDPW TFGQGTKLEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                           218

SEQ ID NO: 96           moltype = AA   length = 108
FEATURE                 Location/Qualifiers
REGION                  1..108
                        note = Synthetic
source                  1..108
                        mol_type = protein
                        organism = synthetic construct
SEQUENCE: 96
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHT                108

SEQ ID NO: 97           moltype = AA   length = 225
FEATURE                 Location/Qualifiers
REGION                  1..225
                        note = Synthetic
source                  1..225
                        mol_type = protein
                        organism = synthetic construct
SEQUENCE: 97
EVQLVQSGSE LKKPGASVKV SCTASGFNIK DDYMYWVRQP PGKGLEWIGW IDPETGDTEY     60
ASKFQDRVTV TADTSTNTAY MELSSLRSED TAVYYCTLWL RRGLDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHT                   225

SEQ ID NO: 98           moltype = AA   length = 225
FEATURE                 Location/Qualifiers
REGION                  1..225
                        note = Synthetic
```

```
source            1..225
                  mol_type = protein
                  organism = synthetic construct
SEQUENCE: 98
EVQLVQSGSE LKKPGASVKV SCTASGFNIK DDYMYWVRQP PGKGLEWIGW IDPESGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHT                  225

SEQ ID NO: 99     moltype = AA   length = 225
FEATURE           Location/Qualifiers
REGION            1..225
                  note = Synthetic
source            1..225
                  mol_type = protein
                  organism = synthetic construct
SEQUENCE: 99
EVQLVQSGSE LKKPGASVKV SCTASGFNIK DDYMYWVRQP PGKGLEWIGW IDPENGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHT                  225

SEQ ID NO: 100    moltype = AA   length = 227
FEATURE           Location/Qualifiers
REGION            1..227
                  note = Synthetic
source            1..227
                  mol_type = protein
                  organism = synthetic construct
SEQUENCE: 100
QVQLQESGPG LVKPSQTLSL TCSVTGYSIT SGYYWNWIRQ PPGKGLEWMG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHT                227

SEQ ID NO: 101    moltype = AA   length = 227
FEATURE           Location/Qualifiers
REGION            1..227
                  note = Synthetic
source            1..227
                  mol_type = protein
                  organism = synthetic construct
SEQUENCE: 101
QVQLQESGPG LVKPSQTLSL TCTVTGYSIT SGYYWNWIRQ PPGKGLEWIG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHT                227

SEQ ID NO: 102    moltype = AA   length = 228
FEATURE           Location/Qualifiers
REGION            1..228
                  note = Synthetic
source            1..228
                  mol_type = protein
                  organism = synthetic construct
SEQUENCE: 102
QVQLVQSGAE VKKPGASVKV SCKASGYSFT DYYINWVRQA PGQGLEWMGW IYPGSGNTRY    60
SERFKGRVTI TRDTSASTAY MELSSLRSED TAVYYCARED YYPYHGMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHT               228

SEQ ID NO: 103    moltype = AA   length = 228
FEATURE           Location/Qualifiers
REGION            1..228
                  note = Synthetic
source            1..228
                  mol_type = protein
                  organism = synthetic construct
SEQUENCE: 103
QVQLVQSGAE VKKPGASVKV SCKASGYSFT DYDINWVRQA PGQGLEWMGW IYPGSGNTRY    60
SERFKGRVTI TRDTSASTAY MELSSLRSED TAVYYCARED YYPYHGMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHT               228

SEQ ID NO: 104    moltype = AA   length = 19
FEATURE           Location/Qualifiers
REGION            1..19
                  note = Synthetic
source            1..19
```

```
                        mol_type = protein
                        organism = synthetic construct
SEQUENCE: 104
MGWSCIILFL VATATGVHS                                              19

SEQ ID NO: 105          moltype = AA   length = 760
FEATURE                 Location/Qualifiers
source                  1..760
                        mol_type = protein
                        organism = Homo sapiens
SEQUENCE: 105
MMDQARSAFS NLFGGEPLSY TRFSLARQVD GDNSHVEMKL AVDEEENADN NTKANVTKPK   60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
APPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGHSTLP ALLENLKLRK  720
QNNGAFNETL FRNQLALATW TIQGAANALS GDVWDIDNEF                       760

SEQ ID NO: 106          moltype = AA   length = 760
FEATURE                 Location/Qualifiers
source                  1..760
                        mol_type = protein
                        organism = Macaca mulatta
SEQUENCE: 106
MMDQARSAFS NLFGGEPLSY TRFSLARQVD GDNSHVEMKL GVDEEENTDN NTKPNGTKPK   60
RCGGNICYGT IAVIIFFLIG FMIGYLGYCK GVEPKTECER LAGTESPARE EPEEDFPAAP  120
RLYWDDLKRK LSEKLDTTDF TSTIKLLNEN LYVPREAGSQ KDENLALYIE NQFREFKLSK  180
VWRDQHFVKI QVKDSAQNSV IIVDKNGGLV YLVENPGGYV AYSKAATVTG KLVHANFGTK  240
KDFEDLDSPV NGSIVIVRAG KITFAEKVAN AESLNAIGVL IYMDQTKFPI VKADLSFFGH  300
AHLGTGDPYT PGFPSFNHTQ FPPSQSSGLP NIPVQTISRA AAEKLFGNME GDCPSDWKTD  360
STCKMVTSEN KSVKLTVSNV LKETKILNIF GVIKGFVEPD HYVVVGAQRD AWGPGAAKSS  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QDVKHPVTGR SLYQDSNWAS KVEKLTLDNA  540
APPFLAYSGI PAVSFCFCED TDYPYLGTTM DTYKELVERI PELNKVARAA AEVAGQFVIK  600
LTHDTELNLD YERYNSQLLL FLRDLNQYRA DVKEMGLSLQ WLYSARGDFF RATSRLTTDF  660
RNAEKRDKFV MKKLNDRVMR VEYYFLSPYV SPKESPFRHV FWGSGHSTLS ALLESLKLRR  720
QNNSAFNETL FRNQLALATW TIQGAANALS GDVWDIDNEF                       760

SEQ ID NO: 107          moltype = AA   length = 760
FEATURE                 Location/Qualifiers
source                  1..760
                        mol_type = protein
                        organism = Macaca fascicularis
SEQUENCE: 107
MMDQARSAFS NLFGGEPLSY TRFSLARQVD GDNSHVEMKL GVDEEENTDN NTKANGTKPK   60
RCGGNICYGT IAVIIFFLIG FMIGYLGYCK GVEPKTECER LAGTESPARE EPEEDFPAAP  120
RLYWDDLKRK LSEKLDTTDF TSTIKLLNEN LYVPREAGSQ KDENLALYIE NQFREFKLSK  180
VWRDQHFVKI QVKDSAQNSV IIVDKNGGLV YLVENPGGYV AYSKAATVTG KLVHANFGTK  240
KDFEDLDSPV NGSIVIVRAG KITFAEKVAN AESLNAIGVL IYMDQTKFPI VKADLSFFGH  300
AHLGTGDPYT PGFPSFNHTQ FPPSQSSGLP NIPVQTISRA AAEKLFGNME GDCPSDWKTD  360
STCKMVTSEN KSVKLTVSNV LKETKILNIF GVIKGFVEPD HYVVVGAQRD AWGPGAAKSS  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QDVKHPVTGR SLYQDSNWAS KVEKLTLDNA  540
APPFLAYSGI PAVSFCFCED TDYPYLGTTM DTYKELVERI PELNKVARAA AEVAGQFVIK  600
LTHDTELNLD YERYNSQLLL FLRDLNQYRA DVKEMGLSLQ WLYSARGDFF RATSRLTTDF  660
RNAEKRDKFV MKKLNDRVMR VEYYFLSPYV SPKESPFRHV FWGSGHSTLS ALLESLKLRR  720
QNNSAFNETL FRNQLALATW TIQGAANALS GDVWDIDNEF                       760

SEQ ID NO: 108          moltype = AA   length = 763
FEATURE                 Location/Qualifiers
source                  1..763
                        mol_type = protein
                        organism = Mus musculus
SEQUENCE: 108
MMDQARSAFS NLFGGEPLSY TRFSLARQVD GDNSHVEMKL AADEEENADN NMKASVRKPK   60
RFNGRLCFAA IALVIFFLIG FMSGYLGYCK RVEQKEECVK LAETEETDKS ETMETEDVPT  120
SSRLYWADLK TLLSEKLNSI EFADTIKQLS QNTYTPREAG SQKDESLAYY IENQFHEFKF  180
SKVWRDEHYV KIQVKSSIGQ NMVTIVQSNG NLDPVESPEG YVAFSKPTEV SGKLVHANFG  240
TKKDFEELSY SVNGSLVIVR AGEITFAEKV ANAQSFNAIG VLIYMDKNKF PVVEADLALF  300
GHAHLGTGDP YTPGFPSFNH TQFPPSQSSG LPNIPVQTIS RAAAEKLFGK MEGSCPARWN  360
IDSSCKLELS QNQNVKLIVK NVLKERRILN IFGVIKGYEE PDRYVVVGAQ RDALGAGVAA  420
KSSVGTGLLL KLAQVFSDMI SKDGFRPSRS IIFASWTAGD FGAVGATEWL EGYLSSLHLK  480
```

```
AFTYINLDKV VLGTSNFKVS ASPLLYTLMG KIMQDVKHPV DGKSLYRDSN WISKVEKLSF  540
DNAAYPFLAY SGIPAVSFCF CEDADYPYLG TRLDTYEALT QKVPQLNQMV RTAAEVAGQL  600
IIKLTHDVEL NLDYEMYNSK LLSFMKDLNQ FKTDIRDMGL SLQWLYSARG DYFRATSRLT  660
TDFHNAEKTN RFVMREINDR IMKVEYHFLS PYVSPRESPF RHIFWGSGSH TLSALVENLK  720
LRQKNITAFN ETLFRNQLAL ATWTIQGVAN ALSGDIWNID NEF                   763

SEQ ID NO: 109           moltype = AA   length = 197
FEATURE                  Location/Qualifiers
REGION                   1..197
                         note = Synthetic
source                   1..197
                         mol_type = protein
                         organism = synthetic construct
SEQUENCE: 109
FVKIQVKDSA QNSVIIVDKN GRLVYLVENP GGYVAYSKAA TVTGKLVHAN FGTKKDFEDL  60
YTPVNGSIVI VRAGKITFAE KVANAESLNA IGVLIYMDQT KFPIVNAELS FFGHAHLGTG  120
DPYTPGFPSF NHTQFPPSRS SGLPNIPVQT ISRAAAEKLF GNMEGDCPSD WKTDSTCRMV  180
TSESKNVKLT VSNVLKE                                                197

SEQ ID NO: 110           moltype = AA   length = 5
FEATURE                  Location/Qualifiers
REGION                   1..5
                         note = Synthetic
source                   1..5
                         mol_type = protein
                         organism = synthetic construct
SEQUENCE: 110
SYWMH                                                              5

SEQ ID NO: 111           moltype = AA   length = 17
FEATURE                  Location/Qualifiers
REGION                   1..17
                         note = Synthetic
source                   1..17
                         mol_type = protein
                         organism = synthetic construct
SEQUENCE: 111
EINPTNGRTN YIEKFKS                                                 17

SEQ ID NO: 112           moltype = AA   length = 7
FEATURE                  Location/Qualifiers
REGION                   1..7
                         note = Synthetic
source                   1..7
                         mol_type = protein
                         organism = synthetic construct
SEQUENCE: 112
GTRAYHY                                                            7

SEQ ID NO: 113           moltype = AA   length = 11
FEATURE                  Location/Qualifiers
REGION                   1..11
                         note = Synthetic
source                   1..11
                         mol_type = protein
                         organism = synthetic construct
SEQUENCE: 113
RASDNLYSNL A                                                       11

SEQ ID NO: 114           moltype = AA   length = 7
FEATURE                  Location/Qualifiers
REGION                   1..7
                         note = Synthetic
source                   1..7
                         mol_type = protein
                         organism = synthetic construct
SEQUENCE: 114
DATNLAD                                                            7

SEQ ID NO: 115           moltype = AA   length = 9
FEATURE                  Location/Qualifiers
REGION                   1..9
                         note = Synthetic
source                   1..9
                         mol_type = protein
                         organism = synthetic construct
SEQUENCE: 115
QHFWGTPLT                                                          9
```

```
SEQ ID NO: 116         moltype = AA  length = 7
FEATURE                Location/Qualifiers
REGION                 1..7
                       note = Synthetic
source                 1..7
                       mol_type = protein
                       organism = synthetic construct
SEQUENCE: 116
GYTFTSY                                                                    7

SEQ ID NO: 117         moltype = AA  length = 6
FEATURE                Location/Qualifiers
REGION                 1..6
                       note = Synthetic
source                 1..6
                       mol_type = protein
                       organism = synthetic construct
SEQUENCE: 117
NPTNGR                                                                     6

SEQ ID NO: 118         moltype = AA  length = 6
FEATURE                Location/Qualifiers
REGION                 1..6
                       note = Synthetic
source                 1..6
                       mol_type = protein
                       organism = synthetic construct
SEQUENCE: 118
TSYWMH                                                                     6

SEQ ID NO: 119         moltype = AA  length = 13
FEATURE                Location/Qualifiers
REGION                 1..13
                       note = Synthetic
source                 1..13
                       mol_type = protein
                       organism = synthetic construct
SEQUENCE: 119
WIGEINPTNG RTN                                                            13

SEQ ID NO: 120         moltype = AA  length = 6
FEATURE                Location/Qualifiers
REGION                 1..6
                       note = Synthetic
source                 1..6
                       mol_type = protein
                       organism = synthetic construct
SEQUENCE: 120
ARGTRA                                                                     6

SEQ ID NO: 121         moltype = AA  length = 7
FEATURE                Location/Qualifiers
REGION                 1..7
                       note = Synthetic
source                 1..7
                       mol_type = protein
                       organism = synthetic construct
SEQUENCE: 121
YSNLAWY                                                                    7

SEQ ID NO: 122         moltype = AA  length = 10
FEATURE                Location/Qualifiers
REGION                 1..10
                       note = Synthetic
source                 1..10
                       mol_type = protein
                       organism = synthetic construct
SEQUENCE: 122
LLVYDATNLA                                                                10

SEQ ID NO: 123         moltype = AA  length = 8
FEATURE                Location/Qualifiers
REGION                 1..8
                       note = Synthetic
source                 1..8
                       mol_type = protein
                       organism = synthetic construct
SEQUENCE: 123
QHFWGTPL                                                                   8
```

```
SEQ ID NO: 124          moltype = AA  length = 116
FEATURE                 Location/Qualifiers
REGION                  1..116
                        note = Synthetic
source                  1..116
                        mol_type = protein
                        organism = synthetic construct
SEQUENCE: 124
QVQLQQPGAE LVKPGASVKL SCKASGYTFT SYWMHWVKQR PGQGLEWIGE INPTNGRTNY   60
IEKFKSKATL TVDKSSSTAY MQLSSLTSED SAVYYCARGT RAYHYWGQGT SVTVSS      116

SEQ ID NO: 125          moltype = AA  length = 107
FEATURE                 Location/Qualifiers
REGION                  1..107
                        note = Synthetic
source                  1..107
                        mol_type = protein
                        organism = synthetic construct
SEQUENCE: 125
DIQMTQSPAS LSVSVGETVT ITCRASDNLY SNLAWYQQKQ GKSPQLLVYD ATNLADGVPS   60
RFSGSGSGTQ YSLKINSLQS EDFGTYYCQH FWGTPLTFGA GTKLELK                107

SEQ ID NO: 126          moltype = AA  length = 9
FEATURE                 Location/Qualifiers
REGION                  1..9
                        note = Synthetic
source                  1..9
                        mol_type = protein
                        organism = synthetic construct
SEQUENCE: 126
QHFAGTPLT                                                          9

SEQ ID NO: 127          moltype = AA  length = 8
FEATURE                 Location/Qualifiers
REGION                  1..8
                        note = Synthetic
source                  1..8
                        mol_type = protein
                        organism = synthetic construct
SEQUENCE: 127
QHFAGTPL                                                           8

SEQ ID NO: 128          moltype = AA  length = 116
FEATURE                 Location/Qualifiers
REGION                  1..116
                        note = Synthetic
source                  1..116
                        mol_type = protein
                        organism = synthetic construct
SEQUENCE: 128
EVQLVQSGAE VKKPGASVKV SCKASGYTFT SYWMHWVRQA PGQRLEWIGE INPTNGRTNY   60
IEKFKSRATL TVDKSASTAY MELSSLRSED TAVYYCARGT RAYHYWGQGT MVTVSS      116

SEQ ID NO: 129          moltype = AA  length = 107
FEATURE                 Location/Qualifiers
REGION                  1..107
                        note = Synthetic
source                  1..107
                        mol_type = protein
                        organism = synthetic construct
SEQUENCE: 129
DIQMTQSPSS LSASVGDRVT ITCRASDNLY SNLAWYQQKP GKSPKLLVYD ATNLADGVPS   60
RFSGSGSGTD YTLTISSLQP EDFATYYCQH FWGTPLTFGA GTKVEIK                107

SEQ ID NO: 130          moltype = AA  length = 330
FEATURE                 Location/Qualifiers
source                  1..330
                        mol_type = protein
                        organism = Homo sapiens
SEQUENCE: 130
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 131          moltype = AA  length = 2859
```

| FEATURE | Location/Qualifiers |
|---|---|
| source | 1..2859 |
| | mol_type = protein |
| | organism = Homo sapiens |

SEQUENCE: 131

```
AGGGGGGCTG GACCAAGGGG TGGGGAGAAG GGGAGGAGGC CTCGGCCGGC CGCAGAGAGA    60
AGTGGCCAGA GAGGCCCAGG GGACAGCCAG GGACAGGCAG ACATGCAGCC AGGGCTCCAG   120
GGCCTGGACA GGGGCTGCCA GGCCCTGTGA CAGGAGGACC CCGAGCCCCC GGCCCGGGGA   180
GGGGCCATGG TGCTGCCTGT CCAACATGTC AGCCGAGGTG CCGCTGAGGC GGCTCCAGCA   240
GCTGGTGTTG GACCCGGGCT TCCTGGGGCT GGAGCCCCTG CTCGACCTTC TCCTGGGCGT   300
CCACCAGGAG CTGGGCGCCT CCGAACTGGC CCAGGACAAG TACGTGGCCG ACTTCTTGCA   360
GTGGGCGGAG CCCATCGTGG TGAGGCTTAA GGAGGTCCGA CTGCAGAGGG ACGACTTCGA   420
GATTCTGAAG GTGATCGGAC GCGGGGCGTT CAGCGAGGTA GCGGTAGTGA AGATGAAGCA   480
GACGGGCCAG GTGTATGCCA TGAAGATCAT GAACAAGTGG GACATGCTGA AGAGGGGCGA   540
GGTGTCGTGC TTCCGTGAGG AGAGGGACGT GTTGGTGAAT GGGGACCGGC GGTGGATCAC   600
GCAGCTGCAC TTCGCCTTCC AGGATGAGAA CTACCTGTAC CTGGTCATGG AGTATTACGT   660
GGGCGGGGAC CTGCTGACAC TGCTGAGCAA GTTTGGGGAG CGGATTCCGG CCGAGATGGC   720
GCGCTTCTAC CTGGCGGAGA TTGTCATGGC CATAGACTCG GTGCACCGGC TTGGCTACGT   780
GCACAGGGAC ATCAAACCCG ACAACATCCT GCTGGACCGC TGTGGCCACA TCCGCCTGGC   840
CGACTTCGGC TCTTGCCTCA AGCTGCGGGC AGATGGAACG GTGCGGTCGC TGGTGGCTGT   900
GGGCACCCCA GACTACCTGT CCCCCGAGAT CCTGCAGGCT GTGGGCGGTG GGCCTGGGAC   960
AGGCGGCTAC GGGCCCGAGT GTGACTGGTG GGCGCTGGGT GTATTCGCCT ATGAAATGTT  1020
CTATGGGCAG ACGCCCTTCT ACGCGGATTC CACGGCGGAG ACCTATGCA AGATCGTCCA  1080
CTACAAGGAG CACCTCTCTC TGCCGCTGGT GGACGAAGGG GTCCCTGAGG AGGCTCGAGA  1140
CTTCATTCAG CGGTTGCTGT GTCCCCCGGA GACACGGCTG GGCCGGGGTG GAGCAGGCGA  1200
CTTCCGGACA CATCCCTTCT TCTTTGGCCT CGACTGGGAT GGTCTCCGGG ACAGCGTGCC  1260
CCCCTTTACA CCGGATTTCG AAGGTGCCAC CGACACATGC AACTTCGACT TGGTGGAGGA  1320
CGGGCTCACT GCCATGGAGA CACTGTCGGA CATTCGGGAA GGTGCGCCGC TAGGGGTCCA  1380
CCTGCCTTTT GTGGGCTACT CCTACTCCTG CATGGCCCTC AGGGACAGTG AGGTCCCAGG  1440
CCCCACACCC ATGGAACTGG AGGCCGAGCA GCTGCTTGGA CACACGTGC AAGCGCCCAG  1500
CCTGGAGCCC TCGGTGTCCC CACAGGATGA AACAGCTGAA GTGGCAGTTC AGCGGCTGT  1560
CCCTGCGGCA GAGGCTGAGG CCGAGGTGAC GCTGCGGGAG CTCCAGGAAG CCCTGGAGGA  1620
GGAGGTGCTC ACCCGGCAGA GCCTGAGCCG GGAGATGGAG GCCATCCGCA CGGACAACCA  1680
GAACTTCGCC AGTCAACTAC GCGAGGCAGA GGCTCGGAAC CGGGACCTAG AGGCACACGT  1740
CCGGCAGTTG CAGGAGCGGA TGGAGTTGCT GCAGGCAGAG GGAGCCACAG CTGTCACGGG  1800
GGTCCCCAGT CCCCGGGCCA CGGATCCACC TTCCCATCTA GATGGCCCCC CGGCCGTGGC  1860
TGTGGGCCAG TGCCCGCTGG TGGGGCCAGG CCCCATGCAC CGCCGCCACC TGCTGCTCCC  1920
TGCCAGGGTC CCTAGGCCTG GCCTATCGGA GGCGCTTTC CTGCTCCTGT TCGCCGTTGT  1980
TCTGTCTCGT GCCGCCGCCC TGGGCTGCAT TGGGTTGGTG GCCCACGCCG GCCAACTCAC  2040
CGCAGTCTGG CGCCGCCCAG GAGCCGCCCG CGCTCCCTGA ACCCTAGAAC TGTCTTCGAC  2100
TCCGGGCCC CGTTGGAAGA CTGAGTGCC GGGGCACGGC ACAGAAGCCG CGCCCACCGC  2160
CTGCCAGTTC ACAACCGCTC CGAGCGTGGG TCTCCGCCCA GCTCCAGTCC TGTGATCCGG  2220
GCCCGCCCC TAGCGCCGG GGAGGGAGGG GCCGGGTCCG CGGCCGGCGA ACGGGGCTCG  2280
AAGGGTCCTT GTAGCCGGGA ATGCTGCTGC TGCTGCTGCT GCTGCTGCTG CTGCTGCTGC  2340
TGCTGCTGCT GCTGCTGCTG CTGGGGGGAT CACAGACCAT TTCTTTCTTT CGGCCAGGCT  2400
GAGGCCCTGA CGTGGATGGG CAAACTCAG GCCTGGGAAG GCAGCAAGCC GGGCCGTCCG  2460
TGTTCCAATC TCCACGCACC CCCACCTATC GTTGGTTCGC AAAGTGCAAA GCTTTCTTGT  2520
GCATGACGCC CTGCTCTGGG GAGCGTCTGG CGCGATCTCT GCCTGCTTAC TCGGGAAATT  2580
TGCTTTTGCC AAACCCGCTT TTTCGGGGAT CCCGCGCCCC CCTCCTCACT TGCGCTGCTC  2640
TCGGAGCCCC AGCCGGCTCC GCCCGCTTCG GCGGTTTGGA TATTTATTGA CCTCGTCCTC  2700
CGACTCGCTG ACAGGCTACA GGACCCCCAA CAACCCCAAT CCACGTTTTG GATGCACTGA  2760
GACCCCGACA TTCCTCGGTA TTTATTGTCT GTCCCCACCT AGGACCCCCA CCCCCGACCC  2820
TCGCGAATAA AAGGCCCTCC ATCTGCCCAA AGCTCTGGA                         2859
```

| SEQ ID NO: 132 | moltype = AA  length = 446 |
|---|---|
| FEATURE | Location/Qualifiers |
| REGION | 1..446 |
| | note = Synthetic |
| source | 1..446 |
| | mol_type = protein |
| | organism = synthetic construct |

SEQUENCE: 132

```
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446
```

| SEQ ID NO: 133 | moltype = AA  length = 214 |
|---|---|
| FEATURE | Location/Qualifiers |
| REGION | 1..214 |
| | note = Synthetic |
| source | 1..214 |
| | mol_type = protein |
| | organism = synthetic construct |

SEQUENCE: 133

```
DIQMTQSPAS LSVSVGETVT ITCRASDNLY SNLAWYQQKQ GKSPQLLVYD ATNLADGVPS    60
RFSGSGSGTQ YSLKINSLQS EDFGTYYCQH FWGTPLTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 134          moltype = AA  length = 446
FEATURE                 Location/Qualifiers
REGION                  1..446
                        note = Synthetic
source                  1..446
                        mol_type = protein
                        organism = synthetic construct
SEQUENCE: 134
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVTPS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 135          moltype = AA  length = 214
FEATURE                 Location/Qualifiers
REGION                  1..214
                        note = Synthetic
source                  1..214
                        mol_type = protein
                        organism = synthetic construct
SEQUENCE: 135
DIQMTQSPSS LSASVGDRVT ITCRASDNLY SNLAWYQQKP GKSPKLLVYD ATNLADGVPS    60
RFSGSGSGTD YTLTISSLQP EDFATYYCQH FWGTPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 136          moltype = AA  length = 226
FEATURE                 Location/Qualifiers
REGION                  1..226
                        note = Synthetic
source                  1..226
                        mol_type = protein
                        organism = synthetic construct
SEQUENCE: 136
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                 226

SEQ ID NO: 137          moltype = AA  length = 226
FEATURE                 Location/Qualifiers
REGION                  1..226
                        note = Synthetic
source                  1..226
                        mol_type = protein
                        organism = synthetic construct
SEQUENCE: 137
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                 226

SEQ ID NO: 138          moltype = AA  length = 7
FEATURE                 Location/Qualifiers
REGION                  1..7
                        note = Synthetic
source                  1..7
                        mol_type = protein
                        organism = synthetic construct
SEQUENCE: 138
ASSLNIA                                                               7

SEQ ID NO: 139          moltype = AA  length = 12
FEATURE                 Location/Qualifiers
REGION                  1..12
                        note = Synthetic
source                  1..12
                        mol_type = protein
                        organism = synthetic construct
SEQUENCE: 139
```

```
SKTFNTHPQS TP                                                                   12

SEQ ID NO: 140          moltype = AA  length = 12
FEATURE                 Location/Qualifiers
REGION                  1..12
                        note = Synthetic
source                  1..12
                        mol_type = protein
                        organism = synthetic construct
SEQUENCE: 140
TARGEHKEEE LI                                                                   12

SEQ ID NO: 141          moltype = AA  length = 9
FEATURE                 Location/Qualifiers
REGION                  1..9
                        note = Synthetic
source                  1..9
                        mol_type = protein
                        organism = synthetic construct
SEQUENCE: 141
CQAQGQLVC                                                                        9

SEQ ID NO: 142          moltype = AA  length = 9
FEATURE                 Location/Qualifiers
REGION                  1..9
                        note = Synthetic
source                  1..9
                        mol_type = protein
                        organism = synthetic construct
SEQUENCE: 142
CSERSMNFC                                                                        9

SEQ ID NO: 143          moltype = AA  length = 9
FEATURE                 Location/Qualifiers
REGION                  1..9
                        note = Synthetic
source                  1..9
                        mol_type = protein
                        organism = synthetic construct
SEQUENCE: 143
CPKTRRVPC                                                                        9

SEQ ID NO: 144          moltype = AA  length = 20
FEATURE                 Location/Qualifiers
REGION                  1..20
                        note = Synthetic
source                  1..20
                        mol_type = protein
                        organism = synthetic construct
SEQUENCE: 144
WLSEAGPVVT VRALRGTGSW                                                           20

SEQ ID NO: 145          moltype = AA  length = 9
FEATURE                 Location/Qualifiers
REGION                  1..9
                        note = Synthetic
source                  1..9
                        mol_type = protein
                        organism = synthetic construct
SEQUENCE: 145
CMQHSMRVC                                                                        9

SEQ ID NO: 146          moltype = AA  length = 7
FEATURE                 Location/Qualifiers
REGION                  1..7
                        note = Synthetic
source                  1..7
                        mol_type = protein
                        organism = synthetic construct
SEQUENCE: 146
DDTRHWG                                                                          7

SEQ ID NO: 147          moltype = DNA  length = 2683
FEATURE                 Location/Qualifiers
source                  1..2683
                        mol_type = genomic DNA
                        organism = Mus musculus
SEQUENCE: 147
gaactggcca gagagaccca agggatagtc agggacgggc agacatgcag ctagggttct              60
```

```
ggggcctgga cagggggcagc caggccctgt gacgggaaga ccccgagctc cggcccgggg    120
aggggccatg gtgttgcctg cccaacatgt cagccgaagt gcggctgagg cagctccagc    180
agctggtgct ggacccaggc ttcctgggac tggagcccct gctcgacctt ctcctgggcg    240
tccaccagga gctgggtgcc tctcacctag cccaggacaa gtatgtggcc gacttcttgc    300
agtgggtgga gcccattgca gcaaggctta aggaggtccg actgcagagg gatgattttg    360
agattttgaa ggtgatcggg cgtggggcgt tcagcgaggt agcggtggtg aagatgaaac    420
agacgggcca agtgtatgcc atgaagatta tgaataagtg ggacatgctg aagagaggcg    480
aggtgtcgtg cttccgggaa gaagggatg tattagtgaa aggggaccgg cgctggatca    540
cacagctgca ctttgccttc caggatgaga actacctgta cctggtcatg gaatactacg    600
tgggcgggga cctgctaacg ctgctgagca agtttgggga gcggatcccc gccgagatgg    660
ctcgcttcta cctggccgag attgtcatgc catagactcc cgtgcaccgg ctgggctacg    720
tgcacaggga catcaaacca gataacattc tgctggaccg atgtgggcac attcgcctgg    780
cagacttcgg ctcctgcctc aaactgcagc ctgatgaat ggtgaggtcg ctggtggctg    840
tgggcacccc ggactacctg tctcctgaga ttctgcaggc cgttggtgga gggcagact    900
caggcagcta cgggcagag tgtgactggt gggcactggg cgtgttcgcc tatgagatgt    960
tctatgggca gacccccttc tacgcggact ccacagccga gacatatgcc aagattgtgc   1020
actacaggga acacttgtcg ctgccgctgg cagacacagt tgtccccgag gaagctcagg   1080
acctcattcg tgggctgctg tgtcctgctg agataaggct aggtcgaggt ggggcagact   1140
tcgagggtgc cacggacaca tgcaatttgc atgtggtgga ggaccggctc actgccatgg   1200
tgagcggggg cggggagacg ctgtcagaca tgcaggaaga catgcccctt ggggtgcgcc   1260
tgcccttcgt gggctactcc tactgctgca tggccttcag agacaatcag gtcccggacc   1320
ccacccctat ggaactagag gccctgcagt tgcctgtc agacttgcaa gggcttgact   1380
tgcagccccc agtgtcccca ccggatcaag tggctgaaga ggctgaccta gtggctgtcc   1440
ctgcccctgt ggctgaggca gagaccacgg taacgctgca gcagctccag aagccctgg    1500
aagaagaggt tctcacccgg cagagcctga gccgcgagct ggaggccatc cggaccgcca   1560
accagaaactt ctccagccaa ctacaggagg ccgaggtccg aaaccgagac ctggaggcgg   1620
atgttcggca gctacaggaa cggatggaga tgctgcaggc cccaggagcc gcagccatca   1680
cgggggtccc cagtccccgg gccacggatc caccttccca tctagatggc ccccggccg    1740
tggctgtggg ccagtgcccg ctggtggggc caggccccat gcaccgcgt cacctgctgc   1800
tccctgccag gatccctagg cctgcctat ccgaggcgg ttgcctgctc ctgttcgtga    1860
ctgctctggc tgctgccgcc acactgggct gcactgggtt ggtggcctat accggcggtc   1920
tcaccccagt ctggtgtttc ccgggagcca ccttcgcccc ctgaaccta agactccaag    1980
ccatctttca tttaggcctc ctaggaaggt cgagcgacca gggagcgacc caaagcgtct   2040
ctgtgcccat cgcgcccccc ccccccccc accgctccgc tccacacttc tgtgagcctg   2100
ggtccccacc cagctccgct cctgtgatcc aggcctgcca cctgcgcc ggggaggagg    2160
gaacagggct cgtgcccagc acccctggtt cctgcagagc tggtagccac cgctgctgca   2220
gcagctgggc attcgccgac cttgctttac tcagccccga cgtggatggg caaactgctc   2280
agctcatccg atttcacttt ttcactctcc cagccatcag ttacaagcca taagcatgag   2340
ccccctattt ccagggacat cccattccca tagtgatgga tcagcaagac ctctgccagc   2400
acacacggag tctttggctt cggacagcct cactcctggg ggttgctgca actccttccc   2460
cgtgtacacg tctgcactct aacaacgagg ccacagctgc actcccccct ccccaaagc    2520
agtgtgggta tttattgatc ttgttatctg actcactgac agactccggg acccacgttt   2580
tagatgcatt gagactcgac attcctcggt atttattgtc tgtccccacc tacgacctcc   2640
actcccgacc cttgcgaata aaatacttct ggtctgccct aaa                    2683

SEQ ID NO: 148          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 148
ggacggcccg gcttgctgcc                                                 20

SEQ ID NO: 149          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 149
gggcccggat cacaggactg                                                 20

SEQ ID NO: 150          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 150
caaacttgct cagcagtgtc                                                 20

SEQ ID NO: 151          moltype = RNA   length = 20
FEATURE                 Location/Qualifiers
misc_feature            1..20
                        note = Synthetic
```

```
source                          1..20
                                mol_type = other RNA
                                organism = synthetic construct
SEQUENCE: 151
aaacttgctc agcagtgtca                                                        20

SEQ ID NO: 152                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 152
cggatggcct ccatctcccg                                                        20

SEQ ID NO: 153                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 153
ctcggccgga atccgctccc                                                        20

SEQ ID NO: 154                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 154
tctcggccgg aatccgctcc                                                        20

SEQ ID NO: 155                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 155
tgctcagcag tgtcagcagg                                                        20

SEQ ID NO: 156                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 156
ttgtcgggtt tgatgtccct                                                        20

SEQ ID NO: 157                  moltype = RNA   length = 19
FEATURE                         Location/Qualifiers
misc_feature                    1..19
                                note = Synthetic
source                          1..19
                                mol_type = other RNA
                                organism = synthetic construct
SEQUENCE: 157
gttgcgggtt tgatgtccc                                                         19

SEQ ID NO: 158                  moltype = RNA   length = 20
FEATURE                         Location/Qualifiers
misc_feature                    1..20
                                note = Synthetic
source                          1..20
                                mol_type = other RNA
                                organism = synthetic construct
SEQUENCE: 158
tccgccaggt agaagcgcgc                                                        20

SEQ ID NO: 159                  moltype = RNA   length = 20
FEATURE                         Location/Qualifiers
misc_feature                    1..20
```

```
                    note = Synthetic
source              1..20
                    mol_type = other RNA
                    organism = synthetic construct
SEQUENCE: 159
catggcatac acctggcccg                                               20

SEQ ID NO: 160      moltype = RNA   length = 20
FEATURE             Location/Qualifiers
misc_feature        1..20
                    note = Synthetic
source              1..20
                    mol_type = other RNA
                    organism = synthetic construct
SEQUENCE: 160
aacttgctca gcagtgtcag                                               20

SEQ ID NO: 161      moltype = RNA   length = 20
FEATURE             Location/Qualifiers
misc_feature        1..20
                    note = Synthetic
source              1..20
                    mol_type = other RNA
                    organism = synthetic construct
SEQUENCE: 161
cagctgcgtg atccaccgcc                                               20

SEQ ID NO: 162      moltype = RNA   length = 20
FEATURE             Location/Qualifiers
misc_feature        1..20
                    note = Synthetic
source              1..20
                    mol_type = other RNA
                    organism = synthetic construct
SEQUENCE: 162
cgaatgtccg acagtgtctc                                               20

SEQ ID NO: 163      moltype = RNA   length = 20
FEATURE             Location/Qualifiers
misc_feature        1..20
                    note = Synthetic
source              1..20
                    mol_type = other RNA
                    organism = synthetic construct
SEQUENCE: 163
gaagtcggcc aggcggatgt                                               20

SEQ ID NO: 164      moltype = RNA   length = 20
FEATURE             Location/Qualifiers
misc_feature        1..20
                    note = Synthetic
source              1..20
                    mol_type = other RNA
                    organism = synthetic construct
SEQUENCE: 164
tgtcgggttt gatgtccctg                                               20

SEQ ID NO: 165      moltype = RNA   length = 20
FEATURE             Location/Qualifiers
misc_feature        1..20
                    note = Synthetic
source              1..20
                    mol_type = other RNA
                    organism = synthetic construct
SEQUENCE: 165
ggatggcctc catctcccgg                                               20

SEQ ID NO: 166      moltype = RNA   length = 20
FEATURE             Location/Qualifiers
misc_feature        1..20
                    note = Synthetic
source              1..20
                    mol_type = other RNA
                    organism = synthetic construct
SEQUENCE: 166
aggatgttgt cgggtttgat                                               20

SEQ ID NO: 167      moltype = RNA   length = 20
FEATURE             Location/Qualifiers
```

```
misc_feature              1..20
                          note = Synthetic
source                    1..20
                          mol_type = other RNA
                          organism = synthetic construct
SEQUENCE: 167
gtcgggtttg atgtccctgt                                                      20

SEQ ID NO: 168            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 168
aatactccat gaccaggtac                                                      20

SEQ ID NO: 169            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 169
cttgttcatg atcttcatgg                                                      20

SEQ ID NO: 170            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 170
tcagtgcatc caaaacgtgg                                                      20

SEQ ID NO: 171            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 171
ctgtcccgga gaccatccca                                                      20

SEQ ID NO: 172            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 172
gggcctggga cctcactgtc                                                      20

SEQ ID NO: 173            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 173
cccacgtaat actccatgac                                                      20

SEQ ID NO: 174            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 174
ctctgccgca gggacagccg                                                      20

SEQ ID NO: 175            moltype = RNA   length = 20
```

```
FEATURE              Location/Qualifiers
misc_feature         1..20
                     note = Synthetic
source               1..20
                     mol_type = other RNA
                     organism = synthetic construct
SEQUENCE: 175
ctgtgcacgt agccaagccg                                                    20

SEQ ID NO: 176       moltype = RNA  length = 20
FEATURE              Location/Qualifiers
misc_feature         1..20
                     note = Synthetic
source               1..20
                     mol_type = other RNA
                     organism = synthetic construct
SEQUENCE: 176
tgcccatcca cgtcagggcc                                                    20

SEQ ID NO: 177       moltype = RNA  length = 20
FEATURE              Location/Qualifiers
misc_feature         1..20
                     note = Synthetic
source               1..20
                     mol_type = other RNA
                     organism = synthetic construct
SEQUENCE: 177
agcgcctccg ataggccagg                                                    20

SEQ ID NO: 178       moltype = RNA  length = 20
FEATURE              Location/Qualifiers
misc_feature         1..20
                     note = Synthetic
source               1..20
                     mol_type = other RNA
                     organism = synthetic construct
SEQUENCE: 178
tgtgcacgta gccaagccgg                                                    20

SEQ ID NO: 179       moltype = RNA  length = 20
FEATURE              Location/Qualifiers
misc_feature         1..20
                     note = Synthetic
source               1..20
                     mol_type = other RNA
                     organism = synthetic construct
SEQUENCE: 179
gaccaggtac aggtagttct                                                    20

SEQ ID NO: 180       moltype = RNA  length = 20
FEATURE              Location/Qualifiers
misc_feature         1..20
                     note = Synthetic
source               1..20
                     mol_type = other RNA
                     organism = synthetic construct
SEQUENCE: 180
ccatctcggc cggaatccgc                                                    20

SEQ ID NO: 181       moltype = RNA  length = 20
FEATURE              Location/Qualifiers
misc_feature         1..20
                     note = Synthetic
source               1..20
                     mol_type = other RNA
                     organism = synthetic construct
SEQUENCE: 181
catctcggcc ggaatccgct                                                    20

SEQ ID NO: 182       moltype = RNA  length = 20
FEATURE              Location/Qualifiers
misc_feature         1..20
                     note = Synthetic
source               1..20
                     mol_type = other RNA
                     organism = synthetic construct
SEQUENCE: 182
ttgccatagg tctccgccgt                                                    20
```

-continued

```
SEQ ID NO: 183              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 183
acagcggtcc agcaggatgt                                                    20

SEQ ID NO: 184              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 184
aaagcgcctc cgataggcca                                                    20

SEQ ID NO: 185              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 185
gccaaagaag aagggatgtg                                                    20

SEQ ID NO: 186              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 186
cacgtaatac tccatgacca                                                    20

SEQ ID NO: 187              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 187
atctcggccg gaatccgctc                                                    20

SEQ ID NO: 188              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 188
gcttcatctt cactaccgct                                                    20

SEQ ID NO: 189              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 189
gccatctcgg ccggaatccg                                                    20

SEQ ID NO: 190              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 190
cagggacagc cgctggaact                                                    20
```

```
SEQ ID NO: 191              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 191
atgacaatct ccgccaggta                                                       20

SEQ ID NO: 192              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 192
ggccatgaca atctccgcca                                                       20

SEQ ID NO: 193              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 193
atactccatg accaggtaca                                                       20

SEQ ID NO: 194              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 194
gcctctgcct cgcgtagttg                                                       20

SEQ ID NO: 195              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 195
gaatgtccga cagtgtctcc                                                       20

SEQ ID NO: 196              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 196
cgttccatct gcccgcagct                                                       20

SEQ ID NO: 197              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 197
ccttgtagtg gacgatcttg                                                       20

SEQ ID NO: 198              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 198
```
atctccgcca ggtagaagcg 20

SEQ ID NO: 199    moltype = RNA   length = 20
FEATURE           Location/Qualifiers
misc_feature      1..20
                  note = Synthetic
source            1..20
                  mol_type = other RNA
                  organism = synthetic construct
SEQUENCE: 199
ctcaggctct gccgggtgag 20

SEQ ID NO: 200    moltype = RNA   length = 20
FEATURE           Location/Qualifiers
misc_feature      1..20
                  note = Synthetic
source            1..20
                  mol_type = other RNA
                  organism = synthetic construct
SEQUENCE: 200
tgcttcatct tcactaccgc 20

SEQ ID NO: 201    moltype = RNA   length = 20
FEATURE           Location/Qualifiers
misc_feature      1..20
                  note = Synthetic
source            1..20
                  mol_type = other RNA
                  organism = synthetic construct
SEQUENCE: 201
gcaggatgtt gtcgggtttg 20

SEQ ID NO: 202    moltype = RNA   length = 20
FEATURE           Location/Qualifiers
misc_feature      1..20
                  note = Synthetic
source            1..20
                  mol_type = other RNA
                  organism = synthetic construct
SEQUENCE: 202
ggcctcagcc tctgccgcag 20

SEQ ID NO: 203    moltype = RNA   length = 20
FEATURE           Location/Qualifiers
misc_feature      1..20
                  note = Synthetic
source            1..20
                  mol_type = other RNA
                  organism = synthetic construct
SEQUENCE: 203
tgttgtcggg tttgatgtcc 20

SEQ ID NO: 204    moltype = RNA   length = 20
FEATURE           Location/Qualifiers
misc_feature      1..20
                  note = Synthetic
source            1..20
                  mol_type = other RNA
                  organism = synthetic construct
SEQUENCE: 204
ccacgtaata ctccatgacc 20

SEQ ID NO: 205    moltype = RNA   length = 20
FEATURE           Location/Qualifiers
misc_feature      1..20
                  note = Synthetic
source            1..20
                  mol_type = other RNA
                  organism = synthetic construct
SEQUENCE: 205
ccgttccatc tgcccgcagc 20

SEQ ID NO: 206    moltype = RNA   length = 20
FEATURE           Location/Qualifiers
misc_feature      1..20
                  note = Synthetic
source            1..20
                  mol_type = other RNA
                  organism = synthetic construct

```
SEQUENCE: 206
ttcccgagta agcaggcaga                                                    20

SEQ ID NO: 207           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 207
tgatcttcat ggcatacacc                                                    20

SEQ ID NO: 208           moltype = DNA   length = 20
FEATURE                  Location/Qualifiers
misc_feature             1..20
                         note = Synthetic
source                   1..20
                         mol_type = other DNA
                         organism = synthetic construct
modified_base            17
                         mod_base = OTHER
                         note = Uracil
SEQUENCE: 208
agggacagcc gctggaactg                                                    20

SEQ ID NO: 209           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 209
gggtttgatg tccctgtgca                                                    20

SEQ ID NO: 210           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 210
tgacaatctc cgccaggtag                                                    20

SEQ ID NO: 211           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 211
cacagcggtc cagcaggatg                                                    20

SEQ ID NO: 212           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 212
gcgtagaagg gcgtctgccc                                                    20

SEQ ID NO: 213           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 213
ctcagcctct gccgcaggga                                                    20

SEQ ID NO: 214           moltype = RNA   length = 20
FEATURE                  Location/Qualifiers
misc_feature             1..20
```

```
                        note = Synthetic
source                  1..20
                        mol_type = other RNA
                        organism = synthetic construct
SEQUENCE: 214
gtctcagtgc atccaaaacg                                                    20

SEQ ID NO: 215          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 215
ggacgatctt gccataggtc                                                    20

SEQ ID NO: 216          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 216
tcagcagtgt cagcaggtcc                                                    20

SEQ ID NO: 217          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 217
gctcctgggc ggcgccagac                                                    20

SEQ ID NO: 218          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 218
agcaggatgt tgtcgggttt                                                    20

SEQ ID NO: 219          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 219
atccgctcct gcaactgccg                                                    20

SEQ ID NO: 220          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 220
aggagcaggg aaagcgcctc                                                    20

SEQ ID NO: 221          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 221
acacctggcc cgtctgcttc                                                    20

SEQ ID NO: 222          moltype = RNA   length = 20
FEATURE                 Location/Qualifiers
```

```
misc_feature               1..20
                           note = Synthetic
source                     1..20
                           mol_type = other RNA
                           organism = synthetic construct
SEQUENCE: 222
cccagcgccc accagtcaca                                                    20

SEQ ID NO: 223             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 223
gctccctctg cctgcagcaa                                                    20

SEQ ID NO: 224             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 224
gctcaggctc tgccgggtga                                                    20

SEQ ID NO: 225             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 225
ttgatgtccc tgtgcacgta                                                    20

SEQ ID NO: 226             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 226
gcctcagcct ctgccgcagg                                                    20

SEQ ID NO: 227             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 227
ggtagttctc atcctggaag                                                    20

SEQ ID NO: 228             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 228
cagcgcccac cagtcacact                                                    20

SEQ ID NO: 229             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 229
cccaaacttg ctcagcagtg                                                    20

SEQ ID NO: 230             moltype = RNA   length = 20
```

```
FEATURE                 Location/Qualifiers
misc_feature            1..20
                        note = Synthetic
source                  1..20
                        mol_type = other RNA
                        organism = synthetic construct
SEQUENCE: 230
cttgccatag gtctccgccg                                                    20

SEQ ID NO: 231          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 231
tacacctggc ccgtctgctt                                                    20

SEQ ID NO: 232          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 232
ccagcgccca ccagtcacac                                                    20

SEQ ID NO: 233          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 233
ggcctcagcc tggccgaaag                                                    20

SEQ ID NO: 234          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 234
aatctccgcc aggtagaagc                                                    20

SEQ ID NO: 235          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 235
atggcataca cctggcccgt                                                    20

SEQ ID NO: 236          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 236
ccatgacaat ctccgccagg                                                    20

SEQ ID NO: 237          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 237
tccccaaact tgctcagcag                                                    20
```

| | |
|---|---|
| SEQ ID NO: 238<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 238
gatgttgtcg ggtttgatgt                                          20

| | |
|---|---|
| SEQ ID NO: 239<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 239
gtttgcccat ccacgtcagg                                          20

| | |
|---|---|
| SEQ ID NO: 240<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 240
cggacggccc ggcttgctgc                                          20

| | |
|---|---|
| SEQ ID NO: 241<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 241
ctccgccagg tagaagcgcg                                          20

| | |
|---|---|
| SEQ ID NO: 242<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 242
gtacaggtag ttctcatcct                                          20

| | |
|---|---|
| SEQ ID NO: 243<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 243
agggcgtctg cccatagaac                                          20

| | |
|---|---|
| SEQ ID NO: 244<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 244
tggccacagc ggtccagcag                                          20

| | |
|---|---|
| SEQ ID NO: 245<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct |

SEQUENCE: 245
cgtagttgac tggcgaagtt                                          20

```
SEQ ID NO: 246          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 246
tctgccgcag ggacagccgc                                                     20

SEQ ID NO: 247          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 247
aagcgcctcc gataggccag                                                     20

SEQ ID NO: 248          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 248
gacagaacaa cggcgaacag                                                     20

SEQ ID NO: 249          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 249
gctcagcagt gtcagcaggt                                                     20

SEQ ID NO: 250          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 250
atgatcttca tggcatacac                                                     20

SEQ ID NO: 251          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 251
tttgcccatc cacgtcaggg                                                     20

SEQ ID NO: 252          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 252
acttgctcag cagtgtcagc                                                     20

SEQ ID NO: 253          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 253
```

```
tgatgtccct gtgcacgtag                                                    20

SEQ ID NO: 254         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 254
aaataccgag gaatgtcggg                                                    20

SEQ ID NO: 255         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 255
ggcgaataca cccagcgccc                                                    20

SEQ ID NO: 256         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 256
agacaataaa taccgaggaa                                                    20

SEQ ID NO: 257         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 257
cccgtctgct tcatcttcac                                                    20

SEQ ID NO: 258         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 258
ctgcctgcag caactccatc                                                    20

SEQ ID NO: 259         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 259
cctcagcctc tgccgcaggg                                                    20

SEQ ID NO: 260         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 260
gtgtccggaa gtcgcctgct                                                    20

SEQ ID NO: 261         moltype = RNA  length = 20
FEATURE                Location/Qualifiers
misc_feature           1..20
                       note = Synthetic
source                 1..20
                       mol_type = other RNA
                       organism = synthetic construct
```

```
SEQUENCE: 261
tgcacgtgtg gctcaagcag                                                    20

SEQ ID NO: 262         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 262
gacaataaat accgaggaat                                                    20

SEQ ID NO: 263         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 263
gccatgacaa tctccgccag                                                    20

SEQ ID NO: 264         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 264
gctgtcccgg agaccatccc                                                    20

SEQ ID NO: 265         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 265
catgaccagg tacaggtagt                                                    20

SEQ ID NO: 266         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 266
agcgcccacc agtcacactc                                                    20

SEQ ID NO: 267         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 267
tctcagtgca tccaaaacgt                                                    20

SEQ ID NO: 268         moltype = RNA  length = 20
FEATURE                Location/Qualifiers
misc_feature           1..20
                       note = Synthetic
source                 1..20
                       mol_type = other RNA
                       organism = synthetic construct
SEQUENCE: 268
tttgggcaga tggagggcct                                                    20

SEQ ID NO: 269         moltype = RNA  length = 20
FEATURE                Location/Qualifiers
misc_feature           1..20
                       note = Synthetic
source                 1..20
                       mol_type = other RNA
```

```
                        organism = synthetic construct
SEQUENCE: 269
gatgtccctg tgcacgtagc                                               20

SEQ ID NO: 270          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 270
cagcagtgtc agcaggtccc                                               20

SEQ ID NO: 271          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 271
catgacaatc tccgccaggt                                               20

SEQ ID NO: 272          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 272
acttgttcat gatcttcatg                                               20

SEQ ID NO: 273          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 273
gtggaatccg cgtagaaggg                                               20

SEQ ID NO: 274          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 274
tggccatgac aatctccgcc                                               20

SEQ ID NO: 275          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 275
gggacagaca ataaataccg                                               20

SEQ ID NO: 276          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 276
ccgctcccca aacttgctca                                               20

SEQ ID NO: 277          moltype = RNA   length = 20
FEATURE                 Location/Qualifiers
misc_feature            1..20
                        note = Synthetic
source                  1..20
```

```
                        mol_type = other RNA
                        organism = synthetic construct
SEQUENCE: 277
cggctcaggc tctgccgggt                                                  20

SEQ ID NO: 278          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 278
ggctcctggg cggcgccaga                                                  20

SEQ ID NO: 279          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 279
tttcccgagt aagcaggcag                                                  20

SEQ ID NO: 280          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 280
ggatgttgtc gggtttgatg                                                  20

SEQ ID NO: 281          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 281
caggtagttc tcatcctgga                                                  20

SEQ ID NO: 282          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 282
tgcccataga acatttcata                                                  20

SEQ ID NO: 283          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 283
tagttctcat cctggaaggc                                                  20

SEQ ID NO: 284          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 284
atgtccctgt gcacgtagcc                                                  20

SEQ ID NO: 285          moltype = RNA  length = 20
FEATURE                 Location/Qualifiers
misc_feature            1..20
                        note = Synthetic
```

```
source                   1..20
                         mol_type = other RNA
                         organism = synthetic construct
SEQUENCE: 285
cgggcccgga tcacaggact                                              20

SEQ ID NO: 286           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 286
tggacgatct tgccataggt                                              20

SEQ ID NO: 287           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 287
gttggccggc gtgggccacc                                              20

SEQ ID NO: 288           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 288
ctcagtgcat ccaaaacgtg                                              20

SEQ ID NO: 289           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 289
tcgaagttgc atgtgtcggt                                              20

SEQ ID NO: 290           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 290
tggaacacgg acggcccggc                                              20

SEQ ID NO: 291           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 291
ccgagagcag cgcaagtgag                                              20

SEQ ID NO: 292           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 292
tcctgcaact gccggacgtg                                              20

SEQ ID NO: 293           moltype = RNA   length = 20
FEATURE                  Location/Qualifiers
misc_feature             1..20
```

```
                         note = Synthetic
source                   1..20
                         mol_type = other RNA
                         organism = synthetic construct
SEQUENCE: 293
tcaccaacac gtccctctcc                                                20

SEQ ID NO: 294           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 294
tgcctgcagc aactccatcc                                                20

SEQ ID NO: 295           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 295
ttggccggcg tgggccacca                                                20

SEQ ID NO: 296           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 296
gagcctctgc ctcgcgtagt                                                20

SEQ ID NO: 297           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 297
aagggcgtct gcccatagaa                                                20

SEQ ID NO: 298           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 298
acagacaata aataccgagg                                                20

SEQ ID NO: 299           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 299
ggacagacaa taaataccga                                                20

SEQ ID NO: 300           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 300
acgtgtgcct ctaggtcccg                                                20

SEQ ID NO: 301           moltype = RNA   length = 20
FEATURE                  Location/Qualifiers
```

```
                        -continued misc_feature            1..20
                        note = Synthetic
source                  1..20
                        mol_type = other RNA
                        organism = synthetic construct
SEQUENCE: 301
ggcacgagac agaacaacgg                                              20

SEQ ID NO: 302          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 302
tgaccaggta caggtagttc                                              20

SEQ ID NO: 303          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 303
ctctgccggg tgagcacctc                                              20

SEQ ID NO: 304          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 304
gacaatctcc gccaggtaga                                              20

SEQ ID NO: 305          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 305
tctccgccag gtagaagcgc                                              20

SEQ ID NO: 306          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 306
ctctgcctcg cgtagttgac                                              20

SEQ ID NO: 307          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 307
ctttgggcag atggagggcc                                              20

SEQ ID NO: 308          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 308
acaggtagtt ctcatcctgg                                              20

SEQ ID NO: 309          moltype = DNA  length = 20
```

```
FEATURE              Location/Qualifiers
misc_feature         1..20
                     note = Synthetic
source               1..20
                     mol_type = other DNA
                     organism = synthetic construct
modified_base        7..8
                     mod_base = OTHER
                     note = Uracil
modified_base        18
                     mod_base = OTHER
                     note = Uracil
modified_base        20
                     mod_base = OTHER
                     note = Uracil
SEQUENCE: 309
ccaaacttgc tcagcagtgt                                                     20

SEQ ID NO: 310       moltype = RNA  length = 20
FEATURE              Location/Qualifiers
misc_feature         1..20
                     note = Synthetic
source               1..20
                     mol_type = other RNA
                     organism = synthetic construct
SEQUENCE: 310
tcgggtttga tgtccctgtg                                                     20

SEQ ID NO: 311       moltype = RNA  length = 20
FEATURE              Location/Qualifiers
misc_feature         1..20
                     note = Synthetic
source               1..20
                     mol_type = other RNA
                     organism = synthetic construct
SEQUENCE: 311
ggcttgctgc cttcccaggc                                                     20

SEQ ID NO: 312       moltype = RNA  length = 20
FEATURE              Location/Qualifiers
misc_feature         1..20
                     note = Synthetic
source               1..20
                     mol_type = other RNA
                     organism = synthetic construct
SEQUENCE: 312
tacaggtagt tctcatcctg                                                     20

SEQ ID NO: 313       moltype = RNA  length = 20
FEATURE              Location/Qualifiers
misc_feature         1..20
                     note = Synthetic
source               1..20
                     mol_type = other RNA
                     organism = synthetic construct
SEQUENCE: 313
ttgcccatcc acgtcagggc                                                     20

SEQ ID NO: 314       moltype = RNA  length = 20
FEATURE              Location/Qualifiers
misc_feature         1..20
                     note = Synthetic
source               1..20
                     mol_type = other RNA
                     organism = synthetic construct
SEQUENCE: 314
aggtacaggt agttctcatc                                                     20

SEQ ID NO: 315       moltype = RNA  length = 20
FEATURE              Location/Qualifiers
misc_feature         1..20
                     note = Synthetic
source               1..20
                     mol_type = other RNA
                     organism = synthetic construct
SEQUENCE: 315
gacagacaat aaataccgag                                                     20

SEQ ID NO: 316       moltype = RNA  length = 20
```

```
FEATURE              Location/Qualifiers
misc_feature         1..20
                     note = Synthetic
source               1..20
                     mol_type = other RNA
                     organism = synthetic construct
SEQUENCE: 316
tagaacattt cataggcgaa                                                     20

SEQ ID NO: 317       moltype = RNA   length = 20
FEATURE              Location/Qualifiers
misc_feature         1..20
                     note = Synthetic
source               1..20
                     mol_type = other RNA
                     organism = synthetic construct
SEQUENCE: 317
agggcctttt attcgcgagg                                                     20

SEQ ID NO: 318       moltype = RNA   length = 20
FEATURE              Location/Qualifiers
misc_feature         1..20
                     note = Synthetic
source               1..20
                     mol_type = other RNA
                     organism = synthetic construct
SEQUENCE: 318
gcctcgcgta gttgactggc                                                     20

SEQ ID NO: 319       moltype = RNA   length = 20
FEATURE              Location/Qualifiers
misc_feature         1..20
                     note = Synthetic
source               1..20
                     mol_type = other RNA
                     organism = synthetic construct
SEQUENCE: 319
ccagcaggat gttgtcgggt                                                     20

SEQ ID NO: 320       moltype = RNA   length = 20
FEATURE              Location/Qualifiers
misc_feature         1..20
                     note = Synthetic
source               1..20
                     mol_type = other RNA
                     organism = synthetic construct
SEQUENCE: 320
gtagttgact ggcgaagttc                                                     20

SEQ ID NO: 321       moltype = RNA   length = 20
FEATURE              Location/Qualifiers
misc_feature         1..20
                     note = Synthetic
source               1..20
                     mol_type = other RNA
                     organism = synthetic construct
SEQUENCE: 321
tgcggatggc ctccatctcc                                                     20

SEQ ID NO: 322       moltype = RNA   length = 20
FEATURE              Location/Qualifiers
misc_feature         1..20
                     note = Synthetic
source               1..20
                     mol_type = other RNA
                     organism = synthetic construct
SEQUENCE: 322
acaatctccg ccaggtagaa                                                     20

SEQ ID NO: 323       moltype = RNA   length = 20
FEATURE              Location/Qualifiers
misc_feature         1..20
                     note = Synthetic
source               1..20
                     mol_type = other RNA
                     organism = synthetic construct
SEQUENCE: 323
gcgaatacac ccagcgccca                                                     20
```

```
SEQ ID NO: 324          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 324
gtagttctca tcctggaagg                                                    20

SEQ ID NO: 325          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 325
ggctcaggct ctgccgggtg                                                    20

SEQ ID NO: 326          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 326
ccattcacca acacgtccct                                                    20

SEQ ID NO: 327          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 327
accaggtaca ggtagttctc                                                    20

SEQ ID NO: 328          moltype = DNA   length = 20
FEATURE                 Location/Qualifiers
misc_feature            1..20
                        note = Synthetic
source                  1..20
                        mol_type = other DNA
                        organism = synthetic construct
modified_base           7..9
                        mod_base = OTHER
                        note = Uracil
modified_base           15
                        mod_base = OTHER
                        note = Uracil
SEQUENCE: 328
ctgcagtttg cccatccacg                                                    20

SEQ ID NO: 329          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 329
ttgttcatga tcttcatggc                                                    20

SEQ ID NO: 330          moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 330
ttgatgtccc tgtgcacgt                                                     19

SEQ ID NO: 331          moltype = RNA   length = 20
FEATURE                 Location/Qualifiers
misc_feature            1..20
```

```
                    note = Synthetic
source              1..20
                    mol_type = other RNA
                    organism = synthetic construct
SEQUENCE: 331
gcggtccagc aggatgttgt                                                20

SEQ ID NO: 332      moltype = RNA   length = 20
FEATURE             Location/Qualifiers
misc_feature        1..20
                    note = Synthetic
source              1..20
                    mol_type = other RNA
                    organism = synthetic construct
SEQUENCE: 332
gtctatggcc atgacaatct                                                20

SEQ ID NO: 333      moltype = RNA   length = 20
FEATURE             Location/Qualifiers
misc_feature        1..20
                    note = Synthetic
source              1..20
                    mol_type = other RNA
                    organism = synthetic construct
SEQUENCE: 333
ggagcaggga aagcgcctcc                                                20

SEQ ID NO: 334      moltype = RNA   length = 20
FEATURE             Location/Qualifiers
misc_feature        1..20
                    note = Synthetic
source              1..20
                    mol_type = other RNA
                    organism = synthetic construct
SEQUENCE: 334
tgcctcgcgt agttgactgg                                                20

SEQ ID NO: 335      moltype = RNA   length = 20
FEATURE             Location/Qualifiers
misc_feature        1..20
                    note = Synthetic
source              1..20
                    mol_type = other RNA
                    organism = synthetic construct
SEQUENCE: 335
gcggatggcc tccatctccc                                                20

SEQ ID NO: 336      moltype = RNA   length = 20
FEATURE             Location/Qualifiers
misc_feature        1..20
                    note = Synthetic
source              1..20
                    mol_type = other RNA
                    organism = synthetic construct
SEQUENCE: 336
tttcataggc gaatacaccc                                                20

SEQ ID NO: 337      moltype = RNA   length = 20
FEATURE             Location/Qualifiers
misc_feature        1..20
                    note = Synthetic
source              1..20
                    mol_type = other RNA
                    organism = synthetic construct
SEQUENCE: 337
gcctgtcagc gagtcggagg                                                20

SEQ ID NO: 338      moltype = RNA   length = 20
FEATURE             Location/Qualifiers
misc_feature        1..20
                    note = Synthetic
source              1..20
                    mol_type = other RNA
                    organism = synthetic construct
SEQUENCE: 338
ccacttcagc tgtttcatcc                                                20

SEQ ID NO: 339      moltype = RNA   length = 20
FEATURE             Location/Qualifiers
```

```
misc_feature                1..20
                            note = Synthetic
source                      1..20
                            mol_type = other RNA
                            organism = synthetic construct
SEQUENCE: 339
catccgctcc tgcaactgcc                                                    20

SEQ ID NO: 340              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 340
tctagggttc agggagcgcg                                                    20

SEQ ID NO: 341              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 341
caccaacacg tccctctcct                                                    20

SEQ ID NO: 342              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 342
caggagcagg gaaagcgcct                                                    20

SEQ ID NO: 343              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 343
caatctccgc caggtagaag                                                    20

SEQ ID NO: 344              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 344
atgttgtcgg gtttgatgtc                                                    20

SEQ ID NO: 345              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 345
ccatccgctc ctgcaactgc                                                    20

SEQ ID NO: 346              moltype = RNA  length = 20
FEATURE                     Location/Qualifiers
misc_feature                1..20
                            note = Synthetic
source                      1..20
                            mol_type = other RNA
                            organism = synthetic construct
SEQUENCE: 346
gcgtcacctc ggcctcagcc                                                    20

SEQ ID NO: 347              moltype = RNA  length = 20
```

```
FEATURE                 Location/Qualifiers
misc_feature            1..20
                        note = Synthetic
source                  1..20
                        mol_type = other RNA
                        organism = synthetic construct
SEQUENCE: 347
gagggccttt tattcgcgag                                                         20

SEQ ID NO: 348          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 348
agcggcagag agaggtgctc                                                         20

SEQ ID NO: 349          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 349
catccaaaac gtggattggg                                                         20

SEQ ID NO: 350          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 350
ttgggcagat ggagggcctt                                                         20

SEQ ID NO: 351          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 351
cctctgcctc gcgtagttga                                                         20

SEQ ID NO: 352          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 352
acagaacaac ggcgaacagg                                                         20

SEQ ID NO: 353          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 353
caggatgttg tcgggtttga                                                         20

SEQ ID NO: 354          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 354
cggcctcagc ctctgccgca                                                         20
```

| | | |
|---|---|---|
| SEQ ID NO: 355<br>FEATURE<br>misc_feature<br><br>source<br><br><br>SEQUENCE: 355<br>cagcaggatg ttgtcgggtt | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 356<br>FEATURE<br>misc_feature<br><br>source<br><br><br>SEQUENCE: 356<br>gcagagagag gtgctccttg | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 357<br>FEATURE<br>misc_feature<br><br>source<br><br><br>SEQUENCE: 357<br>tccagttcca tgggtgtggg | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 358<br>FEATURE<br>misc_feature<br><br>source<br><br><br>SEQUENCE: 358<br>cctcagcctg gccgaaagaa | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 359<br>FEATURE<br>misc_feature<br><br>source<br><br><br>SEQUENCE: 359<br>gggcctttta ttcgcgaggg | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 360<br>FEATURE<br>misc_feature<br><br>source<br><br><br>SEQUENCE: 360<br>gtcggccagg cggatgtggc | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 361<br>FEATURE<br>misc_feature<br><br>source<br><br><br>SEQUENCE: 361<br>gcttgctgcc ttcccaggcc | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |
| SEQ ID NO: 362<br>FEATURE<br>misc_feature<br><br>source<br><br><br>SEQUENCE: 362<br>ggtccagcag gatgttgtcg | moltype = RNA   length = 20<br>Location/Qualifiers<br>1..20<br>note = Synthetic<br>1..20<br>mol_type = other RNA<br>organism = synthetic construct<br><br> | <br><br><br><br><br><br><br><br>20 |

```
SEQ ID NO: 363         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 363
cggagaccat cccagtcgag                                                  20

SEQ ID NO: 364         moltype = RNA   length = 19
FEATURE                Location/Qualifiers
misc_feature           1..19
                       note = Synthetic
source                 1..19
                       mol_type = other RNA
                       organism = synthetic construct
SEQUENCE: 364
tctgcctcgc gtagtgact                                                   19

SEQ ID NO: 365         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 365
aggtagttct catcctggaa                                                  20

SEQ ID NO: 366         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 366
tccttgtagt ggacgatctt                                                  20

SEQ ID NO: 367         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 367
gcatccaaaa cgtggattgg                                                  20

SEQ ID NO: 368         moltype = RNA   length = 19
FEATURE                Location/Qualifiers
misc_feature           1..19
                       note = Synthetic
source                 1..19
                       mol_type = other RNA
                       organism = synthetic construct
SEQUENCE: 368
gtccagcagg atgtgtcgg                                                   19

SEQ ID NO: 369         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 369
agctcccgca gcgtcacctc                                                  20

SEQ ID NO: 370         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 370
```
cgagagcagc gcaagtgagg                                                20

SEQ ID NO: 371          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 371
cagggaaagc gcctccgata                                                20

SEQ ID NO: 372          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 372
atttcatagg cgaatacacc                                                20

SEQ ID NO: 373          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 373
tcggccaggc ggatgtggcc                                                20

SEQ ID NO: 374          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 374
aagggatgtg tccggaagtc                                                20

SEQ ID NO: 375          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 375
cttgtagtgg acgatcttgc                                                20

SEQ ID NO: 376          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 376
agtcggccag gcggatgtgg                                                20

SEQ ID NO: 377          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 377
gcctcagcct ggccgaaaga                                                20

SEQ ID NO: 378          moltype = RNA   length = 20
FEATURE                 Location/Qualifiers
misc_feature            1..20
                        note = Synthetic
source                  1..20
                        mol_type = other RNA
                        organism = synthetic construct -continued

| | | |
|---|---|---|
| SEQUENCE: 378 | | |
| agcgtcacct cggcctcagc | | 20 |
| | | |
| SEQ ID NO: 379 | moltype = DNA length = 20 | |
| FEATURE | Location/Qualifiers | |
| misc_feature | 1..20 | |
| | note = Synthetic | |
| source | 1..20 | |
| | mol_type = other DNA | |
| | organism = synthetic construct | |
| modified_base | 17 | |
| | mod_base = OTHER | |
| | note = Uracil | |
| SEQUENCE: 379 | | |
| cagcggcaga gagaggtgct | | 20 |
| | | |
| SEQ ID NO: 380 | moltype = RNA length = 20 | |
| FEATURE | Location/Qualifiers | |
| misc_feature | 1..20 | |
| | note = Synthetic | |
| source | 1..20 | |
| | mol_type = other RNA | |
| | organism = synthetic construct | |
| SEQUENCE: 380 | | |
| ccagcggcag agagaggtgc | | 20 |
| | | |
| SEQ ID NO: 381 | moltype = RNA length = 20 | |
| FEATURE | Location/Qualifiers | |
| misc_feature | 1..20 | |
| | note = Synthetic | |
| source | 1..20 | |
| | mol_type = other RNA | |
| | organism = synthetic construct | |
| SEQUENCE: 381 | | |
| ttgtagtgga cgatcttgcc | | 20 |
| | | |
| SEQ ID NO: 382 | moltype = RNA length = 20 | |
| FEATURE | Location/Qualifiers | |
| misc_feature | 1..20 | |
| | note = Synthetic | |
| source | 1..20 | |
| | mol_type = other RNA | |
| | organism = synthetic construct | |
| SEQUENCE: 382 | | |
| agggaaagcg cctccgatag | | 20 |
| | | |
| SEQ ID NO: 383 | moltype = RNA length = 20 | |
| FEATURE | Location/Qualifiers | |
| misc_feature | 1..20 | |
| | note = Synthetic | |
| source | 1..20 | |
| | mol_type = other RNA | |
| | organism = synthetic construct | |
| SEQUENCE: 383 | | |
| gggaaagcgc ctccgatagg | | 20 |
| | | |
| SEQ ID NO: 384 | moltype = DNA length = 20 | |
| FEATURE | Location/Qualifiers | |
| misc_feature | 1..20 | |
| | note = Synthetic | |
| source | 1..20 | |
| | mol_type = other DNA | |
| | organism = synthetic construct | |
| SEQUENCE: 384 | | |
| ggcagcaagc cgggccgtcc | | 20 |
| | | |
| SEQ ID NO: 385 | moltype = DNA length = 20 | |
| FEATURE | Location/Qualifiers | |
| misc_feature | 1..20 | |
| | note = Synthetic | |
| source | 1..20 | |
| | mol_type = other DNA | |
| | organism = synthetic construct | |
| SEQUENCE: 385 | | |
| cagtcctgtg atccgggccc | | 20 |
| | | |
| SEQ ID NO: 386 | moltype = DNA length = 20 | |
| FEATURE | Location/Qualifiers | |
| misc_feature | 1..20 | |

```
                    note = Synthetic
source              1..20
                    mol_type = other DNA
                    organism = synthetic construct
SEQUENCE: 386
gacactgctg agcaagtttg                                               20

SEQ ID NO: 387      moltype = DNA   length = 20
FEATURE             Location/Qualifiers
misc_feature        1..20
                    note = Synthetic
source              1..20
                    mol_type = other DNA
                    organism = synthetic construct
SEQUENCE: 387
tgacactgct gagcaagttt                                               20

SEQ ID NO: 388      moltype = DNA   length = 20
FEATURE             Location/Qualifiers
misc_feature        1..20
                    note = Synthetic
source              1..20
                    mol_type = other DNA
                    organism = synthetic construct
SEQUENCE: 388
cgggagatgg aggccatccg                                               20

SEQ ID NO: 389      moltype = DNA   length = 20
FEATURE             Location/Qualifiers
misc_feature        1..20
                    note = Synthetic
source              1..20
                    mol_type = other DNA
                    organism = synthetic construct
SEQUENCE: 389
gggagcggat tccggccgag                                               20

SEQ ID NO: 390      moltype = DNA   length = 20
FEATURE             Location/Qualifiers
misc_feature        1..20
                    note = Synthetic
source              1..20
                    mol_type = other DNA
                    organism = synthetic construct
SEQUENCE: 390
ggagcggatt ccggccgaga                                               20

SEQ ID NO: 391      moltype = DNA   length = 20
FEATURE             Location/Qualifiers
misc_feature        1..20
                    note = Synthetic
source              1..20
                    mol_type = other DNA
                    organism = synthetic construct
SEQUENCE: 391
cctgctgaca ctgctgagca                                               20

SEQ ID NO: 392      moltype = DNA   length = 20
FEATURE             Location/Qualifiers
misc_feature        1..20
                    note = Synthetic
source              1..20
                    mol_type = other DNA
                    organism = synthetic construct
SEQUENCE: 392
agggacatca aacccgacaa                                               20

SEQ ID NO: 393      moltype = DNA   length = 20
FEATURE             Location/Qualifiers
misc_feature        1..20
                    note = Synthetic
source              1..20
                    mol_type = other DNA
                    organism = synthetic construct
SEQUENCE: 393
gggacatcaa acccgacaac                                               20

SEQ ID NO: 394      moltype = DNA   length = 20
FEATURE             Location/Qualifiers
```

```
misc_feature                 1..20
                             note = Synthetic
source                       1..20
                             mol_type = other DNA
                             organism = synthetic construct
SEQUENCE: 394
gcgcgcttct acctggcgga                                                    20

SEQ ID NO: 395               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 395
cgggccaggt gtatgccatg                                                    20

SEQ ID NO: 396               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 396
ctgacactgc tgagcaagtt                                                    20

SEQ ID NO: 397               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 397
ggcggtggat cacgcagctg                                                    20

SEQ ID NO: 398               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 398
gagacactgt cggacattcg                                                    20

SEQ ID NO: 399               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 399
acatccgcct ggccgacttc                                                    20

SEQ ID NO: 400               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 400
cagggacatc aaacccgaca                                                    20

SEQ ID NO: 401               moltype = DNA  length = 20
FEATURE                      Location/Qualifiers
misc_feature                 1..20
                             note = Synthetic
source                       1..20
                             mol_type = other DNA
                             organism = synthetic construct
SEQUENCE: 401
ccgggagatg gaggccatcc                                                    20

SEQ ID NO: 402               moltype = DNA  length = 20
```

```
FEATURE                 Location/Qualifiers
misc_feature            1..20
                        note = Synthetic
source                  1..20
                        mol_type = other DNA
                        organism = synthetic construct
SEQUENCE: 402
atcaaacccg acaacatcct                                                         20

SEQ ID NO: 403          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 403
acagggacat caaacccgac                                                         20

SEQ ID NO: 404          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 404
gtacctggtc atggagtatt                                                         20

SEQ ID NO: 405          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 405
ccatgaagat catgaacaag                                                         20

SEQ ID NO: 406          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 406
ccacgttttg gatgcactga                                                         20

SEQ ID NO: 407          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 407
tgggatggtc tccgggacag                                                         20

SEQ ID NO: 408          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 408
gacagtgagg tcccaggccc                                                         20

SEQ ID NO: 409          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 409
gtcatggagt attacgtggg                                                         20
```

```
SEQ ID NO: 410          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 410
cggctgtccc tgcggcagag                                                    20

SEQ ID NO: 411          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 411
cggcttggct acgtgcacag                                                    20

SEQ ID NO: 412          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 412
ggccctgacg tggatgggca                                                    20

SEQ ID NO: 413          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 413
cctggcctat cggaggcgct                                                    20

SEQ ID NO: 414          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 414
ccggcttggc tacgtgcaca                                                    20

SEQ ID NO: 415          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 415
agaactacct gtacctggtc                                                    20

SEQ ID NO: 416          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 416
gcggattccg gccgagatgg                                                    20

SEQ ID NO: 417          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 417
agcggattcc ggccgagatg                                                    20
```

| | | |
|---|---|---|
| SEQ ID NO: 418<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 418<br>acggcggaga cctatggcaa | | 20 |
| SEQ ID NO: 419<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 419<br>acatcctgct ggaccgctgt | | 20 |
| SEQ ID NO: 420<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 420<br>tggcctatcg gaggcgcttt | | 20 |
| SEQ ID NO: 421<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 421<br>cacatccctt cttctttggc | | 20 |
| SEQ ID NO: 422<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 422<br>tggtcatgga gtattacgtg | | 20 |
| SEQ ID NO: 423<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 423<br>gagcggattc cggccgagat | | 20 |
| SEQ ID NO: 424<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 424<br>agcggtagtg aagatgaagc | | 20 |
| SEQ ID NO: 425<br>FEATURE<br>misc_feature<br><br>source | moltype = DNA length = 20<br>Location/Qualifiers<br>1..20<br>note = Synthetic<br>1..20<br>mol_type = other DNA<br>organism = synthetic construct | |
| SEQUENCE: 425 | | | cggattccgg ccgagatggc                                               20

SEQ ID NO: 426          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 426
agttccagcg gctgtccctg                                               20

SEQ ID NO: 427          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 427
tacctggcgg agattgtcat                                               20

SEQ ID NO: 428          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 428
tggcggagat tgtcatggcc                                               20

SEQ ID NO: 429          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 429
tgtacctggt catggagtat                                               20

SEQ ID NO: 430          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 430
caactacgcg aggcagaggc                                               20

SEQ ID NO: 431          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 431
ggagacactg tcggacattc                                               20

SEQ ID NO: 432          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 432
agctgcgggc agatggaacg                                               20

SEQ ID NO: 433          moltype = DNA   length = 20
FEATURE                 Location/Qualifiers
misc_feature            1..20
                        note = Synthetic
source                  1..20
                        mol_type = other DNA
                        organism = synthetic construct -continued

```
SEQUENCE: 433
caagatcgtc cactacaagg                                               20

SEQ ID NO: 434           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 434
cgcttctacc tggcggagat                                               20

SEQ ID NO: 435           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 435
ctcacccggc agagcctgag                                               20

SEQ ID NO: 436           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 436
gcggtagtga agatgaagca                                               20

SEQ ID NO: 437           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 437
caaacccgac aacatcctgc                                               20

SEQ ID NO: 438           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 438
ctgcggcaga ggctgaggcc                                               20

SEQ ID NO: 439           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 439
ggacatcaaa cccgacaaca                                               20

SEQ ID NO: 440           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 440
ggtcatggag tattacgtgg                                               20

SEQ ID NO: 441           moltype = DNA  length = 20
FEATURE                  Location/Qualifiers
misc_feature             1..20
                         note = Synthetic
source                   1..20
                         mol_type = other DNA
```

```
                               -continued

SEQUENCE: 441
gctgcgggca gatggaacgg                                               20

SEQ ID NO: 442          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 442
tctgcctgct tactcgggaa                                               20

SEQ ID NO: 443          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 443
ggtgtatgcc atgaagatca                                               20

SEQ ID NO: 444          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 444
cagttccagc ggctgtccct                                               20

SEQ ID NO: 445          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 445
tgcacaggga catcaaaccc                                               20

SEQ ID NO: 446          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 446
ctacctggcg gagattgtca                                               20

SEQ ID NO: 447          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 447
catcctgctg gaccgctgtg                                               20

SEQ ID NO: 448          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 448
gggcagacgc ccttctacgc                                               20

SEQ ID NO: 449          moltype = DNA  length = 20
FEATURE                 Location/Qualifiers
misc_feature            1..20
                        note = Synthetic
source                  1..20
```

```
                         mol_type = other DNA
                         organism = synthetic construct
SEQUENCE: 449
tccctgcggc agaggctgag                                             20

SEQ ID NO: 450           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 450
cgttttggat gcactgagac                                             20

SEQ ID NO: 451           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 451
gacctatggc aagatcgtcc                                             20

SEQ ID NO: 452           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 452
ggacctgctg acactgctga                                             20

SEQ ID NO: 453           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 453
gtctggcgcc gcccaggagc                                             20

SEQ ID NO: 454           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 454
aaacccgaca acatcctgct                                             20

SEQ ID NO: 455           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 455
cggcagttgc aggagcggat                                             20

SEQ ID NO: 456           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 456
gaggcgcttt ccctgctcct                                             20

SEQ ID NO: 457           moltype = DNA   length = 20
FEATURE                  Location/Qualifiers
misc_feature             1..20
                         note = Synthetic
```

```
                                   -continued source              1..20
                    mol_type = other DNA
                    organism = synthetic construct
SEQUENCE: 457
gaagcagacg ggccaggtgt                                                   20

SEQ ID NO: 458      moltype = DNA  length = 20
FEATURE             Location/Qualifiers
misc_feature        1..20
                    note = Synthetic
source              1..20
                    mol_type = other DNA
                    organism = synthetic construct
SEQUENCE: 458
tgtgactggt gggcgctggg                                                   20

SEQ ID NO: 459      moltype = DNA  length = 20
FEATURE             Location/Qualifiers
misc_feature        1..20
                    note = Synthetic
source              1..20
                    mol_type = other DNA
                    organism = synthetic construct
SEQUENCE: 459
ttgctgcagg cagagggagc                                                   20

SEQ ID NO: 460      moltype = DNA  length = 20
FEATURE             Location/Qualifiers
misc_feature        1..20
                    note = Synthetic
source              1..20
                    mol_type = other DNA
                    organism = synthetic construct
SEQUENCE: 460
tcacccggca gagcctgagc                                                   20

SEQ ID NO: 461      moltype = DNA  length = 20
FEATURE             Location/Qualifiers
misc_feature        1..20
                    note = Synthetic
source              1..20
                    mol_type = other DNA
                    organism = synthetic construct
SEQUENCE: 461
tacgtgcaca gggacatcaa                                                   20

SEQ ID NO: 462      moltype = DNA  length = 20
FEATURE             Location/Qualifiers
misc_feature        1..20
                    note = Synthetic
source              1..20
                    mol_type = other DNA
                    organism = synthetic construct
SEQUENCE: 462
cctgcggcag aggctgaggc                                                   20

SEQ ID NO: 463      moltype = DNA  length = 20
FEATURE             Location/Qualifiers
misc_feature        1..20
                    note = Synthetic
source              1..20
                    mol_type = other DNA
                    organism = synthetic construct
SEQUENCE: 463
cttccaggat gagaactacc                                                   20

SEQ ID NO: 464      moltype = DNA  length = 20
FEATURE             Location/Qualifiers
misc_feature        1..20
                    note = Synthetic
source              1..20
                    mol_type = other DNA
                    organism = synthetic construct
SEQUENCE: 464
agtgtgactg gtgggcgctg                                                   20

SEQ ID NO: 465      moltype = DNA  length = 20
FEATURE             Location/Qualifiers
misc_feature        1..20
```

```
                    note = Synthetic
source              1..20
                    mol_type = other DNA
                    organism = synthetic construct
SEQUENCE: 465
cactgctgag caagtttggg                                              20

SEQ ID NO: 466      moltype = DNA  length = 20
FEATURE             Location/Qualifiers
misc_feature        1..20
                    note = Synthetic
source              1..20
                    mol_type = other DNA
                    organism = synthetic construct
SEQUENCE: 466
cggcggagac ctatggcaag                                              20

SEQ ID NO: 467      moltype = DNA  length = 20
FEATURE             Location/Qualifiers
misc_feature        1..20
                    note = Synthetic
source              1..20
                    mol_type = other DNA
                    organism = synthetic construct
SEQUENCE: 467
aagcagacgg gccaggtgta                                              20

SEQ ID NO: 468      moltype = DNA  length = 20
FEATURE             Location/Qualifiers
misc_feature        1..20
                    note = Synthetic
source              1..20
                    mol_type = other DNA
                    organism = synthetic construct
SEQUENCE: 468
gtgtgactgg tgggcgctgg                                              20

SEQ ID NO: 469      moltype = DNA  length = 20
FEATURE             Location/Qualifiers
misc_feature        1..20
                    note = Synthetic
source              1..20
                    mol_type = other DNA
                    organism = synthetic construct
SEQUENCE: 469
ctttcggcca ggctgaggcc                                              20

SEQ ID NO: 470      moltype = DNA  length = 20
FEATURE             Location/Qualifiers
misc_feature        1..20
                    note = Synthetic
source              1..20
                    mol_type = other DNA
                    organism = synthetic construct
SEQUENCE: 470
gcttctacct ggcggagatt                                              20

SEQ ID NO: 471      moltype = DNA  length = 20
FEATURE             Location/Qualifiers
misc_feature        1..20
                    note = Synthetic
source              1..20
                    mol_type = other DNA
                    organism = synthetic construct
SEQUENCE: 471
acgggccagg tgtatgccat                                              20

SEQ ID NO: 472      moltype = DNA  length = 20
FEATURE             Location/Qualifiers
misc_feature        1..20
                    note = Synthetic
source              1..20
                    mol_type = other DNA
                    organism = synthetic construct
SEQUENCE: 472
cctggcggag attgtcatgg                                              20

SEQ ID NO: 473      moltype = DNA  length = 20
FEATURE             Location/Qualifiers
```

```
misc_feature           1..20
                       note = Synthetic
source                 1..20
                       mol_type = other DNA
                       organism = synthetic construct
SEQUENCE: 473
ctgctgagca agtttgggga                                                   20

SEQ ID NO: 474         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 474
acatcaaacc cgacaacatc                                                   20

SEQ ID NO: 475         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 475
cctgacgtgg atgggcaaac                                                   20

SEQ ID NO: 476         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 476
gcagcaagcc gggccgtccg                                                   20

SEQ ID NO: 477         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 477
cgcgcttcta cctggcggag                                                   20

SEQ ID NO: 478         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 478
aggatgagaa ctacctgtac                                                   20

SEQ ID NO: 479         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 479
gttctatggg cagacgccct                                                   20

SEQ ID NO: 480         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 480
ctgctggacc gctgtggcca                                                   20

SEQ ID NO: 481         moltype = DNA  length = 20
```

```
FEATURE                 Location/Qualifiers
misc_feature            1..20
                        note = Synthetic
source                  1..20
                        mol_type = other DNA
                        organism = synthetic construct
SEQUENCE: 481
aacttcgcca gtcaactacg                                                        20

SEQ ID NO: 482          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 482
gcggctgtcc ctgcggcaga                                                        20

SEQ ID NO: 483          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 483
ctggcctatc ggaggcgctt                                                        20

SEQ ID NO: 484          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 484
ctgttcgccg ttgttctgtc                                                        20

SEQ ID NO: 485          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 485
acctgctgac actgctgagc                                                        20

SEQ ID NO: 486          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 486
gtgtatgcca tgaagatcat                                                        20

SEQ ID NO: 487          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 487
ccctgacgtg gatgggcaaa                                                        20

SEQ ID NO: 488          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 488
gctgacactg ctgagcaagt                                                        20
```

| | |
|---|---|
| SEQ ID NO: 489<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 489<br>ctacgtgcac agggacatca | 20 |
| SEQ ID NO: 490<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 490<br>cccgacattc ctcggtattt | 20 |
| SEQ ID NO: 491<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 491<br>gggcgctggg tgtattcgcc | 20 |
| SEQ ID NO: 492<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 492<br>ttcctcggta tttattgtct | 20 |
| SEQ ID NO: 493<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 493<br>gtgaagatga agcagacggg | 20 |
| SEQ ID NO: 494<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 494<br>gatggagttg ctgcaggcag | 20 |
| SEQ ID NO: 495<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 495<br>ccctgcggca gaggctgagg | 20 |
| SEQ ID NO: 496<br>FEATURE<br>misc_feature<br>source | moltype = DNA length = 20<br>Location/Qualifiers<br>1..20<br>note = Synthetic<br>1..20<br>mol_type = other DNA<br>organism = synthetic construct |
| SEQUENCE: 496<br>agcaggcgac ttccggacac | 20 |

```
SEQ ID NO: 497              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 497
ctgcttgagc cacacgtgca                                                         20

SEQ ID NO: 498              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 498
attcctcggt atttattgtc                                                         20

SEQ ID NO: 499              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 499
ctggcggaga ttgtcatggc                                                         20

SEQ ID NO: 500              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 500
gggatggtct ccgggacagc                                                         20

SEQ ID NO: 501              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 501
actacctgta cctggtcatg                                                         20

SEQ ID NO: 502              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 502
gagtgtgact ggtgggcgct                                                         20

SEQ ID NO: 503              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 503
acgttttgga tgcactgaga                                                         20

SEQ ID NO: 504              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 504
```
aggccctcca tctgcccaaa                                                    20

SEQ ID NO: 505          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 505
gctacgtgca cagggacatc                                                    20

SEQ ID NO: 506          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 506
gggacctgct gacactgctg                                                    20

SEQ ID NO: 507          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 507
acctggcgga gattgtcatg                                                    20

SEQ ID NO: 508          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 508
catgaagatc atgaacaagt                                                    20

SEQ ID NO: 509          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 509
cccttctacg cggattccac                                                    20

SEQ ID NO: 510          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 510
ggcggagatt gtcatggcca                                                    20

SEQ ID NO: 511          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 511
cggtatttat tgtctgtccc                                                    20

SEQ ID NO: 512          moltype = DNA   length = 20
FEATURE                 Location/Qualifiers
misc_feature            1..20
                        note = Synthetic
source                  1..20
                        mol_type = other DNA
                        organism = synthetic construct

| | | |
|---|---|---|
| SEQUENCE: 512 tgagcaagtt tggggagcgg | | 20 |
| SEQ ID NO: 513 FEATURE misc_feature source | moltype = DNA length = 20 Location/Qualifiers 1..20 note = Synthetic 1..20 mol_type = other DNA organism = synthetic construct | |
| SEQUENCE: 513 acccggcaga gcctgagccg | | 20 |
| SEQ ID NO: 514 FEATURE misc_feature source | moltype = DNA length = 20 Location/Qualifiers 1..20 note = Synthetic 1..20 mol_type = other DNA organism = synthetic construct | |
| SEQUENCE: 514 tctggcgccg cccaggagcc | | 20 |
| SEQ ID NO: 515 FEATURE misc_feature source | moltype = DNA length = 20 Location/Qualifiers 1..20 note = Synthetic 1..20 mol_type = other DNA organism = synthetic construct | |
| SEQUENCE: 515 ctgcctgctt actcgggaaa | | 20 |
| SEQ ID NO: 516 FEATURE misc_feature source | moltype = DNA length = 20 Location/Qualifiers 1..20 note = Synthetic 1..20 mol_type = other DNA organism = synthetic construct | |
| SEQUENCE: 516 catcaaaccc gacaacatcc | | 20 |
| SEQ ID NO: 517 FEATURE misc_feature source | moltype = DNA length = 20 Location/Qualifiers 1..20 note = Synthetic 1..20 mol_type = other DNA organism = synthetic construct | |
| SEQUENCE: 517 tccaggatga gaactacctg | | 20 |
| SEQ ID NO: 518 FEATURE misc_feature source | moltype = DNA length = 20 Location/Qualifiers 1..20 note = Synthetic 1..20 mol_type = other DNA organism = synthetic construct | |
| SEQUENCE: 518 tatgaaatgt tctatgggca | | 20 |
| SEQ ID NO: 519 FEATURE misc_feature source | moltype = DNA length = 20 Location/Qualifiers 1..20 note = Synthetic 1..20 mol_type = other DNA organism = synthetic construct | |
| SEQUENCE: 519 gccttccagg atgagaacta | | 20 |
| SEQ ID NO: 520 FEATURE misc_feature source | moltype = DNA length = 20 Location/Qualifiers 1..20 note = Synthetic 1..20 mol_type = other DNA | |

-continued

```
                          organism = synthetic construct
SEQUENCE: 520
ggctacgtgc acagggacat                                                       20

SEQ ID NO: 521            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 521
agtcctgtga tccgggcccg                                                       20

SEQ ID NO: 522            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 522
acctatggca agatcgtcca                                                       20

SEQ ID NO: 523            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 523
ggtggcccac gccggccaac                                                       20

SEQ ID NO: 524            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 524
cacgttttgg atgcactgag                                                       20

SEQ ID NO: 525            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 525
accgacacat gcaacttcga                                                       20

SEQ ID NO: 526            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 526
gccgggccgt ccgtgttcca                                                       20

SEQ ID NO: 527            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 527
ctcacttgcg ctgctctcgg                                                       20

SEQ ID NO: 528            moltype = DNA  length = 20
FEATURE                   Location/Qualifiers
misc_feature              1..20
                          note = Synthetic
source                    1..20
```

```
                            mol_type = other DNA
                            organism = synthetic construct
SEQUENCE: 528
cacgtccggc agttgcagga                                                    20

SEQ ID NO: 529              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 529
ggagagggac gtgttggtga                                                    20

SEQ ID NO: 530              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 530
ggatggagtt gctgcaggca                                                    20

SEQ ID NO: 531              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 531
tggtggccca cgccggccaa                                                    20

SEQ ID NO: 532              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 532
actacgcgag gcagaggctc                                                    20

SEQ ID NO: 533              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 533
ttctatgggc agacgcccTT                                                    20

SEQ ID NO: 534              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 534
cctcggtatt tattgtctgt                                                    20

SEQ ID NO: 535              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 535
tcggtattta ttgtctgtcc                                                    20

SEQ ID NO: 536              moltype = DNA   length = 20
FEATURE                     Location/Qualifiers
misc_feature                1..20
                            note = Synthetic
```

| | | |
|---|---|---|
| source | 1..20<br>mol_type = other DNA<br>organism = synthetic construct | |
| SEQUENCE: 536<br>cgggacctag aggcacacgt | | 20 |
| SEQ ID NO: 537<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 537<br>ccgttgttct gtctcgtgcc | | 20 |
| SEQ ID NO: 538<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 538<br>gaactacctg tacctggtca | | 20 |
| SEQ ID NO: 539<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 539<br>gaggtgctca cccggcagag | | 20 |
| SEQ ID NO: 540<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 540<br>tctacctggc ggagattgtc | | 20 |
| SEQ ID NO: 541<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 541<br>gcgcttctac ctggcggaga | | 20 |
| SEQ ID NO: 542<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 542<br>gtcaactacg cgaggcagag | | 20 |
| SEQ ID NO: 543<br>FEATURE<br>misc_feature<br>source | moltype = DNA  length = 20<br>Location/Qualifiers<br>1..20<br>note = Synthetic<br>1..20<br>mol_type = other DNA<br>organism = synthetic construct | |
| SEQUENCE: 543<br>ggccctccat ctgcccaaag | | 20 |
| SEQ ID NO: 544<br>FEATURE<br>misc_feature | moltype = DNA  length = 20<br>Location/Qualifiers<br>1..20 | |

```
                          note = Synthetic
source                    1..20
                          mol_type = other DNA
                          organism = synthetic construct
SEQUENCE: 544
ccaggatgag aactacctgt                                                    20

SEQ ID NO: 545            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 545
acactgctga gcaagtttgg                                                    20

SEQ ID NO: 546            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 546
cacagggaca tcaaacccga                                                    20

SEQ ID NO: 547            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 547
gcctgggaag gcagcaagcc                                                    20

SEQ ID NO: 548            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 548
caggatgaga actacctgta                                                    20

SEQ ID NO: 549            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 549
gccctgacgt ggatgggcaa                                                    20

SEQ ID NO: 550            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 550
gatgagaact acctgtacct                                                    20

SEQ ID NO: 551            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 551
ctcggtattt attgtctgtc                                                    20

SEQ ID NO: 552            moltype = DNA  length = 20
FEATURE                   Location/Qualifiers
```

```
misc_feature               1..20
                           note = Synthetic
source                     1..20
                           mol_type = other DNA
                           organism = synthetic construct
SEQUENCE: 552
ttcgcctatg aaatgttcta                                                   20

SEQ ID NO: 553             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 553
cctcgcgaat aaaaggccct                                                   20

SEQ ID NO: 554             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 554
gccagtcaac tacgcgaggc                                                   20

SEQ ID NO: 555             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 555
acccgacaac atcctgctgg                                                   20

SEQ ID NO: 556             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 556
gaacttcgcc agtcaactac                                                   20

SEQ ID NO: 557             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 557
ggagatggag gccatccgca                                                   20

SEQ ID NO: 558             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 558
ttctacctgg cggagattgt                                                   20

SEQ ID NO: 559             moltype = DNA  length = 20
FEATURE                    Location/Qualifiers
misc_feature               1..20
                           note = Synthetic
source                     1..20
                           mol_type = other DNA
                           organism = synthetic construct
SEQUENCE: 559
tgggcgctgg gtgtattcgc                                                   20

SEQ ID NO: 560             moltype = DNA  length = 20
```

```
FEATURE               Location/Qualifiers
misc_feature          1..20
                      note = Synthetic
source                1..20
                      mol_type = other DNA
                      organism = synthetic construct
SEQUENCE: 560
ccttccagga tgagaactac                                                    20

SEQ ID NO: 561        moltype = DNA  length = 20
FEATURE               Location/Qualifiers
misc_feature          1..20
                      note = Synthetic
source                1..20
                      mol_type = other DNA
                      organism = synthetic construct
SEQUENCE: 561
cacccggcag agcctgagcc                                                    20

SEQ ID NO: 562        moltype = DNA  length = 20
FEATURE               Location/Qualifiers
misc_feature          1..20
                      note = Synthetic
source                1..20
                      mol_type = other DNA
                      organism = synthetic construct
SEQUENCE: 562
agggacgtgt tggtgaatgg                                                    20

SEQ ID NO: 563        moltype = DNA  length = 20
FEATURE               Location/Qualifiers
misc_feature          1..20
                      note = Synthetic
source                1..20
                      mol_type = other DNA
                      organism = synthetic construct
SEQUENCE: 563
gagaactacc tgtacctggt                                                    20

SEQ ID NO: 564        moltype = DNA  length = 20
FEATURE               Location/Qualifiers
misc_feature          1..20
                      note = Synthetic
source                1..20
                      mol_type = other DNA
                      organism = synthetic construct
SEQUENCE: 564
cgtggatggg caaactgcag                                                    20

SEQ ID NO: 565        moltype = DNA  length = 20
FEATURE               Location/Qualifiers
misc_feature          1..20
                      note = Synthetic
source                1..20
                      mol_type = other DNA
                      organism = synthetic construct
SEQUENCE: 565
gccatgaaga tcatgaacaa                                                    20

SEQ ID NO: 566        moltype = DNA  length = 20
FEATURE               Location/Qualifiers
misc_feature          1..20
                      note = Synthetic
source                1..20
                      mol_type = other DNA
                      organism = synthetic construct
SEQUENCE: 566
acgtgcacag ggacatcaaa                                                    20

SEQ ID NO: 567        moltype = DNA  length = 20
FEATURE               Location/Qualifiers
misc_feature          1..20
                      note = Synthetic
source                1..20
                      mol_type = other DNA
                      organism = synthetic construct
SEQUENCE: 567
acaacatcct gctggaccgc                                                    20
```

```
SEQ ID NO: 568          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 568
agattgtcat ggccatagac                                                   20

SEQ ID NO: 569          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 569
ggaggcgctt tccctgctcc                                                   20

SEQ ID NO: 570          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 570
ccagtcaact acgcgaggca                                                   20

SEQ ID NO: 571          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 571
gggagatgga ggccatccgc                                                   20

SEQ ID NO: 572          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 572
gggtgtattc gcctatgaaa                                                   20

SEQ ID NO: 573          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 573
cctccgactc gctgacaggc                                                   20

SEQ ID NO: 574          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 574
ggatgaaaca gctgaagtgg                                                   20

SEQ ID NO: 575          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 575
ggcagttgca ggagcggatg                                                   20
```

```
SEQ ID NO: 576           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 576
cgcgctccct gaaccctaga                                                     20

SEQ ID NO: 577           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 577
aggagaggga cgtgttggtg                                                     20

SEQ ID NO: 578           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 578
aggcgctttc cctgctcctg                                                     20

SEQ ID NO: 579           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 579
cttctacctg gcggagattg                                                     20

SEQ ID NO: 580           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 580
gacatcaaac ccgacaacat                                                     20

SEQ ID NO: 581           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 581
gcagttgcag gagcggatgg                                                     20

SEQ ID NO: 582           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 582
ggctgaggcc gaggtgacgc                                                     20

SEQ ID NO: 583           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 583
```
ctcgcgaata aaaggccctc                                                   20

SEQ ID NO: 584          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 584
gagcacctct ctctgccgct                                                   20

SEQ ID NO: 585          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 585
cccaatccac gttttggatg                                                   20

SEQ ID NO: 586          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 586
aaggccctcc atctgcccaa                                                   20

SEQ ID NO: 587          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 587
tcaactacgc gaggcagagg                                                   20

SEQ ID NO: 588          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 588
cctgttcgcc gttgttctgt                                                   20

SEQ ID NO: 589          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 589
tcaaacccga caacatcctg                                                   20

SEQ ID NO: 590          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 590
tgcggcagag gctgaggccg                                                   20

SEQ ID NO: 591          moltype = DNA   length = 20
FEATURE                 Location/Qualifiers
misc_feature            1..20
                        note = Synthetic
source                  1..20
                        mol_type = other DNA
                        organism = synthetic construct

```
SEQUENCE: 591
aacccgacaa catcctgctg                                                   20

SEQ ID NO: 592         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 592
caaggagcac ctctctctgc                                                   20

SEQ ID NO: 593         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 593
cccacaccca tggaactgga                                                   20

SEQ ID NO: 594         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 594
ttctttcggc caggctgagg                                                   20

SEQ ID NO: 595         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 595
ccctcgcgaa taaaaggccc                                                   20

SEQ ID NO: 596         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 596
gccacatccg cctggccgac                                                   20

SEQ ID NO: 597         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 597
ggcctgggaa ggcagcaagc                                                   20

SEQ ID NO: 598         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 598
cgacaacatc ctgctggacc                                                   20

SEQ ID NO: 599         moltype = DNA  length = 20
FEATURE                Location/Qualifiers
misc_feature           1..20
                       note = Synthetic
source                 1..20
                       mol_type = other DNA
```

```
                        organism = synthetic construct
SEQUENCE: 599
ctcgactggg atggtctccg                                                   20

SEQ ID NO: 600          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 600
agtcaactac gcgaggcaga                                                   20

SEQ ID NO: 601          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 601
ttccaggatg agaactacct                                                   20

SEQ ID NO: 602          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 602
aagatcgtcc actacaagga                                                   20

SEQ ID NO: 603          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 603
ccaatccacg ttttggatgc                                                   20

SEQ ID NO: 604          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 604
ccgacaacat cctgctggac                                                   20

SEQ ID NO: 605          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 605
gaggtgacgc tgcgggagct                                                   20

SEQ ID NO: 606          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 606
cctcacttgc gctgctctcg                                                   20

SEQ ID NO: 607          moltype = DNA   length = 20
FEATURE                 Location/Qualifiers
misc_feature            1..20
                        note = Synthetic
source                  1..20
```

```
                        mol_type = other DNA
                        organism = synthetic construct
SEQUENCE: 607
tatcggaggc gctttccctg                                                   20

SEQ ID NO: 608          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 608
ggtgtattcg cctatgaaat                                                   20

SEQ ID NO: 609          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 609
ggccacatcc gcctggccga                                                   20

SEQ ID NO: 610          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 610
gacttccgga cacatccctt                                                   20

SEQ ID NO: 611          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 611
gcaagatcgt ccactacaag                                                   20

SEQ ID NO: 612          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 612
ccacatccgc ctggccgact                                                   20

SEQ ID NO: 613          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 613
tctttcggcc aggctgaggc                                                   20

SEQ ID NO: 614          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 614
gctgaggccg aggtgacgct                                                   20

SEQ ID NO: 615          moltype = DNA   length = 20
FEATURE                 Location/Qualifiers
misc_feature            1..20
                        note = Synthetic
```

```
source                  1..20
                        mol_type = other DNA
                        organism = synthetic construct
SEQUENCE: 615
agcacctctc tctgccgctg                                                   20

SEQ ID NO: 616          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 616
gcacctctct ctgccgctgg                                                   20

SEQ ID NO: 617          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 617
ggcaagatcg tccactacaa                                                   20

SEQ ID NO: 618          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 618
ctatcggagg cgctttccct                                                   20

SEQ ID NO: 619          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 619
cctatcggag gcgctttccc                                                   20

SEQ ID NO: 620          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 620
accattttct tccacagggc t                                                 21

SEQ ID NO: 621          moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 621
taggcactca cccactgcaa ga                                                22

SEQ ID NO: 622          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 622
cggagctcac caggtagttc t                                                 21

SEQ ID NO: 623          moltype = DNA   length = 21
FEATURE                 Location/Qualifiers
misc_feature            1..21
```

```
                      note = Synthetic
source                1..21
                      mol_type = other DNA
                      organism = synthetic construct
SEQUENCE: 623
agggcagtgc ttacctgagg g                                              21

SEQ ID NO: 624        moltype = DNA  length = 21
FEATURE               Location/Qualifiers
misc_feature          1..21
                      note = Synthetic
source                1..21
                      mol_type = other DNA
                      organism = synthetic construct
SEQUENCE: 624
caggtgacag ttcaggtgca g                                              21

SEQ ID NO: 625        moltype = DNA  length = 21
FEATURE               Location/Qualifiers
misc_feature          1..21
                      note = Synthetic
source                1..21
                      mol_type = other DNA
                      organism = synthetic construct
SEQUENCE: 625
tccaccctga ctccaggtga c                                              21

SEQ ID NO: 626        moltype = DNA  length = 22
FEATURE               Location/Qualifiers
misc_feature          1..22
                      note = Synthetic
source                1..22
                      mol_type = other DNA
                      organism = synthetic construct
SEQUENCE: 626
gagaaggaaa taagacccag tt                                             22

SEQ ID NO: 627        moltype = DNA  length = 22
FEATURE               Location/Qualifiers
misc_feature          1..22
                      note = Synthetic
source                1..22
                      mol_type = other DNA
                      organism = synthetic construct
SEQUENCE: 627
ccttctctct gcctctcagc tt                                             22

SEQ ID NO: 628        moltype = DNA  length = 19
FEATURE               Location/Qualifiers
misc_feature          1..19
                      note = Synthetic
source                1..19
                      mol_type = other DNA
                      organism = synthetic construct
SEQUENCE: 628
ccaccctctg tctgtctcc                                                 19

SEQ ID NO: 629        moltype = DNA  length = 23
FEATURE               Location/Qualifiers
misc_feature          1..23
                      note = Synthetic
source                1..23
                      mol_type = other DNA
                      organism = synthetic construct
SEQUENCE: 629
tccgctgggt ggtgggaaaa gaa                                            23

SEQ ID NO: 630        moltype = DNA  length = 21
FEATURE               Location/Qualifiers
misc_feature          1..21
                      note = Synthetic
source                1..21
                      mol_type = other DNA
                      organism = synthetic construct
SEQUENCE: 630
atgggctccg ctgggtggtg g                                              21

SEQ ID NO: 631        moltype = DNA  length = 18
FEATURE               Location/Qualifiers
```

```
                                    -continued
misc_feature           1..18
                       note = Synthetic
source                 1..18
                       mol_type = other DNA
                       organism = synthetic construct
SEQUENCE: 631
acgatgggct ccgctggg                                                    18

SEQ ID NO: 632         moltype = DNA   length = 20
FEATURE                Location/Qualifiers
misc_feature           1..20
                       note = Synthetic
source                 1..20
                       mol_type = other DNA
                       organism = synthetic construct
SEQUENCE: 632
ccatccttgg gcagagacct                                                  20

SEQ ID NO: 633         moltype = DNA   length = 21
FEATURE                Location/Qualifiers
misc_feature           1..21
                       note = Synthetic
source                 1..21
                       mol_type = other DNA
                       organism = synthetic construct
SEQUENCE: 633
atgaccaggt actgagaagg g                                                21

SEQ ID NO: 634         moltype = DNA   length = 21
FEATURE                Location/Qualifiers
misc_feature           1..21
                       note = Synthetic
source                 1..21
                       mol_type = other DNA
                       organism = synthetic construct
SEQUENCE: 634
aggtactgag aagggttcgt c                                                21

SEQ ID NO: 635         moltype = DNA   length = 22
FEATURE                Location/Qualifiers
misc_feature           1..22
                       note = Synthetic
source                 1..22
                       mol_type = other DNA
                       organism = synthetic construct
SEQUENCE: 635
tagggacctg cggagagggc ga                                               22

SEQ ID NO: 636         moltype = DNA   length = 21
FEATURE                Location/Qualifiers
misc_feature           1..21
                       note = Synthetic
source                 1..21
                       mol_type = other DNA
                       organism = synthetic construct
SEQUENCE: 636
gcctagggac ctgcgggaga g                                                21

SEQ ID NO: 637         moltype = DNA   length = 22
FEATURE                Location/Qualifiers
misc_feature           1..22
                       note = Synthetic
source                 1..22
                       mol_type = other DNA
                       organism = synthetic construct
SEQUENCE: 637
gcctttatt cgcgagggtc gg                                                22

SEQ ID NO: 638         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 638
tggagggcct tttattcgcg agg                                              23
```

MUSCLE TARGETING COMPLEXES AND USES THEREOF FOR TREATING MYOTONIC DYSTROPHY

RELATED APPLICATIONS

This application is a continuation of U.S. application Ser. No. 18/495,086, filed Oct. 26, 2023, which is a continuation-in-part of U.S. application Ser. No. 18/490,905, filed Oct. 20, 2023, which is a continuation of U.S. application Ser. No. 18/181,795, filed Mar. 10, 2023, now U.S. Pat. No. 11,839,660, granted Dec. 12, 2023, which is a continuation of U.S. application Ser. No. 17/811,401, filed Jul. 8, 2022, now U.S. Pat. No. 11,672,872, granted Jun. 13, 2023, which claims priority under 35 U.S.C. § 119(e) of U.S. Provisional Application No. 63/220,043, filed Jul. 9, 2021. U.S. application Ser. No. 18/495,086 is a continuation-in-part of U.S. application Ser. No. 18/349,631, filed Jul. 10, 2023, which is a continuation of U.S. application Ser. No. 17/811,370, filed Jul. 8, 2022, now U.S. Pat. No. 11,771,776, granted Oct. 3, 2023, which claim priority under 35 U.S.C. § 119(e) of U.S. Provisional Application No. 63/220,262, filed Jul. 9, 2021. U.S. application Ser. No. 18/495,086 is a continuation-in-part of U.S. application Ser. No. 18/329,781, filed Jun. 6, 2023, now U.S. Pat. No. 11,844,843, granted Dec. 19, 2023, which is a continuation of U.S. application Ser. No. 18/063,795, filed Dec. 9, 2022, now U.S. Pat. No. 11,679,161, granted Jun. 20, 2023, which is a continuation of U.S. application Ser. No. 17/811,380, filed Jul. 8, 2022, now U.S. Pat. No. 11,638,761, granted May 2, 2023, which claims priority under 35 U.S.C. § 119(e) of U.S. Provisional Application No. 63/220,155, filed Jul. 9, 2021. U.S. application Ser. No. 18/495,086 is a continuation-in-part of U.S. application Ser. No. 18/181,700, filed Mar. 10, 2023, now Abandoned, which is a continuation of U.S. application Ser. No. 17/811,424, filed Jul. 8, 2022, now U.S. Pat. No. 11,633,498, granted Apr. 25, 2023, which claims priority under 35 U.S.C. § 119(e) of U.S. Provisional Application No. 63/220,144, filed Jul. 9, 2021. The contents of each of these applications are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO AN ELECTRONIC SEQUENCE LISTING

The contents of the electronic sequence listing (D082470069US06-SEQ-ZJG.xml; Size: 812,642 bytes; and Date of Creation: Mar. 14, 2024) is herein incorporated by reference in its entirety.

BACKGROUND OF INVENTION

Myotonic dystrophy (DM) is a dominantly inherited genetic disease that is characterized by myotonia, muscle loss or degeneration, diminished muscle function, insulin resistance, cardiac arrhythmia, smooth muscle dysfunction, and neurological abnormalities. DM is the most common form of adult-onset muscular dystrophy, with a worldwide incidence of about 1 in 8000 people worldwide. Two types of the disease, myotonic dystrophy type 1 (DM1) and myotonic dystrophy type 2 (DM2), have been described. DM1, the more common form of the disease, results from a repeat expansion of a CTG trinucleotide repeat in the 3' non-coding region of DMPK on chromosome 19; DM2 results from a repeat expansion of a CCTG tetranucleotide repeat in the first intron of ZNF9 on chromosome 3. In DM1 patients, the repeat expansion of a CTG trinucleotide repeat, which may comprise greater than ~50 to ~3,000+ total repeats, leads to generation of toxic RNA repeats capable of forming hairpin structures that bind essential intracellular proteins, e.g. muscleblind-like proteins, with high affinity resulting in protein sequestration and the loss-of-function phenotypes that are characteristic of the disease. Apart from supportive care and treatments to address the symptoms of the disease, no effective therapeutic for DM1 is currently available.

SUMMARY OF INVENTION

In some aspects, the disclosure provides complexes that target muscle cells for purposes of delivering molecular payloads to those cells. In some embodiments, complexes provided herein are particularly useful for delivering molecular payloads that inhibit the expression or activity of a DMPK allele comprising an expanded disease-associated-repeat, e.g., in a subject having or suspected of having myotonic dystrophy. Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can inhibit mutant DMPK expression in the muscle cells. In some embodiments, the oligonucleotides are released by endosomal cleavage of covalent linkers connecting oligonucleotides and muscle-targeting agents of the complexes.

One aspect of the present disclosure relates to a complex comprising an anti-transferrin receptor (TfR) antibody covalently linked to a molecular payload configured for reducing expression or activity of DMPK, wherein the anti-TfR antibody comprises:
   (i) a heavy chain variable region (VH) comprising an amino acid sequence at least 95% identical to SEQ ID NO: 76; and/or a light chain variable region (VL) comprising an amino acid sequence at least 95% identical to SEQ ID NO: 75;
   (ii) a heavy chain variable region (VH) comprising an amino acid sequence at least 95% identical to SEQ ID NO: 69; and/or a light chain variable region (VL) comprising an amino acid sequence at least 95% identical to SEQ ID NO: 70;
   (iii) a heavy chain variable region (VH) comprising an amino acid sequence at least 95% identical to SEQ ID NO: 71; and/or a light chain variable region (VL) comprising an amino acid sequence at least 95% identical to SEQ ID NO: 70;
   (iv) a heavy chain variable region (VH) comprising an amino acid sequence at least 95% identical to SEQ ID NO: 72; and/or a light chain variable region (VL) comprising an amino acid sequence at least 95% identical to SEQ ID NO: 70;

(v) a heavy chain variable region (VH) comprising an amino acid sequence at least 95% identical to SEQ ID NO: 73; and/or a light chain variable region (VL) comprising an amino acid sequence at least 95% identical to SEQ ID NO: 74;
(vi) a heavy chain variable region (VH) comprising an amino acid sequence at least 95% identical to SEQ ID NO: 73; and/or a light chain variable region (VL) comprising an amino acid sequence at least 95% identical to SEQ ID NO: 75;
(vii) a heavy chain variable region (VH) comprising an amino acid sequence at least 95% identical to SEQ ID NO: 76; and/or a light chain variable region (VL) comprising an amino acid sequence at least 95% identical to SEQ ID NO: 74;
(viii) a heavy chain variable region (VH) comprising an amino acid sequence at least 95% identical to SEQ ID NO: 77; and/or a light chain variable region (VL) comprising an amino acid sequence at least 95% identical to SEQ ID NO: 78;
(ix) a heavy chain variable region (VH) comprising an amino acid sequence at least 95% identical to SEQ ID NO: 79; and/or a light chain variable region (VL) comprising an amino acid sequence at least 95% identical to SEQ ID NO: 80; or
(x) a heavy chain variable region (VH) comprising an amino acid sequence at least 95% identical to SEQ ID NO: 77; and/or a light chain variable region (VL) comprising an amino acid sequence at least 95% identical to SEQ ID NO: 80.

In some embodiments, the antibody comprises:
(i) a VH comprising the amino acid sequence of SEQ ID NO: 76 and a VL comprising the amino acid sequence of SEQ ID NO: 75;
(ii) a VH comprising an amino acid sequence of SEQ ID NO: 69 and a VL comprising an amino acid sequence of SEQ ID NO: 70;
(iii) a VH comprising an amino acid sequence of SEQ ID NO: 71 and a VL comprising an amino acid sequence of SEQ ID NO: 70;
(iv) a VH comprising an amino acid sequence of SEQ ID NO: 72 and a VL comprising an amino acid sequence of SEQ ID NO: 70;
(v) a VH comprising an amino acid sequence of SEQ ID NO: 73 and a VL comprising an amino acid sequence of SEQ ID NO: 74;
(vi) a VH comprising an amino acid sequence of SEQ ID NO: 73 and a VL comprising an amino acid sequence of SEQ ID NO: 75;
(vii) a VH comprising an amino acid sequence of SEQ ID NO: 76 and a VL comprising an amino acid sequence of SEQ ID NO: 74;
(viii) a VH comprising an amino acid sequence of SEQ ID NO: 77 and a VL comprising an amino acid sequence of SEQ ID NO: 78;
(ix) a VH comprising an amino acid sequence of SEQ ID NO: 79 and a VL comprising an amino acid sequence of SEQ ID NO: 80; or
(x) a VH comprising an amino acid sequence of SEQ ID NO: 77 and a VL comprising an amino acid sequence of SEQ ID NO: 80.

In some embodiments, the antibody is selected from the group consisting of a Fab fragment, a Fab' fragment, a F(ab')2 fragment, an scFv, an Fv, and a full-length IgG. In some embodiments, the antibody is a Fab fragment.

In some embodiments, the antibody comprises:
(i) a heavy chain comprising an amino acid sequence at least 85% identical to SEQ ID NO: 101; and/or a light chain comprising an amino acid sequence at least 85% identical to SEQ ID NO: 90;
(ii) a heavy chain comprising an amino acid sequence at least 85% identical to SEQ ID NO: 97; and/or a light chain comprising an amino acid sequence at least 85% identical to SEQ ID NO: 85;
(iii) a heavy chain comprising an amino acid sequence at least 85% identical to SEQ ID NO: 98; and/or a light chain comprising an amino acid sequence at least 85% identical to SEQ ID NO: 85;
(iv) a heavy chain comprising an amino acid sequence at least 85% identical to SEQ ID NO: 99; and/or a light chain comprising an amino acid sequence at least 85% identical to SEQ ID NO: 85;
(v) a heavy chain comprising an amino acid sequence at least 85% identical to SEQ ID NO: 100; and/or a light chain comprising an amino acid sequence at least 85% identical to SEQ ID NO: 89;
(vi) a heavy chain comprising an amino acid sequence at least 85% identical to SEQ ID NO: 100; and/or a light chain comprising an amino acid sequence at least 85% identical to SEQ ID NO: 90;
(vii) a heavy chain comprising an amino acid sequence at least 85% identical to SEQ ID NO: 101; and/or a light chain comprising an amino acid sequence at least 85% identical to SEQ ID NO: 89;
(viii) a heavy chain comprising an amino acid sequence at least 85% identical to SEQ ID NO: 102; and/or a light chain comprising an amino acid sequence at least 85% identical to SEQ ID NO: 93;
(ix) a heavy chain comprising an amino acid sequence at least 85% identical to SEQ ID NO: 103; and/or a light chain comprising an amino acid sequence at least 85% identical to SEQ ID NO: 95; or
(x) a heavy chain comprising an amino acid sequence at least 85% identical to SEQ ID NO: 102; and/or a light chain comprising an amino acid sequence at least 85% identical to SEQ ID NO: 95.

In some embodiments, the antibody comprises:
(i) a heavy chain comprising the amino acid sequence of SEQ ID NO: 101 and a light chain comprising the amino acid sequence of SEQ ID NO: 90;
(ii) a heavy chain comprising the amino acid sequence of SEQ ID NO: 97 and a light chain comprising the amino acid sequence of SEQ ID NO: 85;
(iii) a heavy chain comprising the amino acid sequence of SEQ ID NO: 98 and a light chain comprising the amino acid sequence of SEQ ID NO: 85;
(iv) a heavy chain comprising the amino acid sequence of SEQ ID NO: 99 and a light chain comprising the amino acid sequence of SEQ ID NO: 85;
(v) a heavy chain comprising the amino acid sequence of SEQ ID NO: 100 and a light chain comprising the amino acid sequence of SEQ ID NO: 89;
(vi) a heavy chain comprising the amino acid sequence of SEQ ID NO: 100 and a light chain comprising the amino acid sequence of SEQ ID NO: 90;
(vii) a heavy chain comprising the amino acid sequence of SEQ ID NO: 101 and a light chain comprising the amino acid sequence of SEQ ID NO: 89;
(viii) a heavy chain comprising the amino acid sequence of SEQ ID NO: 102 and a light chain comprising the amino acid sequence of SEQ ID NO: 93;

(ix) a heavy chain comprising the amino acid sequence of SEQ ID NO: 103 and a light chain comprising the amino acid sequence of SEQ ID NO: 95; or (x) a heavy chain comprising the amino acid sequence of SEQ ID NO: 102 and a light chain comprising the amino acid sequence of SEQ ID NO: 95.

In some embodiments, the antibody does not specifically bind to the transferrin binding site of the transferrin receptor and/or the antibody does not inhibit binding of transferrin to the transferrin receptor. In some embodiments, the antibody is cross-reactive with extracellular epitopes of two or more of a human, non-human primate and rodent transferrin receptor. In some embodiments, the complex is configured to promote transferrin receptor mediated internalization of the molecular payload into a muscle cell.

In some embodiments, the molecular payload is an oligonucleotide. In some embodiments, the oligonucleotide comprises at least 15 consecutive nucleotides of SEQ ID NOs: 148-383 and 621-638, wherein any one or more of the thymidine bases (T's) in the oligonucleotide may optionally be a uridine base (U) and/or any one or more of the U's may optionally be a T. In some embodiments, the oligonucleotide comprises a sequence comprising any one of SEQ ID NOs: 159, 162, 172, 174, 180, 182, 188, 190, 195, 196, 201, 203, 212, 215, 218, 222, 248, and 264, wherein any one or more of the U's in the oligonucleotide may optionally be a T. In some embodiments, the oligonucleotide comprises a region of complementarity to at least 15 consecutive nucleotides of any one of SEQ ID NO: 384-619.

In some embodiments, the oligonucleotide mediates RNAse H-mediated cleavage of a DMPK mRNA transcript.

In some embodiments, the oligonucleotide comprises a 5'-X—Y—Z-3' formula, wherein X and Z are flanking regions comprising one or more 2'-modified nucleosides selected from the group consisting of: 2'-O-methyl, 2'-fluoro, 2'-O-methoxyethyl, and 2',4'-bridged nucleosides, and wherein Y is a gap region and each nucleoside in Y is a 2'-deoxyribonucleoside.

In some embodiments, the oligonucleotide comprises one or more phosphorothioate internucleoside linkages.

In some embodiments, the antibody is covalently linked to the molecular payload via a cleavable linker. In some embodiments, the cleavable linker comprises a valine-citrulline sequence.

In some embodiments, the antibody is covalently linked to the molecular payload via conjugation to a lysine residue or a cysteine residue of the antibody.

In some embodiments, reducing expression comprises reducing RNA levels of DMPK, optionally wherein the reduced RNA levels are in the nucleus of a cell, optionally wherein the cell is a muscle cell. In some embodiments, the DMPK is encoded from an allele comprising a disease-associated repeat.

Another aspect of the present disclosure relates to a method of reducing DMPK expression in a cell, the method comprising contacting the cell with a complex disclosed herein in an effective amount for promoting internalization of the molecular payload in the cell, optionally wherein the cell is a muscle cell.

Another aspect of the present disclosure relates to a method of treating a subject having an expansion of a disease-associated-repeat of a DMPK allele that is associated with myotonic dystrophy, the method comprising administering to the subject an effective amount of a complex disclosed herein. In some embodiments, the disease-associated-repeat comprises repeating units of a CTG trinucleotide sequence. In some embodiments, the complex is intravenously administered to the subject.

BRIEF DESCRIPTION OF THE DRAWINGS

FIG. 21A shows binding of humanized 3M12 variants to hTfR1. FIG. 21B shows binding of humanized 3M12 variants to cTfR1. FIG. 21C shows binding of humanized 3A4 variants to hTfR1. FIG. 21D shows binding of humanized 3A4 variants to cTfR1. FIG. 21E shows binding of humanized 5H12 variants to hTfR1. FIG. 21F shows binding of humanized 5H12 variants to hTfR1.

FIG. 23A shows the binding of humanized 3M12 variants alone or in conjugates with a DMPK targeting oligo to hTfR1. FIG. 23B shows the binding of humanized 3M12 variants alone or in conjugates with a DMPK targeting oligo to cTfR1. FIG. 23C shows the binding of humanized 3A4 variants alone or in conjugates with a DMPK targeting oligo to hTfR1. FIG. 23D shows the binding of humanized 3A4 variants alone or in conjugates with a DMPK targeting oligo to cTfR1. FIG. 23E shows the binding of humanized 5H12 variants alone or in conjugates with a DMPK targeting oligo to hTfR1. FIG. 23F shows the binding of humanized 5H12 variants alone or in conjugates with a DMPK targeting oligo to cTfR1. The respective $EC_{50}$ values are also shown.

FIG. 30A shows the experimental design (e.g., IV dosage, dosing frequency). DMPK mRNA levels were measured 14 days post first dose in the tibialis anterior (FIG. 30B), gastrocnemius (FIG. 30C), heart (FIG. 30D), and diaphragm (FIG. 30E), of the mice.

FIG. 31A shows that the conjugates reduced mutant DMPK mRNA expression. FIG. 31B shows that the conjugates corrected BIN1 Exon 11 splicing. FIG. 31C shows images of a fluorescence in situ hybridization (FISH) analysis and quantification of the images, demonstrating that the conjugated reduced nuclear foci formed by the mutant DMPK mRNA. In the microscopy images shown in the top panels of FIG. 31C, the light rounded shapes show cell nuclei, and the bright puncta within the nuclei of the DM1 cells (right three microscopy panels) show CUG foci.

DETAILED DESCRIPTION OF INVENTION

Figure 1:
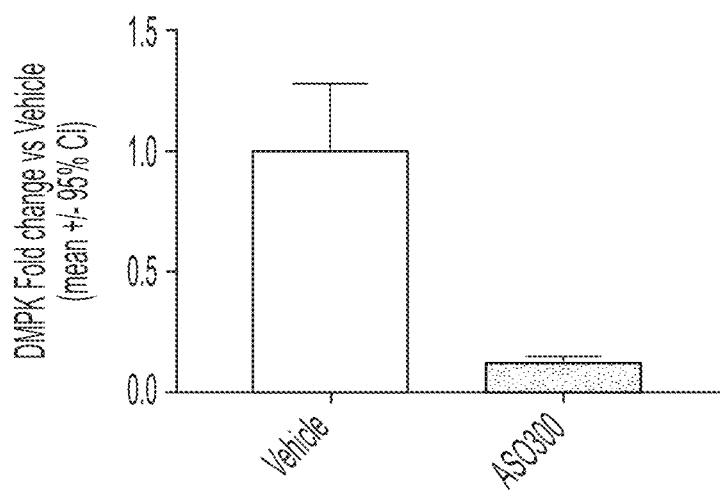
FIG. 1 depicts a non-limiting schematic showing the effect of transfecting Hepa 1-6 cells with an antisense oligonucleotide that targets DMPK (ASO300) on expression levels of DMPK relative to a vehicle transfection.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that inhibit the expression or activity of target genes in muscle cells, e.g., in a subject having or suspected of having a rare muscle disease. For example, in some embodiments, complexes are provided for targeting a DMPK allele that comprises an expanded disease-associated-repeat to treat subjects having DM1. In some embodiments, complexes provided herein may comprise oligonucleotides that inhibit expression of a DMPK allele comprising an expanded disease-associated-repeat. As another example, complexes may comprise oligonucleotides that interfere with the binding of a disease-associated DMPK mRNA to a muscleblind-like protein (e.g., MBNL1, 2, and/or (e.g., and) 3), thereby reducing a toxic effect of a disease-associated DMPK allele. In some embodiments, synthetic nucleic acid payloads (e.g., DNA or RNA payloads) may be used that express one or more proteins that reduce a toxic effect of a disease-associated DMPK allele. In some embodiments, complexes may comprise molecular payloads of synthetic cDNAs and/or (e.g., and) synthetic mRNAs, e.g., that express one or more muscleblind-like-proteins (e.g., MBNL1, 2, and/or (e.g., and) 3) or fragments thereof. In some embodiments, complexes may comprise molecular payloads such as guide molecules (e.g., guide RNAs) that are capable of targeting nucleic acid programmable nucleases (e.g., Cas9) to a sequence at or near a disease-associated repeat sequence of DMPK. In some embodiments, such nucleic programmable nucleases could be used to cleave part or all of a disease-associated repeat sequence from a DMPK gene.

Further aspects of the disclosure, including a description of defined terms, are provided below.

I. Definitions

Administering: As used herein, the terms "administering" or "administration" means to provide a complex to a subject in a manner that is physiologically and/or (e.g., and) pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a Fab', a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or (e.g., and) a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha ($\alpha$), delta ($\Delta$), epsilon ($\varepsilon$), gamma ($\gamma$) or mu ($\mu$) heavy chain. In some embodiments, the heavy chain of an antibody described herein can comprise a human alpha ($\alpha$), delta ($\Delta$), epsilon ($\varepsilon$), gamma ($\gamma$) or mu ($\mu$) heavy chain. In a particular embodiment, an antibody described herein comprises a human gamma 1 CH1, CH2, and/or (e.g., and) CH3 domain. In some embodiments, the amino acid sequence of the VH domain comprises the amino acid sequence of a human gamma ($\gamma$) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or (e.g., and) the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems. Examples of CDR definition systems are provided in Table 1.

TABLE 1

CDR Definitions

|  | IMGT[1] | Kabat[2] | Chothia[3] |
| --- | --- | --- | --- |
| CDR-H1 | 27-38 | 31-35 | 26-32 |
| CDR-H2 | 56-65 | 50-65 | 53-55 |
| CDR-H3 | 105-116/117 | 95-102 | 96-101 |
| CDR-L1 | 27-38 | 24-34 | 26-32 |
| CDR-L2 | 56-65 | 50-56 | 50-52 |
| CDR-L3 | 105-116/117 | 89-97 | 91-96 |

[1]IMGT ®, the international ImMunoGeneTics information system ®, imgt.org, Lefranc, M.-P. et al., Nucleic Acids Res., 27:209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196:901-917 (1987))

CDR-grafted antibody: The term "CDR-grafted antibody" refers to antibodies which comprise heavy and light chain variable region sequences from one species but in which the sequences of one or more of the CDR regions of VH and/or (e.g., and) VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferrin receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Disease-associated-repeat: As used herein, the term "disease-associated-repeat" refers to a repeated nucleotide sequence at a genomic location for which the number of units of the repeated nucleotide sequence is correlated with and/or (e.g., and) directly or indirectly contributes to, or causes, genetic disease. Each repeating unit of a disease associated repeat may be 2, 3, 4, 5 or more nucleotides in length. For example, in some embodiments, a disease associated repeat is a dinucleotide repeat. In some embodiments, a disease associated repeat is a trinucleotide repeat. In some embodiments, a disease associated repeat is a tetranucleotide repeat. In some embodiments, a disease associated repeat is a pentanucleotide repeat. In some embodiments, embodiments, the disease-associated-repeat comprises CAG repeats, CTG repeats, CUG repeats, CGG repeats, CCTG repeats, or a nucleotide complement of any thereof. In some embodiments, a disease-associated-repeat is in a non-coding portion of a gene. However, in some embodiments, a disease-associated-repeat is in a coding region of a gene. In some embodiments, a disease-associated-repeat is expanded from a normal state to a length that directly or indirectly contributes to, or causes, genetic disease. In some embodiments, a disease-associated-repeat is in RNA (e.g., an RNA transcript). In some embodiments, a disease-associated-repeat is in DNA (e.g., a chromosome, a plasmid). In some embodiments, a disease-associated-repeat is expanded in a chromosome of a germline cell. In some embodiments, a disease-associated-repeat is expanded in a chromosome of a somatic cell. In some embodiments, a disease-associated-repeat is expanded to a number of repeating units that is associated with congenital onset of disease. In some embodiments, a disease-associated-repeat is expanded to a number of repeating units that is associated with childhood onset of disease. In some embodiments, a disease-associated-repeat is expanded to a number of repeating units that is associated with adult onset of disease.

DMPK: As used herein, the term "DMPK" refers to a gene that encodes myotonin-protein kinase (also known as myotonic dystrophy protein kinase or dystrophia myotonica protein kinase), a serine/threonine protein kinase. Substrates for this enzyme may include myogenin, the beta-subunit of the L-type calcium channels, and phospholemman. In some embodiments, DMPK may be a human (Gene ID: 1760), non-human primate (e.g., Gene ID: 456139, Gene ID: 715328), or rodent gene (e.g., Gene ID: 13400). In humans, a CTG repeat expansion in the Y non-coding, untranslated region of DMPK is associated with myotonic dystrophy type I (DM1). In addition, multiple human transcript variants (e.g., as annotated under GenBank RefSeq Accession Numbers: NM_001081563.2, NM_004409.4, NM_001081560.2, NM_001081562.2, NM_001288764.1, NM_001288765.1, and NM_001288766.1) have been characterized that encode different protein isoforms.

DMPK allele: As used herein, the term "DMPK allele" refers to any one of alternative forms (e.g., wild-type or mutant forms) of a DMPK gene. In some embodiments, a DMPK allele may encode for wild-type myotonin-protein kinase that retains its normal and typical functions. In some embodiments, a DMPK allele may comprise one or more disease-associated-repeat expansions. In some embodiments, normal subjects have two DMPK alleles comprising in the range of 5 to 37 repeat units. In some embodiments, the number of CTG repeat units in subjects having DM1 is in the range of ~50 to ~3,000+ with higher numbers of repeats leading to an increased severity of disease. In some embodiments, mildly affected DM1 subjects have at least one DMPK allele having in the range of 50 to 150 repeat units. In some embodiments, subjects with classic DM1 have at least one DMPK allele having in the range of 100 to 1,000 or more repeat units. In some embodiments, subjects having DM1 with congenital onset may have at least one DMPK allele comprising more than 2,000 repeat units.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or (e.g., and) VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or (e.g., and) an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or (e.g., and) chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Myotonic dystrophy (DM): As used herein, the term "Myotonic dystrophy (DM)" refers to a genetic disease caused by mutations in the DMPK gene or CNBP (ZNF9) gene that is characterized by muscle loss, muscle weakening, and muscle function. Two types of the disease, myotonic dystrophy type 1 (DM1) and myotonic dystrophy type 2 (DM2), have been described. DM1 is associated with an expansion of a CTG trinucleotide repeat in the 3' non-coding region of DMPK. DM2 is associated with an expansion of a CCTG tetranucleotide repeat in the first intron of ZNF9. In both DM1 and DM2, the nucleotide expansions lead to toxic RNA repeats capable of forming hairpin structures that bind critical intracellular proteins, e.g., muscleblind-like proteins, with high affinity. Myotonic dystrophy, the genetic basis for the disease, and related symptoms are described in the art (see, e.g. Thornton, C. A., "Myotonic Dystrophy" Neurol Clin. (2014), 32(3): 705-719.; and Konieczny et al. "Myotonic dystrophy: candidate small molecule therapeutics" Drug Discovery Today (2017), 22:11.) In some embodiments, subjects are born with a variation of DM1 called congenital myotonic dystrophy. Symptoms of congenital myotonic dystrophy are present from birth and include weakness of all muscles, breathing problems, clubfeet, developmental delays and intellectual disabilities. DM1 is associated with Online Mendelian Inheritance in Man (OMIM) Entry #160900. DM2 is associated with OMIM Entry #602668.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of an oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a disease resulting from a disease-associated-repeat expansion, e.g., in a DMPK allele.

Transferrin receptor: As used herein, the term, "transferrin receptor" (also known as TFRC, CD71, p90, TFR, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

2'-modified nucleoside: As used herein, the terms "2'-modified nucleoside" and "2'-modified ribonucleoside" are used interchangeably and refer to a nucleoside having a sugar moiety modified at the 2' position. In some embodiments, the 2'-modified nucleoside is a 2'-4' bicyclic nucleoside, where the 2' and 4' positions of the sugar are bridged (e.g., via a methylene, an ethylene, or a (S)-constrained ethyl bridge). In some embodiments, the 2'-modified nucleoside is a non-bicyclic 2'-modified nucleoside, e.g., where the 2' position of the sugar moiety is substituted. Non-limiting examples of 2'-modified nucleosides include: 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-0-dimethylaminoethyloxyethyl (2'-O-DMAEOE), 2'-O—N-methylacetamido (2'-O-NMA), locked nucleic acid (LNA, methylene-bridged nucleic acid), ethylene-bridged nucleic acid (ENA), and (S)-constrained ethyl-bridged nucleic acid (cEt). In some embodiments, the 2'-modified nucleosides described herein are high-affinity modified nucleotides and oligonucleotides comprising the 2'-modified nucleotides have increased affinity to a target sequences, relative to an unmodified oligonucleotide. Examples of structures of 2'-modified nucleosides are provided below:

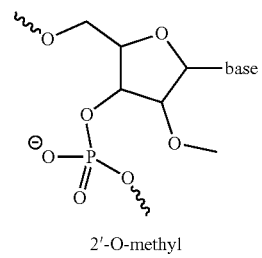

2'-O-methyl

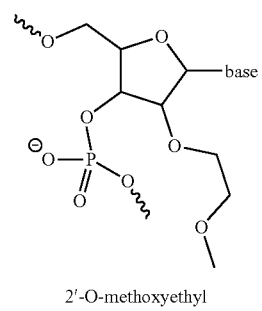

2'-O-methoxyethyl
(MOE)

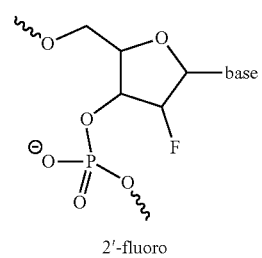

2'-fluoro

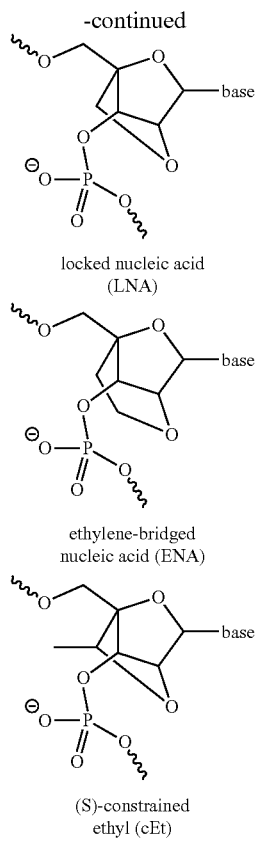

locked nucleic acid (LNA)

ethylene-bridged nucleic acid (ENA)

(S)-constrained ethyl (cEt)

II. Complexes

Provided herein are complexes that comprise a targeting agent, e.g. an antibody, covalently linked to a molecular payload. In some embodiments, a complex comprises a muscle-targeting antibody covalently linked to an oligonucleotide. A complex may comprise an antibody that specifically binds a single antigenic site or that binds to at least two antigenic sites that may exist on the same or different antigens.

A complex may be used to modulate the activity or function of at least one gene, protein, and/or (e.g., and) nucleic acid. In some embodiments, the molecular payload present with a complex is responsible for the modulation of a gene, protein, and/or (e.g., and) nucleic acids. A molecular payload may be a small molecule, protein, nucleic acid, oligonucleotide, or any molecular entity capable of modulating the activity or function of a gene, protein, and/or (e.g., and) nucleic acid in a cell. In some embodiments, a molecular payload is an oligonucleotide that targets a disease-associated repeat in muscle cells.

In some embodiments, a complex comprises a muscle-targeting agent, e.g. an anti-transferrin receptor antibody, covalently linked to a molecular payload, e.g. an antisense oligonucleotide that targets a disease-associated repeat, e.g. DMPK allele.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or (e.g., and) a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or (e.g., and) cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" Nature 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" *J Biol Chem* 1996; 271: 15160-5; and Weisbart R. H. et al., "Cell type specific targeted intracellular delivery into muscle of a monoclonal antibody that binds myosin IIb" *Mol Immunol.* 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to interchangeably as an, transferrin receptor antibody, an anti-transferrin receptor antibody, or an anti-TfR antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or (e.g., and) derivatized using several known methodologies, e.g. library design using phage display. Exemplary methodologies have been characterized in the art and are incorporated by reference (Diez, P. et al. "High-throughput phage-display screening in array format", Enzyme and microbial technology, 2015, 79, 34-41.; Christoph M. H. and Stanley, J. R. "Antibody Phage Display: Technique and Applications" J Invest Dermatol. 2014, 134:2.; Engleman, Edgar (Ed.) "Human Hybridomas and Monoclonal Antibodies." 1985, Springer.). In other embodiments, an anti-transferrin receptor antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522.; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052.).

Provided herein, in some aspects, are new anti-TfR antibodies for use as the muscle targeting agents (e.g., in muscle targeting complexes). In some embodiments, the anti-TfR antibody described herein binds to transferrin receptor with high specificity and affinity. In some embodiments, the anti-TfR antibody described herein specifically binds to any extracellular epitope of a transferrin receptor or an epitope that becomes exposed to an antibody. In some embodiments, anti-TfR antibodies provided herein bind specifically to transferrin receptor from human, non-human primates, mouse, rat, etc. In some embodiments, anti-TfR antibodies provided herein bind to human transferrin receptor. In some embodiments, the anti-TfR antibody described herein binds to an amino acid segment of a human or non-human primate transferrin receptor, as provided in SEQ ID NOs: 105-108. In some embodiments, the anti-TfR antibody described herein binds to an amino acid segment corresponding to amino acids 90-96 of a human transferrin receptor as set forth in SEQ ID NO: 105, which is not in the apical domain of the transferrin receptor.

An example human transferrin receptor amino acid sequence, corresponding to NCBI sequence NP_003225.2 (transferrin receptor protein 1 isoform 1, *Homo sapiens*) is as follows:

(SEQ ID NO: 105)
MMDQARSAFSNLFGGEPLSYTRFSLARQVDGDNSHVEMKLAVDEEENAD

NNTKANVTKPKRCSGSICYGTIAVIVFFLIGFMIGYLGYCKGVEPKTEC

ERLAGTESPVREEPGEDFPAARRLYWDDLKRKLSEKLDSTDFTGTIKLL

NENSYVPREAGSQKDENLALYVENQFREFKLSKVWRDQHFVKIQVKDSA

QNSVIIVDKNGRLVYLVENPGGYVAYSKAATVTGKLVHANFGTKKDFED

LYTPVNGSIVIVRAGKITFAEKVANAESLNAIGVLIYMDQTKFPIVNAE

LSFFGHAHLGTGDPYTPGFPSFNHTQFPPSRSSGLPNIPVQTISRAAAE

KLFGNMEGDCPSDWKTDSTCRMVTSESKNVKLTVSNVLKEIKILNIFGV

IKGFVEPDHYVVVGAQRDAWGPGAAKSGVGTALLLKLAQMFSDMVLKDG

FQPSRSIIFASWSAGDFGSVGATEWLEGYLSSLHLKAFTYINLDKAVLG

TSNFKVSASPLLYTLIEKTMQNVKHPVTGQFLYQDSNWASKVEKLTLDN

AAFPFLAYSGIPAVSFCFCEDTDYPYLGTTMDTYKELIERIPELNKVAR

AAAEVAGQFVIKLTHDVELNLDYERYNSQLLSFVRDLNQYRADIKEMGL

SLQWLYSARGDFFRATSRLTTDFGNAEKTDRFVMKKLNDRVMRVEYHFL

SPYVSPKESPFRHVFWGSGSHTLPALLENLKLRKQNNGAFNETLFRNQL

ALATWTIQGAANALSGDVWDIDNEF.

An example non-human primate transferrin receptor amino acid sequence, corresponding to NCBI sequence NP_001244232.1 (transferrin receptor protein 1, *Macaca mulatta*) is as follows:

(SEQ ID NO: 106)
MMDQARSAFSNLFGGEPLSYTRFSLARQVDGDNSHVEMKLGVDEEENTD

NNTKPNGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPFLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 107)
MMDQARSAFSNLFGGEPLSYTRFSLARQVDGDNSHVEMKLGVDEEENTD

NNTKANGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPFLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 108)
MMDQARSAFSNLFGGEPLSYTRFSLARQVDGDNSHVEMKLAADEEENAD

NNMKASVRKPKRFNGRLCFAAIALVIFFLIGFMSGYLGYCKRVEQKEEC

VKLAETEETDKSETMETEDVPTSSRLYWADLKTLLSEKLNSIEFADTIK

QLSQNTYTPREAGSQKDESLAYYIENQFHEFKFSKVWRDEHYVKIQVKS

SIGQNMVTIVQSNGNLDPVESPEGYVAFSKPTEVSGKLVHANFGTKKDF

EELSYSVNGSLVIVRAGEITFAEKVANAQSFNAIGVLIYMDKNKFPVVE

ADLALFGHAHLGTGDPYTPGFPSFNHTQFPPSQSSGLPNIPVQTISRAA

AEKLFGKMEGSCPARWNIDSSCKLELSQNQNVKLIVKNVLKERRILNIF

GVIKGYEEPDRYVVVGAQRDALGAGVAAKSSVGTGLLLKLAQVFSDMIS

KDGFRPSRSIIFASWTAGDFGAVGATEWLEGYLSSLHLKAFTYINLDKV

VLGTSNFKVSASPLLYTLMGKIMQDVKHPVDGKSLYRDSNWISKVEKLS

FDNAAYPFLAYSGIPAVSFCFCEDADYPYLGTRLDTYEALTQKVPQLNQ

MVRTAAEVAGQLIIKLTHDVELNLDYEMYNSKLLSFMKDLNQFKTDIRD

MGLSLQWLYSARGDYFRATSRLTTDFHNAEKTNRFVMREINDRIMKVEY

HFLSPYVSPRESPFRHIFWGSGSHTLSALVENLKLRQKNITAFNETLFR

NQLALATWTIQGVANALSGDIWNIDNEF

In some embodiments, an anti-transferrin receptor antibody binds to an amino acid segment of the receptor as follows: FVKIQVKDSAQNSVIIVDKNGRLVYLVENPGGYVAYSKAATVTGKLVHANFGTKKDFE DLYTPVNGSIVIVRAGKITFAEKVANAESLN-AIGVLIYMDQTKFPIVNAELSFFGHAHLG TGDPYTPGFPSFNHTQFPPSRSSGLPNIPVQTIS-RAAAEKLFGNMEGDCPSDWKTDSTCR MVTS-ESKNVKLTVSNVLKE (SEQ ID NO: 109) and does not inhibit the binding interactions between transferrin receptors and transferrin and/or (e.g., and) human hemochromatosis protein (also known as HFE). In some embodiments, the anti-transferrin receptor antibody described herein does not bind an epitope in SEQ ID NO: 109.

Appropriate methodologies may be used to obtain and/or (e.g., and) produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988.).

In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, the anti-TfR antibody of the present disclosure comprises a VL domain and/or (e.g., and) VH domain of any one of the anti-TfR antibodies selected from Table 2, and comprises a constant region comprising the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, agents binding to transferrin receptor, e.g., anti-TfR antibodies, are capable of targeting muscle cell and/or (e.g., and) mediate the transportation of an agent across the blood brain barrier. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Antibodies that bind, e.g. specifically bind, to a transferrin receptor may be internalized into the cell, e.g. through receptor-mediated endocytosis, upon binding to a transferrin receptor.

Provided herein, in some aspects, are humanized antibodies that bind to transferrin receptor with high specificity and affinity. In some embodiments, the humanized anti-TfR antibody described herein specifically binds to any extracellular epitope of a transferrin receptor or an epitope that becomes exposed to an antibody. In some embodiments, the humanized anti-TfR antibodies provided herein bind specifically to transferrin receptor from human, non-human primates, mouse, rat, etc. In some embodiments, the humanized anti-TfR antibodies provided herein bind to human transferrin receptor. In some embodiments, the humanized anti-TfR antibody described herein binds to an amino acid segment of a human or non-human primate transferrin receptor, as provided in SEQ ID NOs: 105-108. In some embodiments, the humanized anti-TfR antibody described herein binds to an amino acid segment corresponding to amino acids 90-96 of a human transferrin receptor as set forth in SEQ ID NO: 105, which is not in the apical domain of the transferrin receptor. In some embodiments, the humanized anti-TfR antibodies described herein binds to TfR1 but does not bind to TfR2.

In some embodiments, an anti-TFR antibody specifically binds a TfR1 (e.g., a human or non-human primate TfR1) with binding affinity (e.g., as indicated by Kd) of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, the anti-TfR antibodies described herein binds to TfR1 with a KD of sub-nanomolar range. In some embodiments, the anti-TfR antibodies described herein selectively binds to transferrin receptor 1 (TfR1) but do not bind to transferrin receptor 2 (TfR2). In some embodiments, the anti-TfR antibodies described herein binds to human TfR1 and cyno TfR1 (e.g., with a Kd of $10^{-7}$ M, $10^{-8}$ M, $10^{-9}$ M, $10^{-10}$ M, $10^{-11}$ M, $10^{-12}$ M, $10^{-13}$ M, or less), but does not bind to a mouse TfR1. The affinity and binding kinetics of the anti-TfR antibody can be tested using any suitable method including but not limited to biosensor technology (e.g., OCTET or BIACORE). In some embodiments, binding of any one of the anti-TfR antibody described herein does not complete with or inhibit transferrin binding to the TfR1. In some embodiments, binding of any one of the anti-TfR antibody described herein does not complete with or inhibit HFE-beta-2-microglobulin binding to the TfR1.

The anti-TfR antibodies described herein are humanized antibodies. The CDR and variable region amino acid sequences of the mouse monoclonal anti-TfR antibody from which the humanized anti-TfR antibodies described herein are derived are provided in Table 2.

TABLE 2

Mouse Monoclonal Anti-TfR Antibodies

| Ab | | IMGT | Kabat | Chothia |
|---|---|---|---|---|
| 3-A4 | CDR-H1 | GFNIKDDY (SEQ ID NO: 1) | DDYMY (SEQ ID NO: 7) | GFNIKDD (SEQ ID NO: 12) |
| | CDR-H2 | IDPENGDT (SEQ ID NO: 2) | WIDPENGDTEYASKFQD (SEQ ID NO: 8) | ENG (SEQ ID NO: 13) |
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPENGDTEYASKFQDKATVTADTSSNTAYLQLSSLTSEDTAVYYCTLWLRRGLDYWGQGTSVTVSS (SEQ ID NO: 17) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-A4 N54T* | CDR-H1 | GFNIKDDY (SEQ ID NO: 1) | DDYMY (SEQ ID NO: 7) | GFNIKDD (SEQ ID NO: 12) |
| | CDR-H2 | IDPETGDT (SEQ ID NO: 19) | WIDPETGDTEYASKFQD (SEQ ID NO: 20) | ETG (SEQ ID NO: 21) |
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPETGDTEYASKFQDKATVTADTSSNTAYLQLSSLTSEDTAVYYCTLWLRRGLDYWGQGTSVTVSS (SEQ ID NO: 22) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-A4 N54S* | CDR-H1 | GFNIKDDY (SEQ ID NO: 1) | DDYMY (SEQ ID NO: 7) | GFNIKDD (SEQ ID NO: 12) |
| | CDR-H2 | IDPESGDT (SEQ ID NO: 23) | WIDPESGDTEYASKFQD (SEQ ID NO: 24) | ESG (SEQ ID NO: 25) |
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPESGDTEYASKFQDKATVTADTSSNTAYLQLSSLTSEDTAVYYCTLWLRRGLDYWGQGTSVTVSS (SEQ ID NO: 26) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-M12 | CDR-H1 | GYSITSGYY (SEQ ID NO: 27) | SGYYWN (SEQ ID NO: 33) | GYSITSGY (SEQ ID NO: 38) |
| | CDR-H2 | ITFDGAN (SEQ ID NO: 28) | YITFDGANNYNPSLKN (SEQ ID NO: 34) | FDG (SEQ ID NO: 39) |
| | CDR-H3 | TRSSYDYDVLDY (SEQ ID NO: 29) | SSYDYDVLDY (SEQ ID NO: 35) | SYDYDVLD (SEQ ID NO: 40) |
| | CDR-L1 | QDISNF (SEQ ID NO: 30) | RASQDISNFLN (SEQ ID NO: 36) | SQDISNF (SEQ ID NO: 41) |
| | CDR-L2 | YTS (SEQ ID NO: 31) | YTSRLHS (SEQ ID NO: 37) | YTS (SEQ ID NO: 31) |
| | CDR-L3 | QQGHTLPYT (SEQ ID NO: 32) | QQGHTLPYT (SEQ ID NO: 32) | GHTLPY (SEQ ID NO: 42) |
| | VH | DVQLQESGPGLVKPSQSLSLTCSVTGYSITSGYYWNWIRQFPGNKLEWMGYITFDGANNYNPSLKNRISITRDTSKNQFFLKTSVTTEDTATYYCTRSSYDYDVLDYWGQGTTLTVSS (SEQ ID NO: 43) | | |
| | VL | DIQMTQTTSSLSASLGDRVTISCRASQDISNFLNWYQQRPDGTVKLLIYYTSRLHSGVPSRFSGSGSGTDFSLTVSNLEQEDIATYFCQQGHTLPYTFGGGTKLEIK (SEQ ID NO: 44) | | |

TABLE 2-continued

Mouse Monoclonal Anti-TfR Antibodies

| Ab | | IMGT | Kabat | Chothia |
|---|---|---|---|---|
| 5-H12 | CDR-H1 | GYSFTDYC (SEQ ID NO: 45) | DYCIN (SEQ ID NO: 51) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYCINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 61) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |
| 5-H12 C33Y* | CDR-H1 | GYSFTDYY (SEQ ID NO: 63) | DYYIN (SEQ ID NO: 64) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYYINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 65) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |
| 5-H12 C33D* | CDR-H1 | GYSFTDYD (SEQ ID NO: 66) | DYDIN (SEQ ID NO: 67) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYDINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 68) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |

*mutation positions are according to Kabat numbering of the respective VH sequences containing the mutations In some embodiments, the anti-TfR antibody of the present disclosure is a humanized variant of any one of the anti-TfR antibodies provided in Table 2. In some embodiments, the anti-TfR antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 in any one of the anti-TfR antibodies provided in Table 2, and comprises a humanized heavy chain variable region and/or (e.g., and) a humanized light chain variable region.

Humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

Humanized antibodies and methods of making them are known, e.g., as described in Almagro et al., Front. Biosci. 13:1619-1633 (2008); Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005); Padlan et al., Mol. Immunol. 28:489-498 (1991); Dall'Acqua et al., Methods 36:43-60 (2005); Osbourn et al., Methods 36:61-68 (2005); and Klimka et al., Br. J. Cancer, 83:252-260 (2000), the contents of all of which are incorporated herein by reference. Human framework regions that may be used for humanization are described in e.g., Sims et al. J. Immunol. 151:2296 (1993); Carter et al., Proc. Natl. Acad. Sci. USA, 89:4285 (1992); Presta et al., J. Immunol., 151:2623 (1993); Almagro et al., Front. Biosci. 13:1619-1633 (2008)); Baca et al., J. Biol. Chem. 272:10678-10684 (1997); and Rosok et al., J Biol. Chem. 271:22611-22618 (1996), the contents of all of which are incorporated herein by reference.

In some embodiments, the humanized anti-TfR antibody of the present disclosure comprises a humanized VH comprising one or more amino acid variations (e.g., in the VH framework region) as compared with any one of the VHs listed in Table 2, and/or (e.g., and) a humanized VL comprising one or more amino acid variations (e.g., in the VL framework region) as compared with any one of the VLs listed in Table 2.

In some embodiments, the humanized anti-TfR antibody of the present disclosure comprises a humanized VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH of any of the anti-TfR antibodies listed in Table 2 (e.g., any one of SEQ ID NOs: 17, 22, 26, 43, 61, 65, and 68). Alternatively or in addition (e.g., in addition), the humanized anti-TfR antibody of the present disclosure comprises a humanized VL containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL of any one of the anti-TfR antibodies listed in Table 2 (e.g., any one of SEQ ID NOs: 18, 44, and 62).

In some embodiments, the humanized anti-TfR antibody of the present disclosure comprises a humanized VH comprising an amino acid sequence that is at least 75% (e.g., 75%, 80%, 85%, 90%, 95%, 98%, or 99%) identical in the framework regions to the VH of any of the anti-TfR antibodies listed in Table 2 (e.g., any one of SEQ ID NOs: 17, 22, 26, 43, 61, 65, and 68). Alternatively or in addition (e.g., in addition), In some embodiments, the humanized anti-TfR antibody of the present disclosure comprises a humanized VL comprising an amino acid sequence that is at least 75% (e.g., 75%, 80%, 85%, 90%, 95%, 98%, or 99%) identical in the framework regions to the VL of any of the anti-TfR antibodies listed in Table 2 (e.g., any one of SEQ ID NOs: 18, 44, and 62).

In some embodiments, the humanized anti-TfR antibody of the present disclosure comprises a humanized VH comprising a CDR-H1 having the amino acid sequence of SEQ ID NO: 1 (according to the IMGT definition system), a CDR-H2 having the amino acid sequence of SEQ ID NO: 2, SEQ ID NO: 19, or SEQ ID NO: 23 (according to the IMGT definition system), a CDR-H3 having the amino acid sequence of SEQ ID NO: 3 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22, or SEQ ID NO: 26. Alternatively or in addition (e.g., in addition), the anti-TfR antibody of the present disclosure comprises a humanized VL comprising a CDR-L1 having the amino acid sequence of SEQ ID NO: 4 (according to the IMGT definition system), a CDR-L2 having the amino acid sequence of SEQ ID NO: 5 (according to the IMGT definition system), and a CDR-L3 having the amino acid sequence of SEQ ID NO: 6 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 1 (according to the IMGT definition system), a CDR-H2 having the amino acid sequence of SEQ ID NO: 2, SEQ ID NO: 19, or SEQ ID NO: 23 (according to the IMGT definition system), a CDR-H3 having the amino acid sequence of SEQ ID NO: 3 (according to the IMGT definition system), and is at least 75% (e.g., 75%, 80%, 85%, 90%, 95%, 98%, or 99%) identical in the framework regions to the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 4 (according to the IMGT definition system), a CDR-L2 having the amino acid sequence of SEQ ID NO: 5 (according to the IMGT definition system), and a CDR-L3 having the amino acid sequence of SEQ ID NO: 6 (according to the IMGT definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 7 (according to the Kabat definition system), a CDR-H2 having the amino acid sequence of SEQ ID NO: 8, SEQ ID NO: 20, or SEQ ID NO: 24 (according to the Kabat definition system), a CDR-H3 having the amino acid sequence of SEQ ID NO: 9 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 10 (according to the Kabat definition system), a CDR-L2 having the amino acid sequence of SEQ ID NO: 11 (according to the Kabat definition system), and a CDR-L3 having the amino acid sequence of SEQ ID NO: 6 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 7 (according to the Kabat definition system), a CDR-H2 having the amino acid sequence of SEQ ID NO: 8, SEQ ID NO: 20, or SEQ ID NO: 24 (according to the Kabat definition system), a CDR-H3 having the amino acid sequence of SEQ ID NO: 9 (according to the Kabat definition system), and is at least 75% (e.g., 75%, 80%, 85%, 90%, 95%, 98%, or 99%) identical in the framework regions to the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 10 (according to the Kabat definition system), a CDR-L2 having the amino acid sequence of SEQ ID NO: 11 (according to the Kabat definition system), and a CDR-L3 having the amino acid sequence of SEQ ID NO: 6 (according to the Kabat definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 12 (according to the Chothia definition system), a CDR-H2 having the amino acid sequence of SEQ ID NO: 13, SEQ ID NO: 21, or SEQ ID NO: 25 (according to the Chothia definition system), a CDR-H3 having the amino acid sequence of SEQ ID NO: 14 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22 or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 15 (according to the Chothia definition system), a CDR-L2 having the amino acid sequence of SEQ ID NO: 5 (according to the Chothia definition system), and a CDR-L3 having the amino acid sequence of SEQ ID NO: 16 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 12 (according to the Chothia definition system), a CDR-H2 having the amino acid sequence of SEQ ID NO: 13, SEQ ID NO: 21, or SEQ ID NO: 25 (according to the Chothia definition system), a CDR-H3 having the amino acid sequence of SEQ ID NO: 14 (according to the Chothia definition system), and is at least 75% (e.g., 75%, 80%, 85%, 90%, 95%, 98%, or 99%) identical in the framework regions to the VH as set forth in SEQ ID NO: SEQ ID NO: 17, SEQ ID NO: 22 or SEQ ID NO: 26. Alternatively or in addition (e.g., in addition), the anti-TfR antibody of the present disclosure comprises a humanized VL comprising a CDR-L1 having the amino acid sequence of SEQ ID NO: 15 (according to the Chothia definition system), a CDR-L2 having the amino acid sequence of SEQ ID NO: 5 (according to the Chothia definition system), and a CDR-L3 having the amino acid sequence of SEQ ID NO: 16 (according to the Chothia definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 27 (according to the IMGT definition system), a CDR-H2 having the amino acid sequence of SEQ ID NO: 28 (according to the IMGT definition system), a CDR-H3 having the amino acid sequence of SEQ ID NO: 29 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 30 (according to the IMGT definition system), a CDR-L2 having the amino acid sequence of SEQ ID NO: 31 (according to the IMGT definition system), and a CDR-L3 having the amino acid sequence of SEQ ID NO: 32 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 27 (according to the IMGT definition system), a CDR-H2 having the amino acid sequence of SEQ ID NO: 28 (according to the IMGT definition system), a CDR-H3 having the amino acid sequence of SEQ ID NO: 29 (according to the IMGT definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 30 (according to the IMGT definition system), a CDR-L2 having the amino acid sequence of SEQ ID NO: 31 (according to the IMGT definition system), and a CDR-L3 having the amino acid sequence of SEQ ID NO: 32 (according to the IMGT definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 33 (according to the Kabat definition system), a CDR-H2 having the amino acid sequence of SEQ ID NO: 34 (according to the Kabat definition system), a CDR-H3 having the amino acid sequence of SEQ ID NO: 35 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 36 (according to the Kabat definition system), a CDR-L2 having the amino acid sequence of SEQ ID NO: 37 (according to the Kabat definition system), and a CDR-L3 having the amino acid sequence of SEQ ID NO: 32 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 33 (according to the Kabat definition system), a CDR-H2 having the amino acid sequence of SEQ ID NO: 34 (according to the Kabat definition system), a CDR-H3 having the amino acid sequence of SEQ ID NO: 35 (according to the Kabat definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 36 (according to the Kabat definition system), a CDR-L2 having the amino acid sequence of SEQ ID NO: 37 (according to the Kabat definition system), and a CDR-L3 having the amino acid sequence of SEQ ID NO: 32 (according to the Kabat definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 38 (according to the Chothia definition system), a CDR-H2 having the amino acid sequence of SEQ ID NO: 39 (according to the Chothia definition system), a CDR-H3 having the amino acid sequence of SEQ ID NO: 40 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 41 (according to the Chothia definition system), a CDR-L2 having the amino acid sequence of SEQ ID NO: 31 (according to the Chothia definition system), and a CDR-L3 having the amino acid sequence of SEQ ID NO: 42 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 38 (according to the Chothia definition system), a CDR-H2 having the amino acid sequence of SEQ ID NO: 39 (according to the Chothia definition system), a CDR-H3 having the amino acid sequence of SEQ ID NO: 40 (according to the Chothia definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 41 (according to the Chothia definition system), a CDR-L2 having the amino acid sequence of SEQ ID NO: 31 (according to the Chothia definition system), and a CDR-L3 having the amino acid sequence of SEQ ID NO: 42 (according to the Chothia definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 45, SEQ ID NO: 63, or SEQ ID NO: 66 (according to the IMGT definition system), a CDR-H2 having the amino acid sequence of SEQ ID NO: 46 (according to the IMGT definition system), a CDR-H3 having the amino acid sequence of SEQ ID NO: 47 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, or SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 48 (according to the IMGT definition system), a CDR-L2 having the amino acid sequence of SEQ ID NO: 49 (according to the IMGT definition system), and a CDR-L3 having the amino acid sequence of SEQ ID NO: 50 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 45, SEQ ID NO: 63, or SEQ ID NO: 66 (according to the IMGT definition system), a CDR-H2 having the amino acid sequence of SEQ ID NO: 46 (according to the IMGT definition system), a CDR-H3 having the amino acid sequence of SEQ ID NO: 47 (according to the IMGT definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 48 (according to the IMGT definition system), a CDR-L2 having the amino acid sequence of SEQ ID NO: 49 (according to the IMGT definition system), and a CDR-L3 having the amino acid sequence of SEQ ID NO: 50 (according to the IMGT definition system), and is at least 75% (e.g., 75%, 80%, 85%, 90%, 95%, 98%, or 99%) identical in the framework regions to the VL as set forth in SEQ ID NO: 62.

In some embodiments, the humanized anti-TfR antibody of the present disclosure comprises a humanized VH comprising a CDR-H1 having the amino acid sequence of SEQ ID NO: 51, SEQ ID NO: 64, or SEQ ID NO: 67 (according to the Kabat definition system), a CDR-H2 having the amino acid sequence of SEQ ID NO: 52 (according to the Kabat definition system), a CDR-H3 having the amino acid sequence of SEQ ID NO: 53 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 54 (according to the Kabat definition system), a CDR-L2 having the amino acid sequence of SEQ ID NO: 55 (according to the Kabat definition system), and a CDR-L3 having the amino acid sequence of SEQ ID NO: 50 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 51, SEQ ID NO: 64, or SEQ ID NO: 67 (according to the Kabat definition system), a CDR-H2 having the amino acid sequence of SEQ ID NO: 52 (according to the Kabat definition system), a CDR-H3 having the amino acid sequence of SEQ ID NO: 53 (according to the Kabat definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 54 (according to the Kabat definition system), a CDR-L2 having the amino acid sequence of SEQ ID NO: 55 (according to the Kabat definition system), and a CDR-L3 having the amino acid sequence of SEQ ID NO: 50 (according to the Kabat definition system), and is at least 75% (e.g., 75%, 80%, 85%, 90%, 95%, 98%, or 99%) identical in the framework regions to the VL as set forth in SEQ ID NO: 62.

In some embodiments, the humanized anti-TfR antibody of the present disclosure comprises a humanized VH comprising a CDR-H1 having the amino acid sequence of SEQ ID NO: 56 (according to the Chothia definition system), a CDR-H2 having the amino acid sequence of SEQ ID NO: 57 (according to the Chothia definition system), a CDR-H3 having the amino acid sequence of SEQ ID NO: 58 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 59 (according to the Chothia definition system), a CDR-L2 having the amino acid sequence of SEQ ID NO: 49 (according to the Chothia definition system), and a CDR-L3 having the amino acid sequence of SEQ ID NO: 60 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 56 (according to the Chothia definition system), a CDR-H2 having the amino acid sequence of SEQ ID NO: 57 (according to the Chothia definition system), a CDR-H3 having the amino acid sequence of SEQ ID NO: 58 (according to the Chothia definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 59 (according to the Chothia definition system), a CDR-L2 having the amino acid sequence of SEQ ID NO: 49 (according to the Chothia definition system), and a CDR-L3 having the amino acid sequence of SEQ ID NO: 60 (according to the Chothia definition system), and is at least 75% (e.g., 75%, 80%, 85%, 90%, 95%, 98%, or 99%) identical in the framework regions to the VL as set forth in SEQ ID NO: 62.

Examples of amino acid sequences of the humanized anti-TfR antibodies described herein are provided in Table 3.

TABLE 3

Variable Regions of Humanized Anti-TfR Antibodies

| Antibody | Variable Region Amino Acid Sequence** |
|---|---|
| 3A4<br>VH3 (N54T*)/Vκ4 | V$_H$:<br>EVQLVQSGSELKKPGASVKVSCTASGFNIKDDYMYWVRQPPGKGLEWIGWIDP<br>ETGDTEYASKFQDRVTVTADTSTNTAYMELSSLRSEDTAVYYCTLWLRRGLD<br>YWGQGTLVTVSS (SEQ ID NO: 69)<br>V$_L$:<br>DIVMTQSPLSLPVTPGEPASISCRSSKSLLHSNGYTYLFWFQQRPGQSPRLLIYR<br>MSNLASGVPDRFSGSGSGTDFTLKISRVEAEDVGVYYCMQHLEYPFTFGGGTK<br>VEIK (SEQ ID NO: 70) |
| 3A4<br>VH3 (N54S*)/Vκ4 | V$_H$:<br>EVQLVQSGSELKKPGASVKVSCTASGFNIKDDYMYWVRQPPGKGLEWIGWIDP<br>ESGDTEYASKFQDRVTVTADTSTNTAYMELSSLRSEDTAVYYCTLWLRRGLD<br>YWGQGTLVTVSS (SEQ ID NO: 71)<br>V$_L$: |

TABLE 3-continued

Variable Regions of Humanized Anti-TfR Antibodies

| Antibody | Variable Region Amino Acid Sequence** |
|---|---|
| | DIVMTQSPLSLPVTPGEPASISCRSSKSLLHSNGYTYLFWFQQRPGQSPRLLIYRMSNLASGVPDRFSGSGSGTDFTLKISRVEAEDVGVYYCMQHLEYPFTFGGGTKVEIK (SEQ ID NO: 70) |
| 3A4 VH3/Vκ4 | VH: EVQLVQSGSELKKPGASVKVSCTASGFNIKDDYMYWVRQPPGKGLEWIGWIDPENGDTEYASKFQDRVTVTADTSTNTAYMELSSLRSEDTAVYYCTLWLRRGLDYWGQGTLVTVSS (SEQ ID NO: 72)<br>VL: DIVMTQSPLSLPVTPGEPASISCRSSKSLLHSNGYTYLFWFQQRPGQSPRLLIYRMSNLASGVPDRFSGSGSGTDFTLKISRVEAEDVGVYYCMQHLEYPFTFGGGTKVEIK (SEQ ID NO: 70) |
| 3M12 VH3/Vκ2 | VH: QVQLQESGPGLVKPSQTLSLTCSVTGYSITSGYYWNWIRQPPGKGLEWMGYITFDGANNYNPSLKNRVSISRDTSKNQFSLKLSSVTAEDTATYYCTRSSYDYDVLDYWGQGTTVTVSS (SEQ ID NO: 73)<br>VL: DIQMTQSPSSLSASVGDRVTITCRASQDISNFLNWYQQKPGQPVKLLIYYTSRLHSGVPSRFSGSGSGTDFTLTISSLQPEDFATYFCQQGHTLPYTFGQGTKLEIK (SEQ ID NO: 74) |
| 3M12 VH3/Vκ3 | VH: QVQLQESGPGLVKPSQTLSLTCSVTGYSITSGYYWNWIRQPPGKGLEWMGYITFDGANNYNPSLKNRVSISRDTSKNQFSLKLSSVTAEDTATYYCTRSSYDYDVLDYWGQGTTVTVSS (SEQ ID NO: 73)<br>VL: DIQMTQSPSSLSASVGDRVTITCRASQDISNFLNWYQQKPGQPVKLLIYYTSRLHSGVPSRFSGSGSGTDFTLTISSLQPEDFATYYCQQGHTLPYTFGQGTKLEIK (SEQ ID NO: 75) |
| 3M12 VH4/Vκ2 | VH: QVQLQESGPGLVKPSQTLSLTCTVTGYSITSGYYWNWIRQPPGKGLEWIGYITFDGANNYNPSLKNRVSISRDTSKNQFSLKLSSVTAEDTATYYCTRSSYDYDVLDYWGQGTTVTVSS (SEQ ID NO: 76)<br>VL: DIQMTQSPSSLSASVGDRVTITCRASQDISNFLNWYQQKPGQPVKLLIYYTSRLHSGVPSRFSGSGSGTDFTLTISSLQPEDFATYFCQQGHTLPYTFGQGTKLEIK (SEQ ID NO: 74) |
| 3M12 VH4/Vκ3 | VH: QVQLQESGPGLVKPSQTLSLTCTVTGYSITSGYYWNWIRQPPGKGLEWIGYITFDGANNYNPSLKNRVSISRDTSKNQFSLKLSSVTAEDTATYYCTRSSYDYDVLDYWGQGTTVTVSS (SEQ ID NO: 76)<br>VL: DIQMTQSPSSLSASVGDRVTITCRASQDISNFLNWYQQKPGQPVKLLIYYTSRLHSGVPSRFSGSGSGTDFTLTISSLQPEDFATYYCQQGHTLPYTFGQGTKLEIK (SEQ ID NO: 75) |
| 5H12 VH5 (C33Y*)/Vκ3 | VH: QVQLVQSGAEVKKPGASVKVSCKASGYSFTDYYINWVRQAPGQGLEWMGWIYPGSGNTRYSERFKGRVTITRDTSASTAYMELSSLRSEDTAVYYCAREDYYPYHGMDYWGQGTLVTVSS (SEQ ID NO: 77)<br>VL: DIVLTQSPDSLAVSLGERATINCRASESVDGYDNSFMHWYQQKPGQPPKLLIFRASNLESGVPDRFSGSGSRTDFTLTISSLQAEDVAVYYCQQSSEDPWTFGQGTKLEIK (SEQ ID NO: 78) |
| 5H12 VH5 (C33D*)/Vκ4 | VH: QVQLVQSGAEVKKPGASVKVSCKASGYSFTDYDINWVRQAPGQGLEWMGWIYPGSGNTRYSERFKGRVTITRDTSASTAYMELSSLRSEDTAVYYCAREDYYPYHGMDYWGQGTLVTVSS (SEQ ID NO: 79)<br>VL: DIVMTQSPDSLAVSLGERATINCRASESVDGYDNSFMHWYQQKPGQPPKLLIFRASNLESGVPDRFSGSGSGTDFTLTISSLQAEDVAVYYCQQSSEDPWTFGQGTKLEIK (SEQ ID NO: 80) |

TABLE 3-continued

Variable Regions of Humanized Anti-TfR Antibodies

| Antibody | Variable Region Amino Acid Sequence** |
|---|---|
| 5H12<br>VH5 (C33Y*)/Vκ4 | VH:<br>QVQLVQSGAEVKKPGASVKVSCKASGYSFTDYYINWVRQAPGQGLEWMGWIY<br>PGSGNTRYSERFKGRVTITRDTSASTAYMELSSLRSEDTAVYYCAREDYYPYH<br>GMDYWGQGTLVTVSS (SEQ ID NO: 77)<br>VL:<br>DIVMTQSPDSLAVSLGERATINCRASESVDGYDNSFMHWYQQKPGQPPKLLIFR<br>ASNLESGVPDRFSGSGSGTDFTLTISSLQAEDVAVYYCQQSSEDPWTFGQGTKL<br>EIK (SEQ ID NO: 80) |

*mutation positions are according to Kabat numbering of the respective VH sequences containing the mutations
**CDRs according to the Kabat numbering system are bolded In some embodiments, the humanized anti-TfR antibody of the present disclosure comprises a humanized VH comprising the CDR-H1, CDR-H2, and CDR-H3 of any one of the anti-TfR antibodies provided in Table 2 and comprises one or more (e.g., 1, 2, 3, 4, 5, 6, 7, 8, 9, 10 or more) amino acid variations in the framework regions as compared with the respective humanized VH provided in Table 3. Alternatively or in addition (e.g., in addition), the humanized anti-TfR antibody of the present disclosure comprises a humanized VL comprising the CDR-L1, CDR-L2, and CDR-L3 of any one of the anti-TfR antibodies provided in Table 2 and comprises one or more (e.g., 1, 2, 3, 4, 5, 6, 7, 8, 9, 10 or more) amino acid variations in the framework regions as compared with the respective humanized VL provided in Table 3.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 69, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 69 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 71, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 71 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 72, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 72 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 73, and/or (e.g., and) a humanized VL comprising an amino acid sequence that is at least 80% identical (e.g., 80%, 85%, 90%, 95%, 98%, or 99%) to SEQ ID NO: 74. In some embodiments, the humanized anti-TfR antibody of the present disclosure comprises a humanized VH comprising the amino acid sequence of SEQ ID NO: 73 and a humanized VL comprising the amino acid sequence of SEQ ID NO: 74.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 73, and/or (e.g., and) a humanized VL comprising an amino acid sequence that is at least 80% identical (e.g., 80%, 85%, 90%, 95%, 98%, or 99%) to SEQ ID NO: 75. In some embodiments, the humanized anti-TfR antibody of the present disclosure comprises a humanized VH comprising the amino acid sequence of SEQ ID NO: 73 and a humanized VL comprising the amino acid sequence of SEQ ID NO: 75.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 76, and/or (e.g., and) a humanized VL comprising an amino acid sequence that is at least 80% identical (e.g., 80%, 85%, 90%, 95%, 98%, or 99%) to SEQ ID NO: 74. In some embodiments, the humanized anti-TfR antibody of the present disclosure comprises a humanized VH comprising the amino acid sequence of SEQ ID NO: 76 and a humanized VL comprising the amino acid sequence of SEQ ID NO: 74.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 76, and/or (e.g., and) a humanized VL comprising an amino acid sequence that is at least 80% identical (e.g., 80%, 85%, 90%, 95%, 98%, or 99%) to SEQ ID NO: 75. In some embodiments, the humanized anti-TfR antibody of the present disclosure comprises a humanized VH comprising the amino acid sequence of SEQ ID NO: 76 and a humanized VL comprising the amino acid sequence of SEQ ID NO: 75.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 77, and/or (e.g., and) a humanized VL comprising an amino acid sequence that is at least 80% identical (e.g., 80%, 85%, 90%, 95%, 98%, or 99%) to SEQ ID NO: 78. In some embodiments, the humanized anti-TfR antibody of the present disclosure comprises a humanized VH comprising the amino acid sequence of SEQ ID NO: 77 and a humanized VL comprising the amino acid sequence of SEQ ID NO: 78.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 79, and/or (e.g., and) a humanized VL comprising an amino acid sequence that is at least 80% identical (e.g., 80%, 85%, 90%, 95%, 98%, or 99%) to SEQ ID NO: 80. In some embodiments, the humanized anti-TfR antibody of the present disclosure comprises a humanized VH comprising the amino acid sequence of SEQ ID NO: 79 and a humanized VL comprising the amino acid sequence of SEQ ID NO: 80.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 77, and/or (e.g., and) a humanized VL comprising an amino acid sequence that is at least 80% identical (e.g., 80%, 85%, 90%, 95%, 98%, or 99%) to SEQ ID NO: 80. In some embodiments, the humanized anti-TfR antibody of the present disclosure comprises a humanized VH comprising the amino acid sequence of SEQ ID NO: 77 and a humanized VL comprising the amino acid sequence of SEQ ID NO: 80.

In some embodiments, the humanized anti-TfR antibody described herein is a full-length IgG, which can include a heavy constant region and a light constant region from a human antibody. In some embodiments, the heavy chain of any of the anti-TfR antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An example of a human IgG1 constant region is given below:

(SEQ ID NO: 81)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In some embodiments, the heavy chain of any of the anti-TfR antibodies described herein comprises a mutant human IgG1 constant region. For example, the introduction of LALA mutations (a mutant derived from mAb b12 that has been mutated to replace the lower hinge residues Leu234 Leu235 with Ala234 and Ala235) in the CH2 domain of human IgG1 is known to reduce Fcγ receptor binding (Bruhns, P., et al. (2009) and Xu, D. et al. (2000)). The mutant human IgG1 constant region is provided below (mutations bonded and underlined):

(SEQ ID NO: 82)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPEAAGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In some embodiments, the light chain of any of the anti-TfR antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

(SEQ ID NO: 83)
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC

Other antibody heavy and light chain constant regions are well known in the art, e.g., those provided in the IMGT database (www.imgt.org) or at www.vbase2.org/vbstat.php., both of which are incorporated by reference herein.

In some embodiments, the humanized anti-TfR antibody described herein comprises a heavy chain comprising any one of the VH as listed in Table 3 or any variants thereof and a heavy chain constant region that is at least 80%, at least 85%, at least 90%, at least 95%, or at least 99% identical to SEQ ID NO: 81 or SEQ ID NO: 82. In some embodiments, the humanized anti-TfR antibody described herein comprises a heavy chain comprising any one of the VH as listed in Table 3 or any variants thereof and a heavy chain constant region that contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 81 or SEQ ID NO: 82. In some embodiments, the humanized anti-TfR antibody described herein comprises a heavy chain comprising any one of the VH as listed in Table 3 or any variants thereof and a heavy chain constant region as set forth in SEQ ID NO: 81. In some embodiments, the humanized anti-TfR antibody described herein comprises heavy chain comprising any one of the VH as listed in Table 3 or any variants thereof and a heavy chain constant region as set forth in SEQ ID NO: 82.

In some embodiments, the humanized anti-TfR antibody described herein comprises a light chain comprising any one of the VL as listed in Table 3 or any variants thereof and a light chain constant region that is at least 80%, at least 85%, at least 90%, at least 95%, or at least 99% identical to SEQ ID NO: 83. In some embodiments, the humanized anti-TfR antibody described herein comprises a light chain comprising any one of the VL as listed in Table 3 or any variants thereof and a light chain constant region contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 83. In some embodiments, the humanized anti-TfR antibody described herein comprises a light chain comprising any one of the VL as listed in Table 3 or any variants thereof and a light chain constant region set forth in SEQ ID NO: 83.

Examples of IgG heavy chain and light chain amino acid sequences of the anti-TfR antibodies described are provided in Table 4 below.

TABLE 4

Heavy chain and light chain sequences of examples of humanized anti-TfR IgGs

| Antibody | IgG Heavy Chain/Light Chain Sequences** |
|---|---|
| 3A4 VH3 (N54T*)/Vκ4 | Heavy Chain (with wild type human IgG1 constant region) EVQLVQSGSELKKPGASVKVSCTASGFNIKDDYMYWVRQPPGKGLEWIGWIDPE TGDTEYASKFQDRVTVTADTSTNTAYMELSSLRSEDTAVYYCTLWLRRGLDYW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 84) Light Chain (with kappa light chain constant region) DIVMTQSPLSLPVTPGEPASISCRSSKSLLHSNGYTYLFWFQQRPGQSPRLLIYRMS NLASGVPDRFSGSGSGTDFTLKISRVEAEDVGVYYCMQHLEYPFTFGGGTKVEIK RTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 85) |
| 3A4 VH3 (N54S*)/Vκ4 | Heavy Chain (with wild type human IgG1 constant region) EVQLVQSGSELKKPGASVKVSCTASGFNIKDDYMYWVRQPPGKGLEWIGWIDPE SGDTEYASKFQDRVTVTADTSTNTAYMELSSLRSEDTAVYYCTLWLRRGLDYW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 86) Light Chain (with kappa light chain constant region) DIVMTQSPLSLPVTPGEPASISCRSSKSLLHSNGYTYLFWFQQRPGQSPRLLIYRMS NLASGVPDRFSGSGSGTDFTLKISRVEAEDVGVYYCMQHLEYPFTFGGGTKVEIK RTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 85) |
| 3A4 VH3/Vκ4 | Heavy Chain (with wild type human IgG1 constant region) EVQLVQSGSELKKPGASVKVSCTASGFNIKDDYMYWVRQPPGKGLEWIGWIDPE NGDTEYASKFQDRVTVTADTSTNTAYMELSSLRSEDTAVYYCTLWLRRGLDYW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 87) Light Chain (with kappa light chain constant region) DIVMTQSPLSLPVTPGEPASISCRSSKSLLHSNGYTYLFWFQQRPGQSPRLLIYRMS NLASGVPDRFSGSGSGTDFTLKISRVEAEDVGVYYCMQHLEYPFTFGGGTKVEIK RTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 85) |
| 3M12 VH3/Vκ2 | Heavy Chain (with wild type human IgG1 constant region) QVQLQESGPGLVKPSQTLSLTCSVTGYSITSGYYWNWIRQPPGKGLEWMGYITFD GANNYNPSLKNRVSISRDTSKNQFSLKLSSVTAEDTATYYCTRSSYDYDVLDYWG QGTTVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 88) Light Chain (with kappa light chain constant region) DIQMTQSPSSLSASVGDRVTITCRASQDISNFLNWYQQKPGQPVKLLIYYTSRLHS GVPSRFSGSGSGTDFTLTISSLQPEDFATYFCQQGHTLPYTFGQGTKLEIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC (SEQ ID NO: 89) |
| 3M12 VH3/Vκ3 | Heavy Chain (with wild type human IgG1 constant region) QVQLQESGPGLVKPSQTLSLTCSVTGYSITSGYYWNWIRQPPGKGLEWMGYITFD GANNYNPSLKNRVSISRDTSKNQFSLKLSSVTAEDTATYYCTRSSYDYDVLDYWG QGTTVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN |

TABLE 4-continued

Heavy chain and light chain sequences of examples of humanized anti-TfR IgGs

| Antibody | IgG Heavy Chain/Light Chain Sequences** |
|---|---|
| | WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 88)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYTFGQGTKLEIKRTVAA<br>PSVFIFPPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 3M12<br>VH4/Vκ2 | Heavy Chain (with wild type human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPGK (SEQ ID NO: 91)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH4/Vκ3 | Heavy Chain (with wild type human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPGK (SEQ ID NO: 91)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYTFGQGTKLEIKRTVAA<br>PSVFIFPPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 5H12<br>VH5 (C33Y*)/Vκ3 | Heavy Chain (with wild type human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 92)<br>Light Chain (with kappa light chain constant region)<br>DIVLTQSPDSLAVSLGERATINCRASESVDGYDNSFMHWYQQKPGQPPKLLIFRAS<br>NLESGVPDRFSGSGSRTDFTLTISSLQAEDVAVYYCQQSSEDPWTFGQGTKLEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC (SEQ ID NO: 93) |
| 5H12<br>VH5 (C33D*)/Vκ4 | Heavy Chain (with wild type human IgG1 constant region)<br>QVQLVQSGAEVKKPGASVKVSCKASGYSFTDYDINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 94) |

TABLE 4-continued

Heavy chain and light chain sequences of examples of humanized anti-TfR IgGs

| Antibody | IgG Heavy Chain/Light Chain Sequences** |
|---|---|
| | Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ ID NO: 95) |
| 5H12<br>VH5 (C33Y*)/VK4 | Heavy Chain (with wild type human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 92)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ ID NO: 95) |

*mutation positions are according to Kabat numbering of the respective VH sequences containing the mutations
**CDRs according to the Kabat numbering system are bolded; VH/VL sequences underlined In some embodiments, the humanized anti-TfR antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 84, 86, 87, 88, 91, 92, and 94. Alternatively or in addition (e.g., in addition), the humanized anti-TfR antibody of the present disclosure comprises a light chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the light chain as set forth in any one of SEQ ID NOs: 85, 89, 90, 93, and 95.

In some embodiments, the humanized anti-TfR antibody described herein comprises a heavy chain comprising an amino acid sequence that is at least 75% (e.g., 75%, 80%, 85%, 90%, 95%, 98%, or 99%) identical to any one of SEQ ID NOs: 84, 86, 87, 88, 91, 92, and 94. Alternatively or in addition (e.g., in addition), the humanized anti-TfR antibody described herein comprises a light chain comprising an amino acid sequence that is at least 75% (e.g., 75%, 80%, 85%, 90%, 95%, 98%, or 99%) identical to any one of SEQ ID NOs: 85, 89, 90, 93, and 95. In some embodiments, the anti-TfR antibody described herein comprises a heavy chain comprising the amino acid sequence of any one of SEQ ID NOs: 84, 86, 87, 88, 91, 92, and 94. Alternatively or in addition (e.g., in addition), the anti-TfR antibody described herein comprises a light chain comprising the amino acid sequence of any one of SEQ ID NOs: 85, 89, 90, 93, and 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 84, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 84 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 86, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 86 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 87, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 87 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 88, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 88 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 88, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 88 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 91, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 91 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 91, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 91 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 92, and/or (e.g., and) a light chain comprising an amino acid sequence that is at least 80% identical (e.g., 80%, 85%, 90%, 95%, 98%, or 99%) to SEQ ID NO: 93. In some embodiments, the humanized anti-TfR antibody of the present disclosure comprises a heavy chain comprising the amino acid sequence of SEQ ID NO: 92 and a light chain comprising the amino acid sequence of SEQ ID NO: 93.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 94, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 94 and a light chain comprising the amino acid sequence of SEQ ID NO: 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 92, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 92 and a light chain comprising the amino acid sequence of SEQ ID NO: 95.

In some embodiments, the anti-TfR antibody is a Fab fragment, Fab' fragment, or F(ab')$_2$ fragment of an intact antibody (full-length antibody). Antigen binding fragment of an intact antibody (full-length antibody) can be prepared via routine methods (e.g., recombinantly or by digesting the heavy chain constant region of a full length IgG using an enzyme such as papain). For example, F(ab')$_2$ fragments can be produced by pepsin or papain digestion of an antibody molecule, and Fab' fragments that can be generated by reducing the disulfide bridges of F(ab')$_2$ fragments. In some embodiments, a heavy chain constant region in a Fab fragment of the anti-TfR1 antibody described herein comprises the amino acid sequence of:

(SEQ ID NO: 96)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHT

In some embodiments, the humanized anti-TfR antibody described herein comprises a heavy chain comprising any one of the VH as listed in Table 3 or any variants thereof and a heavy chain constant region that is at least 80%, at least 85%, at least 90%, at least 95%, or at least 99% identical to SEQ ID NO: 96. In some embodiments, the humanized anti-TfR antibody described herein comprises a heavy chain comprising any one of the VH as listed in Table 3 or any variants thereof and a heavy chain constant region that contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 96. In some embodiments, the humanized anti-TfR antibody described herein comprises a heavy chain comprising any one of the VH as listed in Table 3 or any variants thereof and a heavy chain constant region as set forth in SEQ ID NO: 96.

In some embodiments, the humanized anti-TfR antibody described herein comprises a light chain comprising any one of the VL as listed in Table 3 or any variants thereof and a light chain constant region that is at least 80%, at least 85%, at least 90%, at least 95%, or at least 99% identical to SEQ ID NO: 83. In some embodiments, the humanized anti-TfR antibody described herein comprises a light chain comprising any one of the VL as listed in Table 3 or any variants thereof and a light chain constant region contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 83. In some embodiments, the humanized anti-TfR antibody described herein comprises a light chain comprising any one of the VL as listed in Table 3 or any variants thereof and a light chain constant region set forth in SEQ ID NO: 83.

Examples of Fab heavy chain and light chain amino acid sequences of the anti-TfR antibodies described are provided in Table 5 below.

TABLE 5

Heavy chain and light chain sequences of examples of humanized anti-TfR Fabs

| Antibody | Fab Heavy Chain/Light Chain Sequences** |
|---|---|
| 3A4<br>VH3 (N54T*)/Vκ4 | Heavy Chain (with partial human IgG1 constant region)<br>EVQLVQSGSELKKPGASVKVSCTASGFNI KDDYMYWVRQPPGKGLEWIGWIDPE<br>TGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 97)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3A4<br>VH3 (N54S*)/Vκ4 | Heavy Chain (with partial human IgG1 constant region)<br>EVQLVQSGSELKKPGASVKVSCTASGFNI KDDYMYWVRQPPGKGLEWIGWIDPE<br>SGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 98)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3A4<br>VH3/Vκ4 | Heavy Chain (with partial human IgG1 constant region)<br>EVQLVQSGSELKKPGASVKVSCTASGFNI KDDYMYWVRQPPGKGLEWIGWIDPE<br>NGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 99)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3M12<br>VH3/Vκ2 | Heavy Chain (with partial human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHT (SEQ ID NO: 100)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH3/Vκ3 | Heavy Chain (with partial human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHT (SEQ ID NO: 100)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYTFGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 3M12<br>VH4/Vκ2 | Heavy Chain (with partial human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHT (SEQ ID NO: 101)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |

TABLE 5-continued

Heavy chain and light chain sequences of examples of humanized anti-TfR Fabs

| Antibody | Fab Heavy Chain/Light Chain Sequences** |
|---|---|
| 3M12<br>VH4/Vκ3 | Heavy Chain (with partial human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHT (SEQ ID NO: 101)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYTFGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 5H12<br>VH5 (C33Y*)/Vκ3 | Heavy Chain (with partial human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 102)<br>Light Chain (with kappa light chain constant region)<br>DIVLTQSPDSLAVSLGERATINCRASESVDGYDNSFMHWYQQKPGQPPKLLIFRAS<br>NLESGVPDRFSGSGSRTDFTLTISSLQAEDVAVYYCQQSSEDPWTFGQGTKLEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC (SEQ ID NO: 93) |
| 5H12<br>VH5 (C33D*)/Vκ4 | Heavy Chain (with partial human IgG1 constant region)<br>QVQLVQSGAEVKKPGASVKVSCKASGYSFTDYDINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 103)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ ID NO: 95) |
| 5H12<br>VH5 (C33Y*)/Vκ4 | Heavy Chain (with partial human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 102)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ ID NO: 95) |

*mutation positions are according to Kabat numbering of the respective VH sequences containing the mutations
**CDRs according to the Kabat numbering system are bolded; VH/VL sequences underlined In some embodiments, the humanized anti-TfR antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 97-103. Alternatively or in addition (e.g., in addition), the humanized anti-TfR antibody of the present disclosure comprises a light chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the light chain as set forth in any one of SEQ ID NOs: 85, 89, 90, 93, and 95.

In some embodiments, the humanized anti-TfR antibody described herein comprises a heavy chain comprising an amino acid sequence that is at least 75% (e.g., 75%, 80%, 85%, 90%, 95%, 98%, or 99%) identical to any one of SEQ ID NOs: 97-103. Alternatively or in addition (e.g., in addition), the humanized anti-TfR antibody described herein comprises a light chain comprising an amino acid sequence that is at least 75% (e.g., 75%, 80%, 85%, 90%, 95%, 98%, or 99%) identical to any one of SEQ ID NOs: 85, 89, 90, 93, and 95. In some embodiments, the anti-TfR antibody described herein comprises a heavy chain comprising the amino acid sequence of any one of SEQ ID NOs: 97-103. Alternatively or in addition (e.g., in addition), the anti-TfR antibody described herein comprises a light chain comprising the amino acid sequence of any one of SEQ ID NOs: 85, 89, 90, 93, and 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 97, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 97 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 98, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 98 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 99, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 99 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 100, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 100 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 100, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 100 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 101, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 101 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 101, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 101 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 102, and/or (e.g., and) a light chain comprising an amino acid sequence that is at least 80% identical (e.g., 80%, 85%, 90%, 95%, 98%, or 99%) to SEQ ID NO: 93. In some embodiments, the humanized anti-TfR antibody of the present disclosure comprises a heavy chain comprising the amino acid sequence of SEQ ID NO: 102 and a light chain comprising the amino acid sequence of SEQ ID NO: 93.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 103, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 103 and a light chain comprising the amino acid sequence of SEQ ID NO: 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 102, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 102 and a light chain comprising the amino acid sequence of SEQ ID NO: 95.

In some embodiments, the humanized anti-TfR receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, humanized the anti-TfR antibody described herein is a scFv. In some embodiments, the humanized anti-TfR antibody described herein is a scFv-Fab (e.g., scFv fused to a portion of a constant region). In some embodiments, the anti-TfR receptor antibody described herein is a scFv fused to a constant region (e.g., human IgG1 constant region as set forth in SEQ ID NO: 81 or SEQ ID NO: 82, or a portion thereof such as the Fc portion) at either the N-terminus of C-terminus.

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of an anti-TfR antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to alter one or more functional properties of the antibody, such as serum half-life, complement fixation, Fc receptor binding and/or (e.g., and) antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-anti-TfR antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or (e.g., and) the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-anti-TfR antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of an anti-TfR antibody described herein can be replaced with a different amino acid residue such that the antibody has altered C1q binding and/or (e.g., and) reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or (e.g., and) to increase the affinity of the antibody for an Fcγ receptor. This approach is described further in International Publication No. WO 00/42072.

In some embodiments, the heavy and/or (e.g., and) light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, any one of the anti-TfR1 antibodies described herein may comprise a signal peptide in the heavy and/or (e.g., and) light chain sequence (e.g., a N-terminal signal peptide). In some embodiments, the anti-TfR1 antibody described herein comprises any one of the VH and VL sequences, any one of the IgG heavy chain and light chain sequences, or any one of the Fab heavy chain and light chain sequences described herein, and further comprises a signal peptide (e.g., a N-terminal signal peptide). In some embodiments, the signal peptide comprises the amino acid sequence of MGWSCIILFLVATATGVHS (SEQ ID NO: 104).

Other Known Anti-Transferrin Receptor Antibodies

Any other appropriate anti-transferrin receptor antibodies known in the art may be used as the muscle-targeting agent in the complexes disclosed herein. Examples of known anti-transferrin receptor antibodies, including associated references and binding epitopes, are listed in Table 6. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 6.

TABLE 8

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |
| (From Genentech) 7A4, 8A2, 15D2, 10D11, 7B10, 15G11, 16G5, 13C3, 16G4, 16F6, 7G7, 4C2, 1B12, and 13D4 | WO 2016/081643, filed May 26, 2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. patent application 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A Streptococcus invasion. Cellular microbiology. 16:1806-21. | |
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | U.S. patent application 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |

TABLE 8-continued

List of anti-transferrin receptor antibody clones, including associated
references and binding epitope information.

| Antibody Clone Name | Reference(s) | Epitope/Notes |
|---|---|---|
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I. S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 (BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K. C. et al. "Transferrin receptors in human tissues: their distribution and possible clinical relevance." J Clin Pathol. 1983 May; 36(5):539-45. | |

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 6. In some embodiments, transferrin receptor antibodies include the CDR-H1, CDR-H2, and CDR-H3 as provided for any one of the anti-transferrin receptor antibodies selected from Table 6. In some embodiments, anti-transferrin receptor antibodies include the CDR-L1, CDR-L2, and CDR-L3 as provided for any one of the anti-transferrin receptor antibodies selected from Table 6. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 6. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 6. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or (e.g., and) light chain CDR3s of any one of the anti-transferrin receptor antibodies selected from Table 6.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/or (e.g., and) CDR-L3 sequences from one of the anti-transferrin receptor antibodies selected from Table 6. In some embodiments, the position of one or more CDRs along the VH (e.g., CDR-H1, CDR-H2, or CDR-H3) and/or (e.g., and) VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or (e.g., and) C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or (e.g., and) VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or (e.g., and) CDR-H3 described herein may be one, two, three, four, five or more amino acids shorter than one or more of the CDRs described herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or (e.g., and) CDR-H3 described herein may be one, two, three, four, five or more amino acids longer than one or more of the CDRs described herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or (e.g., and) CDR-H3 described herein can be extended by one, two, three, four, five or more amino acids compared to one or more of the CDRs described herein (e.g., CDRs from any of the anti-transferrin receptor antibodies selected from Table 6) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or (e.g., and) CDR-H3 described herein can be extended by one, two, three, four, five or more amino acids compared to one or more of the CDRs described herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or (e.g., and) CDR-H3 described herein can be shortened by one, two, three, four, five or more amino acids compared to one or more of the CDRs described herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or (e.g., and) CDR-H3 described herein can be shortened by one, two, three, four, five or more amino acids compared to one or more of the CDRs described herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 6. For example, the antibodies may include one or more CDR sequence(s) from any of the anti-transferrin receptor antibodies selected from Table 6 containing up to 5, 4, 3, 2, or 1 amino acid residue variations as compared to the corresponding CDR region in any one of the CDRs provided herein (e.g., CDRs from any of the anti-transferrin receptor antibodies selected from Table 6) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or (e.g., and) light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 6. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 6.

In some embodiments, anti-transferrin receptor antibodies of the disclosure include any antibody that includes a heavy chain variable domain and/or (e.g., and) a light chain variable domain of any anti-transferrin receptor antibody, such as any one of the anti-transferrin receptor antibodies selected from Table 6. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 6.

Aspects of the disclosure provide anti-transferrin receptor antibodies having a heavy chain variable (VH) and/or (e.g., and) a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 6. In some embodiments, the homologous heavy chain variable and/or (e.g., and) a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or (e.g., and) a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 6.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 6. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 6. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 6. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 6. In some embodiments, the light chain variable framework region that is derived from said amino acid sequence consists of said amino acid sequence but for the presence of up to 10 amino acid substitutions, deletions, and/or (e.g., and) insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 6. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 6. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 6. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 6.

In some embodiments, the anti-transferrin receptor antibody is any anti-transferrin receptor antibody, such as any one of the anti-transferrin receptor antibodies selected from Table 6.

In some embodiments, an anti-transferrin receptor antibody comprises a VL domain comprising the amino acid sequence of any anti-transferrin receptor antibody, such as any one of the anti-transferrin receptor antibodies selected from Table 6, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, the muscle-targeting agent is a transferrin receptor antibody (e.g., the antibody and variants thereof as described in International Application Publication WO 2016/081643, incorporated herein by reference).

The heavy chain and light chain CDRs of the antibody according to different definition systems are provided in Table 7. The different definition systems, e.g., the Kabat definition, the Chothia definition, and/or (e.g., and) the contact definition have been described. See, e.g., (e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

TABLE 7

Heavy chain and light chain CDRs of a mouse transferrin receptor antibody

| CDRs | Kabat | Chothia | Contact |
|---|---|---|---|
| CDR-H1 | SYWMH (SEQ ID NO: 110) | GYTFTSY (SEQ ID NO: 116) | TSYWMH (SEQ ID NO: 118) |
| CDR-H2 | EINPTNGRTNYIEKFKS (SEQ ID NO: 111) | NPTNGR (SEQ ID NO: 117) | WIGEINPTNGRTN (SEQ ID NO: 119) |
| CDR-H3 | GTRAYHY (SEQ ID NO: 112) | GTRAYHY (SEQ ID NO: 112) | ARGTRA (SEQ ID NO: 120) |
| CDR-L1 | RASDNLYSNLA (SEQ ID NO: 113) | RASDNLYSNLA (SEQ ID NO: 113) | YSNLAWY (SEQ ID NO: 121) |

TABLE 7-continued

Heavy chain and light chain CDRs of a mouse transferrin receptor antibody

| CDRs | Kabat | Chothia | Contact |
|---|---|---|---|
| CDR-L2 | DATNLAD (SEQ ID NO: 114) | DATNLAD (SEQ ID NO: 114) | LLVYDATNLA (SEQ ID NO: 122) |
| CDR-L3 | QHFWGTPLT (SEQ ID NO: 115) | QHFWGTPLT (SEQ ID NO: 115) | QHFWGTPL (SEQ ID NO: 123) |

The heavy chain variable domain (VH) and light chain variable domain sequences are also provided:

VH
(SEQ ID NO: 124)
QVQLQQPGAELVKPGASVKLSCKASGYTFTSYWMHWVKQRPGQGLEWIG

EINPTNGRTNYIEKFKSKATLTVDKSSSTAYMQLSSLTSEDSAVYYCAR

GTRAYHYWGQGTSVTVSS

VL
(SEQ ID NO: 125)
DIQMTQSPASLSVSVGETVTITCRASDNLYSNLAWYQQKQGKSPQLLVY

DATNLADGVPSRFSGSGSGTQYSLKINSLQSEDFGTYYCQHFWGTPLTF

GAGTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 7. Alternatively or in addition (e.g., in addition), the transferrin receptor antibody of the present disclosure comprises a CDR-L1, a CDR-L2, and a CDR-L3 that are the same as the CDR-L1, CDR-L2, and CDR-L3 shown in Table 7.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 7. "Collectively" means that the total number of amino acid variations in all of the three heavy chain CDRs is within the defined range. Alternatively or in addition (e.g., in addition), the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 7.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 7. Alternatively or in addition (e.g., in addition), the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 7.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 7. In some embodiments, the transferrin receptor antibody of the present disclosure comprises a CDR-L3 containing one amino acid variation as compared with the CDR-L3 as shown in Table 7. In some embodiments, the transferrin receptor antibody of the present disclosure comprises a CDR-L3 of QHFAGTPLT (SEQ ID NO: 126) according to the Kabat and Chothia definition system) or QHFAGTPL (SEQ ID NO: 127) according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 7, and comprises a CDR-L3 of QHFAGTPLT (SEQ ID NO: 126) according to the Kabat and Chothia definition system) or QHFAGTPL (SEQ ID NO: 127) according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 7. Alternatively or in addition (e.g., in addition), the transferrin receptor antibody of the present disclosure comprises light chain CDRs that collectively are at least 80% (e.g., 80%, 85%, 90%, 95%, or 98%) identical to the light chain CDRs as shown in Table 7.

In some embodiments, the transferrin receptor antibody of the present disclosure comprises a VH comprising the amino acid sequence of SEQ ID NO: 124. Alternatively or in addition (e.g., in addition), the transferrin receptor antibody of the present disclosure comprises a VL comprising the amino acid sequence of SEQ ID NO: 125.

In some embodiments, the transferrin receptor antibody of the present disclosure comprises a VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 124. Alternatively or in addition (e.g., in addition), the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 125.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 124. Alternatively or in addition (e.g., in addition), the transferrin receptor antibody of the present disclosure comprises a VL comprising an amino acid sequence that is at least 80% (e.g., 80%, 85%, 90%, 95%, or 98%) identical to the VL as set forth in SEQ ID NO: 125.

In some embodiments, the transferrin receptor antibody of the present disclosure is a humanized antibody (e.g., a humanized variant of an antibody). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 7, and comprises a humanized heavy chain variable region and/or (e.g., and) a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 7) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 125, and/or (e.g., and) one or more amino acid substitutions at positions 1, 5, 7, 11, 12, 20, 38, 40, 44, 66, 75, 81, 83, 87, and 108 as compared with the VH as set forth in SEQ ID NO: 124. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 125, and/or (e.g., and) amino acid substitutions at all of positions 1, 5, 7, 11, 12, 20, 38, 40, 44, 66, 75, 81, 83, 87, and 108 as compared with the VH as set forth in SEQ ID NO: 124.

In some embodiments, the transferrin receptor antibody of the present disclosure is a humanized antibody and contains the residues at positions 43 and 48 of the VL as set forth in SEQ ID NO: 125. Alternatively or in addition (e.g., in addition), the transferrin receptor antibody of the present disclosure is a humanized antibody and contains the residues at positions 48, 67, 69, 71, and 73 of the VH as set forth in SEQ ID NO: 124.

The VH and VL amino acid sequences of an example humanized antibody that may be used in accordance with the present disclosure are provided:

Humanized VH
(SEQ ID NO: 128)
EVQLVQSGAEVKKPGASVKVSCKASGYTFTSYWMHWVRQAPGQRLEWIG

EINPTNGRTNYIEKFKSRATLTVDKSASTAYMELSSLRSEDTAVYYCAR

GTRAYHYWGQGTMVTVSS

Humanized VL
(SEQ ID NO: 129)
DIQMTQSPSSLSASVGDRVTITCRASDNLYSNLAWYQQKPGKSPKLLVY

DATNLADGVPSRFSGSGSGTDYTLTISSLQPEDFATYYCQHFWGTPLTF

GQGTKVEIK

In some embodiments, the transferrin receptor antibody of the present disclosure comprises a VH comprising the amino acid sequence of SEQ ID NO: 128. Alternatively or in addition (e.g., in addition), the transferrin receptor antibody of the present disclosure comprises a VL comprising the amino acid sequence of SEQ ID NO: 129.

In some embodiments, the transferrin receptor antibody of the present disclosure comprises a VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 128. Alternatively or in addition (e.g., in addition), the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 129.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 128. Alternatively or in addition (e.g., in addition), the transferrin receptor antibody of the present disclosure comprises a VL comprising an amino acid sequence that is at least 80% (e.g., 80%, 85%, 90%, 95%, or 98%) identical to the VL as set forth in SEQ ID NO: 129.

In some embodiments, the transferrin receptor antibody of the present disclosure is a humanized variant comprising amino acid substitutions at one or more of positions 43 and 48 as compared with the VL as set forth in SEQ ID NO: 125, and/or (e.g., and) amino acid substitutions at one or more of positions 48, 67, 69, 71, and 73 as compared with the VH as set forth in SEQ ID NO: 124. In some embodiments, the transferrin receptor antibody of the present disclosure is a humanized variant comprising a S43A and/or (e.g., and) a V48L mutation as compared with the VL as set forth in SEQ ID NO: 125, and/or (e.g., and) one or more of A67V, L69I, V71R, and K73T mutations as compared with the VH as set forth in SEQ ID NO: 124.

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 125, and/or (e.g., and) amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 124.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or (e.g., and) the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or (e.g., and) the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An example of human IgG1 constant region is given below:

```
                                       (SEQ ID NO: 130)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                        (SEQ ID NO: 83)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC
```

Other antibody heavy and light chain constant regions are well known in the art, e.g., those provided in the IMGT database (www.imgt.org) or at www.vbase2.org/vbstat.php., both of which are incorporated by reference herein.

Examples of heavy chain and light chain amino acid sequences of the transferrin receptor antibodies described are provided below:

```
Heavy Chain (VH + human IgG1 constant region)
                                        (SEQ ID NO: 132)
QVQLQQPGAELVKPGASVKLSCKASGYTFTSYWMHWVKQRPGQGLEWIG

EINPTNGRTNYIEKFKSKATLTVDKSSSTAYMQLSSLTSEDSAVYYCAR

GTRAYHYWGQGTSVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Light Chain (VL + kappa light chain)
                                        (SEQ ID NO: 133)
DIQMTQSPASLSVSVGETVTITCRASDNLYSNLAWYQQKQGKSPQLLVY

DATNLADGVPSRFSGSGSGTQYSLKINSLQSEDFGTYYCQHFWGTPLTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy Chain (humanized VH + human IgG1 constant
region)
                                        (SEQ ID NO: 134)
EVQLVQSGAEVKKPGASVKVSCKASGYTFTSYWMHWVRQAPGQRLEWIG

EINPTNGRTNYIEKFKSRATLTVDKSASTAYMELSSLRSEDTAVYYCAR

GTRAYHYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Light Chain (humanized VL + kappa light chain)
                                        (SEQ ID NO: 135)
DIQMTQSPSSLSASVGDRVTITCRASDNLYSNLAWYQQKPGKSPKLLVY

DATNLADGVPSRFSGSGSGTDYTLTISSLQPEDFATYYCQHFWGTPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

In some embodiments, the transferrin receptor antibody described herein comprises a heavy chain comprising an amino acid sequence that is at least 80% (e.g., 80%, 85%, 90%, 95%, or 98%) identical to SEQ ID NO: 132. Alternatively or in addition (e.g., in addition), the transferrin receptor antibody described herein comprises a light chain comprising an amino acid sequence that is at least 80% (e.g., 80%, 85%, 90%, 95%, or 98%) identical to SEQ ID NO: 133. In some embodiments, the transferrin receptor antibody described herein comprises a heavy chain comprising the amino acid sequence of SEQ ID NO: 132. Alternatively or in addition (e.g., in addition), the transferrin receptor antibody described herein comprises a light chain comprising the amino acid sequence of SEQ ID NO: 133.

In some embodiments, the transferrin receptor antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 132. Alternatively or in addition (e.g., in addition), the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 133.

In some embodiments, the transferrin receptor antibody described herein comprises a heavy chain comprising an amino acid sequence that is at least 80% (e.g., 80%, 85%, 90%, 95%, or 98%) identical to SEQ ID NO: 134. Alternatively or in addition (e.g., in addition), the transferrin receptor antibody described herein comprises a light chain comprising an amino acid sequence that is at least 80% (e.g., 80%, 85%, 90%, 95%, or 98%) identical to SEQ ID NO: 135. In some embodiments, the transferrin receptor antibody described herein comprises a heavy chain comprising the amino acid sequence of SEQ ID NO: 134. Alternatively or in addition (e.g., in addition), the transferrin receptor antibody described herein comprises a light chain comprising the amino acid sequence of SEQ ID NO: 135.

In some embodiments, the transferrin receptor antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain of humanized antibody as set forth in SEQ ID NO: 134. Alternatively or in addition (e.g., in addition), the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 135.

In some embodiments, the transferrin receptor antibody is an antigen binding fragment (Fab) of an intact antibody (full-length antibody). Antigen binding fragment of an intact antibody (full-length antibody) can be prepared via routine methods. For example, F(ab')2 fragments can be produced by pepsin digestion of an antibody molecule, and Fab' fragments that can be generated by reducing the disulfide bridges of F(ab')2 fragments. Examples of Fab amino acid sequences of the transferrin receptor antibodies described herein are provided below:

```
Heavy Chain Fab (VH + a portion of human IgG1
constant region)
                                       (SEQ ID NO: 136)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain Fab (humanized VH + a portion of human
IgG1 constant region)
                                       (SEQ ID NO: 137)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP
```

In some embodiments, the transferrin receptor antibody described herein comprises a heavy chain comprising the amino acid sequence of SEQ ID NO: 136. Alternatively or in addition (e.g., in addition), the transferrin receptor antibody described herein comprises a light chain comprising the amino acid sequence of SEQ ID NO: 133.

In some embodiments, the transferrin receptor antibody described herein comprises a heavy chain comprising the amino acid sequence of SEQ ID NO: 137. Alternatively or in addition (e.g., in addition), the transferrin receptor antibody described herein comprises a light chain comprising the amino acid sequence of SEQ ID NO: 135.

The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 130).

In some embodiments, any one of the anti-TfR antibodies described herein is produced by recombinant DNA technology in Chinese hamster ovary (CHO) cell suspension culture, optionally in CHO-K1 cell (e.g., CHO-K1 cells derived from European Collection of Animal Cell Culture, Cat. No. 85051005) suspension culture.

In some embodiments, an antibody provided herein may have one or more post-translational modifications. In some embodiments, N-terminal cyclization, also called pyroglutamate formation (pyro-Glu), may occur in the antibody at N-terminal Glutamate (Glu) and/or Glutamine (Gln) residues during production. As such, it should be appreciated that an antibody specified as having a sequence comprising an N-terminal glutamate or glutamine residue encompasses antibodies that have undergone pyroglutamate formation resulting from a post-translational modification. In some embodiments, pyroglutamate formation occurs in a heavy chain sequence. In some embodiments, pyroglutamate formation occurs in a light chain sequence.

b. Other Muscle-Targeting Antibodies

In some embodiments, the muscle-targeting antibody is an antibody that specifically binds hemojuvelin, caveolin-3, Duchenne muscular dystrophy peptide, myosin IIb, or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to alter one or more functional properties of the antibody, such as serum half-life, complement fixation, Fc receptor binding and/or (e.g., and) antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or (e.g., and) the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered C1q binding and/or (e.g., and) reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or (e.g., and) to increase the affinity of the antibody for an Fcγ receptor. This approach is described further in International Publication No. WO 00/42072.

In some embodiments, the heavy and/or (e.g., and) light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" Biochim Biophys Acta 2008, 1786: 126-38; Jarver P., et al., "In vivo biodistribution and efficacy of peptide mediated delivery" Trends Pharmacol Sci 2010; 31: 528-35; Samoylova T. I., et al., "Elucidation of muscle-binding peptides by phage display screening" Muscle Nerve 1999; 22: 460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." Biomol Eng 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 138) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 138). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." Int J Pharm 2002; 231: 177-84; the entire contents of which are hereby incorporated by reference. Here, a 12 amino acid peptide having the sequence SKTFNTHPQSTP (SEQ ID NO: 139) was identified and this muscle-targeting peptide showed improved binding to C2C12 cells relative to the ASSLNIA (SEQ ID NO: 138) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" *J Virol* 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEH-KEEELI (SEQ ID NO: 140) appeared most frequently. Accordingly, in some embodiments, the muscle-targeting agent comprises the amino acid sequence TARGEHKEEELI (SEQ ID NO: 140).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or (e.g., and) derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cai, D. "BDNF-mediated enhancement of inflammation and injury in the aging heart." Physiol Genomics. 2006, 24:3, 191-7.; Zhang, L. "Molecular profiling of heart endothelial cells." Circulation, 2005, 112:11, 1601-11.; McGuire, M. J. et al. "In vitro selection of a peptide with high selectivity for cardiomyocytes in vivo." J Mol Biol. 2004, 342:1, 171-82.). Exemplary muscle-targeting peptides comprise an amino acid sequence of the following group: CQAQGQLVC (SEQ ID NO: 141), CSERSMNFC (SEQ ID NO: 142), CPKTRRVPC (SEQ ID NO: 143), WLSEAGPVVTVRALRGTGSW (SEQ ID NO: 144), ASSLNIA (SEQ ID NO: 138), CMQHSMRVC (SEQ ID NO: 145), and DDTRHWG (SEQ ID NO: 146). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include 3-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147.).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or (e.g., and) derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20.; Germer, K. et al. "RNA aptamers and their therapeutic and diagnostic applications." Int. J. Biochem. Mol. Biol. 2013; 4: 27-40.). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214.; Thiel, W. H. et al. "Smooth Muscle Cell-targeted RNA Aptamer Inhibits Neointimal Formation." Mol Ther. 2016, 24:4, 779-87.). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or (e.g., and) lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a DMPK allele comprising a disease-associated-repeat expansion. Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to caused degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Examples of oligonucleotides useful for targeting DMPK are provided in US Patent Application Publication 20100016215A1, published on Jan. 1, 2010, entitled Compound And Method For Treating Myotonic Dystrophy; US Patent Application Publication 20130237585A1, published Jul. 19, 2010, Modulation Of Dystrophia Myotonica-Protein Kinase (DMPK) Expression; US Patent Application Publication 20150064181A1, published on Mar. 5, 2015, entitled "Antisense Conjugates For Decreasing Expression Of Dmpk"; US Patent Application Publication 20150238627A1, published on Aug. 27, 2015, entitled "Peptide-Linked Morpholino Antisense Oligonucleotides For Treatment Of Myotonic Dystrophy"; and US Patent Application Publication 20160304877A1, published on Oct. 20, 2016, entitled "Compounds And Methods For Modulation Of Dystrophia Myotonica-Protein Kinase (Dmpk) Expression," the contents of each of which are incorporated herein in their entireties.

Examples of oligonucleotides for promoting DMPK gene editing include US Patent Application Publication 20170088819A1, published on Mar. 3, 2017, entitled "Genetic Correction Of Myotonic Dystrophy Type 1"; and International Patent Application Publication WO18002812A1, published on Apr. 1, 2018, entitled "Materials And Methods For Treatment Of Myotonic Dystrophy Type 1 (DM1) And Other Related Disorders," the contents of each of which are incorporated herein in their entireties.

In some embodiments, oligonucleotides may have a region of complementarity to a sequence set forth as follows, which is an example human DMPK gene sequence (Gene ID 1760; NM_001081560.2):

(SEQ ID NO: 131)
AGGGGGGCTGGACCAAGGGGTGGGGAGAAGGGGAGGAGGCCTCGGCCGGC

CGCAGAGAGAAGTGGCCAGAGAGGCCCAGGGGACAGCCAGGGACAGGCAG

ACATGCAGCCAGGGCTCCAGGGCCTGGACAGGGGCTGCCAGGCCCTGTGA

CAGGAGGACCCCGAGCCCCCGGCCCGGGGAGGGGCCATGGTGCTGCCTGT

CCAACATGTCAGCCGAGGTGCGGCTGAGGCGGCTCCAGCAGCTGGTGTTG

GACCCGGGCTTCCTGGGGCTGGAGCCCCTGCTCGACCTTCTCCTGGGCGT

CCACCAGGAGCTGGGCGCCTCCGAACTGGCCCAGGACAAGTACGTGGCCG

ACTTCTTGCAGTGGGCGGAGCCCATCGTGGTGAGGCTTAAGGAGGTCCGA

CTGCAGAGGGACGACTTCGAGATTCTGAAGGTGATCGGACGCGGGCGTT

CAGCGAGGTAGCGGTAGTGAAGATGAAGCAGACGGGCCAGGTGTATGCCA

TGAAGATCATGAACAAGTGGGACATGCTGAAGAGGGGCGAGGTGTCGTGC

TTCCGTGAGGAGAGGGACGTGTTGGTGAATGGGGACCGGCGGTGGATCAC

GCAGCTGCACTTCGCCTTCCAGGATGAGAACTACCTGTACCTGGTCATGG

AGTATTACGTGGGCGGGGACCTGCTGACACTGCTGAGCAAGTTTGGGGAG

CGGATTCCGGCCGAGATGGCGCGCTTCTACCTGGCGGAGATTGTCATGGC

CATAGACTCGGTGCACCGGCTTGGCTACGTGCACAGGGACATCAAACCCG

ACAACATCCTGCTGGACCGCTGTGGCCACATCCGCCTGGCCGACTTCGGC

TCTTGCCTCAAGCTGCGGGCAGATGGAACGGTGCGGTCGCTGGTGGCTGT

GGGCACCCCAGACTACCTGTCCCCCGAGATCCTGCAGGCTGTGTGGGCGGTG

GGCCTGGGACAGGCAGCTACGGGCCCGAGTGTGACTGGTGGGCGCTGGGT

GTATTCGCCTATGAAATGTTCTATGGGCAGACGCCCTTCTACGCGGATTC

CACGGCGGAGACCTATGGCAAGATCGTCCACTACAAGGAGCACCTCTCTC

TGCCGCTGGTGGACGAAGGGGTCCCTGAGGAGGCTCGAGACTTCATTCAG

CGGTTGCTGTGTCCCCCGGAGACACGGCTGGGCCGGGGTGGAGCAGGCGA

CTTCCGGACACATCCCTTCTTCTTTGGCCTCGACTGGGATGGTCTCCGGG

ACAGCGTGCCCCCCTTTACACCGGATTTCGAAGGTGCCACCGACACATGC

AACTTCGACTTGGTGGAGGACGGGCTCACTGCCATGGAGACACTGTCGGA

CATTCGGGAAGGTGCGCCGCTAGGGGTCCACCTGCCTTTTGTGGGCTACT

CCTACTCCTGCATGGCCCTCAGGGACAGTGAGGTCCCAGGCCCCACACCC

ATGGAACTGGAGGCCGAGCAGCTGCTTGAGCCACACGTGCAAGCGCCCAG

CCTGGAGCCCTCGGTGTCCCCACAGGATGAAACAGCTGAAGTGGCAGTTC

CAGCGGCTGTCCCTGCGGCAGAGGCTGAGGCCGAGGTGACGCTGCGGAG

CTCCAGGAAGCCCTGGAGGAGGAGGTGCTCACCCGGCAGAGCCTGAGCCG

GGAGATGGAGGCCATCCGCACGGACAACCAGAACTTCGCCAGTCAACTAC

GCGAGGCAGAGGCTCGGAACCGGGACCTAGAGGCACACGTCCGGCAGTTG

CAGGAGCGGATGGAGTTGCTGCAGGCAGAGGGAGCCACAGCTGTCACGGG

GGTCCCCAGTCCCCGGGCCACGGATCCACCTTCCCATCTAGATGGCCCCC

CGGCCGTGGCTGTGGGCCAGTGCCCGCTGGTGGGGCCAGGCCCCATGCAC

CGCCGCCACCTGCTGCTCCCTGCCAGGGTCCCTAGGCCTGGCCTATCGGA

GGCGCTTTCCCTGCTCCTGTTCGCCGTTGTTCTGTCTCGTGCCGCCGCCC

TGGGCTGCATTGGGTTGGTGGCCCACGCCGGCCAACTCACCGCAGTCTGG

CGCCGCCCAGGAGCCGCCCGCGCTCCCTGAACCCTAGAACTGTCTTCGAC

TCCGGGGCCCCGTTGGAAGACTGAGTGCCCGGGGCACGGCACAGAAGCCG

CGCCCACCGCCTGCCAGTTCACAACCGCTCCGAGCGTGGGTCTCCGCCCA

GCTCCAGTCCTGTGATCCGGGCCCGCCCCCTAGCGGCCGGGGAGGGAGGG

GCCGGGTCCGCGGCCGGCGAACGGGGCTCGAAGGGTCCTTGTAGCCGGGA

ATGCTGCTGCTGCTGCTGCTGCTGCTGCTGCTGCTGCTGCTGCT

GCTGCTGCTGCTGGGGGGATCACAGACCATTTCTTTCTTTCGGCCAGGCT

GAGGCCCTGACGTGGATGGGCAAACTGCAGGCCTGGGAAGGCAGCAAGCC

GGGCCGTCCGTGTTCCATCCTCCACGCACCCCCACCTATCGTTGGTTCGC

AAAGTGCAAAGCTTTCTTGTGCATGACGCCCTGCTCTGGGGAGCGTCTGG

CGCGATCTCTGCCTGCTTACTCGGGAAATTTGCTTTTGCCAAACCCGCTT

TTTCGGGGATCCCGCGCCCCCCTCCTCACTTGCGCTGCTCTCGGAGCCCC

AGCCGGCTCCGCCCGCTTCGGCGGTTTGGATATTTATTGACCTCGTCCTC

CGACTCGCTGACAGGCTACAGGACCCCCAACAACCCCAATCCACGTTTTG

GATGCACTGAGACCCCGACATTCCTCGGTATTTATTGTCTGTCCCCACCT

AGGACCCCCACCCCCGACCCTCGCGAATAAAAGGCCCTCCATCTGCCCAA

AGCTCTGGA.

In some embodiments, oligonucleotides may have a region of complementarity to a sequence set forth as follows, which is an example mouse DMPK gene sequence (Gene ID 13400; NM_001190490.1).
GAACTGGCCAGAGAGACCCAAGGGA-TAGTCAGGGACGGGCAGACATGCAGCTAGG GTTCTGGGGCCTGGACAGGGGCAGCCAGGCCC TGTGACGGGAAGACCCCGAGCTCC GGCCCGGG-GAGGGGCCATGGTGTTGCCTGCCCAA-CATGTCAGCCGAAGTGCGGCTG AGGCAGCTCCAGCAGCTGGTGCTGGACCC AGGCTTCCTGGGACTGGAGCCCCTGCT CGACCTTCTCCTGGGCGTCCACCAG-GAGCTGGGTGCCTCTCACCTAGCCCAGGACA AGTATGTGGCCGACTTCTTGCAGTGGGTGGAGCC-CATTGCAGCAAGGCTTAAGGAG GTCCGACTGCAGAGGGATGATTTGAGATTTT-GAAGGTGATCGGGCGTGGGCGTT CAGCGAGGTAGCGGTGGTGAAGATGAAACA-GACGGGCCAAGTGTATGCCATGAAG ATTAT-GAATAAGTGGGACATGCT-GAAGAGAGGCGAGGTGTCGTGCTTCCGGGAAGA AAGGGATGTATTAGTGAAAGGGGACCGGCGCTG-GATCACACAGCTGCACTTTGCCT TCCAGGAT-GAGAACTACCTGTACCTGGTCATGGAATAC- TACGTGGGCGGGGACCTG CTAACGCTGCTGAGCAAGTTTGGGGAGCG-GATCCCCGCCGAGATGGCTCGCTTCTA CCTGGCCGAGATTGTCATGGCCATA-GACTCCGTGCACCGGCTGGGCTACGTGCACA GGGACATCAAACCAGATAACATTCTGCTGGACC-GATGTGGGCACATTCGCCTGGCA GACTTCGGCTCCTGCCTCAAACTGCAGCCTGATG-GAATGGTGAGGTCGCTGGTGGCT GTGGGCACCCCGGACTACCTGTCTCCTGAGAT-TCTGCAGGCCGTTGGTGGAGGGCCT GGGGCAGGCAGC-TACGGGCCAGAGTGTGACTGGTGGGCACTGGG CGTGTTCGCCTA TGAGATGTTCTATGGGCA-GACCCCCTTCTACGCGGACTCCACAGCCGAGA-CATATG CCAAGATTGTGCACTACAGG-GAACACTTGTCGCTGCCGCTGGCAGACACAGT TGTC CCCGAGGAAGCTCAGGACCTCAT-TCGTGGGCTGCTGTGTCCTGCTGAGATAAGGCT AGGTCGAGGTGGGGCAGACTTCGAGGGTGC-CACGGACACATGCAATTTCGATGTGG TGGAGGACCGGCTCACTGCCATGGT-GAGCGGGGCGCGGGGAGACGCTGTCAGACAT GCAGGAAGA-CATGCCCCTTGGGGTGCGCCTGCCCTTCGTGGGC-TACTCCTACTGCTG CATGGCCTTCAGA-GACAATCAGGTCCCGGACCCCACCCCTATG GAACTAGAGGCCC TGCAGTTGCCTGTGTCA-GACTTGCAAGGGCTTGACTTGCAGCCCCC AGTGTCCCCAC CGGATCAAGTGGCT-GAAGAGGCTGACCTAGTGGCTGTCCCTGCC CCTGTGGCTGAG GCAGAGAC-CACGGTAACGCTGCAGCAGCTCCAGGAAGCCCTG-GAAGAAGAGGTTC TCACCCGGCAGAGCCT-GAGCCGCGAGCTGGAGGCCATCCGGACCGC CAACCAGAAC TTCTCCAGCCAACTACAG-GAGGCCGAGGTCCGAAACCGAGACCTGGAGGCG-CATGT TCGGCAGCTACAGGAACGGATG-GAGATGCTGCAGGCCCCAGGAGCCGCAGCCATC ACGGGGTCCCCAGTCCCCGGGCCACGGATC-CACCTTCCCATCTAGATGGCCCCC GGCCGTGGCTGTGGGCCAGTGCCCGCT GGTGGGGCCAGGCCCCATGCACCGCCGTC ACCTGCTGCTCCCTGCCAG-GATCCCTAGGCCTGGCC-TATCCGAGGCGCGTTGCCTGC TCCTGTTCGCCGCTGCTCTGGCTGCTGCCGC-CACACTGGGCTGCACTGGGTTGGTGG CCTATACCGGCGGTCT-CACCCCAGTCTGGTGTTTCCCGGGAGC-CACCTTCGCCCCT GAACCCTAAGACTCCAAGC-CATCTTTCATTTAGGCCTCCTAGGAAGGTCGA GCGAC CAGGGAGCGACCCAAAGCGTCTCTGTGCC-CATCGCGCCCCCCCCCCCCCCACCG CTCCGCTC-CACACTTCTGTGAGCCTGGGTCCC-CACCCAGCTCCGCTCCTGTGATCCA GGCCTGCCACCTGGCGGCCGGGGAGGGAG-GAACAGGGCTCGTGCCCAGCACCCCTG GTTCCTGCAGAGCTGGTAGC-CACCGCTGCTGCAGCAGCTGGGCAT-TCGCCGACCTTG CTTTACTCAGCCCCGACGTG-GATGGGCAAACTGCTCAGCTCATCCGATTTCA CTTTT TCACTCTCCCAGCCATCAGTTACAAGCCAT-AAGCATGAGCCCCCTATTTCCAGGGAC ATCCCAT-TCCCATAGTGATGGATCAGCAA-GACCTCTGCCAGCACACACGGAGTCTTT GGCTTCGGACAGCCT-CACTCCTGGGGGTTGCTGCAACTCCTTCCCCG TGTACACGTC TGCACTCTAACAACGGAGC-CACAGCTGCACTCCCCCCTCCCC-CAAAGCAGTGTGGG TATTTATTGATCTTGT-TATCTGACTCACTGACAGACTCCGGGAC CCACGTTTTAGAT GCATTGAGACTCGACAT-TCCTCGGTATTTATTGTCTGTCCCCACC-TACGACCTCCACT CCCGACCCTTGCGAATAAAATACTTCT GGTCTGCCCTAAA (SEQ ID NO: 147). In some embodiments, an oligonucleotide may have a region of complementarity to DMPK gene sequences of multiple species, e.g., selected from human, mouse and non-human species.

In some embodiments, the oligonucleotide may have region of complementarity to a mutant form of DMPK, for example, a mutant form as reported in Botta A. et al. "The CTG repeat expansion size correlates with the splicing defects observed in muscles from myotonic dystrophy type 1 patients." J Med Genet. 2008 October; 45(10):639-46.; and Machuca-Tzili L. et al. "Clinical and molecular aspects of the myotonic dystrophies: a review." Muscle Nerve. 2005 July; 32(1):1-18.; the contents of each of which are incorporated herein by reference in their entireties.

In some embodiments, the oligonucleotide may target lncRNA or mRNA, e.g., for degradation. In some embodiments, the oligonucleotide may target, e.g., for degradation, a nucleic acid encoding a protein involved in a mismatch repair pathway, e.g., MSH2, MutLalpha, MutSbeta, MutLalpha. Non-limiting examples of proteins involved in mismatch repair pathways, for which mRNAs encoding such proteins may be targeted by oligonucleotides described herein, are described in Iyer, R. R. et al., "DNA triplet repeat expansion and mismatch repair" Annu Rev Biochem. 2015; 84:199-226.; and Schmidt M. H. and Pearson C. E., "Disease-associated repeat instability and mismatch repair" DNA Repair (Amst). 2016 February; 38:117-26.

In some embodiments, an oligonucleotide provided herein is an antisense oligonucleotide targeting DMPK. In some embodiments, the oligonucleotide targeting is any one of the antisense oligonucleotides (e.g., a Gapmer) targeting DMPK as described in US Patent Application Publication US20160304877A1, published on Oct. 20, 2016, entitled "Compounds And Methods For Modulation Of Dystrophia Myotonica-Protein Kinase (DMPK) Expression," incorporated herein by reference). In some embodiments, the DMPK targeting oligonucleotide targets a region of the DMPK gene sequence as set forth in Genbank accession No. NM_001081560.2 (SEQ ID NO: 131) or as set forth in Genbank accession No. NG_009784.1.

In some embodiments, the DMPK targeting oligonucleotide comprises a nucleotide sequence comprising a region complementary to a target region that is at least 10 continuous nucleotides (e.g., at least 10, at least 12, at least 14, at least 16, or more continuous nucleotides) in SEQ ID NO: 131.

In some embodiments, the DMPK targeting oligonucleotide comprise a gapmer motif. "Gapmer" means a chimeric antisense compound in which an internal region having a plurality of nucleotides that support RNase H cleavage is positioned between external regions having one or more nucleotides, wherein the nucleotides comprising the internal region are chemically distinct from the nucleotide or nucleotides comprising the external regions. The internal region can be referred to as a "gap segment" and the external regions can be referred to as "wing segments." In some embodiments, the DMPK targeting oligonucleotide comprises one or more modified nucleotides, and/or (e.g., and) one or more modified internucleotide linkages. In some embodiments, the internucleotide linkage is a phosphorothioate linkage. In some embodiments, the oligonucleotide comprises a full phosphorothioate backbone. In some embodiments, the oligonucleotide is a DNA gapmer with cET ends (e.g., 3-10-3; cET-DNA-cET). In some embodiments, the DMPK targeting oligonucleotide comprises one or more 6'-(S)—CH$_3$ biocyclic nucleotides, one or more β-D-2'-deoxyribonucleotides, and/or (e.g., and) one or more 5-methylcytosine nucleotides.

In some embodiments, the DMPK targeting oligonucleotide is a gapmer having the formula 5'-X—Y—Z-3', with X and Z as wing segments and Y as the gap segment. In some embodiments, the DMPK targeting oligonucleotide is a gapmer having a 5'-4-8-4-3' formula. In some embodiments, the DMPK targeting oligonucleotide is a gapmer having a 5'-5-10-5-3' formula. In some embodiments, the DMPK targeting oligonucleotide is a gapmer having a 5'-3-10-3-3' formula. In some embodiments, the DMPK targeting oligonucleotide is a gapmer comprising one or more of 5-methylcytosine nucleotides, 2'OMe nucleotides, 2'fluoro nucleotides, LNAs, and/or (e.g., and) 2'-O-methoxyethyl (2'-O-MOE) nucleotides. In some embodiments, the DMPK targeting oligonucleotide is a gapmer comprising one or more modified internucleotide (e.g., a phosphorothioate linkage). In some embodiments, the DMPK targeting oligonucleotide is a gapmer comprising a full phosphorothioate backbone.

In some embodiments, any one of the oligonucleotides can be in salt form, e.g., as sodium, potassium, or magnesium salts.

In some embodiments, the 5' or 3' nucleoside (e.g., terminal nucleoside) of any one of the oligonucleotides described herein is conjugated to an amine group, optionally via a spacer. In some embodiments, the spacer comprises an aliphatic moiety. In some embodiments, the spacer comprises a polyethylene glycol moiety. In some embodiments, a phosphodiester linkage is present between the spacer and the 5' or 3' nucleoside of the oligonucleotide. In some embodiments, the 5' or 3' nucleoside (e.g., terminal nucleoside) of any of the oligonucleotides described herein is conjugated to a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof; each R$^A$ is independently hydrogen or substituted or unsubstituted alkyl. In certain embodiments, the spacer is a substituted or unsubstituted alkylene, substituted or unsubstituted heterocyclylene, substituted or unsubstituted heteroarylene, —O—, —N(R$^A$)—, or —C(=O)N(R$^A$)$_2$, or a combination thereof.

In some embodiments, the 5' or 3' nucleoside of any one of the oligonucleotides described herein is conjugated to a compound of the formula —NH$_2$—(CH$_2$)$_n$—, wherein n is an integer from 1 to 12. In some embodiments, n is 6, 7, 8, 9, 10, 11, or 12. In some embodiments, a phosphodiester linkage is present between the compound of the formula NH$_2$—(CH$_2$)$_n$— and the 5' or 3' nucleoside of the oligonucleotide. In some embodiments, a compound of the formula NH$_2$—(CH$_2$)$_6$— is conjugated to the oligonucleotide via a reaction between 6-amino-1-hexanol (NH$_2$—(CH$_2$)$_6$—OH) and the 5' phosphate of the oligonucleotide.

In some embodiments, the oligonucleotide is conjugated to a targeting agent, e.g., a muscle targeting agent such as an anti-TfR antibody, e.g., via the amine group.

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of a target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

In some embodiments, an oligonucleotide comprises at least 10, 11, 12, 13, 14, 15, 16, 17, 18, 19, or 20 consecutive nucleotides of a sequence comprising any one of SEQ ID NO: 148-383 and 621-638. In some embodiments, an oligonucleotide comprises a sequence comprising any one of SEQ ID NO: 148-383 and 621-638. In some embodiments, an oligonucleotide comprises a sequence that shares at least 70%, 75%, 80%, 85%, 90%, 95%, or 97% sequence identity with at least 12 or at least 15 consecutive nucleotides of any one of SEQ ID NO: 148-383 and 621-638.

In some embodiments, an oligonucleotide comprises a sequence that targets a DMPK sequence comprising any one of SEQ ID NO: 384-619. In some embodiments, an oligonucleotide comprises at least 10, 11, 12, 13, 14, 15, 16, 17, 18, 19, or 20 nucleotides (e.g., consecutive nucleotides) that are complementary to a DMPK sequence comprising any one of SEQ ID NO: 384-619. In some embodiments, an oligonucleotide comprises a sequence that is at least 70%, 75%, 80%, 85%, 90%, 95%, or 97% complementary with at least 12 or at least 15 consecutive nucleotides of any one of SEQ ID NO: 384-619.

In some embodiments, the oligonucleotide is complementary (e.g., at least 85% at least 90%, at least 95%, or 100%) to a target sequence of any one of the oligonucleotides provided herein (e.g., the oligonucleotides listed in Table 8 or Table 17). In some embodiments, such target sequence is 100% complementary to the oligonucleotide listed in Table 8 or Table 17.

In some embodiments, any one or more of the thymine bases (T's) in any one of the oligonucleotides provided herein (e.g., the oligonucleotides listed in Table 8 or Table 17) may optionally be uracil bases (U's), and/or any one or more of the U's may optionally be T's.

b. Oligonucleotide Modifications:

The oligonucleotides described herein may be modified, e.g., comprise a modified sugar moiety, a modified internucleoside linkage, a modified nucleotide and/or (e.g., and) combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleosides

In some embodiments, the oligonucleotide described herein comprises at least one nucleoside modified at the 2' position of the sugar. In some embodiments, an oligonucleotide comprises at least one 2'-modified nucleoside. In some embodiments, all of the nucleosides in the oligonucleotide are 2'-modified nucleosides.

In some embodiments, the oligonucleotide described herein comprises one or more non-bicyclic 2'-modified nucleosides, e.g., 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleoside.

In some embodiments, the oligonucleotide described herein comprises one or more 2'-4' bicyclic nucleosides in which the ribose ring comprises a bridge moiety connecting two atoms in the ring, e.g., connecting the 2'-O atom to the 4'-C atom via a methylene (LNA) bridge, an ethylene (ENA) bridge, or a (S)-constrained ethyl (cEt) bridge. Examples of LNAs are described in International Patent Application Publication WO/2008/043753, published on Apr. 17, 2008, and entitled "RNA Antagonist Compounds For The Modulation Of PCSK9", the contents of which are incorporated herein by reference in its entirety. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties. Examples of cEt are provided in U.S. Pat. Nos. 7,101,993; 7,399,845 and 7,569,686, each of which is herein incorporated by reference in its entirety.

In some embodiments, the oligonucleotide comprises a modified nucleoside disclosed in one of the following United States Patent or Patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-Modified Bicyclic Nucleic Acid Analogs"; U.S. Pat. No. 7,569,686, issued on Aug. 4, 2009, and entitled "Compounds And Methods For Synthesis Of Bicyclic Nucleic Acid Analogs"; U.S. Pat. No. 7,335,765, issued on Feb. 26, 2008, and entitled "Novel Nucleoside And Oligonucleotide Analogues"; U.S. Pat. No. 7,314,923, issued on Jan. 1, 2008, and entitled "Novel Nucleoside And Oligonucleotide Analogues"; U.S. Pat. No. 7,816,333, issued on Oct. 19, 2010, and entitled "Oligonucleotide Analogues And Methods Utilizing The Same" and US Publication Number 2011/0009471 now U.S. Pat. No. 8,957,201, issued on Feb. 17, 2015, and entitled "Oligonucleotide Analogues And Methods Utilizing The Same", the entire contents of each of which are incorporated herein by reference for all purposes.

In some embodiments, the oligonucleotide comprises at least one modified nucleoside that results in an increase in Tm of the oligonucleotide in a range of 1° C., 2° C., 3° C., 4° C., or 5° C. compared with an oligonucleotide that does not have the at least one modified nucleoside. The oligonucleotide may have a plurality of modified nucleosides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleoside.

The oligonucleotide may comprise a mix of nucleosides of different kinds. For example, an oligonucleotide may comprise a mix of 2'-deoxyribonucleosides or ribonucleosides and 2'-fluoro modified nucleosides. An oligonucleotide may comprise a mix of deoxyribonucleosides or ribonucleosides and 2'-O-Me modified nucleosides. An oligonucleotide may comprise a mix of 2'-fluoro modified nucleosides and 2'-O-Me modified nucleosides. An oligonucleotide may comprise a mix of 2'-4' bicyclic nucleosides and 2'-MOE, 2'-fluoro, or 2'-O-Me modified nucleosides. An oligonucleotide may comprise a mix of non-bicyclic 2'-modified nucleosides (e.g., 2'-MOE, 2'-fluoro, or 2'-O-Me) and 2'-4' bicyclic nucleosides (e.g., LNA, ENA, cEt).

The oligonucleotide may comprise alternating nucleosides of different kinds. For example, an oligonucleotide may comprise alternating 2'-deoxyribonucleosides or ribonucleosides and 2'-fluoro modified nucleosides. An oligonucleotide may comprise alternating deoxyribonucleosides or ribonucleosides and 2'-O-Me modified nucleosides. An oligonucleotide may comprise alternating 2'-fluoro modified nucleosides and 2'-O-Me modified nucleosides. An oligonucleotide may comprise alternating 2'-4' bicyclic nucleosides and 2'-MOE, 2'-fluoro, or 2'-O-Me modified nucleosides. An oligonucleotide may comprise alternating non-bicyclic 2'-modified nucleosides (e.g., 2'-MOE, 2'-fluoro, or 2'-O-Me) and 2'-4' bicyclic nucleosides (e.g., LNA, ENA, cEt).

In some embodiments, an oligonucleotide described herein comprises a 5'-vinylphosphonate modification, one or more abasic residues, and/or one or more inverted abasic residues.

d. Internucleoside Linkages/Backbones

In some embodiments, oligonucleotide may contain a phosphorothioate or other modified internucleoside linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleoside linkages at the first, second, and/or (e.g., and) third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563, 253; 5,571,799; 5,587,361; and 5,625,050.

In some embodiments, oligonucleotides may have heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides by adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides comprise nucleoside units that are joined together by either substantially all Sp or substantially all Rp phosphorothioate intersugar linkages are provided. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, an oligonucleotide described herein is a gapmer. A gapmer oligonucleotide generally has the formula 5'-X—Y—Z-3', with X and Z as flanking regions around a gap region Y. In some embodiments, flanking region X of formula 5'-X—Y—Z-3' is also referred to as X region, flanking sequence X, 5' wing region X, or 5' wing segment. In some embodiments, flanking region Z of formula 5'-X—Y—Z-3' is also referred to as Z region, flanking sequence Z, 3' wing region Z, or 3' wing segment. In some embodiments, gap region Y of formula 5'-X—Y—Z-3' is also referred to as Y region, Y segment, or gap-segment Y. In some embodiments, each nucleoside in the gap region Y is a 2'-deoxyribonucleoside, and neither the 5' wing region X or the 3' wing region Z contains any 2'-deoxyribonucleosides.

In some embodiments, the Y region is a contiguous stretch of nucleotides, e.g., a region of 6 or more DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleosides, e.g., one to six high-affinity modified nucleosides. Examples of high affinity modified nucleosides include, but are not limited to, $2^T$-modified nucleosides (e.g., 2'-MOE, 2'O-Me, 2'-F) or 2'-4' bicyclic nucleosides (e.g., LNA, cEt, ENA). In some embodiments, the flanking sequences X and Z may be of 1-20 nucleotides, 1-8 nucleotides, or 1-5 nucleotides in length. The flanking sequences X and Z may be of similar length or of dissimilar lengths. In some embodiments, the gap-segment Y may be a nucleotide sequence of 5-20 nucleotides, 5-15 twelve nucleotides, or 6-10 nucleotides in length.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleoside linkages. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,015,315; 7,101,993; 7,399,845; 7,432,250; 7,569,686; 7,683,036; 7,750,131; 8,580,756; 9,045,754; 9,428,534; 9,695,418; 10,017,764; 10,260,069; 9,428,534; 8,580,756; U.S. patent publication Nos. US20050074801, US20090221685; US20090286969, US20100197762, and US20110112170; PCT publication Nos. WO2004069991; WO2005023825; WO2008049085 and WO2009090182; and EP Patent No. EP2,149,605, each of which is herein incorporated by reference in its entirety.

In some embodiments, a gapmer is 10-40 nucleosides in length. For example, a gapmer may be 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40 nucleosides in length. In some embodiments, a gapmer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleosides in length.

In some embodiments, the gap region Y in a gapmer is 5-20 nucleosides in length. For example, the gap region Y may be 5-20, 5-15, 5-10, 10-20, 10-15, or 15-20 nucleosides in length. In some embodiments, the gap region Y is 5, 6, 7, 8, 9, 10, 11, 12, 13, 14, 15, 16, 17, 18, 19, or 20 nucleosides in length. In some embodiments, each nucleoside in the gap region Y is a 2'-deoxyribonucleoside. In some embodiments, all nucleosides in the gap region Y are 2'-deoxyribonucleosides. In some embodiments, one or more of the nucleosides in the gap region Y is a modified nucleoside (e.g., a 2' modified nucleoside such as those described herein). In some embodiments, one or more cytosines in the gap region Y are optionally 5-methyl-cytosines. In some embodiments, each cytosine in the gap region Y is a 5-methyl-cytosines.

In some embodiments, the 5'wing region of a gapmer (X in the 5'-X—Y—Z-3' formula) and the 3'wing region of a gapmer (Z in the 5'-X—Y—Z-3' formula) are independently 1-20 nucleosides long. For example, the 5'wing region of a gapmer (X in the 5'-X—Y—Z-3' formula) and the 3'wing region of the gapmer (Z in the 5'-X—Y—Z-3' formula) may be independently 1-20, 1-15, 1-10, 1-7, 1-5, 1-3, 1-2, 2-5, 2-7, 3-5, 3-7, 5-20, 5-15, 5-10, 10-20, 10- 15, or 15-20 nucleosides long. In some embodiments, the 5'wing region of the gapmer (X in the 5'-X—Y—Z-3' formula) and the 3'wing region of the gapmer (Z in the 5'-X—Y—Z-3' formula) are independently 1, 2, 3, 4, 5, 6, 7, 8, 9, 10, 11, 12, 13, 14, 15, 16, 17, 18, 19, or 20 nucleosides long. In some embodiments, the 5'wing region of the gapmer (X in the 5'-X—Y—Z-3' formula) and the 3'wing region of the gapmer (Z in the 5'-X—Y—Z-3' formula) are of the same length. In some embodiments, the 5'wing region of the gapmer (X in the 5'-X—Y—Z-3' formula) and the 3'wing region of the gapmer (Z in the 5'-X—Y—Z-3' formula) are of different lengths. In some embodiments, the 5'wing region of the gapmer (X in the 5'-X—Y—Z-3' formula) is longer than the 3'wing region of the gapmer (Z in the 5'-X—Y—Z-3' formula). In some embodiments, the 5'wing region of the gapmer (X in the 5'-X—Y—Z-3' formula) is shorter than the 3'wing region of the gapmer (Z in the 5'-X—Y—Z-3' formula).

In some embodiments, a gapmer comprises a 5'-X—Y—Z-3' of 5-10-5, 4-12-4, 3-14-3, 2-16-2, 1-18-1, 3-10-3, 2-10-2, 1-10-1, 2-8-2, 4-6-4, 3-6-3, 2-6-2, 4-7-4, 3-7-3, 2-7-2, 4-8-4, 3-8-3, 2-8-2, 1-8-1, 2-9-2, 1-9-1, 2-10-2, 1-10-1, 1-12-1, 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6- 11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12- 8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. The numbers indicate the number of nucleosides in X, Y, and Z regions in the 5'-X—Y—Z-3' gapmer.

In some embodiments, one or more nucleosides in the 5'wing region of a gapmer (X in the 5'-X—Y—Z-3' formula) or the 3'wing region of a gapmer (Z in the 5'-X—Y—Z-3' formula) are modified nucleotides (e.g., high-affinity modified nucleosides). In some embodiments, the modified nucleoside (e.g., high-affinity modified nucleosides) is a 2'-modified nucleoside. In some embodiments, the 2'-modified nucleoside is a 2'-4' bicyclic nucleoside or a non-bicyclic 2'-modified nucleoside. In some embodiments, the high-affinity modified nucleoside is a 2'-4' bicyclic nucleoside (e.g., LNA, cEt, or ENA) or a non-bicyclic 2'-modified nucleoside (e.g., 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA)).

In some embodiments, one or more nucleosides in the 5'wing region of a gapmer (X in the 5'-X—Y—Z-3' formula) are high-affinity modified nucleosides. In some embodiments, each nucleoside in the 5'wing region of the gapmer (X in the 5'-X—Y—Z-3' formula) is a high-affinity modified nucleoside. In some embodiments, one or more nucleosides in the 3'wing region of a gapmer (Z in the 5'-X—Y—Z-3' formula) are high-affinity modified nucleosides. In some embodiments, each nucleoside in the 3'wing region of the gapmer (Z in the 5'-X—Y—Z-3' formula) is a high-affinity modified nucleoside. In some embodiments, one or more nucleosides in the 5'wing region of the gapmer (X in the 5'-X—Y—Z-3' formula) are high-affinity modified nucleosides and one or more nucleosides in the 3'wing region of the gapmer (Z in the 5'-X—Y—Z-3' formula) are high-affinity modified nucleosides. In some embodiments, each nucleoside in the 5'wing region of the gapmer (X in the 5'-X—Y—Z-3' formula) is a high-affinity modified nucleoside and each nucleoside in the 3'wing region of the gapmer (Z in the 5'-X—Y—Z-3' formula) is high-affinity modified nucleoside.

In some embodiments, the 5'wing region of a gapmer (X in the 5'-X—Y—Z-3' formula) comprises the same high affinity nucleosides as the 3'wing region of the gapmer (Z in the 5'-X—Y—Z-3' formula). For example, the 5'wing region of the gapmer (X in the 5'-X—Y—Z-3' formula) and the 3'wing region of the gapmer (Z in the 5'-X—Y—Z-3' formula) may comprise one or more non-bicyclic 2'-modified nucleosides (e.g., 2'-MOE or 2'-O-Me). In another example, the 5'wing region of the gapmer (X in the 5'-X—Y—Z-3' formula) and the 3'wing region of the gapmer (Z in the 5'-X—Y—Z-3' formula) may comprise one or more 2'-4' bicyclic nucleosides (e.g., LNA or cEt). In some embodiments, each nucleoside in the 5'wing region of the gapmer (X in the 5'-X—Y—Z-3' formula) and the 3'wing region of the gapmer (Z in the 5'-X—Y—Z-3' formula) is a non-bicyclic 2'-modified nucleosides (e.g., 2'-MOE or 2'-O-Me). In some embodiments, each nucleoside in the 5'wing region of the gapmer (X in the 5'-X—Y—Z-3' formula) and the 3'wing region of the gapmer (Z in the 5'-X—Y—Z-3' formula) is a 2'-4' bicyclic nucleosides (e.g., LNA or cEt).

In some embodiments, a gapmer comprises a 5'-X—Y—Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X and Z is a non-bicyclic 2'-modified nucleosides (e.g., 2'-MOE or 2'-O-Me) and each nucleoside in Y is a 2'-deoxyribonucleoside. In some embodiments, the gapmer comprises a 5'-X—Y—Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X and Z is a 2'-4' bicyclic nucleosides (e.g., LNA or cEt) and each nucleoside in Y is a 2'-deoxyribonucleoside. In some embodiments, the 5'wing region of the gapmer (X in the 5'-X—Y—Z-3' formula) comprises different high affinity nucleosides as the 3'wing region of the gapmer (Z in the 5'-X—Y—Z-3' formula). For example, the 5'wing region of the gapmer (X in the 5'-X—Y—Z-3' formula) may comprise one or more non-bicyclic 2'-modified nucleosides (e.g., 2'-MOE or 2'-O-Me) and the 3'wing region of the gapmer (Z in the 5'-X—Y—Z-3' formula) may comprise one or more 2'-4' bicyclic nucleosides (e.g., LNA or cEt). In another example, the 3'wing region of the gapmer (Z in the 5'-X—Y—Z-3' formula) may comprise one or more non-bicyclic 2'-modified nucleosides (e.g., 2'-MOE or 2'-O-Me) and the 5'wing region of the gapmer (X in the 5'-X—Y—Z-3' formula) may comprise one or more 2'-4' bicyclic nucleosides (e.g., LNA or cEt).

In some embodiments, a gapmer comprises a 5'-X—Y—Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X is a non-bicyclic 2'-modified nucleosides (e.g., 2'-MOE or 2'-O-Me), each nucleoside in Z is a 2'-4' bicyclic nucleosides (e.g., LNA or cEt), and each nucleoside in Y is a 2'-deoxyribonucleoside. In some embodiments, the gapmer comprises a 5'-X—Y—Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X is a 2'-4' bicyclic nucleosides (e.g., LNA or cEt), each nucleoside in Z is a non-bicyclic 2'-modified nucleosides (e.g., 2'-MOE or 2'-O-Me) and each nucleoside in Y is a 2'-deoxyribonucleoside.

In some embodiments, the 5'wing region of a gapmer (X in the 5'-X—Y—Z-3' formula) comprises one or more non-bicyclic 2'-modified nucleosides (e.g., 2'-MOE or 2'-O-Me) and one or more 2'-4' bicyclic nucleosides (e.g., LNA or cEt). In some embodiments, the 3'wing region of the gapmer (Z in the 5'-X—Y—Z-3' formula) comprises one or more non-bicyclic 2'-modified nucleosides (e.g., 2'-MOE or 2'-O-Me) and one or more 2'-4' bicyclic nucleosides (e.g., LNA or cEt). In some embodiments, both the 5'wing region of the gapmer (X in the 5'-X—Y—Z-3' formula) and the 3'wing region of the gapmer (Z in the 5'-X—Y—Z-3' formula) comprise one or more non-bicyclic 2'-modified nucleosides (e.g., 2'-MOE or 2'-O-Me) and one or more 2'-4' bicyclic nucleosides (e.g., LNA or cEt).

In some embodiments, a gapmer comprises a 5'-X—Y—Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside. In some embodiments, the gapmer comprises a 5'-X—Y—Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in Z (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside. In some embodiments, the gapmer comprises a 5'-X—Y—Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X and at least one of positions but not all (e.g., 1, 2, 3, 4, 5, or 6) 1, 2, 3, 4, 5, 6, or 7 in Z (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside.

Non-limiting examples of gapmers configurations with a mix of non-bicyclic 2'-modified nucleoside (e.g., 2'-MOE or 2'-O-Me) and 2'-4' bicyclic nucleosides (e.g., LNA or cEt) in the 5'wing region of the gapmer (X in the 5'-X—Y—Z-3' formula) and/or the 3'wing region of the gapmer (Z in the 5'-X—Y—Z-3' formula) include: BBB-(D)n-BBBAA; KKK-(D)n-KKKAA; LLL-(D)n-LLLAA; BBB-(D)n-BBBEE; KKK-(D)n-KKKEE; LLL-(D)n-LLLEE; BBB-(D)n-BBBAA; KKK-(D)n-KKKAA; LLL-(D)n-LLLAA; BBB-(D)n-BBBEE; KKK-(D)n-KKKEE; LLL-(D)n-LLLEE; BBB-(D)n-BBBAAA; KKK-(D)n-KKKAAA; LLL-(D)n-LLLAAA; BBB-(D)n-BBBEEE; KKK-(D)n-KKKEEE; LLL-(D)n-LLLEEE; BBB-(D)n-BBBAAA; KKK-(D)n-KKKAAA; LLL-(D)n-LLLAAA; BBB-(D)n-BBBEEE; KKK-(D)n-KKKEEE; LLL-(D)n-LLLEEE; BABA-(D)n-ABAB; KAKA-(D)n-AKAK; LALA-(D)n-ALAL; BEBE-(D)n-EBEB; KEKE-(D)n-EKEK; LELE-(D)n-ELEL; BABA-(D)n-ABAB; KAKA-(D)n-AKAK; LALA-(D)n-ALAL; BEBE-(D)n-EBEB; KEKE-(D)n-EKEK; LELE-(D)n-ELEL; ABAB-(D)n-ABAB; AKAK-(D)n-AKAK; ALAL-(D)n-ALAL; EBEB-(D)n-EBEB; EKEK-(D)n-EKEK; ELEL-(D)n-ELEL; ABAB-(D)n-ABAB; AKAK-(D)n-AKAK; ALAL-(D)n-ALAL; EBEB-(D)n-EBEB; EKEK-(D)n-EKEK; ELEL-(D)n-ELEL; AABB-(D)n-BBAA; BBAA-(D)n-AABB; AAKK-(D)n-KKAA; AALL-(D)n-LLAA; EEBB-(D)n-BBEE; EEKK-(D)n-KKEE; EELL-(D)n-LLEE; AABB-(D)n-BBAA; AAKK-(D)n-KKAA; AALL-(D)n-LLAA; EEBB-(D)n-BBEE; EEKK-(D)n-KKEE; EELL-(D)n-LLEE; BBB-(D)n-BBA; KKK-(D)n-KKA; LLL-(D)n-LLA; BBB-(D)n-BBE; KKK-(D)n-KKE; LLL-(D)n-LLE; BBB-(D)n-BBA; KKK-(D)n-KKA; LLL-(D)n-LLA; BBB-(D)n-BBE; KKK-(D)n-KKE; LLL-(D)n-LLE; BBB-(D)n-BBA; KKK-(D)n-KKA; LLL-(D)n-LLA; BBB-(D)n-BBE; KKK-(D)n-KKE; LLL-(D)n-LLE; ABBB-(D)n-BBBA; AKKK-(D)n-KKKA; ALLL-(D)n-LLLA; EBBB-(D)n-BBBE; EKKK-(D)n-KKKE; ELLL-(D)n-LLLE; ABBB-(D)n-BBBA; AKKK-(D)n-KKKA; ALLL-(D)n-LLLA; EBBB-(D)n-BBBE; EKKK-(D)n-KKKE; ELLL-(D)n-LLLE; ABBB-(D)n-BBBAA; AKKK-(D)n-KKKAA; ALLL-(D)n-LLLAA; EBBB-(D)n-BBBEE; EKKK-(D)n-KKKEE; ELLL-(D)n-LLLEE; ABBB-(D)n-BBBAA; AKKK-(D)n-KKKAA; ALLL-(D)n-LLLAA; EBBB-(D)n-BBBEE; EKKK-(D)n-KKKEE; ELLL-(D)n-LLLEE; AABBB-(D)n-BBB; AAKKK-(D)n-KKK; AALLL-(D)n-LLL; EEBBB-(D)n-BBB; EEKKK-(D)n-KKK; EELLL-(D)n-LLL; AABBB-(D)n-BBB; AAKKK-(D)n-KKK; AALLL-(D)n-LLL; EEBBB-(D)n-BBB; EEKKK-(D)n-KKK; EELLL-(D)n-LLL; AABBB-(D)n-BBBA; AAKKK-(D)n-KKKA; AALLL-(D)n-LLLA; EEBBB-(D)n-BBBE; EEKKK-(D)n-KKKE; EELLL-(D)n-LLLE; AABBB-(D)n-BBBA; AAKKK-(D)n-KKKA; AALLL-(D)n-LLLA; EEBBB-(D)n-BBBE; EEKKK-(D)n-KKKE; EELLL-(D)n-LLLE; ABBAABB-(D)n-BB; AKKAAKK-(D)n-KK; ALLAALLL-(D)n-LL; EBBEEBB-(D)n-BB; EKKEEKK-(D)n-KK; ELLEELL-(D)n-LL; ABBAABB-(D)n-BB; AKKAAKK-(D)n-KK; ALLAALL-(D)n-LL; EBBEEBB-(D)n-BB; EKKEEKK-(D)n-KK; ELLEELL-(D)n-LL; ABBABB-(D)n-BBB; AKKAKK-(D)n-KKK; ALLALLL-(D)n-LLL; EBBEBB-(D)n-BBB; EKKEKK-(D)n-KKK; ELLELL-(D)n-LLL; ABBABB-(D)n-BBB; AKKAKK-(D)n-KKK; ALLALL-(D)n-LLL; EBBEBB-(D)n-BBB; EKKEKK-(D)n-KKK; ELLELL-(D)n-LLL; EEEK-(D)n-EEEEEEEE; EEK-(D)n-EEEEEEEE; EK-(D)n-EEEEEEEE; EK-(D)n-EEEKK; K-(D)n-EEEKEKE; K-(D)n-EEEKEKEE; K-(D)n-EEEKEK; EK-(D)n-EEEEKEKE; EK-(D)n-EEEEKEK; EEK-(D)n-KEEKE; EK-(D)n-EEEKEK; EK-(D)n-KEEK; EEK-(D)n-EEEKEK; EK-(D)n-KEEE-KEE; EK-(D)n-EEEKEKE; EK-(D)n-EEEEKEKE; and EK-(D)n-EEEEKEK. "A" nucleosides comprise a 2'-modified nucleoside; "B" represents a 2'-4' bicyclic nucleoside; "K" represents a constrained ethyl nucleoside (cEt); "L" represents an LNA nucleoside; and "E" represents a 2'-MOE modified ribonucleoside; "D" represents a 2'-deoxyribonucleoside; "n" represents the length of the gap segment (Y in the 5'-X—Y—Z-3' configuration) and is an integer between 1-20.

In some embodiments, any one of the gapmers described herein comprises one or more modified nucleoside linkages (e.g., a phosphorothioate linkage) in each of the X, Y, and Z regions. In some embodiments, each internucleoside linkage in the any one of the gapmers described herein is a phosphorothioate linkage. In some embodiments, each of the X, Y, and Z regions independently comprises a mix of phosphorothioate linkages and phosphodiester linkages. In some embodiments, each internucleoside linkage in the gap region Y is a phosphorothioate linkage, the 5'wing region X comprises a mix of phosphorothioate linkages and phosphodiester linkages, and the 3'wing region Z comprises a mix of phosphorothioate linkages and phosphodiester linkages.

i. Mixmers

In some embodiments, an oligonucleotide described herein may be a mixmer or comprise a mixmer sequence pattern. In general, mixmers are oligonucleotides that comprise both naturally and non-naturally occurring nucleosides or comprise two different types of non-naturally occurring nucleosides typically in an alternating pattern. Mixmers generally have higher binding affinity than unmodified oligonucleotides and may be used to specifically bind a target molecule, e.g., to block a binding site on the target molecule. Generally, mixmers do not recruit an RNase to the target molecule and thus do not promote cleavage of the target molecule. Such oligonucleotides that are incapable of recruiting RNase H have been described, for example, see WO2007/112754 or WO2007/112753.

In some embodiments, the mixmer comprises or consists of a repeating pattern of nucleoside analogues and naturally occurring nucleosides, or one type of nucleoside analogue and a second type of nucleoside analogue. However, a mixmer need not comprise a repeating pattern and may instead comprise any arrangement of modified nucleoside s and naturally occurring nucleoside s or any arrangement of one type of modified nucleoside and a second type of modified nucleoside. The repeating pattern, may, for instance be every second or every third nucleoside is a modified nucleoside, such as LNA, and the remaining nucleoside s are naturally occurring nucleosides, such as DNA, or are a 2' substituted nucleoside analogue such as 2'-MOE or 2' fluoro analogues, or any other modified nucleoside described herein. It is recognized that the repeating pattern of modified nucleoside, such as LNA units, may be combined with modified nucleoside at fixed positions—e.g. at the 5' or 3' termini.

In some embodiments, a mixmer does not comprise a region of more than 5, more than 4, more than 3, or more than 2 consecutive naturally occurring nucleosides, such as DNA nucleosides. In some embodiments, the mixmer comprises at least a region consisting of at least two consecutive modified nucleoside, such as at least two consecutive LNAs. In some embodiments, the mixmer comprises at least a region consisting of at least three consecutive modified nucleoside units, such as at least three consecutive LNAs.

In some embodiments, the mixmer does not comprise a region of more than 7, more than 6, more than 5, more than 4, more than 3, or more than 2 consecutive nucleoside analogues, such as LNAs. In some embodiments, LNA units may be replaced with other nucleoside analogues, such as those referred to herein.

Mixmers may be designed to comprise a mixture of affinity enhancing modified nucleosides, such as in non-limiting example LNA nucleosides and 2'-O-Me nucleosides. In some embodiments, a mixmer comprises modified internucleoside linkages (e.g., phosphorothioate internucleoside linkages or other linkages) between at least two, at least three, at least four, at least five or more nucleosides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleosides. For example, in some embodiments, a mixmer may comprise morpholino nucleosides mixed (e.g., in an alternating manner) with one or more other nucleosides (e.g., DNA, RNA nucleosides) or modified nucleosides (e.g., LNA, 2'-O-Me nucleosides).

In some embodiments, mixmers are useful for splice correcting or exon skipping, for example, as reported in Touznik A., et al., LNA/DNA mixmer-based antisense oligonucleotides correct alternative splicing of the SMN2 gene and restore SMN protein expression in type 1 SMA fibroblasts Scientific Reports, volume 7, Article number: 3672 (2017), Chen S. et al., Synthesis of a Morpholino Nucleic Acid (MNA)-Uridine Phosphoramidite, and Exon Skipping Using MNA/2'-O-Methyl Mixmer Antisense Oligonucleotide, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective. In some embodiments, the siRNA molecules are 7, 8, 9, 10, 11, 12, 13, 14, 15, 16, 17, 18, 19, 20, 21, 22, 23, 24, 25, 26, 27, 28, 29, 30, 35, 40, 45, 50, or more base pairs in length. In some embodiments, the siRNA molecules are 8 to 30 base pairs in length, 10 to 15 base pairs in length, 10 to 20 base pairs in length, 15 to 25 base pairs in length, 19 to 21 base pairs in length, 21 to 23 base pairs in length.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791). The siRNA molecule can be double stranded (i.e. a dsRNA molecule comprising an antisense strand and a complementary sense strand that hybridizes to form the dsRNA) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

In some embodiments, the antisense strand of the siRNA molecule is 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides in length. In some embodiments, the antisense strand is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 19 to 21 nucleotides in length, 21 to 23 nucleotides in lengths.

In some embodiments, the sense strand of the siRNA molecule is 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides in length. In some embodiments, the sense strand is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 19 to 21 nucleotides in length, 21 to 23 nucleotides in lengths.

In some embodiments, siRNA molecules comprise an antisense strand comprising a region of complementarity to a target region in a target mRNA. In some embodiments, the region of complementarity is at least 80%, at least 85%, at least 90%, at least 91%, at least 92%, at least 93%, at least 94%, at least 95%, at least 96%, at least 97%, at least 98%, at least 99% or 100% complementary to a target region in a target mRNA. In some embodiments, the target region is a region of consecutive nucleotides in the target mRNA. In some embodiments, a complementary nucleotide sequence need not be 100% complementary to that of its target to be specifically hybridizable or specific for a target RNA sequence.

In some embodiments, siRNA molecules comprise an antisense strand that comprises a region of complementarity to a target RNA sequence and the region of complementarity is in the range of 8 to 15, 8 to 30, 8 to 40, or 10 to 50, or 5 to 50, or 5 to 40 nucleotides in length. In some embodiments, a region of complementarity is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more consecutive nucleotides of a target RNA sequence. In some embodiments, siRNA molecules comprise a nucleotide sequence that contains no more than 1, 2, 3, 4, or 5 base mismatches compared to the portion of the consecutive nucleotides of target RNA sequence. In some embodiments, siRNA molecules comprise a nucleotide sequence that has up to 3 mismatches over 15 bases, or up to 2 mismatches over 10 bases.

In some embodiments, siRNA molecules comprise an antisense strand comprising a nucleotide sequence that is complementary (e.g., at least 85%, at least 90%, at least 95%, or 100%) to the target RNA sequence of the oligonucleotides provided herein. In some embodiments, siRNA molecules comprise an antisense strand comprising a nucleotide sequence that is at least 85%, at least 90%, at least 95%, or 100% identical to the oligonucleotides provided herein. In some embodiments, siRNA molecules comprise an antisense strand comprising at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more consecutive nucleotides of the oligonucleotides provided herein.

Double-stranded siRNA may comprise sense and antisense RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or (e.g., and) the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or (e.g., and) the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule. The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule. In some embodiments, the siRNA molecule comprises 3' overhangs of about 1 to about 3 nucleotides on the sense strand. In some embodiments, the siRNA molecule comprises 3' overhangs of about 1 to about 3 nucleotides on the antisense strand. In some embodiments, the siRNA molecule comprises 3' overhangs of about 1 to about 3 nucleotides on both the sense strand and the antisense strand.

In some embodiments, the siRNA molecule comprises one or more modified nucleotides (e.g. 1, 2, 3, 4, 5, 6, 7, 8, 9, 10 or more). In some embodiments, the siRNA molecule comprises one or more modified nucleotides and/or (e.g., and) one or more modified internucleotide linkages. In some embodiments, the modified nucleotide is a modified sugar moiety (e.g. a 2' modified nucleotide). In some embodiments, the siRNA molecule comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, each nucleotide of the siRNA molecule is a modified nucleotide (e.g., a 2'-modified nucleotide). In some embodiments, the siRNA molecule comprises one or more phosphorodiamidate morpholinos. In some embodiments, each nucleotide of the siRNA molecule is a phosphorodiamidate morpholino.

In some embodiments, the siRNA molecule contains a phosphorothioate or other modified internucleotide linkage. In some embodiments, the siRNA molecule comprises phosphorothioate internucleoside linkages. In some embodiments, the siRNA molecule comprises phosphorothioate internucleoside linkages between at least two nucleotides. In some embodiments, the siRNA molecule comprises phosphorothioate internucleoside linkages between all nucleotides. For example, in some embodiments, the siRNA molecule comprises modified internucleotide linkages at the first, second, and/or (e.g., and) third internucleoside linkage at the 5' or 3' end of the siRNA molecule.

In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of siRNA molecules described herein can be combined with each other. For example, one, two, three, four, five, or more different types of modifications can be included within the same siRNA molecule.

In some embodiments, the antisense strand comprises one or more modified nucleotides (e.g. 1, 2, 3, 4, 5, 6, 7, 8, 9, 10 or more). In some embodiments, the antisense strand comprises one or more modified nucleotides and/or (e.g., and) one or more modified internucleotide linkages. In some embodiments, the modified nucleotide comprises a modified sugar moiety (e.g. a 2' modified nucleotide). In some embodiments, the antisense strand comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, each nucleotide of the antisense strand is a modified nucleotide (e.g., a 2'-modified nucleotide). In some embodiments, the antisense strand comprises one or more phosphorodiamidate morpholinos. In some embodiments, the antisense strand is a phosphorodiamidate morpholino oligomer (PMO).

In some embodiments, antisense strand contains a phosphorothioate or other modified internucleotide linkage. In some embodiments, the antisense strand comprises phosphorothioate internucleoside linkages. In some embodiments, the antisense strand comprises phosphorothioate internucleoside linkages between at least two nucleotides. In some embodiments, the antisense strand comprises phosphorothioate internucleoside linkages between all nucleotides. For example, in some embodiments, the antisense strand comprises modified internucleotide linkages at the first, second, and/or (e.g., and) third internucleoside linkage at the 5' or 3' end of the siRNA molecule. In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of the antisense strand described herein can be combined with each other. For example, one, two, three, four, five, or more different types of modifications can be included within the same antisense strand.

In some embodiments, the sense strand comprises one or more modified nucleotides (e.g. 1, 2, 3, 4, 5, 6, 7, 8, 9, 10 or more). In some embodiments, the sense strand comprises one or more modified nucleotides and/or (e.g., and) one or more modified internucleotide linkages. In some embodiments, the modified nucleotide is a modified sugar moiety (e.g. a 2' modified nucleotide). In some embodiments, the sense strand comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, each nucleotide of the sense strand is a modified nucleotide (e.g., a 2'-modified nucleotide). In some embodiments, the sense strand comprises one or more phosphorodiamidate morpholinos. In some embodiments, the antisense strand is a phosphorodiamidate morpholino oligomer (PMO). In some embodiments, the sense strand contains a phosphorothioate or other modified internucleotide linkage. In some embodiments, the sense strand comprises phosphorothioate internucleoside linkages. In some embodiments, the sense strand comprises phosphorothioate internucleoside linkages between at least two nucleotides. In some embodiments, the sense strand comprises phosphorothioate internucleoside linkages between all nucleotides. For example, in some embodiments, the sense strand comprises modified internucleotide linkages at the first, second, and/or (e.g., and) third internucleoside linkage at the 5' or 3' end of the sense strand.

In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of the sense strand described herein can be combined with each other. For example, one, two, three, four, five, or more different types of modifications can be included within the same sense strand.

In some embodiments, the antisense or sense strand of the siRNA molecule comprises modifications that enhance or reduce RNA-induced silencing complex (RISC) loading. In some embodiments, the antisense strand of the siRNA molecule comprises modifications that enhance RISC loading. In some embodiments, the sense strand of the siRNA molecule comprises modifications that reduce RISC loading and reduce off-target effects. In some embodiments, the antisense strand of the siRNA molecule comprises a 2'-O-methoxyethyl (2'-MOE) modification. The addition of the 2'-O-methoxyethyl (2'-MOE) group at the cleavage site improves both the specificity and silencing activity of siRNAs by facilitating the oriented RNA-induced silencing complex (RISC) loading of the modified strand, as described in Song et al., (2017) Mol Ther Nucleic Acids 9:242-250, incorporated herein by reference in its entirety. In some embodiments, the antisense strand of the siRNA molecule comprises a 2'-OMe-phosphorodithioate modification, which increases RISC loading as described in Wu et al., (2014) Nat Commun 5:3459, incorporated herein by reference in its entirety.

In some embodiments, the sense strand of the siRNA molecule comprises a 5'-morpholino, which reduces RISC loading of the sense strand and improves antisense strand selection and RNAi activity, as described in Kumar et al., (2019) Chem Commun (Camb) 55(35):5139-5142, incorporated herein by reference in its entirety. In some embodiments, the sense strand of the siRNA molecule is modified with a synthetic RNA-like high affinity nucleotide analogue, Locked Nucleic Acid (LNA), which reduces RISC loading of the sense strand and further enhances antisense strand incorporation into RISC, as described in Elman et al., (2005) Nucleic Acids Res. 33(1): 439-447, incorporated herein by reference in its entirety. In some embodiments, the sense strand of the siRNA molecule comprises a 5' unlocked nucleic acid (UNA) modification, which reduce RISC loading of the sense strand and improve silencing potency of the antisense strand, as described in Snead et al., (2013) Mol Ther Nucleic Acids 2(7):e103, incorporated herein by reference in its entirety. In some embodiments, the sense strand of the siRNA molecule comprises a 5-nitroindole modification, which decreased the RNAi potency of the sense strand and reduces off-target effects as described in Zhang et al., (2012) Chembiochem 13(13):1940-1945, incorporated herein by reference in its entirety. In some embodiments, the sense strand comprises a 2'-O'methyl (2'-O-Me) modification, which reduces RISC loading and the off-target effects of the sense strand, as described in Zheng et al., FASEB (2013) 27(10): 4017-4026, incorporated herein by reference in its entirety. In some embodiments, the sense strand of the siRNA molecule is fully substituted with morpholino, 2'-MOE or 2'-O-Me residues, and are not recognized by RISC as described in Kole et al., (2012) Nature reviews. Drug Discovery 11(2):125-140, incorporated herein by reference in its entirety. In some embodiments the antisense strand of the siRNA molecule comprises a 2'-MOE modification and the sense strand comprises an 2'-O-Me modification (see e.g., Song et al., (2017) Mol Ther Nucleic Acids 9:242-250). In some embodiments at least one (e.g., at least 2, at least 3, at least 4, at least 5, at least 10) siRNA molecule is linked (e.g., covalently) to a muscle-targeting agent. In some embodiments, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). In some embodiments, the muscle-targeting agent is an antibody. In some embodiments, the muscle-targeting agent is an anti-transferrin receptor antibody (e.g., any one of the anti-TfR antibodies provided herein). In some embodiments, the muscle-targeting agent may be linked to the 5' end of the sense strand of the siRNA molecule. In some embodiments, the muscle-targeting agent may be linked to the 3' end of the sense strand of the siRNA molecule. In some embodiments, the muscle-targeting agent may be linked internally to the sense strand of the siRNA molecule. In some embodiments, the muscle-targeting agent may be linked to the 5' end of the antisense strand of the siRNA molecule. In some embodiments, the muscle-targeting agent may be linked to the 3' end of the antisense strand of the siRNA molecule. In some embodiments, the muscle-targeting agent may be linked internally to the antisense strand of the siRNA molecule.

k. microRNA (miRNAs)

In some embodiments, an oligonucleotide may be a microRNA (miRNA). MicroRNAs (referred to as "miRNAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or (e.g., and) loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via an oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled Methods of delivering multiple targeting oligonucleotides to a cell using cleavable linkers, which was published on Nov. 5, 2015; US Patent Application Number 2015/0247141 A1, entitled Multimeric Oligonucleotide Compounds, which was published on Sep. 3, 2015, US Patent Application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules:

Any suitable small molecule may be used as a molecular payload, as described herein. In some embodiments, the small molecule is as described in US Patent Application Publication 2016052914A1, published on Feb. 25, 2016, entitled "Compounds And Methods For Myotonic Dystrophy Therapy". Further examples of small molecule payloads are provided in Lopez-Morato M, et al., Small Molecules Which Improve Pathogenesis of Myotonic Dystrophy Type 1, (Review) Front. Neurol., 18 May 2018. For example, in some embodiments, the small molecule is an MBNL1 upregulator such as phenylbuthazone, ketoprofen, ISOX, or vorinostat. In some embodiments, the small molecule is an H-Ras pathway inhibitor such as manumycin A. In some embodiments, the small molecule is a protein kinase modulator such as Ro-318220, C16, C51, Metformin, AICAR, lithium chloride, TDZD-8 or Bio. In some embodiments, the small molecule is a plant alkaloid such as harmine. In some embodiments, the small molecule is a transcription inhibitor such as pentamidine, propamidine, heptamidiine or actinomycin D. In some embodiments, the small molecule is an inhibitor of Glycogen synthase kinase 3 beta (GSK3B), for example, as disclosed in Jones K, et al., GSK3β mediates muscle pathology in myotonic dystrophy. J Clin Invest. 2012 December; 122(12):4461-72; and Wei C, et al., GSK3β is a new therapeutic target for myotonic dystrophy type 1. Rare Dis. 2013; 1: e26555; and Palomo V, et al., Subtly Modulating Glycogen Synthase Kinase 3β: Allosteric Inhibitor Development and Their Potential for the Treatment of Chronic Diseases. J Med Chem. 2017 Jun. 22; 60(12):4983-5001, the contents of each of which are incorporated herein by reference in their entireties. In some embodiments, the small molecule is a substituted pyrido[2,3-d]pyrimidines and pentamidine-like compound, as disclosed in Gonzalez A L, et al., In silico discovery of substituted pyrido[2,3-d] pyrimidines and pentamidine-like compounds with biological activity in myotonic dystrophy models. PLoS One. 2017 Jun. 5; 12(6):e0178931, the contents of which are incorporated herein by reference in its entirety. In some embodiments, the small molecule is an MBNL1 modulator, for example, as disclosed in: Zhange F, et al., A flow cytometry-based screen identifies MBNL1 modulators that rescue splicing defects in myotonic dystrophy type I. Hum Mol Genet. 2017 Aug. 15; 26(16):3056-3068, the contents of which are incorporated herein by reference in its entirety.

iii. Peptides

Any suitable peptide or protein may be used as a molecular payload, as described herein. A peptide or protein payload may correspond to a sequence of a protein that preferentially binds to a nucleic acid, e.g. a disease-associated repeat, or a protein, e.g. MBNL1, found in muscle cells. In some embodiments, peptides or proteins may be produced, synthesized, and/or (e.g., and) derivatized using several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.).

In some embodiments, the peptide is as described in US Patent Application 2018/0021449, published on Jan. 25, 2018, "Antisense conjugates for decreasing expression of DMPK". In some embodiments, the peptide is as described in Garcia-Lopez et al., "In vivo discovery of a peptide that prevents CUG-RNA hairpin formation and reverses RNA toxicity in myotonic dystrophy models", PNAS Jul. 19, 2011. 108 (29) 11866-11871. In some embodiments, the peptide or protein may target, e.g., bind to, a disease-associated repeat, e.g. an RNA CUG repeat expansion.

In some embodiments, the peptide or protein comprises a fragment of an MBNL protein, e.g., MBNL1. In some embodiments, the peptide or protein comprises at least one zinc finger. In some embodiments, the peptide or protein may comprise about 2-25 amino acids, about 2-20 amino acids, about 2-15 amino acids, about 2-10 amino acids, or about 2-5 amino acids. The peptide or protein may comprise naturally-occurring amino acids, e.g. cysteine, alanine, or non-naturally-occurring or modified amino acids. Non-naturally occurring amino acids include j-amino acids, homo-amino acids, proline derivatives, 3-substituted alanine derivatives, linear core amino acids, N-methyl amino acids, and others known in the art. In some embodiments, the peptide may be linear; in other embodiments, the peptide may be cyclic, e.g. bicyclic.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5'-methyl cap. In some embodiments, a mRNA may comprise a polyA tail, optionally of up to 160 nucleotides in length. A gene expression construct may encode a sequence of a protein that preferentially binds to a nucleic acid, e.g. a disease-associated repeat, or a protein, e.g. MBNL1, found in muscle cells. In some embodiments, the gene expression construct may be expressed, e.g., overexpressed, within the nucleus of a muscle cell. In some embodiments, the gene expression construct encodes a MBNL protein, e.g., MBNL1. In some embodiments, the gene expression construct encodes a protein that comprises at least one zinc finger. In some embodiments, the gene expression construct encodes a protein that binds to a disease-associated repeat. In some embodiments, the gene expression construct encodes a protein that leads to a reduction in the expression of a disease-associated repeat. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "Closed-Ended Linear Duplex Dna For Non-Viral Gene Transfer"; U.S. Pat. No. 8,853,377B2, issued on Oct. 7, 2014, entitled, "mRNA For Use In Treatment Of Human Genetic Diseases"; and US Patent U.S. Pat. No. 8,822,663B2, issued on Sep. 2, 2014, Engineered Nucleic Acids And Methods Of Use Thereof," the contents of each of which are incorporated herein by reference in their entireties.

C. Linkers

Complexes described herein generally comprise a linker that connects any one of the anti-TfR antibodies described herein to a molecular payload. A linker comprises at least one covalent bond. In some embodiments, a linker may be a single bond, e.g., a disulfide bond or disulfide bridge, that connects an anti-TfR antibody to a molecular payload. However, in some embodiments, a linker may connect any one of the anti-TfR antibodies described herein to a molecular payload through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the anti-TfR antibody or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493.; Jain, N. et al. "Current ADC Linker Chemistry" Pharm Res. 2015, 32:11, 3526-3540.; McCombs, J. R. and Owen, S. C. "Antibody Drug Conjugates: Design and Selection of Linker, Payload and Conjugation Chemistry" AAPS J. 2015, 17:2, 339-351.).

A precursor to a linker typically will contain two different reactive species that allow for attachment to both the anti-TfR antibody and a molecular payload. In some embodiments, the two different reactive species may be a nucleophile and/or (e.g., and) an electrophile. In some embodiments, a linker is connected to an anti-TfR antibody via conjugation to a lysine residue or a cysteine residue of the anti-TfR antibody. In some embodiments, a linker is connected to a cysteine residue of an anti-TfR antibody via a maleimide-containing linker, wherein optionally the maleimide-containing linker comprises a maleimidocaproyl or maleimidomethyl cyclohexane-1-carboxylate group. In some embodiments, a linker is connected to a cysteine residue of an anti-TfR antibody or thiol functionalized molecular payload via a 3-arylpropionitrile functional group. In some embodiments, a linker is connected to a lysine residue of an anti-TfR antibody. In some embodiments, a linker is connected to an anti-TfR antibody and/or (e.g., and) a molecular payload via an amide bond, a carbamate bond, a hydrazide, a trizaole, a thioether, or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include 3-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or (e.g., and) an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by a disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

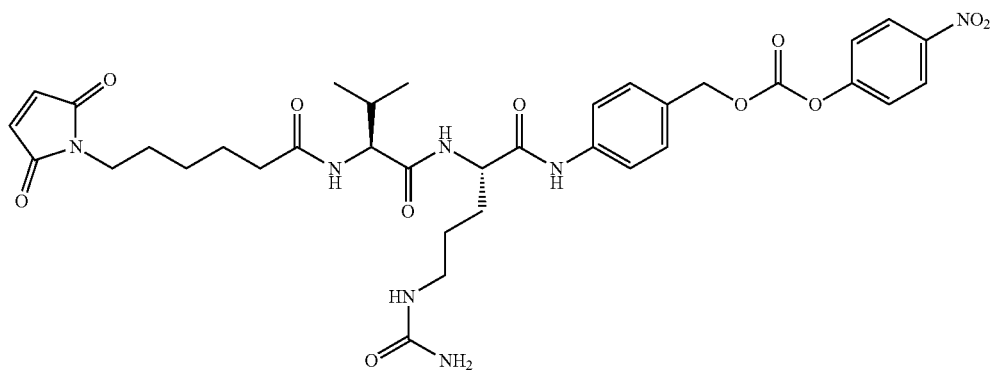 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of:

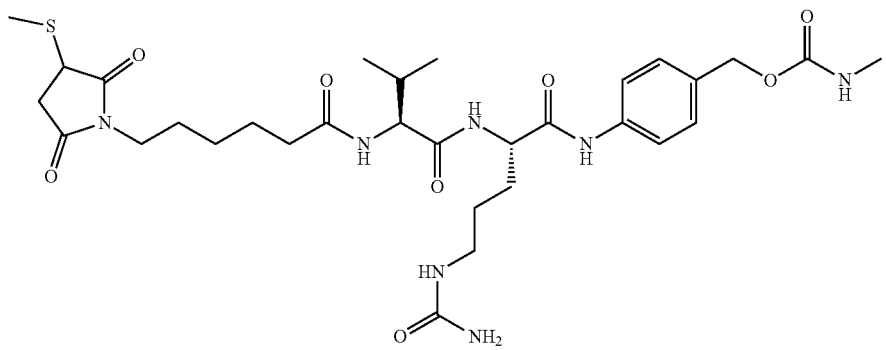

In some embodiments, the Val-cit linker is attached to a reactive chemical moiety (e.g., SPAAC for click chemistry conjugation). In some embodiments, before click chemistry conjugation, the val-cit linker attached to a reactive chemical moiety (e.g., SPAAC for click chemistry conjugation) has the structure of:

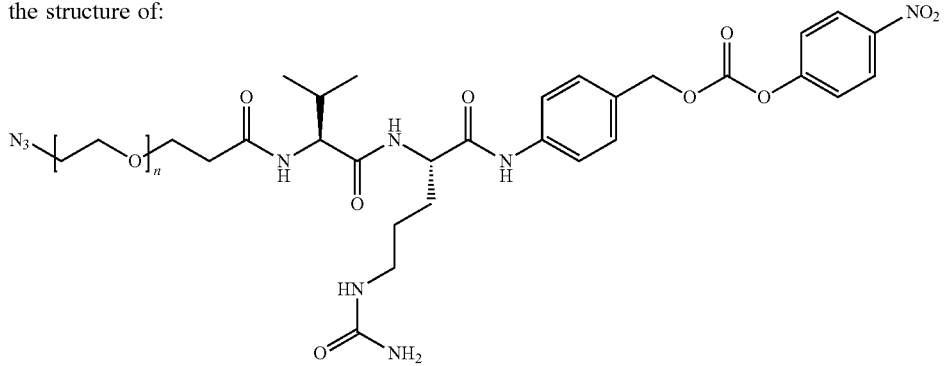

wherein n is any number from 0-10. In some embodiments, n is 3.

In some embodiments, the val-cit linker attached to a reactive chemical moiety (e.g., SPAAC for click chemistry conjugation) is conjugated (e.g., via a different chemical moiety) to a molecular payload (e.g., an oligonucleotide). In some embodiments, the val-cit linker attached to a reactive chemical moiety (e.g., SPAAC for click chemistry conjugation) and conjugated to a molecular payload (e.g., an oligonucleotide) has the structure of (before click chemistry conjugation):

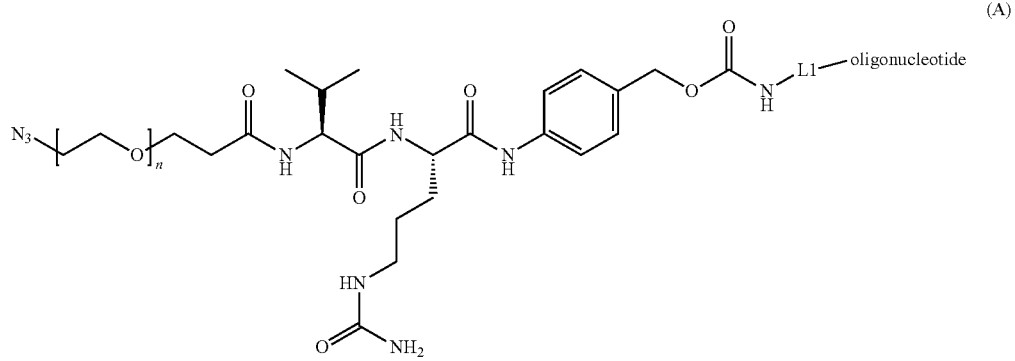

(A)

wherein n is any number from 0-10. In some embodiments, n is 3.

In some embodiments, after conjugation to a molecular payload (e.g., an oligonucleotide), the val-cit linker has a structure of:

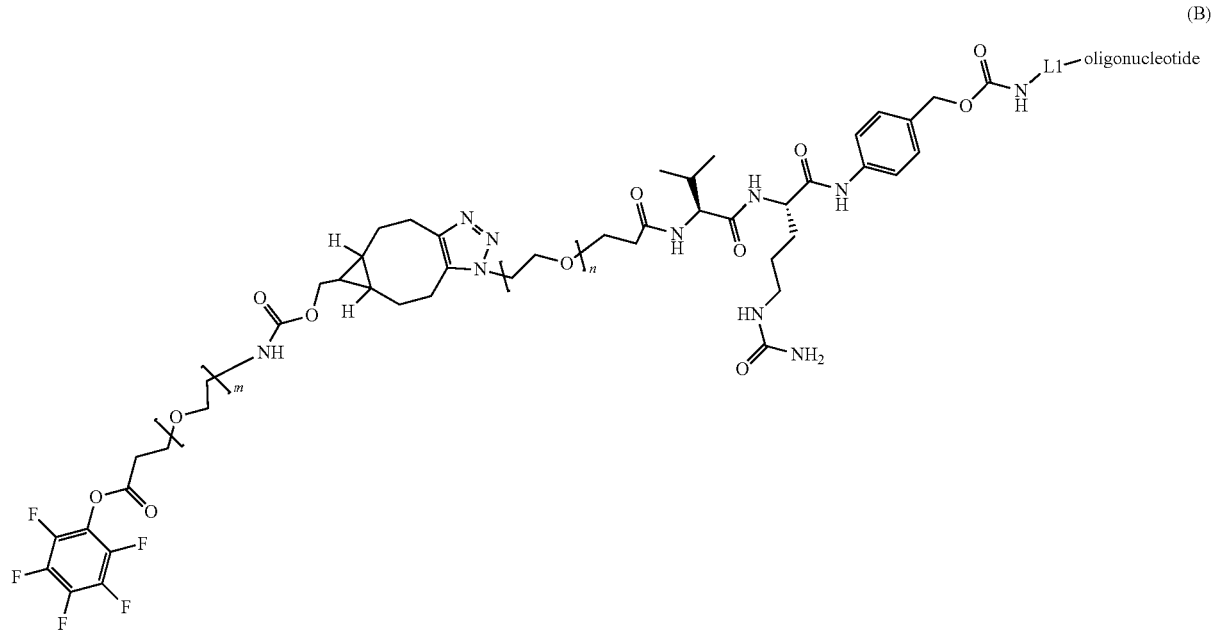

(B)

wherein n is any number from 0-10, and wherein m is any number from 0-10. In some embodiments, n is 3 and m is 4.

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or (e.g., and) an alkoxy-amine linker. In some embodiments, sortase-mediated ligation will be utilized to covalently link an anti-TfR antibody comprising a LPXT sequence to a molecular payload comprising a (G)n sequence (see, e.g. Proft T. Sortase-mediated protein ligation: an emerging biotechnology tool for protein modification and immobilization. Biotechnol Lett. 2010, 32(1): 1-10.).

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S; an optionally substituted heterocyclylene further comprising at least one heteroatom selected from N, O, and S; an imino, an optionally substituted nitrogen species, an optionally substituted oxygen species O, an optionally substituted sulfur species, or a poly(alkylene oxide), e.g. polyethylene oxide or polypropylene oxide.

iii. Linker Conjugation

In some embodiments, a linker is connected to an anti-TfR antibody and/or (e.g., and) molecular payload via a phosphate, thioether, ether, carbon-carbon, carbamate, or amide bond. In some embodiments, a linker is connected to an oligonucleotide through a phosphate or phosphorothioate group, e.g. a terminal phosphate of an oligonucleotide backbone. In some embodiments, a linker is connected to an anti-TfR antibody, through a lysine or cysteine residue present on the anti-TfR antibody.

In some embodiments, a linker is connected to an anti-TfR antibody and/or (e.g., and) molecular payload by a cycloaddition reaction between an azide and an alkyne to form a triazole, wherein the azide and the alkyne may be located on the anti-TfR antibody, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "Fused Cyclooctyne Compounds And Their Use In Metal-free Click Reactions". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase". In some embodiments, a cycloaddition reaction between an azide and an alkyne to form a triazole, wherein the azide and the alkyne may be located on the anti-TfR antibody, molecular payload, or the linker is as described in International Patent Application Publication WO2014065661, published on May 1, 2014, entitled, "Modified antibody, antibody-conjugate and process for the preparation thereof"; or International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase".

In some embodiments, a linker further comprises a spacer, e.g., a polyethylene glycol spacer or an acyl/carbomoyl sulfamide spacer, e.g., a HydraSpace™ spacer. In some embodiments, a spacer is as described in Verkade, J. M. M. et al., "*A Polar Sulfamide Spacer Significantly Enhances the Manufacturability, Stability, and Therapeutic Index of Antibody-Drug Conjugates*", Antibodies, 2018, 7, 12.

In some embodiments, a linker is connected to an anti-TfR antibody and/or (e.g., and) molecular payload by the Diels-Alder reaction between a dienophile and a diene/hetero-diene, wherein the dienophile and the diene/hetero-diene may be located on the anti-TfR antibody, molecular payload, or the linker. In some embodiments a linker is connected to an anti-TfR antibody and/or (e.g., and) molecular payload by other pericyclic reactions, e.g. ene reaction. In some embodiments, a linker is connected to an anti-TfR antibody and/or (e.g., and) molecular payload by an amide, thioamide, or sulfonamide bond reaction. In some embodiments, a linker is connected to an anti-TfR antibody and/or (e.g., and) molecular payload by a condensation reaction to form an oxime, hydrazone, or semicarbazide group existing between the linker and the anti-TfR antibody and/or (e.g., and) molecular payload.

In some embodiments, a linker is connected to an anti-TfR antibody and/or (e.g., and) molecular payload by a conjugate addition reactions between a nucleophile, e.g. an amine or a hydroxyl group, and an electrophile, e.g. a carboxylic acid, carbonate, or an aldehyde. In some embodiments, a nucleophile may exist on a linker and an electrophile may exist on an anti-TfR antibody or molecular payload prior to a reaction between a linker and an anti-TfR antibody or molecular payload. In some embodiments, an electrophile may exist on a linker and a nucleophile may exist on an anti-TfR antibody or molecular payload prior to a reaction between a linker and an anti-TfR antibody or molecular payload. In some embodiments, an electrophile may be an azide, pentafluorophenyl, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or (e.g., and) an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

In some embodiments, the val-cit linker attached to a reactive chemical moiety (e.g., SPAAC for click chemistry conjugation) is conjugated to the anti-TfR antibody by a structure of:

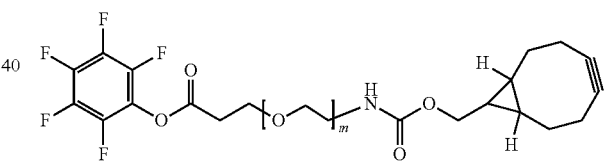

wherein m is any number from 0-10. In some embodiments, m is 4.

In some embodiments, the val-cit linker attached to a reactive chemical moiety (e.g., SPAAC for click chemistry conjugation) is conjugated to an anti-TfR antibody having a structure of:

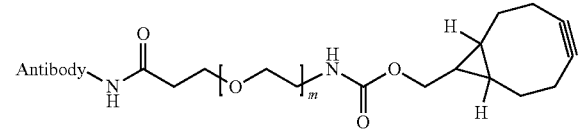

wherein m is any number from 0-10. In some embodiments, m is 4.

In some embodiments, the val-cit linker attached to a reactive chemical moiety (e.g., SPAAC for click chemistry conjugation) and conjugated to an anti-TfR antibody has a structure o

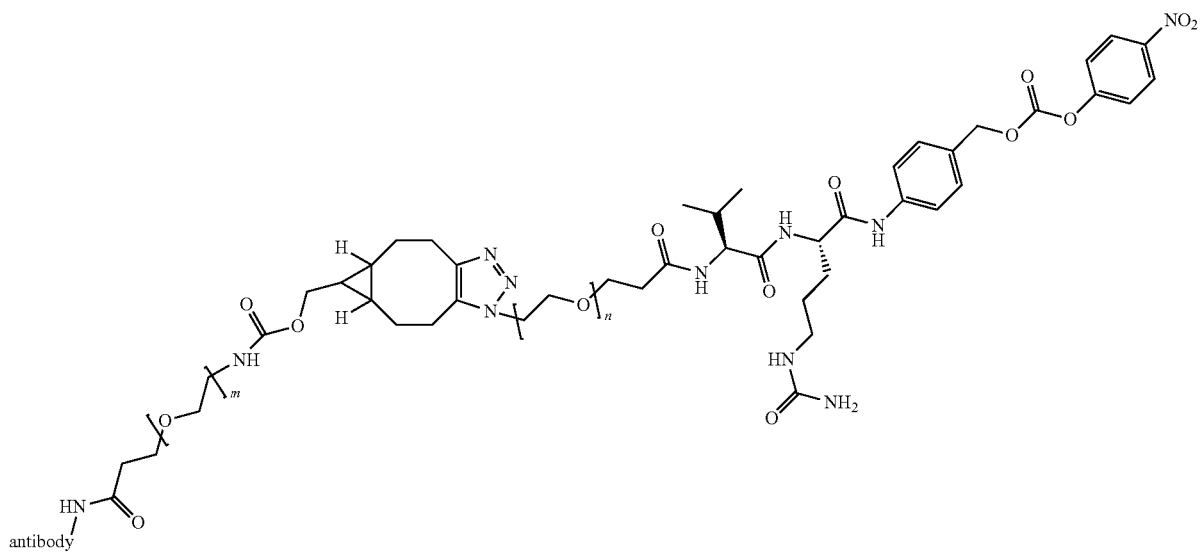

wherein n is any number from 0-10, wherein m is any number from 0-10. In some embodiments, n is 3 and/or (e.g., and) m is 4.

In some embodiments, the val-cit linker that links the antibody and the molecular payload has a structure of:

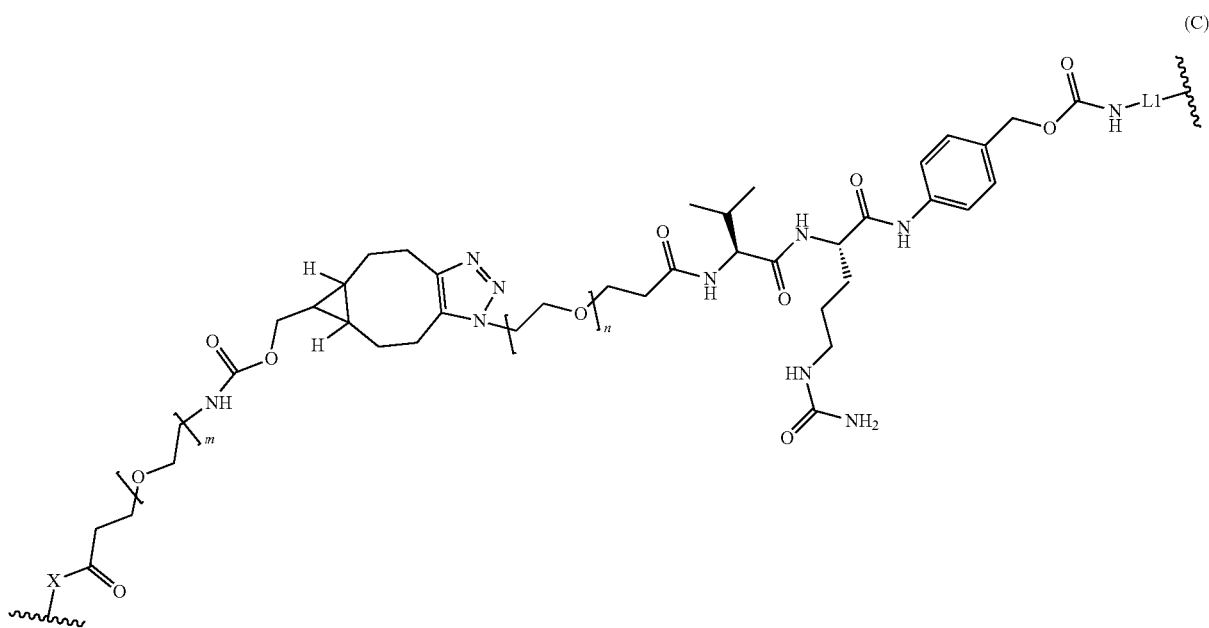

(C)

wherein n is any number from 0-10, wherein m is any number from 0-10. In some embodiments, n is 3 and/or (e.g., and) m is 4. In some embodiments, n is 3 and/or (e.g., and) m is 4. In some embodiments, X is NH (e.g., NH from an amine group of a lysine), S (e.g., S from a thiol group of a cysteine), or O (e.g., O from a hydroxyl group of a serine, threonine, or tyrosine) of the antibody.

In some embodiments, the val-cit linker used to covalently link an anti-TfR antibody and a molecular payload (e.g., an oligonucleotide) has a structure of:

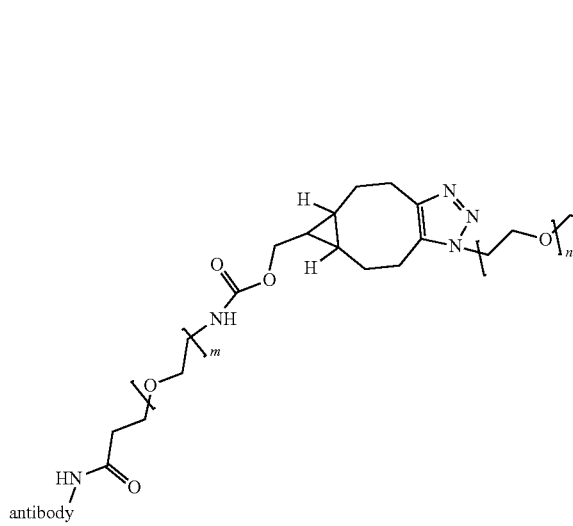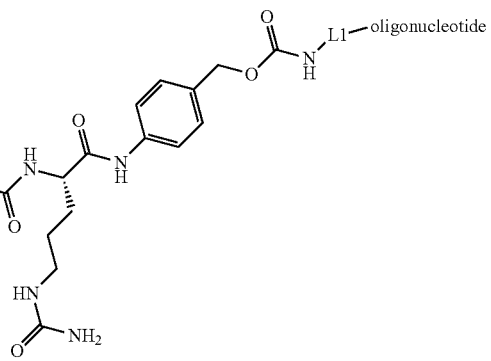

wherein n is any number from 0-10, wherein m is any number from 0-10. In some embodiments, n is 3 and m is 4.

In structures formula (A), (B), (C), and (D), L1, in some embodiments, is a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof. In some embodiments, L1 is

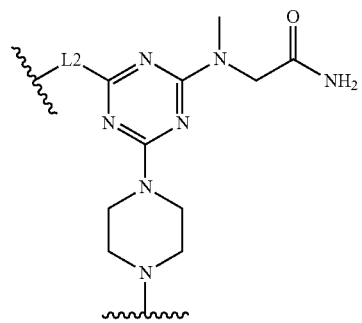

wherein the piperazine moiety links to the oligonucleotide, wherein L2 is

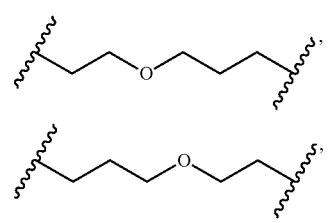

-continued

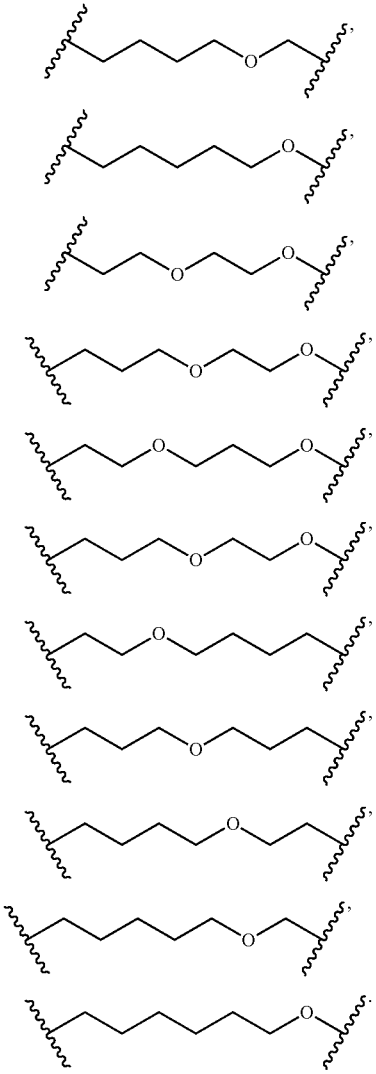

In some embodiments, L1 is:

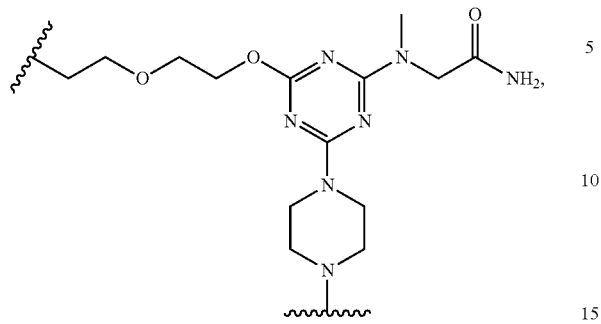

wherein the piperazine moiety links to the oligonucleotide.

In some embodiments, L1 is

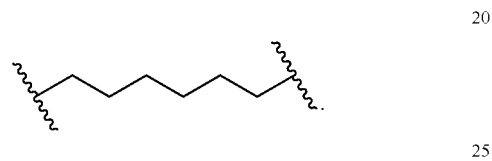

In some embodiments, L1 is linked to a 5' phosphate of the oligonucleotide.

In some embodiments, L1 is optional (e.g., need not be present).

In some embodiments, any one of the complexes described herein has a structure of:

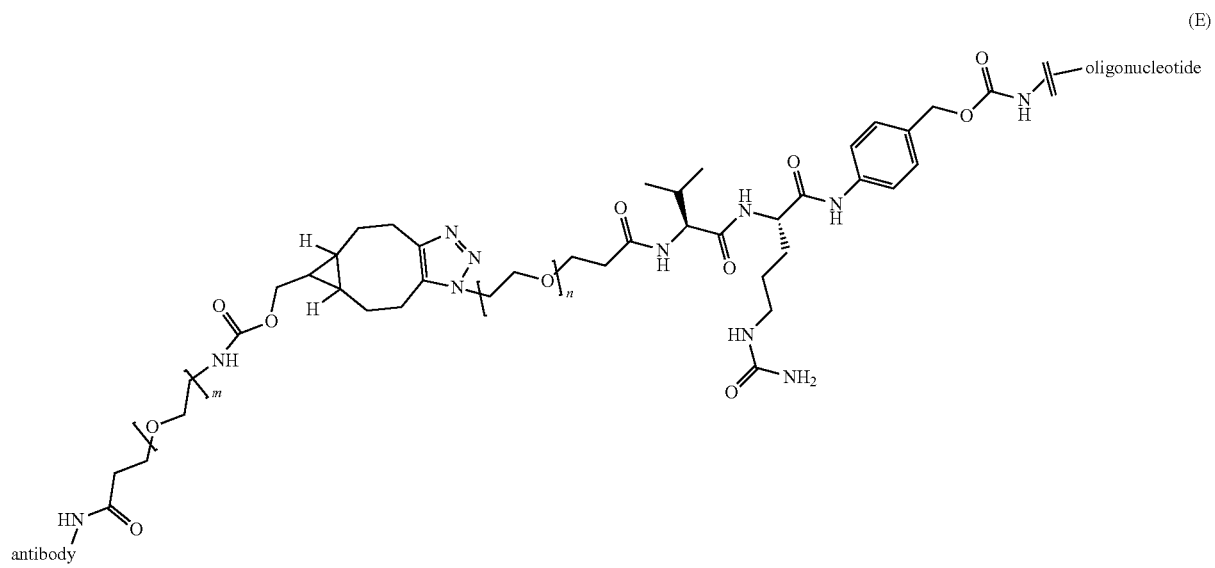

(E)

wherein n is 0-15 (e.g., 3) and m is 0-15 (e.g., 4).

C. Examples of Antibody-Molecular Payload Complexes

Further provided herein are non-limiting examples of complexes comprising any one the anti-TfR antibodies described herein covalently linked to any of the molecular payloads (e.g., an oligonucleotide) described herein. In some embodiments, the anti-TfR antibody (e.g., any one of the anti-TfR antibodies provided in Table 2) is covalently linked to a molecular payload (e.g., an oligonucleotide) via a linker. Any of the linkers described herein may be used. In some embodiments, if the molecular payload is an oligonucleotide, the linker is linked to the 5' end, the 3' end, or internally of the oligonucleotide. In some embodiments, the linker is linked to the anti-TfR antibody via a thiol-reactive linkage (e.g., via a cysteine in the anti-TfR antibody). In some embodiments, the linker (e.g., a Val-cit linker) is linked to the antibody (e.g., an anti-TfR antibody described herein) via an amine group (e.g., via a lysine in the antibody). In some embodiments, the molecular payload is a DMPK-targeting oligonucleotide (e.g., a DMPK-targeting oligonucleotide listed in Table 8 or Table 17).

An example of a structure of a complex comprising an anti-TfR antibody covalently linked to a molecular payload via a Val-cit linker is provided below:

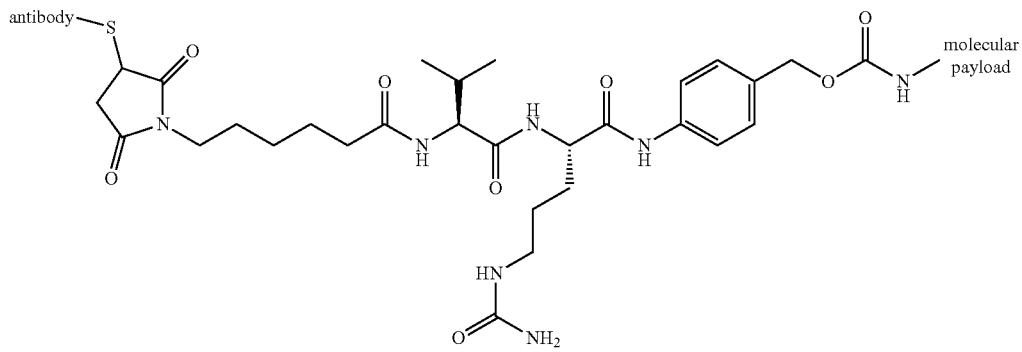

wherein the linker is linked to the antibody via a thiol-reactive linkage (e.g., via a cysteine in the antibody). In some embodiments, the molecular payload is a DMPK-targeting oligonucleotide (e.g., a DMPK-targeting oligonucleotide listed in Table 8 or Table 17).

Another example of a structure of a complex comprising an anti-TfR antibody covalently linked to a molecular payload via a Val-cit linker is provided below:

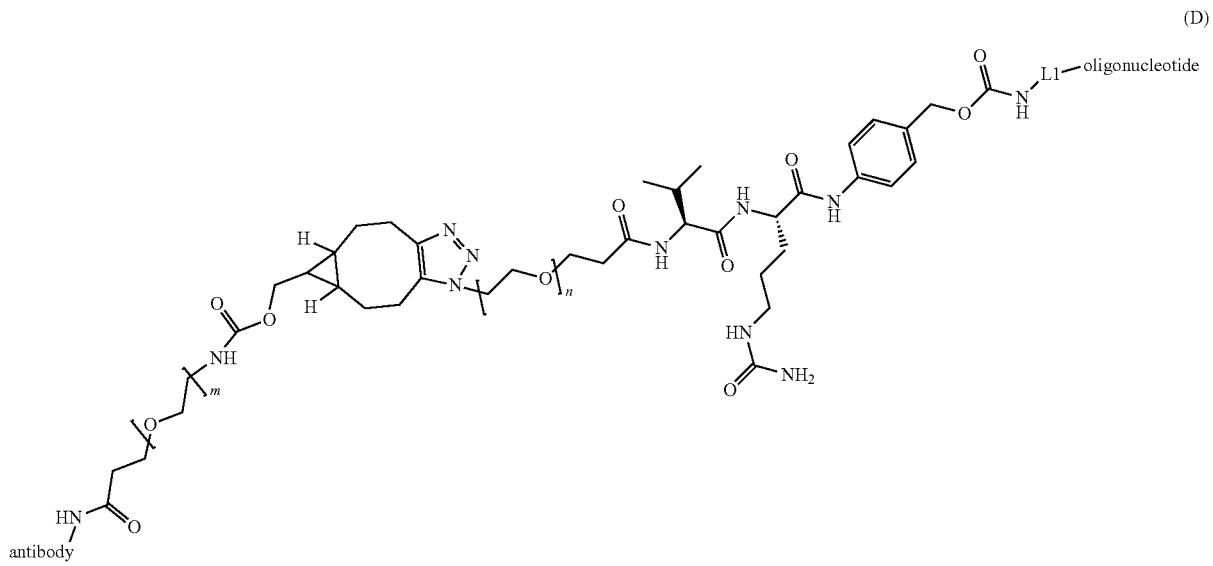

(D)

wherein n is a number between 0-10, wherein m is a number between 0-10, wherein the linker is linked to the antibody via an amine group (e.g., on a lysine residue), and/or (e.g., and) wherein the linker is linked to the oligonucleotide (e.g., at the 5' end, 3' end, or internally). In some embodiments, the linker is linked to the antibody via a lysine, the linker is linked to the oligonucleotide at the 5' end, n is 3, and m is 4. In some embodiments, the molecular payload is an oligonucleotide comprising a sense strand and an antisense strand, and, the linker is linked to the sense strand or the antisense strand at the 5' end or the 3' end. In some embodiments, the molecular payload is a DMPK-targeting oligonucleotide (e.g., a DMPK-targeting oligonucleotide listed in Table 8 or Table 17).

It should be appreciated that antibodies can be linked to molecular payloads with different stoichiometries, a property that may be referred to as a drug to antibody ratios (DAR) with the "drug" being the molecular payload. In some embodiments, one molecular payload is linked to an antibody (DAR=1). In some embodiments, two molecular payloads are linked to an antibody (DAR=2). In some embodiments, three molecular payloads are linked to an antibody (DAR=3). In some embodiments, four molecular payloads are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating molecular payloads to different sites on an antibody and/or (e.g., and) by conjugating multimers to one or more sites on antibody. For example, a DAR of 2 may be achieved by conjugating a single molecular payload to two different sites on an antibody or by conjugating a dimer molecular payload to a single site of an antibody.

In some embodiments, the complex described herein comprises an anti-TfR antibody described herein (e.g., the 3-A4, 3-M12, and 5-H12 antibodies provided in Table 2 in an IgG or Fab form) covalently linked to a molecular payload. In some embodiments, the complex described herein comprises an anti-TfR antibody described herein (e.g., the 3-A4, 3-M12, and 5-H12 antibodies provided in Table 2 in a IgG or Fab form) covalently linked to molecular payload via a linker (e.g., a Val-cit linker). In some embodiments, the linker (e.g., a Val-cit linker) is linked to the antibody (e.g., an anti-TfR antibody described herein) via a thiol-reactive linkage (e.g., via a cysteine in the antibody). In some embodiments, the linker (e.g., a Val-cit linker) is linked to the antibody (e.g., an anti-TfR antibody described herein) via an amine group (e.g., via a lysine in the antibody). In some embodiments, the molecular payload is a DMPK-targeting oligonucleotide (e.g., a DMPK-targeting oligonucleotide listed in Table 8 or Table 17).

In some embodiments, in any one of the examples of complexes described herein, the molecular payload a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a CDR-H1, a CDR-H2, and a CDR-H3 that are the same as the CDR-H1, CDR-H2, and CDR-H3 shown in Table 2; and a CDR-L1, a CDR-L2, and a CDR-L3 that are the same as the CDR-L1, CDR-L2, and CDR-L3 shown in Table 2. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a VH comprising the amino acid sequence of SEQ ID NO: 69, SEQ ID NO: 71, or SEQ ID NO: 72, and a VL comprising the amino acid sequence of SEQ ID NO: 70. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a VH comprising the amino acid sequence of SEQ ID NO: 73 or SEQ ID NO: 76, and a VL comprising the amino acid sequence of SEQ ID NO: 74. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a VH comprising the amino acid sequence of SEQ ID NO: 73 or SEQ ID NO: 76, and a VL comprising the amino acid sequence of SEQ ID NO: 75. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a VH comprising the amino acid sequence of SEQ ID NO: 77, and a VL comprising the amino acid sequence of SEQ ID NO: 78. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a VH comprising the amino acid sequence of SEQ ID NO: 77 or SEQ ID NO: 79, and a VL comprising the amino acid sequence of SEQ ID NO: 80. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 84, SEQ ID NO: 86 or SEQ ID NO: 87 and a light chain comprising the amino acid sequence of SEQ ID NO: 85. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 88 or SEQ ID NO: 91, and a light chain comprising the amino acid sequence of SEQ ID NO: 89. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 88 or SEQ ID NO: 91, and a light chain comprising the amino acid sequence of SEQ ID NO: 90. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 92 or SEQ ID NO: 94, and a light chain comprising the amino acid sequence of SEQ ID NO: 95. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 92, and a light chain comprising the amino acid sequence of SEQ ID NO: 93. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 97, SEQ ID NO: 98, or SEQ ID NO: 99 and a VL comprising the amino acid sequence of SEQ ID NO: 85. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 100 or SEQ ID NO: 101 and a light chain comprising the amino acid sequence of SEQ ID NO: 89. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 100 or SEQ ID NO: 101 and a light chain comprising the amino acid sequence of SEQ ID NO: 90. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 102 and a light chain comprising the amino acid sequence of SEQ ID NO: 93. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked to a molecular payload, wherein the anti-TfR antibody comprises a heavy chain comprising the amino acid sequence of SEQ ID NO: 102 or SEQ ID NO: 103 and a light chain comprising the amino acid sequence of SEQ ID NO: 95. In some embodiments, the molecular payload is a DMPK-targeting oligonucleotide (e.g., a DMPK-targeting oligonucleotide listed in Table 8 or Table 17).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 84 and a light chain comprising the amino acid sequence of in SEQ ID NO: 85; wherein the complex has the structure of:

(D)

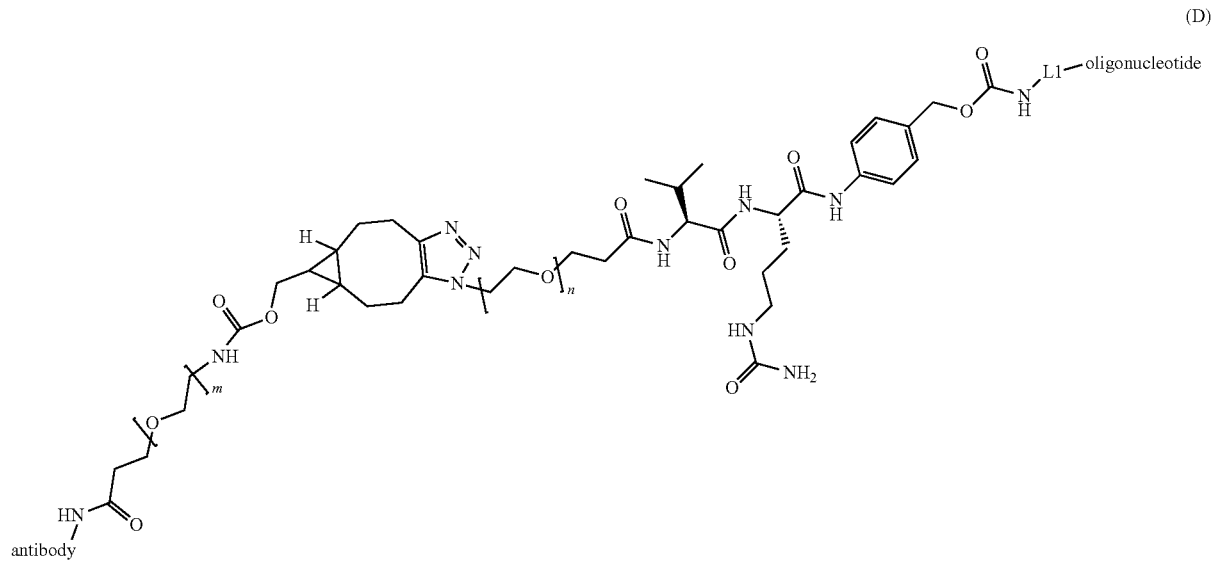

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide, wherein the anti-TfR antibody comprises a heavy chain comprising the amino acid sequence of SEQ ID NO: 86 and a light chain comprising the amino acid sequence of in SEQ ID NO: 85; wherein the complex has the structure of:

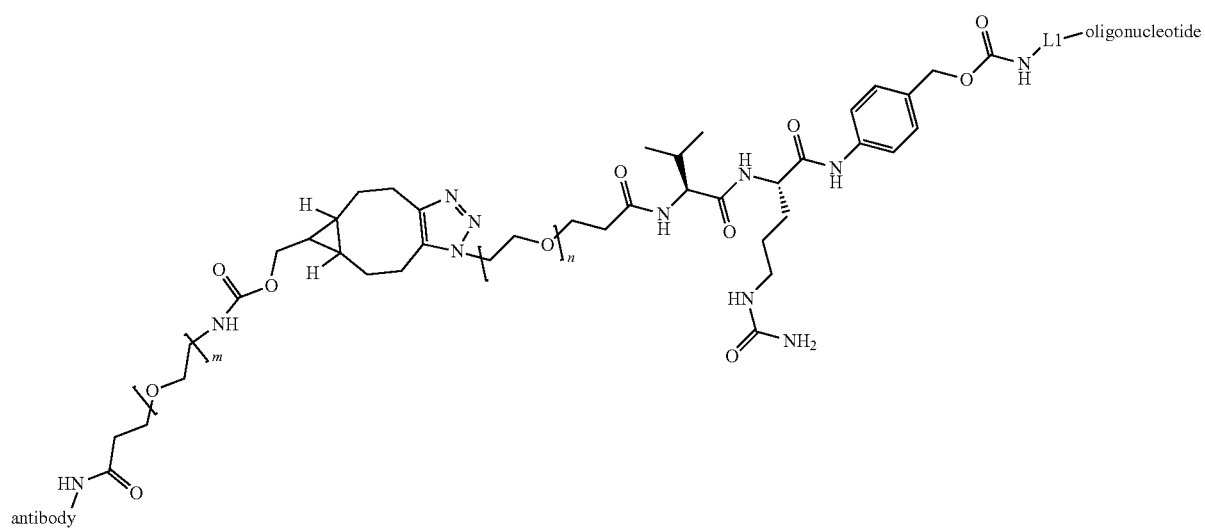

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264). In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 87 and a light chain comprising the amino acid sequence of in SEQ ID NO: 85; wherein the complex has the structure of:

(D)

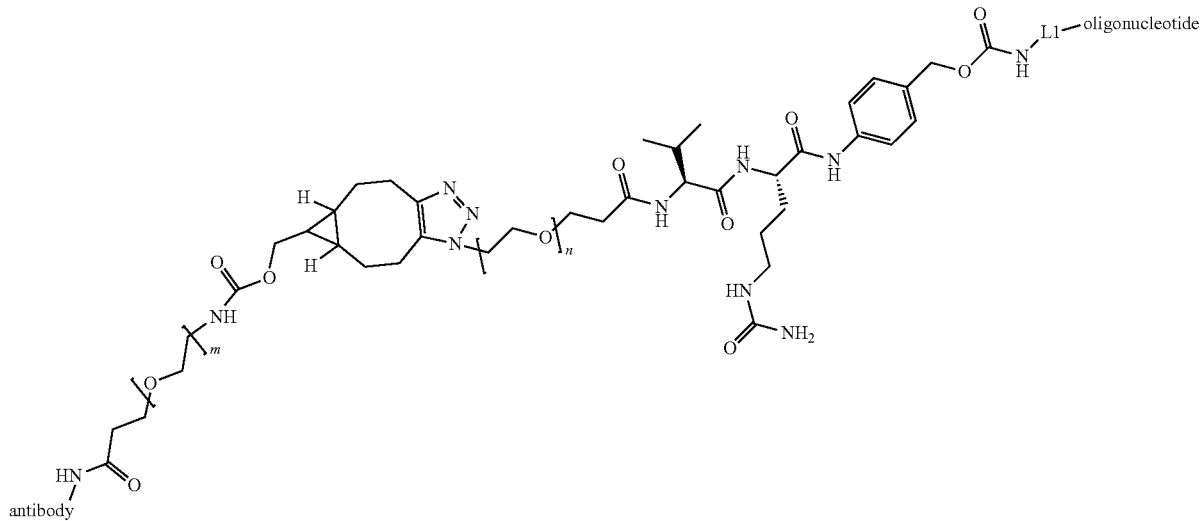

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 88 and a light chain comprising the amino acid sequence of in SEQ ID NO: 89; wherein the complex has the structure of:

(D)

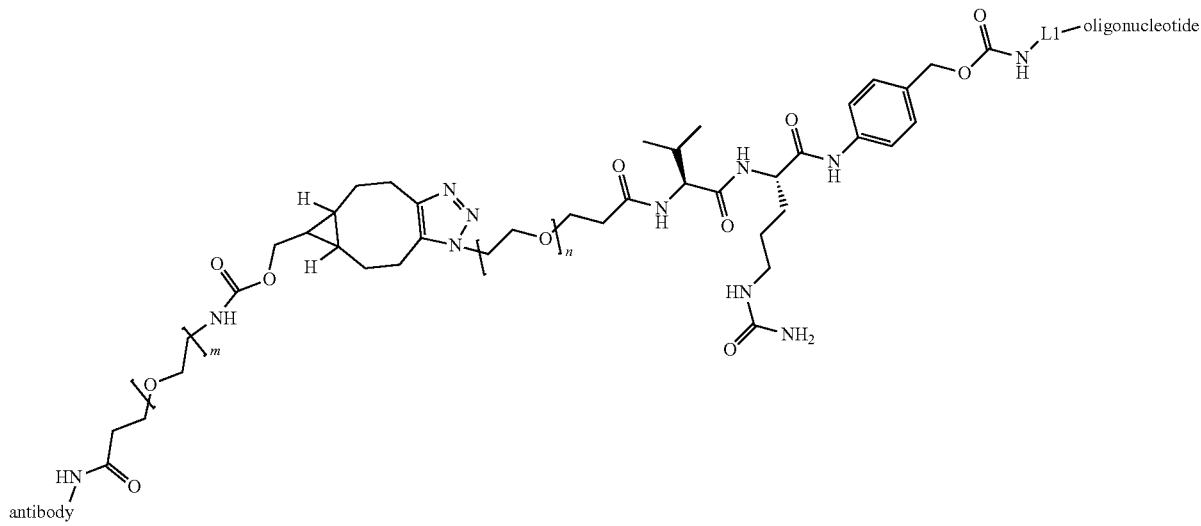

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 88 and a light chain comprising the amino acid sequence of in SEQ ID NO: 90; wherein the complex has the structure of:

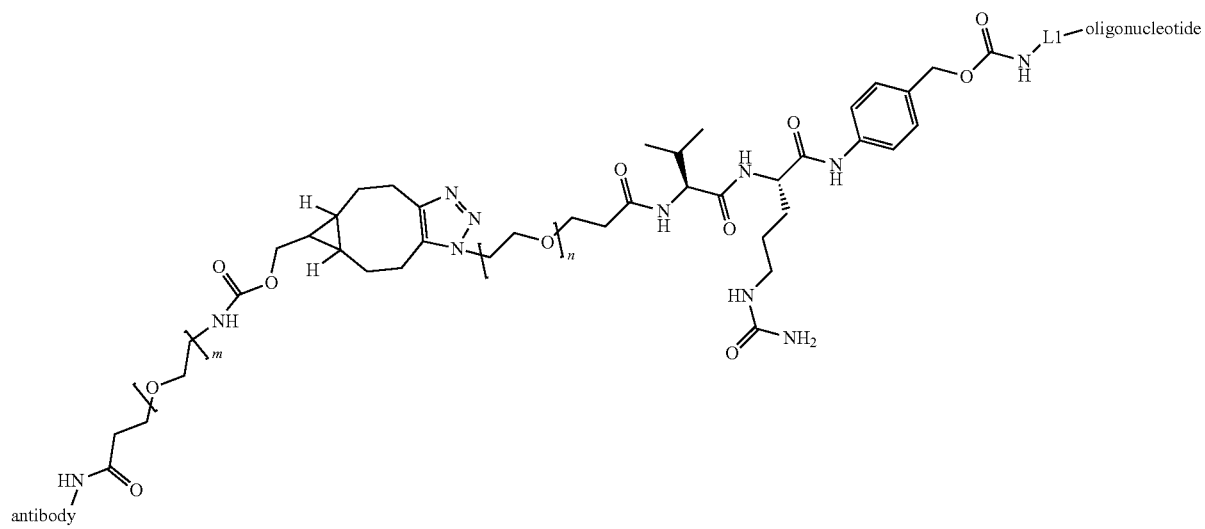

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 91 and a light chain comprising the amino acid sequence of in SEQ ID NO: 89; wherein the complex has the structure of:

(D)

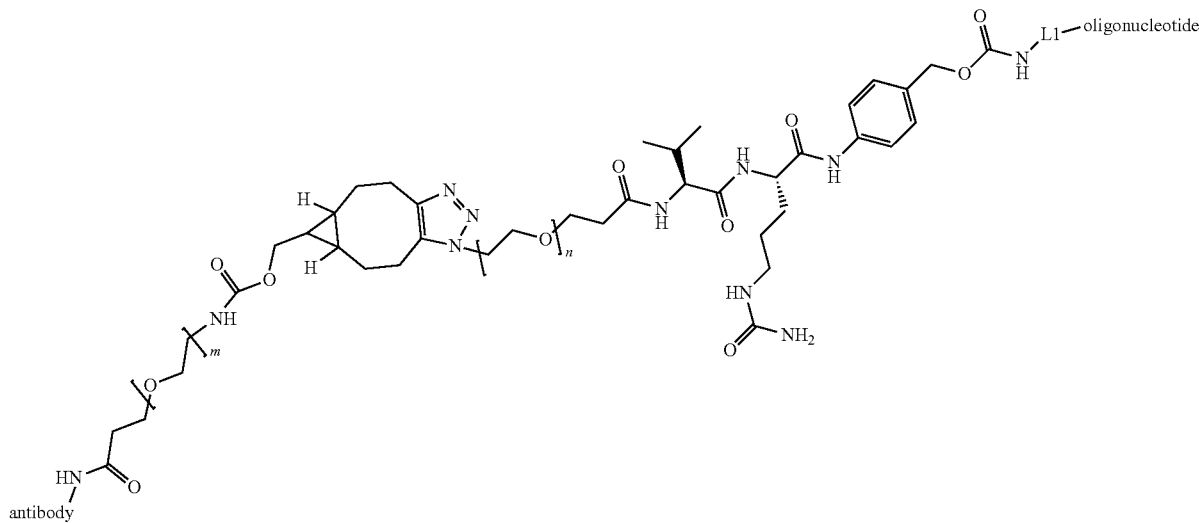

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 91 and a light chain comprising the amino acid sequence of in SEQ ID NO: 90; wherein the complex has the structure of:

(D)

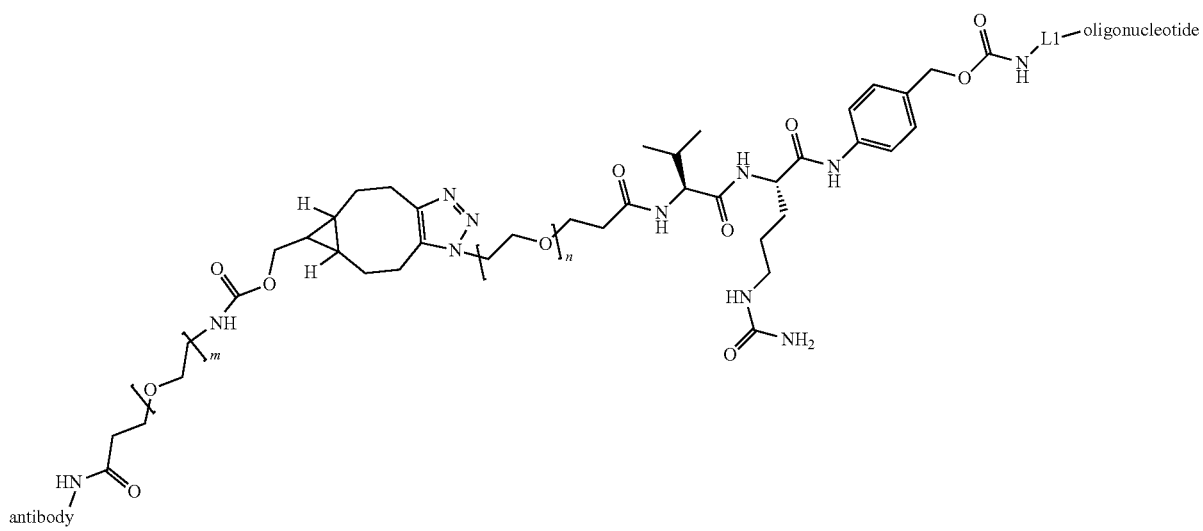

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 92 and a light chain comprising the amino acid sequence of in SEQ ID NO: 93; wherein the complex has the structure of:

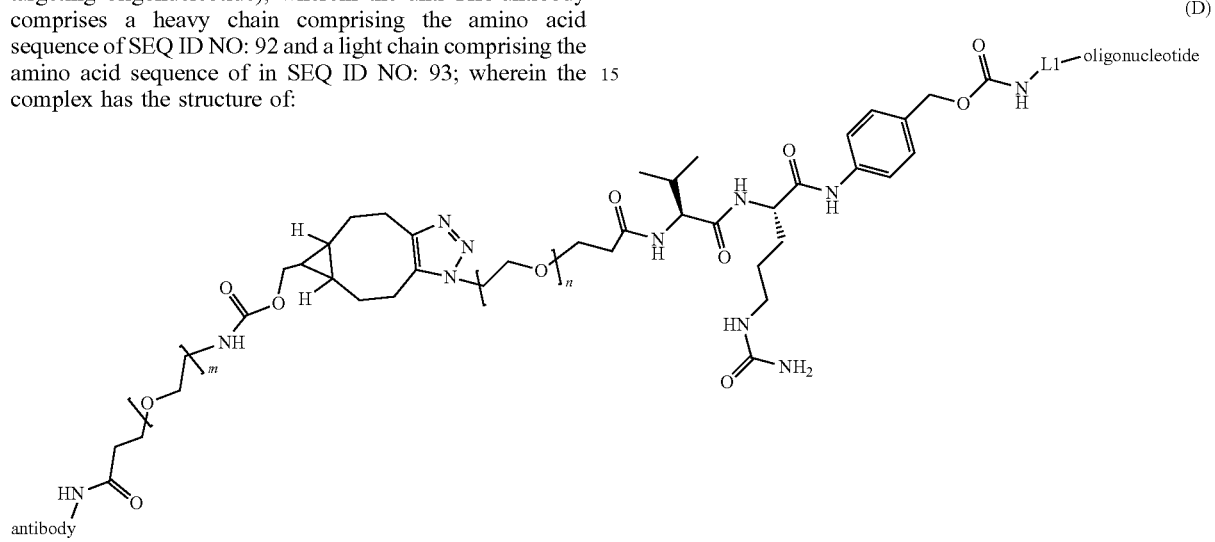

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 94 and a light chain comprising the amino acid sequence of in SEQ ID NO: 95; wherein the complex has the structure of:

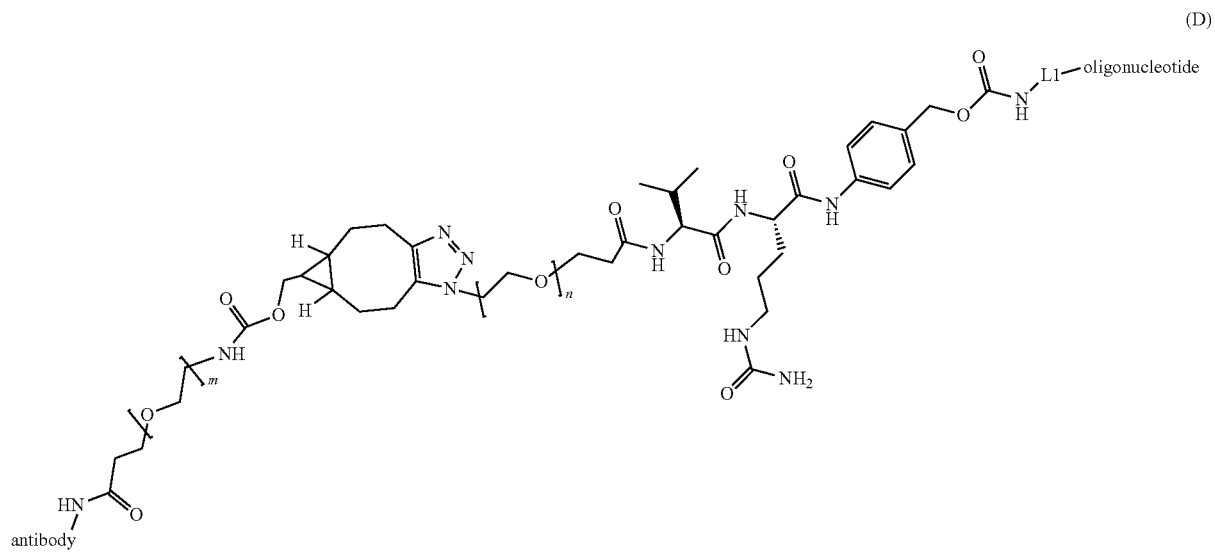

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR antibody covalently linked via a lysine to the 5' end of an oligonucleotide (e.g., a DMPK-targeting oligonucleotide), wherein the anti-TfR antibody comprises a heavy chain comprising the amino acid sequence of SEQ ID NO: 92 and a light chain comprising the amino acid sequence of in SEQ ID NO: 95; wherein the complex has the structure of:

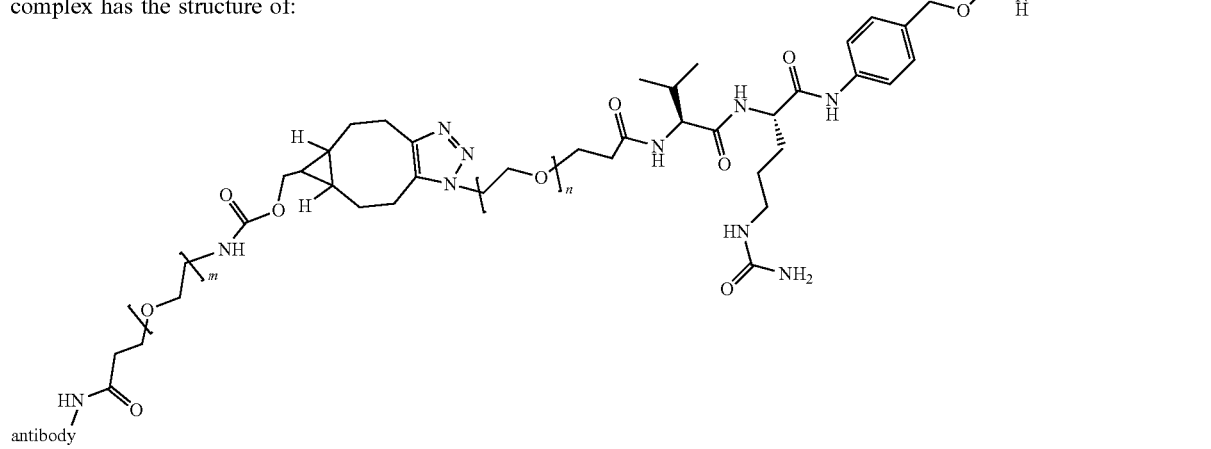

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 69 and a VL comprising the amino acid sequence of in SEQ ID NO: 70; wherein the complex has the structure of:

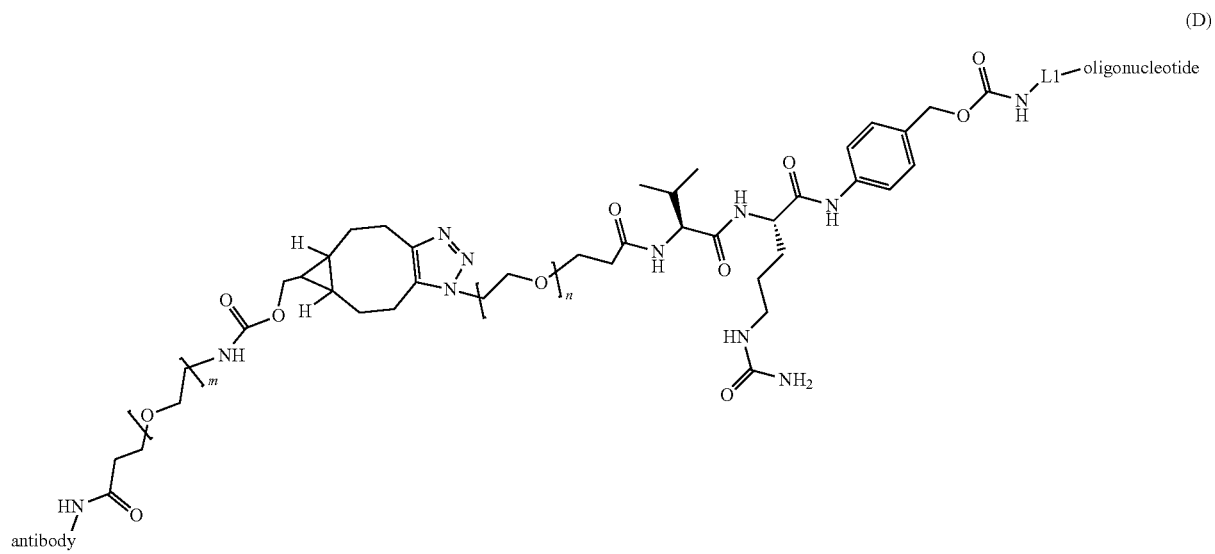

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 71 and a VL comprising the amino acid sequence of in SEQ ID NO: 70; wherein the complex has the structure of:

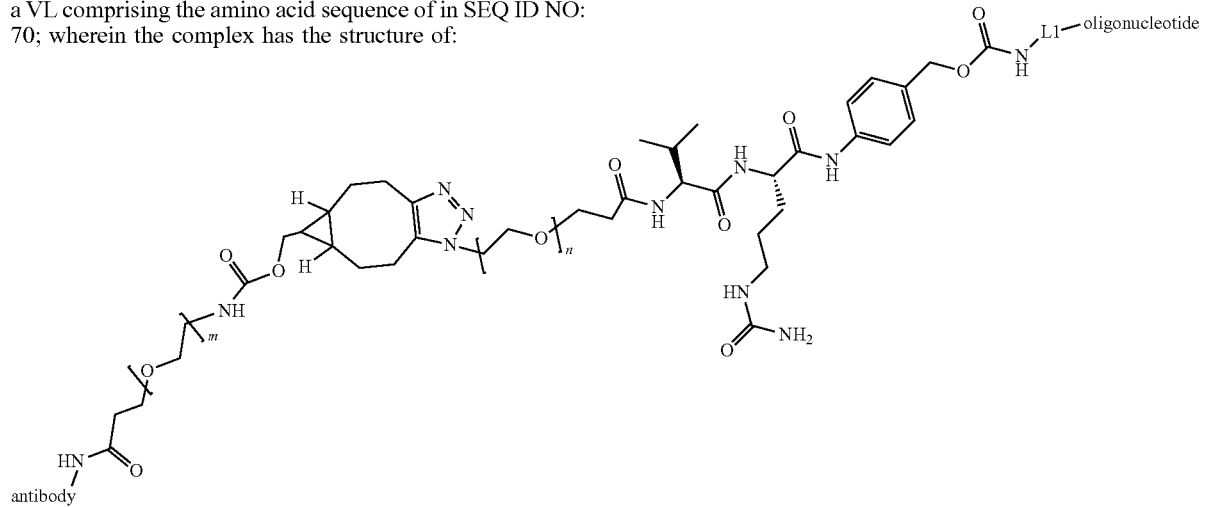

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 72 and a VL comprising the amino acid sequence of in SEQ ID NO: 70; wherein the complex has the structure of:

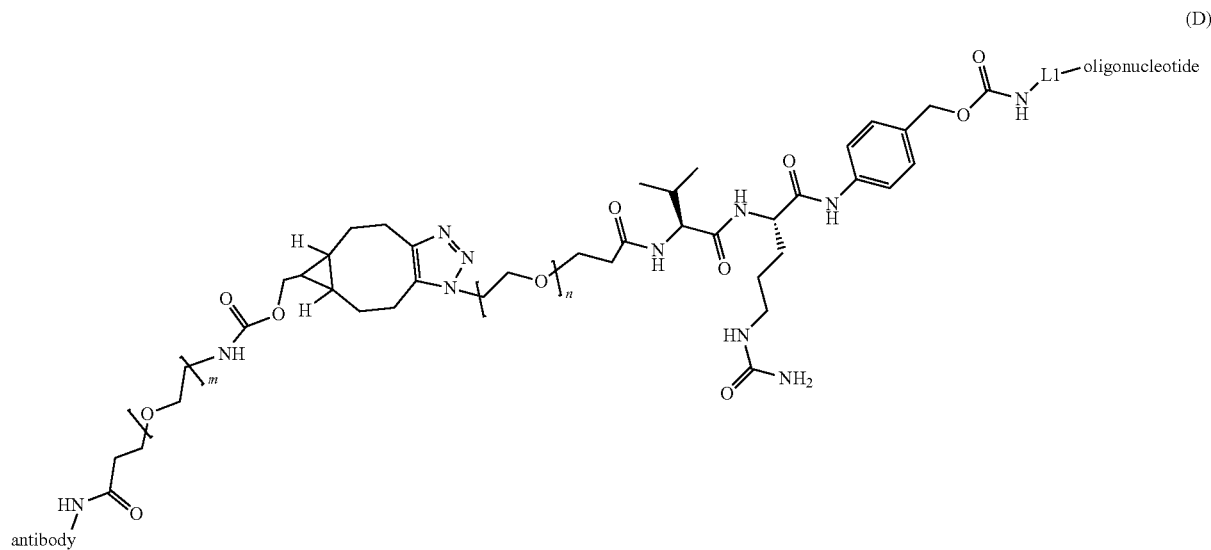

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 73 and a VL comprising the amino acid sequence of in SEQ ID NO: 74; wherein the complex has the structure of:

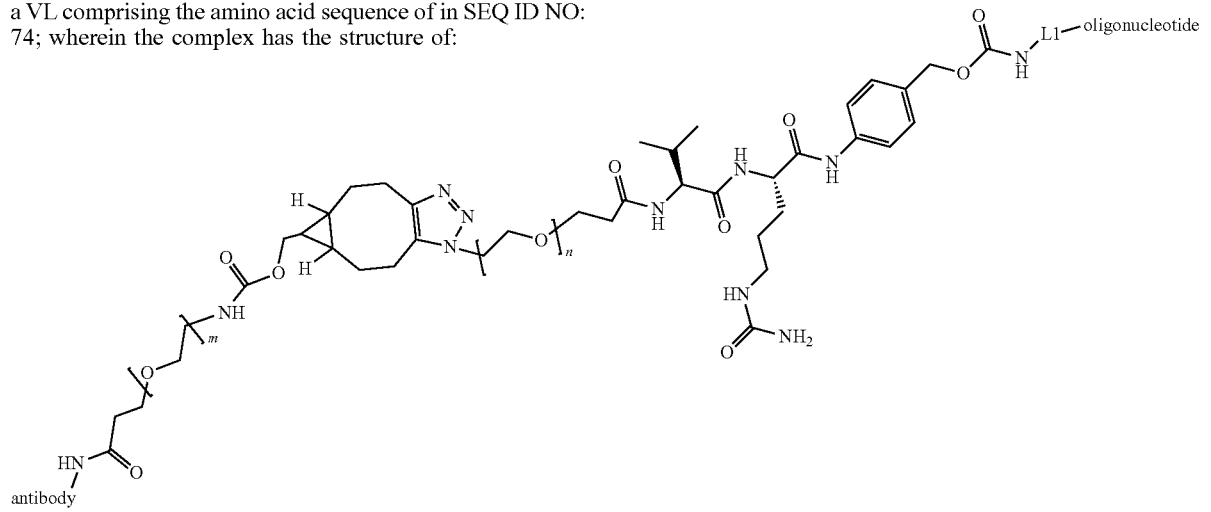

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 73 and a VL comprising the amino acid sequence of in SEQ ID NO: 75; wherein the complex has the structure of:

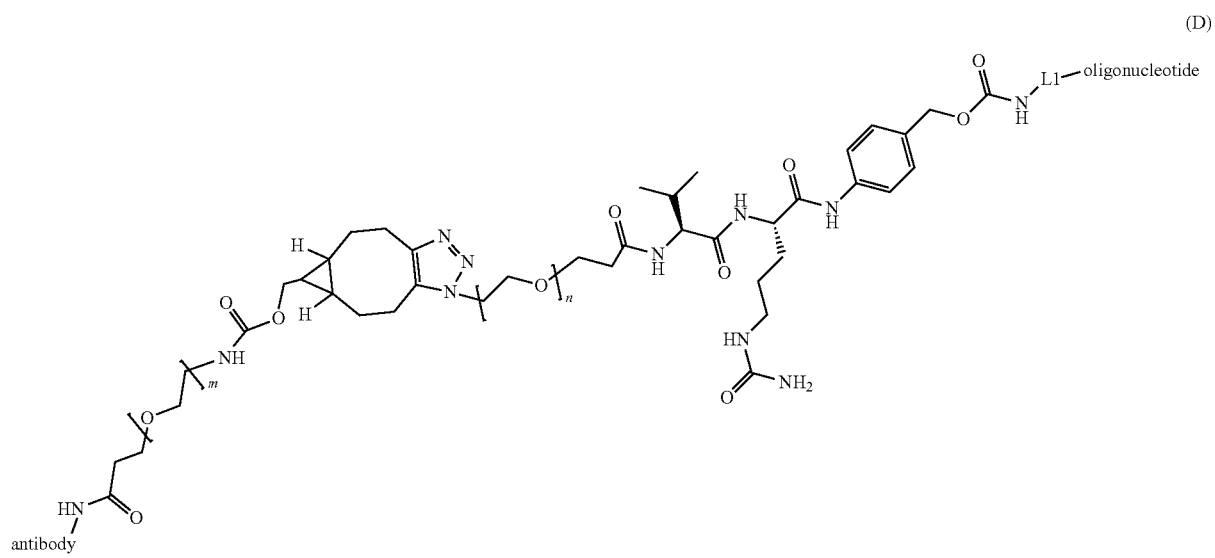

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 76 and a VL comprising the amino acid sequence of in SEQ ID NO: 74; wherein the complex has the structure of:

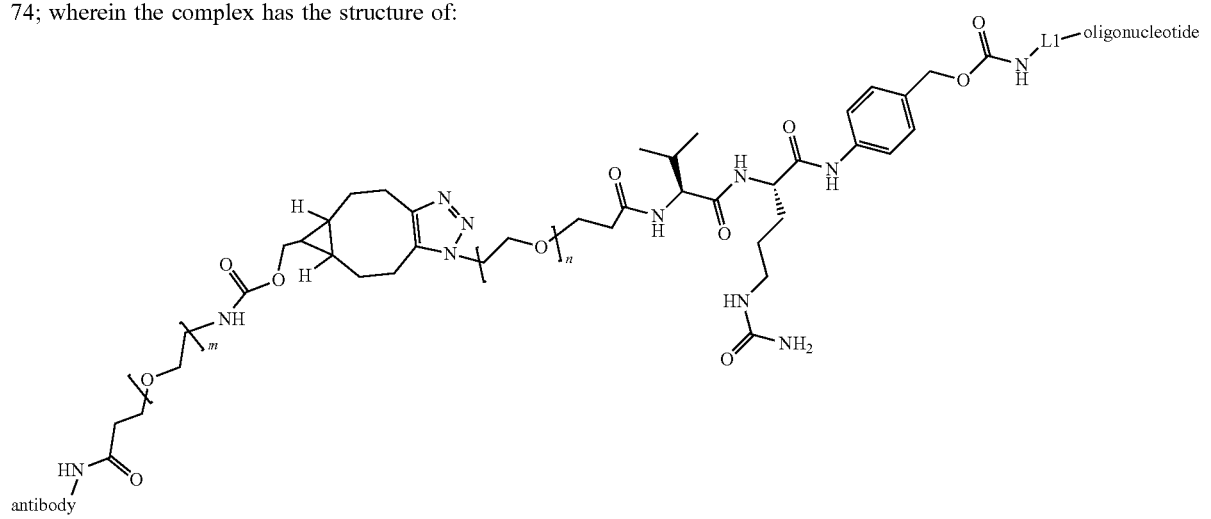

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 76 and a VL comprising the amino acid sequence of in SEQ ID NO: 75; wherein the complex has the structure of:

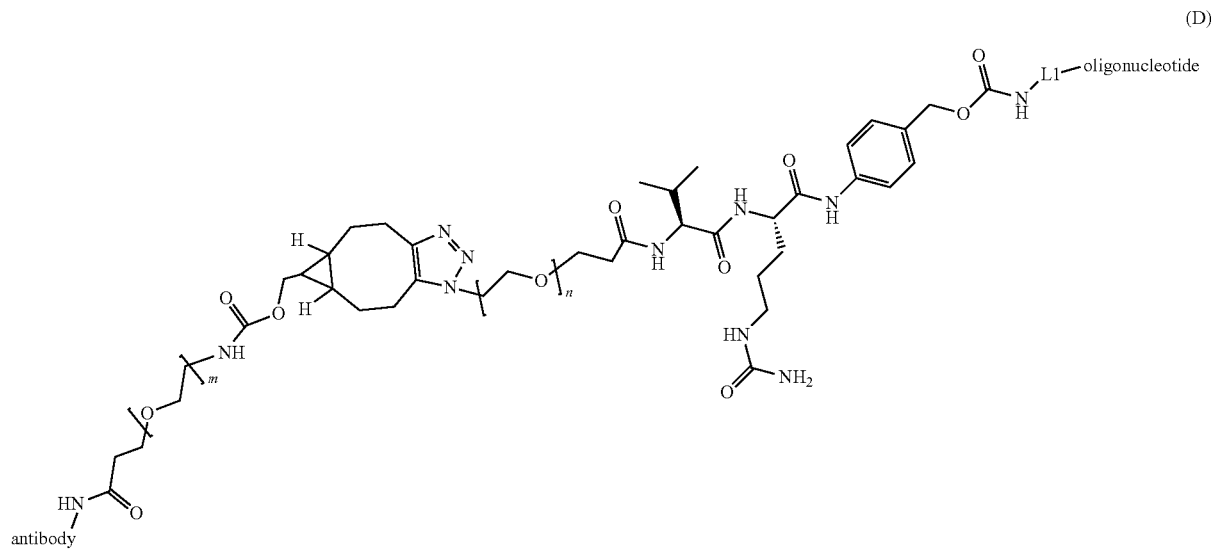

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 77 and a VL comprising the amino acid sequence of in SEQ ID NO: 78; wherein the complex has the structure of:

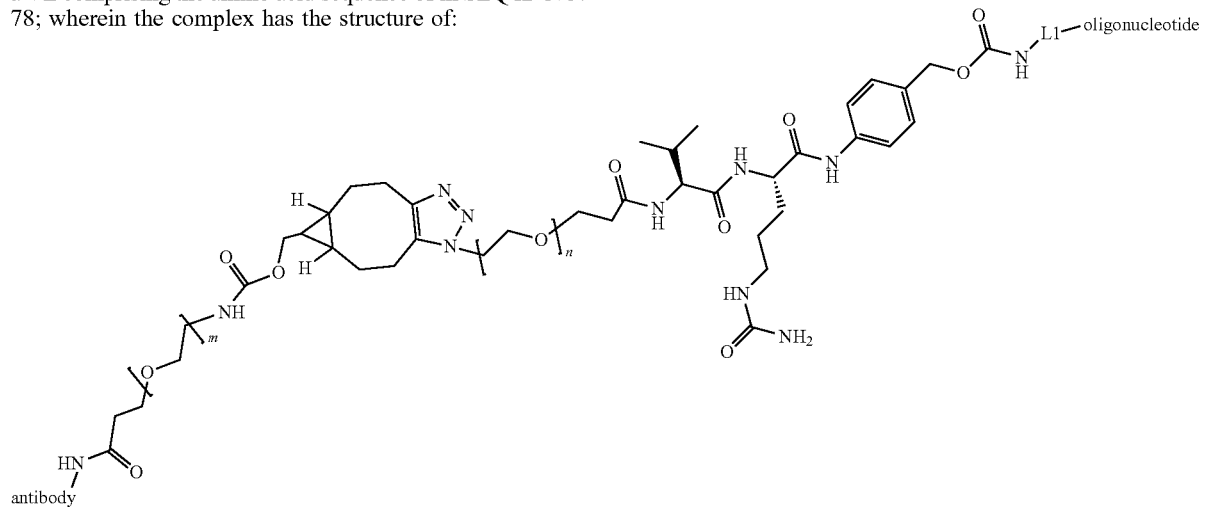

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 79 and a VL comprising the amino acid sequence of in SEQ ID NO: 80; wherein the complex has the structure of:

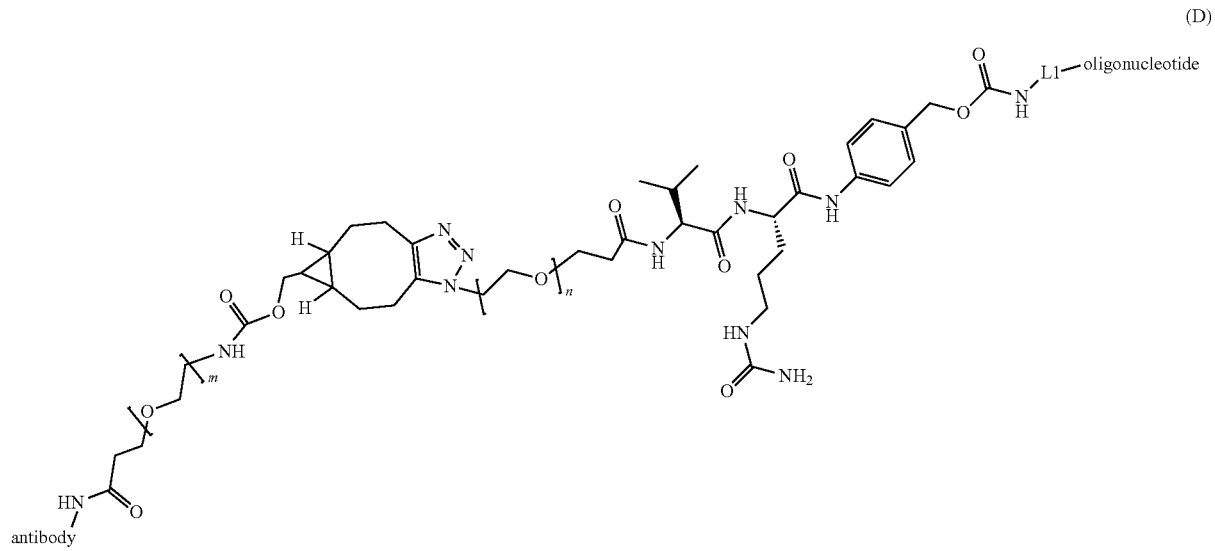

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a VH comprising the amino acid sequence of SEQ ID NO: 77 and a VL comprising the amino acid sequence of in SEQ ID NO: 80; wherein the complex has the structure of:

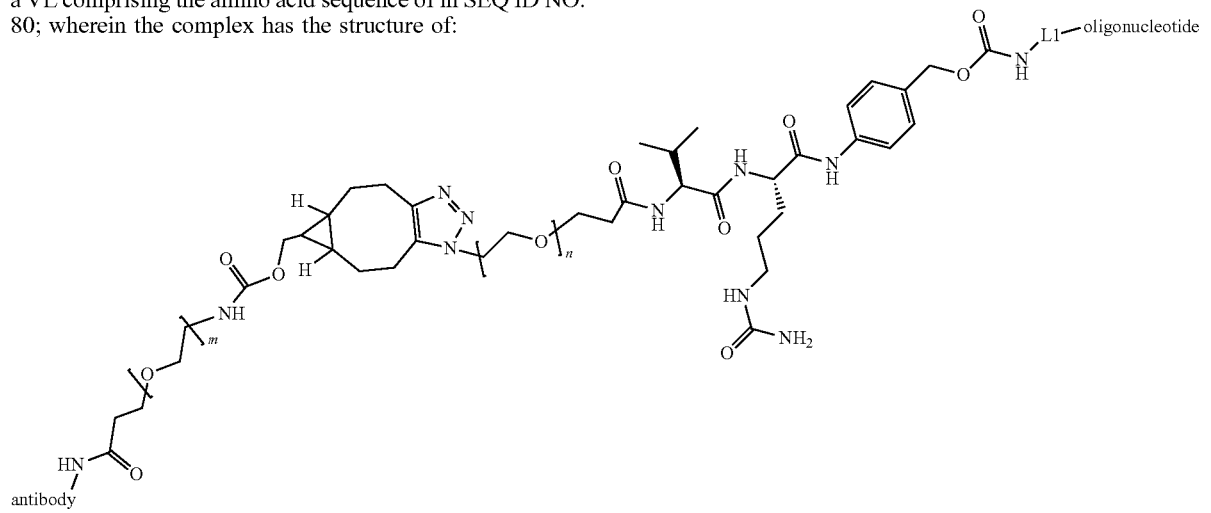

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 97 and a light chain comprising the amino acid sequence of in SEQ ID NO: 85; wherein the complex has the structure of:

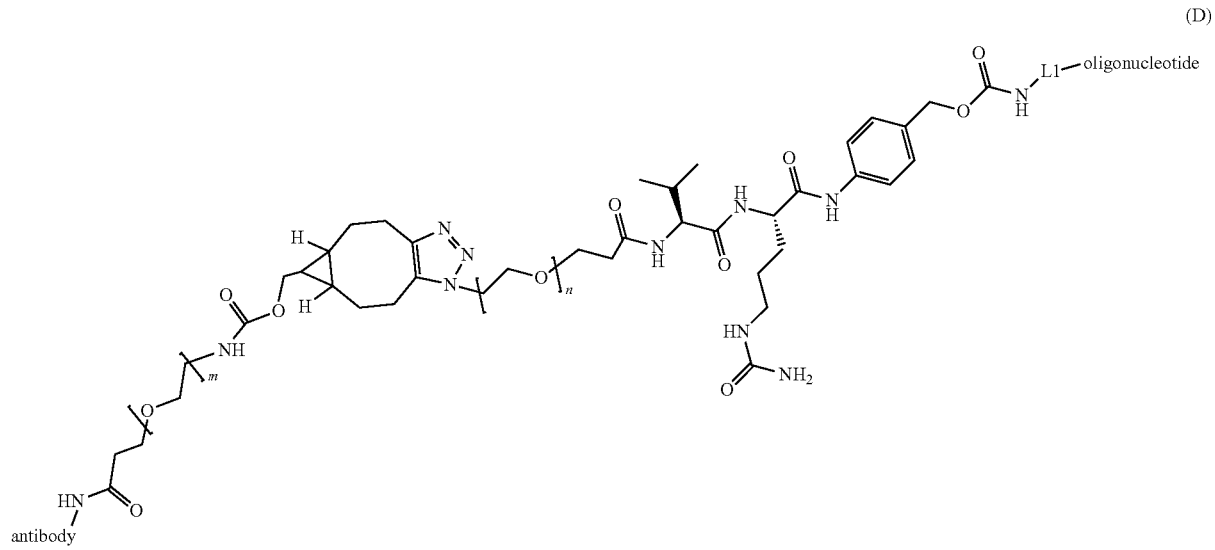

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 98 and a light chain comprising the amino acid sequence of in SEQ ID NO: 85; wherein the complex has the structure of:

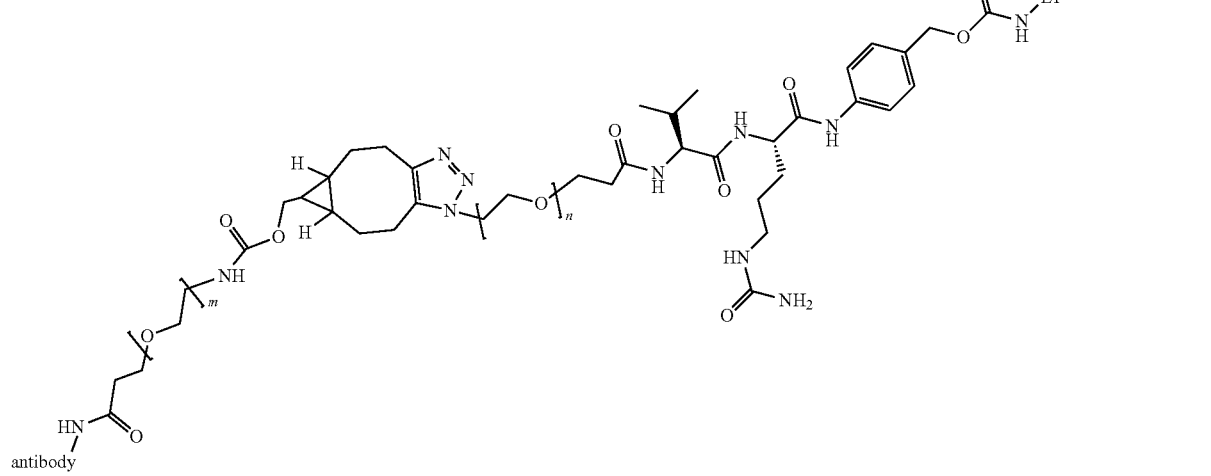

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 99 and a light chain comprising the amino acid sequence of in SEQ ID NO: 85; wherein the complex has the structure of:

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 100 and a light chain comprising the amino acid sequence of in SEQ ID NO: 89; wherein the complex has the structure of:

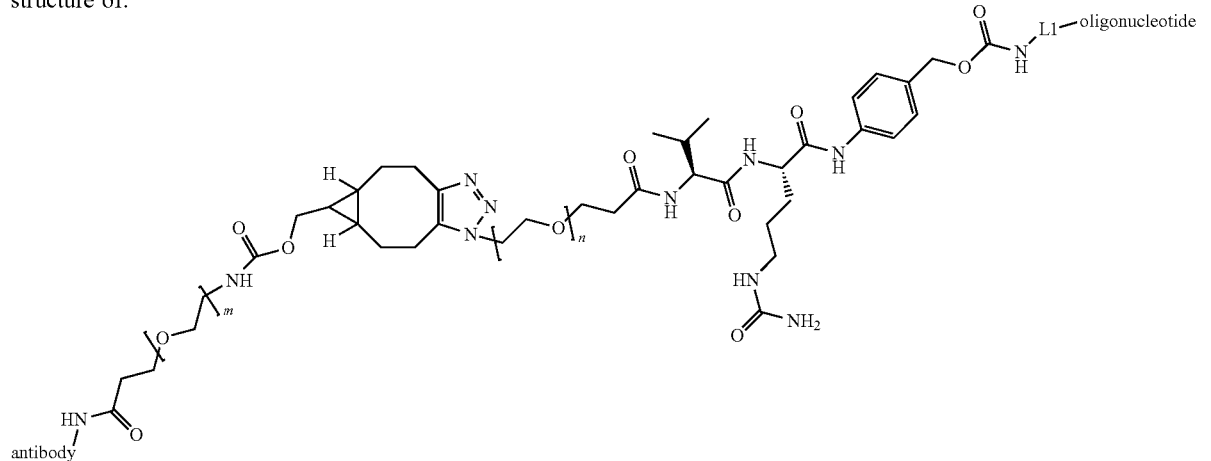

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 100 and a light chain comprising the amino acid sequence of in SEQ ID NO: 90; wherein the complex has the structure of:

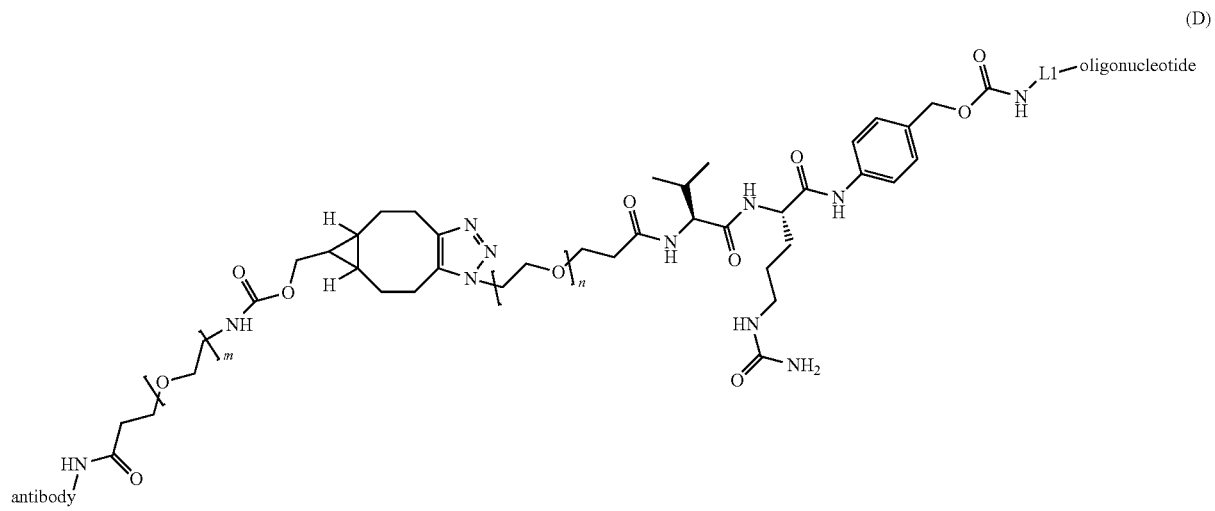

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 101 and a light chain comprising the amino acid sequence of in SEQ ID NO: 89; wherein the complex has the structure of:

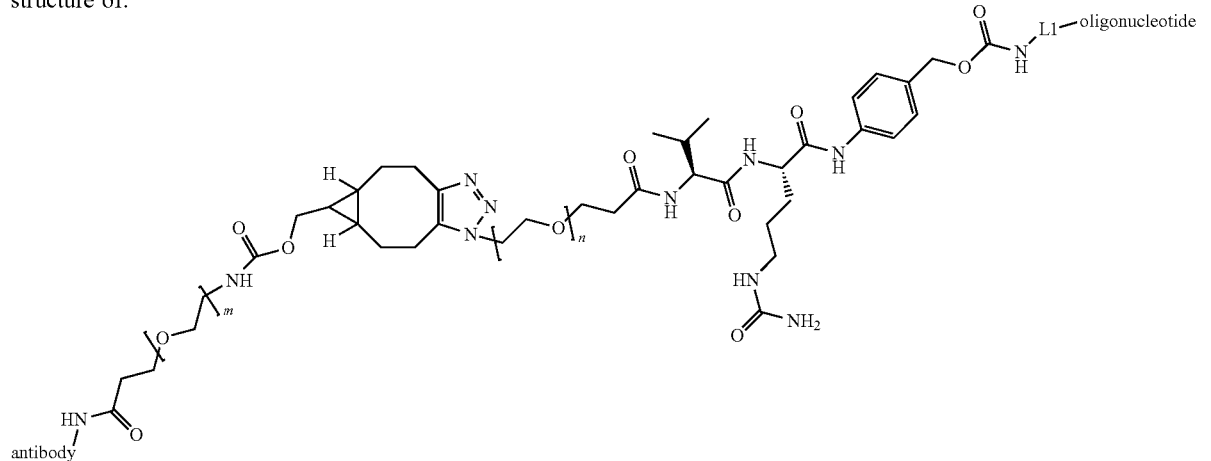

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 101 and a light chain comprising the amino acid sequence of in SEQ ID NO: 90; wherein the complex has the structure of:

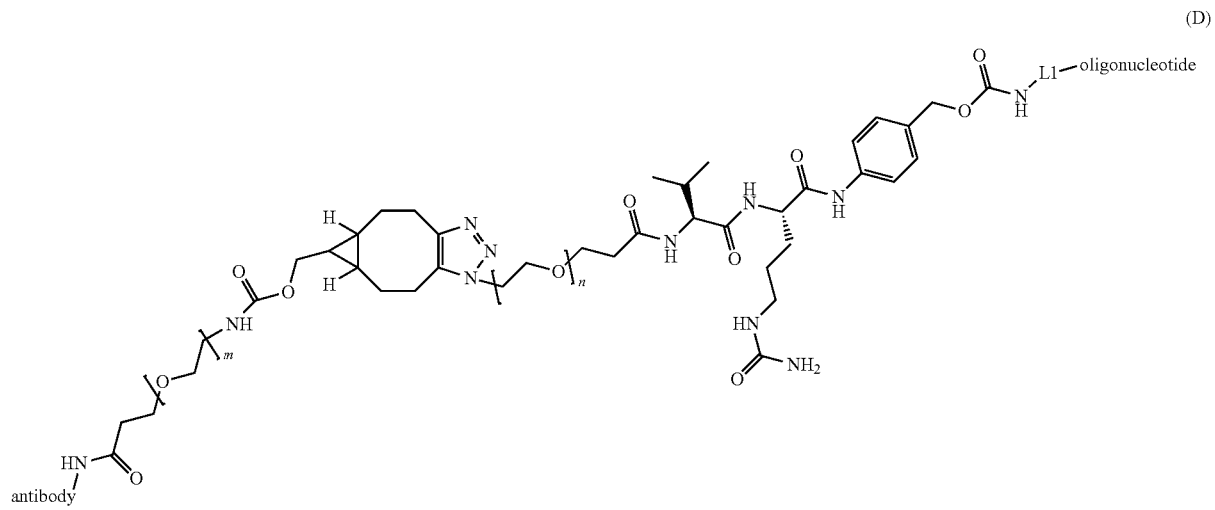

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 102 and a light chain comprising the amino acid sequence of in SEQ ID NO: 93; wherein the complex has the structure of:

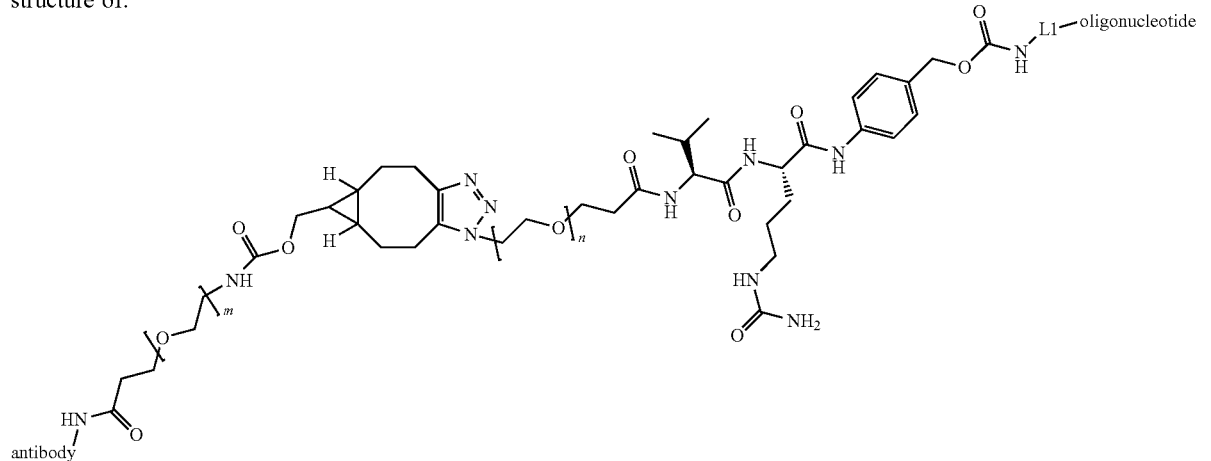

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 103 and a light chain comprising the amino acid sequence of in SEQ ID NO: 95; wherein the complex has the structure of:

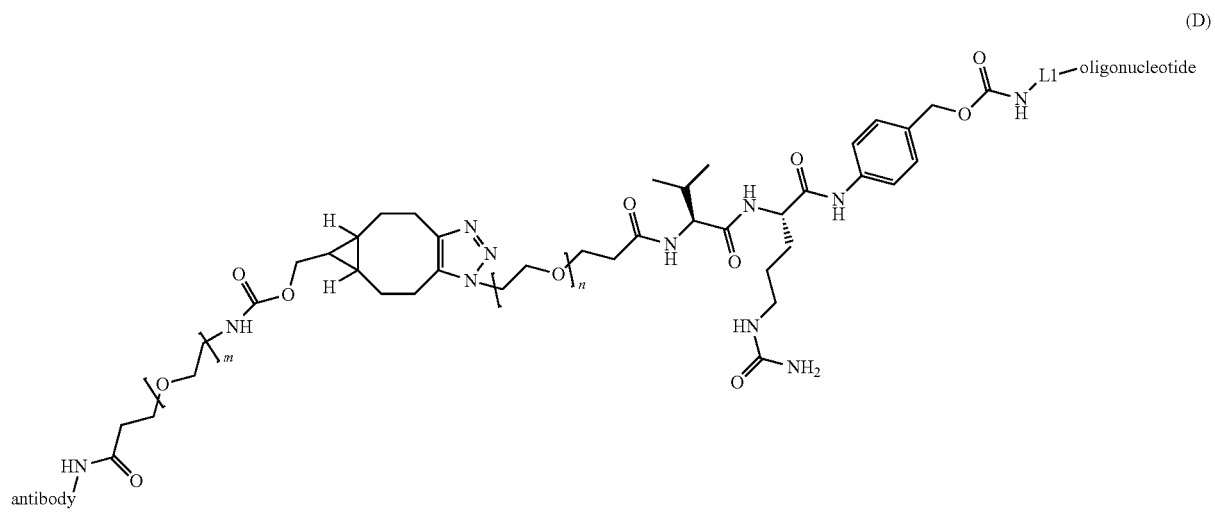

(D)

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, the complex described herein comprises an anti-TfR Fab covalently linked via a lysine to the 5' end of an oligonucleotide (e.g., a DMPK-targeting oligonucleotide), wherein the anti-TfR Fab comprises a heavy chain comprising the amino acid sequence of SEQ ID NO: 102 and a light chain comprising the amino acid sequence of in SEQ ID NO: 95; wherein the complex has the structure of:

wherein the piperazine moiety links to the oligonucleotide, wherein L2 is

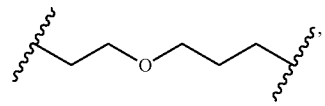

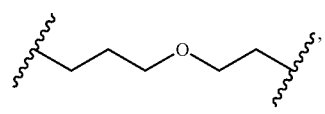

(D)

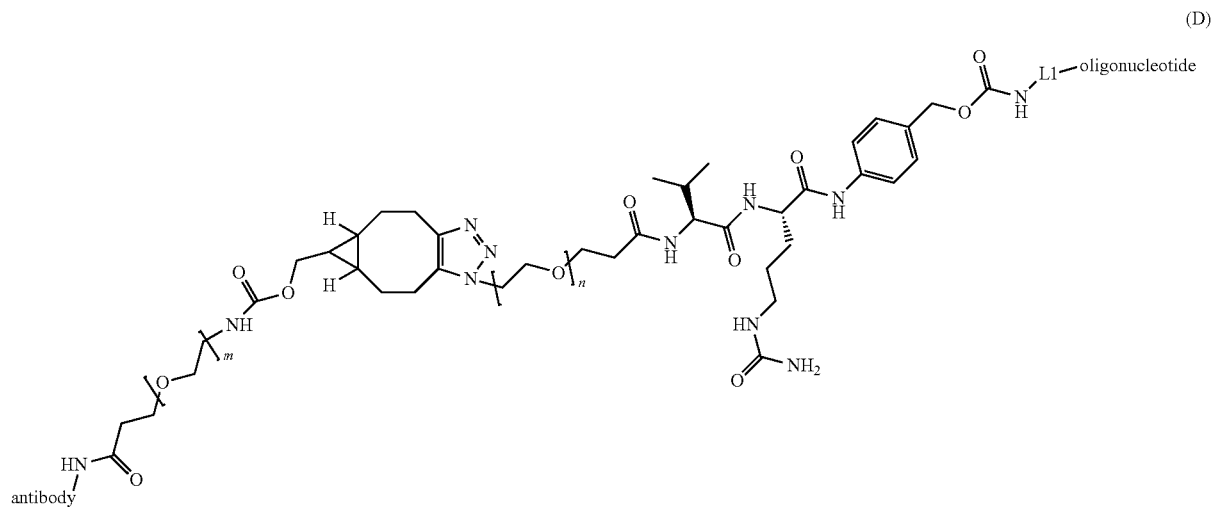

wherein n is 3 and m is 4, optionally wherein the DMPK-targeting oligonucleotide (e.g., a gapmer) comprises at least 10, 11, 12, 13, 14, 15, 16, 17, 18, 19, or 20 consecutive nucleotides (e.g., 10, 11, 12, 13, 14, 15, 16, 17, 18, 19, or 20 consecutive nucleotides) of any one of the oligonucleotides listed in Table 8 or Table 17 (e.g., any one of SEQ ID NOs: 159, 162, 172, 174, 180, 182, 188, 190, 195, 196, 201, 203, 212, 215, 218, 222, 248, and 264).

In some embodiments, in any one of the examples of complexes described herein, L1 is any one of the spacers described herein.

In some embodiments, L1 is:

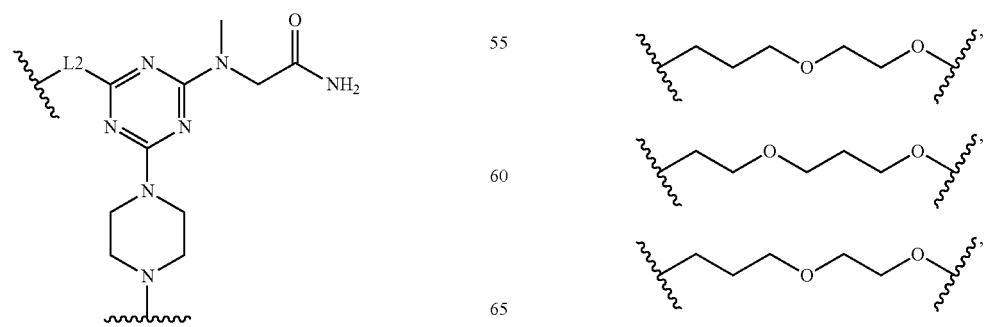

-continued

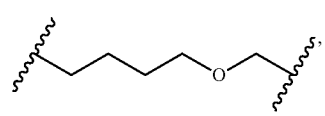

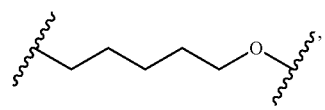

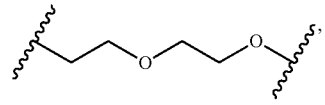

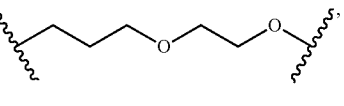

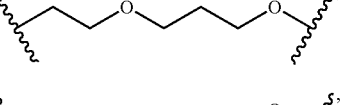

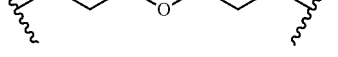

-continued

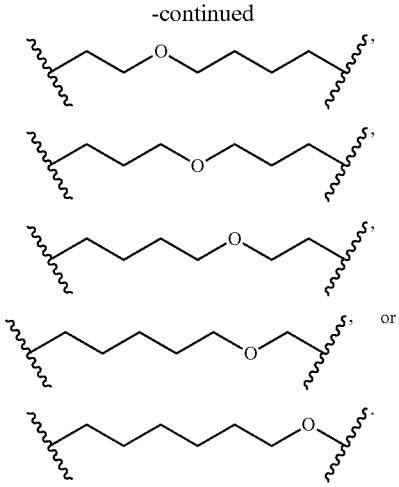

In some embodiments, L1 is:

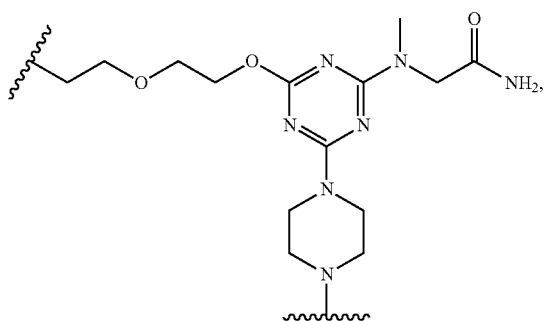 [SMILES: *CCOCCOc1nc(N(C)CC(N)=O)nc(N2CCN(*)CC2)n1]

wherein the piperazine moiety links to the oligonucleotide.

In some embodiments, L1 is

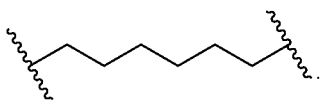 [SMILES: *CCCCCC*]

In some embodiments, L1 is linked to a 5' phosphate of the oligonucleotide.

In some embodiments, L1 is optional (e.g., need not be present).

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or (e.g., and) uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or (e.g., and) therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the complexes in a required amount in a selected solvent with one or a combination of ingredients enumerated above, as required, followed by filtered sterilization.

In some embodiments, a composition may contain at least about 0.1% of the complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently linked to a molecular payload as described herein are effective in treating myotonic dystrophy. In some embodiments, complexes are effective in treating myotonic dystrophy type 1 (DM1). In some embodiments, DM1 is associated with an expansion of a CTG trinucleotide repeat in the 3' non-coding region of DMPK. In some embodiments, the nucleotide expansions lead to toxic RNA repeats capable of forming hairpin structures that bind critical intracellular proteins, e.g., muscleblind-like proteins, with high affinity.

In some embodiments, a subject may be a human subject, a non-human primate subject, a rodent subject, or any suitable mammalian subject. In some embodiments, a subject may have myotonic dystrophy. In some embodiments, a subject has a DMPK allele, which may optionally contain a disease-associated repeat. In some embodiments, a subject may have a DMPK allele with an expanded disease-associated-repeat that comprises about 2-10 repeat units, about 2-50 repeat units, about 2-100 repeat units, about 50-1,000 repeat units, about 50-500 repeat units, about 50-250 repeat units, about 50-100 repeat units, about 500-10,000 repeat units, about 500-5,000 repeat units, about 500-2,500 repeat units, about 500-1,000 repeat units, or about 1,000-10,000 repeat units. In some embodiments, a subject is suffering from symptoms of DM1, e.g. muscle atrophy or muscle loss. In some embodiments, a subject is not suffering from symptoms of DM1. In some embodiments, subjects have congenital myotonic dystrophy.

An aspect of the disclosure includes a method involving administering to a subject an effective amount of a complex as described herein. In some embodiments, an effective amount of a pharmaceutical composition that comprises a complex comprising a muscle-targeting agent covalently linked to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently linked to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently linked to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment.

In some embodiments, an initial candidate dosage is about 1-50, 1-25, 1-10, 1-5, 5-100, 5-50, 5-25, 5-10, 10-100, 10-75, 10-50, 10-25, 10-20, 25-100, 25-75, or 25-50 mg/kg. In some embodiments, an initial candidate dosage is about 1-20, 1-15, 1-10, 1-5, 1-3, 1-2, 5-20, 5-15, or 5-10 mg/kg. In some embodiments, an initial candidate dosage is about 1, 2, 3, 4, 5, 6, 7, 8, 9, 10, 15, or 20 mg/kg.

The efficacy of treatment may be assessed using any suitable methods. In some embodiments, the efficacy of treatment may be assessed by evaluation of observation of symptoms associated with DM1, e.g. muscle atrophy or muscle weakness, through measures of a subject's self-reported outcomes, e.g. mobility, self-care, usual activities, pain/discomfort, and anxiety/depression, or by quality-of-life indicators, e.g. lifespan.

In some embodiments, a pharmaceutical composition that comprises a complex comprising a muscle-targeting agent covalently linked to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently linked to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently linked to a molecular payload described herein to a subject is sufficient to inhibit activity or expression of a target gene for at least 1, 2, 3, 4, 5, 6, 7, 8, 9, 10, 11, 12, 15, 20, or 24 weeks. In some embodiments, a single dose or administration of a pharmaceutical composition that comprises a complex comprising a muscle-targeting agent covalently linked to a molecular payload described herein to a subject is sufficient to inhibit activity or expression of a target gene for at least 1-5, 1-10, 2-5, 2-10, 4-8, 4-12, 5-10, 5-12, 5-15, 8-12, 8-15, 10-12, 10-15, 10-20, 12-15, 12-20, 15-20, or 15-25 weeks. In some embodiments, a single dose or administration of a pharmaceutical composition that comprises a complex comprising a muscle-targeting agent covalently linked to a molecular payload described herein to a subject is sufficient to inhibit activity or expression of a target gene for at least 1, 2, 3, 4, 5, or 6 months.

In some embodiments, a single dose or administration of a pharmaceutical composition that comprises a complex comprising a muscle-targeting agent covalently linked to a molecular payload described herein to a subject persists or remains in the subject for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently linked to a molecular payload described herein to a subject persists or remains in the subject for at least 1, 2, 3, 4, 5, 6, 7, 8, 9, 10, 11, 12, 15, 20, or 24 weeks. In some embodiments, a single dose or administration of a pharmaceutical composition that comprises a complex comprising a muscle-targeting agent covalently linked to a molecular payload described herein to a subject persists or remains in the subject for at least 1-5, 1-10, 2-5, 2-10, 4-8, 4-12, 5-10, 5-12, 5-15, 8-12, 8-15, 10-12, 10-15, 10-20, 12-15, 12-20, 15-20, or 15-25 weeks. In some embodiments, a single dose or administration of a pharmaceutical composition that comprises a complex comprising a muscle-targeting agent covalently linked to a molecular payload described herein to a subject persists or remains in the subject for at least 1, 2, 3, 4, 5, or 6 months.

In some embodiments, multiple doses or administrations of a pharmaceutical composition that comprises a complex comprising a muscle-targeting agent covalently linked to a molecular payload described herein are delivered to a subject. In some embodiments, multiple doses of a pharmaceutical composition comprise delivering 2, 3, 4, 5, 6, 7, 8, 9, or 10 doses to a subject. In some embodiments, multiple doses of a pharmaceutical composition comprise delivering a dose to a subject every 1, 2, 3, 4, 5, 6, 7, 8, 9, 10, 11, 12, 13, 14, 15, or 16 weeks. In some embodiments, multiple doses of a pharmaceutical composition comprise delivering a dose to a subject once every 4 weeks. In some embodiments, multiple doses of a pharmaceutical composition comprise delivering a dose to a subject once every 1-10, 2-5, 2-10, 4-8, 4-12, 5-10, 5-12, 5-15, 8-12, 8-16, 10-12, 10-15, 10-20, 12-15, 12-20, 15-20, or 15-25 weeks. In some embodiments, multiple doses of a pharmaceutical composition comprise delivering a dose to a subject on a biweekly (i.e., every two weeks), bimonthly (i.e., every two months), or quarterly schedule (i.e., every twelve weeks).

In some embodiments, a single dose or administration is about 1-50, 1-25, 1-10, 1-15, 1-5, 5-100, 5-50, 5-25, 5-10, 10-100, 10-75, 10-50, 10-25, 10-20, 25-100, 25-75, or 25-50 mg/kg. In some embodiments, a single dose or administration is about 1-20, 1-15, 1-10, 1-5, 1-3, 1-2, 5-20, 5-15, or 5-10 mg/kg. In some embodiments, a single dose or administration is about 1, 2, 3, 4, 5, 6, 7, 8, 9, 10, 11, 12, 13, 14, 15, or 20 mg/kg.

In some embodiments, a pharmaceutical composition that comprises a complex comprising a muscle-targeting agent covalently linked to a molecular payload described herein is delivered to a subject every 1, 2, 3, 4, 5, 6, 7, 8, 9, 10, 11, 12, 13, 14, 15, or 16 weeks. In some embodiments, a pharmaceutical composition that comprises a complex comprising a muscle-targeting agent covalently linked to a molecular payload described herein is delivered to a subject every 1-10, 2-5, 2-10, 4-8, 4-12, 5-10, 5-12, 5-15, 8-12, 8-16, 9-15, 10-12, 10-14, 10-15, 10-20, 11-13, 11-15, 12-15, 12-16, 12-20, 15-20, or 15-25 weeks. In some embodiments, a pharmaceutical composition that comprises a complex comprising a muscle-targeting agent covalently linked to a molecular payload described herein is delivered to a subject on a biweekly (i.e., every two weeks), bimonthly (i.e., every two months), or quarterly schedule (i.e., every twelve weeks).

In some embodiments, a pharmaceutical composition that comprises a complex comprising a muscle-targeting agent covalently linked to a molecular payload described herein at a concentration of 1-15 mg/kg of RNA is delivered to a subject every 1, 2, 3, 4, 5, 6, 7, 8, 9, 10, 11, 12, 13, 14, 15, or 16 weeks. In some embodiments, a pharmaceutical composition that comprises a complex comprising a muscle-targeting agent covalently linked to a molecular payload described herein at a concentration of 1-15 mg/kg of RNA is delivered to a subject every 1-10, 2-5, 2-10, 4-8, 4-12, 5-10, 5-12, 5-15, 8-12, 8-16, 9-15, 10-12, 10-14, 10-15, 10-20, 11-13, 11-15, 12-15, 12-16, 12-20, 15-20, or 15-25 weeks. In some embodiments, a pharmaceutical composition that comprises a complex comprising a muscle-targeting agent covalently linked to a molecular payload described herein at a concentration of 1-15 mg/kg of RNA is delivered to a subject on a biweekly (i.e., every two weeks), bimonthly (i.e., every two months), or quarterly schedule (i.e., every twelve weeks).

In some embodiments, a pharmaceutical composition may comprise more than one complex comprising a muscle-targeting agent covalently linked to a molecular payload. In some embodiments, a pharmaceutical composition may further comprise any other suitable therapeutic agent for treatment of a subject, e.g. a human subject having DM1. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting DMPK with Transfected Antisense Oligonucleotides

A gapmer antisense oligonucleotide that targets both wild-type and mutant alleles of DMPK (ASO300) was tested in vitro for its ability to reduce expression levels of DMPK in an immortalized cell line. Briefly, Hepa 1-6 cells were transfected with ASO300 (100 nM) formulated with Lipofectamine 2000. DMPK expression levels were evaluated 72 hours following transfection. A control experiment was also performed in which vehicle (phosphate-buffered saline) was delivered to Hepa 1-6 cells in culture and the cells were maintained for 72 hours. As shown in FIG. 1, it was found that ASO300 reduced DMPK expression levels by ~90% compared with controls.

Example 2: Targeting DMPK with a Muscle-Targeting Complex

A muscle-targeting complex was generated comprising the DMPK ASO used in Example 1 (ASO300) covalently linked, via a cathepsin cleavable linker, to DTX-A-002 (RI7 217 Fab), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule was coupled to $NH_2$—$C_6$-ASO300 using an amide coupling reaction. Excess linker and organic solvents were removed by gel permeation chromatography. The purified Val-Cit-linker-ASO300 was then coupled to a thiol on the anti-transferrin receptor antibody (DTX-A-002).

Figure 2A:
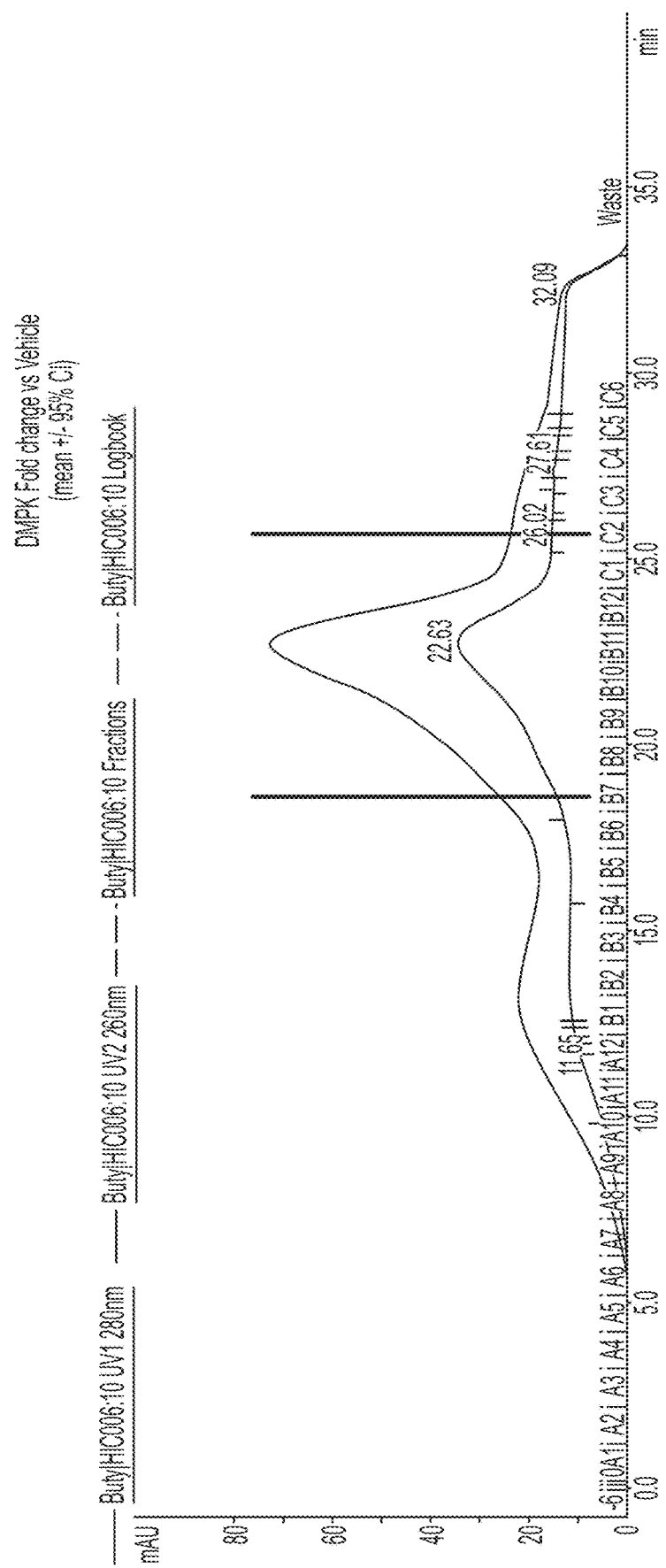
FIG. 2A depicts a non-limiting schematic showing an HIL-HPLC trace obtained during purification of a muscle targeting complex comprising an anti-transferrin receptor antibody covalently linked to a DMPK antisense oligonucleotide.
Figure 2B:
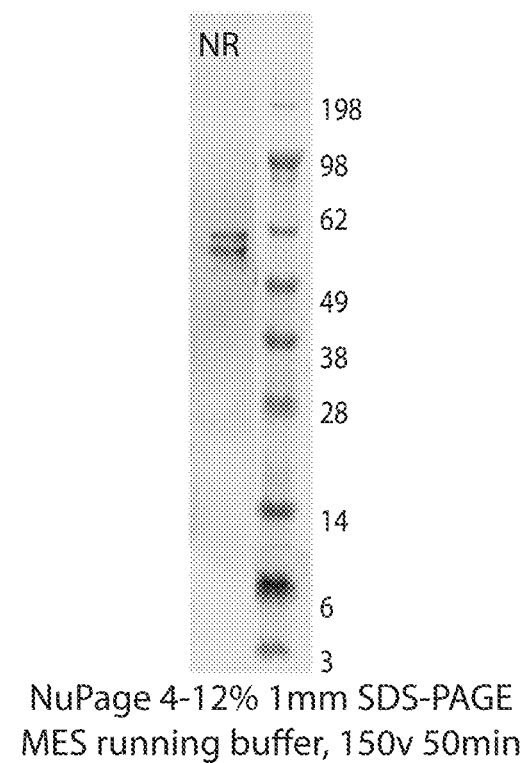
FIG. 2B depicts a non-limiting image of an SDS-PAGE analysis of a muscle targeting complex.

The product of the antibody coupling reaction was then subjected to hydrophobic interaction chromatography (HIC-HPLC). FIG. 2A shows a resulting HIC-HPLC chromatogram, in which fractions B7-C2 of the chromatogram (denoted by vertical lines) contained antibody-oligonucleotide complexes (referred to as DTX-C-008) comprising one or two DMPK ASO molecules covalently attached to DTX-A-002, as determined by SDS-PAGE. These HIC-HPLC fractions were combined and densitometry following additional purification confirmed that this sample of DTX-C-008 complexes had an average ASO to antibody ratio (DAR) of 1.48. SDS-PAGE analysis demonstrated that 86.4% of this sample of DTX-C-008 complexes comprised DTX-A-002 linked to either one or two DMPK ASO molecules (FIG. 2B).

Using the same methods as described above, a control complex was generated comprising the DMPK ASO used in Example 1 (ASO300) covalently linked via a Val-Cit linker to an IgG2a (Fab) antibody (DTX-C-007).

Figure 3:
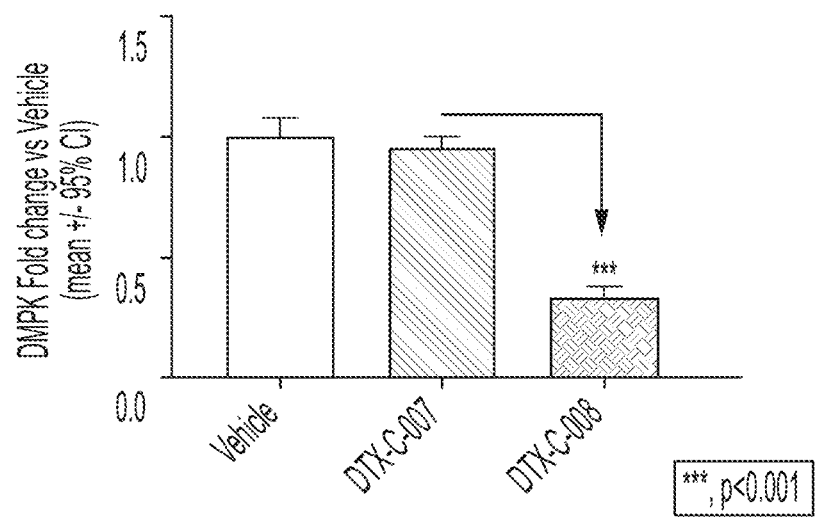
FIG. 3 depicts a non-limiting schematic showing the ability of a muscle targeting RI7 217 Fab antibody-oligonucleotide complex (DTX-C-008) comprising ASO300 to reduce expression levels of DMPK.
Figure 4A:
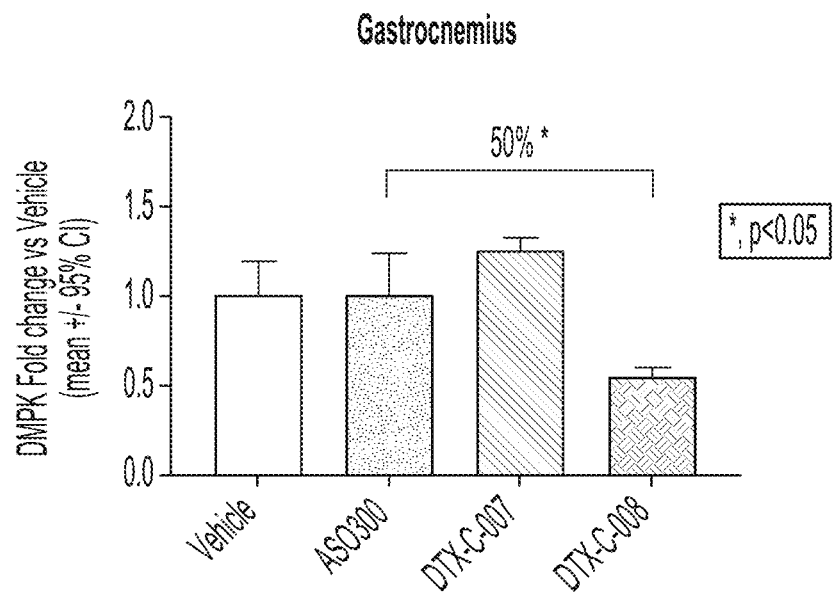
FIGS. 4A-4E depict non-limiting schematics showing the ability of a muscle targeting RI7 217 Fab antibody-oligonucleotide complex (DTX-C-008) comprising ASO300 to reduce expression levels of DMPK in mouse muscle tissues in vivo, relative to a vehicle treatment, treatment with naked ASO300, or treatment with a control non-targeting complex (DTX-C-007). (N=3 C57Bl/6 WT mice)
Figure 4B:
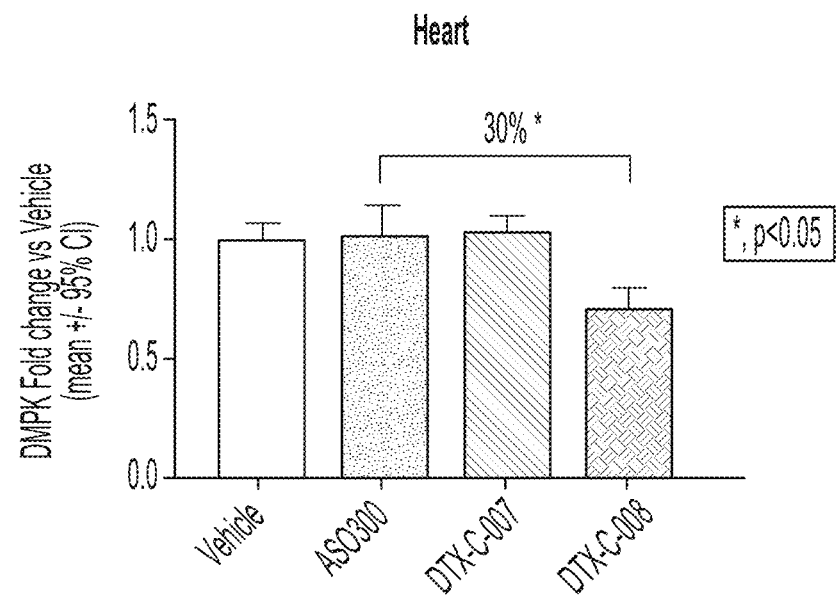
Figure 4C:
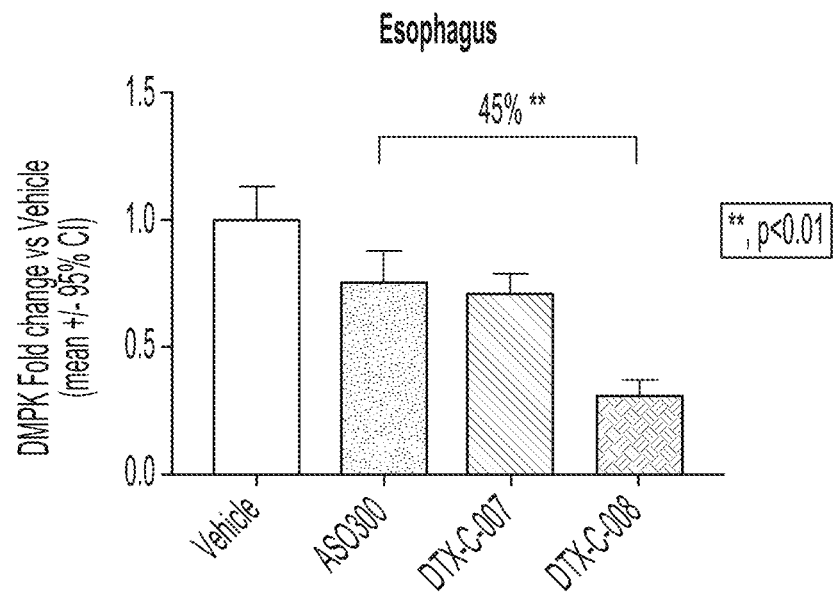
Figure 4D:
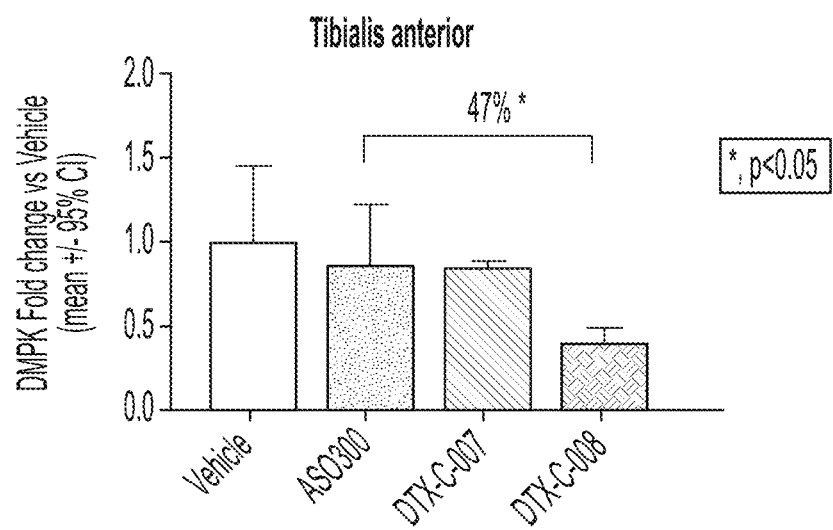
Figure 4E:
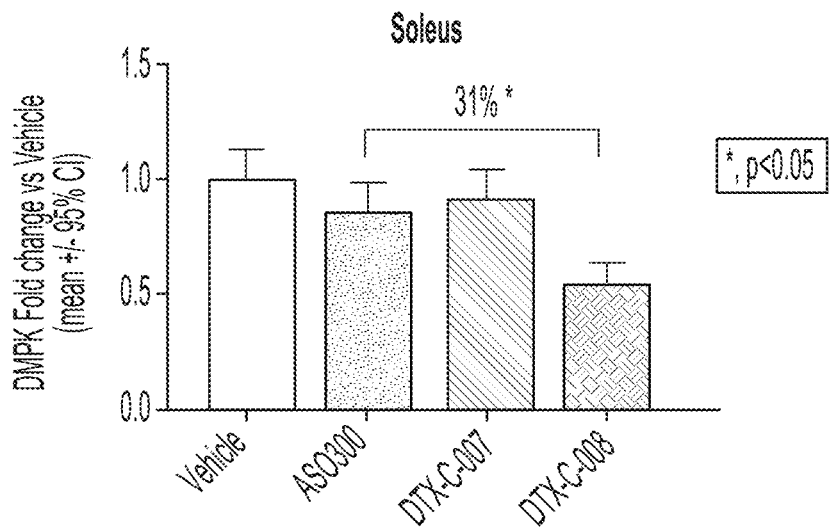

The purified RI7 217 Fab antibody-ASO complex (DTX-C-008) was then tested for cellular internalization and inhibition of DMPK. Hepa 1-6 cells, which have relatively high expression levels of transferrin receptor, were incubated in the presence of vehicle control, DTX-C-008 (100 nM), or DTX-C-007 (100 nM) for 72 hours. After the 72 hour incubation, the cells were isolated and assayed for expression levels of DMPK (FIG. 3). Cells treated with the DTX-C-008 demonstrated a reduction in DMPK expression by ~65% relative to the cells treated with the vehicle control. Meanwhile, cells treated with the DTX-C-007 had DMPK expression levels comparable to the vehicle control (no reduction in DMPK expression). These data indicate that the anti-transferrin receptor antibody of the DTX-C-008 enabled cellular internalization of the complex, thereby allowing the DMPK ASO to inhibit expression of DMPK.

Example 3: Targeting DMPK in Mouse Muscle Tissues with a Muscle-Targeting Complex The muscle-targeting complex described in Example 2, RI7 217 Fab antibody-ASO complex DTX-C-008, was tested for inhibition of DMPK in mouse tissues. C57BL/6 wild-type mice were intravenously injected with a single dose of a vehicle control, naked ASO300 (3 mg/kg of ASO), DTX-C-008 (3 mg/kg of ASO, corresponding to 20 mg/kg antibody conjugate), or DTX-C-007 IgG2a Fab antibody-ASO complex (3 mg/kg of ASO, corresponding to 20 mg/kg antibody conjugate). Naked ASO300, the DMPK ASO as described in Example 1, was used as a control. Each experimental condition was replicated in three individual C57BL/6 wild-type mice. Following a seven-day period after injection, the mice were euthanized and segmented into isolated tissue types. Individual tissue samples were subsequently assayed for expression levels of DMPK (FIGS. 4A-4E and 5A-5B).

Mice treated with the DTX-C-008 complex demonstrated a reduction in DMPK expression in a variety of skeletal, cardiac, and smooth muscle tissues. For example, as shown in FIGS. 4A-4E, DMPK expression levels were significantly reduced in gastrocnemius (50% reduction), heart (30% reduction), esophagus (45% reduction), tibialis anterior (47% reduction), and soleus (31% reduction) tissues, relative to the mice treated with the vehicle control. Meanwhile, mice treated with the DTX-C-007 complex had DMPK expression levels comparable to the vehicle control mice and mice treated with naked ASO300 (no reduction in DMPK expression) for all assayed muscle tissue types.

Figure 5A:
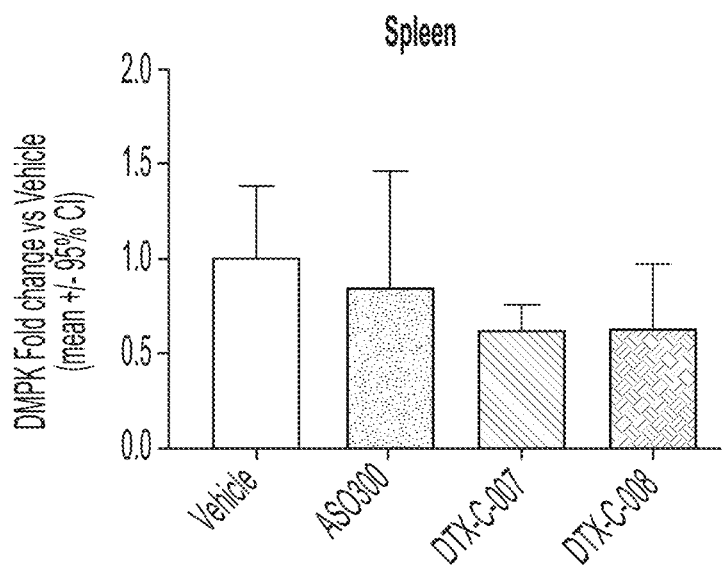
FIGS. 5A-5B depict non-limiting schematics showing the tissue selectivity of a muscle targeting RI7 217 Fab antibody-oligonucleotide complex (DTX-C-008) comprising ASO300. The muscle targeting complex (DTX-C-008) comprising ASO300 does not reduce expression levels of DMPK in mouse brain or spleen tissues in vivo, relative to a vehicle treatment, treatment with naked ASO300, or treatment with a control non-targeting complex (DTX-C-007). (N=3 C57Bl/6 WT mice).
Figure 5B:
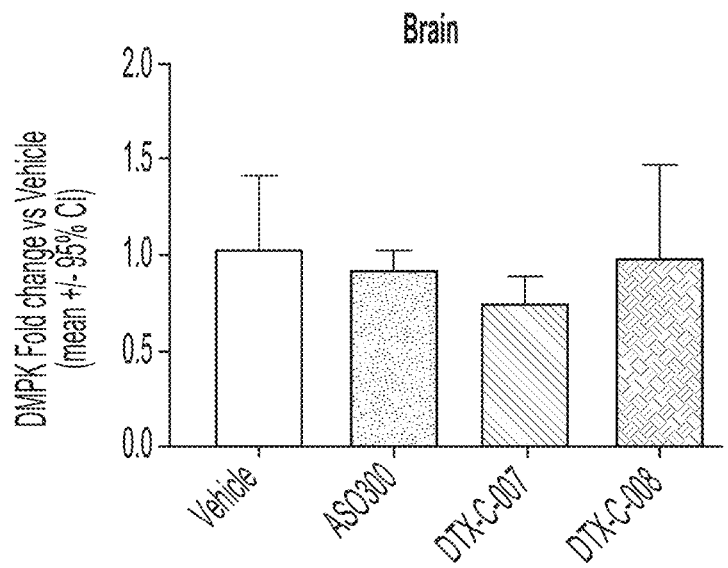
Figure 6A:
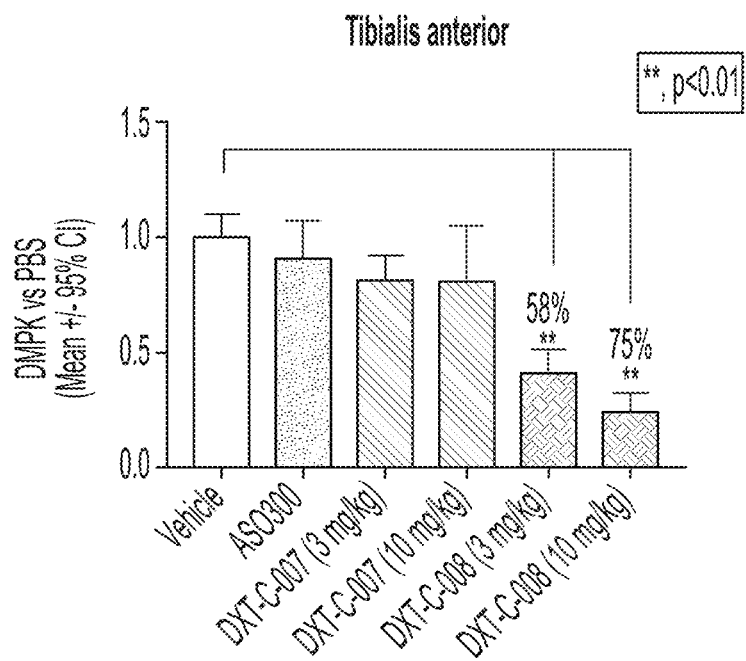
FIGS. 6A-6F depict non-limiting schematics showing the ability of a muscle targeting RI7 217 Fab antibody-oligonucleotide complex (DTX-C-008) comprising ASO300 to reduce expression levels of DMPK in mouse muscle tissues in vivo, relative to a vehicle treatment, treatment with naked ASO300, or treatment with a control non-targeting complex (DTX-C-007). (N=5 C57Bl/6 WT mice)
Figure 6B:
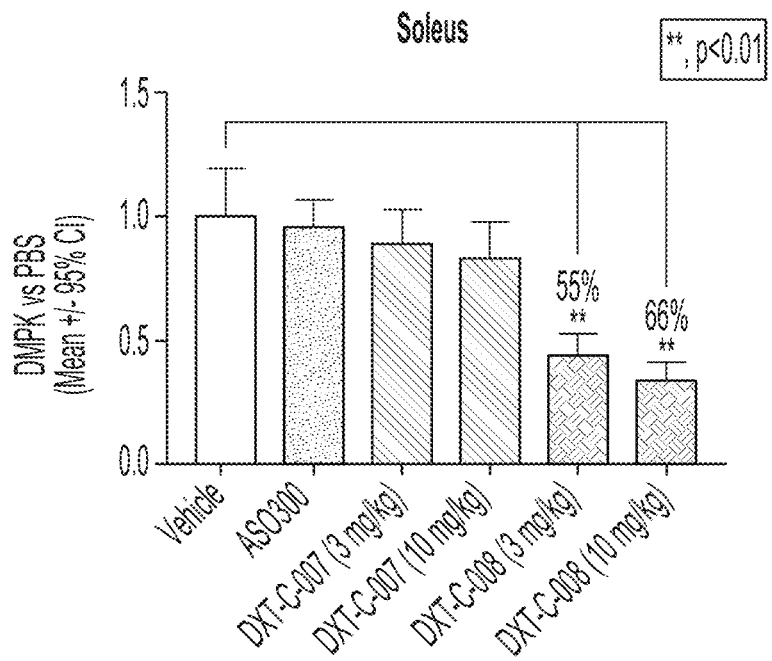
Figure 6C:
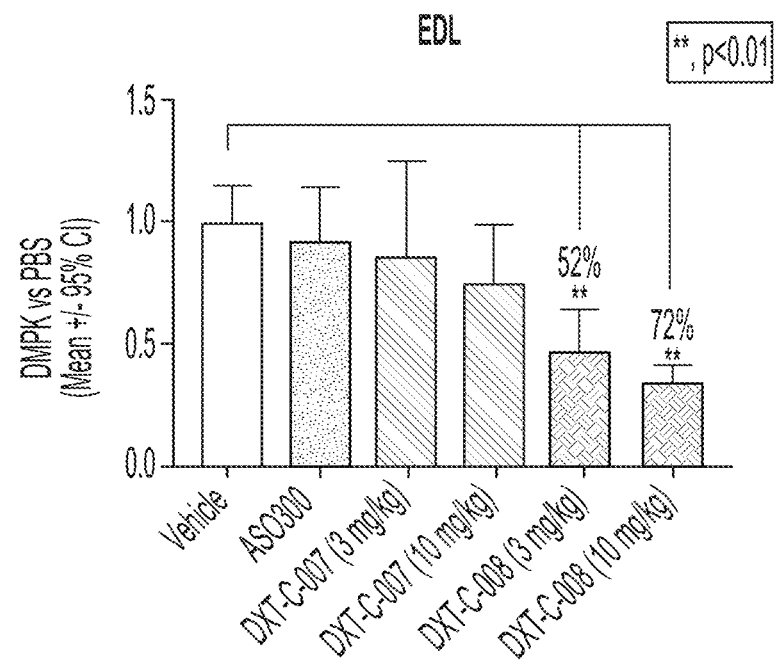
Figure 6D:
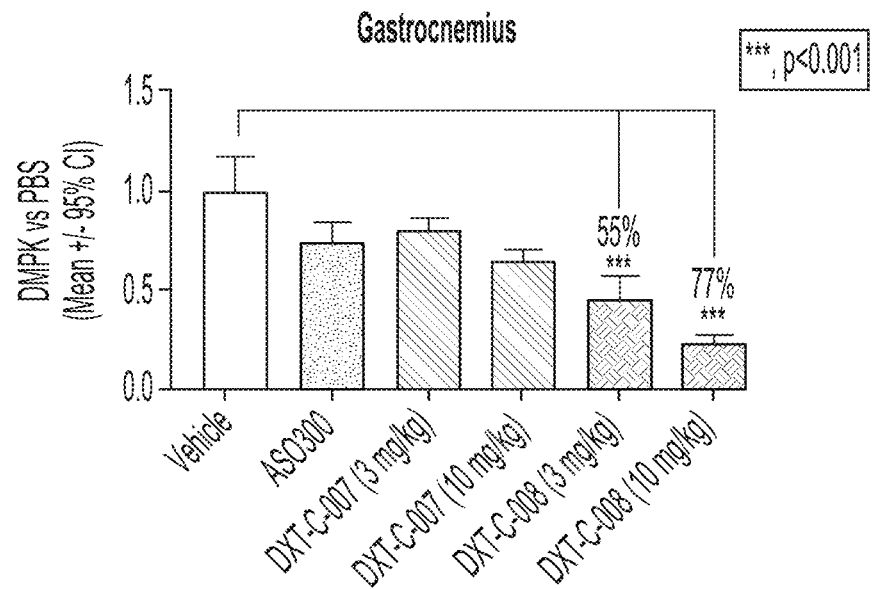
Figure 6E:
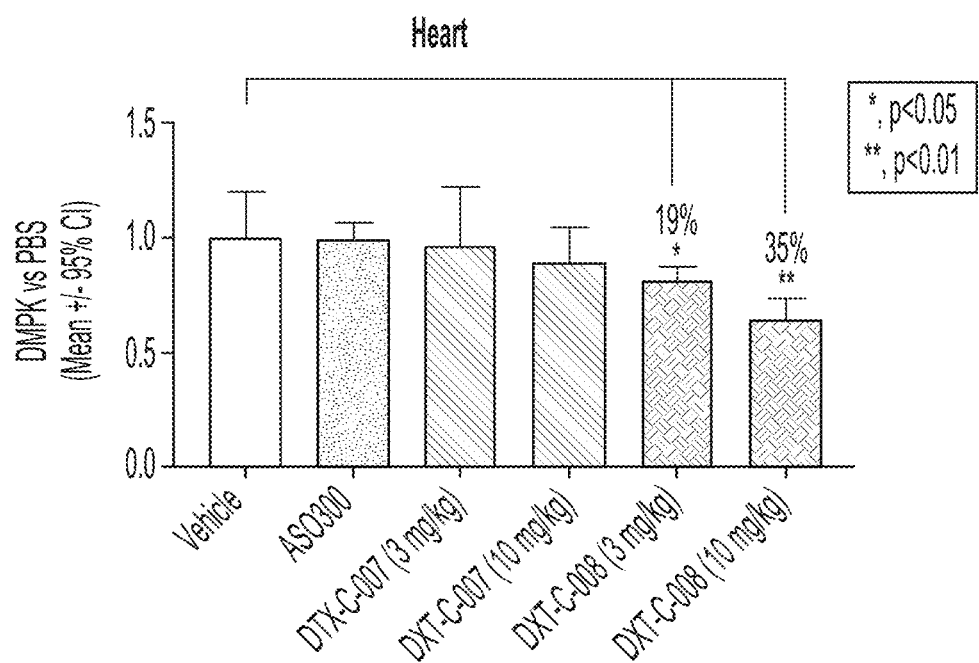
Figure 6F:
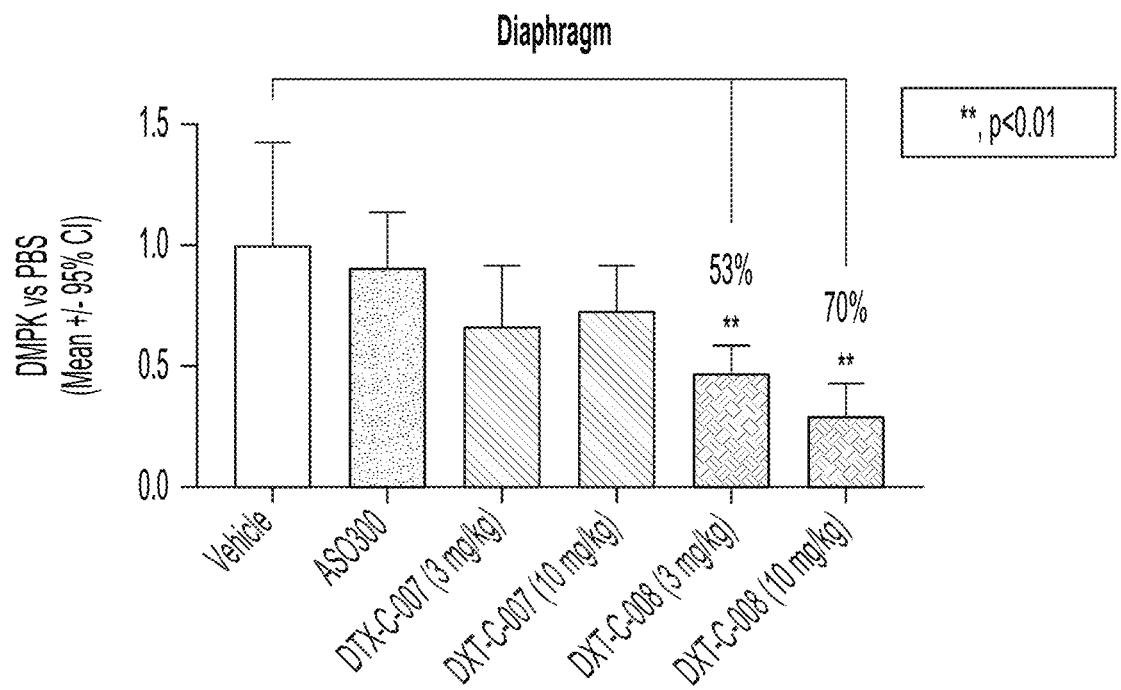

Mice treated with the DTX-C-008 complex demonstrated no change in DMPK expression in non-muscle tissues such as spleen and brain tissues (FIGS. 5A and 5B).

These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues.

Example 4: Targeting DMPK in Mouse Muscle Tissues with a Muscle-Targeting Complex The muscle-targeting complex described in Example 2, RI7 217 Fab antibody-ASO complex DTX-C-008, was tested for dose-dependent inhibition of DMPK in mouse tissues. C57BL/6 wild-type mice were intravenously injected with a single dose of a vehicle control (phosphate-buffered saline, PBS), naked ASO300 (10 mg/kg of ASO), DTX-C-008 (3 mg/kg or 10 mg/kg of ASO, wherein 3 mg/kg corresponds to 20 mg/kg antibody conjugate), or DTX-C-007 IgG2a Fab antibody-ASO complex (3 mg/kg or 10 mg/kg of ASO, wherein 3 mg/kg corresponds to 20 mg/kg antibody conjugate). Naked ASO300, the DMPK ASO as described in Example 1, was used as a control. Each experimental condition was replicated in five individual C57BL/6 wild-type mice. Following a seven-day period after injection, the mice were euthanized and segmented into isolated tissue types. Individual tissue samples were subsequently assayed for expression levels of DMPK (FIGS. 6A-6F).

Mice treated with the DTX-C-008 complex demonstrated a reduction in DMPK expression in a variety of skeletal muscle tissues. As shown in FIGS. 6A-6F, DMPK expression levels were significantly reduced in tibialis anterior (58% and 75% reduction for 3 mg/kg and 10 mg/kg DTX-C-008, respectively), soleus (55% and 66% reduction for 3 mg/kg and 10 mg/kg DTX-C-008, respectively), extensor digitorum longus (EDL) (52% and 72% reduction for 3 mg/kg and 10 mg/kg DTX-C-008, respectively), gastrocnemius (55% and 77% reduction for 3 mg/kg and 10 mg/kg DTX-C-008, respectively), heart (19% and 35% reduction for 3 mg/kg and 10 mg/kg DTX-C-008, respectively), and diaphragm (53% and 70% reduction for 3 mg/kg and 10 mg/kg DTX-C-008, respectively) tissues, relative to the mice treated with the vehicle control. Notably, all assayed muscle tissue types experienced dose-dependent inhibition of DMPK, with greater reduction in DMPK levels at 10 mg/kg antibody conjugate relative to 3 mg/kg antibody conjugate.

Meanwhile, mice treated with the control DTX-C-007 complex had DMPK expression levels comparable to the vehicle control (no reduction in DMPK expression) for all assayed muscle tissue types. These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues for dose-dependent inhibition of DMPK.

Example 5: Targeting DMPK in Cynomolgus Monkey Muscle Tissues with a Muscle-Targeting Complex A muscle-targeting complex comprising ASO300 (DTX-C-012), was generated and purified using methods described in Example 2. DTX-C-012 is a complex comprising a human anti-transferrin receptor antibody covalently linked, via a cathepsin cleavable Val-Cit linker, to ASO300. The anti-TfR antibody used in DTX-C-012 is cross-reactive with cynomolgus and human TfR1. Following HIC-HPLC purification and additional purification, densitometry confirmed that DTX-C-012 had an average ASO to antibody ratio of 1.32, and SDS-PAGE revealed a purity of 92.3%.

DTX-C-012 was tested for inhibition of DMPK in male cynomolgus monkey tissues. Male cynomolgus monkeys (19-31 months; 2-3 kg) were intravenously injected with a single dose of a saline control, naked ASO300 (10 mg/kg of ASO), or DTX-C-012 (10 mg/kg of ASO) on Day 0. Each experimental condition was replicated in three individual male cynomolgus monkeys. On Day 7 after injection, tissue biopsies (including muscle tissues) were collected. DMPK mRNA expression levels, ASO detection assays, serum clinical chemistries, tissue histology, clinical observations, and body weights were analyzed. The monkeys were euthanized on Day 14.

Figure 7A:
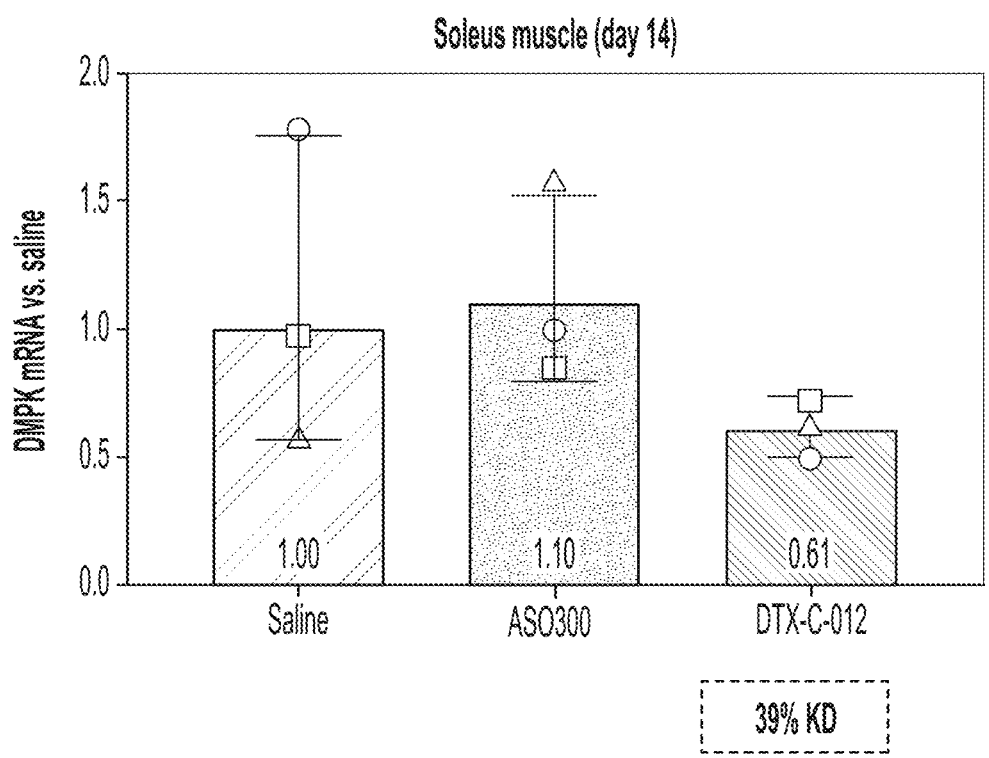
FIGS. 7A-7L depict non-limiting schematics showing the ability of a muscle targeting antibody-oligonucleotide complex (DTX-C-012) comprising ASO300 covalently linked to an anti-hTfR antibody to reduce expression levels of DMPK in cynomolgus monkey muscle tissues in vivo, relative to a vehicle treatment (saline) and compared to naked ASO300. (N=3 male cynomolgus monkeys)
Figure 7B:
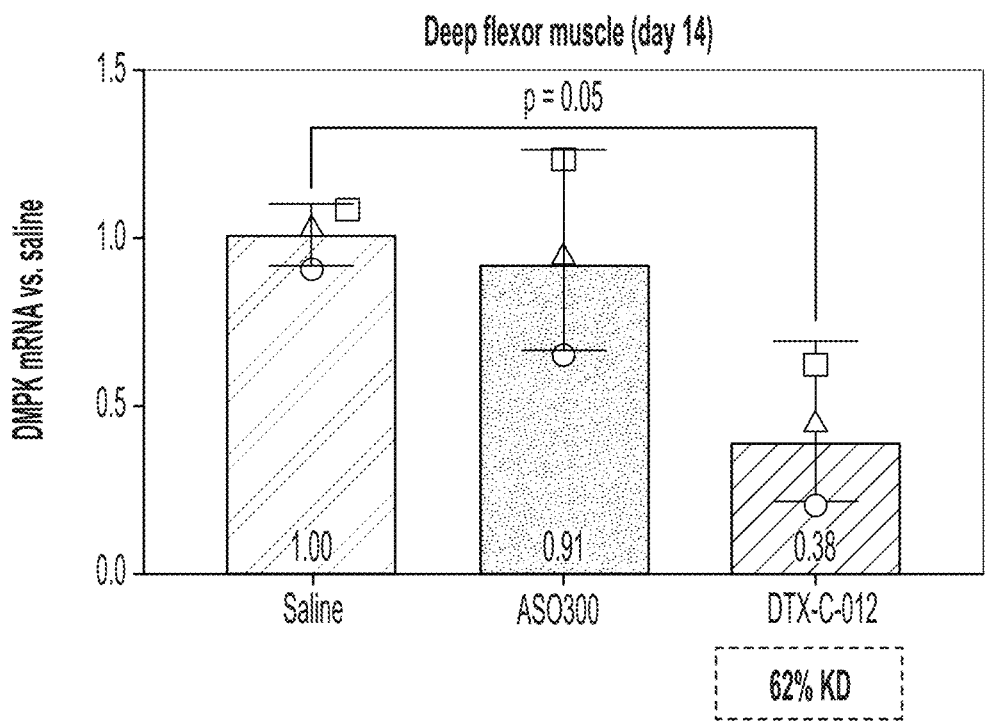
Figure 7C:
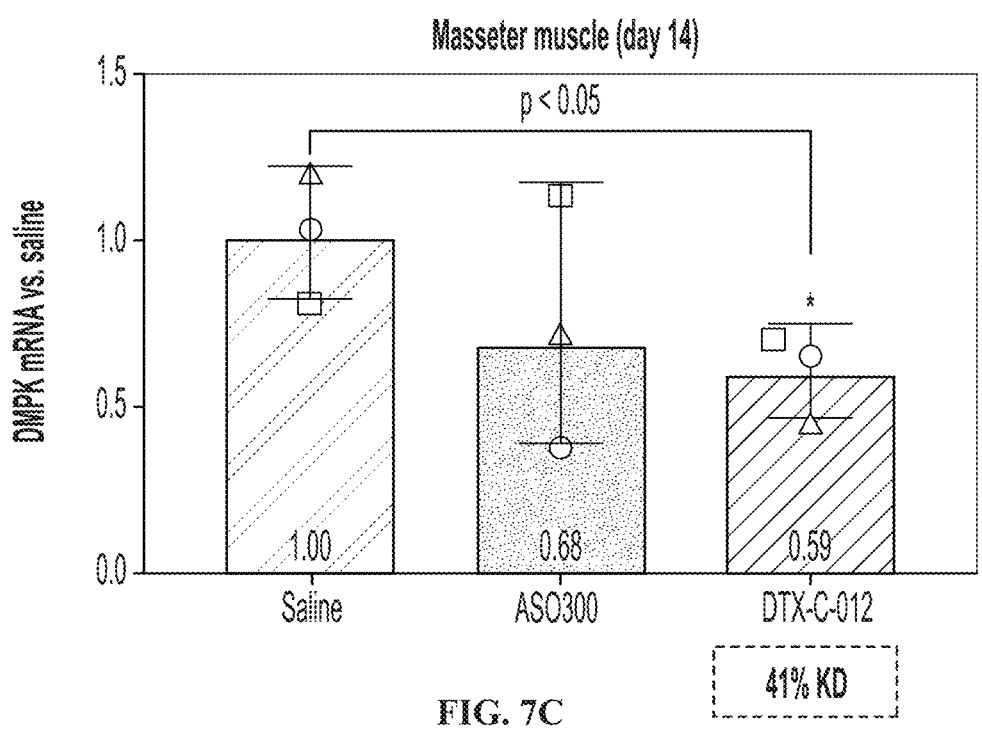
Figure 7D:
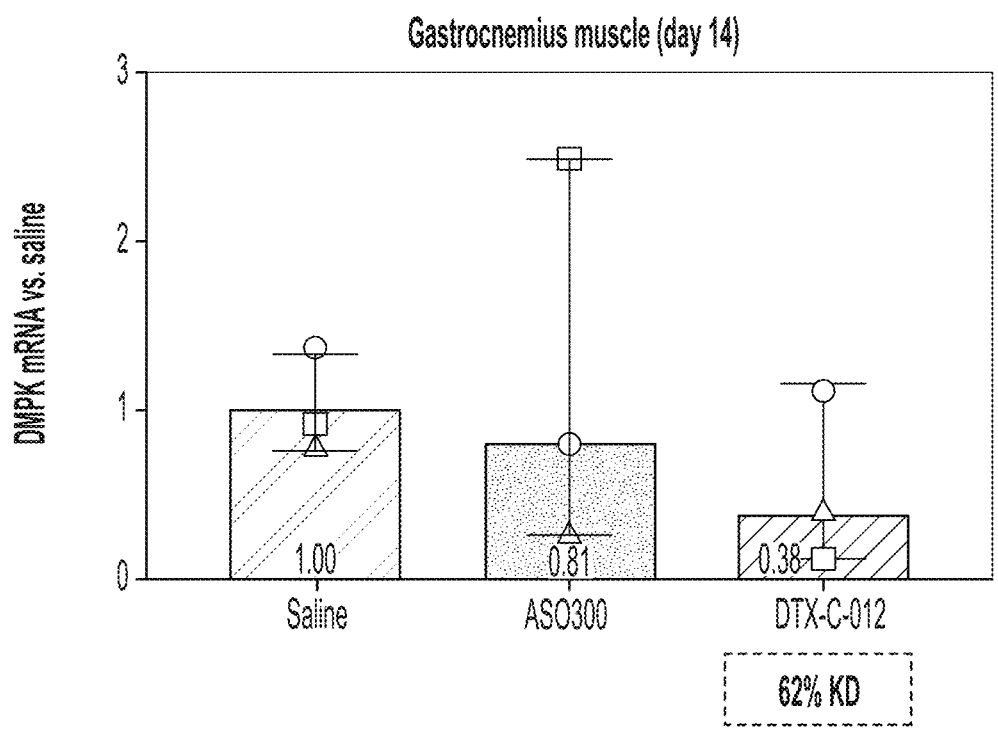
Figure 7E:
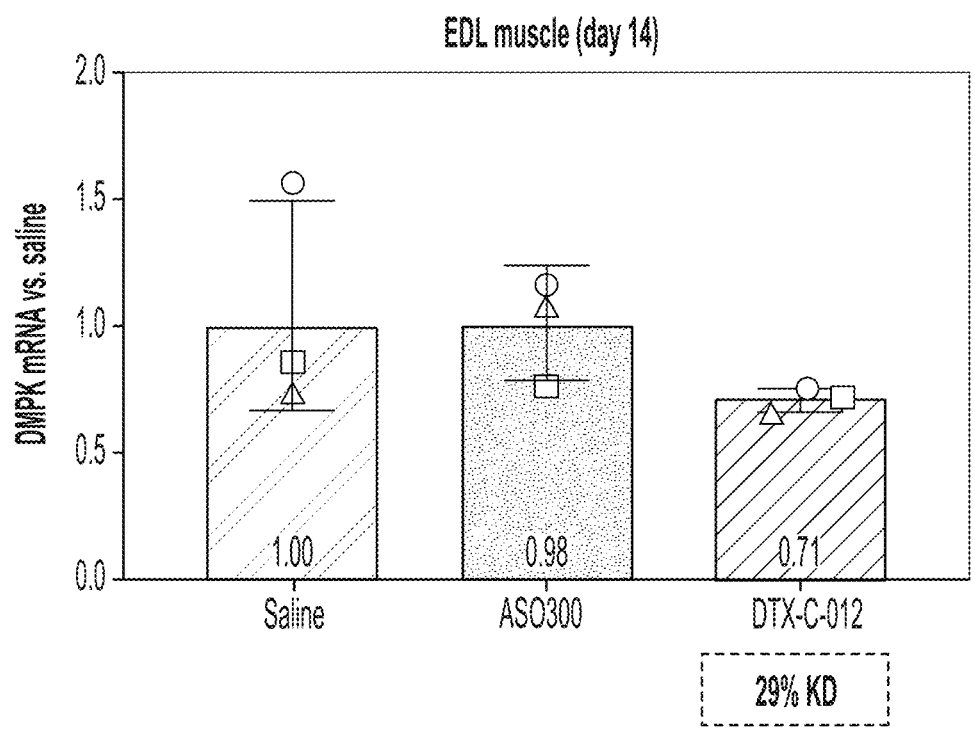
Figure 7F:
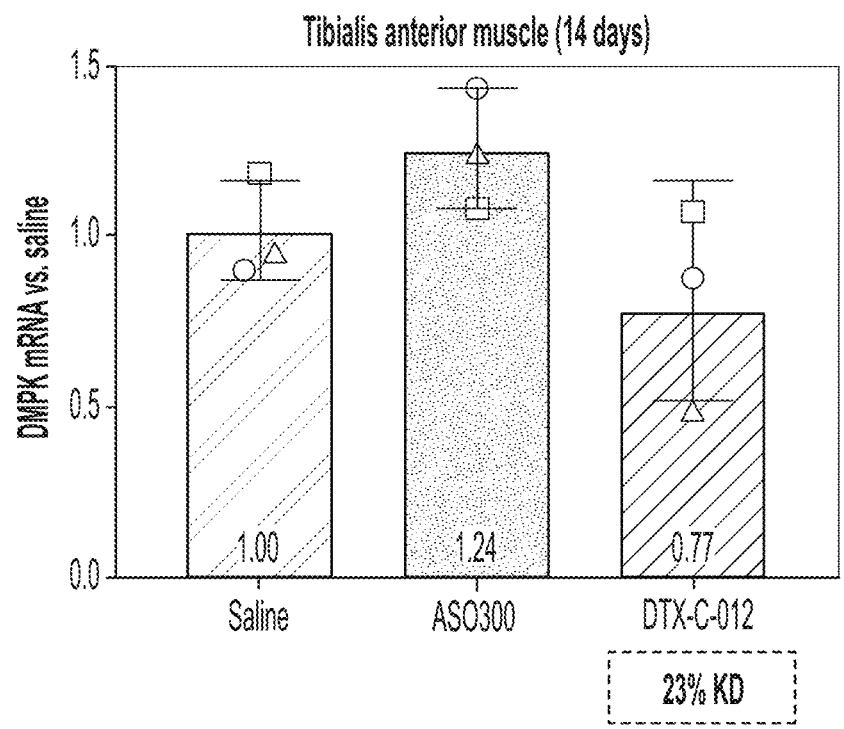
Figure 7G:
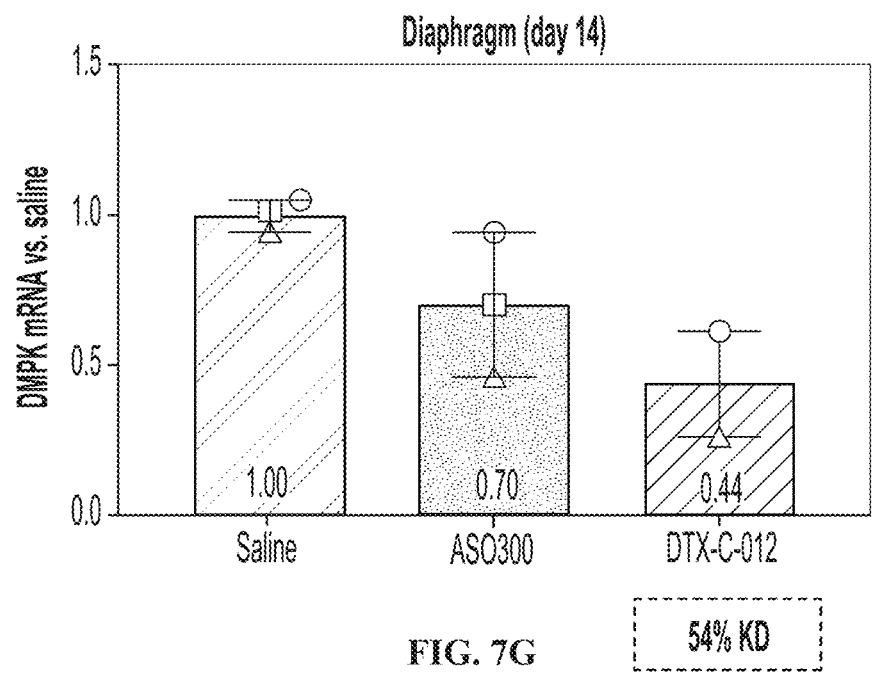
Figure 7H:
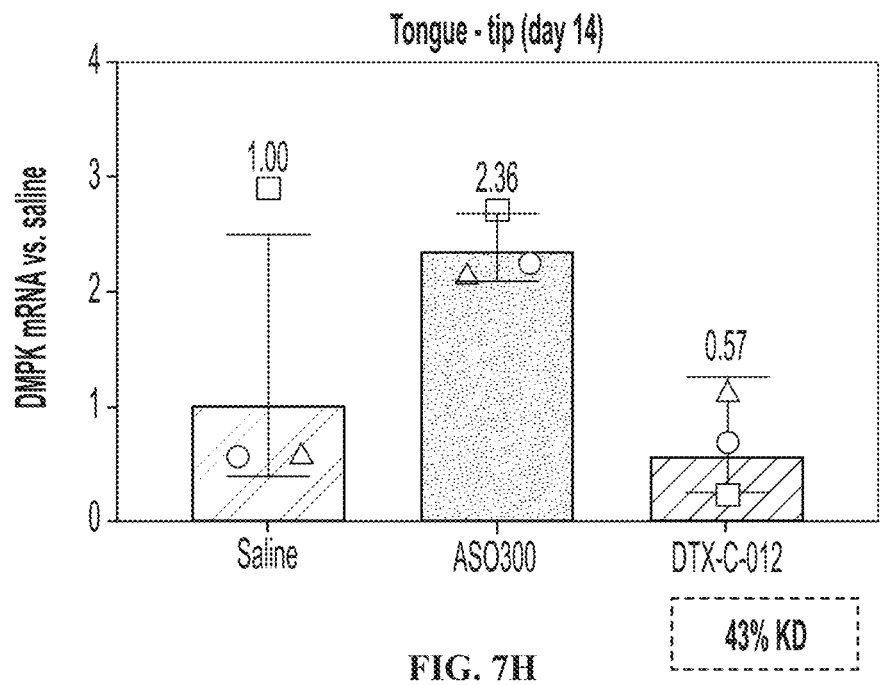
Figure 7I:
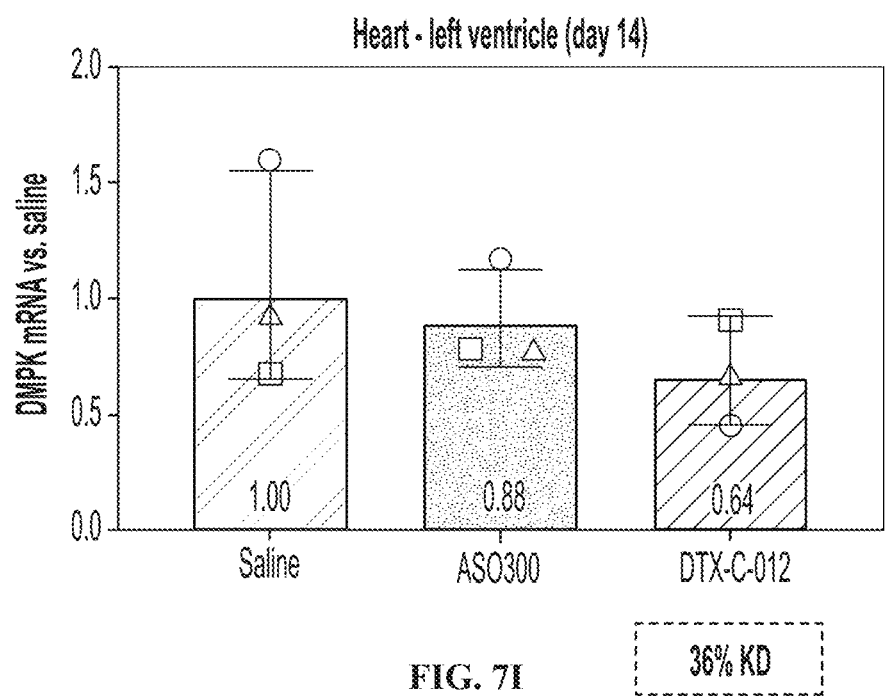
Figure 7J:
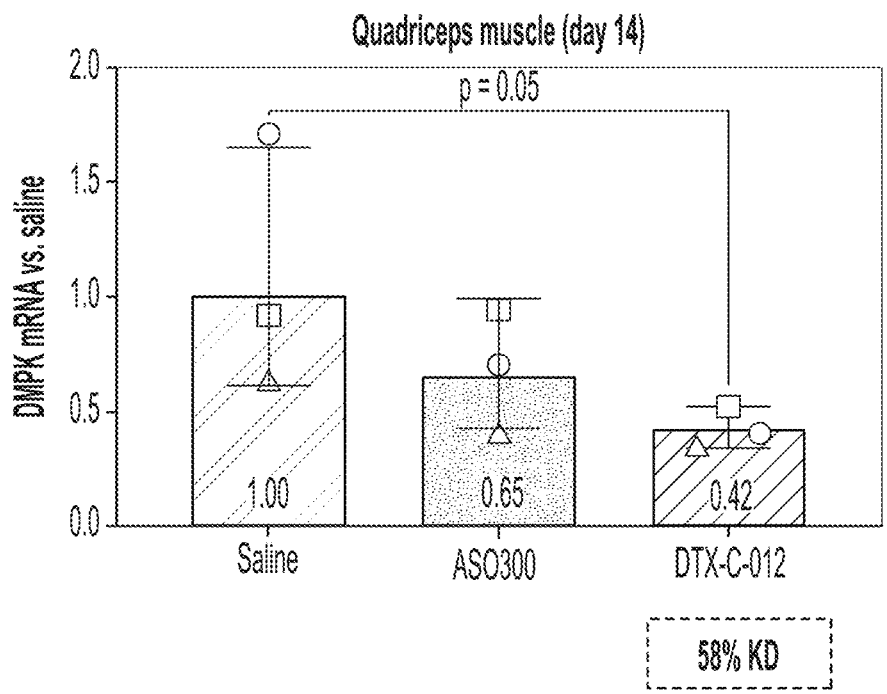
Figure 7K:
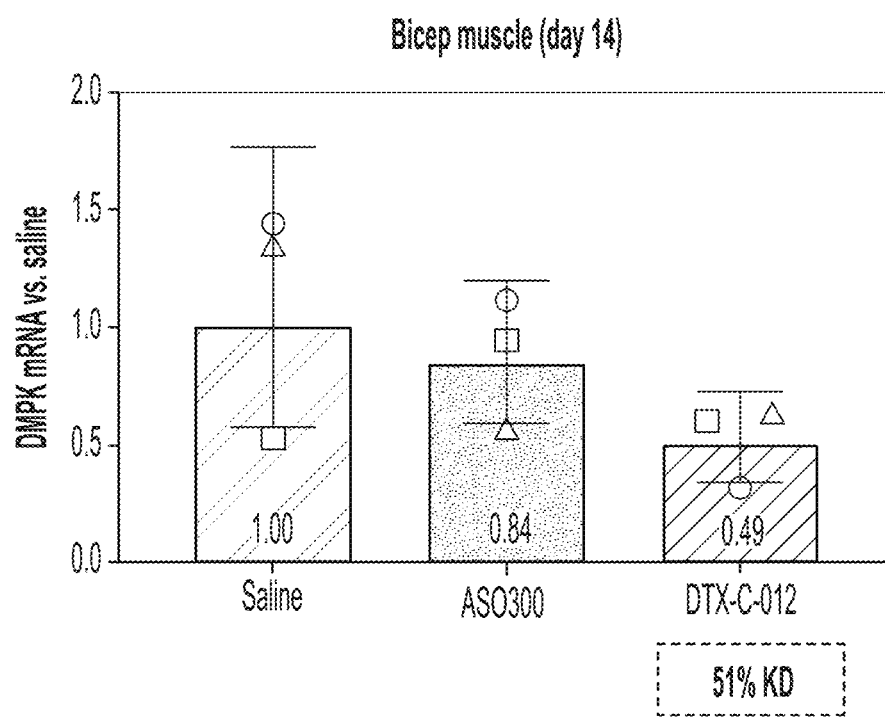
Figure 7L:
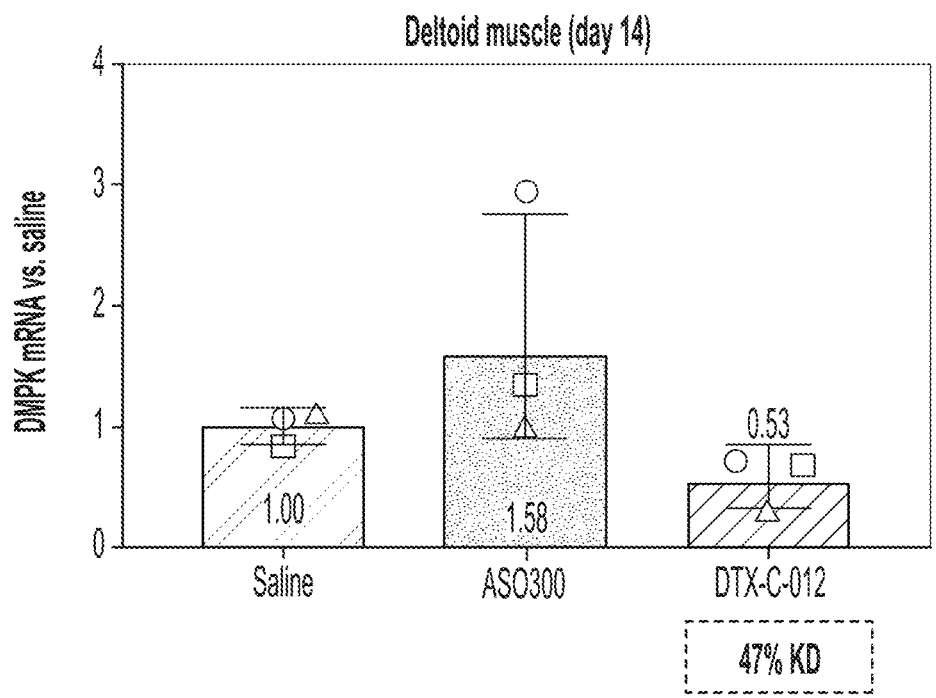
Figure 8A:
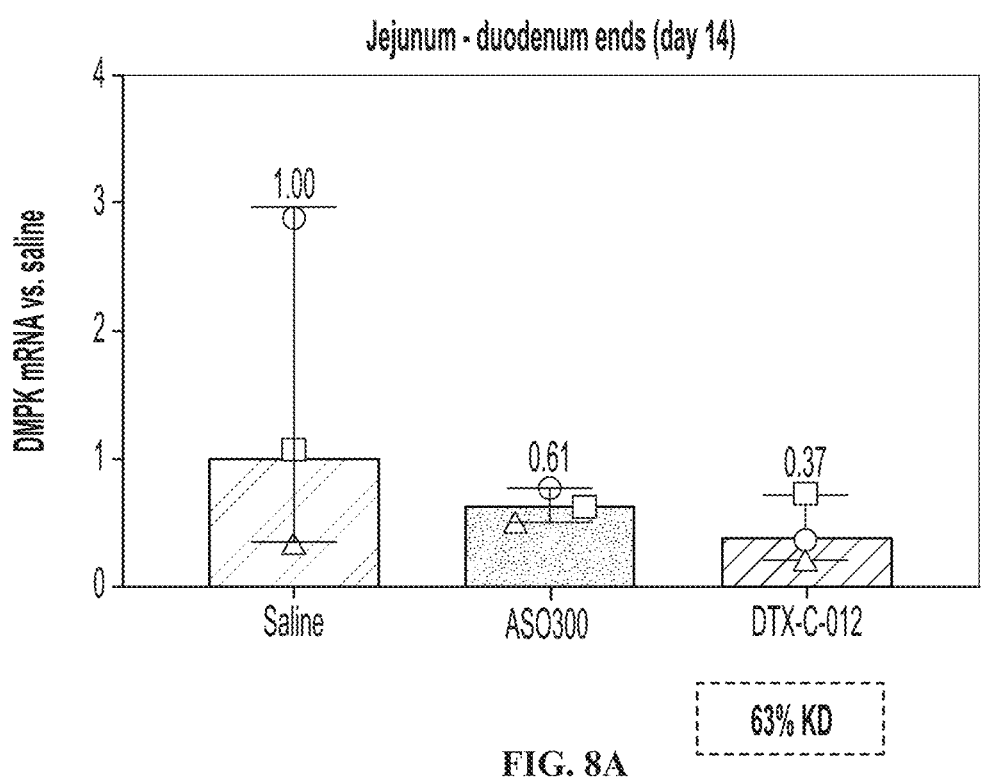
FIGS. 8A-8B depict non-limiting schematics showing the ability of a muscle targeting antibody-oligonucleotide complex (DTX-C-012) comprising ASO300 covalently linked to an anti-hTfR antibody to reduce expression levels of DMPK in cynomolgus monkey smooth muscle tissues in vivo, relative to a vehicle treatment (saline) and compared to naked ASO300. (N=3 male cynomolgus monkeys)
Figure 8B:
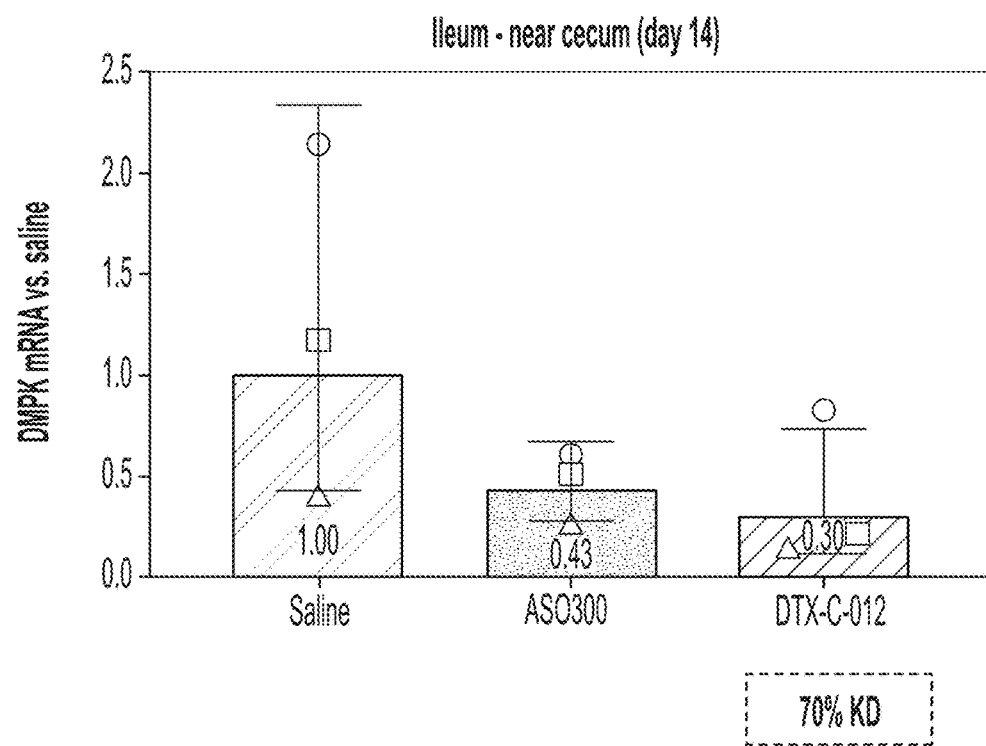
Figure 9A:
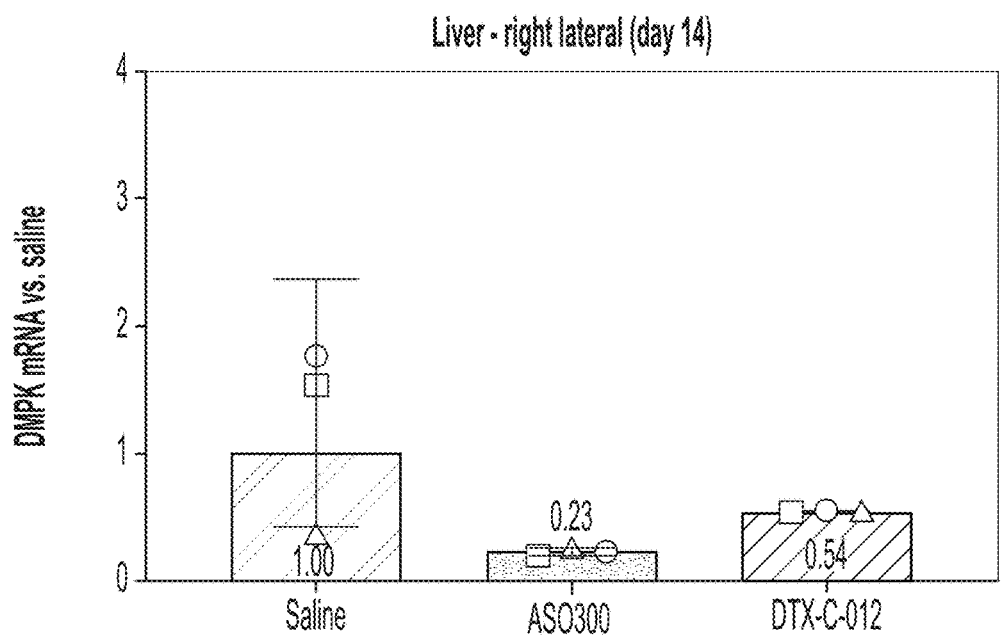
FIGS. 9A-9D depict non-limiting schematics showing the tissue selectivity of a muscle targeting antibody-oligonucleotide complex (DTX-C-012) comprising ASO300 covalently linked to an anti-hTfR antibody. The muscle targeting complex comprising DMPK-ASO does not reduce expression levels of DMPK in cynomolgus monkey kidney, brain, or spleen tissues in vivo, relative to a vehicle treatment. (N=3 male cynomolgus monkeys)
Figure 9B:
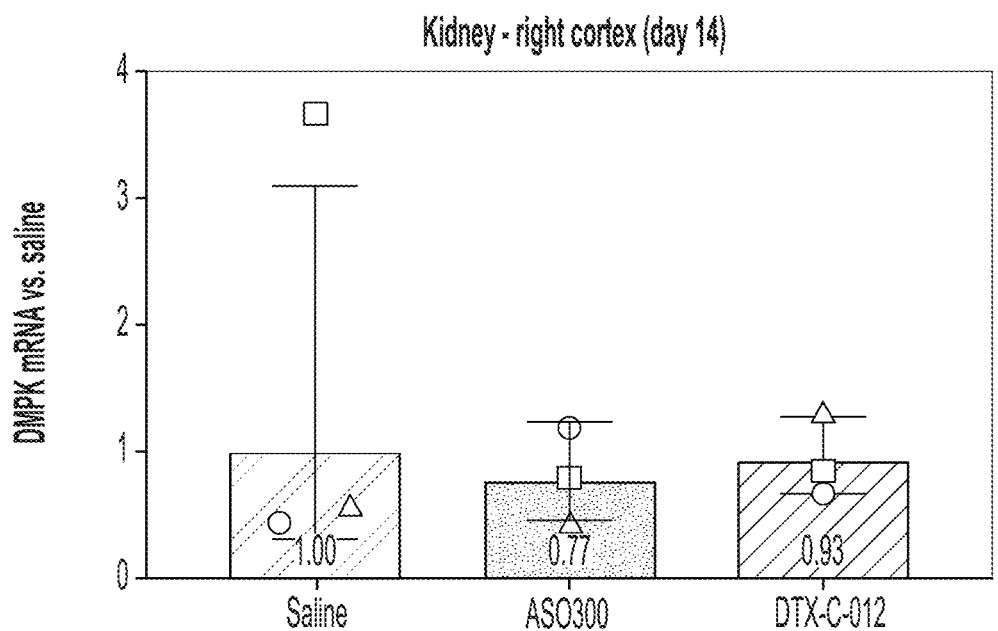
Figure 9C:
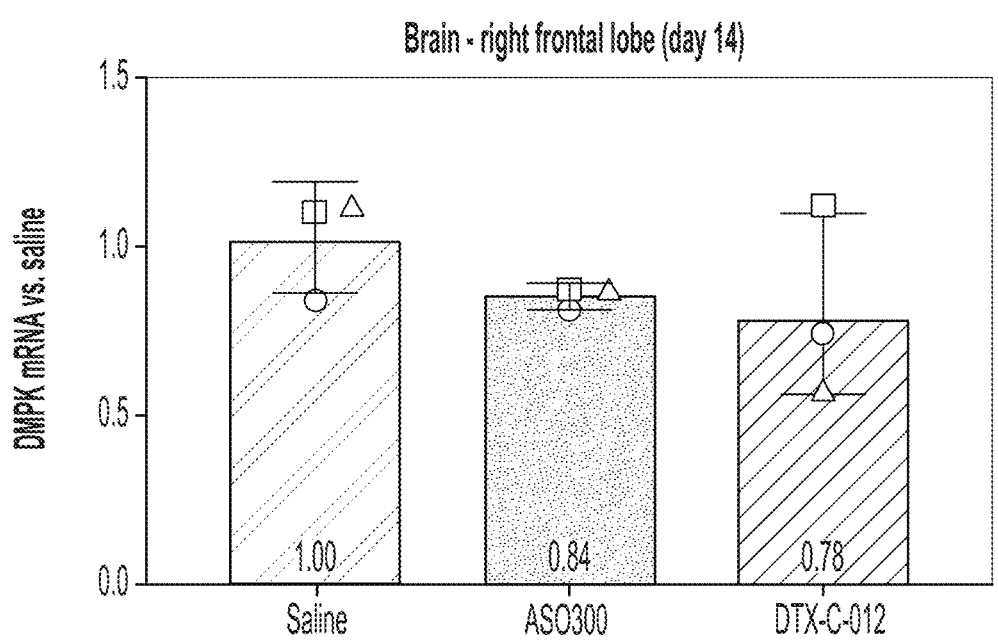
Figure 9D:
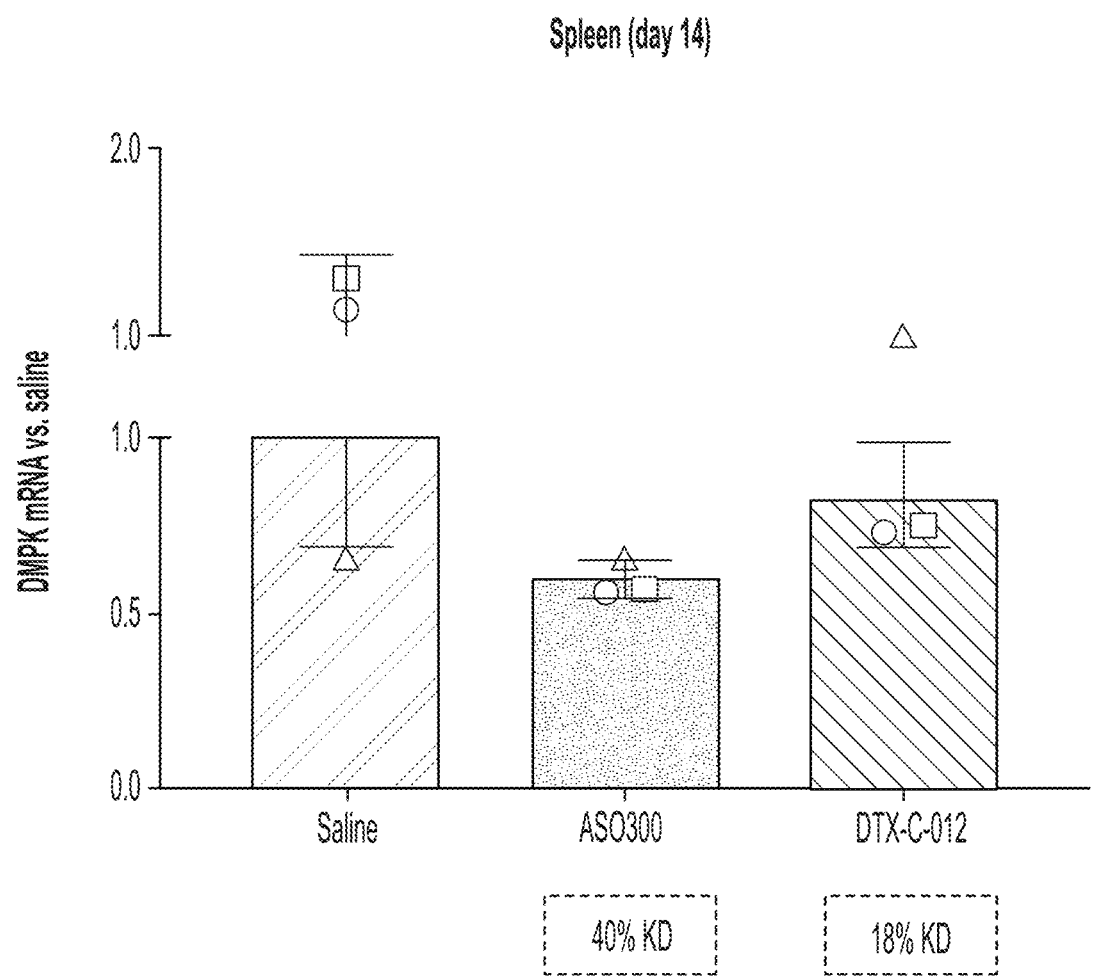
Figure 10:
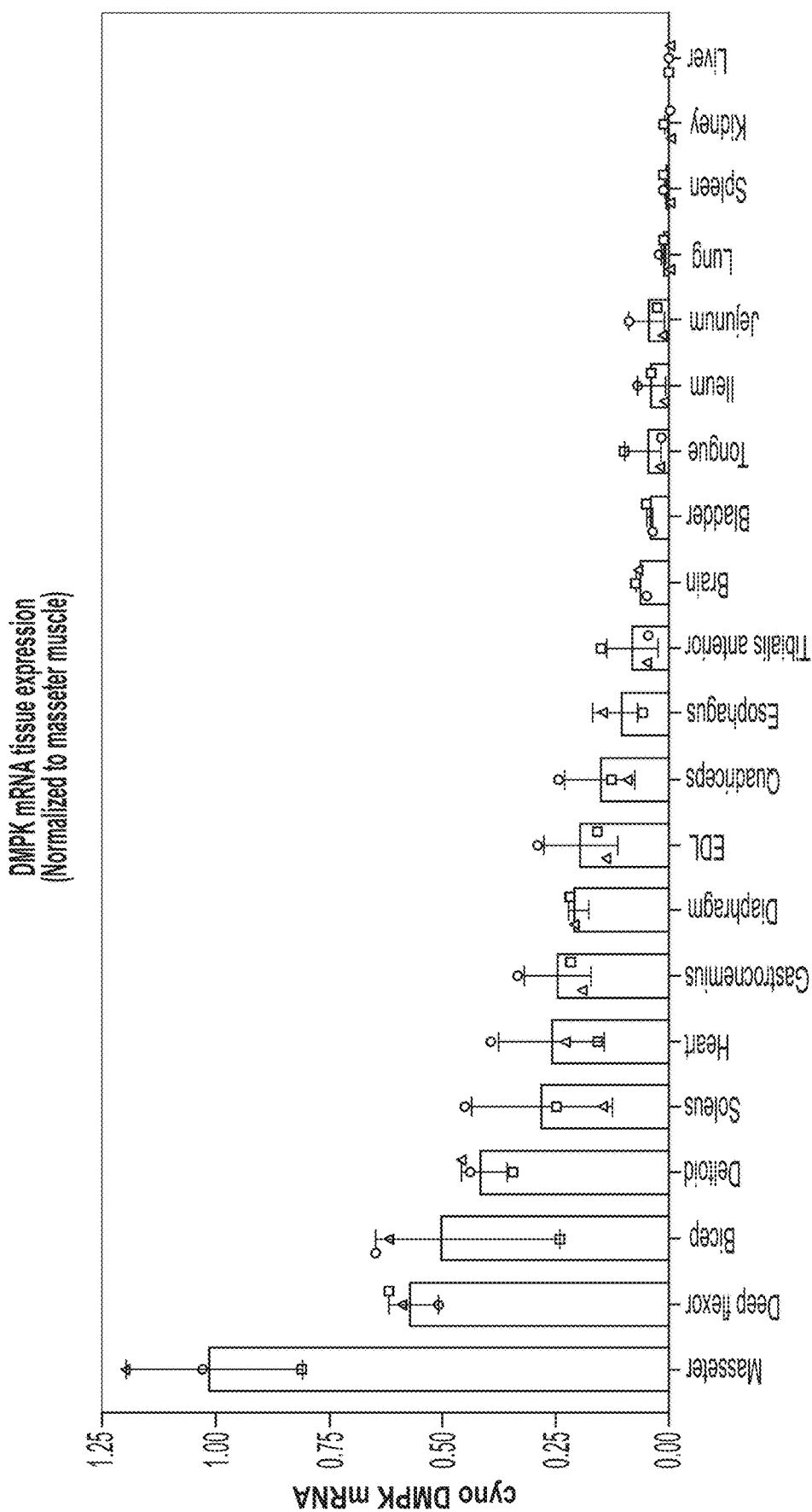
FIG. 10 shows normalized DMPK mRNA tissue expression levels across several tissue types in cynomolgus monkeys. (N=3 male cynomolgus monkeys)

Significant knockdown (KD) of DMPK mRNA expression using DTX-C-012 was observed in soleus, deep flexor, and masseter muscles relative to saline control, with 39% KD, 62% KD, and 41% KD, respectively (FIGS. 7A-7C). Robust knockdown of DMPK mRNA expression by DTX-C-012 was further observed in gastrocnemius (62% KD; FIG. 7D), EDL (29% KD; FIG. 7E), tibialis anterior muscle (23% KD; FIG. 7F), diaphragm (54% KD; FIG. 7G), tongue (43% KD; FIG. 7H), heart muscle (36% KD; FIG. 7I), quadriceps (58% KD; FIG. 7J), bicep (51% KD; FIG. 7K), and deltoid muscles (47% KD; FIG. 7L). Knockdown of DMPK mRNA expression by DTX-C-012 in smooth muscle was also observed in the intestine, with 63% KD at jejunum-duodenum ends (FIG. 8A) and 70% KD in ileum (FIG. 8B). Notably, naked DMPK ASO300 (i.e., not linked to a muscle-targeting agent) had minimal effects on DMPK expression levels relative to the vehicle control (i.e., little or no reduction in DMPK expression) for most assayed muscle tissue types. Monkeys treated with the DTX-C-012 complex demonstrated no change in DMPK expression in most non-muscle tissues, such as kidney, brain, and spleen tissues (FIGS. 9A-9D). Additional tissues were examined, as depicted in FIG. 10, which shows normalized DMPK mRNA tissue expression levels across several tissue types in cynomolgus monkeys. (N=3 male cynomolgus monkeys)

Figure 12:
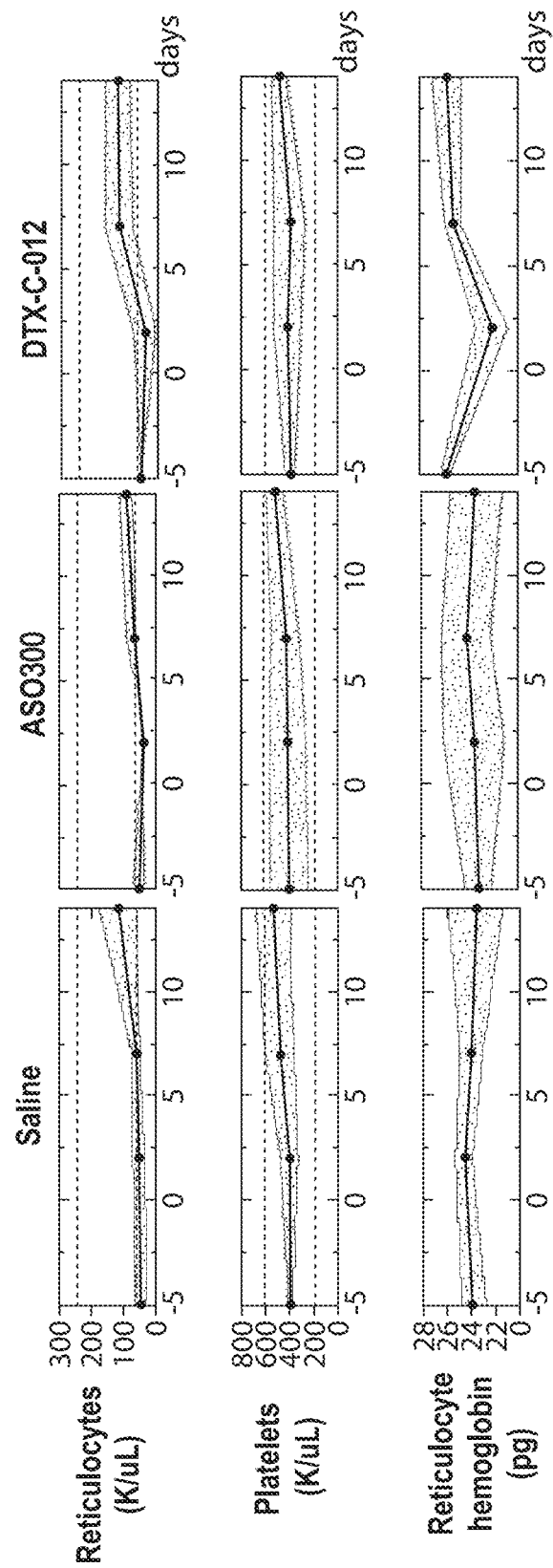
FIG. 12 shows that a single dose of a muscle targeting complex (DTX-C-012) comprising ASO300 covalently linked to an anti-hTFR antibody is safe and tolerated in cynomolgus monkeys. (N=3 male cynomolgus monkeys)

Prior to euthanization, all monkeys were tested for reticulocyte levels, platelet levels, hemoglobin expression, alanine aminotransferase (ALT) expression, aspartate aminotransferase (AST) expression, and blood urea nitrogen (BUN) levels on days 2, 7, and 14 after dosing. As shown in FIG. 12, monkeys dosed with antibody-oligonucleotide complex had normal reticulocyte levels, platelet levels and hemoglobin expression throughout the length of the experiment. Monkeys dosed with DTX-C-012 also had normal alanine aminotransferase (ALT) expression, aspartate aminotransferase (AST) expression, and blood urea nitrogen (BUN) levels throughout the length of the experiment. These data show that a single dose of a complex comprising ASO300 is safe and tolerated in cynomolgus monkeys.

These data demonstrate that the anti-transferrin receptor antibody of the DTX-C-012 complex enabled cellular internalization of the complex into muscle-specific tissues in an in vivo cynomolgus monkey model, thereby allowing the DMPK ASO (ASO300) to inhibit expression of DMPK. These data further demonstrate that the DTX-C-012 complex is capable of specifically targeting muscle tissues for dose-dependent inhibition of DMPK without substantially impacting non-muscle tissues. This is direct contrast with the limited ability of naked DMPK ASO300 (not linked to a muscle-targeting agent), to inhibit expression of DMPK in muscle tissues of an in vivo cynomolgus monkey model.

Figure 11A:
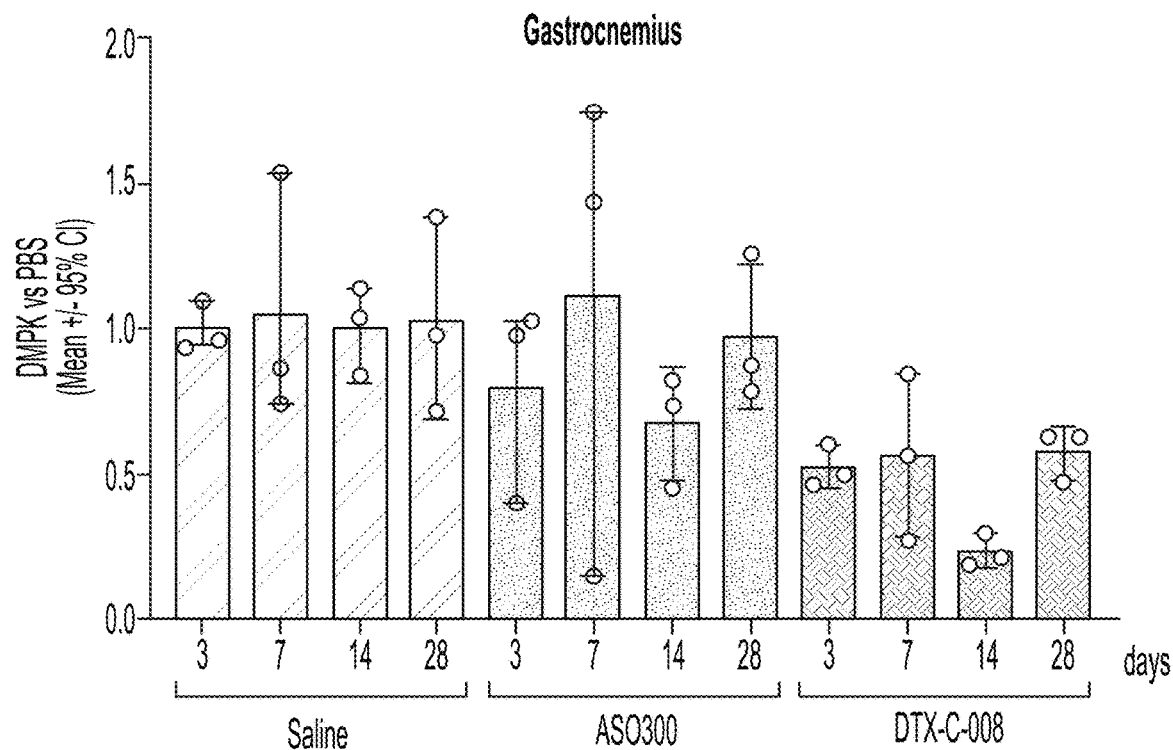
FIGS. 11A-11B depict non-limiting schematics showing the ability of a muscle targeting RI7 217 Fab antibody-oligonucleotide complex (DTX-C-008) comprising ASO300 to reduce expression levels of DMPK in mouse muscle tissues in vivo for up to 28 days after dosing with DTX-C-008, relative to a vehicle treatment (saline) and compared to naked ASO300.
Figure 11B:
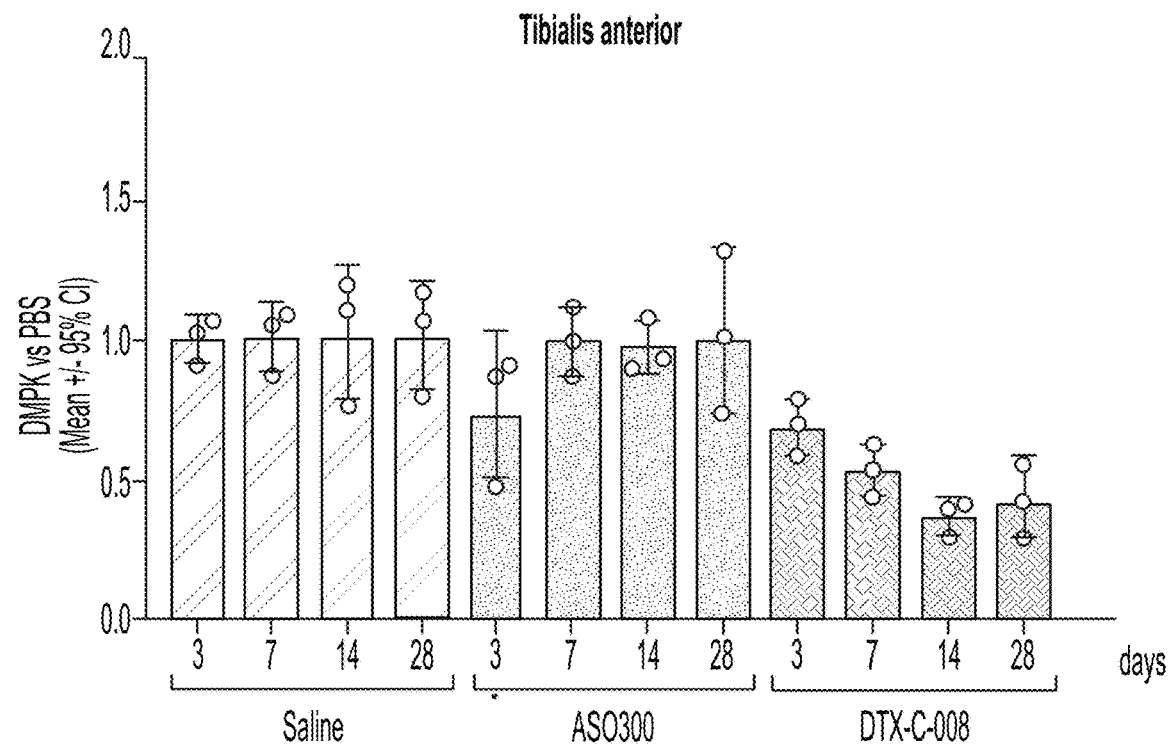

Example 6: Targeting DMPK in Mouse Muscle Tissues with a Muscle-Targeting Complex The RI7 217 Fab antibody-ASO muscle-targeting complex described in Example 2, DTX-C-008, was tested for time-dependent inhibition of DMPK in mouse tissues. C57BL/6 wild-type mice were intravenously injected with a single dose of a vehicle control (saline), naked ASO300 (10 mg/kg of ASO), or DTX-C-008 (10 mg/kg of ASO) and euthanized after a prescribed period of time, as described in Table 13. Following euthanization, the mice were segmented into isolated tissue types and tissue samples were subsequently assayed for expression levels of DMPK (FIGS. 11A-11B).

TABLE 13

| Experimental conditions | | | |
|---|---|---|---|
| Group | Dosage | Days after injection before euthanization | Number of mice |
| 1 | Vehicle (saline) | 3 days | 3 |
| 2 | Vehicle (saline) | 7 days | 3 |
| 3 | Vehicle (saline) | 14 days | 3 |
| 4 | Vehicle (saline) | 28 days | 3 |
| 5 | ASO300 | 3 days | 3 |
| 6 | ASO300 | 7 days | 3 |
| 7 | ASO300 | 14 days | 3 |
| 8 | ASO300 | 28 days | 3 |
| 9 | DTX-C-008 | 3 days | 3 |
| 10 | DTX-C-008 | 7 days | 3 |
| 11 | DTX-C-008 | 14 days | 3 |
| 12 | DTX-C-008 | 28 days | 3 |

Mice treated with the DTX-C-008 complex demonstrated approximately 50% reduction in DMPK expression in gastrocnemius (FIG. 11A) and tibialis anterior (FIG. 11B) muscles for all of Groups 9-12 (3-28 days between injection and euthanization), relative to vehicle. Mice treated with the naked ASO300 oligonucleotide did not demonstrate significant reduction in DMPK expression.

These data indicate that the DTX-C-008 complex was capable of providing persistent reduction in DMPK expression for up to 28 days following dosage of mice with said DTX-C-008 complex.

Example 7: Evaluation of Antisense Oligonucleotides that Target DMPK in Immortalized Myoblasts Two hundred and thirty-six oligonucleotides for targeting DMPK were generated using in silico analysis. Each individual oligonucleotide was evaluated for their ability to target DMPK in cellulo at two doses—0.5 nM (low dose) and 50 nM (high dose).

Briefly, DM1 C15 immortalized myoblasts were cultured in T-75 flasks until near confluency (~80% confluent). Myoblasts were then disrupted with trypsin and seeded into 96-well microplates at a density of 50,000 cells/well. Cells were allowed to recover overnight before the growth media was washed out and replaced with a no-serum media to induce differentiation into myotubes. Differentiation proceeded for seven days prior to treatment with DMPK-targeting oligonucleotides.

On day seven following induction of differentiation, DM1 C15 myotubes were transfected with an individual oligonucleotide using 0.3 μL of Lipofectamine MessengerMax per well. All oligonucleotides were tested at both 0.5 nM and 50 nM final concentrations in biological triplicates. After treatment with oligonucleotides, cells were incubated for 72 hours prior to being harvested for total RNA. cDNA was synthesized from the total RNA extracts and qPCR was performed to determine expression levels of DMPK in technical quadruplicate. All qPCR data were analyzed using a traditional ΔΔCT method and were normalized to a plate-based negative control that comprised cells treated with vehicle control (0.3 μL/well Lipofectamine MessengerMax without any oligonucleotide). Results from these experiments are shown in Table 8. 'Normalized DMPK Remaining' for each antisense oligonucleotide in Table 8 refers to the expression level of DMPK in cell treated with said antisense oligonucleotide relative to the negative control that comprised cells treated with vehicle control (wherein the expression level of the negative control has been normalized to equal 1.00)

The majority of tested DMPK-targeting antisense oligonucleotides demonstrated a reduction in DMPK expression in differentiated myotubes at both the low and high dose concentrations (0.5 nM and 50 nM, respectively). These data demonstrate that the antisense oligonucleotides shown in Table 8 are capable of targeting DMPK in cellulo, suggesting that muscle-targeting complexes comprising these antisense oligonucleotides would be capable of targeting DMPK in muscle tissues in vivo.

TABLE 8

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GGACGGCCCG GCUUGCUGCC | 148 | GGCAGCAAGC CGGGCCGTCC | 384 | 0.42 | 58.25 | 0.31 | 69.30 |
| GGGCCCGGAU CACAGGACUG | 149 | CAGTCCTGTG ATCCGGGCCC | 385 | 0.42 | 57.97 | 0.38 | 61.96 |
| CAAACUUGCU CAGCAGUGUC | 150 | GACACTGCTG AGCAAGTTTG | 386 | 0.69 | 31.45 | 0.46 | 53.93 |
| AAACUUGCUC AGCAGUGUCA | 151 | TGACACTGCT GAGCAAGTTT | 387 | 0.69 | 30.85 | 0.49 | 50.69 |
| CGGAUGGCCU CCAUCUCCCG | 152 | CGGGAGATGG AGGCCATCCG | 388 | 0.71 | 28.92 | 0.44 | 55.57 |
| CUCGGCCGGA AUCCGCUCCC | 153 | GGGAGCGGAT TCCGGCCGAG | 389 | 0.71 | 28.64 | 0.35 | 64.75 |
| UCUCGGCCGG AAUCCGCUCC | 154 | GGAGCGGATT CCGGCCGAGA | 390 | 0.72 | 27.88 | 0.33 | 67.46 |
| UGCUCAGCAG UGUCAGCAGG | 155 | CCTGCTGACA CTGCTGAGCA | 391 | 0.73 | 27.08 | 0.34 | 65.78 |
| UUGUCGGGUU UGAUGUCCCU | 156 | AGGGACATCA AACCCGACAA | 392 | 0.66 | 34.16 | 0.44 | 55.56 |
| GUUGCGGGUU UGAUGUCCC | 157 | GGGACATCAA ACCCGACAAC | 393 | 0.67 | 33.31 | 0.39 | 61.07 |
| UCCGCCAGGU AGAAGCGCGC | 158 | GCGCGCTTCT ACCTGGCGGA | 394 | 0.72 | 27.99 | 0.20 | 80.06 |
| CAUGGCAUAC ACCUGGCCCG | 159 | CGGGCCAGGT GTATGCCATG | 395 | 0.68 | 31.63 | 0.26 | 74.03 |
| AACUUGCUCA GCAGUGUCAG | 160 | CTGACACTGC TGAGCAAGTT | 396 | 0.80 | 19.81 | 0.47 | 52.64 |
| CAGCUGCGUG AUCCACCGCC | 161 | GGCGGTGGAT CACGCAGCTG | 397 | 0.81 | 19.03 | 0.32 | 68.34 |
| CGAAUGUCCG ACAGUGUCUC | 162 | GAGACACTGT CGGACATTCG | 398 | 0.60 | 40.21 | 0.36 | 64.42 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GAAGUCGGCC AGGCGGAUGU | 163 | ACATCCGCCT GGCCGACTTC | 399 | 0.82 | 18.36 | 0.56 | 44.04 |
| UGUCGGGUUU GAUGUCCCUG | 164 | CAGGGACATC AAACCCGACA | 400 | 0.70 | 30.09 | 0.32 | 68.14 |
| GGAUGGCCUC CAUCUCCCGG | 165 | CCGGGAGATG GAGGCCATCC | 401 | 0.75 | 24.93 | 0.39 | 60.77 |
| AGGAUGUUGU CGGGUUUGAU | 166 | ATCAAACCCG ACAACATCCT | 402 | 0.76 | 24.19 | 0.61 | 39.48 |
| GUCGGGUUUG AUGUCCCUGU | 167 | ACAGGGACAT CAAACCCGAC | 403 | 0.71 | 28.89 | 0.36 | 64.15 |
| AAUACUCCAU GACCAGGUAC | 168 | GTACCTGGTC ATGGAGTATT | 404 | 0.71 | 28.86 | 0.48 | 52.07 |
| CUUGUUCAUG AUCUUCAUGG | 169 | CCATGAAGAT CATGAACAAG | 405 | 0.84 | 16.06 | 0.51 | 49.47 |
| UCAGUGCAUC CAAAACGUGG | 170 | CCACGTTTTG ATGCACTGA | 406 | 0.84 | 15.76 | 0.58 | 42.06 |
| CUGUCCCGGA GACCAUCCCA | 171 | TGGGATGGTC TCCGGGACAG | 407 | 0.64 | 35.85 | 0.49 | 50.78 |
| GGGCCUGGGA CCUCACUGUC | 172 | GACAGTGAGG TCCCAGGCCC | 408 | 0.63 | 37.19 | 0.23 | 76.81 |
| CCCACGUAAU ACUCCAUGAC | 173 | GTCATGGAGT ATTACGTGGG | 409 | 0.72 | 28.21 | 0.54 | 45.94 |
| CUCUGCCGCA GGGACAGCCG | 174 | CGGCTGTCCCT GCGGCAGAG | 410 | 0.63 | 37.09 | 0.06 | 93.59 |
| CUGUGCACGU AGCCAAGCCG | 175 | CGGCTTGGCT ACGTGCACAG | 411 | 0.74 | 25.67 | 0.30 | 70.10 |
| UGCCCAUCCA CGUCAGGGCC | 176 | GGCCCTGACG TGGATGGGCA | 412 | 0.86 | 13.63 | 0.67 | 33.09 |
| AGCGCCUCCG AUAGGCCAGG | 177 | CCTGGCCTATC GGAGGCGCT | 413 | 0.79 | 21.19 | 0.38 | 61.91 |
| UGUGCACGUA GCCAAGCCGG | 178 | CCGGCTTGGC TACGTGCACA | 414 | 0.75 | 24.74 | 0.25 | 75.09 |
| GACCAGGUAC AGGUAGUUCU | 179 | AGAACTACCT GTACCTGGTC | 415 | 0.57 | 42.85 | 0.29 | 70.95 |
| CCAUCUCGGC CGGAAUCCGC | 180 | GCGGATTCCG GCCGAGATGG | 416 | 0.79 | 20.50 | 0.40 | 59.76 |
| CAUCUCGGCC GGAAUCCGCU | 181 | AGCGGATTCC GGCCGAGATG | 417 | 0.80 | 20.21 | 0.41 | 59.40 |
| UUGCCAUAGG UCUCCGCCGU | 182 | ACGGCGGAGA CCTATGGCAA | 418 | 0.64 | 36.30 | 0.40 | 60.12 |
| ACAGCGGUCC AGCAGGAUGU | 183 | ACATCCTGCT GGACCGCTGT | 419 | 0.80 | 19.94 | 0.45 | 55.14 |
| AAAGCGCCUC CGAUAGGCCA | 184 | TGGCCTATCG GAGGCGCTTT | 420 | 0.80 | 19.89 | 0.38 | 62.04 |
| GCCAAAGAAG AAGGGAUGUG | 185 | CACATCCCTTC TTCTTTGGC | 421 | 0.75 | 24.87 | 0.44 | 56.19 |

TABLE 8-continued

Ability of DMPK-targeting antisense oligonucleotides to reduce expression of DMPK in cellulo

|  |  |  |  | 0.5 nM | | 50 nM | |
|---|---|---|---|---|---|---|---|
| Antisense Oligonucleotide Sequence | SEQ ID NO: | DMPK Target Sequence | SEQ ID NO: | Normalized DMPK Remaining | Percent DMPK Reduction | Normalized DMPK Remaining | Percent DMPK Reduction |
| CACGUAAUACUCCAUGACCA | 186 | TGGTCATGGAGTATTACGTG | 422 | 0.76 | 24.40 | 0.54 | 46.50 |
| AUCUCGGCCGGAAUCCGCUC | 187 | GAGCGGATTCCGGCCGAGAT | 423 | 0.88 | 11.61 | 0.34 | 65.98 |
| GCUUCAUCUUCACUACCGCU | 188 | AGCGGTAGTGAAGATGAAGC | 424 | 0.69 | 31.44 | 0.48 | 51.78 |
| GCCAUCUCGGCCGGAAUCCG | 189 | CGGATTCCGGCCGAGATGGC | 425 | 0.81 | 18.56 | 0.14 | 86.39 |
| CAGGGACAGCCGCUGGAACU | 190 | AGTTCCAGCGGCTGTCCCTG | 426 | 0.68 | 32.09 | 0.41 | 58.84 |
| AUGACAAUCUCCGCCAGGUA | 191 | TACCTGGCGGAGATTGTCAT | 427 | 0.58 | 42.38 | 0.40 | 60.47 |
| GGCCAUGACAAUCUCCGCCA | 192 | TGGCGGAGATTGTCATGGCC | 428 | 0.58 | 42.38 | 0.25 | 75.00 |
| AUACUCCAUGACCAGGUACA | 193 | TGTACCTGGTCATGGAGTAT | 429 | 0.77 | 23.07 | 0.43 | 56.84 |
| GCCUCUGCCUCGCGUAGUUG | 194 | CAACTACGCGAGGCAGAGGC | 430 | 0.65 | 35.38 | 0.19 | 81.18 |
| GAAUGUCCGACAGUGUCUCC | 195 | GGAGACACTGTCGGACATTC | 431 | 0.70 | 30.09 | 0.37 | 63.41 |
| CGUUCCAUCUGCCCGCAGCU | 196 | AGCTGCGGGCAGATGGAACG | 432 | 0.66 | 33.74 | 0.31 | 68.72 |
| CCUUGUAGUGGACGAUCUUG | 197 | CAAGATCGTCCACTACAAGG | 433 | 0.83 | 17.20 | 0.34 | 65.91 |
| AUCUCCGCCAGGUAGAAGCG | 198 | CGCTTCTACCTGGCGGAGAT | 434 | 0.58 | 42.37 | 0.35 | 65.50 |
| CUCAGGCUCUGCCGGGUGAG | 199 | CTCACCCGGCAGAGCCTGAG | 435 | 0.70 | 30.13 | 0.37 | 63.07 |
| UGCUUCAUCUUCACUACCGC | 200 | GCGGTAGTGAAGATGAAGCA | 436 | 0.71 | 28.82 | 0.40 | 60.24 |
| GCAGGAUGUUGUCGGGUUUG | 201 | CAAACCCGACAACATCCTGC | 437 | 0.56 | 44.39 | 0.22 | 78.03 |
| GGCCUCAGCCUCUGCCGCAG | 202 | CTGCGGCAGAGGCTGAGGCC | 438 | 0.80 | 20.12 | 0.29 | 71.28 |
| UGUUGUCGGGUUUGAUGUCC | 203 | GGACATCAAACCCGACAACA | 439 | 0.79 | 21.00 | 0.58 | 42.19 |
| CCACGUAAUACUCCAUGACC | 204 | GGTCATGGAGTATTACGTGG | 440 | 0.79 | 20.84 | 0.50 | 50.06 |
| CCGUUCCAUCUGCCCGCAGC | 205 | GCTGCGGGCAGATGGAACGG | 441 | 0.68 | 31.74 | 0.23 | 77.46 |
| UUCCCGAGUAAGCAGGCAGA | 206 | TCTGCCTGCTTACTCGGGAA | 442 | 0.69 | 31.49 | 0.50 | 49.81 |
| UGAUCUUCAUGGCAUACACC | 207 | GGTGTATGCCATGAAGATCA | 443 | 0.72 | 27.70 | 0.10 | 89.68 |
| AGGGACAGCCGCUGGAACUG | 208 | CAGTTCCAGCGGCTGTCCCT | 444 | 0.71 | 28.72 | 0.55 | 45.34 |
| GGGUUUGAUGUCCCUGUGCA | 209 | TGCACAGGGACATCAAACCC | 445 | 0.60 | 40.12 | 0.37 | 62.61 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| UGACAAUCUC CGCCAGGUAG | 210 | CTACCTGGCG GAGATTGTCA | 446 | 0.61 | 38.86 | 0.33 | 66.56 |
| CACAGCGGUC CAGCAGGAUG | 211 | CATCCTGCTG GACCGCTGTG | 447 | 0.93 | 6.62 | 0.40 | 59.58 |
| GCGUAGAAGG GCGUCUGCCC | 212 | GGGCAGACGC CCTTCTACGC | 448 | 0.60 | 39.53 | 0.22 | 77.91 |
| CUCAGCCUCU GCCGCAGGGA | 213 | TCCCTGCGGC AGAGGCTGAG | 449 | 0.82 | 17.86 | 0.20 | 79.58 |
| GUCUCAGUGC AUCCAAAACG | 214 | CGTTTTGGATG CACTGAGAC | 450 | 0.81 | 18.85 | 0.54 | 46.13 |
| GGACGAUCUU GCCAUAGGUC | 215 | GACCTATGGC AAGATCGTCC | 451 | 0.70 | 29.82 | 0.51 | 48.97 |
| UCAGCAGUGU CAGCAGGUCC | 216 | GGACCTGCTG ACACTGCTGA | 452 | 0.67 | 33.46 | 0.39 | 61.11 |
| GCUCCUGGGC GGCGCCAGAC | 217 | GTCTGGCGCC GCCCAGGAGC | 453 | 0.91 | 8.52 | 0.21 | 78.79 |
| AGCAGGAUGU UGUCGGGUUU | 218 | AAACCCGACA ACATCCTGCT | 454 | 0.59 | 41.05 | 0.26 | 74.02 |
| AUCCGCUCCU GCAACUGCCG | 219 | CGGCAGTTGC AGGAGCGGAT | 455 | 0.87 | 12.80 | 0.60 | 40.06 |
| AGGAGCAGGG AAAGCGCCUC | 220 | GAGGCGCTTT CCCTGCTCCT | 456 | 0.67 | 33.24 | 0.38 | 62.37 |
| ACACCUGGCC CGUCUGCUUC | 221 | GAAGCAGACG GGCCAGGTGT | 457 | 0.67 | 33.00 | 0.45 | 55.40 |
| CCCAGCGCCC ACCAGUCACA | 222 | TGTGACTGGT GGGCGCTGGG | 458 | 0.62 | 37.93 | 0.32 | 67.82 |
| GCUCCCUCUG CCUGCAGCAA | 223 | TTGCTGCAGG CAGAGGGAGC | 459 | 0.74 | 26.41 | 0.30 | 70.15 |
| GCUCAGGCUC UGCCGGGUGA | 224 | TCACCCGGCA GAGCCTGAGC | 460 | 0.74 | 25.69 | 0.39 | 60.71 |
| UUGAUGUCCC UGUGCACGUA | 225 | TACGTGCACA GGGACATCAA | 461 | 0.74 | 25.67 | 0.45 | 55.13 |
| GCCUCAGCCU CUGCCGCAGG | 226 | CCTGCGGCAG AGGCTGAGGC | 462 | 0.84 | 16.37 | 0.54 | 46.42 |
| GGUAGUUCUC AUCCUGGAAG | 227 | CTTCCAGGAT GAGAACTACC | 463 | 0.75 | 25.48 | 0.44 | 56.15 |
| CAGCGCCCAC CAGUCACACU | 228 | AGTGTGACTG GTGGGCGCTG | 464 | 0.63 | 37.28 | 0.35 | 64.93 |
| CCCAAACUUG CUCAGCAGUG | 229 | CACTGCTGAG CAAGTTTGGG | 465 | 0.63 | 37.02 | 0.38 | 61.78 |
| CUUGCCAUAG GUCUCCGCCG | 230 | CGGCGGAGAC CTATGGCAAG | 466 | 0.73 | 27.04 | 0.29 | 71.05 |
| UACACCUGGC CCGUCUGCUU | 231 | AAGCAGACGG GCCAGGTGTA | 467 | 0.69 | 31.10 | 0.43 | 57.43 |
| CCAGCGCCCA CCAGUCACAC | 232 | GTGTGACTGG TGGGCGCTGG | 468 | 0.64 | 36.17 | 0.29 | 70.96 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GGCCUCAGCCUGGCCGAAAG | 233 | CTTTCGGCCAGGCTGAGGCC | 469 | 0.86 | 14.49 | 0.35 | 64.80 |
| AAUCUCCGCCAGGUAGAAGC | 234 | GCTTCTACCTGGCGGAGATT | 470 | 0.64 | 35.85 | 0.35 | 65.27 |
| AUGGCAUACACCUGGCCCGU | 235 | ACGGGCCAGGTGTATGCCAT | 471 | 0.86 | 14.31 | 0.50 | 49.63 |
| CCAUGACAAUCUCCGCCAGG | 236 | CCTGGCGGAGATTGTCATGG | 472 | 0.65 | 34.53 | 0.24 | 76.46 |
| UCCCCAAACUUGCUCAGCAG | 237 | CTGCTGAGCAAGTTTGGGGA | 473 | 0.94 | 5.73 | 0.55 | 44.67 |
| GAUGUUGUCGGGUUUGAUGU | 238 | ACATCAAACCCGACAACATC | 474 | 0.90 | 10.06 | 0.58 | 42.42 |
| GUUUGCCCAUCCACGUCAGG | 239 | CCTGACGTGGATGGGCAAAC | 475 | 0.66 | 34.36 | 0.46 | 54.49 |
| CGGACGGCCCGGCUUGCUGC | 240 | GCAGCAAGCCGGGCCGTCCG | 476 | 0.95 | 5.42 | 0.70 | 30.41 |
| CUCCGCCAGGUAGAAGCGCG | 241 | CGCGCTTCTACCTGGCGGAG | 477 | 0.70 | 30.22 | 0.22 | 78.14 |
| GUACAGGUAGUUCUCAUCCU | 242 | AGGATGAGAACTACCTGTAC | 478 | 0.68 | 31.52 | 0.34 | 65.57 |
| AGGGCGUCUGCCCAUAGAAC | 243 | GTTCTATGGGCAGACGCCCT | 479 | 0.87 | 13.23 | 0.41 | 58.98 |
| UGGCCACAGCGGUCCAGCAG | 244 | CTGCTGGACCGCTGTGGCCA | 480 | 0.70 | 29.59 | 0.31 | 69.44 |
| CGUAGUUGACUGGCGAAGUU | 245 | AACTTCGCCAGTCAACTACG | 481 | 0.75 | 25.26 | 0.38 | 61.52 |
| UCUGCCGCAGGGACAGCCGC | 246 | GCGGCTGTCCCTGCGGCAGA | 482 | 0.77 | 22.97 | 0.18 | 82.10 |
| AAGCGCCUCCGAUAGGCCAG | 247 | CTGGCCTATCGGAGGCGCTT | 483 | 0.91 | 8.91 | 0.56 | 43.93 |
| GACAGAACAACGGCGAACAG | 248 | CTGTTCGCCGTTGTTCTGTC | 484 | 0.79 | 21.41 | 0.30 | 70.49 |
| GCUCAGCAGUGUCAGCAGGU | 249 | ACCTGCTGACACTGCTGAGC | 485 | 0.71 | 29.18 | 0.27 | 73.46 |
| AUGAUCUUCAUGGCAUACAC | 250 | GTGTATGCCATGAAGATCAT | 486 | 0.87 | 12.76 | 0.60 | 39.97 |
| UUUGCCCAUCCACGUCAGGG | 251 | CCCTGACGTGGATGGGCAAA | 487 | 0.67 | 32.79 | 0.41 | 59.36 |
| ACUUGCUCAGCAGUGUCAGC | 252 | GCTGACACTGCTGAGCAAGT | 488 | 0.72 | 27.84 | 0.39 | 60.71 |
| UGAUGUCCCUGUGCACGUAG | 253 | CTACGTGCACAGGGACATCA | 489 | 0.79 | 20.58 | 0.41 | 59.00 |
| AAAUACCGAGGAAUGUCGGG | 254 | CCCGACATTCCTCGGTATTT | 490 | 0.89 | 11.25 | 0.49 | 50.91 |
| GGCGAAUACACCCAGCGCCC | 255 | GGGCGCTGGGTGTATTCGCC | 491 | 0.80 | 19.77 | 0.31 | 68.72 |
| AGACAAUAAAUACCGAGGAA | 256 | TTCCTCGGTATTTATTGTCT | 492 | 0.71 | 29.37 | 0.52 | 48.20 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| CCCGUCUGCUUCAUCUUCAC | 257 | GTGAAGATGAAGCAGACGGG | 493 | 0.80 | 20.31 | 0.56 | 43.97 |
| CUGCCUGCAGCAACUCCAUC | 258 | GATGGAGTTGCTGCAGGCAG | 494 | 0.77 | 23.10 | 0.53 | 46.69 |
| CCUCAGCCUCUGCCGCAGGG | 259 | CCCTGCGGCAGAGGCTGAGG | 495 | 0.89 | 10.87 | 0.45 | 55.22 |
| GUGUCCGGAAGUCGCCUGCU | 260 | AGCAGGCGACTTCCGGACAC | 496 | 0.77 | 22.99 | 0.26 | 73.65 |
| UGCACGUGUGGCUCAAGCAG | 261 | CTGCTTGAGCCACACGTGCA | 497 | 0.89 | 10.81 | 0.36 | 64.18 |
| GACAAUAAAUACCGAGGAAU | 262 | ATTCCTCGGTATTTATTGTC | 498 | 0.71 | 28.97 | 0.52 | 47.51 |
| GCCAUGACAAUCUCCGCCAG | 263 | CTGGCGGAGATTGTCATGGC | 499 | 0.69 | 30.96 | 0.19 | 81.00 |
| GCUGUCCCGGAGACCAUCCC | 264 | GGGATGGTCTCCGGGACAGC | 500 | 0.77 | 22.57 | 0.34 | 66.27 |
| CAUGACCAGGUACAGGUAGU | 265 | ACTACCTGTACCTGGTCATG | 501 | 0.81 | 19.39 | 0.41 | 59.09 |
| AGCGCCCACCAGUCACACUC | 266 | GAGTGTGACTGGTGGGCGCT | 502 | 0.70 | 30.36 | 0.36 | 63.67 |
| UCUCAGUGCAUCCAAAACGU | 267 | ACGTTTTGGATGCACTGAGA | 503 | 0.89 | 10.88 | 0.49 | 51.34 |
| UUUGGGCAGAUGGAGGGCCU | 268 | AGGCCCTCCATCTGCCCAAA | 504 | 0.65 | 35.14 | 0.30 | 70.00 |
| GAUGUCCCUGUGCACGUAGC | 269 | GCTACGTGCACAGGGACATC | 505 | 0.81 | 18.99 | 0.38 | 62.46 |
| CAGCAGUGUCAGCAGGUCCC | 270 | GGGACCTGCTGACACTGCTG | 506 | 0.74 | 25.67 | 0.48 | 51.97 |
| CAUGACAAUCUCCGCCAGGU | 271 | ACCTGGCGGAGATTGTCATG | 507 | 0.71 | 29.45 | 0.29 | 70.52 |
| ACUUGUUCAUGAUCUUCAUG | 272 | CATGAAGATCATGAACAAGT | 508 | 0.75 | 25.47 | 0.47 | 52.89 |
| GUGGAAUCCGCGUAGAAGGG | 273 | CCCTTCTACGCGGATTCCAC | 509 | 0.69 | 30.55 | 0.51 | 49.34 |
| UGGCCAUGACAAUCUCCGCC | 274 | GGCGGAGATTGTCATGGCCA | 510 | 0.70 | 30.46 | 0.27 | 72.55 |
| GGGACAGACAAUAAAUACCG | 275 | CGGTATTTATTGTCTGTCCC | 511 | 0.73 | 27.19 | 0.49 | 50.50 |
| CCGCUCCCCAAACUUGCUCA | 276 | TGAGCAAGTTTGGGGAGCGG | 512 | 1.00 | 0.28 | 0.43 | 56.82 |
| CGGCUCAGGCUCUGCCGGGU | 277 | ACCCGGCAGAGCCTGAGCCG | 513 | 0.82 | 17.97 | 0.31 | 69.03 |
| GGCUCCUGGGCGGCGCCAGA | 278 | TCTGGCGCCGCCCAGGAGCC | 514 | 1.00 | 0.05 | 0.04 | 96.23 |
| UUUCCCGAGUAAGCAGGCAG | 279 | CTGCCTGCTTACTCGGGAAA | 515 | 0.79 | 20.69 | 0.55 | 44.89 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GGAUGUUGUCGGGUUUGAUG | 280 | CATCAAACCCGACAACATCC | 516 | 0.96 | 4.26 | 0.59 | 40.81 |
| CAGGUAGUUCUCAUCCUGGA | 281 | TCCAGGATGAGAACTACCTG | 517 | 0.74 | 25.92 | 0.23 | 76.71 |
| UGCCCAUAGAACAUUUCAUA | 282 | TATGAAATGTTCTATGGGCA | 518 | 0.92 | 7.67 | 0.65 | 34.56 |
| UAGUUCUCAUCCUGGAAGGC | 283 | GCCTTCCAGGATGAGAACTA | 519 | 0.83 | 16.83 | 0.56 | 43.88 |
| AUGUCCCUGUGCACGUAGCC | 284 | GGCTACGTGCACAGGGACAT | 520 | 0.83 | 16.78 | 0.51 | 49.29 |
| CGGGCCCGGAUCACAGGACU | 285 | AGTCCTGTGATCCGGGCCCG | 521 | 0.83 | 17.45 | 0.33 | 67.11 |
| UGGACGAUCUUGCCAUAGGU | 286 | ACCTATGGCAAGATCGTCCA | 522 | 0.81 | 19.20 | 0.57 | 42.52 |
| GUUGGCCGGCGUGGGCACCC | 287 | GGTGGCCCACGCCGGCCAAC | 523 | 1.02 | -1.82 | 0.56 | 43.57 |
| CUCAGUGCAUCCAAAACGUG | 288 | CACGTTTTGGATGCACTGAG | 524 | 0.92 | 7.65 | 0.46 | 54.26 |
| UCGAAGUUGCAUGUGUCGGU | 289 | ACCGACACATGCAACTTCGA | 525 | 0.77 | 22.96 | 0.42 | 58.15 |
| UGGAACACGGACGGCCCGGC | 290 | GCCGGGCCGTCCGTGTTCCA | 526 | 1.02 | -1.90 | 0.39 | 60.96 |
| CCGAGAGCAGCGCAAGUGAG | 291 | CTCACTTGCGCTGCTCTCGG | 527 | 0.84 | 16.13 | 0.59 | 40.93 |
| UCCUGCAACUGCCGGACGUG | 292 | CACGTCCGGCAGTTGCAGGA | 528 | 0.84 | 16.06 | 0.55 | 44.61 |
| UCACCAACACGUCCCUCUCC | 293 | GGAGAGGGACGTGTTGGTGA | 529 | 0.53 | 47.12 | 0.16 | 84.09 |
| UGCCUGCAGCAACUCCAUCC | 294 | GGATGGAGTTGCTGCAGGCA | 530 | 0.86 | 13.99 | 0.50 | 49.75 |
| UUGGCCGGCGUGGGCCACCA | 295 | TGGTGGCCCACGCCGGCCAA | 531 | 1.03 | -3.19 | 0.56 | 44.37 |
| GAGCCUCUGCCUCGCGUAGU | 296 | ACTACGCGAGGCAGAGGCTC | 532 | 0.81 | 18.77 | 0.22 | 77.78 |
| AAGGGCGUCUGCCCAUAGAA | 297 | TTCTATGGGCAGACGCCCTT | 533 | 0.87 | 13.15 | 0.65 | 34.56 |
| ACAGACAAUAAAUACCGAGG | 298 | CCTCGGTATTTATTGTCTGT | 534 | 1.04 | -3.95 | 0.26 | 74.02 |
| GGACAGACAAUAAAUACCGA | 299 | TCGGTATTTATTGTCTGTCC | 535 | 0.77 | 22.57 | 0.47 | 52.51 |
| ACGUGUGCCUCUAGGUCCCG | 300 | CGGGACCTAGAGGCACACGT | 536 | 0.84 | 16.47 | 0.22 | 77.73 |
| GGCACGAGACAGAACAACGG | 301 | CCGTTGTTCTGTCTCGTGCC | 537 | 0.84 | 16.10 | 0.32 | 68.01 |
| UGACCAGGUACAGGUAGUUC | 302 | GAACTACCTGTACCTGGTCA | 538 | 0.78 | 22.00 | 0.36 | 63.73 |
| CUCUGCCGGGUGAGCACCUC | 303 | GAGGTGCTCACCCGGCAGAG | 539 | 0.75 | 25.25 | 0.26 | 74.36 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GACAAUCUCC GCCAGGUAGA | 304 | TCTACCTGGC GGAGATTGTC | 540 | 0.76 | 23.70 | 0.50 | 49.82 |
| UCUCCGCCAG GUAGAAGCGC | 305 | GCGCTTCTACC TGGCGGAGA | 541 | 0.80 | 19.59 | 0.33 | 66.52 |
| CUCUGCCUCG CGUAGUUGAC | 306 | GTCAACTACG CGAGGCAGAG | 542 | 0.83 | 16.61 | 0.09 | 91.21 |
| CUUUGGGCAG AUGGAGGGCC | 307 | GGCCCTCCAT CTGCCCAAAG | 543 | 0.72 | 28.06 | 0.33 | 67.50 |
| ACAGGUAGUU CUCAUCCUGG | 308 | CCAGGATGAG AACTACCTGT | 544 | 0.79 | 20.51 | 0.15 | 85.36 |
| CCAAACUUGC TCAGCAGUGU | 309 | ACACTGCTGA GCAAGTTTGG | 545 | 0.76 | 23.64 | 0.42 | 57.70 |
| UCGGGUUUGA UGUCCCUGUG | 310 | CACAGGGACA TCAAACCCGA | 546 | 0.78 | 22.49 | 0.43 | 57.16 |
| GGCUUGCUGC CUUCCCAGGC | 311 | GCCTGGGAAG GCAGCAAGCC | 547 | 1.06 | -6.32 | 0.52 | 48.15 |
| UACAGGUAGU UCUCAUCCUG | 312 | CAGGATGAGA ACTACCTGTA | 548 | 0.80 | 19.83 | 0.27 | 72.51 |
| UUGCCCAUCC ACGUCAGGGC | 313 | GCCCTGACGT GGATGGGCAA | 549 | 0.78 | 22.23 | 0.33 | 67.15 |
| AGGUACAGGU AGUUCUCAUC | 314 | GATGAGAACT ACCTGTACCT | 550 | 0.81 | 18.68 | 0.41 | 58.92 |
| GACAGACAAU AAAUACCGAG | 315 | CTCGGTATTTA TTGTCTGTC | 551 | 0.82 | 18.26 | 0.62 | 38.07 |
| UAGAACAUUU CAUAGGCGAA | 316 | TTCGCCTATGA AATGTTCTA | 552 | 0.80 | 20.23 | 0.56 | 43.67 |
| AGGGCCUUUU AUUCGCGAGG | 317 | CCTCGCGAAT AAAAGGCCCT | 553 | 0.86 | 13.63 | 0.34 | 66.43 |
| GCCUCGCGUA GUUGACUGGC | 318 | GCCAGTCAAC TACGCGAGGC | 554 | 0.87 | 12.98 | 0.09 | 91.10 |
| CCAGCAGGAU GUUGUCGGGU | 319 | ACCCGACAAC ATCCTGCTGG | 555 | 0.60 | 40.29 | 0.10 | 89.59 |
| GUAGUUGACU GGCGAAGUUC | 320 | GAACTTCGCC AGTCAACTAC | 556 | 0.93 | 7.50 | 0.55 | 45.33 |
| UGCGGAUGGC CUCCAUCUCC | 321 | GGAGATGGAG GCCATCCGCA | 557 | 0.60 | 40.15 | 0.16 | 84.43 |
| ACAAUCUCCG CCAGGUAGAA | 322 | TTCTACCTGGC GGAGATTGT | 558 | 0.81 | 19.09 | 0.50 | 49.75 |
| GCGAAUACAC CCAGCGCCCA | 323 | TGGGCGCTGG GTGTATTCGC | 559 | 0.93 | 6.94 | 0.30 | 69.72 |
| GUAGUUCUCA UCCUGGAAGG | 324 | CCTTCCAGGA TGAGAACTAC | 560 | 0.93 | 7.43 | 0.45 | 55.09 |
| GGCUCAGGCU CUGCCGGGUG | 325 | CACCCGGCAG AGCCTGAGCC | 561 | 0.93 | 7.38 | 0.34 | 65.82 |
| CCAUUCACCA ACACGUCCCU | 326 | AGGGACGTGT TGGTGAATGG | 562 | 0.61 | 39.26 | 0.13 | 86.83 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| ACCAGGUACAGGUAGUUCUC | 327 | GAGAACTACCTGTACCTGGT | 563 | 0.84 | 16.09 | 0.23 | 76.96 |
| CTGCAGUUUGCCCAUCCACG | 328 | CGTGGATGGGCAAACTGCAG | 564 | 1.11 | -10.69 | 0.40 | 60.08 |
| UUGUUCAUGAUCUUCAUGGC | 329 | GCCATGAAGATCATGAACAA | 565 | 0.86 | 14.13 | 0.55 | 45.23 |
| UUGAUGUCCCUGUGCACGU | 330 | ACGTGCACAGGGACATCAAA | 566 | 0.93 | 6.92 | 0.57 | 43.07 |
| GCGGUCCAGCAGGAUGUUGU | 331 | ACAACATCCTGCTGGACCGC | 567 | 0.61 | 38.84 | 0.16 | 83.64 |
| GUCUAUGGCCAUGACAAUCU | 332 | AGATTGTCATGGCCATAGAC | 568 | 1.11 | -11.00 | 0.27 | 73.11 |
| GGAGCAGGGAAAGCGCCUCC | 333 | GGAGGCGCTTTCCCTGCTCC | 569 | 0.79 | 21.46 | 0.12 | 88.35 |
| UGCCUCGCGUAGUUGACUGG | 334 | CCAGTCAACTACGCGAGGCA | 570 | 0.89 | 11.03 | 0.12 | 88.02 |
| GCGGAUGGCCUCCAUCUCCC | 335 | GGGAGATGGAGGCCATCCGC | 571 | 0.79 | 21.25 | 0.28 | 71.77 |
| UUUCAUAGGCGAAUACACCC | 336 | GGGTGTATTCGCCTATGAAA | 572 | 0.94 | 5.56 | 0.47 | 53.28 |
| GCCUGUCAGCGAGUCGGAGG | 337 | CCTCCGACTCGCTGACAGGC | 573 | 0.89 | 10.81 | 0.24 | 75.67 |
| CCACUUCAGCUGUUUCAUCC | 338 | GGATGAAACAGCTGAAGTGG | 574 | 0.78 | 22.40 | 0.36 | 64.20 |
| CAUCCGCUCCUGCAACUGCC | 339 | GGCAGTTGCAGGAGCGGATG | 575 | 0.79 | 21.04 | 0.23 | 76.81 |
| UCUAGGGUUCAGGGAGCGCG | 340 | CGCGCTCCCTGAACCCTAGA | 576 | 0.78 | 21.81 | 0.17 | 83.22 |
| CACCAACACGUCCCUCUCCU | 341 | AGGAGAGGGACGTGTTGGTG | 577 | 0.62 | 37.51 | 0.18 | 81.57 |
| CAGGAGCAGGGAAAGCGCCU | 342 | AGGCGCTTTCCCTGCTCCTG | 578 | 0.88 | 12.48 | 0.48 | 51.82 |
| CAAUCCCGCCAGGUAGAAG | 343 | CTTCTACCTGGCGGAGATTG | 579 | 0.84 | 15.95 | 0.51 | 49.25 |
| AUGUUGUCGGGUUUGAUGUC | 344 | GACATCAAACCCGACAACAT | 580 | 0.83 | 16.93 | 0.47 | 52.83 |
| CCAUCCGCUCCUGCAACUGC | 345 | GCAGTTGCAGGAGCGGATGG | 581 | 0.80 | 19.53 | 0.28 | 71.62 |
| GCGUCACCUCGGCCUCAGCC | 346 | GGCTGAGGCCGAGGTGACGC | 582 | 0.80 | 20.02 | 0.19 | 81.27 |
| GAGGGCCUUUUAUUCGCGAG | 347 | CTCGCGAATAAAAGGCCCTC | 583 | 0.92 | 8.23 | 0.38 | 62.21 |
| AGCGGCAGAGAGAGGUGCUC | 348 | GAGCACCTCTCTCTGCCGCT | 584 | 0.80 | 19.75 | 0.09 | 90.71 |
| CAUCCAAAACGUGGAUUGGG | 349 | CCCAATCCACGTTTTGGATG | 585 | 0.81 | 19.12 | 0.22 | 77.98 |
| UUGGGCAGAUGGAGGGCCUU | 350 | AAGGCCCTCCATCTGCCCAA | 586 | 0.81 | 19.08 | 0.22 | 78.39 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| CCUCUGCCUC GCGUAGUUGA | 351 | TCAACTACGC GAGGCAGAGG | 587 | 0.93 | 7.39 | 0.15 | 85.33 |
| ACAGAACAAC GGCGAACAGG | 352 | CCTGTTCGCCG TTGTTCTGT | 588 | 0.98 | 2.07 | 0.44 | 55.96 |
| CAGGAUGUUG UCGGGUUUGA | 353 | TCAAACCCGA CAACATCCTG | 589 | 0.83 | 17.17 | 0.21 | 79.31 |
| CGGCCUCAGC CUCUGCCGCA | 354 | TGCGGCAGAG GCTGAGGCCG | 590 | 0.93 | 6.71 | 0.40 | 60.06 |
| CAGCAGGAUG UUGUCGGGUU | 355 | AACCCGACAA CATCCTGCTG | 591 | 0.66 | 34.18 | 0.15 | 84.54 |
| GCAGAGAGAG GUGCUCCUUG | 356 | CAAGGAGCAC CTCTCTCTGC | 592 | 0.83 | 17.29 | 0.14 | 85.95 |
| UCCAGUUCCA UGGGUGUGGG | 357 | CCCACACCCA TGGAACTGGA | 593 | 0.84 | 15.66 | 0.22 | 78.48 |
| CCUCAGCCUG GCCGAAAGAA | 358 | TTCTTTCGGCC AGGCTGAGG | 594 | 0.83 | 16.83 | 0.36 | 63.99 |
| GGGCCUUUUA UUCGCGAGGG | 359 | CCCTCGCGAA TAAAAGGCCC | 595 | 0.95 | 5.11 | 0.49 | 50.65 |
| GUCGGCCAGG CGGAUGUGGC | 360 | GCCACATCCG CCTGGCCGAC | 596 | 0.85 | 15.35 | 0.25 | 74.59 |
| GCUUGCUGCC UUCCCAGGCC | 361 | GGCCTGGGAA GGCAGCAAGC | 597 | 0.99 | 1.14 | 0.19 | 81.01 |
| GGUCCAGCAG GAUGUUGUCG | 362 | CGACAACATC CTGCTGGACC | 598 | 0.68 | 31.78 | 0.20 | 79.93 |
| CGGAGACCAU CCCAGUCGAG | 363 | CTCGACTGGG ATGGTCTCCG | 599 | 0.86 | 14.08 | 0.20 | 79.93 |
| UCUGCCUCGC GUAGUGACU | 364 | AGTCAACTAC GCGAGGCAGA | 600 | 0.96 | 3.53 | 0.13 | 86.86 |
| AGGUAGUUCU CAUCCUGGAA | 365 | TTCCAGGATG AGAACTACCT | 601 | 0.93 | 7.36 | 0.37 | 62.62 |
| UCCUUGUAGU GGACGAUCUU | 366 | AAGATCGTCC ACTACAAGGA | 602 | 0.87 | 12.96 | 0.15 | 84.87 |
| GCAUCCAAAA CGUGGAUUGG | 367 | CCAATCCACG TTTTGGATGC | 603 | 0.97 | 2.54 | 0.27 | 72.69 |
| GUCCAGCAGG AUGUGUCGG | 368 | CCGACAACAT CCTGCTGGAC | 604 | 0.70 | 30.00 | 0.17 | 82.64 |
| AGCUCCCGCA GCGUCACCUC | 369 | GAGGTGACGC TGCGGGAGCT | 605 | 0.86 | 13.72 | 0.20 | 80.40 |
| CGAGAGCAGC GCAAGUGAGG | 370 | CCTCACTTGCG CTGCTCTCG | 606 | 1.02 | -2.19 | 0.63 | 37.11 |
| CAGGGAAAGC GCCUCCGAUA | 371 | TATCGGAGGC GCTTTCCCTG | 607 | 0.89 | 11.10 | 0.08 | 91.59 |
| AUUUCAUAGG CGAAUACACC | 372 | GGTGTATTCG CCTATGAAAT | 608 | 1.05 | -4.54 | 0.56 | 44.15 |
| UCGGCCAGGC GGAUGUGGCC | 373 | GGCCACATCC GCCTGGCCGA | 609 | 0.73 | 26.53 | 0.17 | 83.04 |

TABLE 8-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| AAGGGAUGUG UCCGGAAGUC | 374 | GACTTCCGGA CACATCCCTT | 610 | 0.90 | 10.37 | 0.26 | 73.52 |
| CUUGUAGUGG ACGAUCUUGC | 375 | GCAAGATCGT CCACTACAAG | 611 | 0.76 | 24.09 | 0.11 | 89.16 |
| AGUCGGCCAG GCGGAUGUGG | 376 | CCACATCCGC CTGGCCGACT | 612 | 0.94 | 6.15 | 0.33 | 67.44 |
| GCCUCAGCCU GGCCGAAAGA | 377 | TCTTTCGGCCA GGCTGAGGC | 613 | 1.05 | -4.82 | 0.37 | 63.11 |
| AGCGUCACCU CGGCCUCAGC | 378 | GCTGAGGCCG AGGTGACGCT | 614 | 0.78 | 22.10 | 0.35 | 64.70 |
| CAGCGGCAGA GAGAGGUGCT | 379 | AGCACCTCTCT CTGCCGCTG | 615 | 0.96 | 4.49 | 0.14 | 86.00 |
| CCAGCGGCAG AGAGAGGUGC | 380 | GCACCTCTCTC TGCCGCTGG | 616 | 0.97 | 3.23 | 0.15 | 84.55 |
| UUGUAGUGGA CGAUCUUGCC | 381 | GGCAAGATCG TCCACTACAA | 617 | 0.83 | 17.22 | 0.19 | 81.05 |
| AGGGAAAGCG CCUCCGAUAG | 382 | CTATCGGAGG CGCTTTCCCT | 618 | 1.01 | -1.12 | 0.25 | 75.50 |
| GGGAAAGCGC CUCCGAUAGG | 383 | CCTATCGGAG GCGCTTTCCC | 619 | 0.90 | 10.02 | 0.23 | 76.79 |

Example 8: Selected Antisense Oligonucleotides Provided Dose-Dependent Reduction in DMPK Expression in Immortalized Myoblasts Eighteen oligonucleotides from Example 7 were selected to be evaluated for their ability to reduce DMPK expression in a dose-responsive manner. DM1 C15 myoblasts were prepared as in Example 7 to yield differentiated myotubes in 96-well microplates. After seven days of differentiation, cells were transfected with individual oligonucleotides using Lipofectamine MessengerMax. Each oligonucleotide was tested in triplicate at concentrations of 0.046 nM, 0.137 nM, 0.412 nM, 1.235 nM, 3.704 nM, 11.11 nM, 33.33 nM, and 100 nM by 3-fold serial dilutions using 0.3 µL of Lipofectamine MessengerMax per well.

Following addition of oligonucleotide, cells were incubated for 72 hours prior to harvesting for total RNA. cDNA was synthesized from the total RNA extracts and qPCR was performed to determine expression levels of DMPK using a commercially available Taqman probeset in technical quadruplicate. All qPCR data were analyzed using a traditional ΔΔCT method and were normalized to a plate-based negative control that comprised of cells treated with vehicle control (0.3 µL/well Lipofectamine MessengerMax without any oligonucleotide). Data for each oligonucleotide to was fit to sigmoidal curve in order to determine an effective concentration of each oligonucleotide that provided a half-maximal response (EC-50). Results from these experiments are shown in Table 9.

Each of the eighteen antisense oligonucleotides selected for dose-dependent experimentation were capable of dose-dependently reducing DMPK in differentiated myotubes. Further, each of the tested antisense oligonucleotides reduced DMPK with EC-50 values below 25 nM. For example, antisense oligonucleotides comprising SEQ ID NOs: 264, 215, 222, 190, and 212 resulted in EC-50 values of 3.27 nM, 3.59 nM, 5.45 nM, 6.04 nM, and 24.59 nM, respectively. These data demonstrate that the antisense oligonucleotides shown in Table 9 are capable of dose-dependent reduction of DMPK in cellulo, suggesting that muscle-targeting complexes comprising these antisense oligonucleotides would be capable of targeting DMPK in muscle tissues in vivo.

TABLE 9

Ability of DMPK-targeting antisense oligonucleotides to reduce expression of DMPK in dose-dependent manner in cellulo

| Antisense Oligonucleotide Sequence | SEQ ID NO: | DMPK Target Sequence | SEQ ID NO: | Results EC-50 (nM) | Percent DMPK reduction at 100 nM |
|---|---|---|---|---|---|
| GCAGGAUGUUGUCGGGUUUG | 201 | CAAACCCGACAACATCCTGC | 437 | 0.1679 | 89.77 |
| AGCAGGAUGUUGUCGGGUUU | 218 | AAACCCGACAACATCCTGCT | 454 | 0.2266 | 85.81 |
| GCGUAGAAGGGCGUCUGCCC | 212 | GGGCAGACGCCCTTCTACGC | 448 | 24.59 | 95.13 |
| CCCAGCGCCCACCAGUCACA | 222 | TGTGACTGGTGGGCGCTGGG | 458 | 5.454 | 63.69 |
| CCAUCUCGGCCGGAAUCCGC | 180 | GCGGATTCCGGCCGAGATGG | 416 | 0.44 | 95.42 |
| CGUUCCAUCUGCCCGCAGCU | 196 | AGCTGCGGGCAGATGGAACG | 432 | 0.19 | 89.97 |
| CAGGGACAGCCGCUGGAACU | 190 | AGTTCCAGCGGCTGTCCCTG | 426 | 6.04 | 90.59 |
| CAUGGCAUACACCUGGCCCG | 159 | CGGGCCAGGTGTATGCCATG | 395 | 0.42 | 75.28 |
| GCUUCAUCUUCACUACCGCU | 188 | AGCGGTAGTGAAGATGAAGC | 424 | 0.03 | 64.06 |
| GAAUGUCCGACAGUGUCUCC | 195 | GGAGACACTGTCGGACATTC | 431 | 0.07 | 97.23 |
| GGACGAUCUUGCCAUAGGUC | 215 | GACCTATGGCAAGATCGTCC | 451 | 3.59 | 92.18 |
| GCUGUCCCGGAGACCAUCCC | 264 | GGGATGGTCTCCGGGACAGC | 500 | 3.27 | 93.07 |
| GACAGAACAACGGCGAACAG | 248 | CTGTTCGCCGTTGTTCTGTC | 484 | 0.08 | 94.32 |
| UGUUGUCGGGUUUGAUGUCC | 203 | GGACATCAAACCCGACAACA | 439 | 0.21 | 93.95 |
| CGAAUGUCCGACAGUGUCUC | 162 | GAGACACTGTCGGACATTCG | 398 | 0.18 | 95.93 |
| GGGCCUGGGACCUCACUGUC | 172 | GACAGTGAGGTCCCAGGCCC | 408 | 0.07 | 90.58 |
| CUCUGCCGCAGGGACAGCCG | 174 | CGGCTGTCCCTGCGGCAGAG | 410 | 0.42 | 93.66 |
| UUGCCAUAGGUCUCCGCCGU | 182 | ACGGCGGAGACCTATGGCAA | 418 | 0.37 | 93.70 |

Figure 13A:
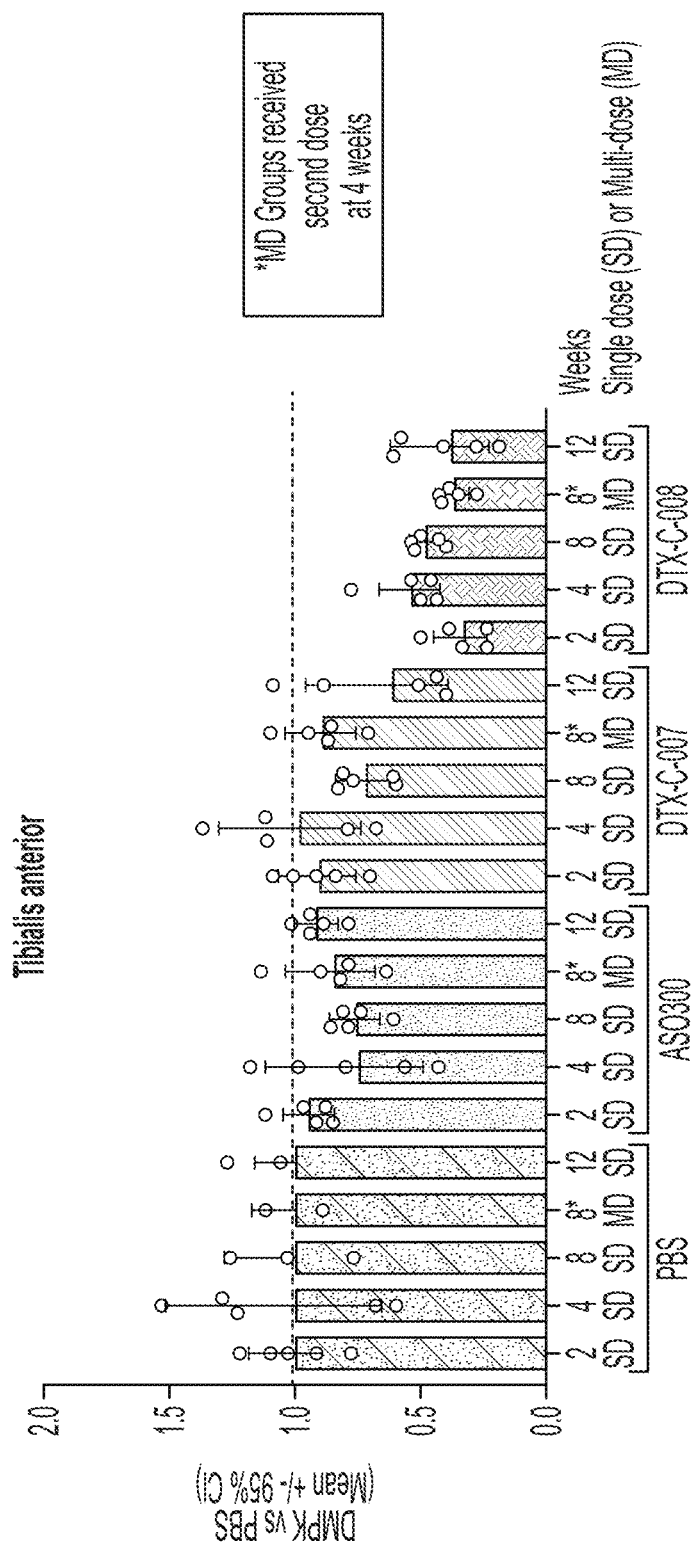
FIGS. 13A-13B depict non-limiting schematics showing the ability of a muscle targeting RI7 217 Fab antibody-oligonucleotide complex (DTX-C-008) comprising ASO300 to reduce expression levels of DMPK in mouse muscle tissues in vivo for up to twelve weeks after dosing with DTX-C-008, relative to a vehicle treatment (PBS); and compared to a control IgG2a Fab antibody-oligonucleotide complex (DTX-C-007) and naked DMPK ASO (ASO300). (N=5 C57Bl/6 WT mice)
Figure 13B:
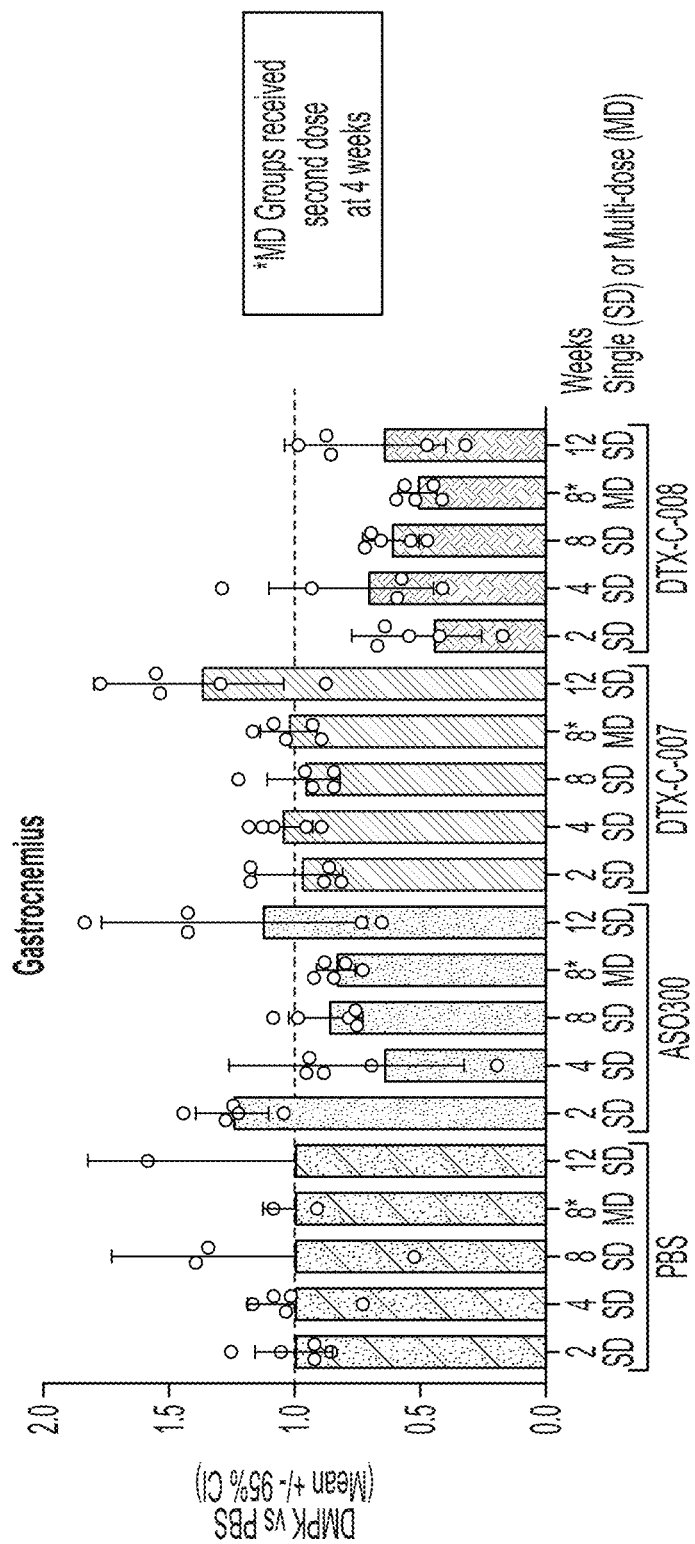

Example 9: Targeting DMPK in Mouse Muscle Tissues with a Muscle-Targeting Complex The RI7 217 Fab antibody-ASO muscle-targeting complex described in Example 2, DTX-C-008, was tested for time-dependent inhibition of DMPK in mouse tissues in vivo. C57BL/6 wild-type mice were intravenously injected with a single dose of a vehicle control (phosphate-buffered saline (PBS)), naked antisense oligonucleotide (ASO300) (10 mg/kg of ASO), DTX-C-007 IgG2a Fab antibody-ASO control complex (10 mg/kg of ASO), or DTX-C-008 (10 mg/kg of ASO) on Day 0 and euthanized after a prescribed period of time, as described in Table 10. One group of mice in each experimental condition was subjected to a second dose (multi-dose groups) at four weeks (Day 28). Following euthanization, the mice were segmented into isolated tissue types and samples of tibialis anterior and gastrocnemius muscle tissues were subsequently assayed for expression levels of DMPK (FIGS. 13A-13B).

TABLE 10

Experimental conditions

| Group | Dosage | Weeks after injection before euthanization | Number of mice |
|---|---|---|---|
| 1 | Single dose of vehicle (PBS) | 2 | 5 |
| 2 | Single dose of vehicle (PBS) | 4 | 5 |
| 3 | Single dose of vehicle (PBS) | 8 | 3 |
| 4 | Multi-dose of vehicle (PBS) | 8 | 2 |
| 5 | Single dose of vehicle (PBS) | 12 | 5 |
| 6 | Single dose of ASO300 | 2 | 5 |
| 7 | Single dose of ASO300 | 4 | 5 |
| 8 | Single dose of ASO300 | 8 | 5 |
| 9 | Multi-dose of ASO300 | 8 | 5 |
| 10 | Single dose of ASO300 | 12 | 5 |
| 11 | Single dose of DTX-C-007 control | 2 | 5 |
| 12 | Single dose of DTX-C-007 control | 4 | 5 |
| 13 | Single dose of DTX-C-007 control | 8 | 5 |
| 14 | Multi-dose of DTX-C-007 control | 8 | 5 |
| 15 | Single dose of DTX-C-007 control | 12 | 5 |
| 16 | Single dose of DTX-C-008 | 2 | 5 |
| 17 | Single dose of DTX-C-008 | 4 | 5 |
| 18 | Single dose of DTX-C-008 | 8 | 5 |
| 19 | Multi-dose of DTX-C-008 | 8 | 5 |
| 20 | Single dose of DTX-C-008 | 12 | 5 |

Mice treated with the RI7 217 Fab antibody-ASO DTX-C-008 complex demonstrated about 50-60% reduction in DMPK expression in tibialis anterior muscle (FIG. 13A) and about 30-50% reduction in DMPK expression in gastrocnemius muscle (FIG. 13B) for all of Groups 16-20 (2-12 weeks between injection and euthanization), relative to vehicle. These data show that a single dose of the muscle-targeting complex DTX-C-008 reduces expression of DMPK for at least twelve weeks following administration of the complex.

In contrast, mice treated with the naked antisense oligonucleotide or the control complex did not demonstrate significant inhibition of DMPK expression across all experimental groups and tissues.

These data demonstrate that a muscle-targeting complex as described herein is capable of providing persistent inhibition of DMPK expression in vivo for up to 12 weeks following a single dose or administration of said muscle targeting complex.

Figure 14A:
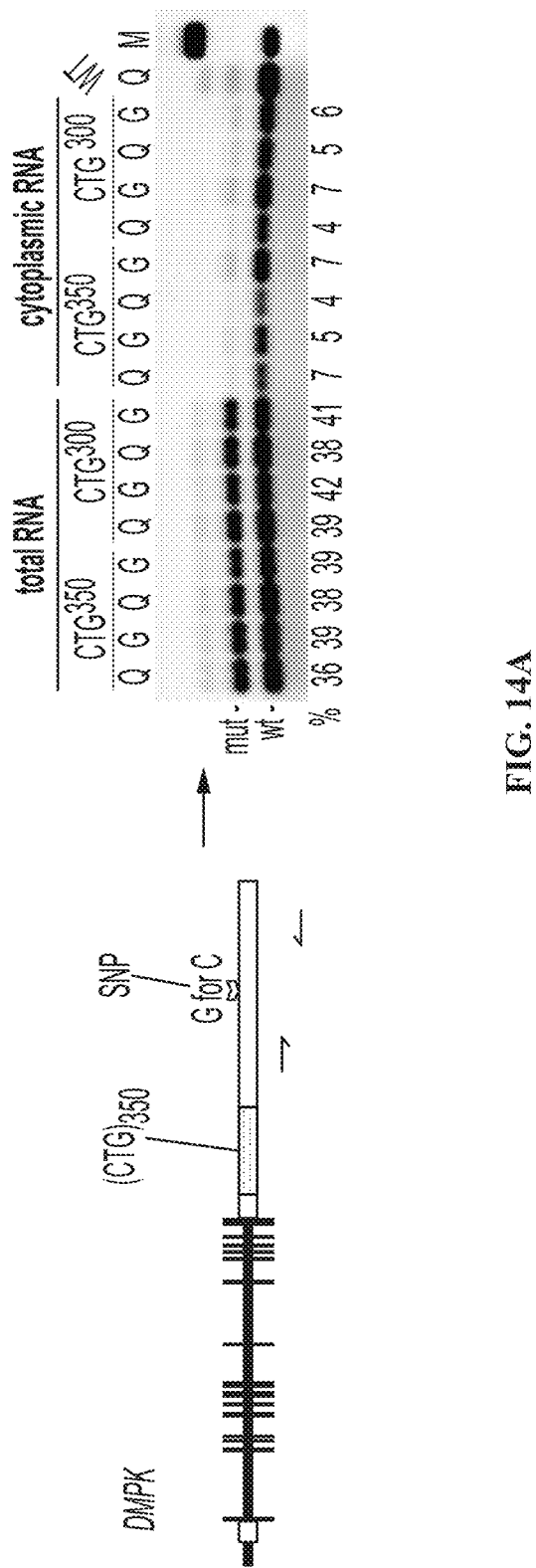
FIGS. 14A-14B depict non-limiting schematics showing the ability of a muscle-targeting RI7 217 Fab antibody-oligonucleotide complex (DTX-C-008) comprising ASO300 to target nuclear mutant DMPK RNA in a mouse model. (N=6 mice)

Example 10: A Muscle-Targeting Complex can Target Gene Expression in the Nucleus The RI7 217 Fab antibody-ASO muscle-targeting complex as described in Example 2, DTX-C-008, was tested for inhibition of nuclear-retained DMPK RNA in mouse muscle tissues. The mice used for this Example have been engineered to express a human mutant DMPK gene (schematic shown in FIG. 14A)—DMPK with a 350 CTG repeat region and a downstream G-for-C single-nucleotide polymorphism. As shown in FIG. 14A, the human mutant DMPK RNA is retained in the nucleus, while the mouse wild-type DMPK RNA is located in the cytoplasm and the nucleus.

Figure 14B:
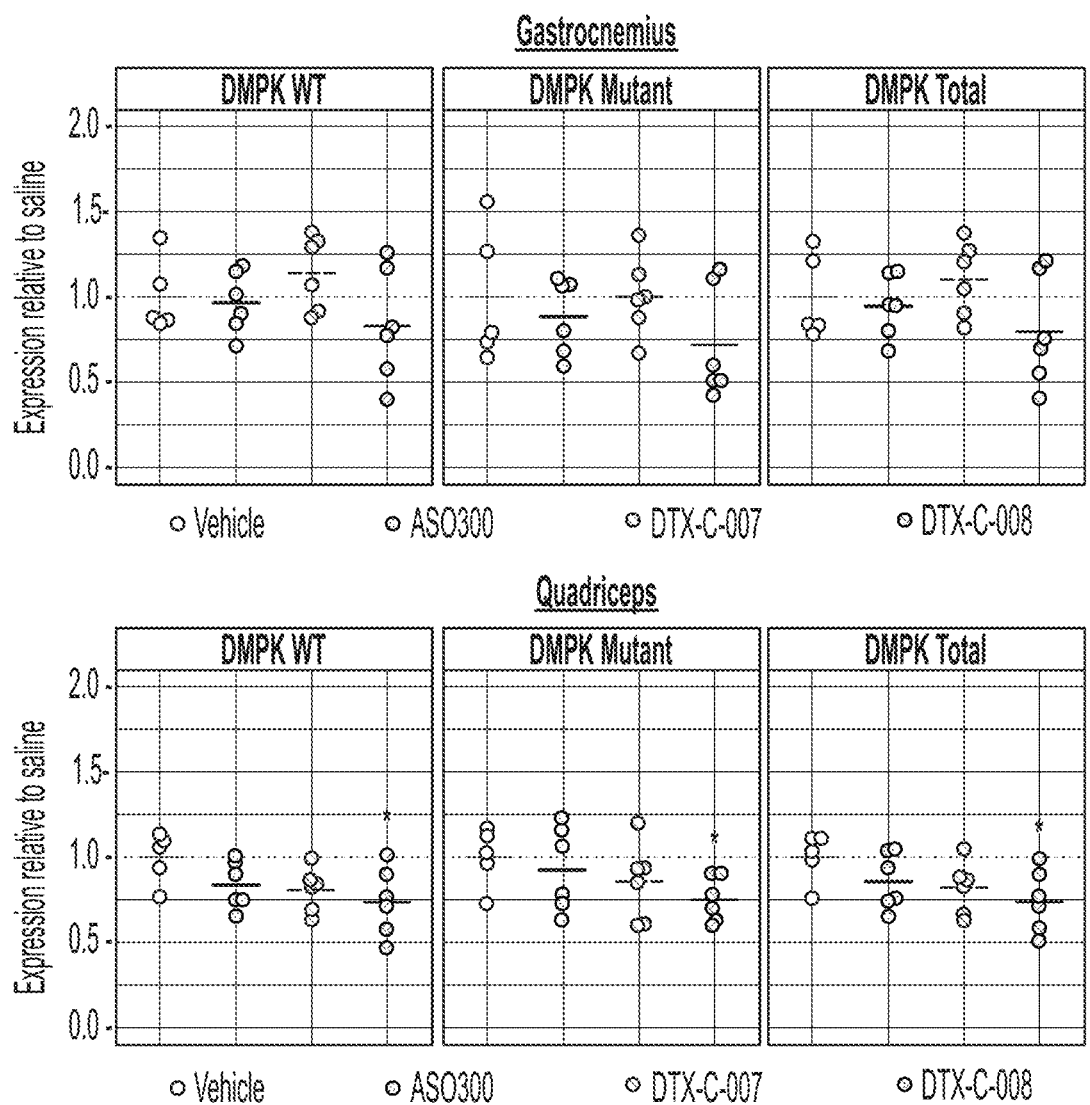

Mice were intravenously injected with a single dose of a vehicle control (saline), an IgG2a Fab-ASO control complex DTX-C-007 (10 mg/kg of ASO), naked ASO300 (10 mg/kg of ASO), or DTX-C-008 (10 mg/kg of ASO) and euthanized after 14 days. Six mice were treated in each experimental condition. Following euthanization, the mice were segmented into isolated tissue types and tissue samples were subsequently assayed for expression levels of mutant and wild-type DMPK (FIG. 14B).

Mice treated with the muscle-targeting RI7 217 Fab antibody-ASO complex DTX-C-008 demonstrated statistically significant reduction in both nuclear-retained mutant DMPK and wild-type DMPK. (p-value <0.05). These data demonstrate that a muscle-targeting complex as described herein is capable of targeting DMPK in the nucleus.

Example 11: A Muscle-Targeting Complex Reverses Myotonia in HSA$^{LR}$ Mouse Model A muscle-targeting complex (DTX-Actin) was generated comprising an antisense oligonucleotide (ASO) that targets actin covalently linked to DTX-A-002 (RI7 217 Fab), an anti-transferrin receptor antibody.

The actin-targeting ASO is an MOE 5-10-5 gapmer that comprises: 5'-NH$_2$—(CH$_2$)$_6$-dA*oC*oC*oA*oT*oT*dT*dT*dC*dT*dT*dC*dC*dA*dC*dA*oG*oG*oG*oC*oT-3' (SEQ ID NO: 620); wherein '*' represents a PS linkage; 'd' represents a deoxynucleic acid; and 'o' represents a 2'-MOE.

Figure 15A:
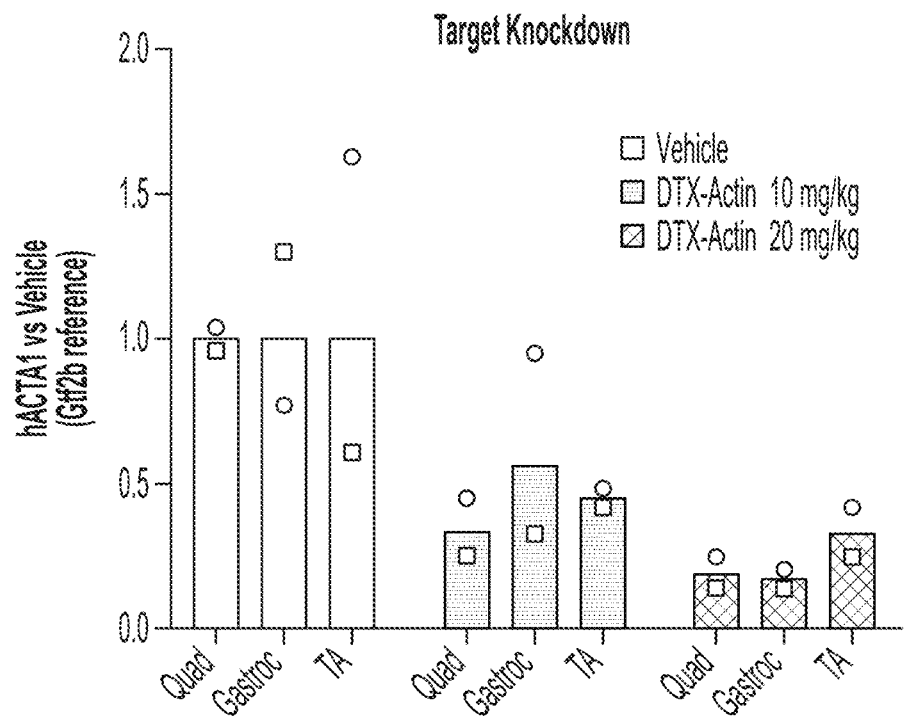
FIGS. 15A-15B depict non-limiting schematics showing the ability of a muscle-targeting RI7 217 Fab antibody-ASO complex (DTX-Actin) comprising an oligonucleotide that targets actin to dose-dependently reduce expression levels of actin and functional grades of myotonia in muscle tissues. (N=2 $HSA^{LR}$ mice)

DTX-Actin was then tested for its ability to reduce target gene expression (hACTA1) and reduce myotonia in HSA$^{LR}$ mice, a mouse model that has a functional myotonia phenotype similar to that observed in human DM1 patients. Details of the HSA$^{LR}$ mouse model are as described in Mankodi, A. et al. Science. 289: 1769, 2000. HSA$^{LR}$ mice were intravenously injected with a single dose of PBS or DTX-Actin (either 10 mg/kg or 20 mg/kg ASO equivalent). Each of these three experimental conditions were replicated in two individual mice. On Day 14 after injection, mice were euthanized and specific muscles were collected—quadriceps (quad), gastrocnemius (gastroc) and tibialis anterior (TA). The muscle tissues were analyzed for expression of hACTA1. DTX-Actin demonstrated reduction of hACTA1 expression in all three muscle tissues relative to vehicle control (FIG. 15A).

Figure 15B:
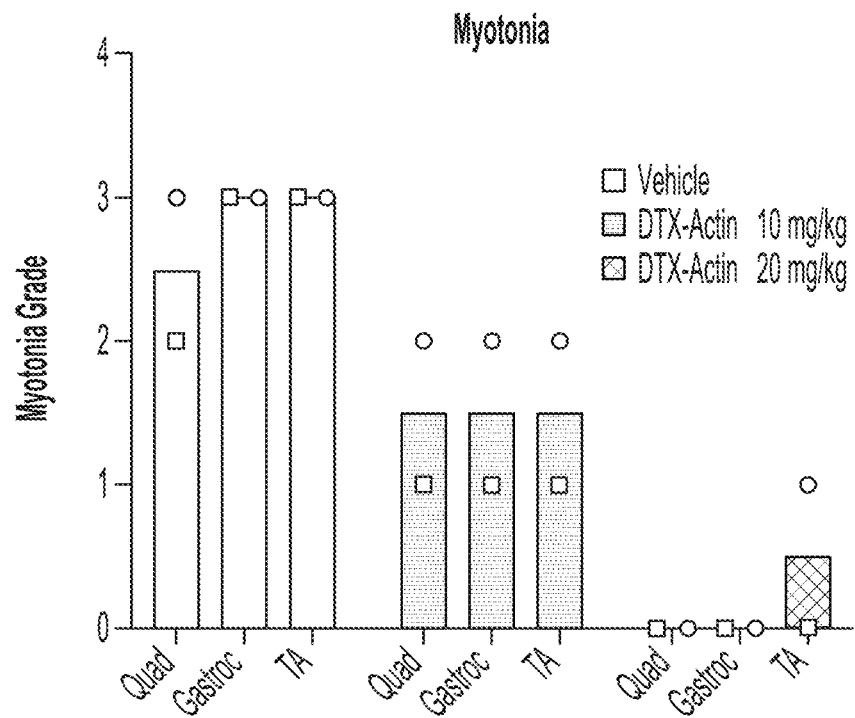

On Day 14 after injection, and prior to the euthanasia and tissue collection described above, electromyography (EMG) was performed on specific muscles. EMG myotonic discharges were graded by a blinded examiner on a 4-point scale: 0, no myotonia; 1, occasional myotonic discharge in less than 50% of needle insertions; 2, myotonic discharge in greater than 50% of needle insertions; and 3: myotonic discharge with nearly every insertion. DTX-Actin demonstrated reduction in graded myotonia in all three muscle tissues relative to vehicle control (FIG. 15B). Mice treated with DTX-Actin at a dose of 20 mg/kg ASO equivalent demonstrated little-to-no myotonia in quadriceps and gastrocnemius muscles.

These data demonstrate that a single dose of a muscle-targeting complex is capable of gene-specific targeting and reduction in functional myotonia in in the HSA$^{LR}$ mice, a mouse model that has a functional myotonia phenotype similar to that observed in human DM1 patients.

Figure 16A:
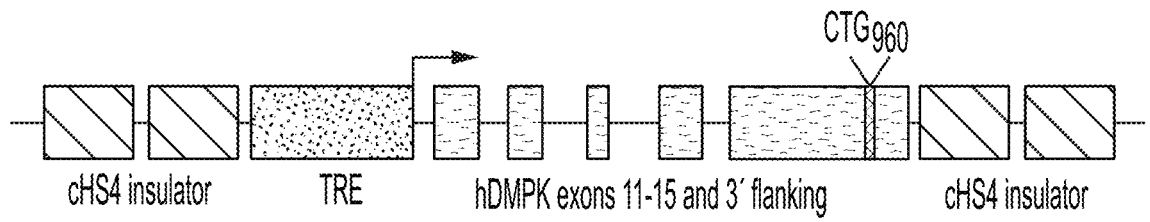
FIGS. 16A-16C depict non-limiting schematics showing that a muscle-targeting RI7 217 Fab antibody-oligonucleotide complex (DTX-C-008) comprising ASO300 is capable of significantly reducing the prolonged QTc interval in a mouse model for validation of the functional correction of arrhythmia in a DM1 cardiac model. (N=10 mice)

Example 12: A Muscle-Targeting Complex can Functionally Correct Arrhythmia in a DM1 Mouse Model The RI7 217 Fab antibody-ASO muscle-targeting complex as described in Example 2, DTX-C-008, was tested for its ability to functionally correct arrythmia in a DM1 mouse model. The mice used for this Example are the offspring of mice expressing myosin heavy chain reverse tet transactivator (MHCrtTA) and mice expressing a mutant form of human DMPK (CUG$_{960}$). FIG. 16A shows the genomic structure of the mutant transgene.

Doxycycline containing chow (2 g doxycycline/kg chow, Bio-Serv) was provided to the mice beginning at postnatal day 1, initially through the nursing dam and subsequently through chow after weaning, to induce selective expression of mutant DM PK in the heart. All mice were maintained on chow containing doxycycline throughout the entire course of the study except the "off Dox Control" group. At 12 weeks of age, all mice underwent a baseline pre-dose ECG evaluation. Mice were then treated intravenously with a single dose of either vehicle (saline), naked ASO300 (10 mg/kg), DTX-C-008 (10 mg/kg ASO equivalent) or DTX-C-008 (20 mg/kg ASO equivalent). Following baseline pre-dose ECG evaluation in the "off Dox Control" group were switched to chow without doxycycline. Post dose ECG evaluations were performed in all mice 7 and 14 days after treatment, or in the case of the "off Dox Control" group 7 and 14 days after reversion to chow without doxycycline. For each of the ECG spectra, QRS and QTc intervals were measured.

Figure 16B:
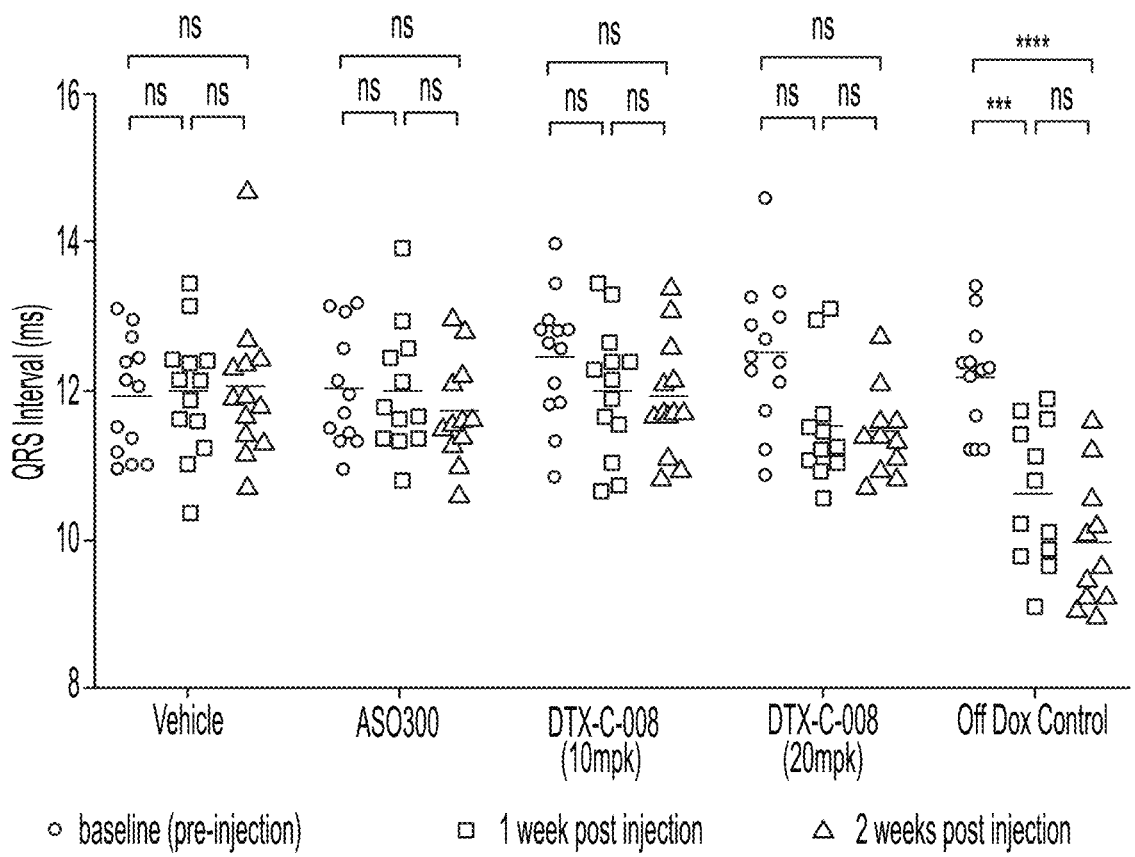
Figure 16C:
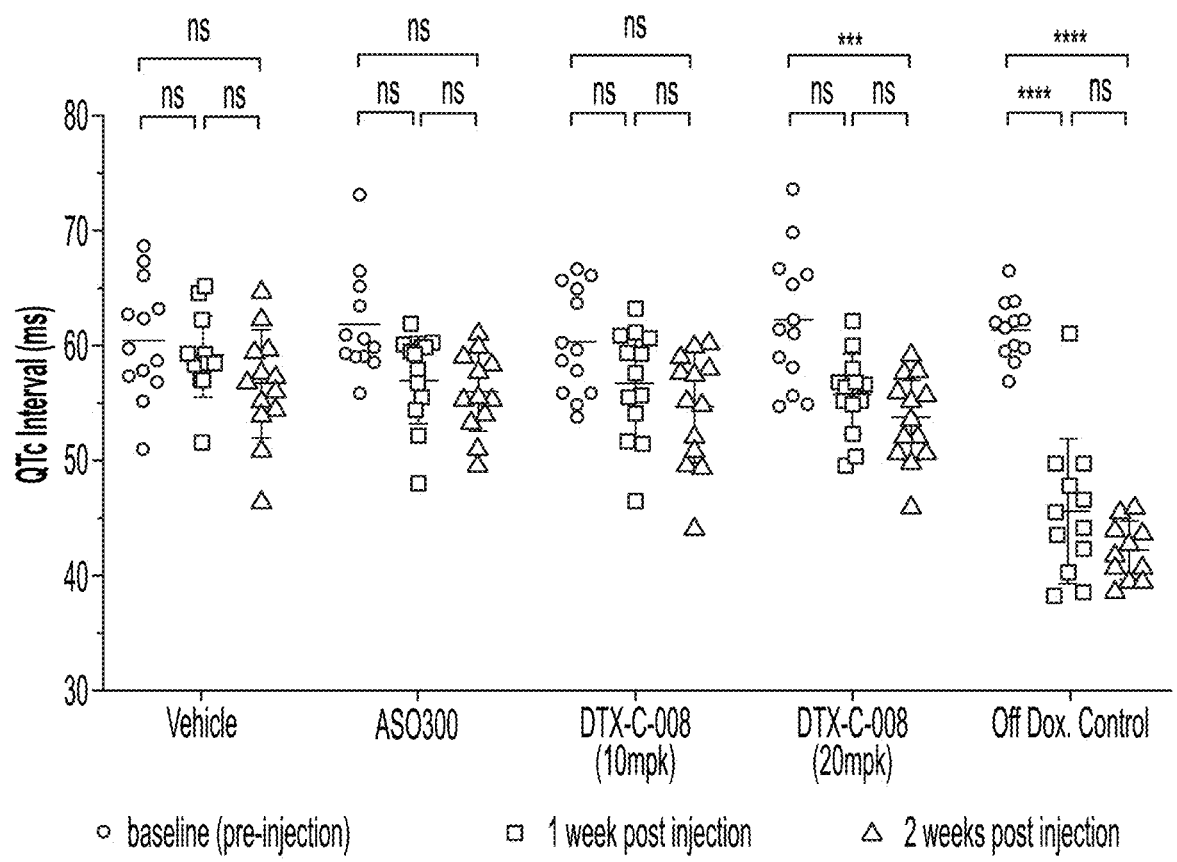

In this model, mice treated with doxycycline exhibit prolongation of QRS and QTC intervals driven by expression of mutant DMPK in the heart, similar to those reported in DM1 patients, and consistent with increased propensity for cardiac arrythmia. Removal of doxycycline for the diet in the "Off Dox Control" group turns off expression of mutant DMPK, resulting in a normalization of QRS (FIG. 16B) and QTC (FIG. 16C) intervals. Mice maintained on doxycycline and treated with 20 mg/kg of the muscle-targeting complex DTX-C-008 demonstrated statistically significant reduction in their QTc intervals after 14 days despite continued expression of mutant DMPK in the heart (FIG. 16C). This reduction in QTc intervals represents a correction in cardiac arrythmia in a DM1 mouse model. These data demonstrate that a muscle-targeting complex as described herein is capable of providing a phenotypic and therapeutic benefit in a DM1 model.

Example 13: A Muscle-Targeting Complex can Target DMPK and Correct DM1-Related Genetic Splicing In isolated muscles cells derived from human DM1 patients, the muscle-targeting complex as described in Example 5, DTX-C-012, was tested for reduction of DMPK expression and subsequent correction of splicing defects in Bin1, a downstream gene of DMPK.

Briefly, patient cells were seeded at a density of 10 k cells/well before being allowed to recover overnight. Cells were then treated with PBS (vehicle control), naked ASO300, or DTX-C-012 (500 nM; equivalent to 55.5 nM ASO). Cells were allowed to differentiate for 14 days. Expression levels of DMPK and % Bin1 exon-11 inclusion were determined on Days 10, 11, 12, 13, and 14 post differentiation.

Figure 17A:
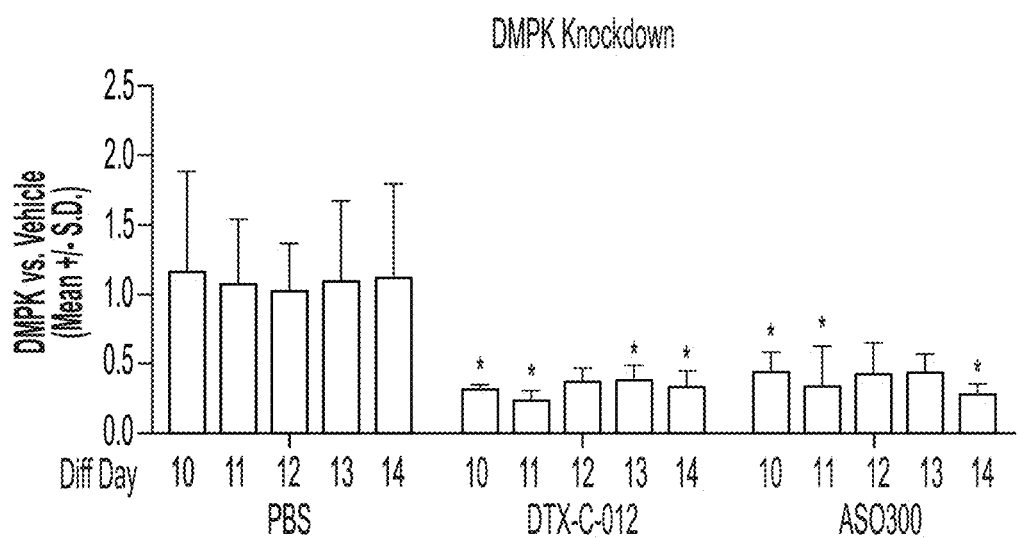
FIGS. 17A-17B depict non-limiting schematics showing that a muscle-targeting antibody-oligonucleotide complex (DTX-C-012) comprising ASO300 antisense oligonucleotide covalently linked to an anti-hTFR antibody is capable of reducing expression levels of DMPK and correcting splicing of a DMPK-specific target gene (Bin1) in human cells from a DM1 patient. (N=3)
Figure 17B:
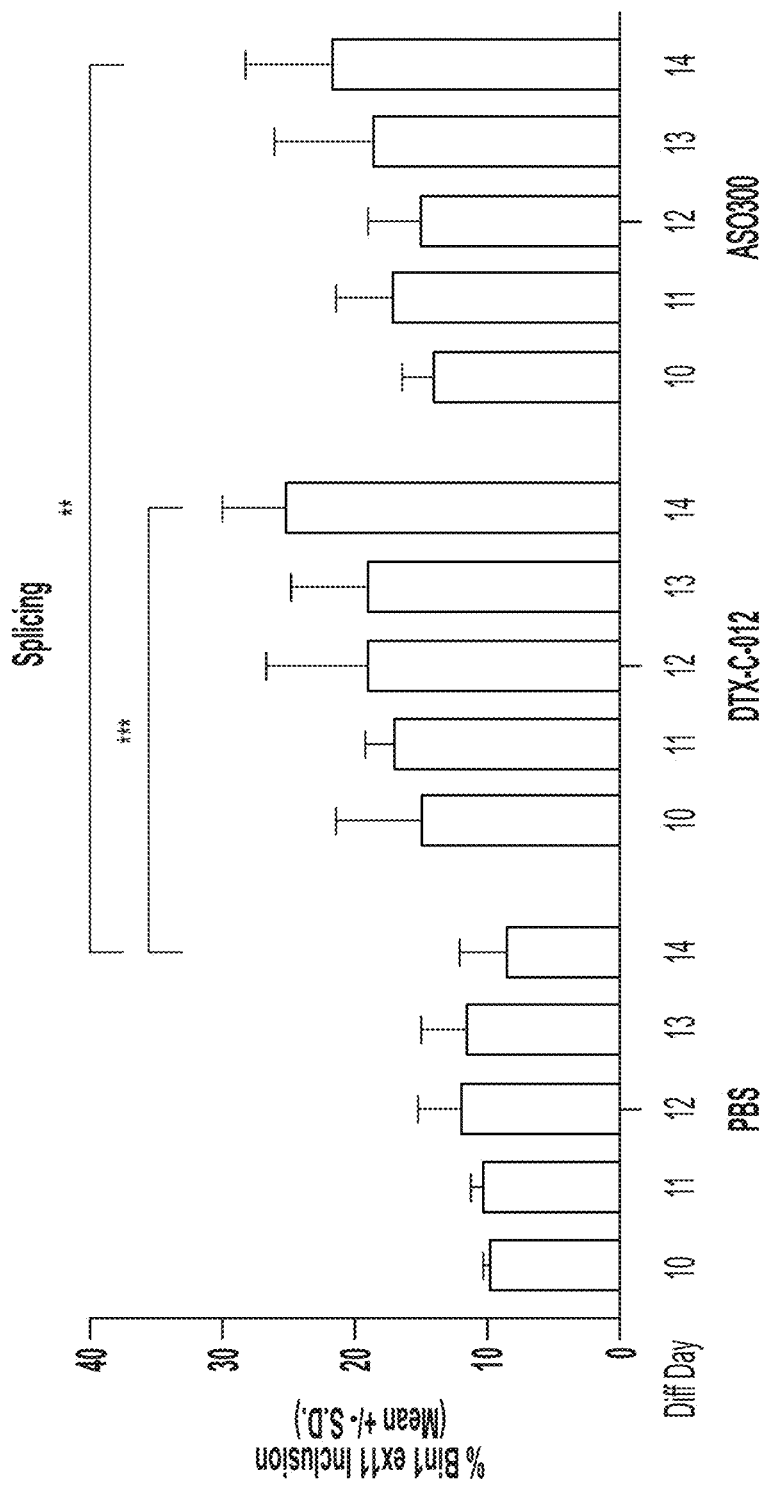
Figure 18A:
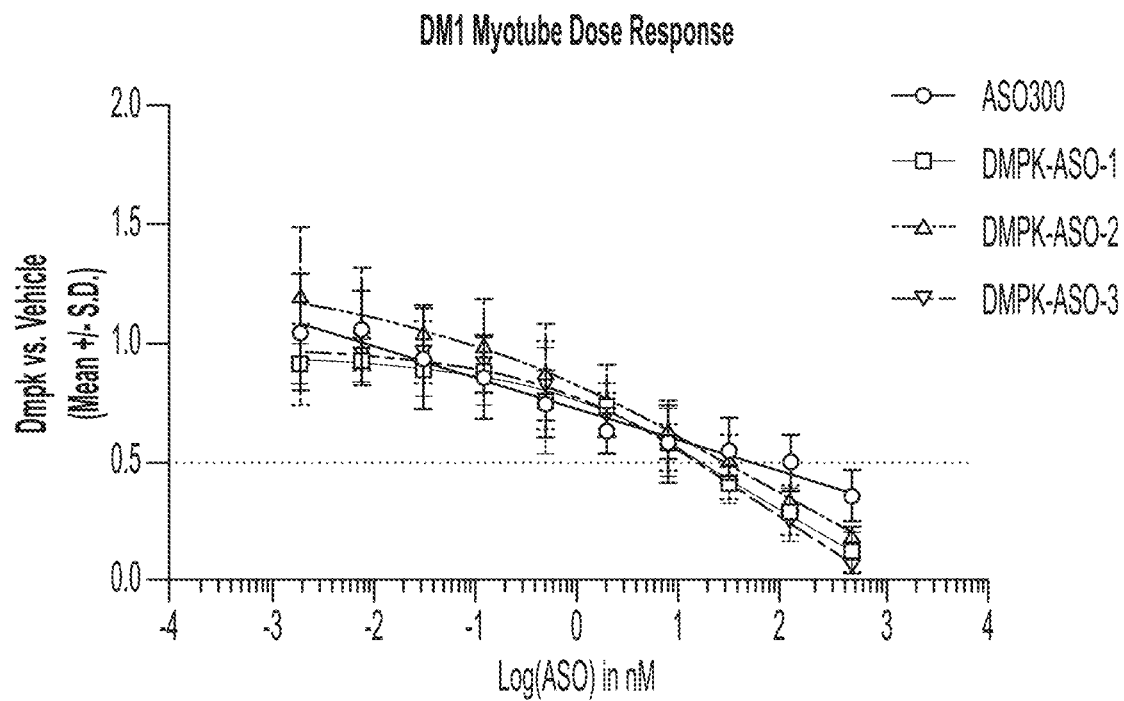
FIGS. 18A-18C depict non-limiting schematics showing the dose response of selected antisense oligonucleotides in DMPK knockdown in human DM1 myotubes. ASO300 was used as control. All tested oligonucleotides showed activity in DMPK knockdown. Statistical analysis: One-way ANOVA with Tukey's HSD post-hoc test vs. naked ASO300 treatment; *p<0.05, p<0.01, *p<0.001, ****p<0.0001.
Figure 18B:
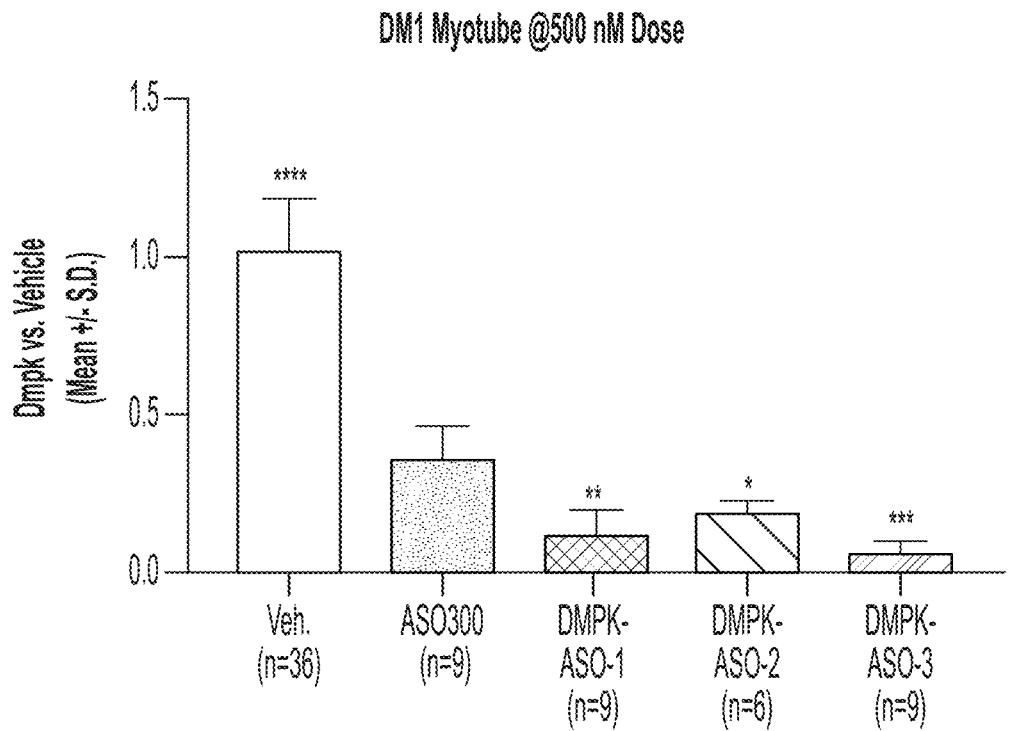
Figures 18C, 19A, 19B:
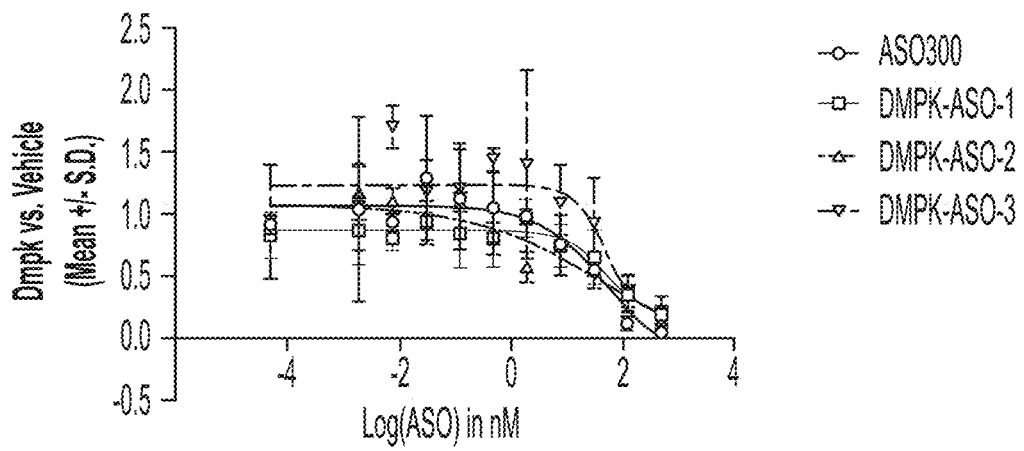
FIGS. 19A-19B depict non-limiting schematics showing the dose response of selected antisense oligonucleotides in DMPK knockdown in non-human primate (NHP) DM1 myotubes. ASO300 was used as control. All tested oligonucleotides showed activity in DMPK knockdown.

Treatment of DM1 patient cells with the DTX-C-012 complex leads to reduction of DMPK levels as early as Day 10 post differentiation (FIG. 17A). Treatment of DM1 patient cells with the DTX-C-012 complex also leads to a statistically significant time-dependent change in Bin1 splicing (FIG. 17B). ($p<0.01$, *$p<0.001$). These data demonstrate that a muscle-targeting complex as described herein is capable of providing phenotypic and therapeutic benefit (increased correction of DM1 gene-specific splicing) in a DM1 model.

Example 14: Selected Antisense Oligonucleotides Provided Dose-Dependent Reduction in DMPK Expression in DM1 and NHP Myotubes The antisense oligonucleotides listed in Table 9 were further assessed to identify oligos that are safe in vivo (e.g., as indicated by low immunogenicity as measured by cytokine induction), and further based on manufacturability and secondary structure considerations. Three antisense oligonucleotides from Table 9, (SEQ ID NO: 212, DMPK-ASO-1), (SEQ ID NO: 222, DMPK-ASO-2), and (SEQ ID NO: 180, DMPK-ASO-3) were selected. These oligonucleotides were then further evaluated for their ability to reduce DMPK expression in DM1 myotubes and NHP myotubes in a dose-responsive manner. Naked ASO300 was used as control. Each of the antisense oligonucleotides were capable of dose-dependently reducing DMPK in DM1 and NHP myotubes (see FIGS. 18A-18C and FIGS. 19A-19B, respectively).

These data demonstrate that these antisense oligonucleotides are safe in vivo and are capable of dose-dependent reduction of DMPK in cellulo, suggesting that muscle-targeting complexes comprising these antisense oligonucleotides would be capable of targeting DMPK in muscle tissues in vivo.

Example 15: Binding Affinity of Selected Anti-TfR1 Antibodies to Human TfR1

Selected anti-TfR1 antibodies were tested for their binding affinity to human TfR1 for measurement of Ka (association rate constant), Kd (dissociation rate constant), and $K_D$(affinity). Two known anti-TfR1 antibodies were used as control, 15G11 and OKT9. The binding experiment was performed on Carterra LSA at 25° C. An anti-mouse IgG and anti-human IgG antibody "lawn" was prepared on a HC30M chip by amine coupling. 59 IgGs (58 mouse mAbs and 1 human mAb) were captured on the chip. Dilution series of hTfR1, cyTfR1, and hTfR2 were injected to the chip for binding (starting from 1000 nM, 1:3 dilution, 8 concentrations).

Binding data were referenced by subtracting the responses from a buffer analyte injection and globally fitting to a 1:1 Langmuir binding model for estimate of Ka (association rate constant), Kd (dissociation rate constant), and $K_D$ (affinity) using the Carterra™ Kinetics software. 5-6 concentrations were used for curve fitting.

The result showed that the mouse mAbs demonstrated binding to hTfR1 with $K_D$ values ranging from 13 pM to 50 nM. A majority of the mouse mAbs had $K_D$ values in the single digit nanomolar to sub-nanomolar range. The tested mouse mAbs showed cross-reactive binding to cyTfR1 with $K_D$ values ranging from 16 pM to 22 nM.

Ka, Kd, and $K_D$ values of anti-TfR1 antibodies are provided in Table 11.

TABLE 11

Ka, Kd, and $K_D$ values of anti-TfR1 antibodies

| Name | $K_D$ (M) | Ka (M) | Kd (M) |
| --- | --- | --- | --- |
| ctrl-15G11 | 2.83E-10 | 3.70E+05 | 1.04E-04 |
| ctrl-OKT9 mIgG | 5.36E-10 | 7.74E+05 | 4.15E-04 |
| 3-A04 | 4.36E-10 | 4.47E+05 | 1.95E-04 |
| 3-M12 | 7.68E-10 | 1.66E+05 | 1.27E-04 |
| 5-H12 | 2.08E-07 | 6.67E+04 | 1.39E-02 |

Example 16: Conjugation of Anti-TfR1 Antibodies with Oligonucleotides

Complexes containing an anti-TfR1 antibody covalently conjugated to ASO300 were generated. First, Fab fragments of anti-TfR antibody clones 3-A4, 3-M12, and 5-H12 were prepared by cutting the mouse monoclonal antibodies with an enzyme in or below the hinge region of the full IgG followed by partial reduction. The Fabs were confirmed to be comparable to mAbs in avidity or affinity.

Muscle-targeting complexes was generated by covalently linking the anti-TfR mAbs to the ASO300 via a cathepsin cleavable linker. Briefly, a Bicyclo[6.1.0]nonyne-PEG3-L-valine-L-citrulline-pentafluorophenyl ester (BCN-PEG3-Val-Cit-PFP) linker molecule was coupled to ASO300 through a carbamate bond. Excess linker and organic solvents were removed by tangential flow filtration (TFF). The purified Val-Cit-linker-ASO was then coupled to an azide functionalized anti-transferrin receptor antibody generated through modifying F-amine on lysine with Azide-PEG4-PFP. A positive control muscle-targeting complex was also generated using 15G11.

The product of the antibody coupling reaction was then subjected to two purification methods to remove free antibody and free payload: 1) hydrophobic interaction chromatography (HIC-HPLC), and 2) Size exclusion chromatography (SEC). The HIC column utilized a decreasing salt gradient to separate free antibody from conjugate. During SEC, fractionation was performed based on A260/A280 traces to specifically collect conjugated material. Concentrations of the conjugates were determined by either Nanodrop A280 or BCA protein assay (for antibody) and Quant-It Ribogreen assay (for payload). Corresponding drug-antibody ratios (DARs) were calculated. DARs ranged between 0.8 and 2.0, and were standardized so that all samples receive equal amounts of payload.

The purified complexes were then tested for cellular internalization and inhibition of the target gene, DMPK. Non-human primate (NHP) or DM1 (donated by DM1 patients) cells were grown in 96-well plates and differentiated into myotubes for 7 days. Cells were then treated with escalating concentrations (0.5 nM, 5 nM, 50 nM) of each complex for 72 hours. Cells were harvested, RNA was isolated, and reverse transcription was performed to generate cDNA. qPCR was performed using TaqMan kits specific for Ppib (control) and DMPK on the QuantStudio 7. The relative amounts of remaining DMPK transcript in treated vs non-treated cells was were calculated and the results are shown in Table 12.

The results demonstrated that the anti-TfR1 antibodies are able to target muscle cells, be internalized by the muscle cells with the molecular payload (ASO300), and that the molecular payload is able to target and knockdown the target gene (DMPK).

payload (e.g., DMPK knockdown) in either cyno cells or human DM1 patient cells, compared to the control antibody 15G11, despite the comparable binding affinity (or, in certain instances, such as 5-H12, lower binding affinity) to human or cyno transferrin receptor between these antibodies and the control antibody 15G11.

Top attributes such as high huTfR1 affinity, >50% knockdown of DMPK in NHP and DM1 patient cell line, identified epitope binding with 3 unique sequences, low/no predicted PTM sites, and good expression and conjugation efficiency led to the selection of the top 3 clones for humanization, 3-A4, 3-M12, and 5-H12.

Example 17: Humanized Anti-TfR1 Antibodies

The anti-TfR antibodies shown in Table 2 were subjected to humanization and mutagenesis to reduce manufacturability liabilities. The humanized variants were screened and tested for their binding properties and biological actives. Humanized variants of anti-TfR1 heavy and light chain variable regions (5 variants each) were designed using Composite Human Technology. Genes encoding Fabs having these heavy and light chain variable regions were synthesized, and vectors were constructed to express each humanized heavy and light chain variant. Subsequently, each vector was expressed on a small scale and the resultant humanized anti-TfR1 Fabs were analyzed. Humanized Fabs were selected for further testing based upon several criteria including Biacore assays of antibody affinity for the target antigen, relative expression, percent homology to human germline sequence, and the number of MHC class II predicted T cell epitopes (determined using iTope™ MCH class II in silico analysis).

Potential liabilities were identified within the parental sequence of some antibodies by introducing amino acid substitutions in the heavy chain and light chain variable regions. These substitutions were chosen based on relative expression levels, iTope™ score and relative $K_D$ from Biacore single cycle kinetics analysis. The humanized variants were tested and variants were selected initially based upon affinity for the target antigen. Subsequently, the selected humanized Fabs were further screened based on a series of biophysical assessments of stability and susceptibility to aggregation and degradation of each analyzed variant, shown in Table 14 and Table 15. The selected Fabs were analyzed for their properties binding to TfR1 by kinetic

TABLE 12

Binding Affinity of anti-TfR1 Antibodies and Efficacy of Conjugates

| Clone Name | huTfR1 Avg $K_D$ (M) (antibody alone) | cyTfR1 Avg $K_D$ (M) (antibody alone) | % knockdown of DMPK in NHP cells using Antibody-DMPK ASO conjugate | % knockdown of DMPK in cells from human DM1 patients using Antibody-DMPK ASO conjugate |
|---|---|---|---|---|
| 15G11 (control) | 8.0E−10 | 1.0E−09 | 36 | 46 |
| 3-A4 | 4.36E−10 | 2.32E−09 | 77 | 70 |
| 3-M12 | 7.68E−10 | 5.18E−09 | 77 | 52 |
| 5-H12 | 2.02316E−07 | 1.20E−08 | 88 | 57 |

Interestingly, the DMPK knockdown results showed a lack of correlation between the binding affinity of the anti-TfR to transferrin receptor and efficacy in delivering a DMPK-targeting ASO to cells for DMPK knockdown. Surprisingly, the anti-TfR antibodies provided herein (e.g., at least 3-A4, 3-M12, and 5-H12) demonstrated superior activity in delivering a payload (e.g., DMPK ASO) to the target cells and achieving the biological effect of the molecular analysis. The results of these analyses are shown in Table 16. For conjugates shown in Table 14 and Table 15, the selected humanized Fabs were conjugated to a DMPK-targeting oligonucleotide ASO300. The selected Fabs are thermally stable, as indicated by the comparable binding affinity to human and cyno TfR1 after been exposed to high temperature (40° C.) for 9 days, compared to before the exposure (see Table 16).

TABLE 14

Biophysical assessment data for humanized anti-TfR Fabs

| Criteria | 3M12 (VH3/Vk2) | 3M12 (VH3/Vk3) | 3M12 (VH4/Vk2) | 3M12 (VH4/Vk3) | 3A4 (VH3-N54T/Vk4) |
|---|---|---|---|---|---|
| Binding Affinity (Biacore d 0) | 395 pM | 345 pM | 396 pM | 341 pM | 3.09 nM |
| Binding Affinity (Biacore d 25) | 567 pM | 515 pM | 510 pM | 486 pM | 3.01 nM |
| Fab binding affinity ELISA (human/cyno TfR1) | 0.8 nM/9.9 nM | 0.6 nM/4.7 nM | 0.4 nM/1.4 nM | 0.5 nM/2.2 nM | 2.6 nM/156 nM* |
| Conjugate binding affinity ELISA (human/cyno TfR1) | 2.2 nM/2.9 nM | N/A | N/A | 1.7 nM/2.1 nM | 2.8 nM/4.7 nM |

. . .

| Criteria | 3A4 (VH3-N54S/Vk4) | 3A4 (VH3/Vk4) | 5H12 (VH5-C33Y/Vk3) | 5H12 (VH5-C33D/Vk4) | 5H12 (VH4-C33Y/Vk4) |
|---|---|---|---|---|---|
| Binding Affinity (Biacore d 0) | 1.34 nM | 1.5 nM | 627 pM | 991 pM | 626 pM |
| Binding Affinity (Biacore d 25) | 1.39 nM | 1.35 nM | 1.07 nM | 3.01 nM | 1.33 nM |
| Fab binding affinity ELISA (human/cyno TfR1) | 1.6 nM/398 nM* | 1.5 nM/122 nM* | 6.3 nM/2.1 nM | 6.0 nM/3.5 nM | 2.8 nM/3.3 nM |
| Conjugate binding affinity ELISA (human/cyno TfR1) | 2.9 nM/7.8 nM | 2.8 nM/7.6 nM | 33.4 nM/2.3 nM | 110 nM/10.2 nM | 23.7 nM/3.3 nM |

*Regains cyno binding after conjugation;

TABLE 15

Thermal Stability for humanized anti-TfR Fabs and conjugates

| Criteria | 3M12 (VH3/Vk2) | 3M12 (VH3/Vk3) | 3M12 (VH4/Vk2) | 3M12 (VH4/Vk3) | 3A4 (VH3-N54T/Vk4) |
|---|---|---|---|---|---|
| Binding affinity hTfR1 d 0 (nM) | 0.8 | 0.6 | 0.4 | 0.5 | 2.6 |
| Binding affinity hTfR1 d 9 (nM) | 0.98 | 1.49 | 0.50 | 0.28 | 0.40 |
| Binding affinity cyno TfR1 d 0 (nM) | 9.9 | 4.7 | 1.4 | 2.2 | 156 |
| Binding affinity cyno TfR1 d 9 (nM) | 19.51 | 15.58 | 5.01 | 16.40 | 127.50 |
| DMPK oligo conjugate binding to hTfR1 (nM) | 1.14 | N/A | N/A | 1.18 | 2.22 |
| DMPK oligo conjugate binding to cyno TfR1 (nM) | 2.26 | N/A | N/A | 1.85 | 5.12 |

. . .

| Criteria | 3A4 (VH3-N54S/Vk4) | 3A4 (VH3/Vk4) | 5H12 (VH5-C33Y/Vk3) | 5H12 (VH5-C33D/Vk4) | 5H12 (VH4-C33Y/Vk4) |
|---|---|---|---|---|---|
| Binding affinity hTfR1 d 0 (nM) | 1.6 | 1.5 | 6.3 | 6 | 2.8 |
| Binding affinity hTfR1 d 9 (nM) | 0.65 | 0.46 | 71.90 | 92.34 | 1731.00 |
| Binding affinity cyno TfR1 d 0 (nM) | 398 | 122 | 2.1 | 3.5 | 3.3 |

TABLE 15-continued

Thermal Stability for humanized anti-TfR Fabs and conjugates

| | | | | | |
|---|---|---|---|---|---|
| Binding affinity cyno TfR1 d 9 (nM) | 248.30 | 878.40 | 0.69 | 0.63 | 0.26 |
| DMPK oligo conjugate binding to hTfR1 (nM) | 2.71 | 2.837 | N/A | 110.5 | 13.9 |
| DMPK oligo conjugate binding to cyno TfR1 (nM) | 4.1 | 7.594 | N/A | 10.18 | 13.9 |

TABLE 16

Kinetic analysis of humanized anti-TfR Fabs binding to TfR1

| Humanized anti-TfR Fabs | $k_a$ (1/Ms) | $k_d$ (1/s) | $K_D$ (M) | $R_{MAX}$ | $Chi^2$ ($RU^2$) |
|---|---|---|---|---|---|
| 3A4 (VH3/Vk4) | 7.65E+10 | 1.15E+02 | 1.50E−09 | 48.0 | 0.776 |
| 3A4 (VH3-N54S/Vk4) | 4.90E+10 | 6.56E+01 | 1.34E−09 | 49.4 | 0.622 |
| 3A4 (VH3-N54T/Vk4) | 2.28E+05 | 7.05E−04 | 3.09E−09 | 61.1 | 1.650 |
| 3M12 (VH3/Vk2) | 2.64E+05 | 1.04E−04 | 3.95E−10 | 78.4 | 0.037 |
| 3M12 (VH3/Vk3) | 2.42E+05 | 8.34E−05 | 3.45E−10 | 91.1 | 0.025 |
| 3M12 (VH4/Vk2) | 2.52E+05 | 9.98E−05 | 3.96E−10 | 74.8 | 0.024 |
| 3M12 (VH4/Vk3) | 2.52E+05 | 8.61E−05 | 3.41E−10 | 82.4 | 0.030 |
| 5H12 (VH5-C33D/Vk4) | 6.78E+05 | 6.72E−04 | 9.91E−10 | 49.3 | 0.093 |
| 5H12 (VH5-C33Y/Vk3) | 1.95E+05 | 1.22E−04 | 6.27E−10 | 68.5 | 0.021 |
| 5H12 (VH5-C33Y/Vk4) | 1.86E+05 | 1.17E−04 | 6.26E−10 | 75.2 | 0.026 |

Binding of Humanized Anti-TfR1 Fabs to TfR1 (ELISA)

Figure 21A:
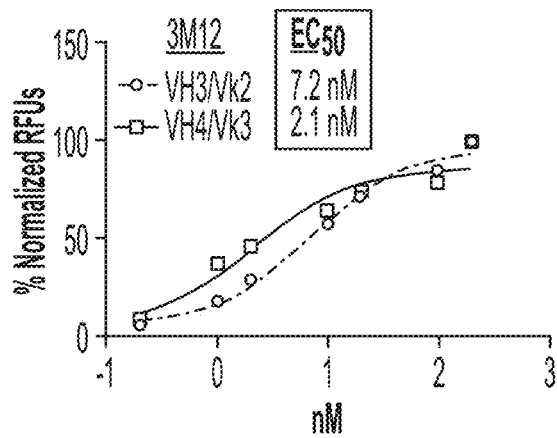
FIGS. 21A-21F show binding of humanized anti-TfR Fabs to human TfR1 (hTfR1) or cynomolgus monkey TfR1 (cTfR1), as measured by ELISA.
Figure 21B:
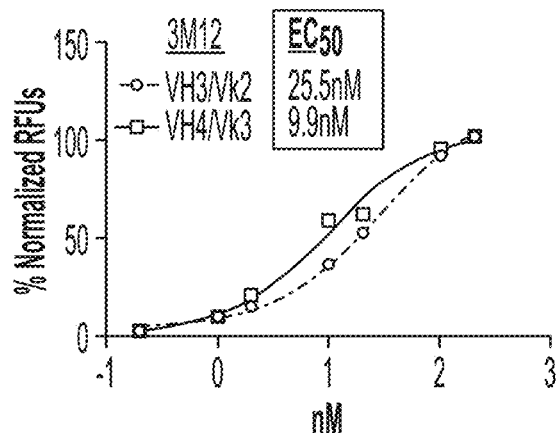
Figure 21C:
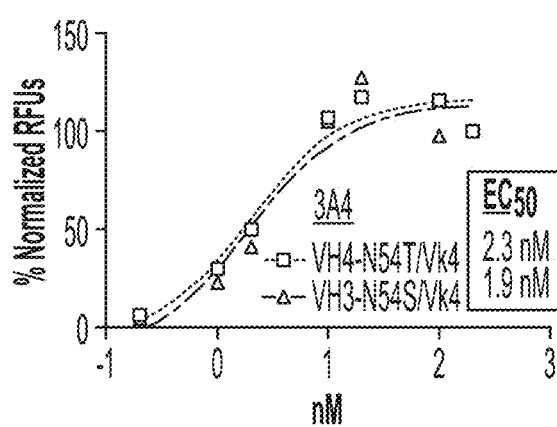
Figure 21D:
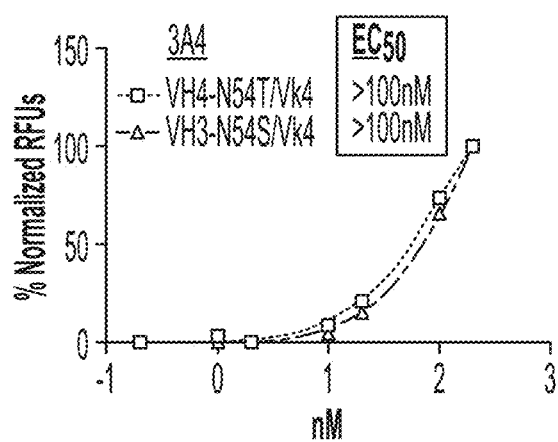
Figure 21E:
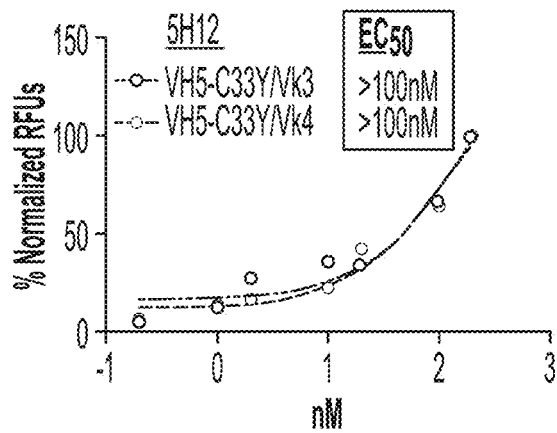
Figure 21F:
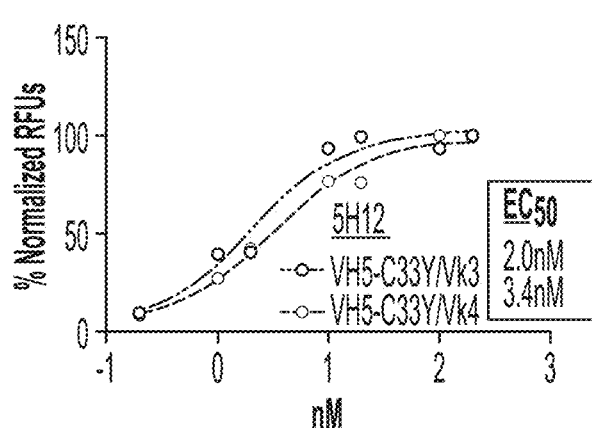

To measure binding of humanized anti-TfR antibodies to TfR1, ELISAs were conducted. High binding, black, flat bottom, 96 well plates (Coning #3925) were first coated with 100 µL/well of recombinant huTfR1 at 1 ag/mL in PBS and incubated at 4° C. overnight. Wells were emptied and residual liquid was removed. Blocking was conducted by adding 200 µL of 1% BSA (w/w) in PBS to each well. Blocking was allowed to proceed for 2 hours at room temperature on a shaker at 300 rpm. After blocking, liquid was removed and wells were washed three times with 300 µL of TBST. Anti-TfR1 antibodies were then added in 0.5% BSA/TBST in triplicate in an 8 point serial dilution (dilution range 5 µg/mL-5 ng/mL). A positive control and isotype controls were also included on the ELISA plate. The plate was incubated at room temperature on an orbital shaker for 60 minutes at 300 rpm, and the plate was washed three times with 300 µL of TBST. Anti-(H+L)IgG-A488 (1:500) (Invitrogen #A11013) was diluted in 0.5% BSA in TBST, and 100 µL was added to each well. The plate was then allowed to incubate at room temperature for 60 minutes at 300 rpm on orbital shaker. The liquid was removed and the plate was washed four times with 300 µL of TBST. Absorbance was then measured at 495 nm excitation and 50 nm emission (with a 15 nm bandwidth) on a plate reader. Data was recorded and analyzed for $EC_{50}$. The data for binding to human TfR1 (hTfR1) for the humanized 3M12, 3A4 and 5H12 Fabs are shown in FIGS. 21A, 21C, and 21E, respectively. ELISA measurements were conducted using cynomolgus monkey (Macaca fascicularis) TfR1 (cTfR1) according to the same protocol described above for hTfR1, and results are shown in FIGS. 21B, 21D, and 21F.

Results of these two sets of ELISA analyses for binding of the humanized anti-TfR Fabs to hTfR1 and cTfR1 demonstrate that humanized 3M12 Fabs show consistent binding to both hTfR1 and cTfR1, and that humanized 3A4 Fabs show decreased binding to cTfR1 relative to hTfR1.

Antibody-oligonucleotide conjugates were prepared using six humanized anti-TfR Fabs, each of which were conjugated to a DMPK targeting oligonucleotide ASO300. Conjugation efficiency and down-stream purification were characterized, and various properties of the product conjugates were measured. The results demonstrate that conjugation efficiency was robust across all 10 variants tested, and that the purification process (hydrophobic interaction chromatography followed by hydroxyapatite resin chromatography) were effective. The purified conjugates showed a >97% purity as analyzed by size exclusion chromatography.

Figure 22:
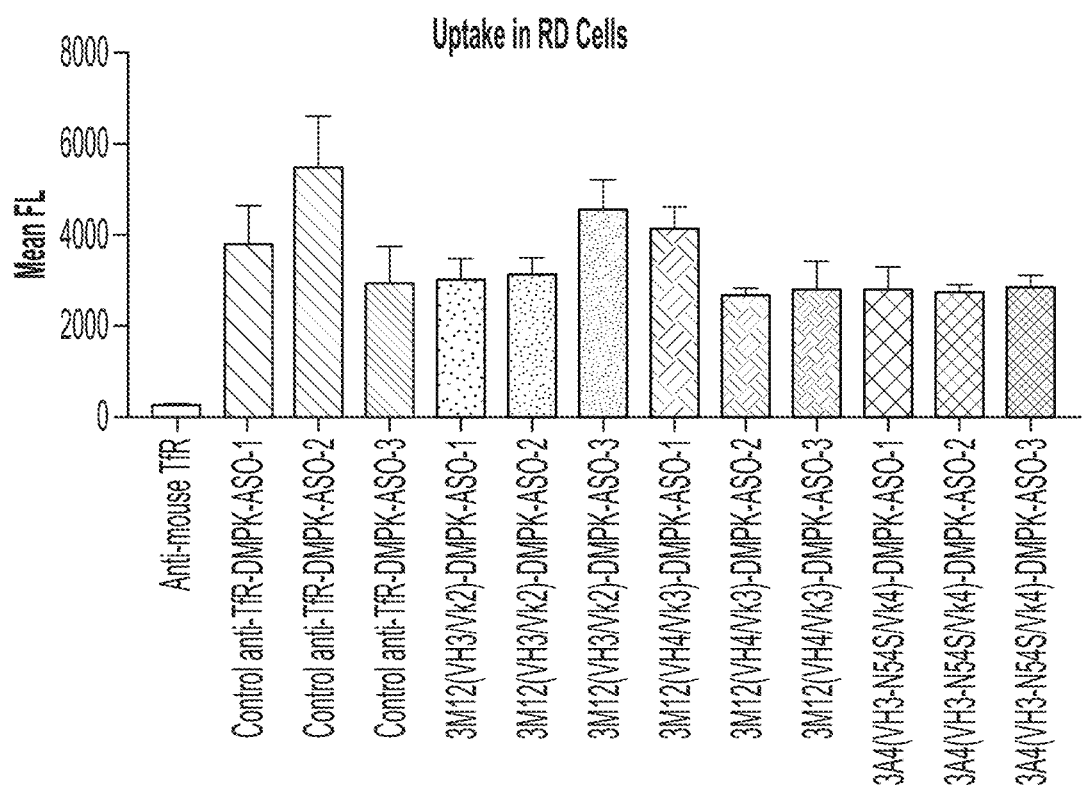
FIG. 22 shows the quantified cellular uptake of anti-TfR Fab conjugates into rhabdomyosarcoma (RD) cells. The molecular payload in the tested conjugates are DMPK-targeting oligonucleotides and the uptake of the conjugates were facilitated by indicated anti-TfR Fabs. Conjugates having a negative control Fab (anti-mouse TfR) or a positive control Fab (anti-human TfR1) are also included this assay. Cells were incubated with indicated conjugate at a concentration of 100 nM for 4 hours. Cellular uptake was measured by mean Cypher5e fluorescence.

Several humanized Fabs were tested in cellular uptake experiments to evaluate TfR1-mediated internalization. To measure such cellular uptake mediated by antibodies, humanized anti-TfR Fab conjugates were labeled with Cypher5e, a pH-sensitive dye. Rhabdomyosarcoma (RD) cells were treated for 4 hours with 100 nM of the conjugates, trypsinized, washed twice, and analyzed by flow cytometry. Mean Cypher5e fluorescence (representing uptake) was calculated using Attune NxT software. As shown in FIG. 22, the humanized anti-TfR Fabs show similar or greater endosomal uptake compared to a positive control anti-TfR1 Fab. Similar internalization efficiencies were observed for different oligonucleotide payloads. An anti-mouse TfR antibody was used as the negative control. Cold (non-internalizing) conditions abrogated the fluorescence signal of the positive control antibody-conjugate (data not shown), indicating that the positive signal in the positive control and humanized anti-TfR Fab-conjugates is due to internalization of the Fab-conjugates.

Figure 23A:
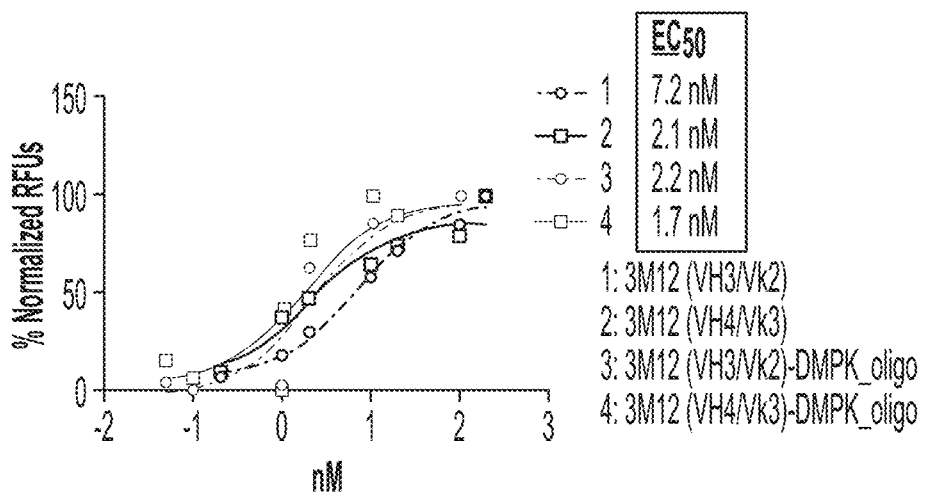
FIGS. 23A-23F show binding of oligonucleotide-conjugated or unconjugated humanized anti-TfR Fabs to human TfR1 (hTfR1) and cynomolgus monkey TfR1 (cTfR1), as measured by ELISA.
Figure 23B:
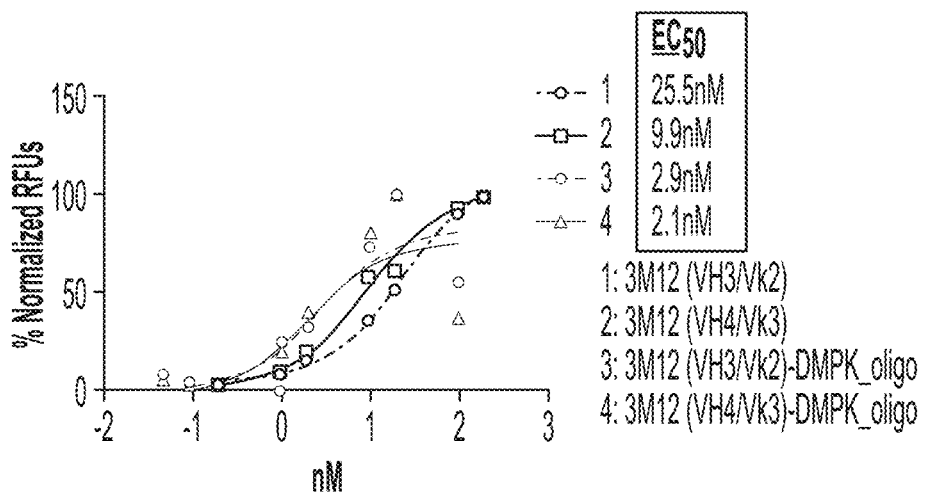
Figure 23C:
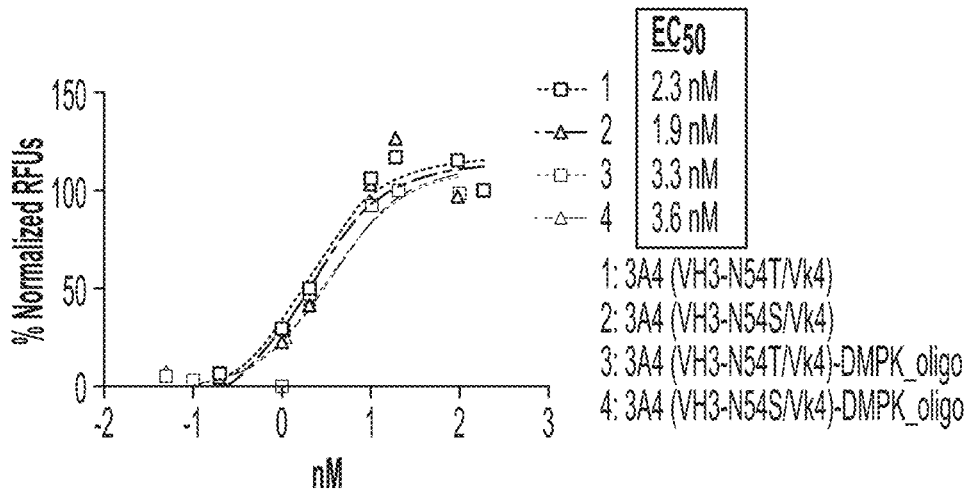
Figure 23D:
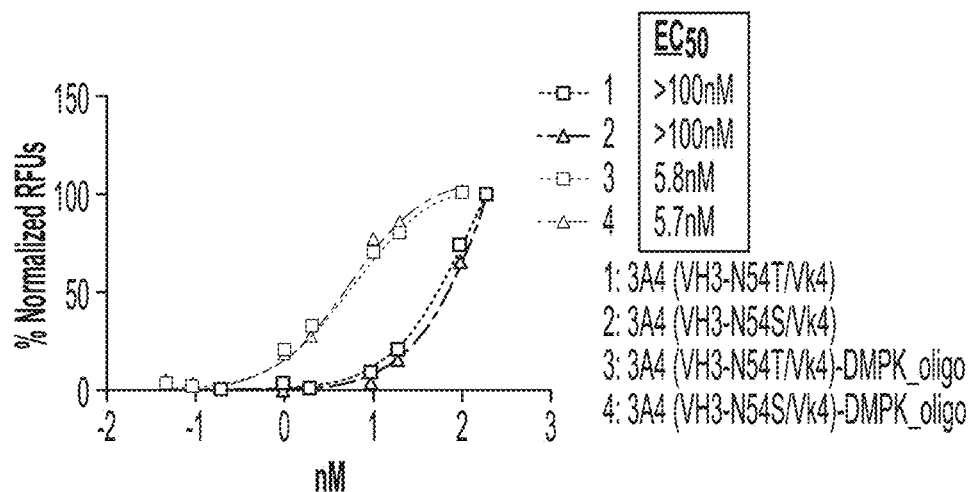
Figure 23E:
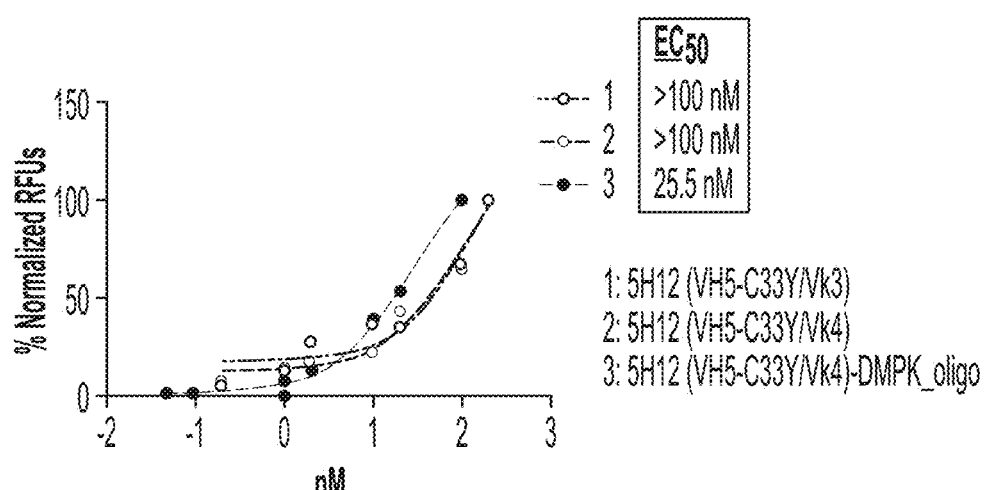
Figure 23F:
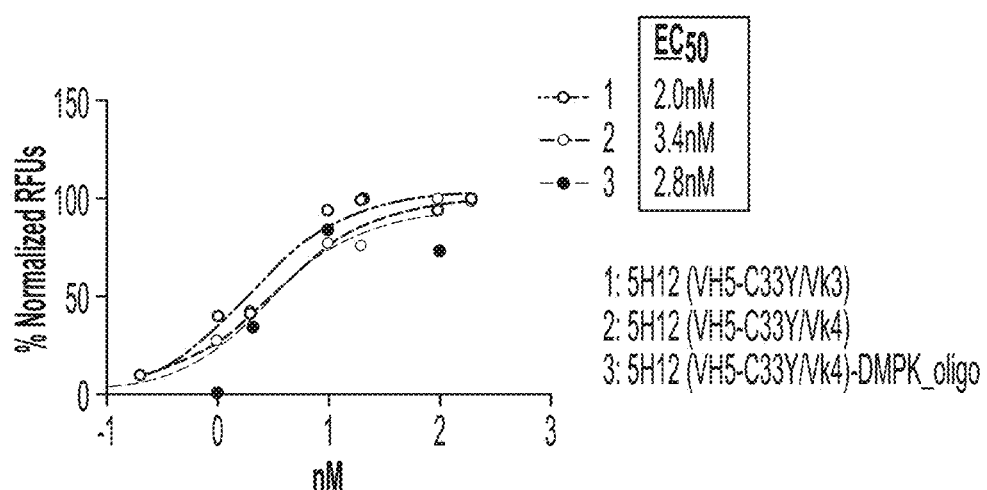

Conjugates of six humanized anti-TfR Fabs of were also tested for binding to hTfR1 and cTfR1 by ELISA, and compared to the unconjugated forms of the humanized Fabs. Results demonstrate that humanized 3M12 and 5H12 Fabs maintain similar levels of hTfR1 and cTfR1 binding after conjugation relative to their unconjugated forms (3M12, FIGS. 23A and 23B; 5H12, FIGS. 23E and 23F). Interestingly, 3A4 clones show improved binding to cTfR1 after conjugation relative to their unconjugated forms (FIGS. 23C and 23D).

As used in this Example, the term 'unconjugated' indicates that the antibody was not conjugated to an oligonucleotide.

Example 18. Knockdown of DMPK mRNA Level Facilitated by Oligonucleotides Conjugates In Vitro DMPK-targeting oligonucleotides (e.g., ASO) were tested in rhabdomyosarcoma (RD) cells for knockdown of DMPK transcript expression. RD cells were cultured in a growth medium of DMEM with glutamine, supplemented with 10% FBS and penicillin/streptomycin until nearly confluent. Cells were then seeded into a 96 well plate at 20K cells per well and were allowed to recover for 24 hours. Cells were then treated with free DMPK-targeting oligonucleotides or by transfection of the oligonucleotides using 0.3 µL per well of Lipofectamine MessengerMAX transfection reagent. After 3 days, total RNA was collected from cells, cDNA was synthesized and DMPK expression was measured by qPCR.

Figure 24:
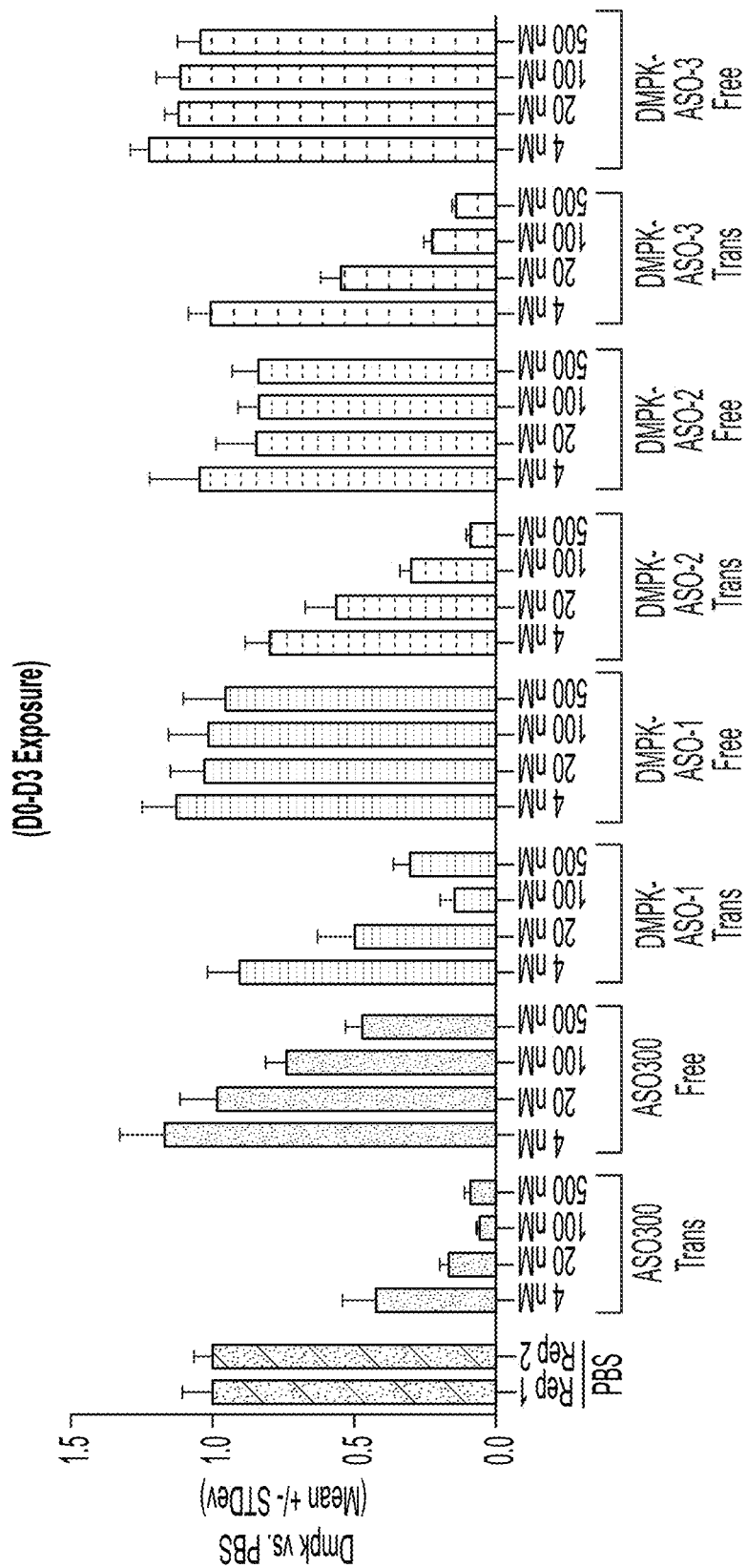
FIG. 24 shows DMPK expression in RD cells treated with DMPK-targeting oligonucleotides relative to cells treated with PBS. The duration treatment was 3 days. DMPK-targeting oligonucleotides were delivered to the cells as free oligonucleotides (gymnotic uptake, "free") or with transfection reagent ("trans").

Results in FIG. 24 show that DMPK expression level was reduced in cells treated with each given DMPK-targeting oligonucleotide, relative to expression in PBS-treated cells. Several DMPK-oligonucleotides showed dose-dependent reduction of DMPK expression level. In FIG. 24, DMPK-ASO-1 has the sequence GCGUAGAAGGGCGUCUGCCC (SEQ ID NO: 212). DMPK-ASO-2 has the sequence CCCAGCGCCCACCAGUCACA (SEQ ID NO: 222). DMPK-ASO-3 has the sequence CCAUCUCGGCCG-GAAUCCGC (SEQ ID NO: 180). ASO300 was also used in this experiment.

Example 19. Knockdown of DMPK mRNA Level Facilitated by Antibody-Oligonucleotide Conjugates In Vitro Conjugates containing humanized anti-TfR Fabs 3M12 (VH3/Vk2), 3M-12 (VH4/Vk3), and 3A4(VH3-N54S/Vk4) were conjugated to a DMPK-targeting oligonucleotide (ASO300) and were tested in rhabdomyosarcoma (RD) cells for knockdown of DMPK transcript expression. Antibodies were conjugated to ASO300 via the linker shown in Formula (C).

RD cells were cultured in a growth medium of DMEM with glutamine, supplemented with 10% FBS and penicillin/streptomycin until nearly confluent. Cells were then seeded into a 96 well plate at 20K cells per well and were allowed to recover for 24 hours. Cells were then treated with the conjugates for 3 days. Total RNA was collected from cells, cDNA was synthesized and DMPK expression was measured by qPCR.

Figure 25:
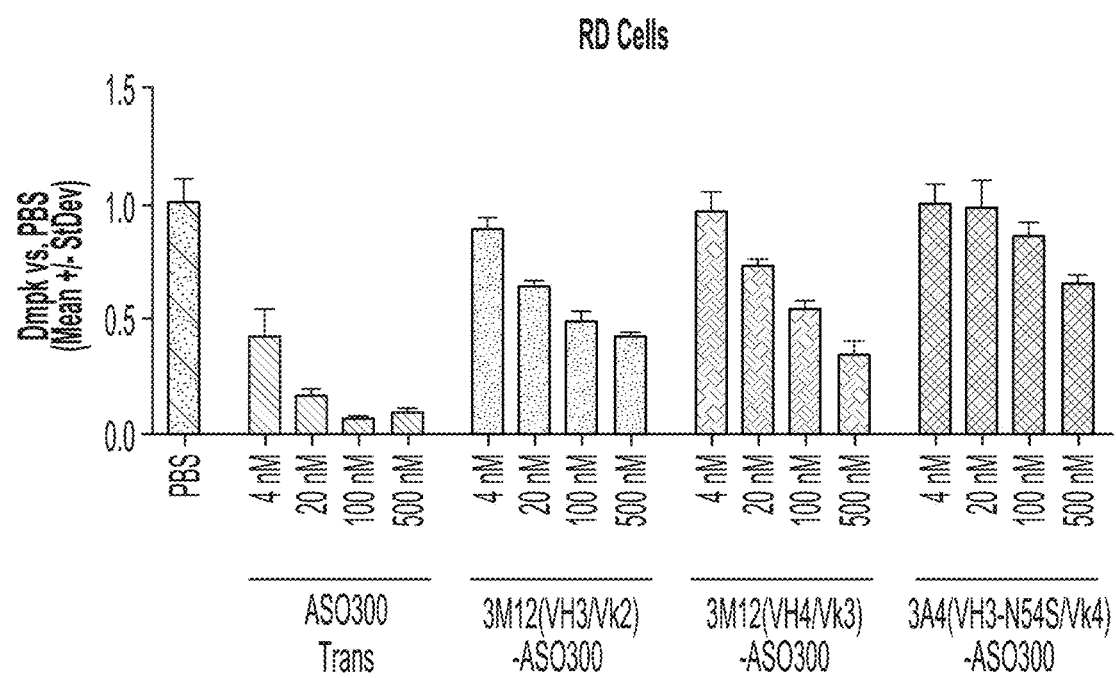
FIG. 25 shows DMPK expression in RD cells treated with various concentrations of conjugates containing the indicated humanized anti-TfR antibodies conjugated to a DMPK-targeting antisense oligonucleotide (ASO300). The duration of treatment was 3 days. ASO300 delivered using transfection agents (labeled "Trans") was used as control.

Results in FIG. 25 show that DMPK expression level was reduced in cells treated with each indicated conjugate, relative to expression in PBS-treated cells, indicating that the humanized anti-TfR Fabs are able to mediate the uptake of the DMPK-targeting oligonucleotide by the RD cells and that the internalized DMPK-targeting oligonucleotide are effective in knocking down DMPK mRNA level.

Example 20. Splicing Correction and Functional Efficacy in HSA-LR Mouse Model of DM1

Correction of splicing in the HSA-LR mouse model of DM1 was demonstrated with conjugates containing anti-TfR antibodies conjugated to oligonucleotides target human skeletal actin (ACTA1). The anti-TfR1 antibody used in this study was RI7 217. The oligonucleotide targeting ACTA1 is an MOE 5-10-5 gapmer that comprises: 5'-NH$_2$—(CH$_2$)$_6$-dA*oC*oC*oA*oT*oT*dT*dT*dC*dT*dT*dC*dC*dA*dC*dA*oG*oG*oG*oC*oT-3 (SEQ ID NO: 620); wherein '*' represents a PS linkage; 'd' represents a deoxynucleic acid; and 'o' represents a 2'-MOE.

The HSA-LR DM1 mouse model is a well-validated model of DM1 that exhibits pathologies that are very similar to human DM1 patients. The HSA-LR model uses the human skeletal actin (ACTA1) promoter to drive expression of CUG long repeats (LR). In this model, toxic DMPK RNA accumulates within the nucleus and sequesters proteins responsible for splicing, such as Muscleblind-like protein (MBNL), resulting in mis-splicing of multiple RNAs, including CLCN1 (chloride channel), ATP2a1 (calcium channel), and others. This mis-splicing causes the mice to also exhibit myotonia which is a hallmark of the DM1 clinical presentation in humans.

The anti-TfR-oligonucleotide conjugate delivered intravenously has been shown to have activity in dose-dependent correction of splicing in multiple RNAs and multiple muscles and was well tolerated by HSA-LR mice. In this study, the ability of the conjugates to correct splicing in more than 30 different RNAs was evaluated. In DM1, significant RNA mis-splicing of these RNAs reduces the ability of multiple muscles to function. The RNAs monitored are critical for contraction and relaxation of muscle in HSA-LR mice. Dose-dependent correction of splicing was observed.

Figure 26:
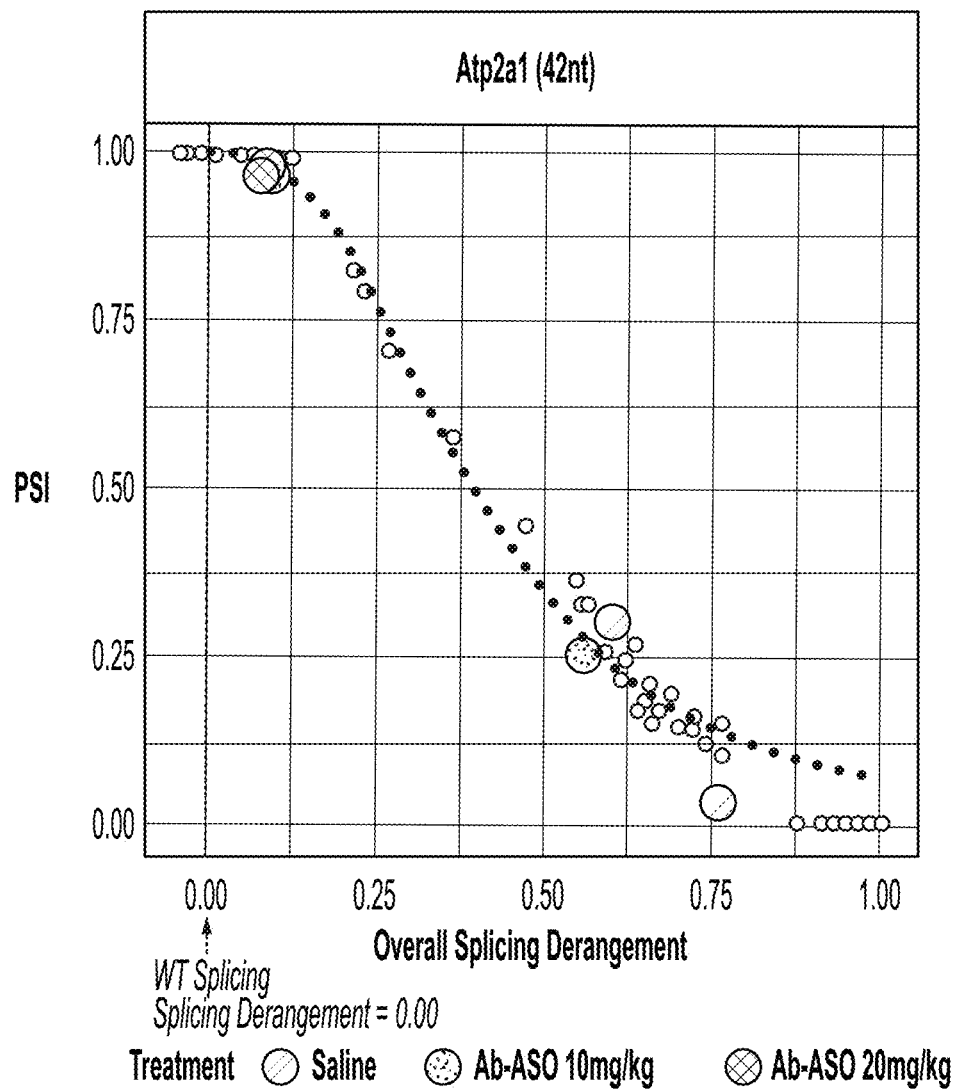
FIG. 26 shows results of splicing correction in Atp2a1 by an anti-TfR1 antibody-oligonucleotide conjugate (Ab-ASO) in the HSA-LR mouse model of DM1, measured in the gastrocnemius muscle. The anti-TfR antibody used is RI7 217 Fab and the oligonucleotide is targeting skeletal actin.

FIG. 26 shows results for Atp2a1, which encodes a calcium channel and contributes to muscle contraction and relaxation. The X-axis represents splice derangement with 1.00 representing severe mis-splicing and 0.00 representing a wild type (WT) splice pattern. Progression from right to left in the figure represents a correction of splicing. The Y-axis represents the percent of the gene spliced in (PSI). Severe mis-splicing of ATP2a1 is caused by exclusion of exon 22 in the ATP2a1 RNA. WT splicing reflects near complete inclusion of exon 22. Results demonstrate that the conjugate corrected splicing of ATP2a1 in a dose-dependent manner in the gastrocnemius muscle.

Figure 27:
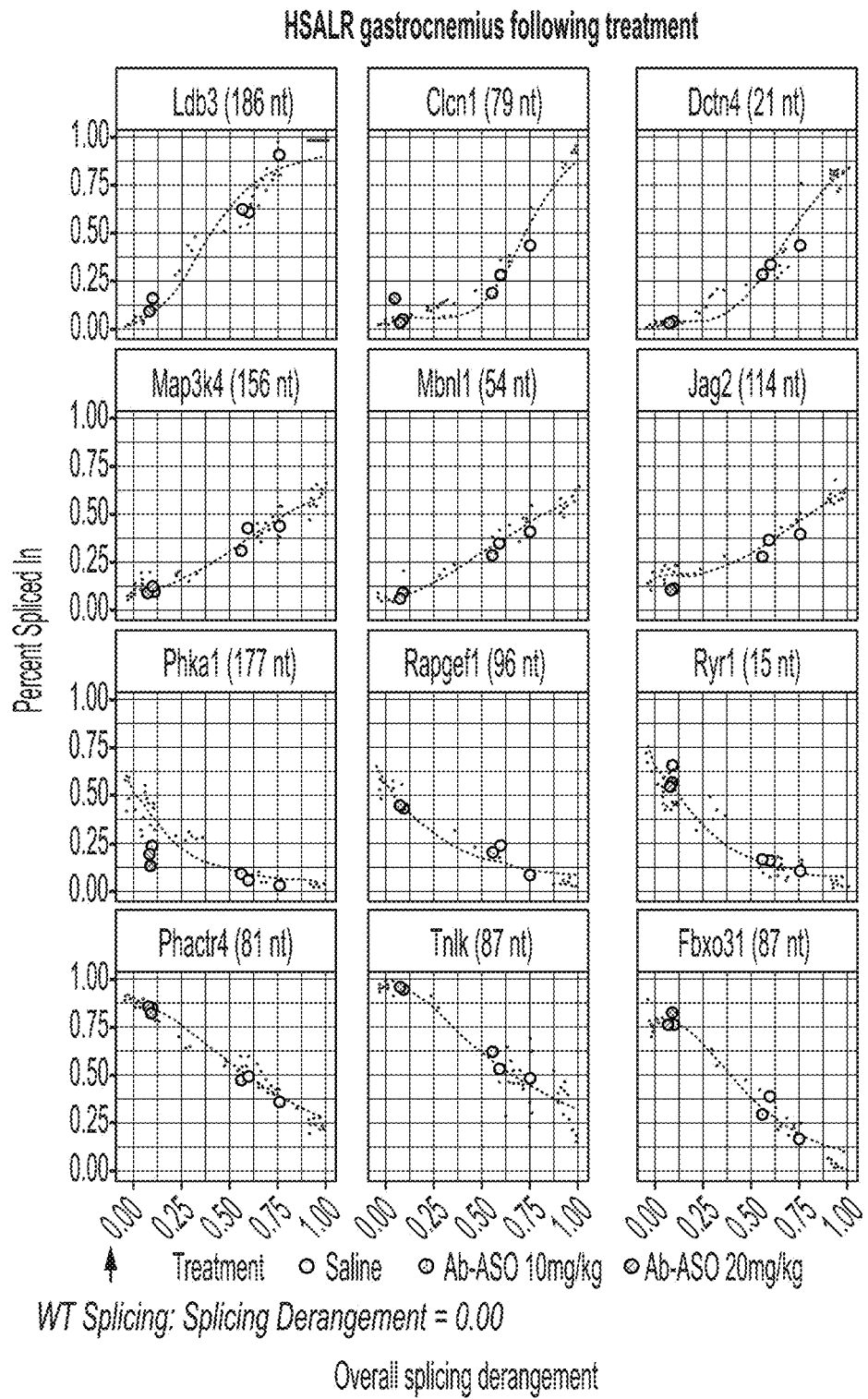
FIG. 27 shows splicing correction in more than 30 different RNAs related to DM1, measured in the gastrocnemius muscle of HSA-LR mice treated anti-TfR1 antibody-oligonucleotide (Ab-ASO) conjugate or saline. The anti-TfR antibody used is RI7 217 Fab and the oligonucleotide is targeting human skeletal actin.
Figure 27:
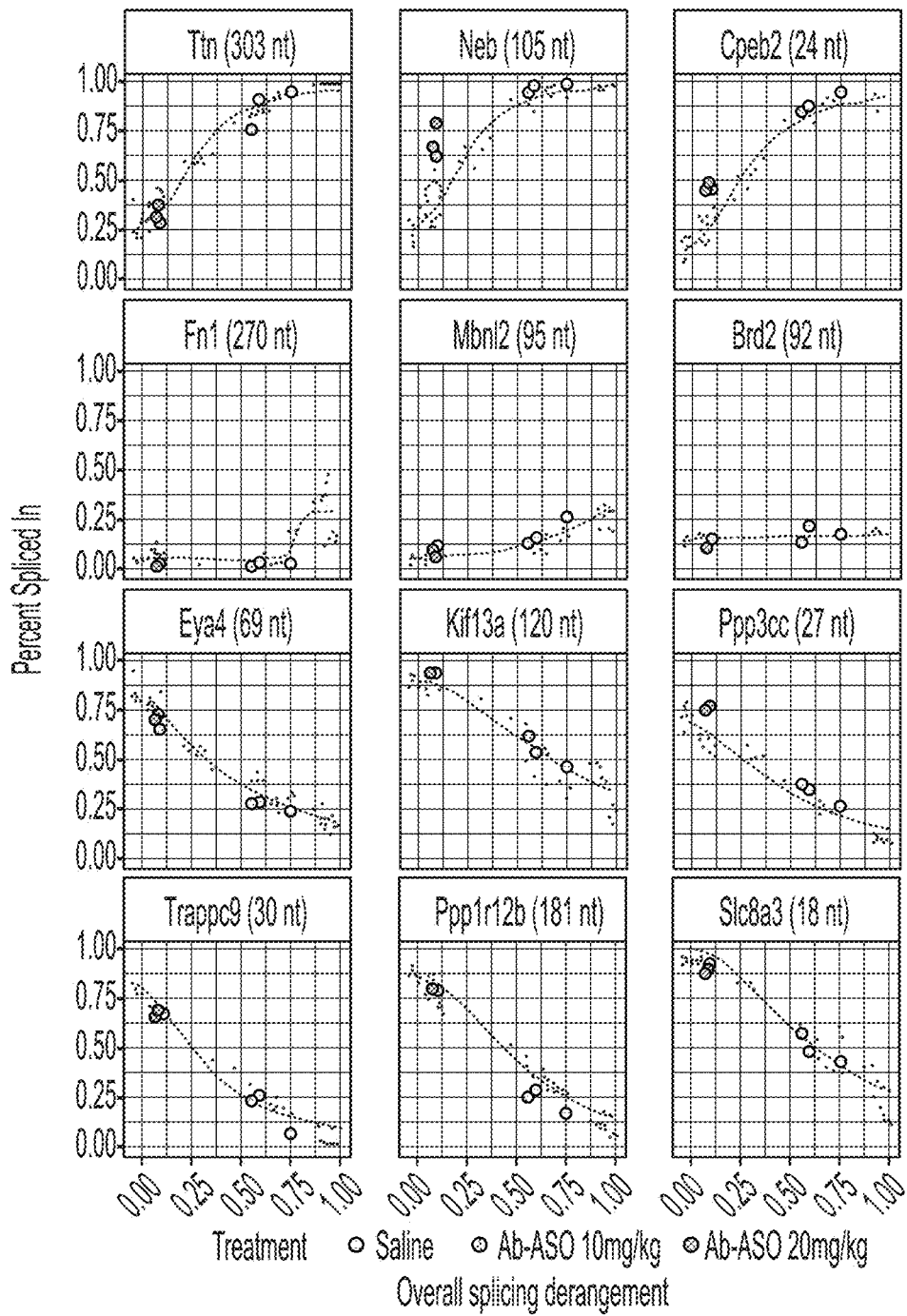
Figure 27:
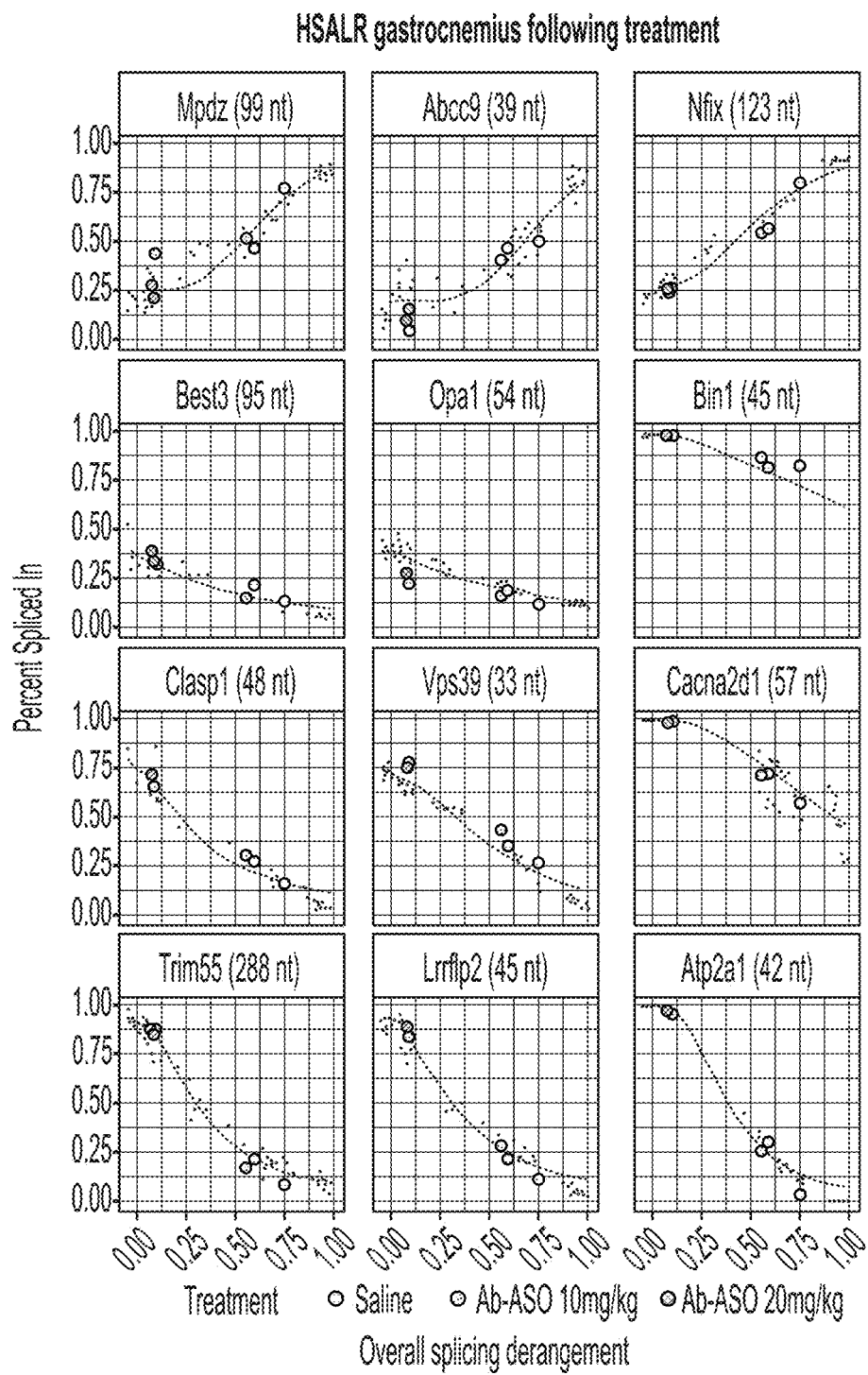
Figure 35A:
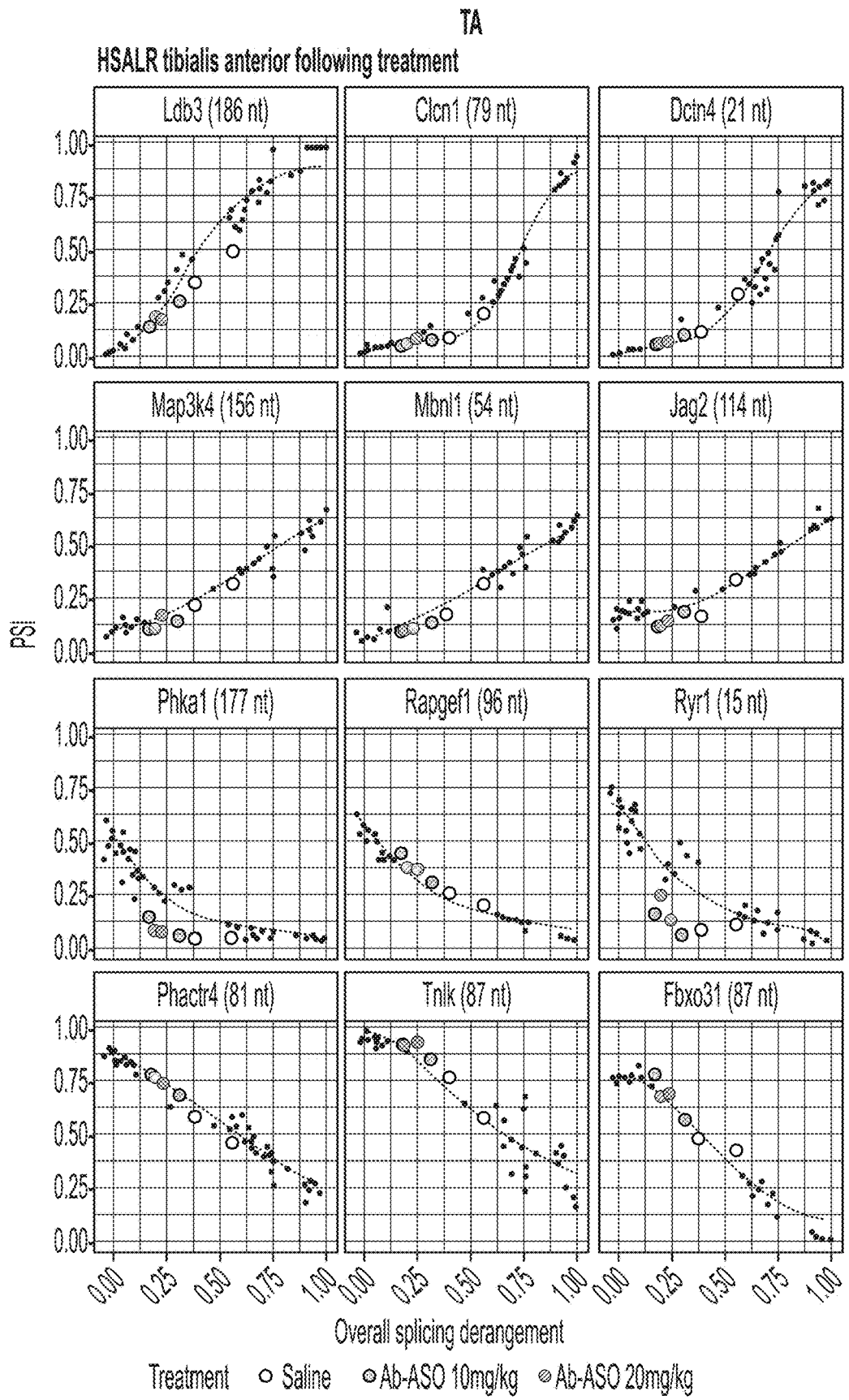
FIGS. 35A-35B show splicing correction in more than 30 different RNAs known to be mis-spliced in DM1 patients, measured in the tibialis anterior (FIG. 35A) or the quadriceps (FIG. 35B) of HSA-LR mice treated with a single dose of anti-TfR antibody-oligonucleotide (Ab-ASO) conjugate or saline. The anti-TfR antibody used is RI7 217 Fab and the oligonucleotide targets skeletal actin (ACTA1).
Figure 35A:
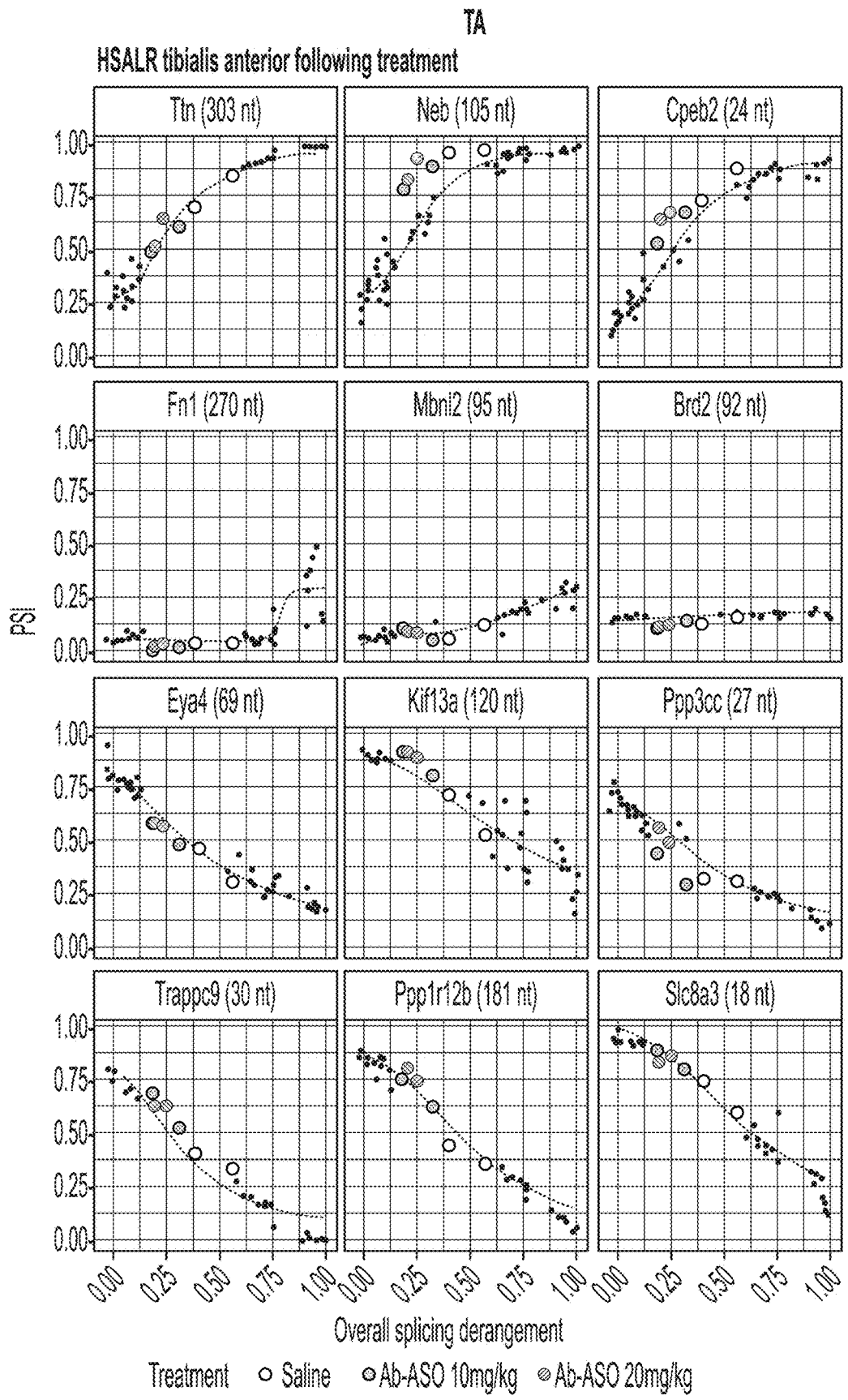
Figure 35A:
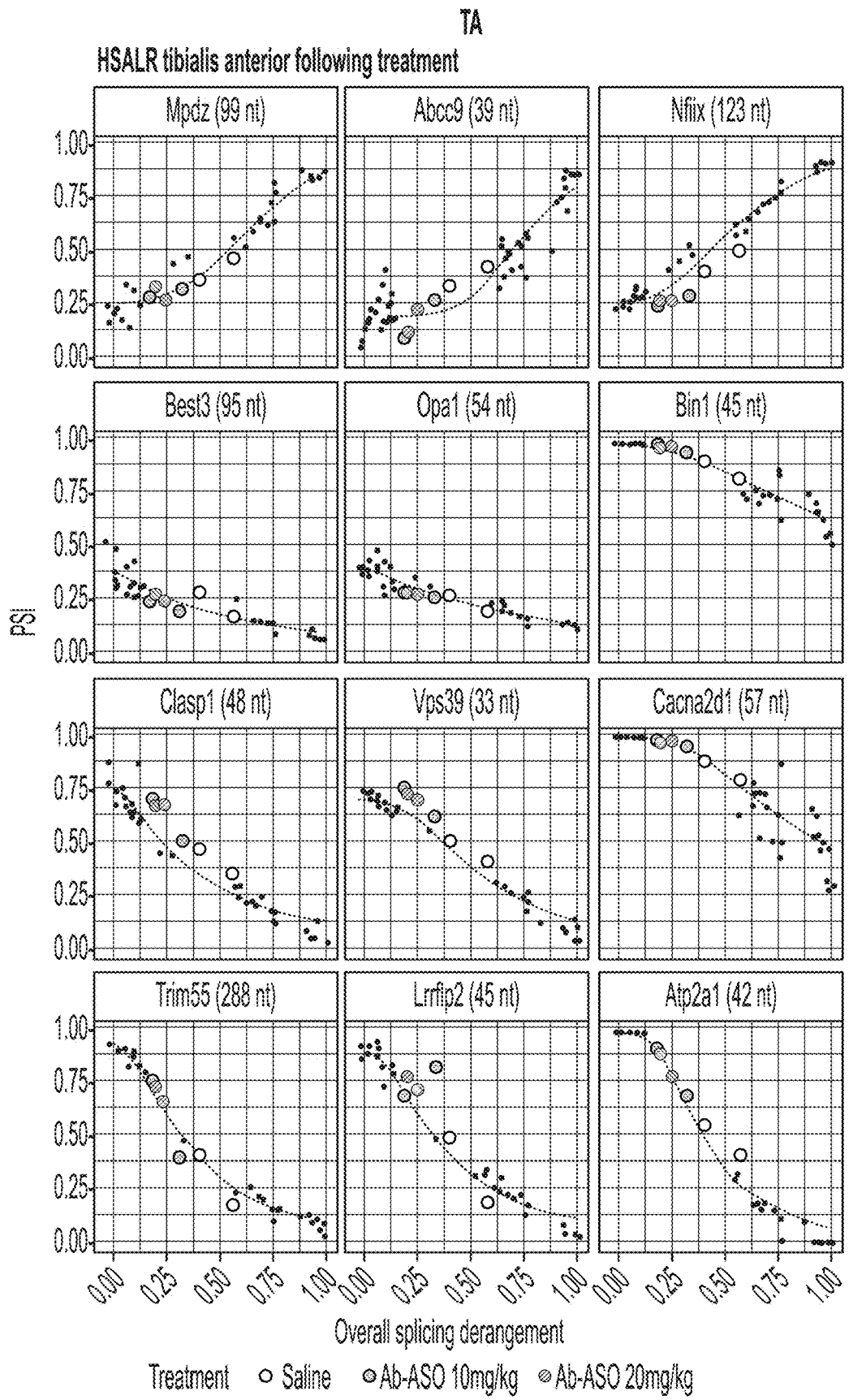
Figure 35B:
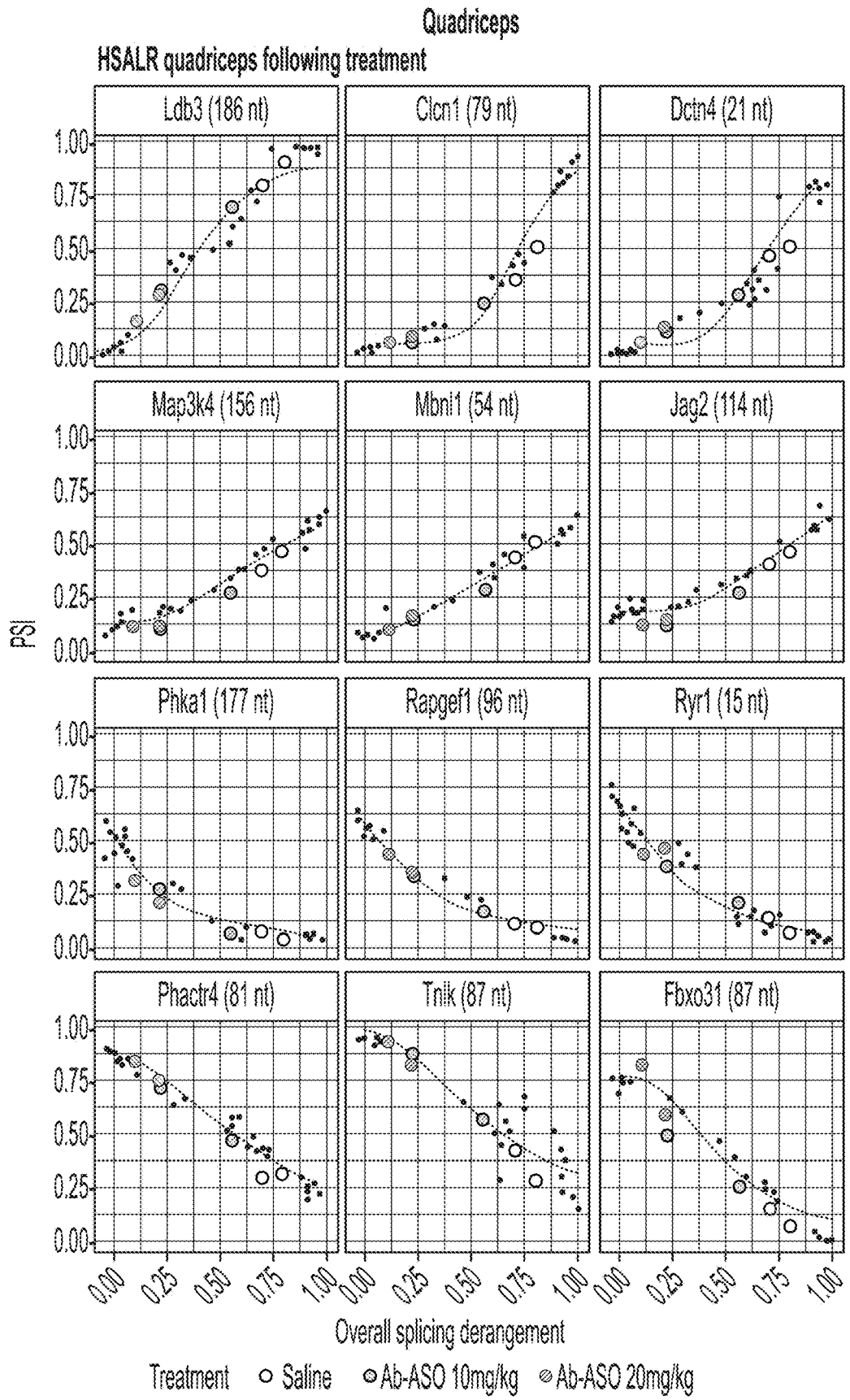
Figure 35B:
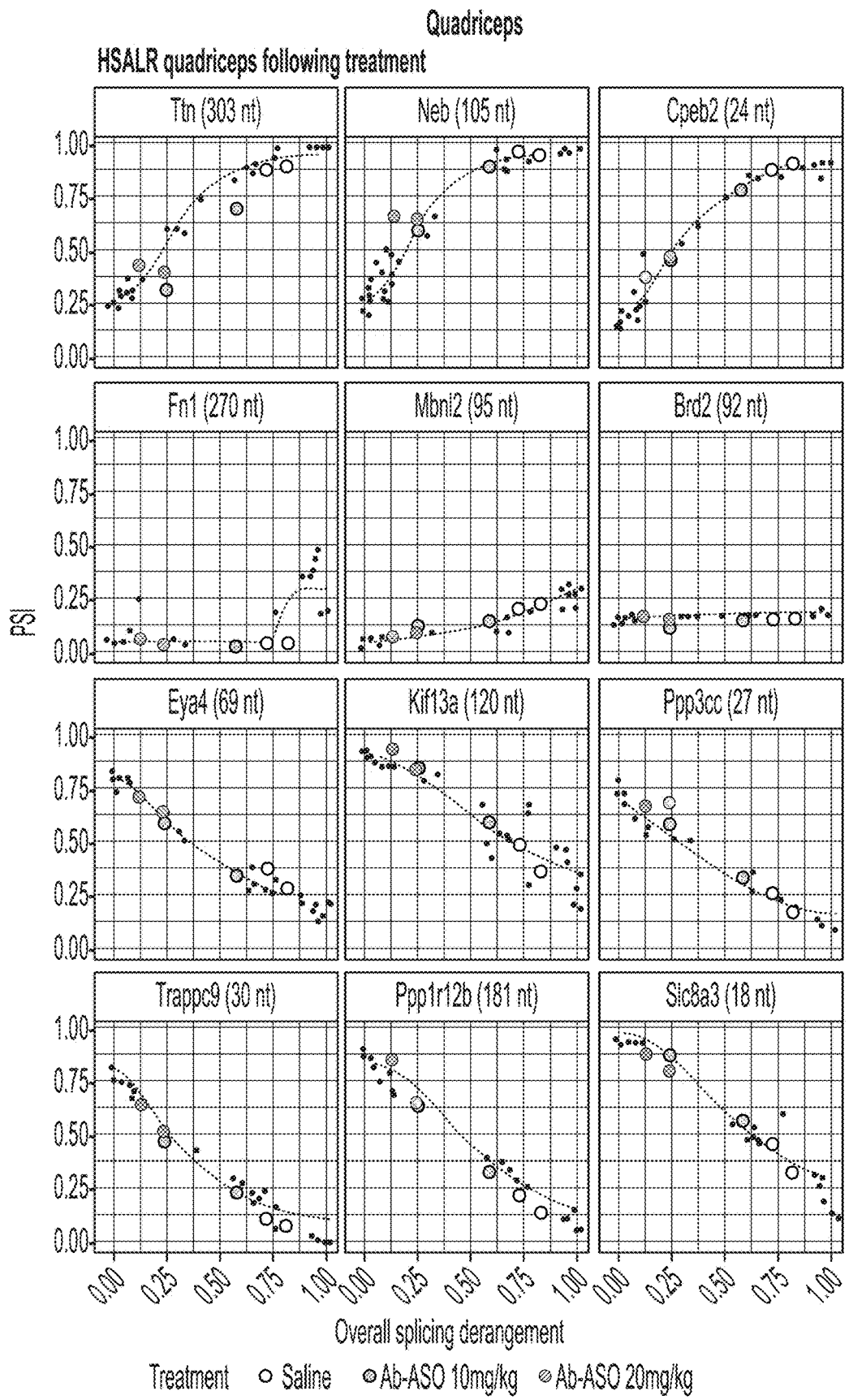
Figure 35B:
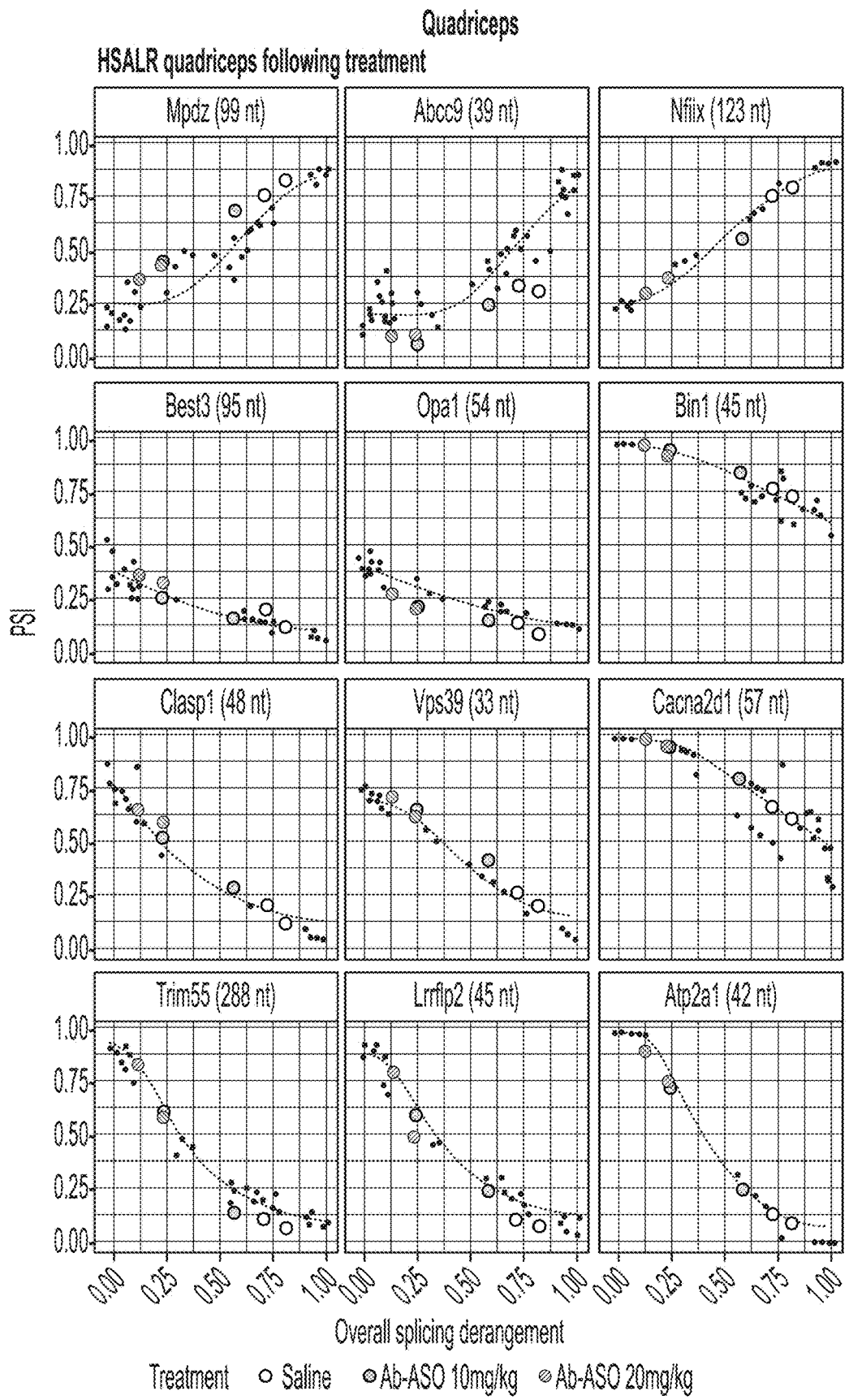

Data for the more than 30 different RNAs that were tested in this study are shown in FIGS. 27, 35A, and 35B. Similar dose-dependent correction of splicing was achieved for all of the tested RNAs in gastrocnemius muscle (FIG. 27), tibialis anterior (FIG. 35A), and quadriceps (FIG. 35B). For some of these RNAs, correction of splicing is reflected by a decrease in PSI, as in FIG. 26, and for other RNAs correction is reflected by an increase in PSI.

Figure 28:
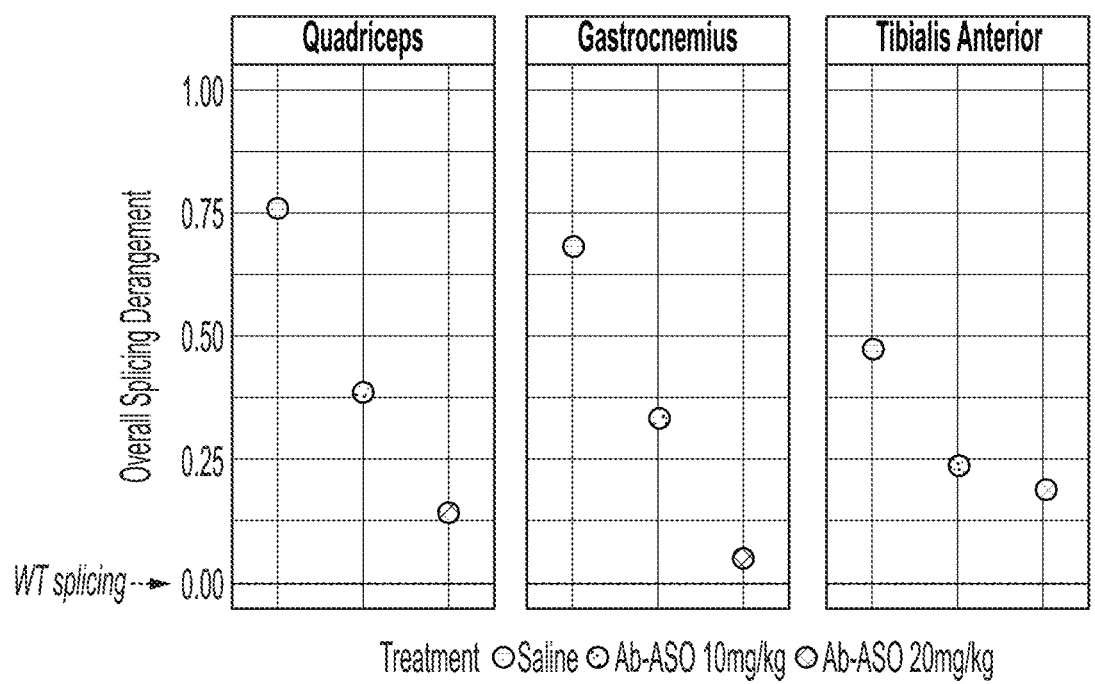
FIG. 28 shows splicing derangement in quadriceps, gastrocnemius, or tibialis anterior muscles of HSA-LR mice treated with anti-TfR1 antibody-oligonucleotide conjugate (Ab-ASO) or saline. The data represent composite splicing derangement measured in the more than 30 RNAs shown in FIG. 27.

Similar dose-dependent improvements in splicing within the set of RNAs were observed in the quadriceps and tibialis anterior muscles, after treatment with the conjugate. FIG. 28 shows composite levels of splicing derangement observed for saline and different doses of the Ab-ASO across the more than 30 RNAs that were tested in each muscle type. Doses of 10 mg/kg and 20 mg/kg were administered in this study.

Figure 29:
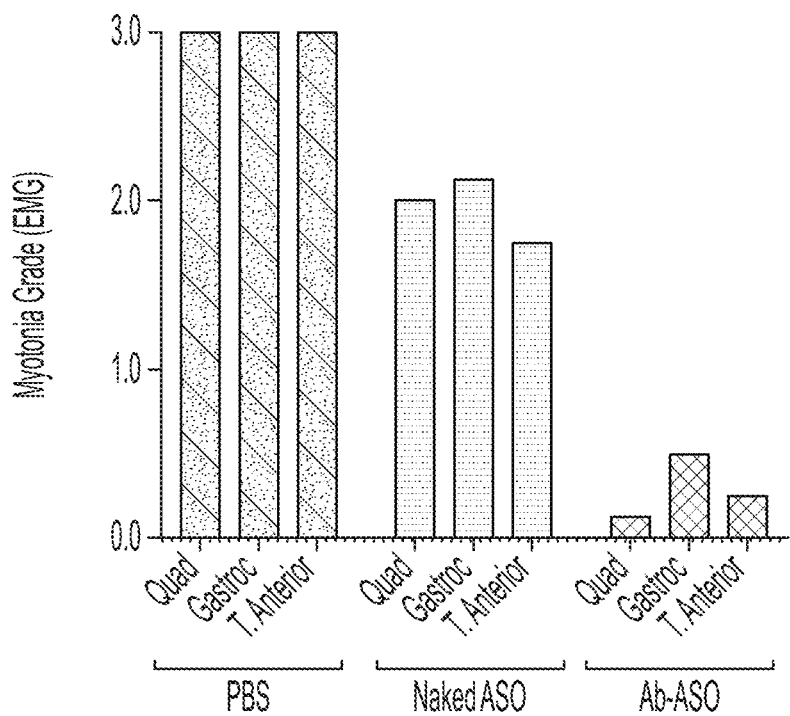
FIG. 29 shows myotonia grade measured in quadriceps, gastrocnemius, and tibialis anterior muscles of HSA-LR mice treated with saline, unconjugated oligonucleotide (ASO), or anti-TfR1 antibody-oligonucleotide conjugate (Ab-ASO). Myotonia was measured by electromyography (EMG), and graded 0, 1, 2, or 3 based on the frequency of myotonic discharge.

In addition to reductions in splicing derangement across multiple genes in several muscles in the HSA-LR model, disease modification was observed in the HSA-LR model. The results in FIG. 29 show that almost complete reversal of myotonia was achieved after a single dose of the conjugate. The severity of myotonia on a four-point scale was evaluated 14 days following dosing with saline (PBS), naked oligonucleotide, or the conjugate. Grade 0 indicates no myotonia was observed, grade 1 indicates myotonic discharge was measured by electromyography (EMG) in less than 50% of needle insertions, grade 2 indicates myotonic discharge was measured in greater than 50% of needle insertions and grade 3 indicates myotonic discharge was measured with nearly every needle insertion.

Example 21. DMPK-Targeting PMOs

Additional DMPK targeting oligonucleotides (PMOs) were designed and tested for their activity in reducing DMPK expression in primary human myotubes. Wild-type primary myoblasts were cultured in PromoCell Skeletal Muscle growth medium with 5% FBS and penicillin/streptomycin until nearly confluent. Cells were then seeded into a 96 well plate at 50K cells per well and allowed to recover for 24 hours. Cells were then differentiated in a differentiation medium of DMEM with glutamine and penicillin/streptomycin for 7 days. Cells were then treated with the unconjugated PMO for 3 days. Total RNA was collected from cells, cDNA was synthesized and DMPK expression was measured by qPCR. The sequences of the PMOs and their activity in knocking down DMPK in vitro are shown in Table 17.

As used in this Example, the term 'unconjugated' indicates that the oligonucleotide was not conjugated to an antibody."

Formula (C). It is important that the linker maintain stability in serum and provide release kinetics that favor sufficient payload accumulation in the targeted muscle cell. This serum stability is important for systemic intravenous administration, stability of the conjugated oligonucleotide in the bloodstream, delivery to muscle tissue and internalization of the therapeutic payload in the muscle cells. The linker has been confirmed to facilitate precise conjugation of multiple types of payloads (including ASOs, siRNAs and PMOs) to Fabs. This flexibility enabled rational selection of the appropriate type of payload to address the genetic basis of each muscle disease. Additionally, the linker and conjugation chemistry allowed the optimization of the ratio of payload molecules attached to each Fab for each type of payload, and enabled rapid design, production and screening of molecules to enable use in various muscle disease applications.

Figure 20:
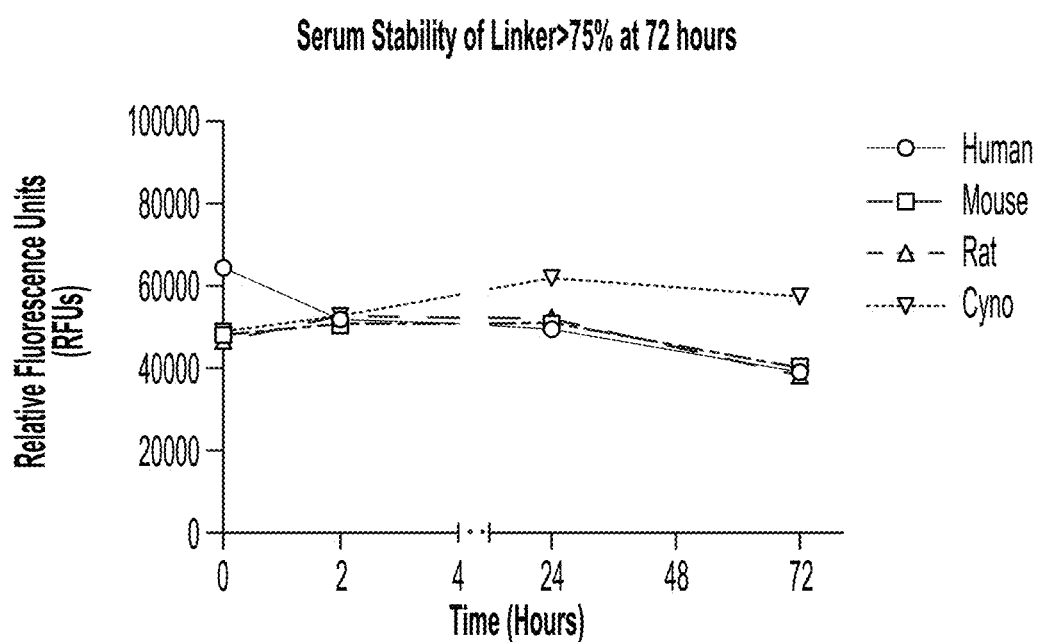
FIG. 20 shows the serum stability of the linker used for linking an anti-TfR antibody and a molecular payload (e.g., an oligonucleotide) in various species over time after intravenous administration.

FIG. 20 shows serum stability of the linker in vivo, which was comparable across multiple species over the course of 72 hours after intravenous dosing. At least 75% stability was measured in each case at 72 hours after dosing.

TABLE 17

DMPK-targeting PMOs and activity in knocking down DMPK in vitro

| PMO Sequence | SEQ ID NO | Target region | % DMPK Knockdown in Primary Human Myotubes |
| --- | --- | --- | --- |
| CAGGTGACAGTTCAGGTGCAG | 624 | Intron 1-2 | 59% |
| TCCACCCTGACTCCAGGTGAC | 625 | Intron 1-2 | 16% |
| GAGAAGGAAATAAGACCCAGTT | 626 | Intron 1-2 | 14% |
| CCTTCTCTCTGCCTCTCAGCTT | 627 | Intron 1-2 | 58% |
| CCACCCTCTGTCTGTCTCC | 628 | Intron 1-2 | 64% |
| TCCGCTGGGTGGTGGGAAAAGAA | 629 | Exon 2 | 9% |
| ATGGGCTCCGCTGGGTGGTGG | 630 | Exon 2 | 11% |
| ACGATGGGCTCCGCTGGG | 631 | Exon 2 | 60% |
| CCATCCTTGGGCAGAGACCT | 632 | Intron 4-5 | 41% |
| ATGACCAGGTACTGAGAAGGG | 633 | Exon 5 | 33% |
| AGGTACTGAGAAGGGTTCGTC | 634 | Exon 5 | 40% |
| TAGGGACCTGCGGAGAGGGCGA | 635 | Exon 15 | 35% |
| GCCTAGGGACCTGCGGGAGAG | 636 | Exon 15 | 62% |
| GCCTTTTATTCGCGAGGGTCGG | 637 | polyA | 73% |
| TGGAGGGCCTTTTATTCGCGAGG | 638 | polyA | 66% |
| TAGGCACTCACCCACTGCAAGA | 621 | Exon 1 | 69% |
| CGGAGCTCACCAGGTAGTTCT | 622 | Intron 4-5 | 73% |
| AGGGCAGTGCTTACCTGAGGG | 623 | Intron 9-10 | 57% |

Example 22. Serum Stability of the Linker Linking the Anti-TfR Antibody and the Molecular Payload Oligonucleotides which were linked to antibodies in examples were conjugated via a cleavable linker shown in

Example 23. In Vivo Activity of Anti-TfR Conjugates in hTfR1 Mice

In DM1, the higher than normal number of CUG repeats form large hairpin loops that remain trapped in the nucleus, forming nuclear foci that bind splicing proteins and inhibit the ability of splicing proteins to perform their normal function. When toxic nuclear DMPK levels are reduced, the nuclear foci are diminished, releasing splicing proteins, allowing restoration of normal mRNA processing, and potentially stopping or reversing disease progression.

The in vivo activity of conjugates containing an anti-TfR Fab (control, 3M12 VH3/VK2, 3M12 VH4/VK3, 3A4 VH3 N54S/VK4) conjugated to the DMPK-targeting oligonucleotide (ASO300) in reducing DMPK mRNA level in multiple muscle tissues following systemic intravenous administration in mice was evaluated.

Figure 30A:
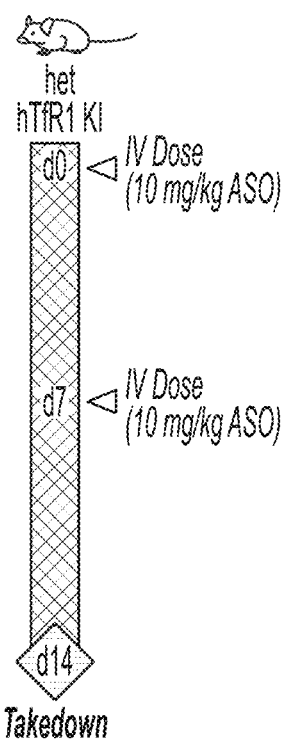
FIGS. 30A-30E show in vivo activity of conjugates containing designated anti-TfR Fabs (control, 3M12 VH3/VK2, 3M12 VH4/VK3, and 3A4 VH3 N54S/VK4) conjugated to DMPK-targeting oligonucleotide in reducing DMPK mRNA expression in mice expressing human TfR1 (hTfR1 knock-in mice).
Figure 30B:
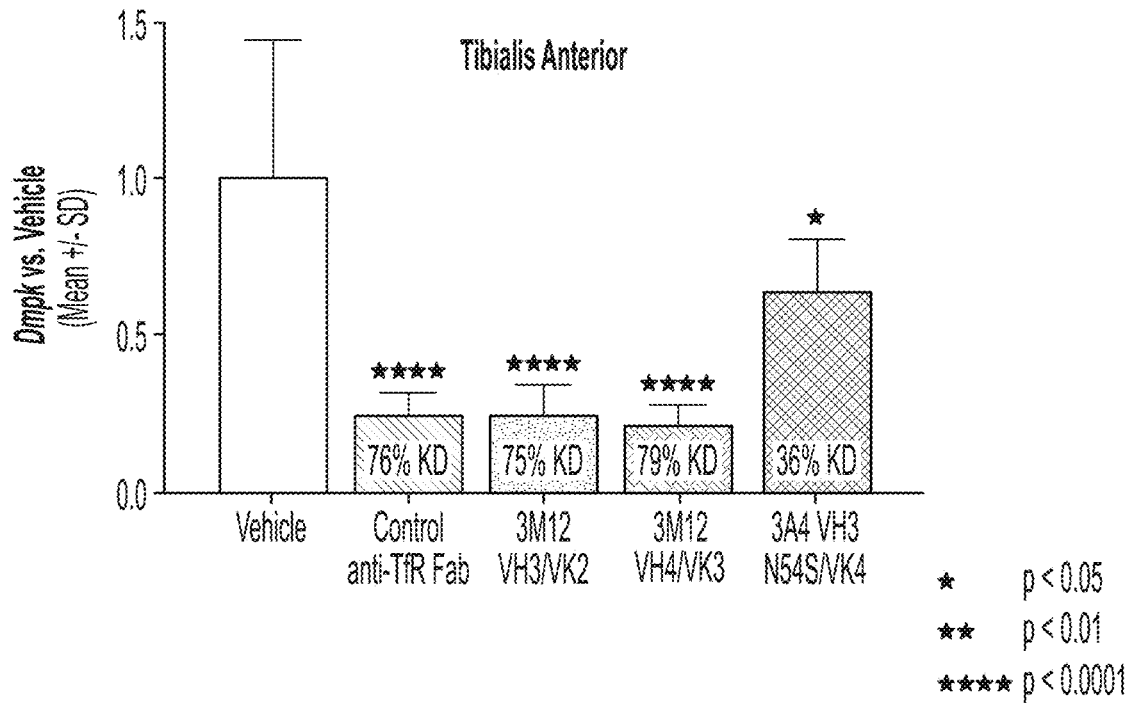
Figure 30C:
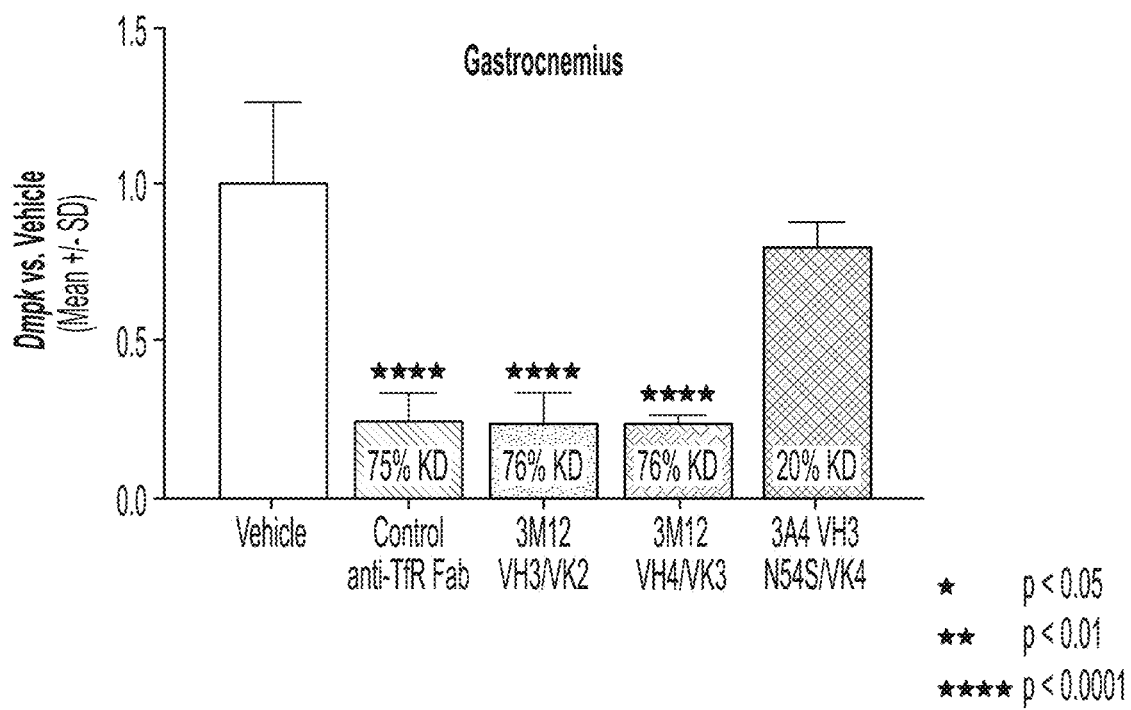
Figure 30D:
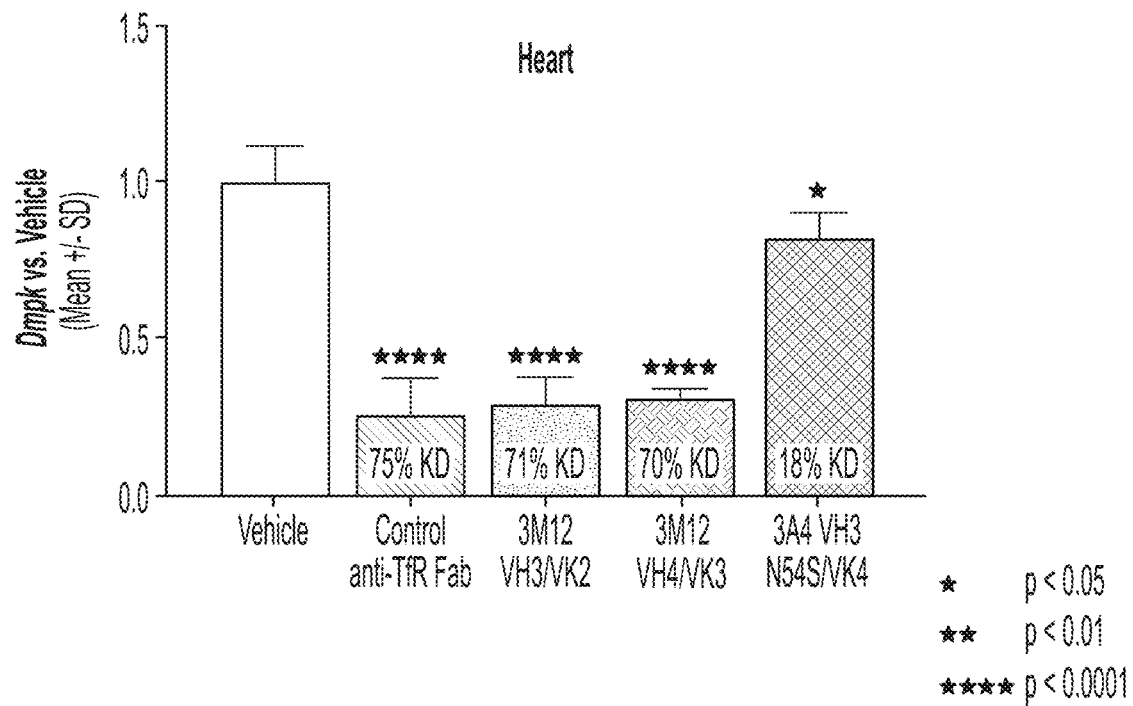
Figure 30E:
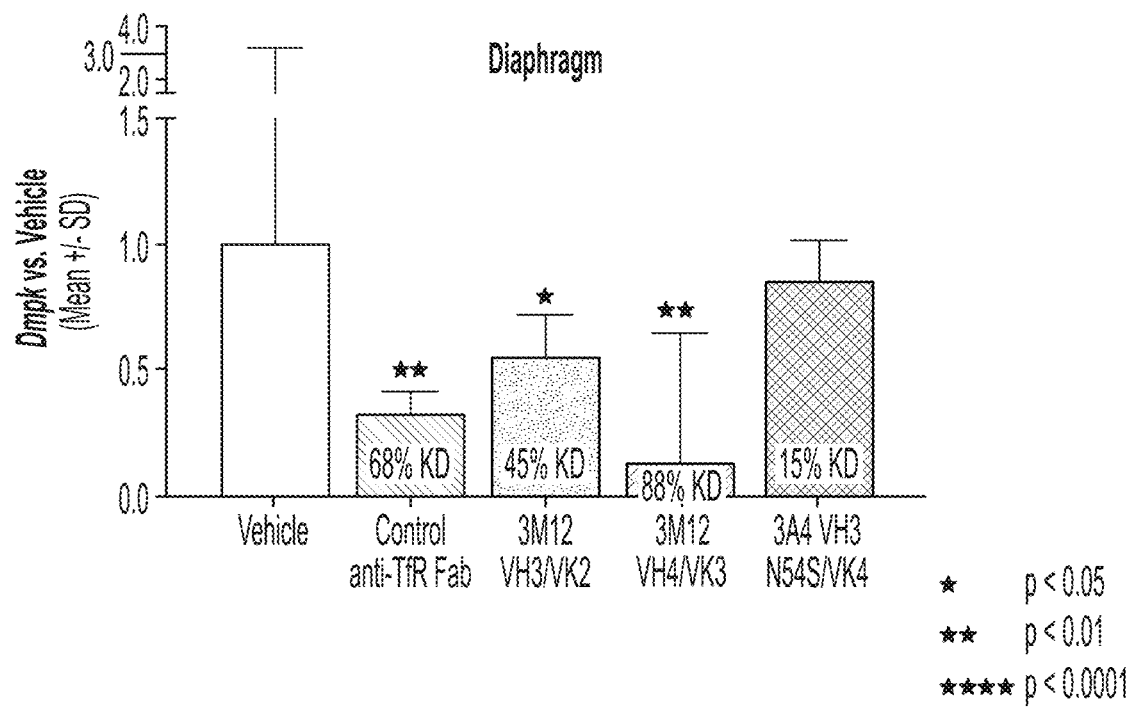

Male and female C57BL/6 mice where one TfR allele was replaced with a human TFR1 allele were administered between the ages of 5 and 15 weeks according to the dosing schedule outlined in Table 18 and in FIG. 30A. Mice were sacrificed 14 days after the first injection and selected muscles collected as indicated in Table 19.

TABLE 18

| Group | Animal No. | Treatment Antibody | Treatment Oligo | Dose Level (mg/kg) | Dose Volume (mL/kg) | Dosing Regimen | Terminal Time Point |
|---|---|---|---|---|---|---|---|
| 1 | 4 | Vehicle | NA | 0 | 10 | Day 0 and Day 7 by IV | Day 14 |
| 2 | 4 | NA | ASO300 | 10 | 5.0 | | |
| 3 | 4 | control anti-TfR Fab | ASO300 | | 10.2 | | |
| 4 | 4 | 3M12 VH3/VK2 | ASO300 | | 11.5 | | |
| 5 | 4 | 3M12 VH4/VK3 | ASO300 | | 10.1 | | |
| 6 | 4 | 3A4 VH3 N54S/VK4 | ASO300 | | 10.7 | | |

TABLE 19

| Tissue | Storage |
|---|---|
| Gastrocnemius | Right leg of each animal stored in RNALater at −80° C. |
| Tibialis Anterior | One leg (R) of each animal stored in RNALater at −80° C. |
| Heart | Dissect transversally and store the apex in RNAlater at −80° C. |
| Diaphragm | Split in half and collect one half in RNAlater at −80° C. |

Total RNA was extracted on a Maxwell Rapid Sample Concentrator (RSC) Instrument using kits provided by the manufacturer (Promega). Purified RNA was reverse-transcribed and levels of Dmpk and Ppib transcripts determined by qRT-PCR with specific TaqMan assays (ThermoFIsher). Log fold changes in Dmpk expression were calculated according to the $2^{-\Delta\Delta C_T}$ method using Ppib as the reference gene and mice injected with vehicle as the control group. Statistical significance in differences of Dmpk expression between control mice and mice administered with the conjugates were determined by one-way ANOVA with Dunnet's correction for multiple comparisons. As shown in FIGS. 30B-30E, the tested conjugates showed robust activity in reducing DMPK mRNA level in vivo in various muscle tissues.

Example 24. In Vitro Activity of Anti-TfR Conjugates in Patient-Derived Cells

An in vitro experiment was conducted to determine the activities of anti-TfR conjugates in reducing DMPK mRNA expression, correcting BIN1 splicing, and reducing nuclear foci in CM-DM1-32F primary cells expressing a mutant DMPK mRNA containing 380 CUG repeats. The CM-DM1-32F primary cell is an immortalized myoblastic cell line isolated from a DM1 patient (CL5 cells; Described in Arandel et al., Dis Model Mech. 2017 Apr. 1; 10(4): 487-497). Conjugate 1 contains an anti-TfR mAb conjugated to DMPK-targeting oligonucleotide (ASO300). Conjugate 2 contains an anti-TfR Fab conjugated to DMPK ASO-1 (GCGUAGAAGGGCGUCUGCCC; SEQ ID NO: 212).

CL5 cells were seeded at a density of 156,000 cells/cm$^2$, allowed to recover for 24 hours, transferred to differentiation media to induce myotube formation, as described (Arandel et al. Dis Model Mech. (2017) 10(4):487-497) and subsequently exposed to conjugate 1 and conjugate 2 at a payload concentration of 500 nM. Parallel cultures exposed to vehicle PBS served as controls. Cells were harvested after 10 days of culture.

For analysis of gene expression, cells were collected with Qiazol for total RNA extraction with a Qiagen miRNAeasy kit. Purified RNA was reverse-transcribed and levels of DMPK, PPIB, BIN1 transcripts and of the BIN1 mRNA isoform containing exon 11 determined by qRT-PCR with specific TaqMan assays (ThermoFIsher). Log fold changes in DMPK expression were calculated according to the $2^{-\Delta\Delta C_T}$ method using PPIB as the reference gene and cells exposed to vehicle as the control group. Log fold changes in the levels BIN1 isoform containing exon 11 were calculated according to the $2^{-\Delta\Delta C_T}$ method using BIN1 as the reference gene and cells exposed to vehicle as the control group.

To measure the area of mutant DMPK nuclear foci, cells were fixed in 4% formalin, permeabilized with 0.1% Triton X-100 and hybridized at 70° C. with a CAG peptide-nucleic acid probe conjugated to the Cy5 fluorophore. After multiple washes in hybridization buffer and 2×SSC solution, nuclei were counterstained with DAPI. Images were collected at a 400× magnification by confocal microscopy and foci area measured as the area of Cy5 signal contained within the area of DAPI signal. Data were expressed as foci area corrected for nuclear area.

Figure 31A:
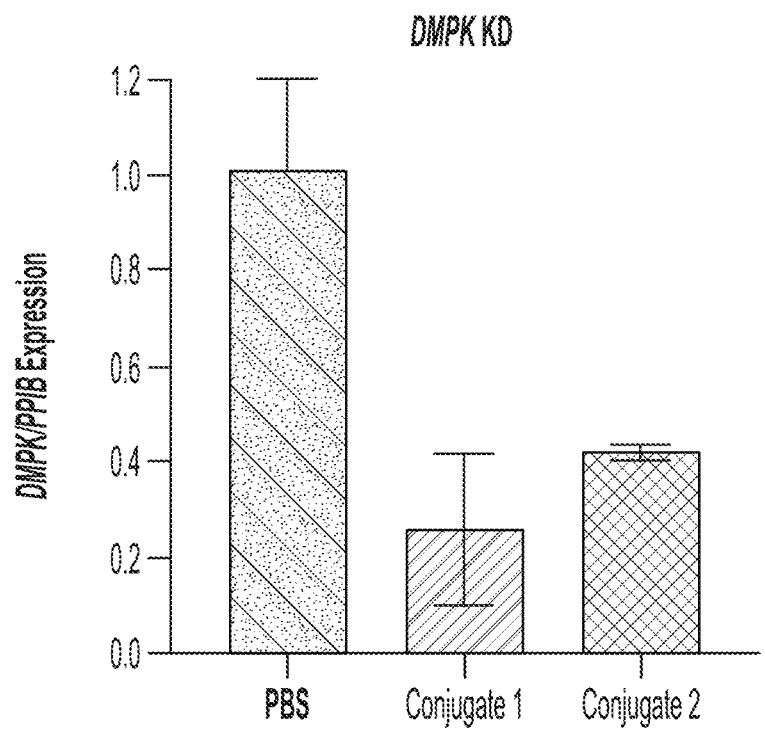
FIGS. 31A-31C show that conjugates containing anti-TfR antibody conjugated to DMPK-targeting oligonucleotide corrected splicing and reduced foci in CM-DM1-32F primary cells expressing a DMPK mutant mRNA containing 380 CUG repeats.
Figure 31B:
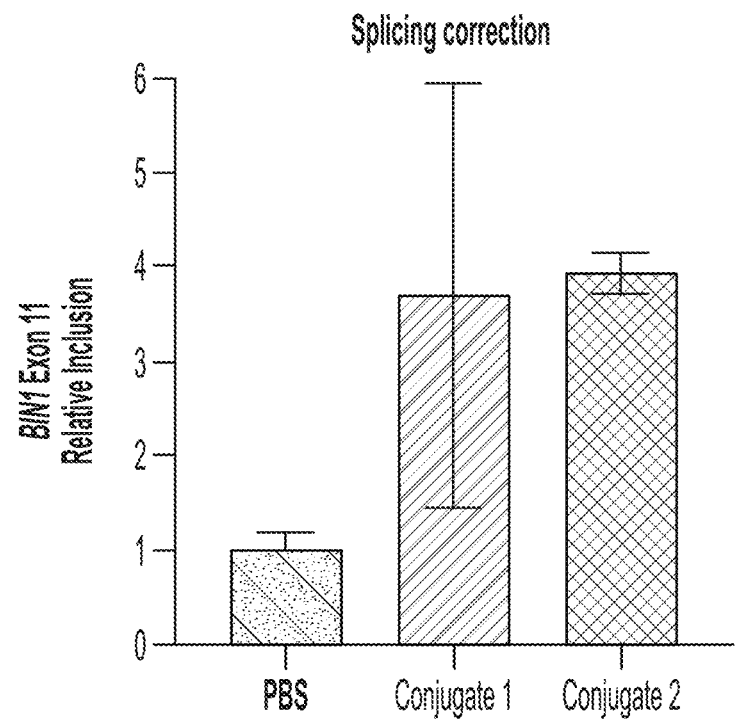
Figure 31C:
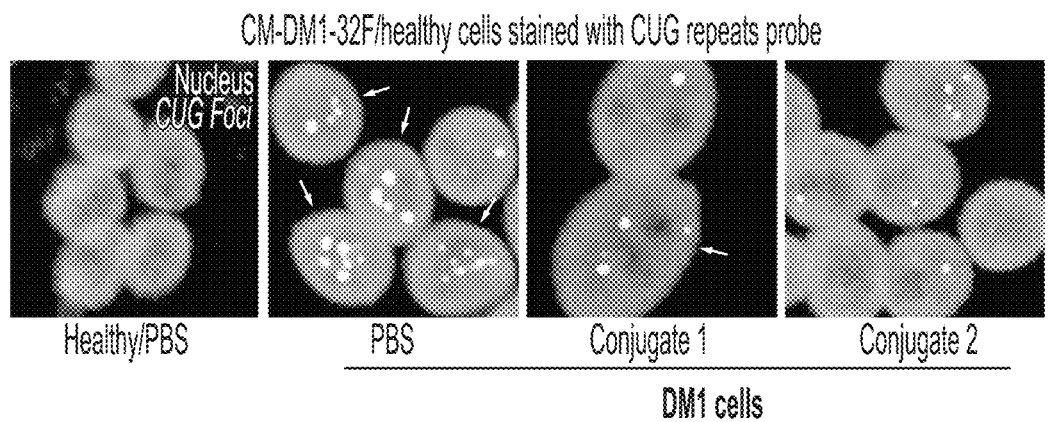
Figure 31C:
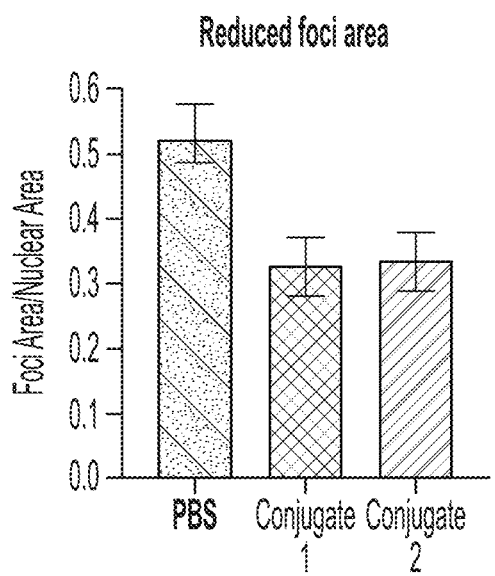

The results show that a single dose of the conjugates containing an anti-TfR (IgG or Fab) conjugated to a DMPK-targeting oligonucleotide (ASO300 or DMPK ASO-1 (SEQ ID NO: 212)) resulted reduced mutant DMPK expression (FIG. 31A), corrected BIN1 splicing (FIG. 31B), and reduced nuclear foci by approximately 40% (FIG. 31C).

Example 25. Characterization of Binding Activities of Anti-TfR Fab 3M12 VH4/Vk3

Figure 32:
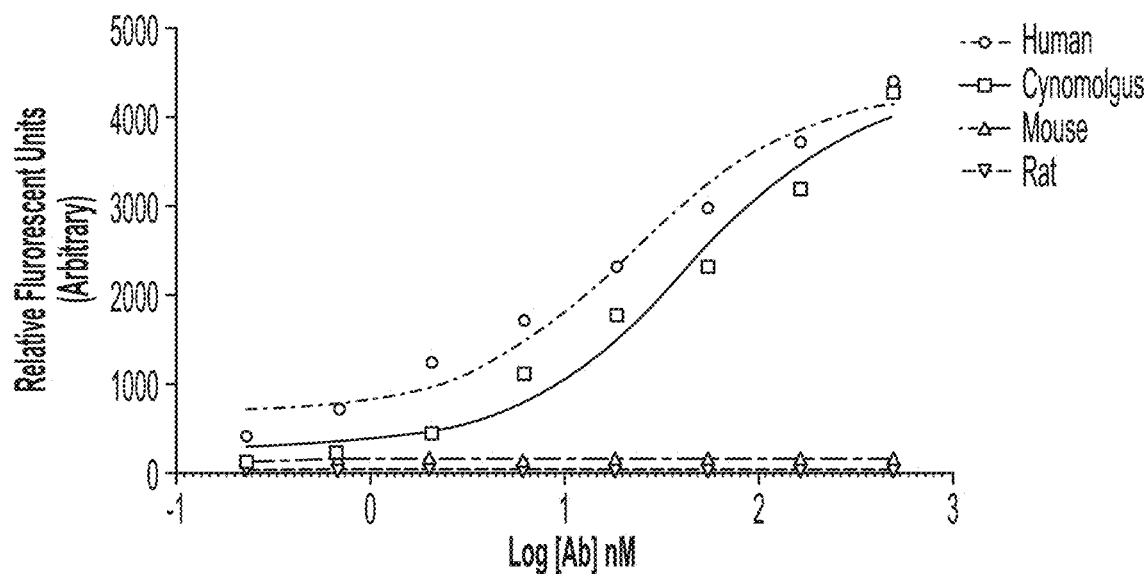
FIG. 32 shows ELISA measurements of binding of anti-TfR Fab 3M12 VH4/Vk3 to recombinant human (circles), cynomolgus monkey (squares), mouse (upward triangles), or rat (downward triangles) TfR1 protein, at a range of concentrations from 230 pM to 500 nM of the Fab. Measurement results show that the anti-TfR Fab is reactive with human and cynomolgus monkey TfR1. Binding was not observed to mouse or rat recombinant TfR1. Data is shown as relative fluorescent units normalized to baseline.

In vitro studies were performed to test the specificity of anti-TfR Fab 3M12 VH4/Vk3 for human and cynomolgus monkey TfR1 binding and to confirm its selectivity for human TfR1 vs TfR2. The binding affinity of anti-TfR Fab 3M12 VH4/Vk3 to TfR1 from various species was determined using an enzyme-linked immunosorbent assay (ELISA). Serial dilutions of the Fab were added to plates precoated with recombinant human, cynomolgus monkey, mouse, or rat TfR1. After a short incubation, binding of the Fab was quantified by addition of a fluorescently tagged anti-(H+L) IgG secondary antibody and measurement of fluorescence intensity at 495 nm excitation and 520 nm emission. The Fab showed strong binding affinity to human and cynomolgus monkey TfR1, and no detectable binding of mouse or rat TfR1 was observed (FIG. 32). Surface plasmon resonance (SPR) measurements were also conducted, and results are shown in Table 20. The $K_d$ of the Fab against the human TfR1 receptor was calculated to be $7.68 \times 10^{-10}$ M and against the cynomolgus monkey TfR1 receptor was calculated to be $5.18 \times 10^{-9}$ M.

TABLE 20

Kinetic analysis of anti-TfR Fab 3M12 VH4/Vk3 binding to human and cynomolgus monkey TfR1 or human TfR2, measured using surface plasmon resonance

| | Anti-TfR Fab 3M12 VH4/Vk3 | | | | |
| --- | --- | --- | --- | --- | --- |
| Target | $K_d$ (M) | $k_a$ ($M^{-1}s^{-1}$) | $k_d$ ($s^{-1}$) | $R_{max}$ | $R_{es}$ SD |
| Human TfR1 | 7.68E−10 | 1.66E+05 | 1.27E−04 | 1.11E+02 | 3.45E+00 |
| Cyno TfR1 | 5.18E−09 | 9.19E+04 | 4.76E−04 | 1.87E+02 | 6.24E+00 |
| Human TfR2 | ND | ND | ND | ND | ND |

ND = No detectable binding by SPR (10 pM-100 uM)

Figure 33:
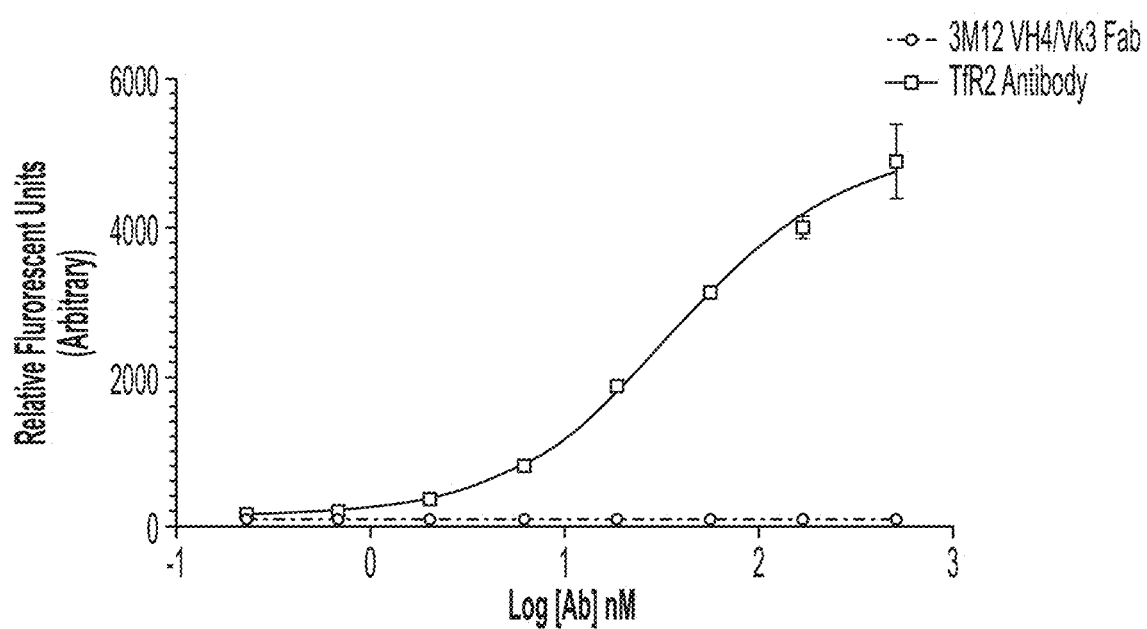
FIG. 33 shows results of an ELISA testing the affinity of anti-TfR Fab 3M12 VH4/Vk3 to recombinant human TfR1 or TfR2 over a range of concentrations from 230 pM to 500 nM of Fab. The data are presented as relative fluorescence units normalized to baseline. The results demonstrate that the Fab does not bind recombinant human TfR2.

To test for cross-reactivity of anti-TfR Fab 3M12 VH4/Vk3 to human TfR2, an ELISA was performed. Recombinant human TfR2 protein was plated overnight at 2 μg/mL and was blocked for 1 hour with 1% bovine serum albumin (BSA) in PBS. Serial dilutions of the Fab or a positive control anti-TfR2 antibody were added in 0.5% BSA/TBST for 1 hour. After washing, anti-(H+L) IgG-A488 (Invitrogen #MA5-25932) fluorescent secondary antibody was added at a 1:500 dilution in 0.5% BSA/TBST and the plate was incubated for 1 hour. Relative fluorescence was measured using a Biotek Synergy plate reader at 495 nm excitation and 520 nm emission. No binding of anti-TfR Fab 3M12 VH4/Vk3 to hTfR2 was observed (FIG. 33).

Example 26. Serum Stability of Anti-TfR Fab-ASO Conjugate

Figure 34:
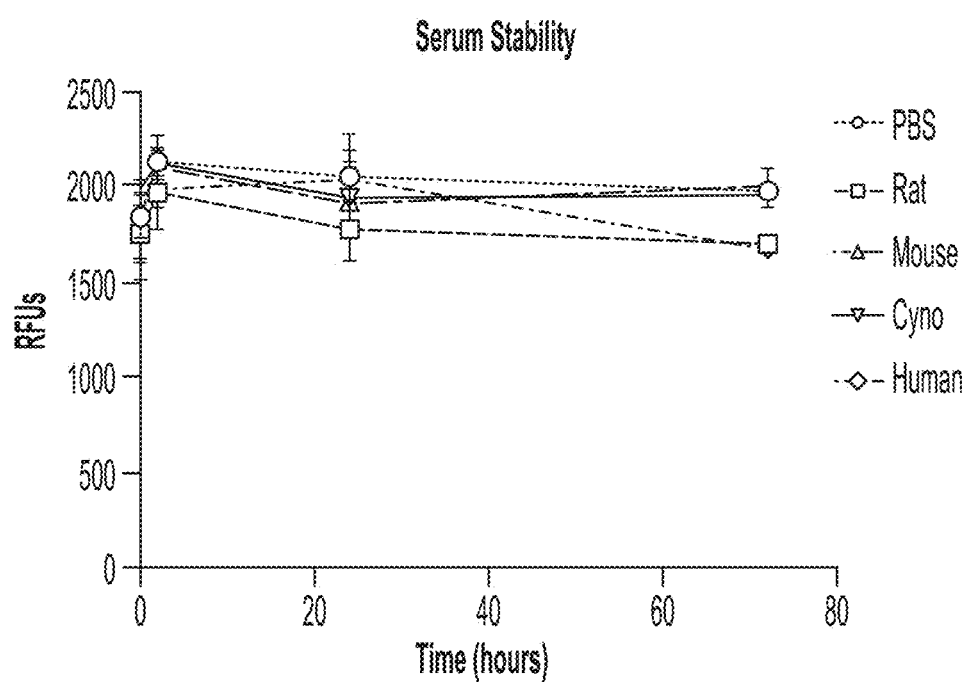
FIG. 34 shows the serum stability of the linker used for linking anti-TfR Fab 3M12 VH4/Vk3 to a control antisense oligonucleotide over 72 hours incubation in PBS or in rat, mouse, cynomolgus monkey or human serum.

Anti-TfR Fab VH4/Vk3 was conjugated to a control antisense oligonucleotide (ASO) via a linker as shown in Formula (C) and the resulting conjugate was tested for stability of the linker conjugating the Fab to the ASO. Serum stability was measured by incubating fluorescently labeled conjugate in PBS or in rat, mouse, cynomolgus monkey, or human serum and measuring relative fluorescence intensity over time, with higher fluorescence indicating more conjugate remaining intact. FIG. 34 shows serum stability was similar across multiple species and remained high after 72 hours.

Example 27. Effect of a Single Dose of an Anti-Mouse TfR Fab Conjugated to an Oligonucleotide (ASO) Against the Human ACTA1 mRNA in HSA$^{LR}$ Mice, a Model of DM1

Six- to 8-week-old homozygous HSA$^{LR}$ mice were allocated randomly to one of five treatment groups and treated with vehicle, a naked oligonucleotide (ASO) targeting human ACTA1 mRNA at a dose of 10 mg/kg or 20 mg/kg, or conjugates containing anti-TfR RI7217 Fab conjugated to the ASO (Ab-ASO) at a dose equivalent to 10 mg/kg or 20 mg/kg of ASO.

Figure 36A:
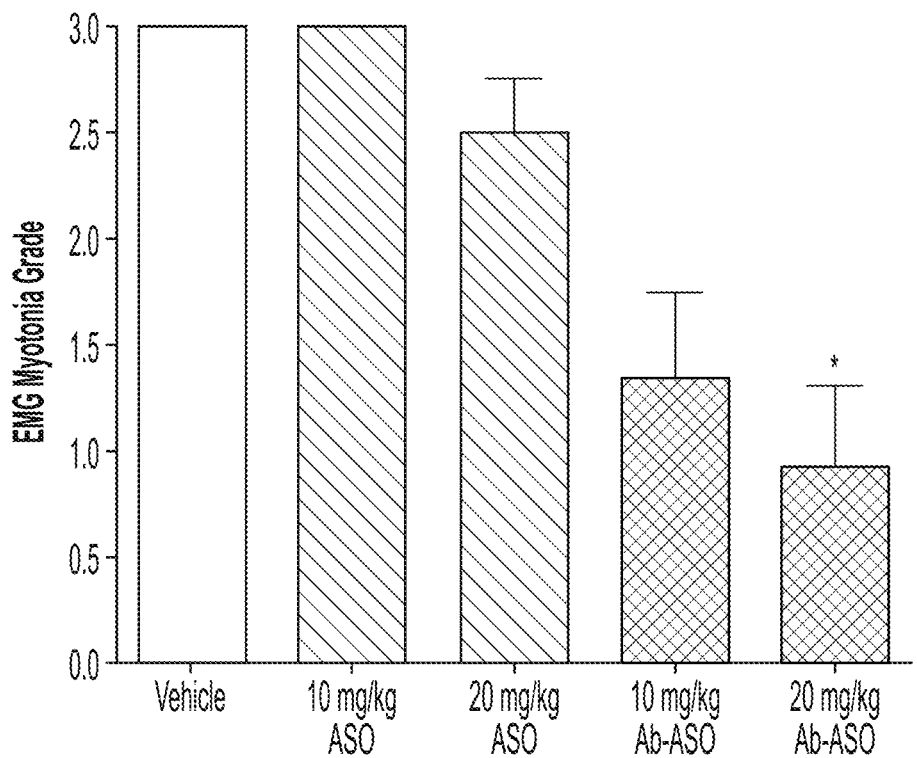
FIGS. 36A-36C show EMG myotonia grade in quadriceps (FIG. 36A), gastrocnemius (FIG. 36B), and tibialis anterior (FIG. 36C) of HSA-LR mice treated with vehicle, a single dose of unconjugated ASO, or a single dose of anti-TfR antibody-ASO conjugate (Ab-ASO). The anti-TfR antibody used is RI7 217 Fab and the oligonucleotide targets human skeletal actin (ACTA1).
Figure 36B:
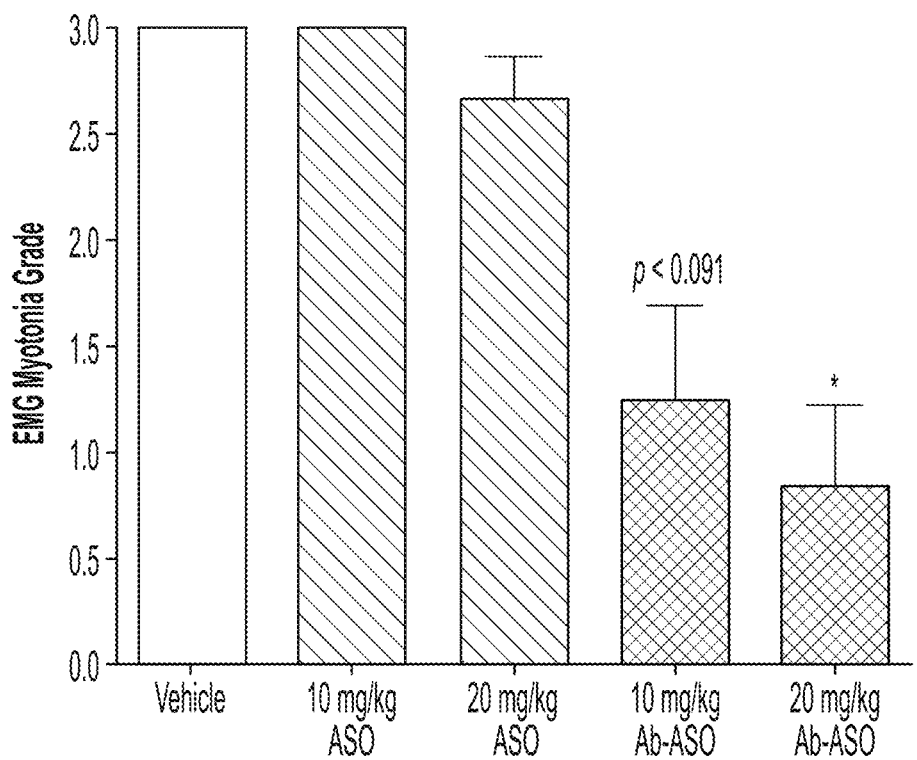
Figure 36C:
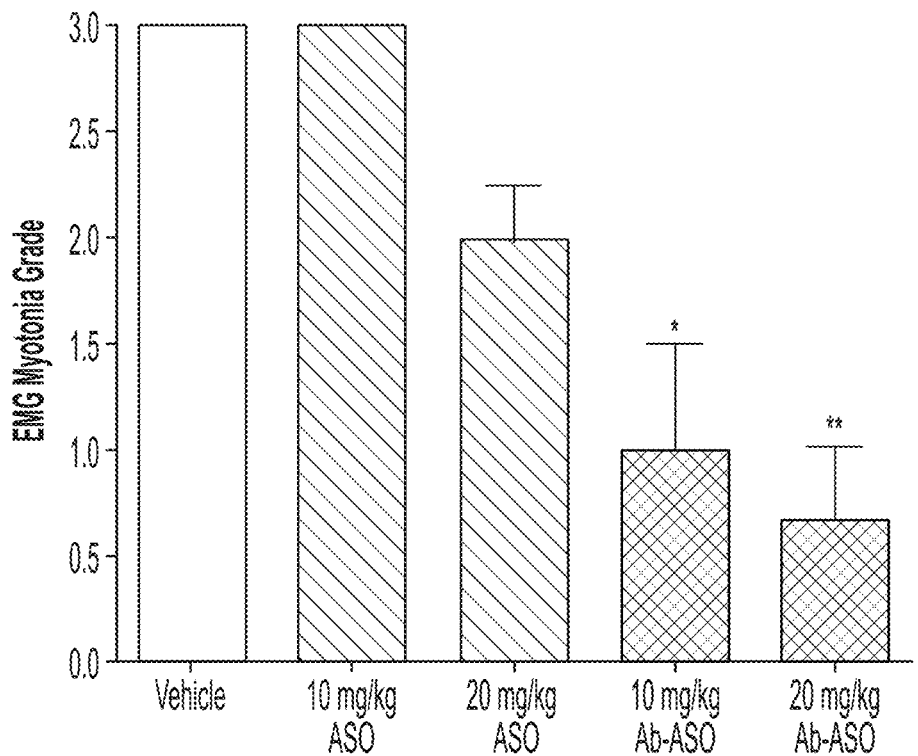

Twenty-eight days after intravenous injections of vehicle, ASO, or Ab-ASO, EMG myotonic discharges in quadriceps (FIG. 36A), gastrocnemius (FIG. 36B), and tibialis anterior (FIG. 36C), were graded by blinded examiner on a 4-point scale in which 0 indicated no myotonia; 1 indicated occasional myotonic discharge in less than 50% of needle insertions; 2 indicated myotonic discharge in greater than 50% of needle insertions; and 3 indicated myotonic discharge with nearly every insertion. A single dose of the conjugate, but not naked ASO, dose-dependently reversed myotonia in the HSA$^{LR}$ DM1 model.

Statistical significance of differences between vehicle-treated group and each experimental arm was determined by Kruskal-Wallis test with Dunn's multiple comparisons test. Data are reported as means±S.E.M.; $*p<0.05$, $**p<0.01$.

Figure 37:
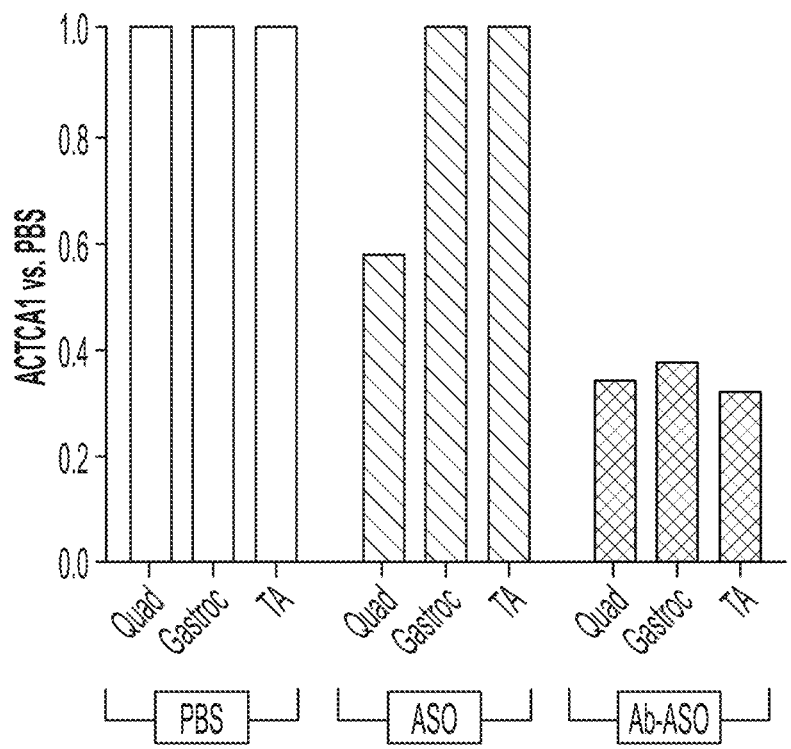
FIG. 37 shows human ACTA1 expression measured by qPCR in $HSA^{LR}$ DM1 mice after a single dose of naked ASO or dose equivalent of anti-TFR antibody-ASO conjugate (Ab-ASO), relative to vehicle-treated mice. The anti-TfR antibody used is RI7 217 Fab and the oligonucleotide targets human skeletal actin (ACTA1).
Figure 38A:
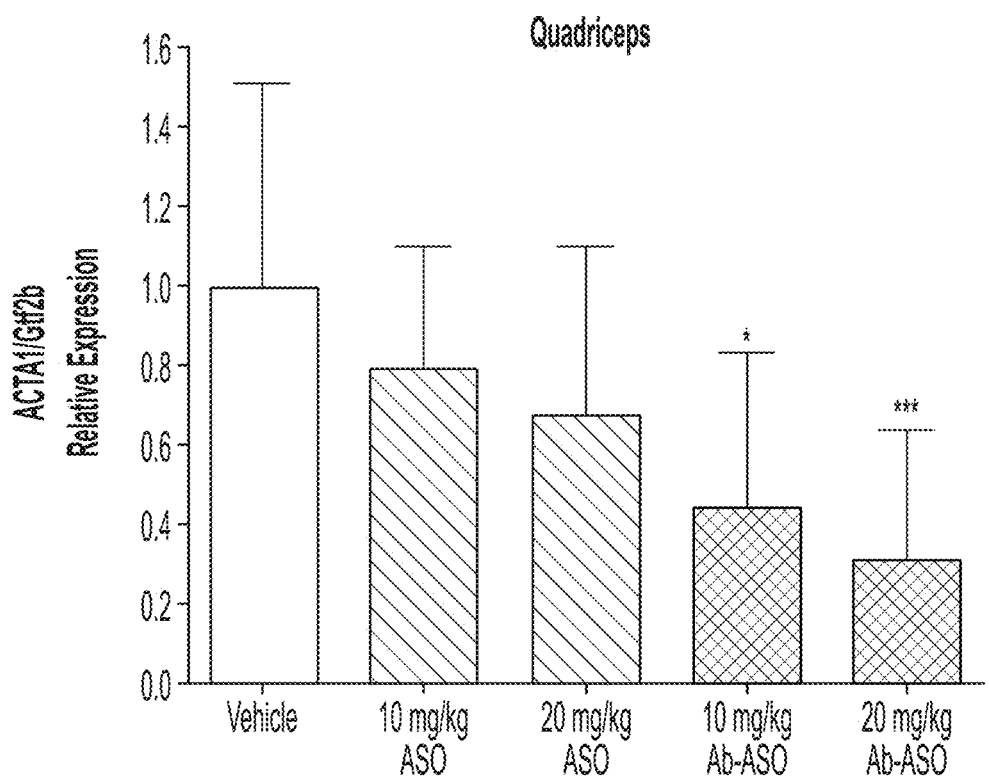
FIGS. 38A-38C show ACTA1 expression in quadriceps (FIG. 38A), gastrocnemius (FIG. 38B), and tibialis anterior (FIG. 38C) in $HSA^{LR}$ DM1 mice after a single dose of 10 mg/kg naked ASO, 20 mg/kg naked ASO, or dose equivalents of anti-TFR antibody-ASO conjugate (Ab-ASO), relative to vehicle-treated mice. The anti-TfR antibody used is RI7 217 Fab and the oligonucleotide targets human skeletal actin (ACTA1). (* $p<0.05$; *** $p<0.001$)
Figure 38B:
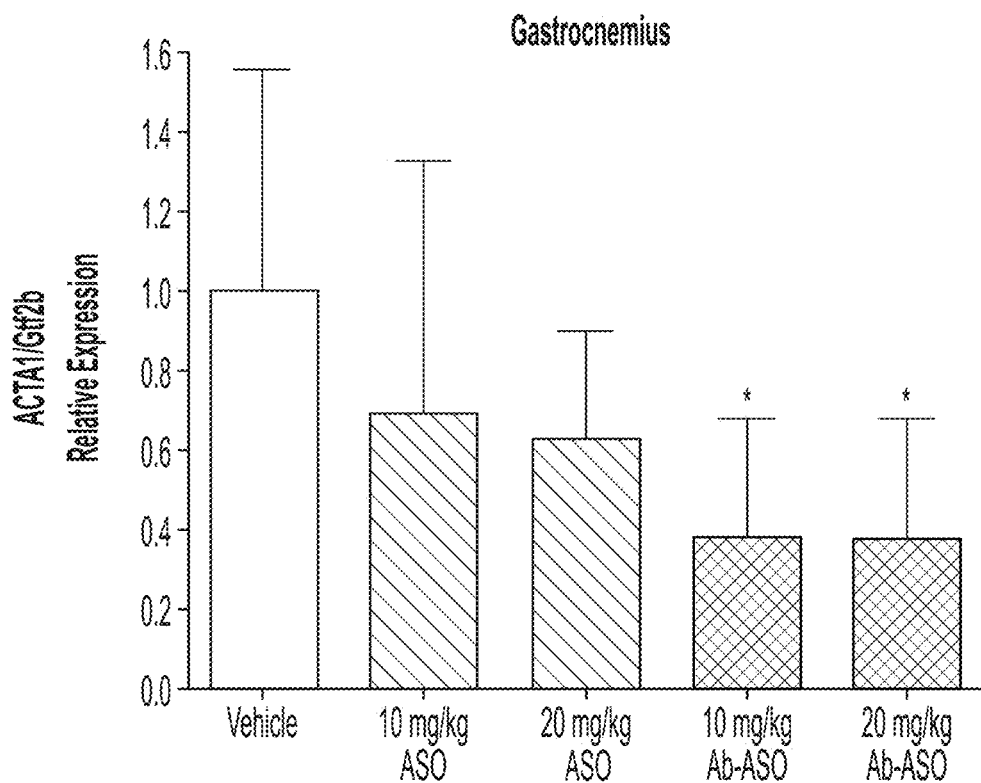
Figure 38C:
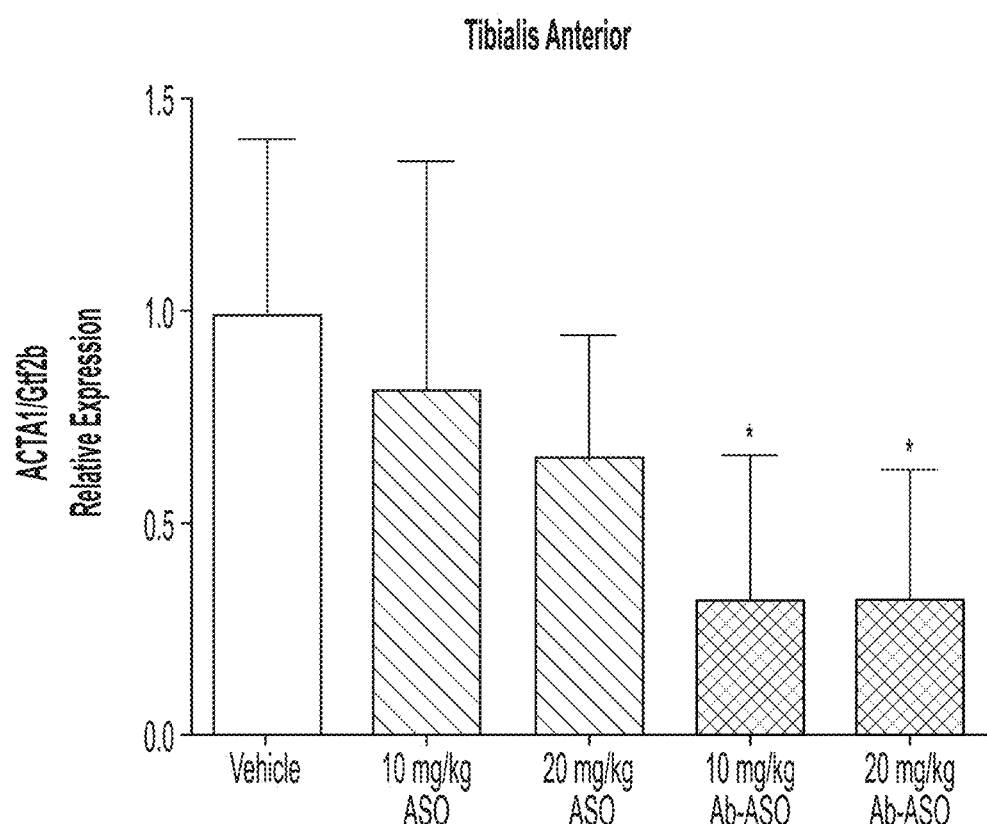

Additionally, fourteen days and twenty-eight days after the treatment mice were sacrificed and quadriceps (quad), gastrocnemius (gastroc) and tibialis anterior (TA) muscles were collected and analyzed for expression of ACTA1. Knockdown (KD) of ACTA1 expression using the Ab-ASO conjugate was observed in quadriceps (quad), gastrocnemius (gastroc) and tibialis anterior (TA) muscles relative to PBS control 14 days following a single administered dose, whereas naked ASO did not facilitate ACTA1 suppression in the same timeframe (FIG. 37). Measurement of ACTA1 in muscle 28 days following the treatment showed that the, the Ab-ASO conjugate reduced ACTA1 expression relative to vehicle control at both tested doses (10 mg/kg ASO equivalent and 20 mg/kg ASO equivalent), whereas the same doses of naked ASO did not facilitate ACTA1 suppression (FIGS. 38A-38C; $*p<0.05$, $**p<0.01$).

ADDITIONAL EMBODIMENTS

1. A complex comprising a muscle-targeting agent covalently linked to a molecular payload configured for inhibiting expression or activity of a DMPK allele comprising a disease-associated-repeat, wherein the muscle-targeting agent specifically binds to an internalizing cell surface receptor on muscle cells,
wherein the muscle targeting agent is a humanized antibody that binds to a transferrin receptor, wherein the antibody comprises:
(i) a heavy chain variable region (VH) comprising an amino acid sequence at least 85% identical to SEQ ID NO: 69; and/or a light chain variable region (VL) comprising an amino acid sequence at least 85% identical to SEQ ID NO: 70;
(ii) a heavy chain variable region (VH) comprising an amino acid sequence at least 85% identical to SEQ ID NO: 71; and/or a light chain variable region (VL) comprising an amino acid sequence at least 85% identical to SEQ ID NO: 70;
(iii) a heavy chain variable region (VH) comprising an amino acid sequence at least 85% identical to SEQ ID NO: 72; and/or a light chain variable region (VL) comprising an amino acid sequence at least 85% identical to SEQ ID NO: 70;
(iv) a heavy chain variable region (VH) comprising an amino acid sequence at least 85% identical to SEQ ID NO: 73; and/or a light chain variable region (VL) comprising an amino acid sequence at least 85% identical to SEQ ID NO: 74;
(v) a heavy chain variable region (VH) comprising an amino acid sequence at least 85% identical to SEQ ID NO: 73; and/or a light chain variable region (VL) comprising an amino acid sequence at least 85% identical to SEQ ID NO: 75;
(vi) a heavy chain variable region (VH) comprising an amino acid sequence at least 85% identical to SEQ ID NO: 76; and/or a light chain variable region (VL) comprising an amino acid sequence at least 85% identical to SEQ ID NO: 74;
(vii) a heavy chain variable region (VH) comprising an amino acid sequence at least 85% identical to SEQ ID NO: 76; and/or a light chain variable region (VL) comprising an amino acid sequence at least 85% identical to SEQ ID NO: 75;
(viii) a heavy chain variable region (VH) comprising an amino acid sequence at least 85% identical to SEQ ID NO: 77; and/or a light chain variable region (VL) comprising an amino acid sequence at least 85% identical to SEQ ID NO: 78;
(ix) a heavy chain variable region (VH) comprising an amino acid sequence at least 85% identical to SEQ ID NO: 79; and/or a light chain variable region (VL) comprising an amino acid sequence at least 85% identical to SEQ ID NO: 80; or
(x) a heavy chain variable region (VH) comprising an amino acid sequence at least 85% identical to SEQ ID NO: 77; and/or a light chain variable region (VL) comprising an amino acid sequence at least 85% identical to SEQ ID NO: 80.

2. The complex of embodiment 1, wherein the antibody comprises:
(i) a VH comprising the amino acid sequence of SEQ ID NO: 69 and a VL comprising the amino acid sequence of SEQ ID NO: 70;
(ii) a VH comprising the amino acid sequence of SEQ ID NO: 71 and a VL comprising the amino acid sequence of SEQ ID NO: 70;
(iii) a VH comprising the amino acid sequence of SEQ ID NO: 72 and a VL comprising the amino acid sequence of SEQ ID NO: 70;
(iv) a VH comprising the amino acid sequence of SEQ ID NO: 73 and a VL comprising the amino acid sequence of SEQ ID NO: 74;
(v) a VH comprising the amino acid sequence of SEQ ID NO: 73 and a VL comprising the amino acid sequence of SEQ ID NO: 75;
(vi) a VH comprising the amino acid sequence of SEQ ID NO: 76 and a VL comprising the amino acid sequence of SEQ ID NO: 74;
(vii) a VH comprising the amino acid sequence of SEQ ID NO: 76 and a VL comprising the amino acid sequence of SEQ ID NO: 75;
(viii) a VH comprising the amino acid sequence of SEQ ID NO: 77 and a VL comprising the amino acid sequence of SEQ ID NO: 78;
(ix) a VH comprising the amino acid sequence of SEQ ID NO: 79 and a VL comprising the amino acid sequence of SEQ ID NO: 80; or
(x) a VH comprising the amino acid sequence of SEQ ID NO: 77 and a VL comprising the amino acid sequence of SEQ ID NO: 80.

3. The complex of embodiment 1 or embodiment 2, wherein the antibody is selected from the group consisting of a full-length IgG, a Fab fragment, a Fab' fragment, a F(ab')2 fragment, a scFv, and a Fv.

4. The complex of embodiment 3, wherein the antibody is a full-length IgG, optionally wherein the full-length IgG comprises a heavy chain constant region of the isotype IgG1, IgG2, IgG3, or IgG4.

5. The complex of embodiment 4, wherein the antibody comprises:
(i) a heavy chain comprising an amino acid sequence at least 85% identical to SEQ ID NO: 84; and/or a light chain comprising an amino acid sequence at least 85% identical to SEQ ID NO: 85;
(ii) a heavy chain comprising an amino acid sequence at least 85% identical to SEQ ID NO: 86; and/or a light chain comprising an amino acid sequence at least 85% identical to SEQ ID NO: 85;
(iii) a heavy chain comprising an amino acid sequence at least 85% identical to SEQ ID NO: 87; and/or a light chain comprising an amino acid sequence at least 85% identical to SEQ ID NO: 85;
(iv) a heavy chain comprising an amino acid sequence at least 85% identical to SEQ ID NO: 88; and/or a light chain comprising an amino acid sequence at least 85% identical to SEQ ID NO: 89;
(v) a heavy chain comprising an amino acid sequence at least 85% identical to SEQ ID NO: 88; and/or a light chain comprising an amino acid sequence at least 85% identical to SEQ ID NO: 90;
(vi) a heavy chain comprising an amino acid sequence at least 85% identical to SEQ ID NO: 91; and/or a light chain comprising an amino acid sequence at least 85% identical to SEQ ID NO: 89;
(vii) a heavy chain comprising an amino acid sequence at least 85% identical to SEQ ID NO: 91; and/or a light chain comprising an amino acid sequence at least 85% identical to SEQ ID NO: 90;
(viii) a heavy chain comprising an amino acid sequence at least 85% identical to SEQ ID NO: 92; and/or a light chain comprising an amino acid sequence at least 85% identical to SEQ ID NO: 93;
(ix) a heavy chain comprising an amino acid sequence at least 85% identical to SEQ ID NO: 94; and/or a light chain comprising an amino acid sequence at least 85% identical to SEQ ID NO: 95; or
(x) a heavy chain comprising an amino acid sequence at least 85% identical to SEQ ID NO: 92; and/or a light chain comprising an amino acid sequence at least 85% identical to SEQ ID NO: 95.

6. The complex of embodiment 3, wherein the antibody is a Fab fragment.

7. The complex of embodiment 6, wherein the antibody comprises:
(i) a heavy chain comprising an amino acid sequence at least 85% identical to SEQ ID NO: 97; and/or a light chain comprising an amino acid sequence at least 85% identical to SEQ ID NO: 85;
(ii) a heavy chain comprising an amino acid sequence at least 85% identical to SEQ ID NO: 98; and/or a light chain comprising an amino acid sequence at least 85% identical to SEQ ID NO: 85;
(iii) a heavy chain comprising an amino acid sequence at least 85% identical to SEQ ID NO: 99; and/or a light chain comprising an amino acid sequence at least 85% identical to SEQ ID NO: 85;
(iv) a heavy chain comprising an amino acid sequence at least 85% identical to SEQ ID NO: 100; and/or a light chain comprising an amino acid sequence at least 85% identical to SEQ ID NO: 89;
(v) a heavy chain comprising an amino acid sequence at least 85% identical to SEQ ID NO: 100; and/or a light chain comprising an amino acid sequence at least 85% identical to SEQ ID NO: 90;
(vi) a heavy chain comprising an amino acid sequence at least 85% identical to SEQ ID NO: 101; and/or a light chain comprising an amino acid sequence at least 85% identical to SEQ ID NO: 89;
(vii) a heavy chain comprising an amino acid sequence at least 85% identical to SEQ ID NO: 101; and/or a light chain comprising an amino acid sequence at least 85% identical to SEQ ID NO: 90;
(viii) a heavy chain comprising an amino acid sequence at least 85% identical to SEQ ID NO: 102; and/or a light chain comprising an amino acid sequence at least 85% identical to SEQ ID NO: 93;
(ix) a heavy chain comprising an amino acid sequence at least 85% identical to SEQ ID NO: 103; and/or a light chain comprising an amino acid sequence at least 85% identical to SEQ ID NO: 95; or
(x) a heavy chain comprising an amino acid sequence at least 85% identical to SEQ ID NO: 102; and/or a light chain comprising an amino acid sequence at least 85% identical to SEQ ID NO: 95.

8. The complex of embodiment 6 or embodiment 7, wherein the antibody comprises:
(i) a heavy chain comprising the amino acid sequence of SEQ ID NO: 97; and a light chain comprising the amino acid sequence of SEQ ID NO: 85;
(ii) a heavy chain comprising the amino acid sequence of SEQ ID NO: 98; and a light chain comprising the amino acid sequence of SEQ ID NO: 85;
(iii) a heavy chain comprising the amino acid sequence of SEQ ID NO: 99; and a light chain comprising the amino acid sequence of SEQ ID NO: 85;
(iv) a heavy chain comprising the amino acid sequence of SEQ ID NO: 100; and a light chain comprising the amino acid sequence of SEQ ID NO: 89;
(v) a heavy chain comprising the amino acid sequence of SEQ ID NO: 100; and a light chain comprising the amino acid sequence of SEQ ID NO: 90;
(vi) a heavy chain comprising the amino acid sequence of SEQ ID NO: 101; and a light chain comprising the amino acid sequence of SEQ ID NO: 89;
(vii) a heavy chain comprising the amino acid sequence of SEQ ID NO: 101; and a light chain comprising the amino acid sequence of SEQ ID NO: 90;
(viii) a heavy chain comprising the amino acid sequence of SEQ ID NO: 102; and a light chain comprising the amino acid sequence of SEQ ID NO: 93;
(ix) a heavy chain comprising the amino acid sequence of SEQ ID NO: 103; and a light chain comprising the amino acid sequence of SEQ ID NO: 95; or
(x) a heavy chain comprising the amino acid sequence of SEQ ID NO: 102; and a light chain comprising the amino acid sequence of SEQ ID NO: 95.

9. The complex of any one of embodiments 1 to 8, wherein the equilibrium dissociation constant ($K_D$) of binding of the antibody to the transferrin receptor is in a range from $10^{-11}$ M to $10^{-6}$ M.

10. The complex of any one of embodiments 1 to 9, wherein the antibody does not specifically bind to the transferrin binding site of the transferrin receptor and/or wherein the antibody does not inhibit binding of transferrin to the transferrin receptor.

11. The complex of any one of embodiments 1 to 10, wherein the antibody is cross-reactive with extracellular epitopes of two or more of a human, non-human primate and rodent transferrin receptor.

12. The complex of any one of embodiments 1 to 11, wherein the complex is configured to promote transferrin receptor mediated internalization of the molecular payload into a muscle cell.

13. The complex of any one of embodiments 1 to 12, wherein the antibody is a chimeric antibody, optionally wherein the chimeric antibody is a humanized monoclonal antibody.

14. The complex of any one of embodiments 1 to 13, wherein the antibody is in the form of a ScFv, Fab fragment, Fab' fragment, F(ab')$_2$ fragment, or Fv fragment.

15. The complex of any one of embodiments 1 to 14, wherein the molecular payload is an oligonucleotide.

16. The complex of embodiment 15, wherein the oligonucleotide comprises at least 15 consecutive nucleotides of a sequence comprising any one of SEQ ID NOs: 148-383 and 621-638.

17. The complex of embodiment 16, wherein the oligonucleotide comprises a sequence comprising any one of SEQ ID NOs: 148-383 and 621-638.

18. The complex of embodiment 17, wherein the oligonucleotide comprises a sequence comprising any one of SEQ ID NOs: 159, 162, 172, 174, 180, 182, 188, 190, 195, 196, 201, 203, 212, 215, 218, 222, 248, and 264.

18.1. The complex of embodiment 18, wherein the oligonucleotide comprises a sequence comprising any one of SEQ ID NOs: 180, 212, and 222.

19. The complex of any one of embodiments 1-14, wherein the oligonucleotide comprises a region of complementarity to any one of SEQ ID NO: 384-619.

20. The complex of embodiment 19, wherein the oligonucleotide comprises a region of complementarity to at least 15 consecutive nucleotides of any one of SEQ ID NO: 384-619.

21. The complex of any one of embodiments 15 to 20, wherein the oligonucleotide comprises a region of complementarity to the DMPK allele comprising the disease-associated-repeat expansion.

22. The complex of any one of embodiments 1 to 14, wherein the molecular payload is a polypeptide.

23. The complex of embodiment 22, wherein the polypeptide is a muscleblind-like (MBNL) polypeptide.

24. The complex of any one of embodiments 15 to 21, wherein the oligonucleotide comprises an antisense strand that hybridizes, in a cell, with a wild-type DMPK mRNA transcript encoded by the allele, wherein the DMPK mRNA transcript comprises repeating units of a CUG trinucleotide sequence.

25. The complex of any one of embodiments 15 to 21, wherein the oligonucleotide comprises an antisense strand that hybridizes, in a cell, with a mutant DMPK mRNA transcript encoded by the allele, wherein the DMPK mRNA transcript comprises repeating units of a CUG trinucleotide sequence.

26. The complex of any one of embodiments 1 to 25, wherein the disease-associated-repeat is 38 to 200 repeating units in length.

27. The complex of embodiment 26, wherein the disease-associated-repeat is associated with late onset myotonic dystrophy.

28. The complex of any one of embodiments 1 to 25, wherein the disease-associated-repeat is 100 to 10,000 repeat units in length.
29. The complex of embodiment 28, wherein the disease-associated-repeat is associated with congenital myotonic dystrophy.
30. The complex of any one of embodiments 15 to 21 and 24 to 29, wherein the oligonucleotide comprises at least one modified internucleotide linkage.
31. The complex of embodiment 30, wherein the at least one modified internucleotide linkage is a phosphorothioate linkage.
32. The complex of embodiment 31, wherein the oligonucleotide comprises phosphorothioate linkages in the Rp stereochemical conformation and/or in the Sp stereochemical conformation.
33. The complex of embodiment 32, wherein the oligonucleotide comprises phosphorothioate linkages that are all in the Rp stereochemical conformation or that are all in the Sp stereochemical conformation.
34. The complex of any one of embodiments 15 to 21 and 24 to 33, wherein the oligonucleotide comprises one or more modified nucleotides.
35. The complex of embodiment 34, wherein the one or more modified nucleotides are 2'-modified nucleotides.
36. The complex of any one of embodiments 15 to 21 and 24 to 35, wherein the oligonucleotide is a gapmer oligonucleotide that directs RNAse H-mediated cleavage of a DMPK mRNA transcript in a cell.
37. The complex of embodiment 36, wherein the gapmer oligonucleotide comprises a central portion of 5 to 15 deoxyribonucleotides flanked by wings of 2 to 8 modified nucleotides.
38. The complex of embodiment 37, wherein the modified nucleotides of the wings are 2'-modified nucleotides.
39. The complex of any one of embodiments 15 to 21 and 24 to 35, wherein the oligonucleotide is a mixmer oligonucleotide.
40. The complex of embodiment 39, wherein the mixmer oligonucleotide inhibits binding of muscleblind-like protein 1, muscleblind-like protein 2, or muscleblind-like protein 3 to the DMPK mRNA transcript.
41. The complex of embodiment 39 or 40, wherein the mixmer oligonucleotide comprises two or more different 2' modified nucleotides.
42. The complex of any one of embodiments 15 or 21 and 24 to 35, wherein the oligonucleotide is an RNAi oligonucleotide that promotes RNAi-mediated cleavage of the DMPK mRNA transcript.
43. The complex of embodiment 42, wherein the RNAi oligonucleotide is a double-stranded oligonucleotide of 19 to 25 nucleotides in length.
44. The complex of embodiment 42 or 43, wherein the RNAi oligonucleotide comprises at least one 2' modified nucleotide.
45. The complex of any one of embodiments 35, 38, 41, or 44, wherein each 2' modified nucleotide is selected from the group consisting of: 2'-O-methyl, 2'-fluoro (2'-F), 2'-O-methoxyethyl (2'-MOE), and 2', 4'-bridged nucleotides.
46. The complex of embodiment 34, wherein the one or more modified nucleotides are bridged nucleotides.
47. The complex of any one of embodiment 35, 38, 41, or 44, wherein at least one 2' modified nucleotide is a 2',4'-bridged nucleotide selected from: 2',4'-constrained 2'-O-ethyl (cEt) and locked nucleic acid (LNA) nucleotides.
48. The complex of any one of embodiments 15 to 21 and 24 to 35, wherein the oligonucleotide comprises a guide sequence for a genome editing nuclease.
49. The complex of any one of embodiments 15 to 21 and 24 to 35, wherein the oligonucleotide is phosphorodiamidite morpholino oligomer.
50. The complex of any one of embodiments 1 to 49, wherein the muscle-targeting agent is covalently linked to the molecular payload via a cleavable linker.
51. The complex of embodiment 50, wherein the cleavable linker is selected from: a protease-sensitive linker, pH-sensitive linker, and glutathione-sensitive linker.
52. The complex of embodiment 51, wherein the cleavable linker is a protease-sensitive linker.
53. The complex of embodiment 52, wherein the protease-sensitive linker comprises a sequence cleavable by a lysosomal protease and/or an endosomal protease.
54. The complex of embodiment 52, wherein the protease-sensitive linker comprises a valine-citrulline dipeptide sequence.
55. The complex of embodiment 51, wherein the linker is pH-sensitive linker that is cleaved at a pH in a range of 4 to 6.
56. The complex of any one of embodiments 1 to 49, wherein the muscle-targeting agent is covalently linked to the molecular payload via a non-cleavable linker.
57. The complex of embodiment 56, wherein the non-cleavable linker is an alkane linker.
58. The complex of any of embodiments 2 to 57, wherein the antibody comprises a non-natural amino acid to which the oligonucleotide is covalently linked.
59. The complex of any of embodiments 2 to 57, wherein the antibody is covalently linked to the oligonucleotide via conjugation to a lysine residue or a cysteine residue of the antibody.
60. The complex of embodiment 59, wherein the antibody is conjugated to the cysteine via a maleimide-containing linker, optionally wherein the maleimide-containing linker comprises a maleimidocaproyl or maleimidomethyl cyclohexane-1-carboxylate group.
61. The complex of any one of embodiments 2 to 60, wherein the antibody is a glycosylated antibody that comprises at least one sugar moiety to which the oligonucleotide is covalently linked.
62. The complex of embodiment 61, wherein the sugar moiety is a branched mannose.
63. The complex of embodiment 61 or 62, wherein the antibody is a glycosylated antibody that comprises one to four sugar moieties each of which is covalently linked to a separate oligonucleotide.
64. The complex of embodiment 61, wherein the antibody is a fully-glycosylated antibody.
65. The complex of embodiment 61, wherein the antibody is a partially-glycosylated antibody.
66. The complex of embodiment 65, wherein the partially-glycosylated antibody is produced via chemical or enzymatic means.
67. The complex of embodiment 65, wherein the partially-glycosylated antibody is produced in a cell, cell that is deficient for an enzyme in the N- or O-glycosylation pathway.
68. A method of delivering a molecular payload to a cell expressing transferrin receptor, the method comprising contacting the cell with the complex of any one of embodiments 1 to 67.
69. A method of inhibiting activity of DMPK in a cell, the method comprising contacting the cell with the complex of any one of embodiments 1 to 67 in an amount effective for promoting internalization of the molecular payload to the cell.
70. The method of embodiment 69, wherein the cell is in vitro.
71. The method of embodiment 69, wherein the cell is in a subject.
72. The method of embodiment 71, wherein the subject is a human.
73. The method of any one of embodiments 69 to 72, wherein the complex inhibits the expression of DMPK.
74. The method of any one of embodiments 69 to 73, wherein the cell is contacted with a single dose of the complex.
75. The method of embodiment 74, wherein a single dose of the complex inhibits the expression of DMPK for at least two, four, eight, or twelve weeks.
76. The method of embodiment 75, wherein the complex inhibits the expression of DMPK by at least 30%, 40%, 50%, or 60% relative to a control.
77. The method of embodiment 75 or 76, the complex inhibits the expression of DMPK in muscle tissues by 40-60% for at least 12 weeks following administration of the single dose, relative to a control
78. A method of treating a subject having an expansion of a disease-associated-repeat of a DMPK allele that is associated with myotonic dystrophy, the method comprising administering to the subject an effective amount of the complex of any one of embodiments 1 to 67.
79. The method of embodiment 78, wherein the disease-associated-repeat comprises repeating units of a trinucleotide sequence.
80. The method of embodiment 78, wherein the trinucleotide sequence is a CTG trinucleotide sequence.
81. The method of any one of embodiments 78 to 80, wherein the disease-associated-repeat is 38 to 200 repeating units in length.
82. The method of 81, wherein the disease-associated-repeat is associated with late onset myotonic dystrophy.
83. The method of any one of embodiments 78 to 80, wherein the disease-associated-repeat is 100 to 10,000 repeating units in length.
84. The method of 83, wherein the disease-associated-repeat is associated with congenital myotonic dystrophy.
85. The method of any one of embodiments 78 to 84, wherein administration of the complex results in inhibition of the expression of DMPK in muscle tissues.
86. The method of any one of embodiments 78 to 85, wherein the complex is intravenously administered to the subject.
87. The method of any one of embodiments 78 to 86, wherein an effective amount of the complex comprises 1-15 mg/kg of RNA.
88. The method of any one of embodiments 78 to 87, wherein the complex is administered to the subject in a single dose.
89. The method of embodiment 88, wherein administration of a single dose of the complex results in inhibition of the expression of DMPK in muscle tissues for at least two, four, eight, or twelve weeks.
90. The method of embodiment 89, wherein the administration of a single dose of the complex results in inhibition of the expression of DMPK in muscle tissues by at least 30%, 40%, 50%, or 60% relative to a control.
91. The method of embodiment 89 or 90, wherein the administration of a single dose of the complex results in inhibition of the expression of DMPK in muscle tissues for at least 12 weeks following administration of the single dose.
92. The method of embodiment 91, wherein the administration of a single dose of the complex results in inhibition of the expression of DMPK in muscle tissues by 40-60%, relative to a control, for at least 12 weeks following administration of the single dose.
93. The method of embodiment 89 or 90, wherein the administration of a single dose of the complex results in inhibition of the expression of DMPK in muscle tissues for a duration of time in the range of 4-8, 5-10, 8-12, 10-14, or 8-16 weeks following administration of the single dose.
94. The method of embodiment 93, wherein the administration of a single dose of the complex results in inhibition of the expression of DMPK in muscle tissues by 40-60%, relative to a control, for a duration of time in the range of 4-8, 5-10, 8-12, 10-14, or 8-16 weeks following administration of the single dose.
95. The method of embodiment 89 or 90, wherein the administration of a single dose of the complex results in inhibition of the expression of DMPK in muscle tissues by 40-60%, relative to a control, at 12 weeks following administration of the single dose.
96. The method of any one of embodiments 78 to 87, wherein the complex is administered to the subject in a single dose once every 4-8, 5-10, 8-12, or 8-16 weeks.
97. The method of embodiment 96, wherein the complex is administered to the subject in a single dose once every 12 weeks.
98. The method of any one of embodiments 88 to 97, wherein the single dose comprises the complex at a concentration of 1-15 mg/kg of RNA.
99. The method of embodiment 98, wherein the single dose comprises the complex at a concentration of 10 mg/kg of RNA.
100. A method of treating a subject having an expansion of a disease-associated-repeat of a DMPK allele that is associated with myotonic dystrophy, the method comprising administering the complex of any one of embodiments 1 to 67 to the subject,
wherein the administration results in inhibition of DMPK expression in muscle tissues by 40-60%, relative to a control, for a duration of time in the range of 4-8, 5-10, 8-12, 10-14, or 8-16 weeks following administration of the complex.
101. A method of inhibiting DMPK expression in a subject, the method comprising administering the complex of any one of embodiments 1 to 67,
wherein the administration results in inhibition of DMPK expression in muscle tissues by 40-60%, relative to a control, for a duration of time in the range of 4-8, 5-10, 8-12, 10-14, or 8-16 weeks following administration of the complex.
102. The method of embodiment 100 or 101, wherein the molecular payload is an oligonucleotide.
103. The method of embodiment 102, wherein the concentration of the complex is 1-15 mg/kg of RNA.
104. A complex comprising an anti-transferrin receptor (TfR) antibody covalently linked to a molecular payload configured for reducing expression or activity of DMPK, wherein the anti-TfR antibody comprises:
(i) a heavy chain variable region (VH) comprising an amino acid sequence at least 85% identical to SEQ ID NO: 76; and/or a light chain variable region (VL) comprising an amino acid sequence at least 85% identical to SEQ ID NO: 75;

(ii) a heavy chain variable region (VH) comprising an amino acid sequence at least 85% identical to SEQ ID NO: 69; and/or a light chain variable region (VL) comprising an amino acid sequence at least 85% identical to SEQ ID NO: 70;

(iii) a heavy chain variable region (VH) comprising an amino acid sequence at least 85% identical to SEQ ID NO: 71; and/or a light chain variable region (VL) comprising an amino acid sequence at least 85% identical to SEQ ID NO: 70;

(iv) a heavy chain variable region (VH) comprising an amino acid sequence at least 85% identical to SEQ ID NO: 72; and/or a light chain variable region (VL) comprising an amino acid sequence at least 85% identical to SEQ ID NO: 70;

(v) a heavy chain variable region (VH) comprising an amino acid sequence at least 85% identical to SEQ ID NO: 73; and/or a light chain variable region (VL) comprising an amino acid sequence at least 85% identical to SEQ ID NO: 74;

(vi) a heavy chain variable region (VH) comprising an amino acid sequence at least 85% identical to SEQ ID NO: 73; and/or a light chain variable region (VL) comprising an amino acid sequence at least 85% identical to SEQ ID NO: 75;

(vii) a heavy chain variable region (VH) comprising an amino acid sequence at least 85% identical to SEQ ID NO: 76; and/or a light chain variable region (VL) comprising an amino acid sequence at least 85% identical to SEQ ID NO: 74;

(viii) a heavy chain variable region (VH) comprising an amino acid sequence at least 85% identical to SEQ ID NO: 77; and/or a light chain variable region (VL) comprising an amino acid sequence at least 85% identical to SEQ ID NO: 78;

(ix) a heavy chain variable region (VH) comprising an amino acid sequence at least 85% identical to SEQ ID NO: 79; and/or a light chain variable region (VL) comprising an amino acid sequence at least 85% identical to SEQ ID NO: 80; or (x) a heavy chain variable region (VH) comprising an amino acid sequence at least 85% identical to SEQ ID NO: 77; and/or a light chain variable region (VL) comprising an amino acid sequence at least 85% identical to SEQ ID NO: 80.

105. A complex comprising an anti-transferrin receptor (TfR) antibody covalently linked to a molecular payload configured for reducing expression or activity of DMPK, wherein the anti-TfR antibody has undergone pyroglutamate formation resulting from a post-translational modification.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or (e.g., and) one or more modified nucleotides and/or (e.g., and) one or more modified internucleotide linkages and/or (e.g., and) one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising an anti-transferrin receptor (TfR) antibody covalently linked to at least one oligonucleotide, wherein the antibody comprises:
   (i) a heavy chain comprising a heavy chain variable region (VH) and a human IgG CH1 domain and lacking a human IgG CH2 domain and CH3 domain, wherein the heavy chain comprises the amino acid sequence of SEQ ID NO: 101, and
   (ii) a light chain comprising a light chain variable region (VL) and a human kappa light chain constant region, wherein the light chain comprises the amino acid sequence of SEQ ID NO: 90;
   wherein each oligonucleotide is covalently linked to a lysine residue of the anti-TfR antibody, and wherein the oligonucleotide targets a Dystrophia Myotonica Protein Kinase (DMPK) RNA.

2. The complex of claim 1, wherein the heavy chain of the antibody comprises an N-terminal pyroglutamate.

3. The complex of claim 1, wherein the oligonucleotide comprises a 5'-X—Y—Z-3' formula, wherein X and Z are flanking regions comprising one or more 2'-modified nucleosides selected from the group consisting of: 2'-O-methyl, 2'-fluoro, 2'-O-methoxyethyl, 2',4'-bridged nucleosides, and combinations thereof, and wherein Y is a gap region and each nucleoside in Y is a 2'-deoxyribonucleoside.

4. The complex of claim 1, wherein the oligonucleotide comprises a region of complementarity to any one of SEQ ID NOs: 384-619, wherein the region of complementarity is 15-20 nucleotides in length.

5. The complex of claim 1, wherein the oligonucleotide comprises a region of complementarity to SEQ ID NO: 458, wherein the region of complementarity is 15-20 nucleotides in length.

6. The complex of claim 1, wherein the oligonucleotide comprises at least 15 consecutive nucleotides of SEQ ID NOs: 148-383, wherein any one or more of the thymine bases (T's) in the oligonucleotide may optionally be a uracil base (U).

7. The complex of claim 1, wherein the oligonucleotide comprises one or more phosphorothioate internucleoside linkages.

8. The complex of claim 1, wherein the antibody is covalently linked to each oligonucleotide via a cleavable linker.

9. The complex of claim 8, wherein the linker comprises a valine-citrulline sequence.

10. The complex of claim 9, wherein the complex comprises a structure of:

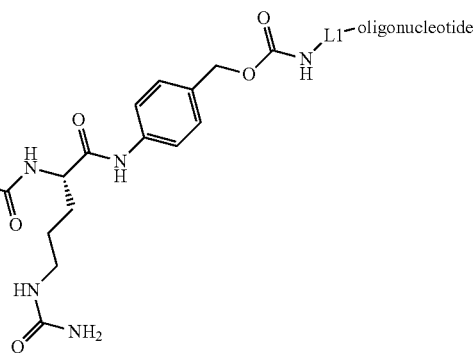
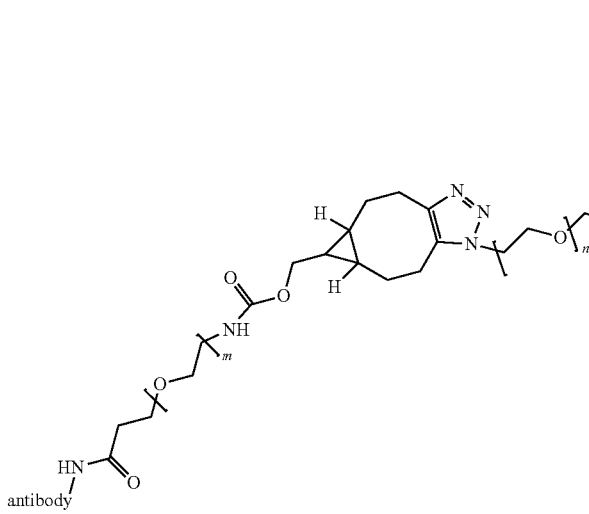

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$, —NR$^A$S(O)$_2$—, or a combination thereof, wherein each R$^A$ is independently hydrogen or substituted or unsubstituted alkyl.

11. The complex of claim 10, wherein L1 comprises

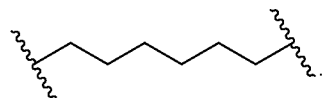 [SMILES: *CCCCCC*]

12. A method of reducing DMPK expression in muscle cells of a subject, the method comprising administering to the subject a composition comprising the complex of claim 1.

13. The method of claim 12, wherein the subject is human.

14. The method of claim 12, wherein the subject has myotonic dystrophy, type 1 (DM1).

15. The method of claim 12, wherein the heavy chain of the antibody comprises an N-terminal pyroglutamate.

16. A complex comprising an anti-transferrin receptor (TfR) antibody covalently linked to at least one oligonucleotide, wherein the antibody comprises:
   (i) a heavy chain comprising a heavy chain variable region (VH) and a portion of a heavy chain constant region, wherein the VH comprises the amino acid sequence of SEQ ID NO: 76 and the portion of the heavy chain constant region consists of the amino acid sequence of SEQ ID NO: 96, and
(ii) a light chain comprising the amino acid sequence of SEQ ID NO: 90;
wherein each oligonucleotide is covalently linked to a lysine residue of the anti-TfR antibody, and wherein the oligonucleotide targets a Dystrophia Myotonica Protein Kinase (DMPK) RNA.

17. The complex of claim 16, wherein the heavy chain of the antibody comprises an N-terminal pyroglutamate.

18. The complex of claim 16, wherein the portion of the heavy chain constant region consists of a CH1 domain and a portion of a hinge region.

19. The complex of claim 16, wherein the oligonucleotide comprises a 5'-X—Y—Z-3' formula, wherein X and Z are flanking regions comprising one or more 2'-modified nucleosides selected from the group consisting of: 2'-O-methyl, 2'-fluoro, 2'-O-methoxyethyl, 2',4'-bridged nucleosides, and combinations thereof, and wherein Y is a gap region and each nucleoside in Y is a 2'-deoxyribonucleoside.

20. The complex of claim 16, wherein the oligonucleotide comprises a region of complementarity to any one of SEQ ID NO: 384-619, wherein the region of complementarity is 15-20 nucleotides in length.

21. The complex of claim 16, wherein the oligonucleotide comprises a region of complementarity to SEQ ID NO: 458, wherein the region of complementarity is 15-20 nucleotides in length.

22. The complex of claim 16, wherein the oligonucleotide comprises at least 15 consecutive nucleotides of SEQ ID NOs: 148-383, wherein any one or more of the thymine bases (T's) in the oligonucleotide may optionally be a uracil base (U).

23. The complex of claim 16, wherein the oligonucleotide comprises one or more phosphorothioate internucleoside linkages.

24. The complex of claim 16, wherein the antibody is covalently linked to each oligonucleotide via a cleavable linker comprising a valine-citrulline sequence.

25. The complex of claim 24, wherein the complex comprises a structure of:

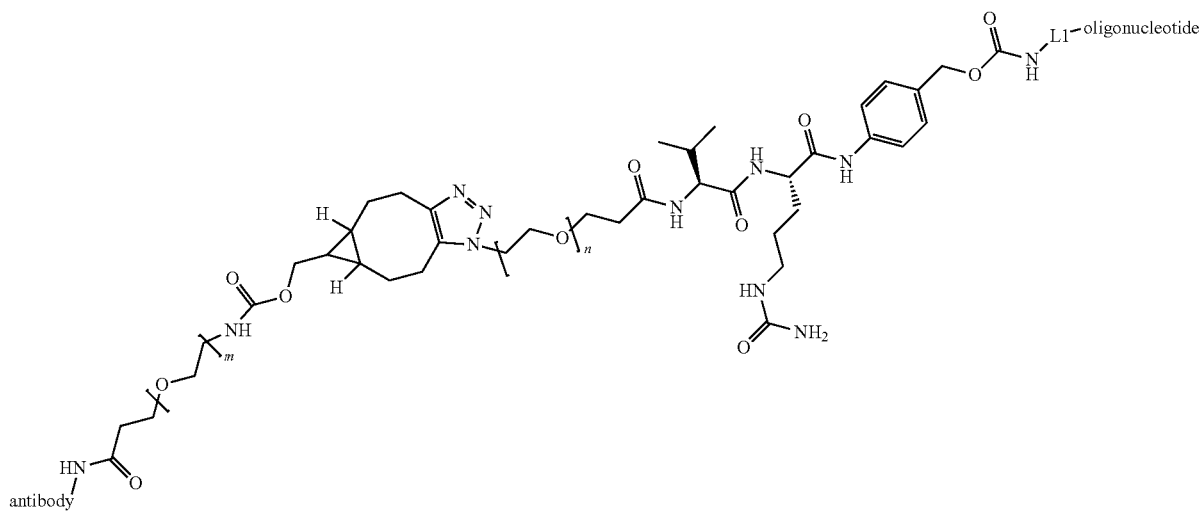

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof, wherein each R$^A$ is independently hydrogen or substituted or unsubstituted alkyl.

26. The complex of claim 25, wherein L1 comprises

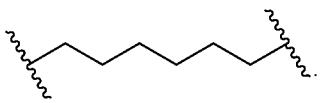 [SMILES: *CCCCCC*]

27. A method of reducing DMPK expression in muscle cells of a subject, the method comprising administering to the subject a composition comprising the complex of claim 16.

28. The method of claim 27, wherein the subject is human.

29. The method of claim 27, wherein the subject has myotonic dystrophy, type 1 (DM1).

30. The method of claim 27, wherein the heavy chain of the antibody comprises an N-terminal pyroglutamate.

* * * * *

UNITED STATES PATENT AND TRADEMARK OFFICE
CERTIFICATE OF CORRECTION

PATENT NO. : 12,102,687 B2
APPLICATION NO. : 18/609032
DATED : October 1, 2024
INVENTOR(S) : Romesh R. Subramanian et al.

Page 1 of 3

It is certified that error appears in the above-identified patent and that said Letters Patent is hereby corrected as shown below:

In the Claims

At Column 398, Claim 10, Lines 6-44:
10. The complex of claim 9, wherein the complex comprises a structure of:

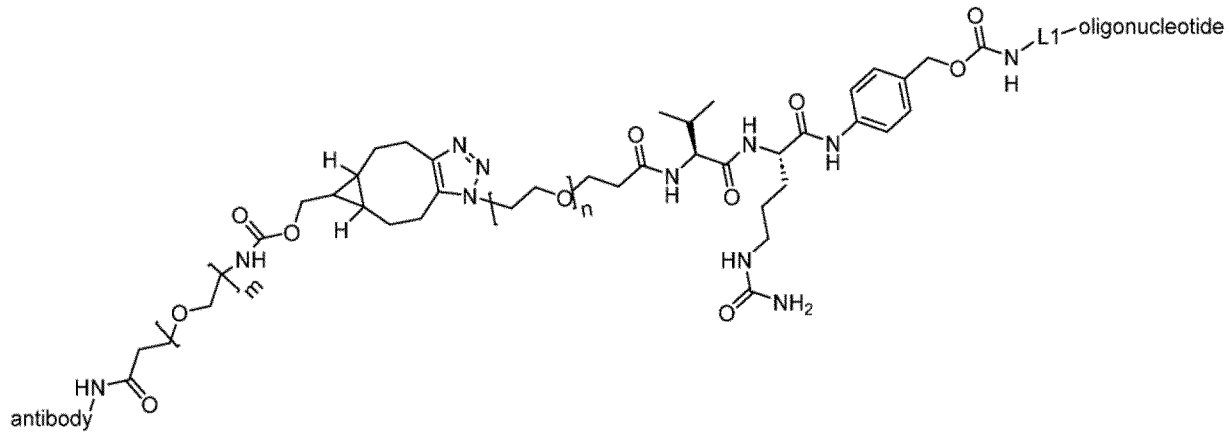

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, -O-, -N($R^A$)-, -S-, -C(=O)-, -C(=O)O-, -C(=O)N$R^A$-, -N$R^A$C(=O)-, -N$R^A$C(=O)$R^A$-, -C(=O)$R^A$-, -N$R^A$C(=O)O-, -N$R^A$C(=O)N($R^A$)-, -OC(-O)-, -OC(=O)O-, -OC(=O)N($R^A$)-, -S(O)$_2$N$R^A$, -N$R^A$S(O)$_2$-, or a combination thereof, wherein each $R^A$ is independently hydrogen or substituted or unsubstituted alkyl.

Should read:
10. The complex of Claim 9, wherein the complex comprises a structure of:

Signed and Sealed this
Third Day of December, 2024

*Katherine Kelly Vidal*

Katherine Kelly Vidal
*Director of the United States Patent and Trademark Office*

CERTIFICATE OF CORRECTION (continued)
U.S. Pat. No. 12,102,687 B2

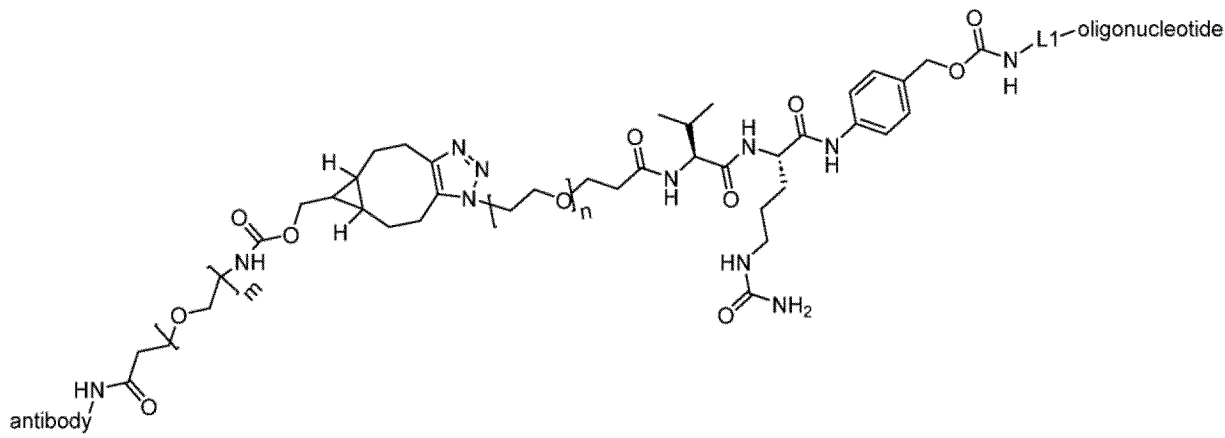

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, -O-, -N($R^A$)-, -S-, -C(=O)-, -C(=O)O-, -C(=O)N$R^A$-, -N$R^A$C(=O)-, -N$R^A$C(=O)$R^A$-, -C(=O)$R^A$-, -N$R^A$C(=O)O-, -N$R^A$C(=O)N($R^A$)-, -OC(=O)-, -OC(=O)O-, -OC(=O)N($R^A$)-, -S(O)$_2$N$R^A$, -N$R^A$S(O)$_2$-, or a combination thereof, wherein each $R^A$ is independently hydrogen or substituted or unsubstituted alkyl.

At Columns 400 and 401, Claim 25, Lines 22 through 15:
25. The complex of claim 24, wherein the complex comprises a structure of:

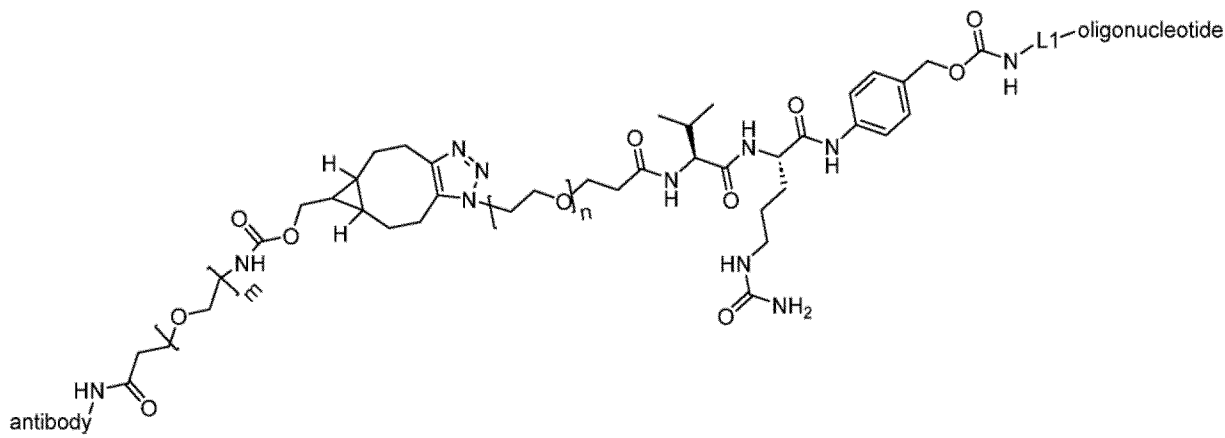

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, -O-, -N($R^A$)-, -S-, -C(=O)-, -C(=O)O-, -C(-O)N$R^A$-, -N$R^A$C(=O)-, -N$R^A$C(=O)$R^A$-, -C(=O)$R^A$-, -N$R^A$C(=O)O-, -N$R^A$C(=O)N($R^A$)-, -OC(=O)-, -OC(=O)O-, -OC(=O)N($R^A$)-, -S(O)$_2$N$R^A$-, -N$R^A$S(O)$_2$-, or a combination thereof, wherein each $R^A$ is independently hydrogen or substituted or unsubstituted alkyl.

Should read:
25. The complex of claim 24, wherein the complex comprises a structure of:

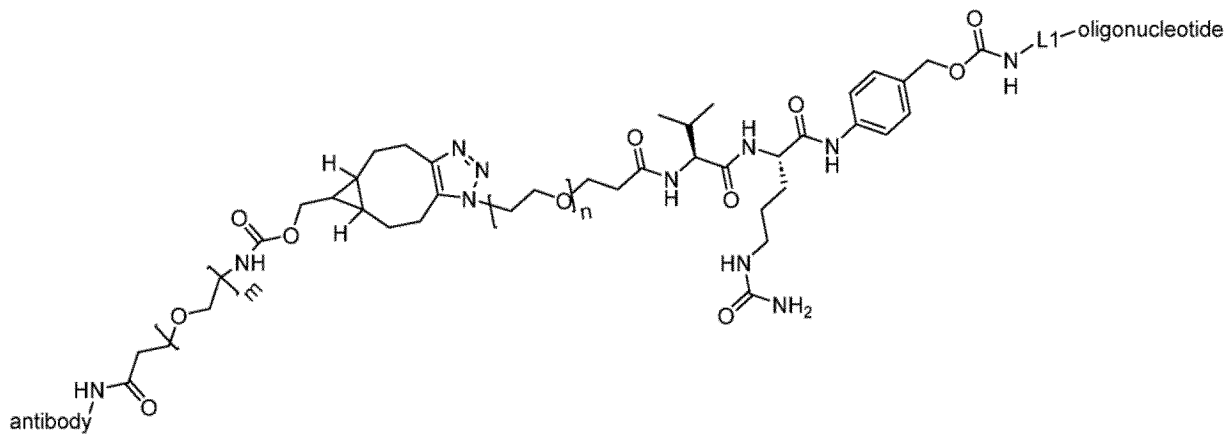

wherein n is 3 and m is 4, wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, -O-, -N($R^A$)-, -S-, -C(=O)-, -C(=O)O-, -C(=O)N$R^A$-, -$NR^A$C(=O)-, -$NR^A$C(=O)$R^A$-, -C(=O)$R^A$-, -$NR^A$C(=O)O-, -$NR^A$C(=O)N($R^A$)-, -OC(=O)-, -OC(=O)O-, -OC(=O)N($R^A$)-, -S(O)$_2$N$R^A$-, -$NR^A$S(O)$_2$-, or a combination thereof, wherein each $R^A$ is independently hydrogen or substituted or unsubstituted alkyl.